United States Patent
Pierce et al.

(10) Patent No.: US 9,743,672 B2
(45) Date of Patent: *Aug. 29, 2017

(54) CONTINUOUS METHODS FOR TREATING LIQUIDS AND MANUFACTURING CERTAIN CONSTITUENTS (E.G., NANOPARTICLES) IN LIQUIDS, APPARATUSES AND NANOPARTICLES AND NANOPARTICLE/LIQUID SOLUTION(S) RESULTING THEREFROM

(71) Applicants: David K. Pierce, Elkton, MD (US); Mark G. Mortenson, North East, MD (US); David A. Bryce, Elkton, MD (US)

(72) Inventors: David K. Pierce, Elkton, MD (US); Mark G. Mortenson, North East, MD (US); David A. Bryce, Elkton, MD (US)

(73) Assignee: GR INTELLECTUAL RESERVE, LLC

( * ) Notice: Subject to any disclaimer, the term of this patent is extended or adjusted under 35 U.S.C. 154(b) by 0 days.

This patent is subject to a terminal disclaimer.

(21) Appl. No.: 14/081,725

(22) Filed: Nov. 15, 2013

(65) Prior Publication Data
US 2015/0093453 A1    Apr. 2, 2015

Related U.S. Application Data

(62) Division of application No. 12/668,181, filed as application No. PCT/US2008/008558 on Jul. 11, 2008, now Pat. No. 8,617,360.
(Continued)

(51) Int. Cl.
*A01N 59/16* (2006.01)
*B22F 3/00* (2006.01)
(Continued)

(52) U.S. Cl.
CPC .......... *A01N 59/16* (2013.01); *A01N 59/00* (2013.01); *B01J 19/088* (2013.01); *B22F 3/003* (2013.01);
(Continued)

(58) Field of Classification Search
CPC ....... B01J 2219/0811; B01J 2219/0894; B22F 9/14; B82Y 40/00; H05H 1/48; H05H 2001/483
See application file for complete search history.

(56) References Cited

U.S. PATENT DOCUMENTS 5,478,533 A    12/1995   Inculet
5,876,663 A    3/1999    Laroussi
(Continued)

FOREIGN PATENT DOCUMENTS

AU    PCT/AU96/00768 A1    6/1997
EP    12908                 5/1910
(Continued)

OTHER PUBLICATIONS

Cushing, et al., Recent Advances in the Liquid-Phase Synthesis of Inorganic Nanoparices; Chem. Rev. 2004, 104, 3893-3946.
(Continued)

*Primary Examiner* — Steven A. Friday
(74) *Attorney, Agent, or Firm* — Mark G Mortenson

(57) ABSTRACT

This invention relates generally to novel methods and novel devices for the continuous manufacture of nanoparticles, microparticles and nanoparticle/liquid solution(s). The nanoparticles (and/or micron-sized particles) comprise a variety of possible compositions, sizes and shapes. The particles (e.g., nanoparticles) are caused to be present (e.g., created) in a liquid (e.g., water) by, for example, preferably utilizing at least one adjustable plasma (e.g., created by at least one AC and/or DC power source), which plasma
(Continued)

communicates with at least a portion of a surface of the liquid. At least one subsequent and/or substantially simultaneous adjustable electrochemical processing technique is also preferred. Multiple adjustable plasmas and/or adjustable electrochemical processing techniques are preferred. The continuous process causes at least one liquid to flow into, through and out of at least one trough member, such liquid being processed, conditioned and/or effected in said trough member(s). Results include constituents formed in the liquid including micron-sized particles and/or nanoparticles (e.g., metallic-based nanoparticles) of novel size, shape, composition and properties present in a liquid.

23 Claims, 246 Drawing Sheets

Related U.S. Application Data

(60) Provisional application No. 60/949,175, filed on Jul. 11, 2007, provisional application No. 60/949,312, filed on Jul. 12, 2007.

(51) Int. Cl.
    *B01J 19/08*    (2006.01)
    *C22B 3/02*     (2006.01)
    *C22B 3/22*     (2006.01)
    *A01N 59/00*    (2006.01)
    *H05H 1/48*     (2006.01)
    *C22B 4/00*     (2006.01)
    *C22B 4/08*     (2006.01)

(52) U.S. Cl.
    CPC .................. *C22B 3/02* (2013.01); *C22B 3/22* (2013.01); *H05H 1/48* (2013.01); *B01J 2219/0811* (2013.01); *B01J 2219/0894* (2013.01); *B22F 2999/00* (2013.01); *C22B 4/005* (2013.01); *C22B 4/08* (2013.01); *H05H 2001/483* (2013.01); *Y02P 10/234* (2015.11)

(56) References Cited

U.S. PATENT DOCUMENTS

| | | | |
|---|---|---|---|
| 5,965,994 | A | 10/1999 | Seo et al. |
| 6,214,299 | B1 | 4/2001 | Holladay et al. |
| 6,358,398 | B1 | 3/2002 | Halldorson et al. |
| 6,743,348 | B2 | 6/2004 | Holladay et al. |
| 6,749,759 | B2 | 6/2004 | Denes et al. |
| 6,802,981 | B2 | 10/2004 | Ryazanova et al. |
| 7,033,415 | B2 | 4/2006 | Mirkin et al. |
| 7,118,852 | B2 | 10/2006 | Purdum |
| 7,135,054 | B2 | 11/2006 | Jin et al. |
| 7,135,055 | B2 | 11/2006 | Mirkin et al. |
| 7,135,195 | B2 | 11/2006 | Holladay et al. |
| 7,276,283 | B2 | 10/2007 | Denes et al. |
| 7,438,882 | B2 | 10/2008 | Goodwin et al. |
| 8,088,193 | B2 | 1/2012 | Zeng et al. |
| 8,540,942 | B2 | 9/2013 | Pierce et al. |
| 8,617,360 | B2 | 12/2013 | Pierce et al. |
| 2002/0014400 | A1 | 2/2002 | Zadiraka et al. |
| 2002/0071792 | A1* | 6/2002 | Holladay .............. C02F 1/4606 422/186.04 |
| 2003/0012718 | A1* | 1/2003 | Josephson et al. .......... 423/241 |
| 2003/0121775 | A1* | 7/2003 | Liu et al. ................... 204/293 |
| 2004/0022702 | A1 | 2/2004 | Christensen |
| 2004/0131524 | A1 | 7/2004 | Josephson et al. |
| 2006/0068026 | A1 | 3/2006 | Hu et al. |
| 2006/0249705 | A1 | 11/2006 | Wang et al. |
| 2007/0080054 | A1 | 4/2007 | Parkansky et al. |
| 2007/0108056 | A1 | 5/2007 | Nyberg et al. |
| 2007/0267289 | A1 | 11/2007 | Jabs et al. |
| 2008/0169182 | A1 | 7/2008 | Denes |
| 2008/0277272 | A1 | 11/2008 | Pierce et al. |
| 2009/0178933 | A1 | 7/2009 | Zeng |
| 2011/0278178 | A1 | 11/2011 | Pierce et al. |
| 2015/0064278 | A1 | 3/2015 | Pierce et al. |
| 2015/0093453 | A1 | 4/2015 | Pierce et al. |

FOREIGN PATENT DOCUMENTS

| | | |
|---|---|---|
| EP | 432101 | 7/1935 |
| EP | 0857695 A2 | 4/2001 |
| WO | PCT/US05/47699 | 7/2006 |
| WO | PCT/US2008/008558 | 1/2009 |
| WO | PCT/US2010/041427 | 1/2011 |
| WO | PCT/US2010.00088 | 11/2011 |

OTHER PUBLICATIONS

Wiley, et al., Shape-Controlled Synthesis of Metal Nanostructures: The Case of Silver, Chem. Eur. J. 2005, 11, 454-463.
Wu, C.; Zeng, T., Size-Tunable Synthesis of Metallic Nanoparticles in a Continuous and Steady-Flow Reactor, Chem. Mater 2007, 112-125, vol. 19, No. 2.
Ultra Professional Instructions for Making Premium AC Colloidal Silver with your HVAC Ultra Professional System.
HVAC ARC Silver Solutions, System Tech Engineering, http://web.archive.org/web/20021125133241l/http://www.hvacsilver.com: Nov. 12, 2008.
Plasma (physics); Wikipedia; http://en.wikipedia.org/wiki/plasma_ (physics); 2010.
Taylor cone; Wikipeia; http://en.wikipedia.org/wiki/Taylor_cone; 2010.
Manolache, S; Shamamian, V.; Denes F., Dense Medium Plasma-Plasma-Enhanced Decontamination of Water of Aromatic Compounds, J. of Environ Eng. Jan. 17-25, 2004.
Riegel, E. R.; Osthoff, R.C.; Flach D.O. Bredig Sols: A Lecture Demonstration, J. Chem. Educ, 1949, p. 519, vol. 26, No. 10.
Weiser, Harry Boyer, Inorganic Colloid Chemistry, 1933, p.1, 8-17, 45-46, 116-117, 124-125, 132-135, John Wiley & Sons, Inc., New York.
Kraemer, E.O., Svedberg, T., Formation of Colloid Solutions by Electrical Pulverization in the High-Frequency Alternating Current Arc, J. Am. Chem Soc. 1924, 46(9) p. 1980-1991.
Rodriguez-Sanchez, L., Blanco, M.C., Lopez-Quintela, M.A., Electrochemical Synthesis of Silver Nanoparticles, J. Phys. Chem. B., 2000, 104, p. 9683-9688.
Liu, Yu-Chuan, et al., Active Catalysts of Electrochemically Prepared Gold Nanoparticles for the Decomposition of Aldehyde in Alcohol Solutions. Electrochemistry Communications, 2006, 1163-1167, 8.
Hickling, A., et al. Contact Glow-Discharge Electrolysis. Trans Faraday Soc., 1964, 783-793, 60.
Toriyabe, Yu. et al. Controlled Formation of Metallic Nanoballs During Plasma Electrolysis. Applied Physics Letters, 2007, 041501-1-041501-3, 91.
Wuthrich, Rolf, et al., Electrochemical Discharges-Discovery and Early Applications. Etettochimica Acta, 2009. 4031-4035, 54.
Locke, B. R. et al., Electrohydraulic Discharge and Nonthermal Plasma for Water Treatment, Ind. Eng. Chem. Res., 2006, 882-905, 45.
Meiss, Sebastian A., Employing Plasmas as Gaseous Electrodes at the Free Surface of Ionic Liquids: Deposition of Nanocrystalline Silver Particles. ChemPhsyChem, 2007, 50-53, 8.
Hickling, A., et al., Glow-Discharge Electrolysis. J. Electroanal. Chem, 1964, 65-81, 8.
Chaffin, John H., et al., Hydrogen Production by Plasma Electrolysis. Journal of Energy Engineering, 2006, 104-108, 132:3.
Aqil, A., et al.: Preparation of Stable Suspensions of Gold Nanoparticles in Water by Sonoelectrochernistry. Ultrasonics Sonochemistry, 2008, 1055-1061, 15.
Liu, Yu-Chen, et al. Size-Controlled Synthesis of Gold Nanoparticles from Bulk Gold Substrates by Sonoelectrochemical Methods. J. Phys. Chem. B, 2004, 19237-19240, 108.

(56) References Cited

OTHER PUBLICATIONS

Torimoto Tsukasa, et al. Sputter deposition onto ionic liquids: Simple and clean synthesis of highly dispersed ultrafine metal nanoparticles. Applied Physics Letters, 2006, 243117-1-243117-3, 89.

Nagata, Yoshio, et al. Sonochemical Formation of Gold Particles in Aqueous Solution. Radiation Research, 1996, 333-336, 146.

Saez, Veronica, et al. Sonoelectrochemical Synthesis of Nanoparticles. Molecules, 2009, 4284-4299, 14.

Flijimoto, Taku, et al. Sonolytical Preparation cif Various Types of Metal Nanoparticles Aqueous Solution Scripta mater., 2001, 2183-2186, 44.

Vasudevamurthy, Gokul, et al. "Effect of System Parameters on Size Distribution of 304 Stainless Steel Particles Produced by Electrical Discharge Mechanism", Materials Letters, 2007, p. 4872-4874, vol. 61.

Staack, David, et al. Nanoscale Corona Discharge in Liquids. Enabling Nanosecond Optical Emission Spectroscopy. Angew. Chem.Int.Ed., 2008, 8020-6024, 47.

Kravechenko A.V., et al., On the Change in Properties of Water Subjected to Low Temperature Plasma Electrolysis. High Energy Chemistry, vol. 38, No. 5. 2004, pp. 333-337.

Koo, II Gyo, et al., Platinum Nanoparticles Prepared by a Plasma-Chemical Reduction Method. J. Mater Chem., 2005, 15, 4125-4128.

Tas, M.A., Van Hardeveld, R., Van Veldhuizen, E.M.: Reactions of NO in a Positive Streamer Corona Plasma; Plasma Chem and Plasma Proc; 1997, p. 371-391, vol. 17, No. 4.

Yan, K., Corona Plasma Generation, 2001, Technische Universiteit Eindhoven.

Hoeben, W.F.L.M., Pulsed Corona-Induced Degradation of Organic Materials in Water, 2000, Technische Universiteit Eindhoven.

Lofton, C., Sigmund, W.: Mechanisms Controlling Crystal Habits of Gold and Silver Colloids, Adv. Funct. Mater. 2005, p. 1197-1208, 15.

Martinez, S.S., Gallegos, A.A., Martinez, E.; Electrolytically Generated Silver and Copper Ions to Treat Cooling Water: An Environmentally Friendly Novel Alternative, International Journal of Hydrogen Energy, 2004, p. 921-932, 29.

Bhattacharyya, S., et al.; Localized Synthesis of Metal Nanoparticles, Using Nanoscale Corona Discharge in Aqueous Solutions, Adv. Mater, 2009, p. 4039-4044, 21.

Mucalo, M.R., Bullen, C R.; Electric Arc Generated (Bredig) Palladium Nanoparticles: Surface Analysis by X-Ray Photoelectron Spectroscopy for Samples Prepared at Different pH, J. Mat. Sci. Let., 2001, p. 1853-1856, 20.

Lange, H., et al., Nanocarbon Production by Arc Discharge in Water, Carbon, 2003, pp. 1617-1623, 41.

Ma, H; Yin, B; Wang, S; Jiao, Y; Pan, W; Huang, S: Chen, S: Meng, F; Synthesis of Silver and Gold Nanoparticles by a Novel Electrochemical Method, ChemPhysChem, 2004, 5, 68-75.

Powell, J., Our Mightiest Germ Fighter, Science Digest, 1978 p. 57-59.

Svedberg, T., The Formation of Colloids, 1921, p. 22-41, D. Van Nostrand Company, New York.

Zsigmondy, R., The Chemistry of Colloids, 1917, p. 11, 19, 30, 68, 86-95, 114-119, 122-123, 127-128, John Wiley & Sons, Inc., New York.

Bechhold, H., Colloids in Biology and Medicine, 1919. p. 89-127. D. Van Nostrand Company, New York.

Federal Register/vol. 64, No. 158/Aug. 17, 1999/Rules and Regulations, p. 44653-44658.

Gibbs, R. J., Silver Coolids, Do They Work?, 1999, Ronald J. Gibbs, Newark, DE.

Grier, Silver and Its Compounds. Disinfection, Sterilization,and Preservation, 2001, p. 403-407. Lippincott Williams & Wilkins. Philadelphia.

Pacheco, G., Studies on the Action of Metallic Colloids on Immunisation. Mem. Inst. Oswaldo Cruz. 1925, vol. 18, n. 1, pp. 119-149.

DeVries, C.A M.; De Hoog, F.J.; Schram, D.C.; Ionic Species in a Negative Corona in Humid Air, 1983, p. 317-321, Eindhoven University of Technology, The Netherlands.

Liu, Yu-Chuan, et al., New Pathway for the Synthesis of Ultrafine Silver Naneparticles From Bulk Silver Substrates in Aqueous Solutions by Sonoelectrochemical Methods, Electrochemistry Communications. 2004, 1163-1168, 6.

Bruggeman, Peter, et al., Non-Thermal Plasmas in and in Contact With Liquids; J.Phys.D:Appl.Phys, 2009.

Burda, et al., Chemistry and Properties of Nanocrystals of Different Shapes; Chem. Rev. 2005, 1025-1102.

Lelievre, J., et al., Electrolysis Processes in D.C. Corona Discharges in Humid Air. J.Phys. III France 5 (1995).

* cited by examiner

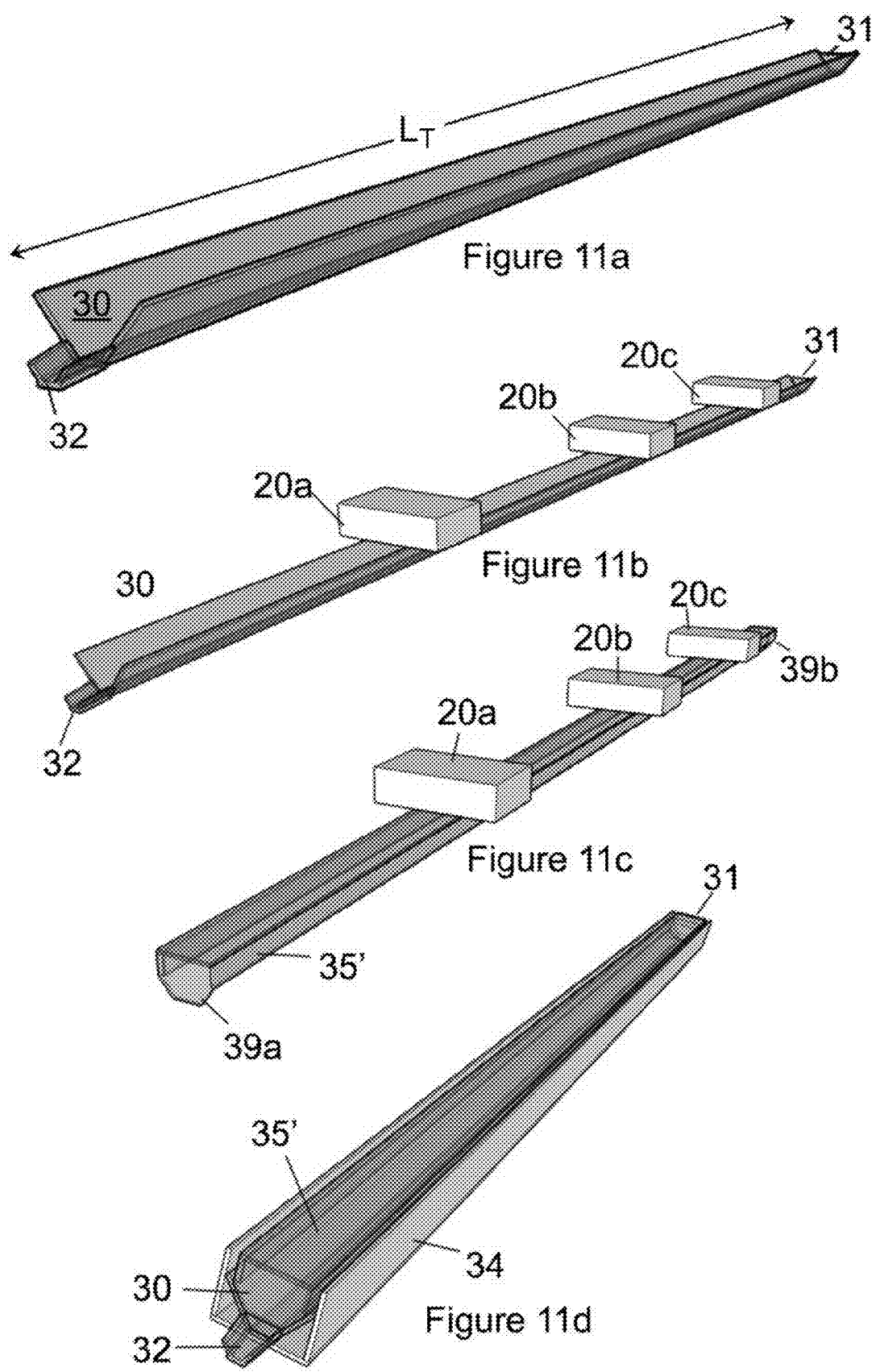

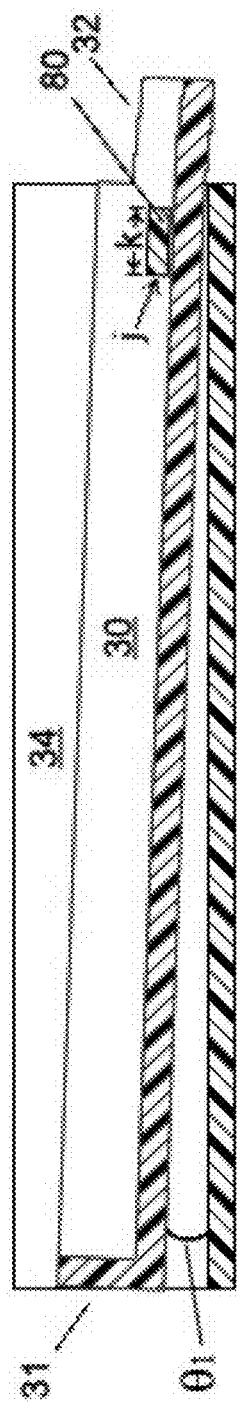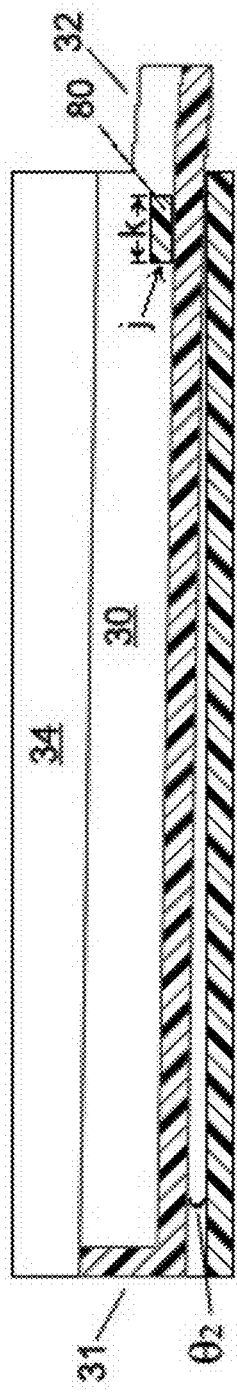
Figure 15a
Figure 15b

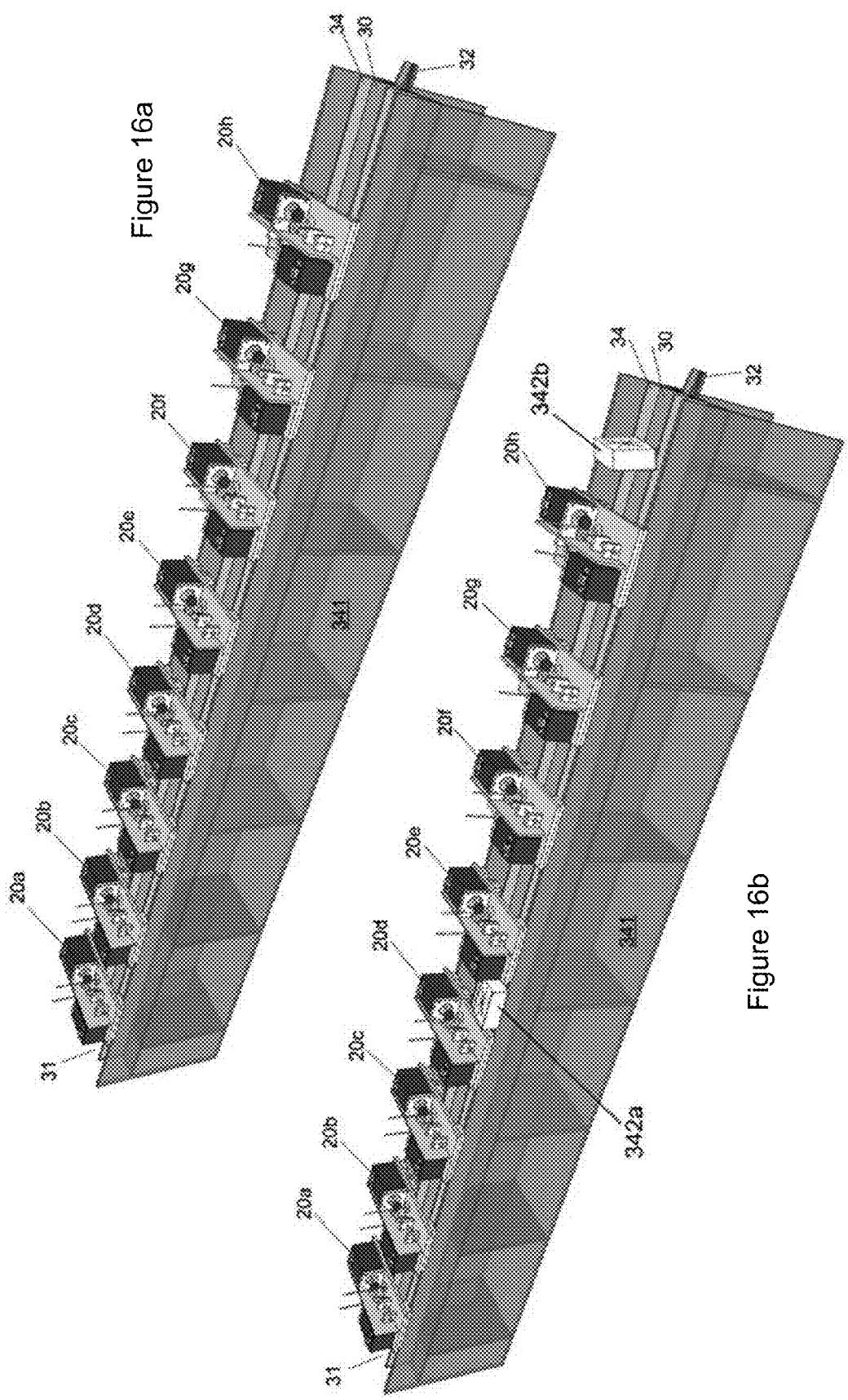

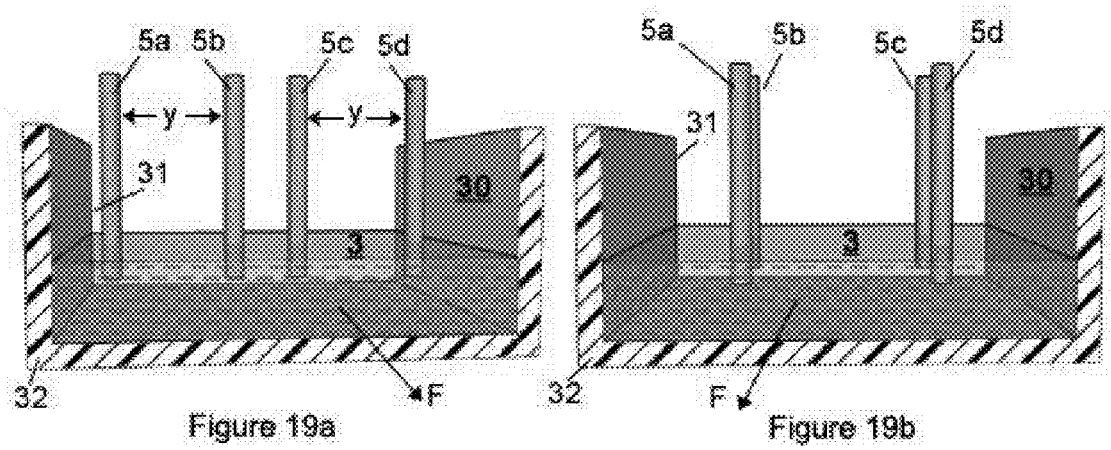
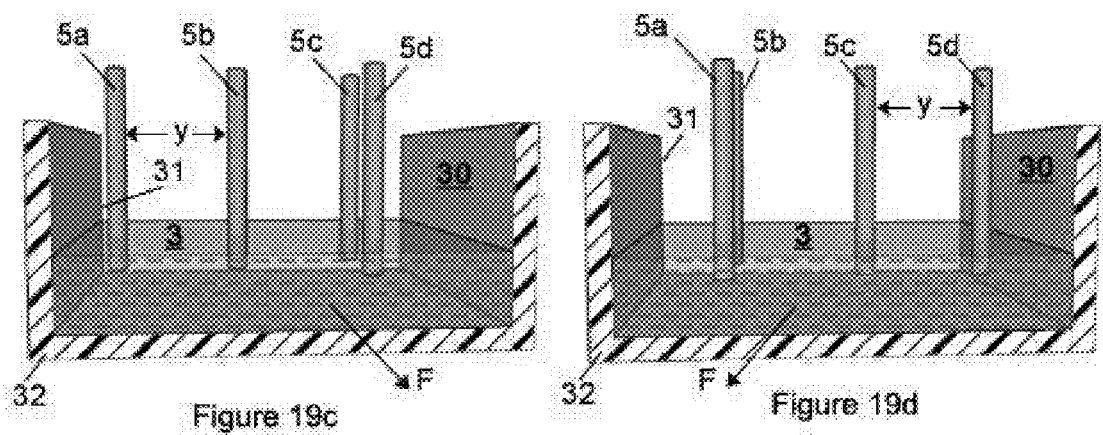

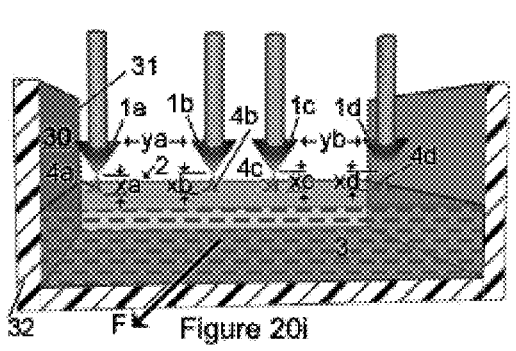

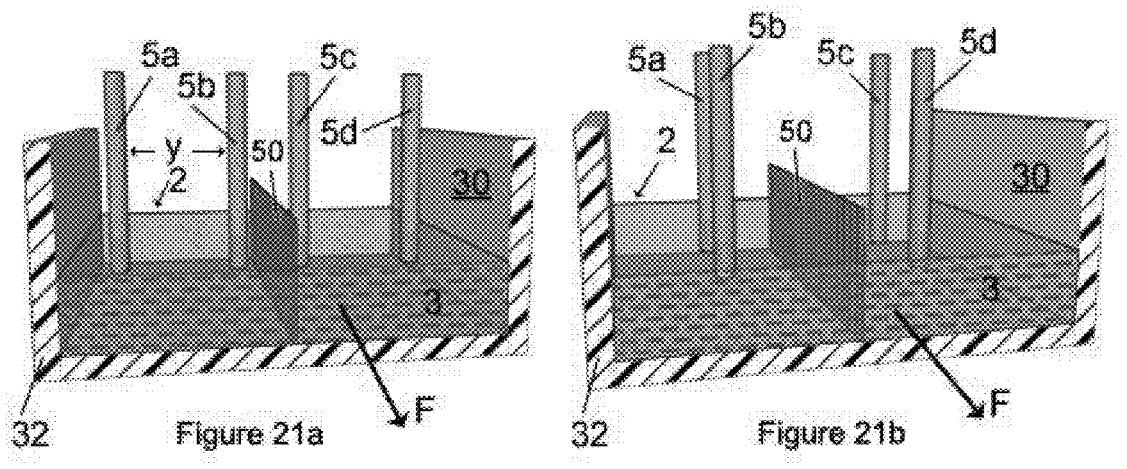
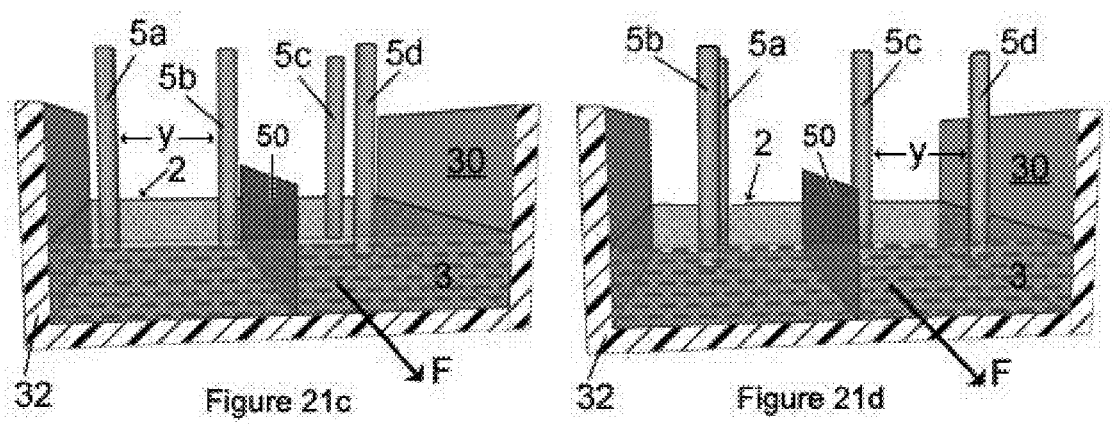

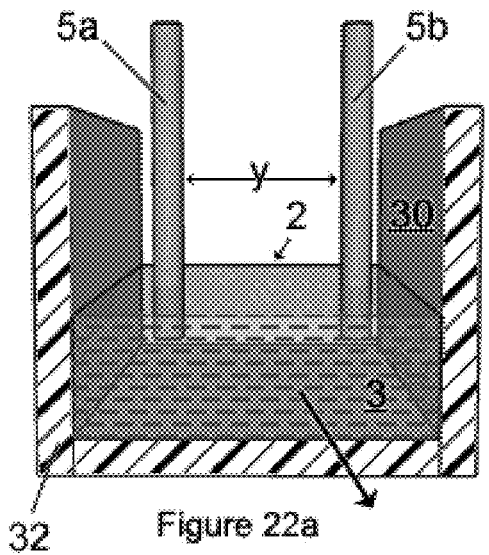
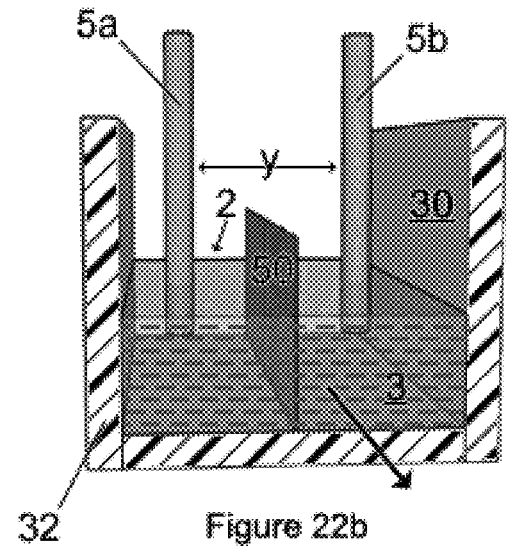
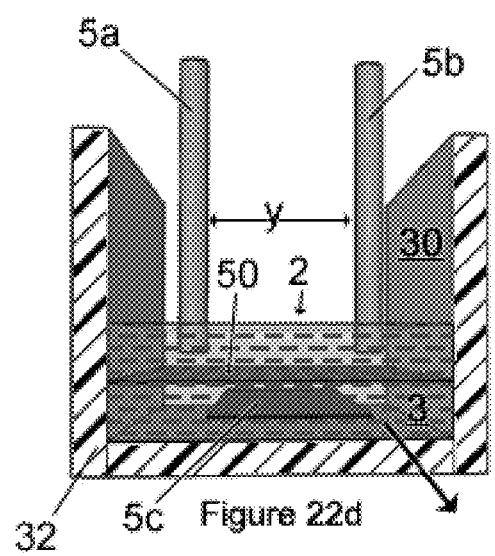

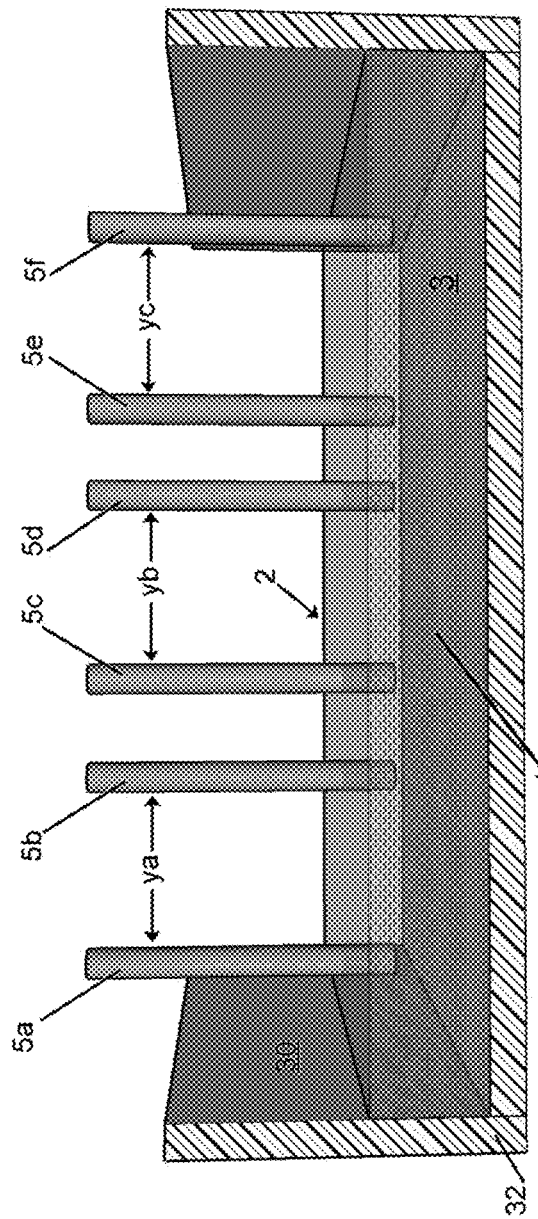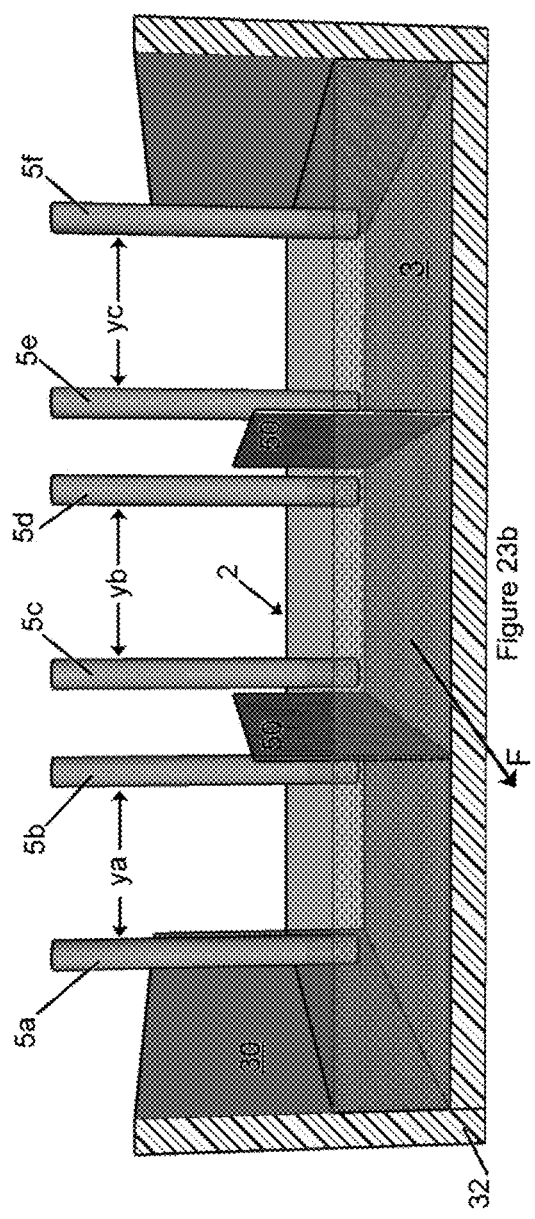

$$V_{out} = \frac{V_1(R_2 \| R_L)}{(R_1 + R_2 \| R_L)}$$

$R_L$ = 10M Ohm input impedance of Multimeter

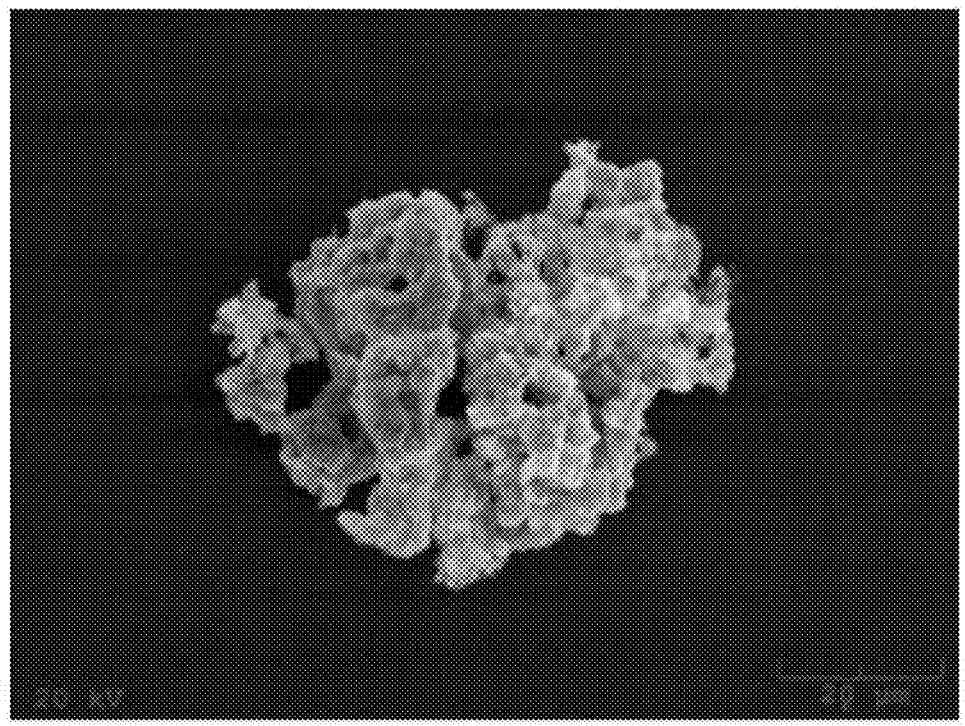
i.
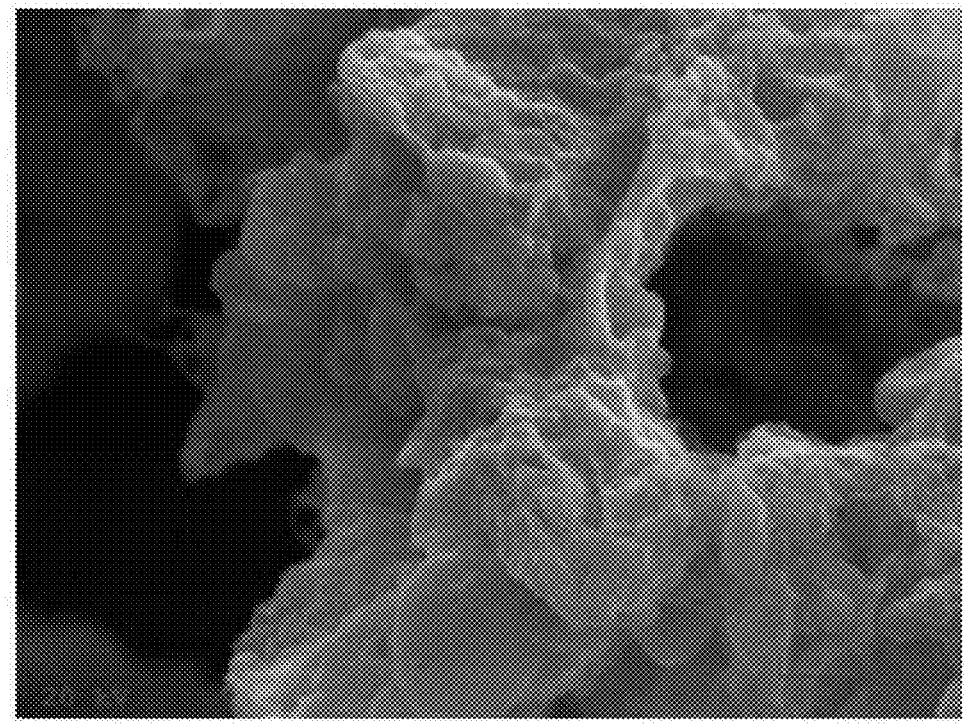
ii.
Figure 43a

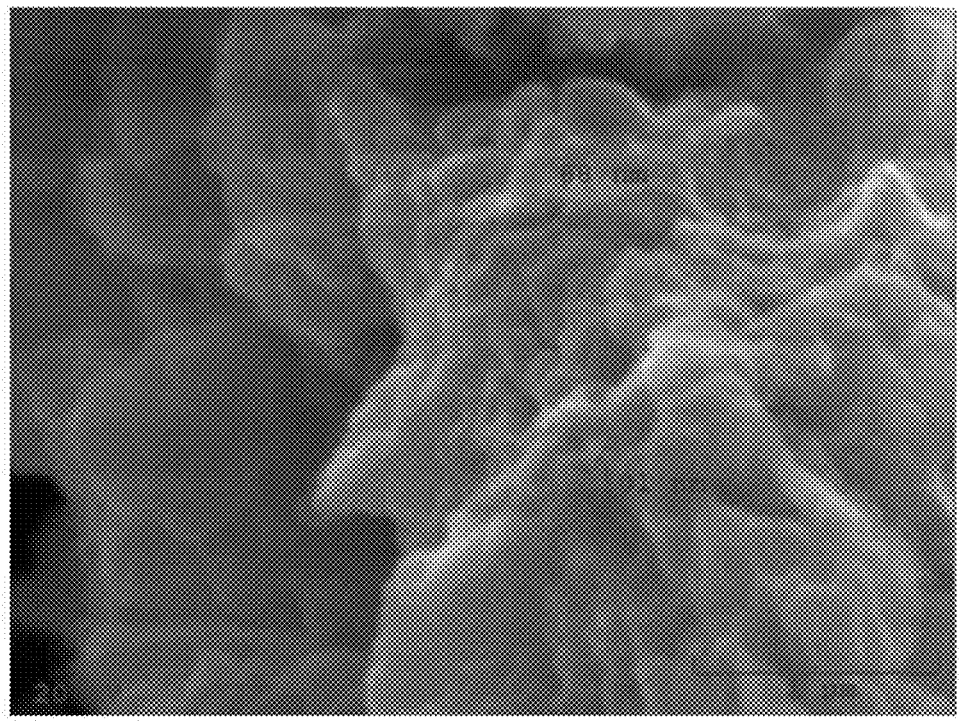
iii.
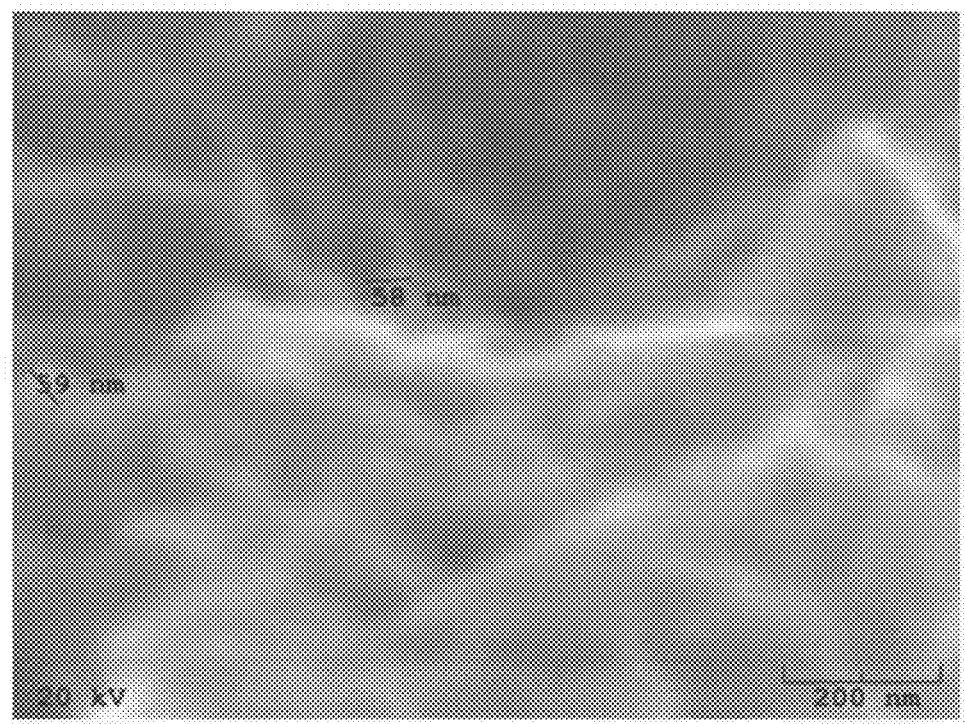
iv.
Figure 43a

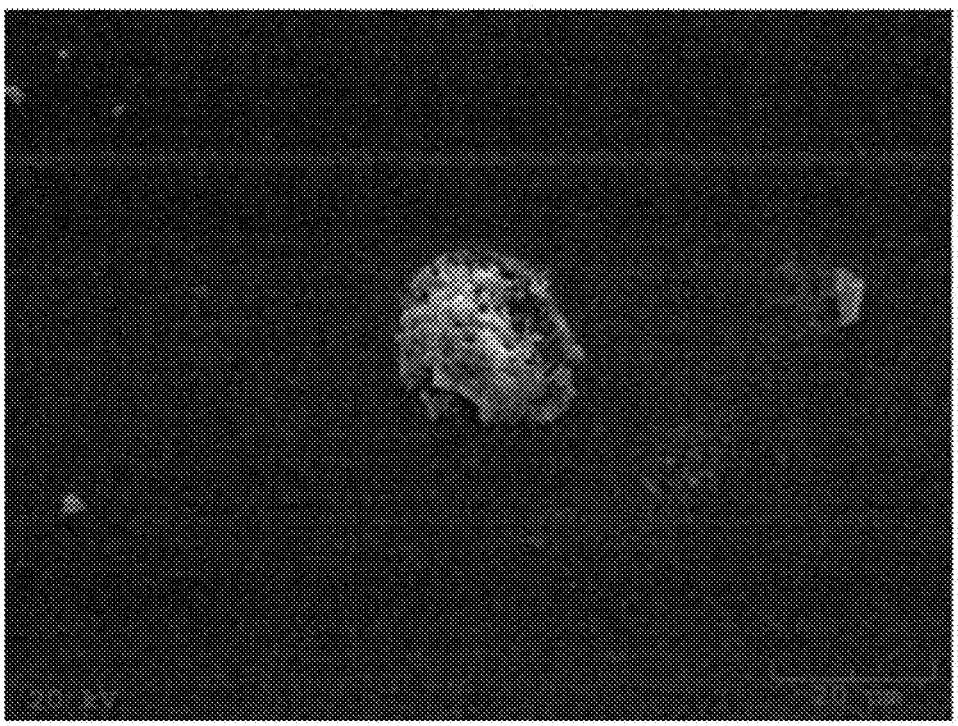
i.
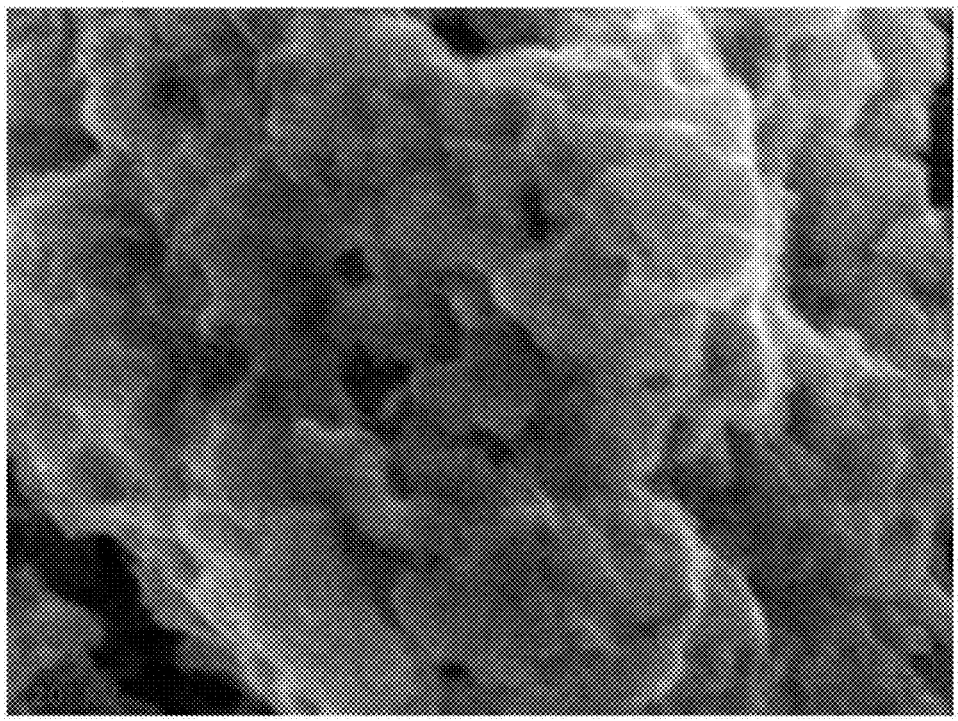
ii.
Figure 43b

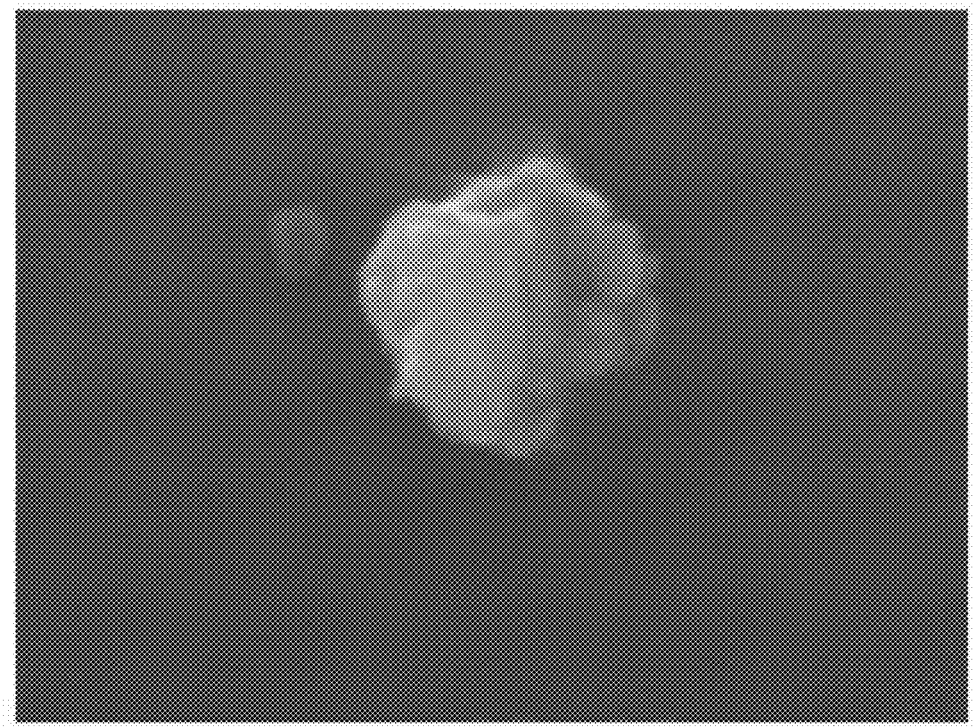
iii.
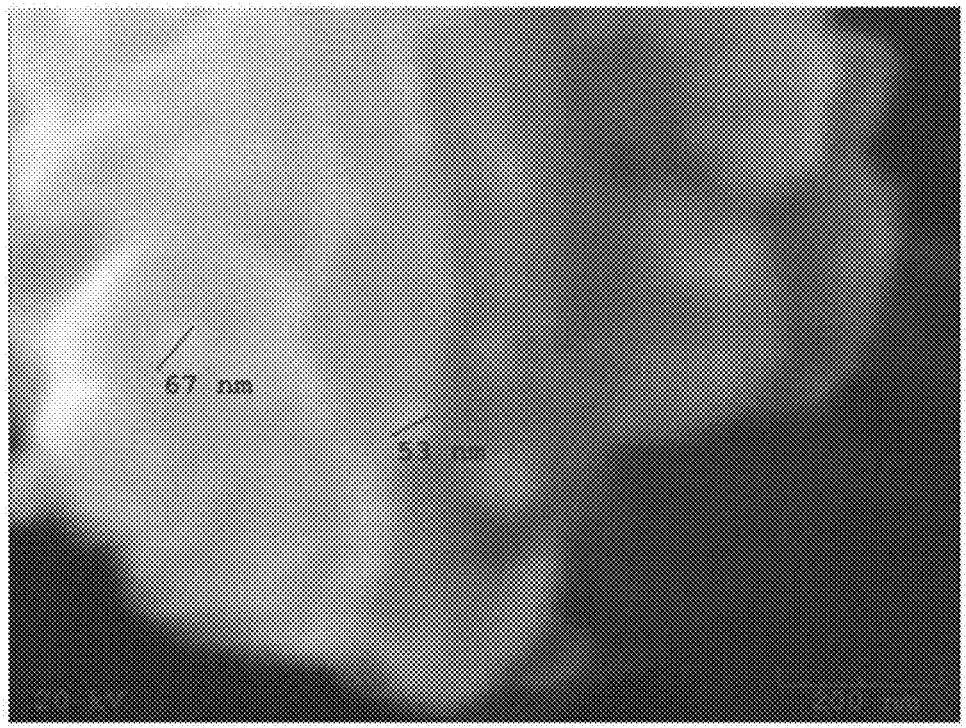
iv.
Figure 43b

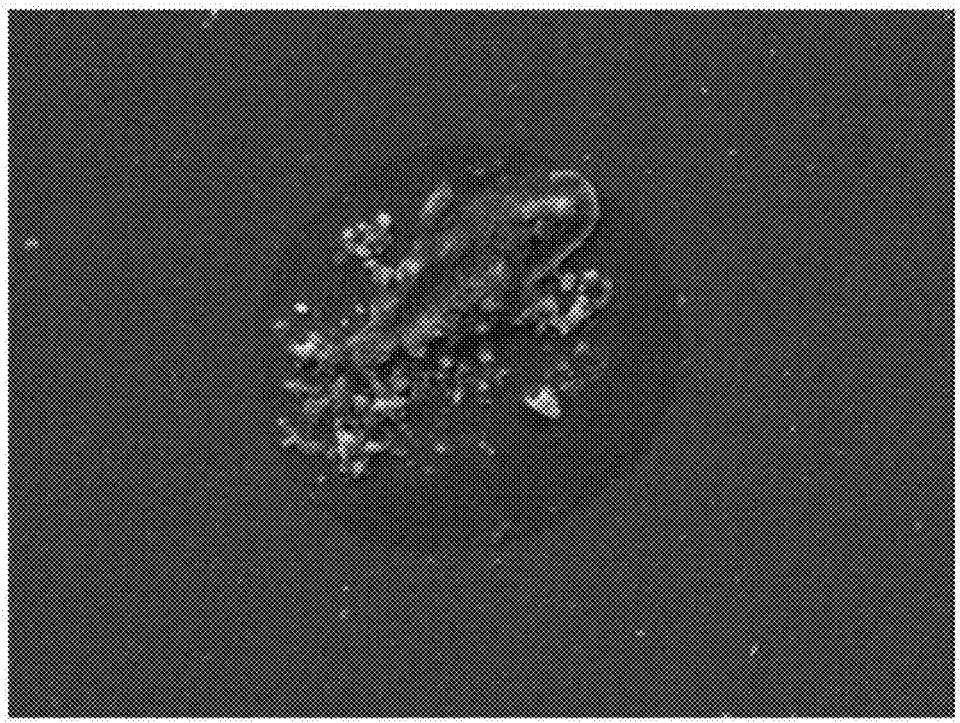
i.
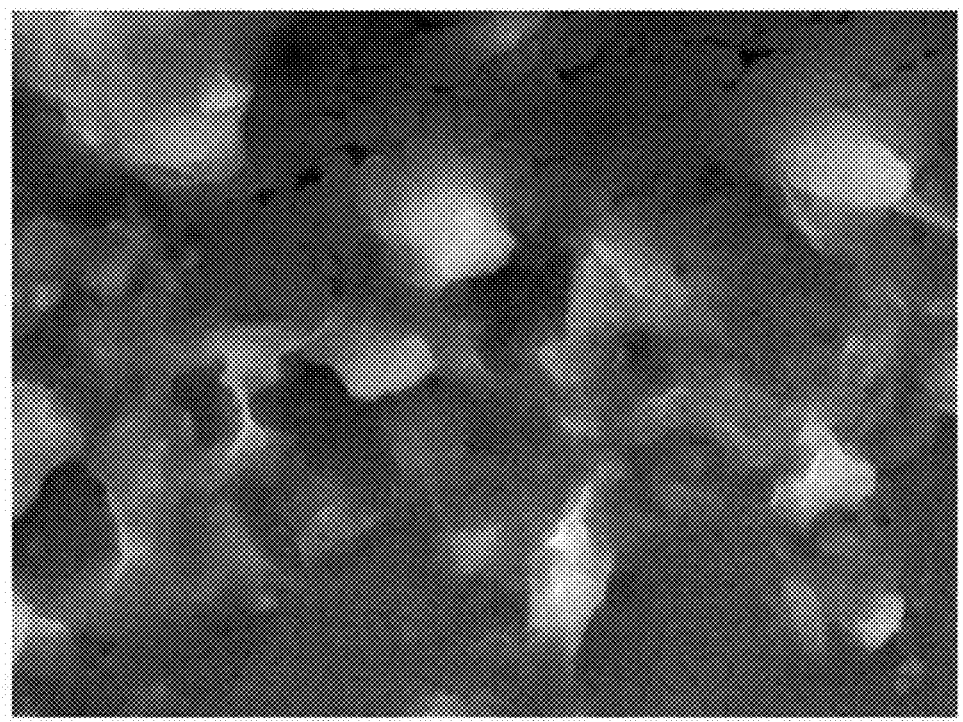
ii.
Figure 43c

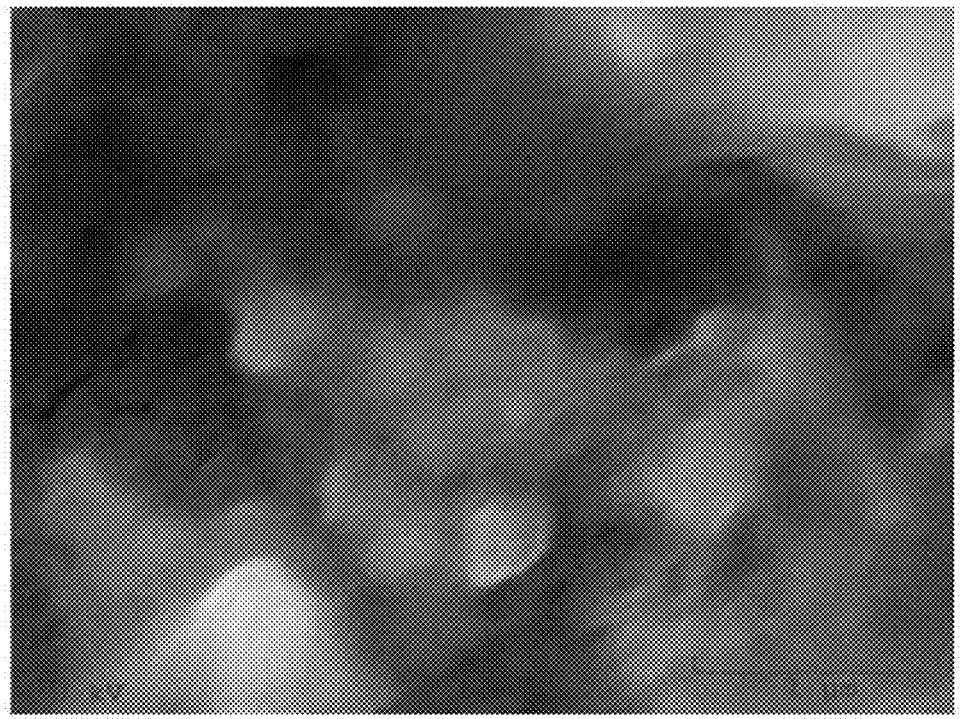
iii.
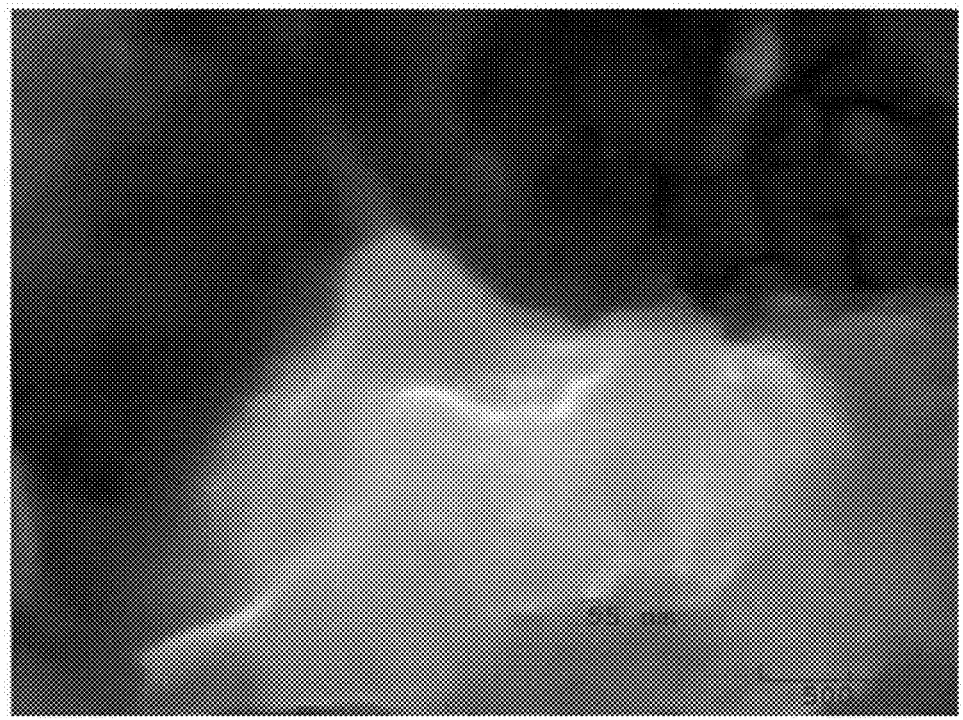
iv.
Figure 43c

i.
ii.
Figure 43d

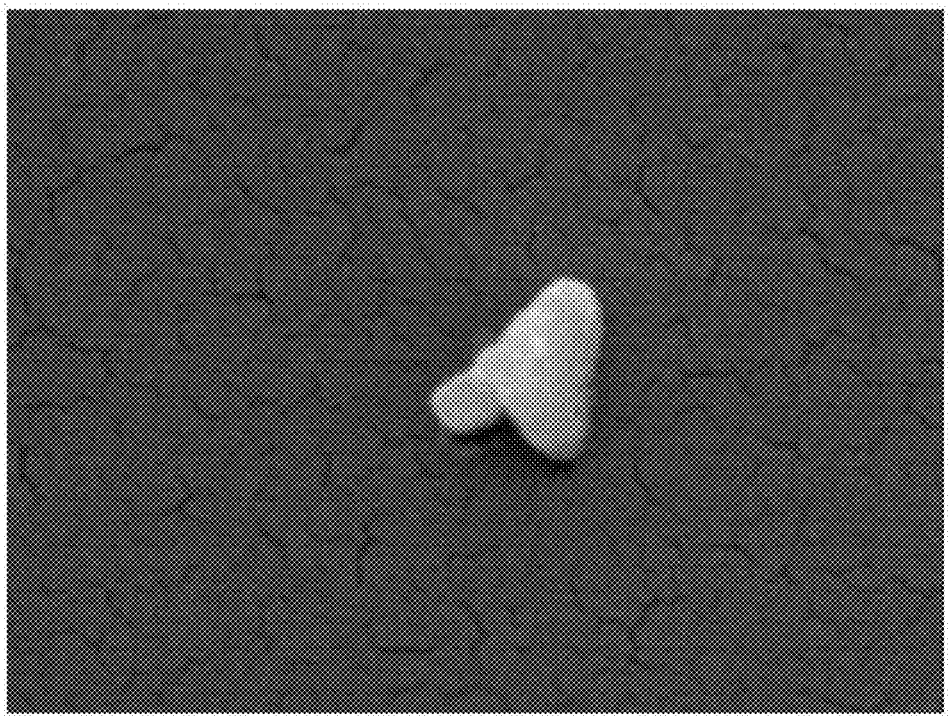
iii.
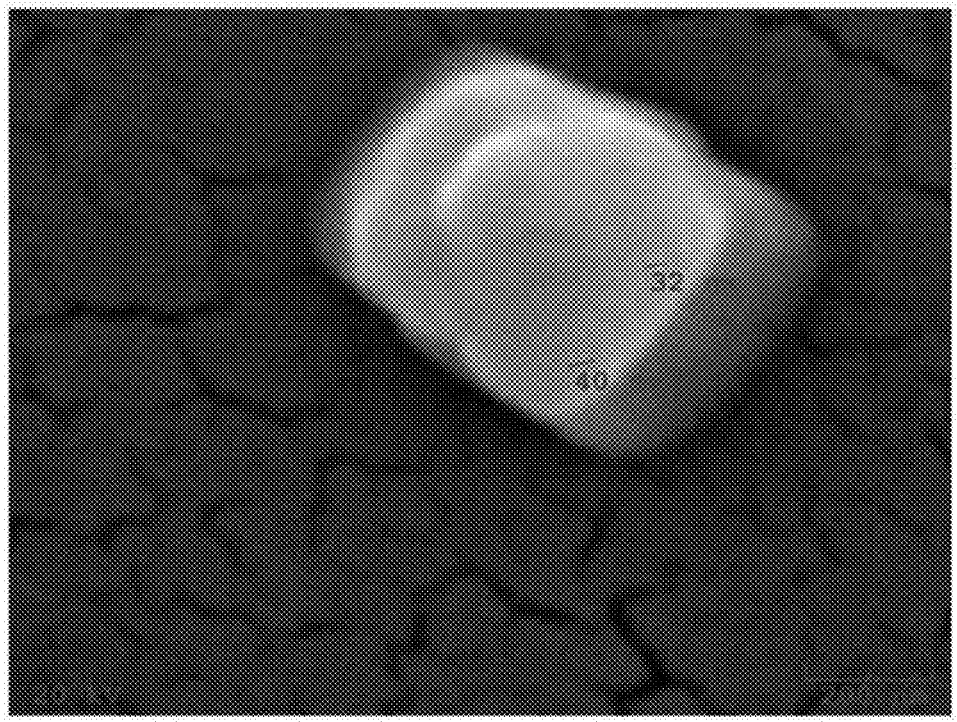
iv.
Figure 43d

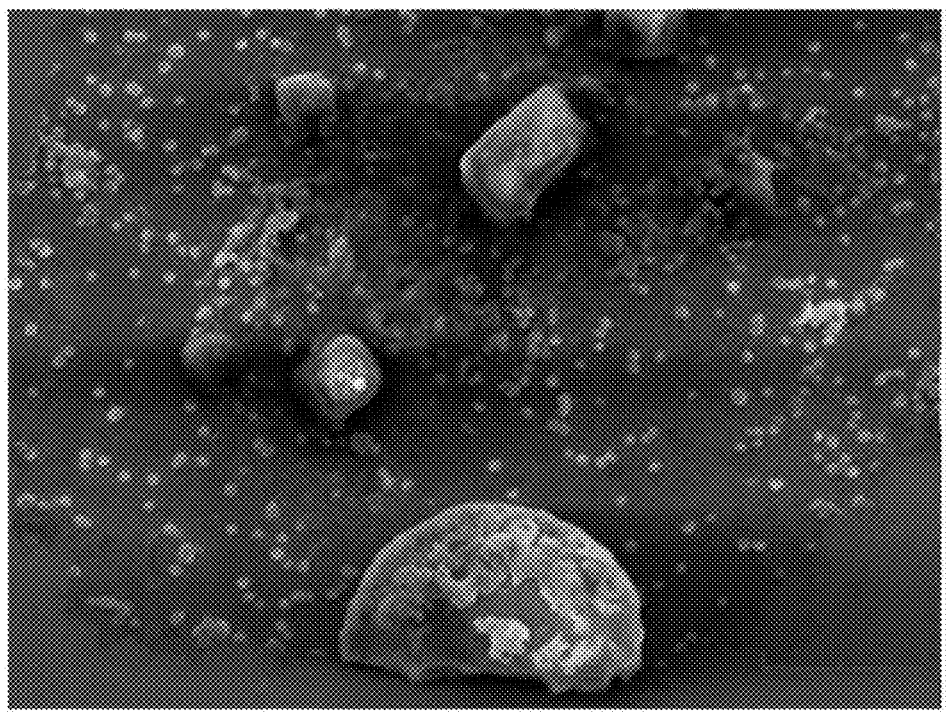
i.
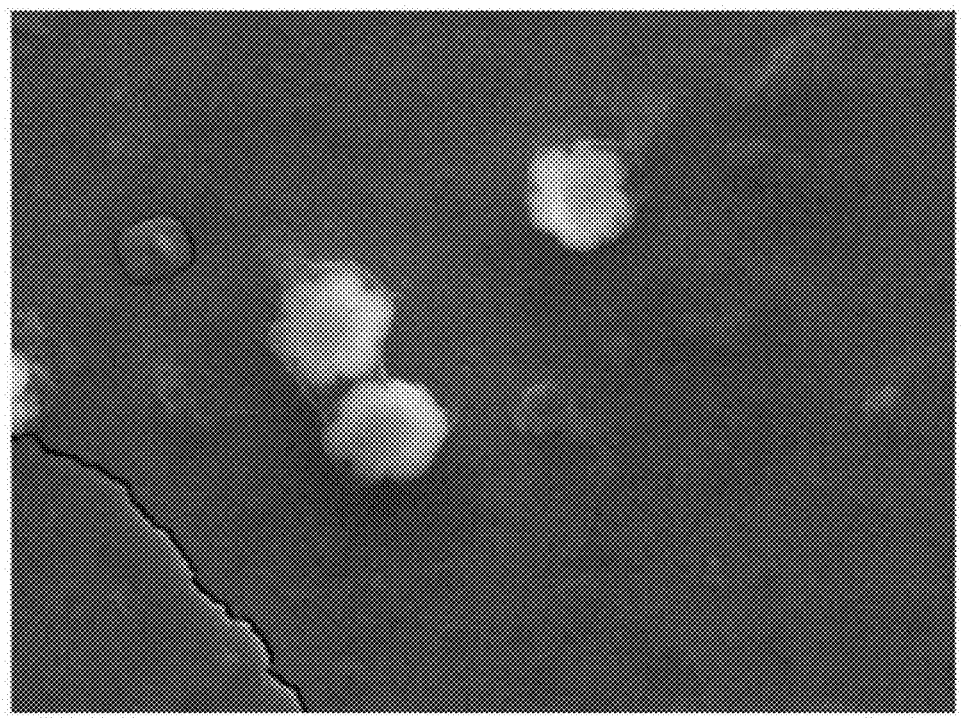
ii.
Figure 43e

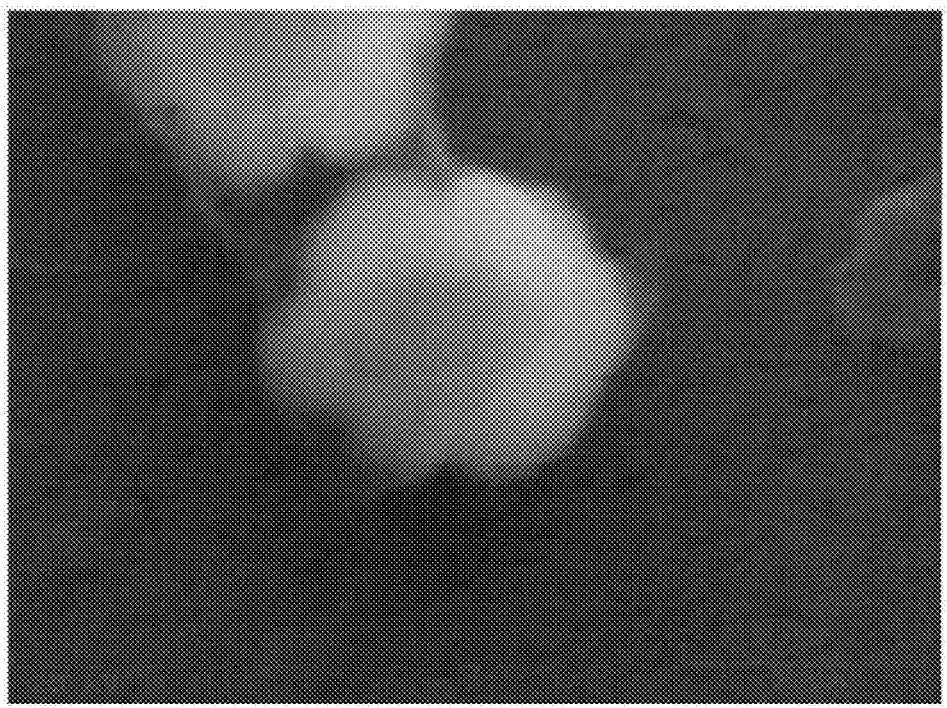
iii.
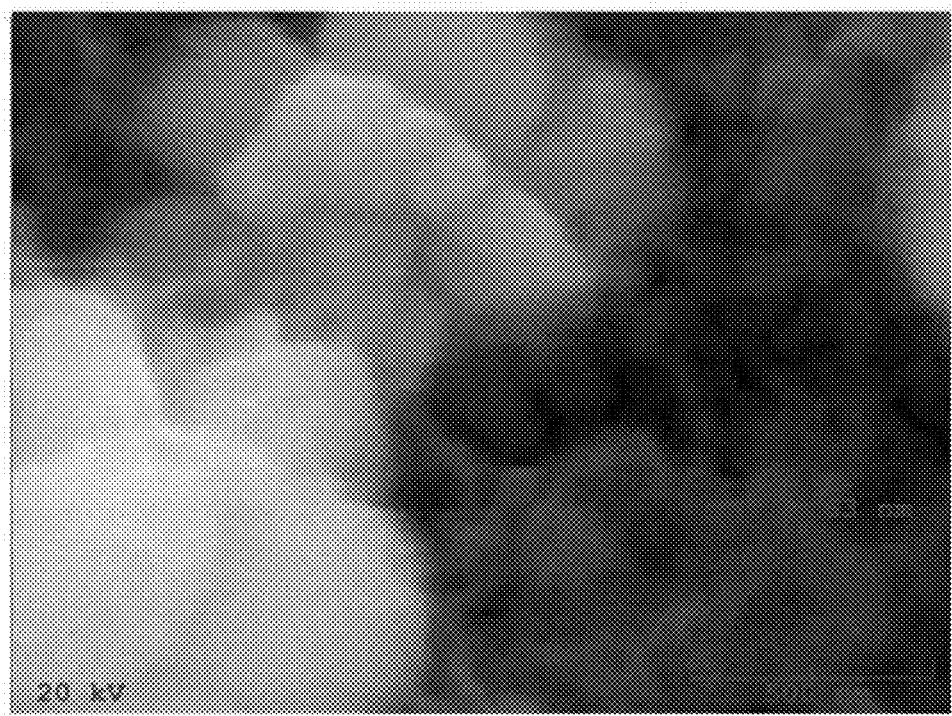
iv.
Figure 43e

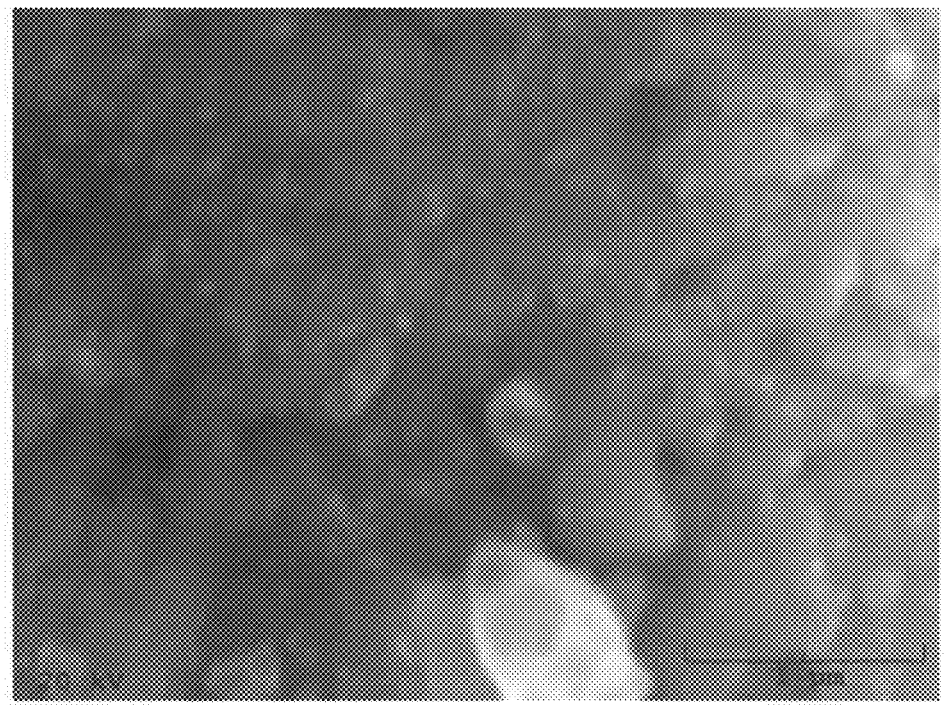
iii.
iv.
Figure 43f

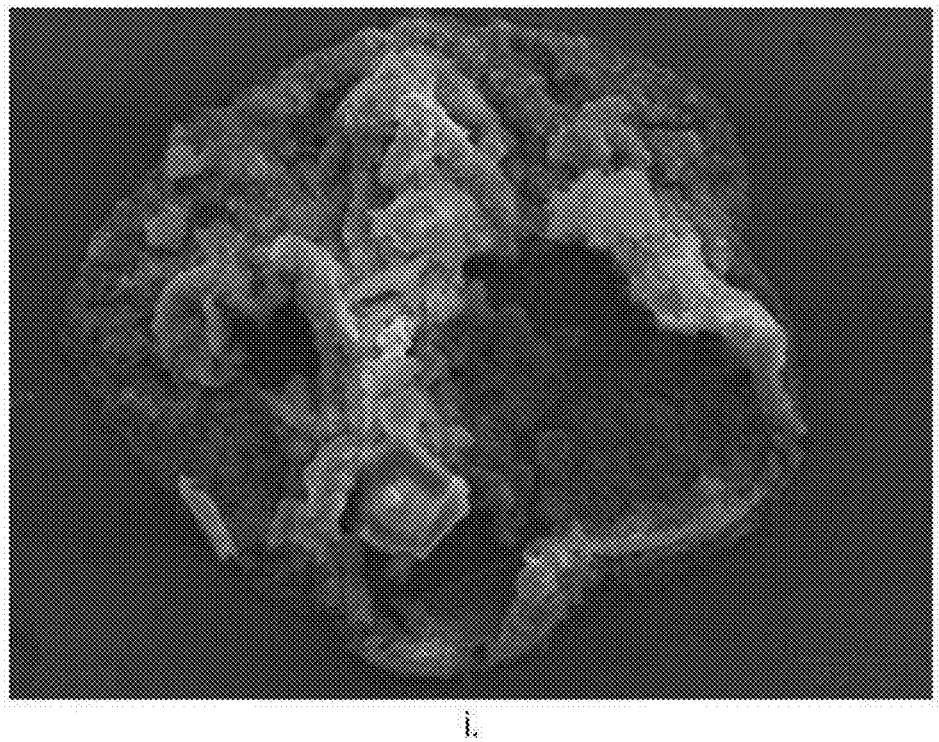
i.
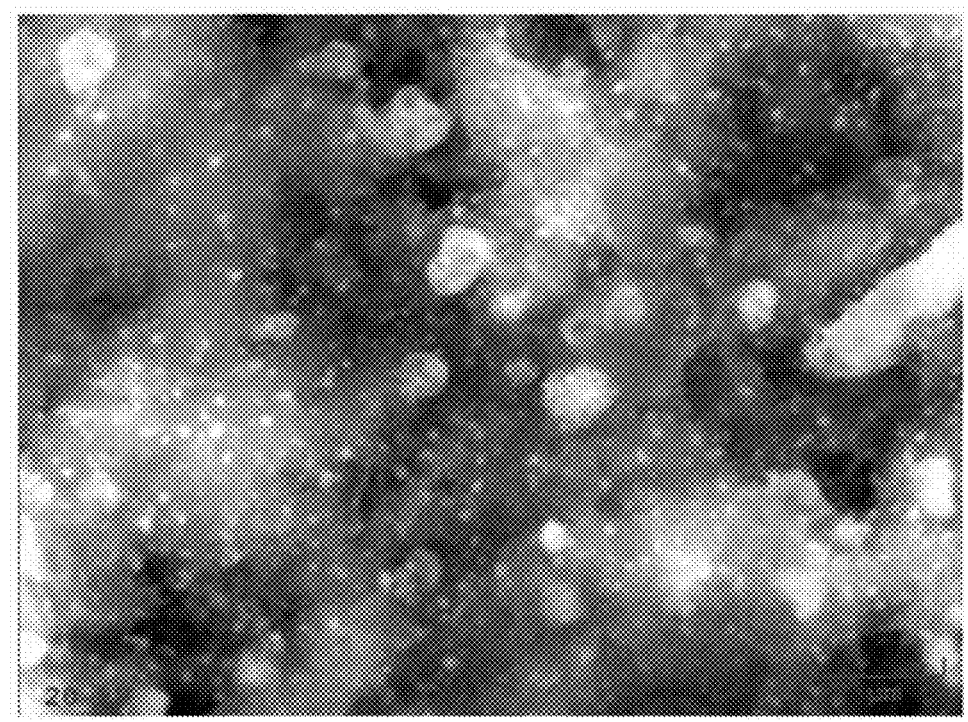
ii.
Figure 43g

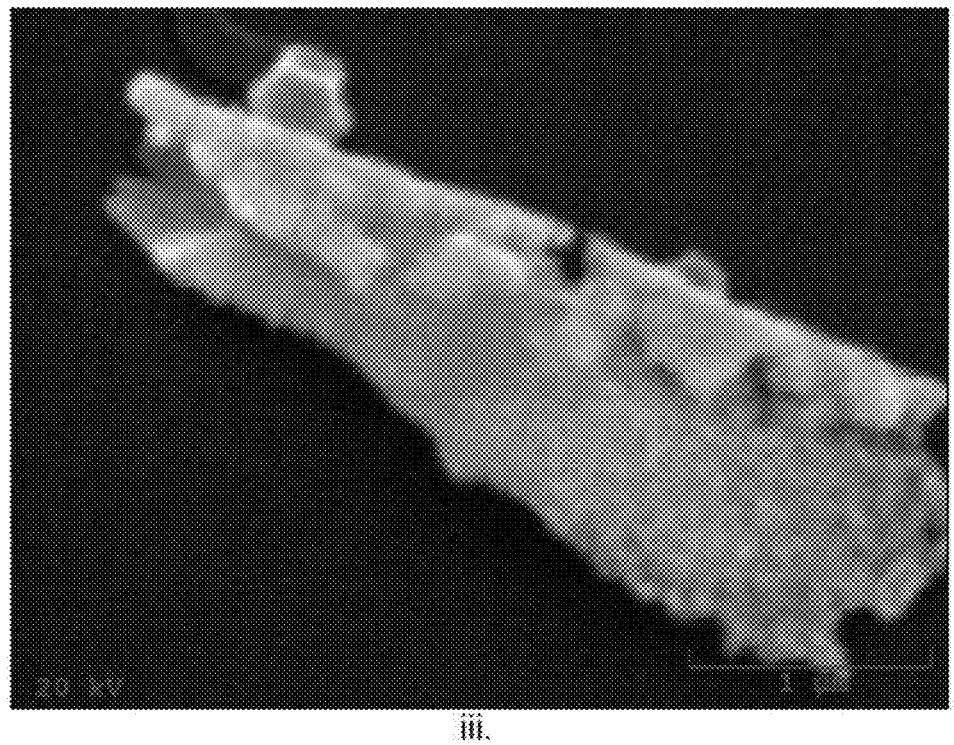
iii.
iv.
Figure 43g

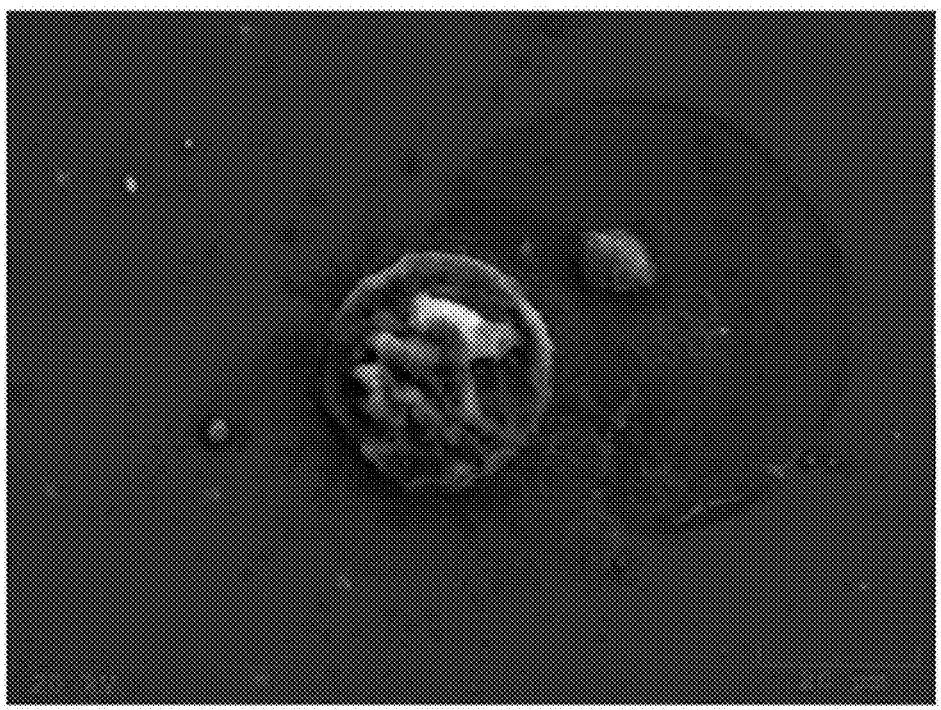
i.
ii.
Figure 43h

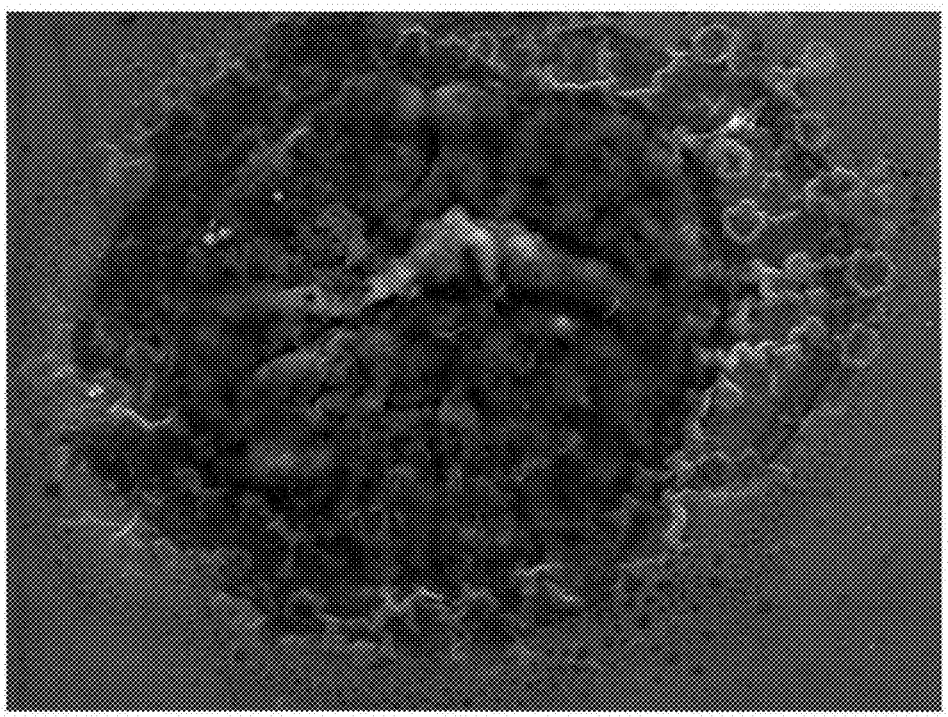
i.
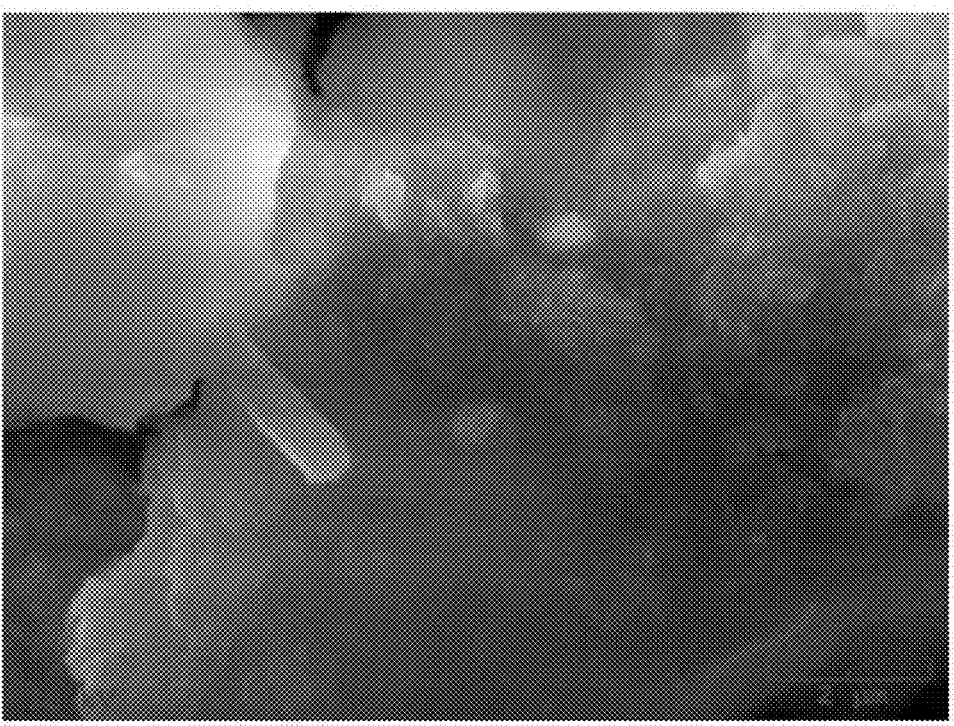
ii.
Figure 43i

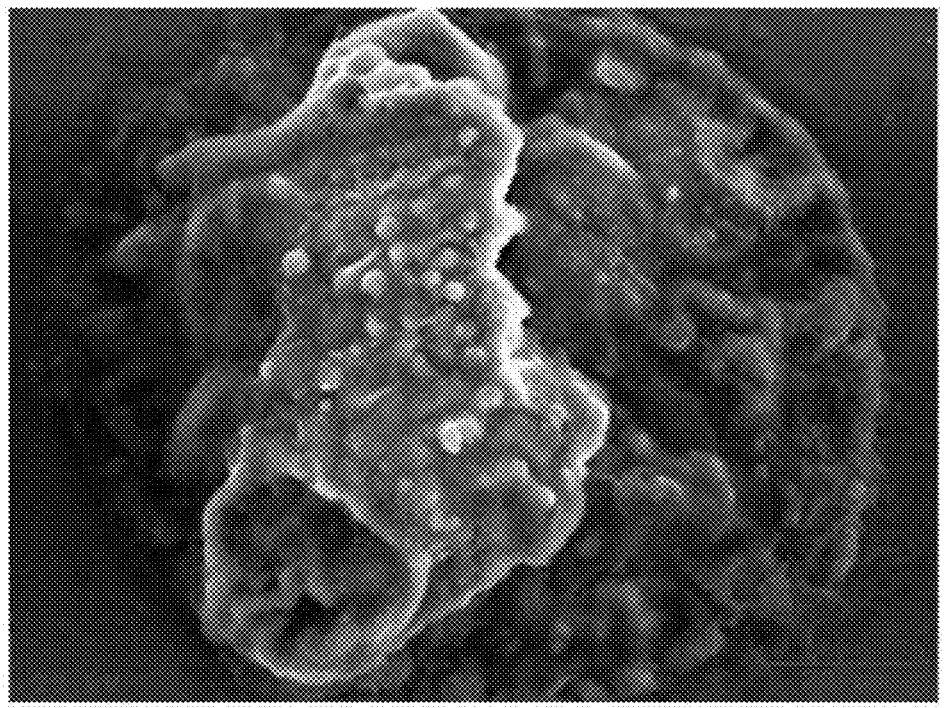
i.
ii.
Figure 43j

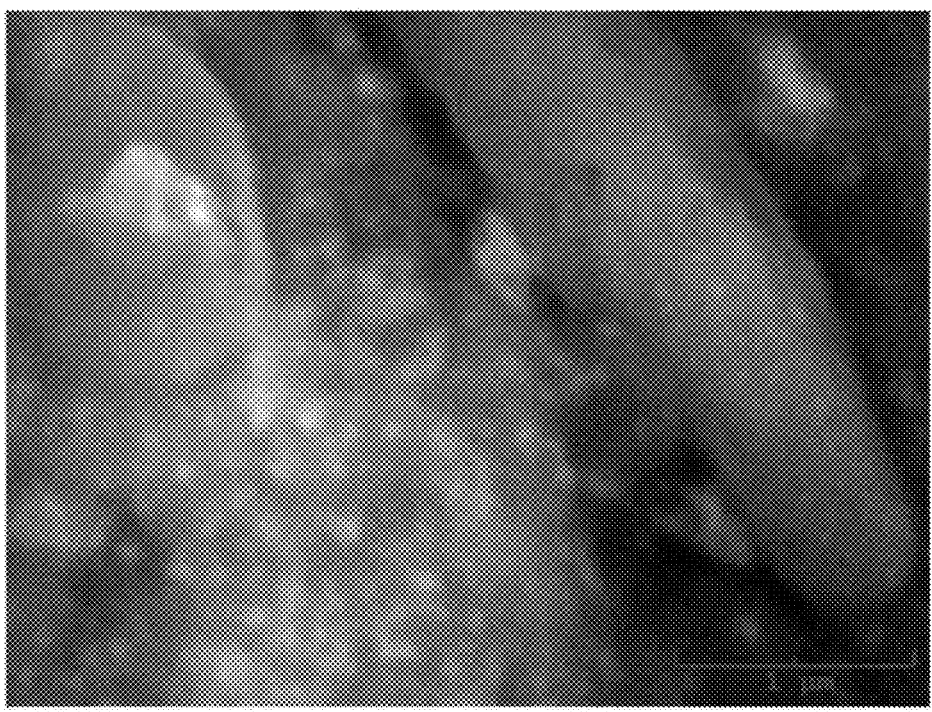
iii.
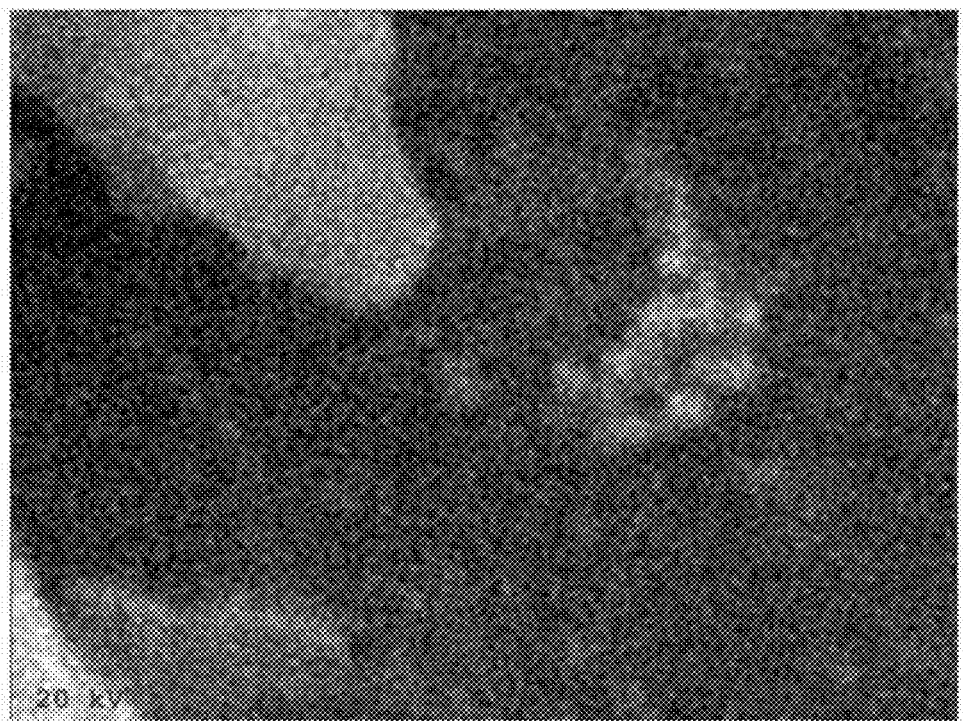
iv.
Figure 43j

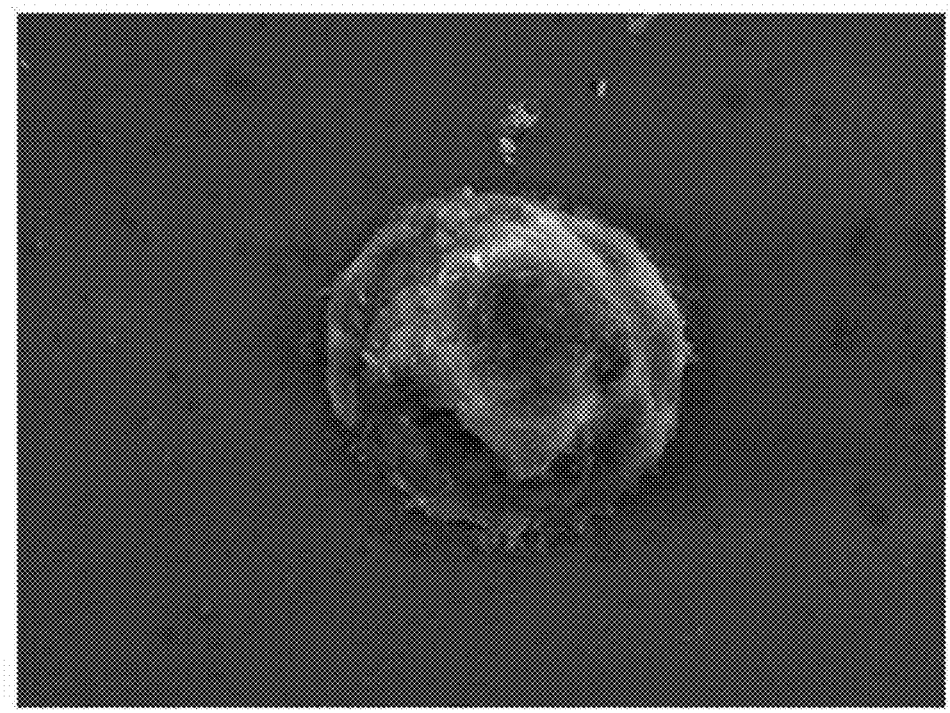
i.
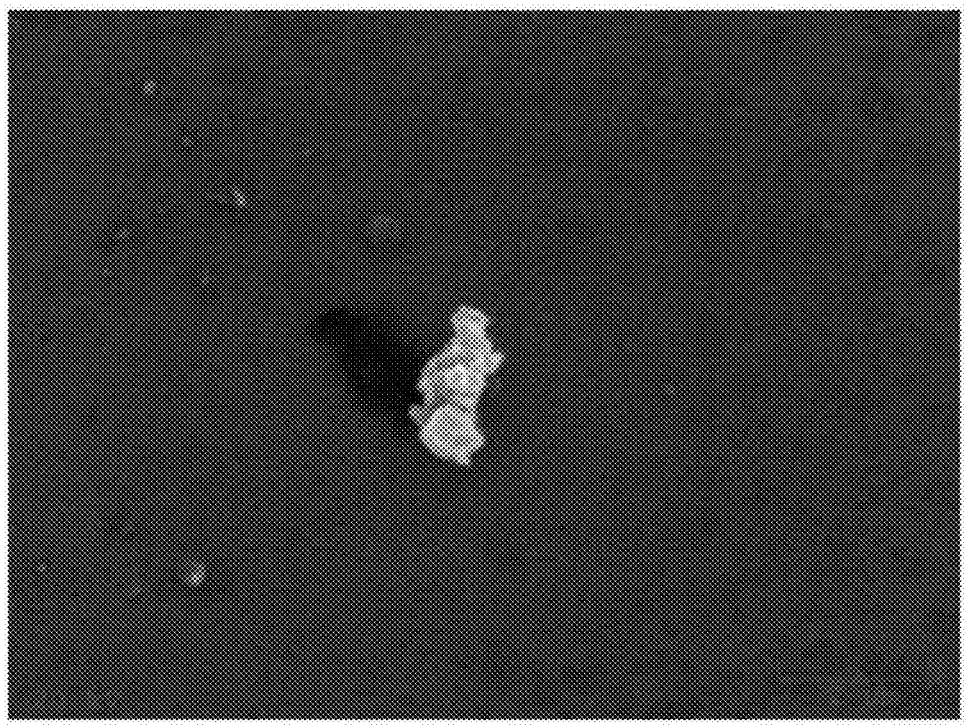
ii.
Figure 43k

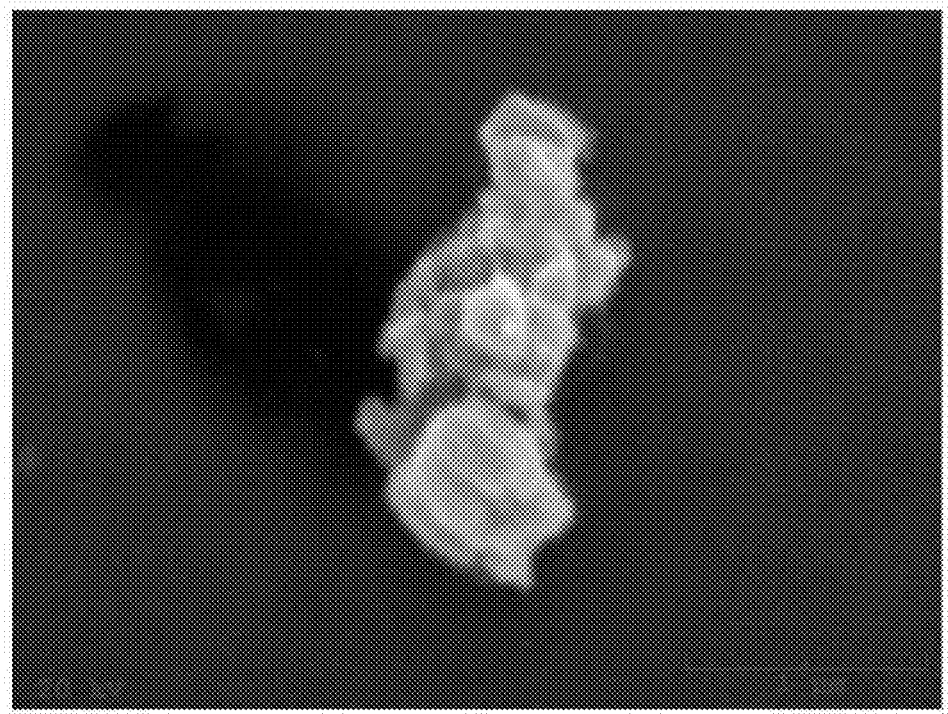
iii.
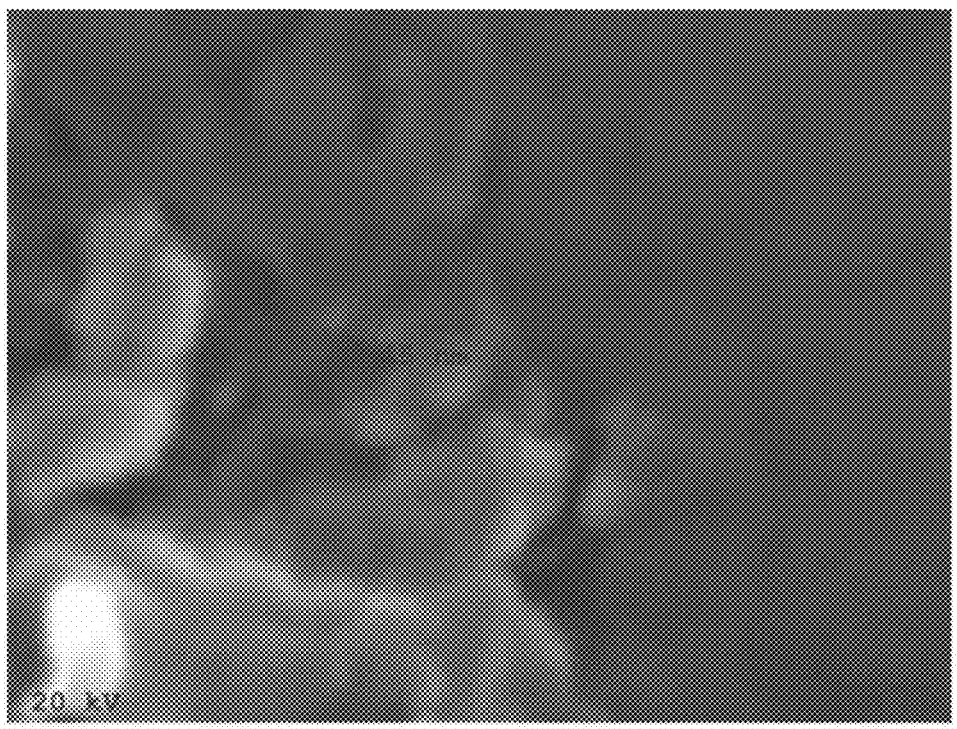
iv.
Figure 43k

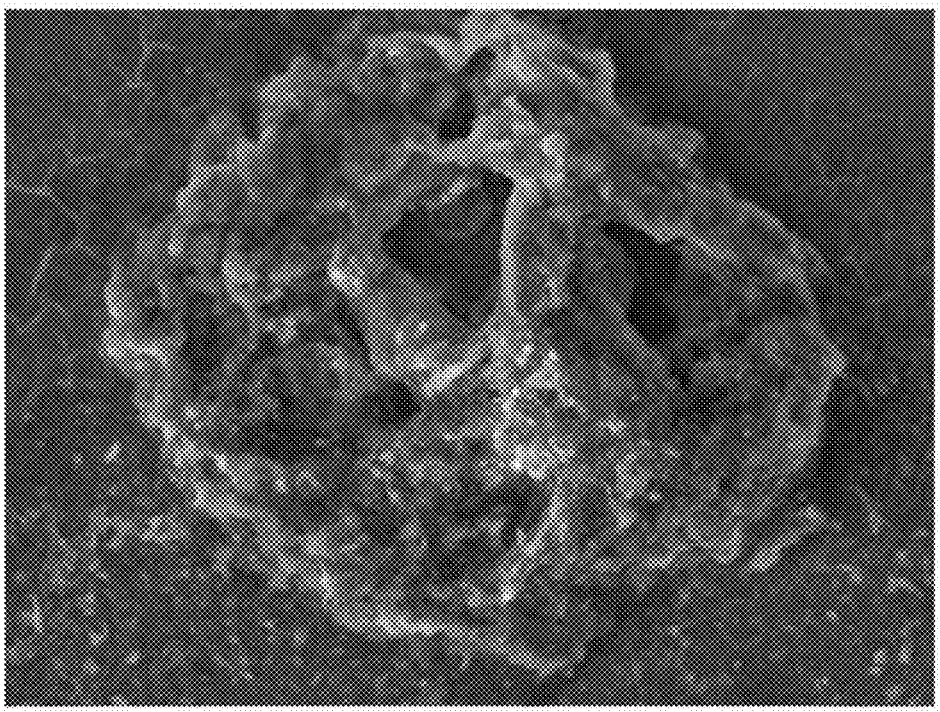
i.

ii.
Figure 43I

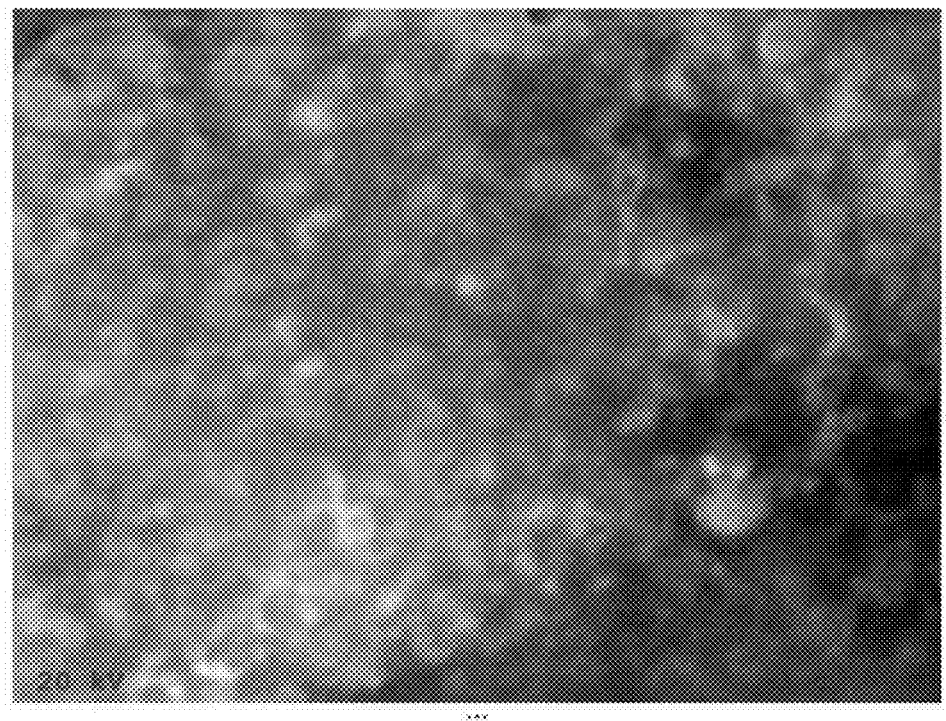
iii.
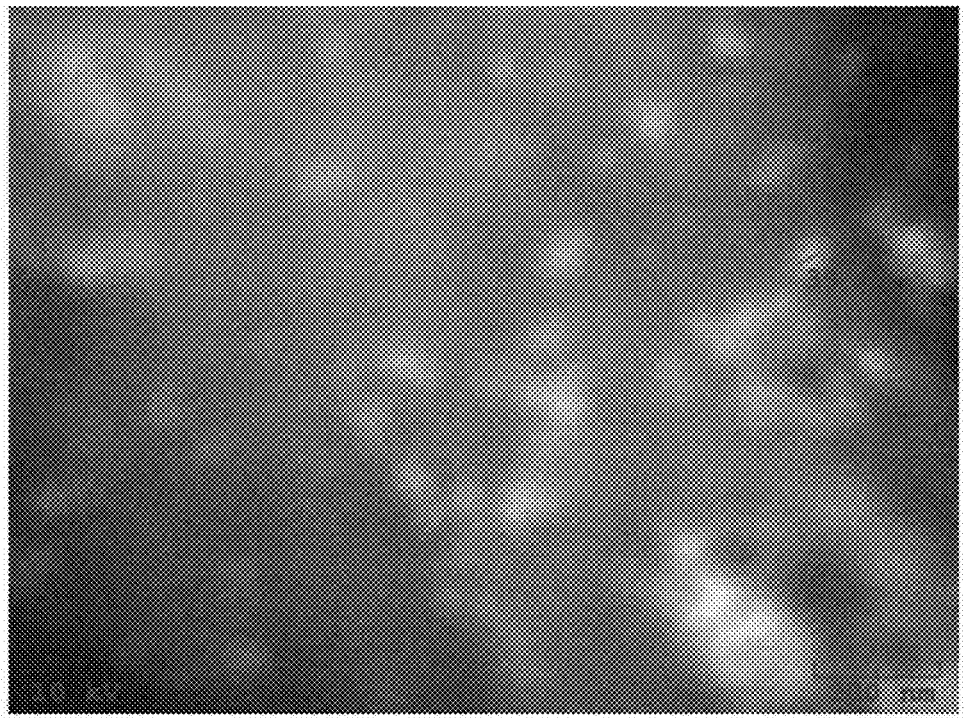
iv.
Figure 43I

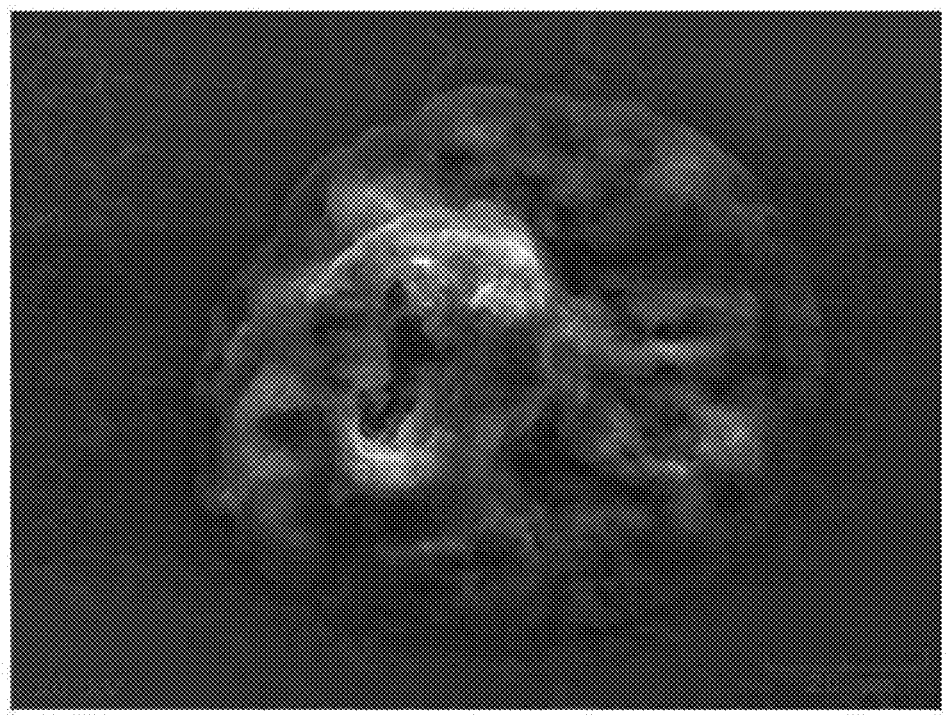
i.
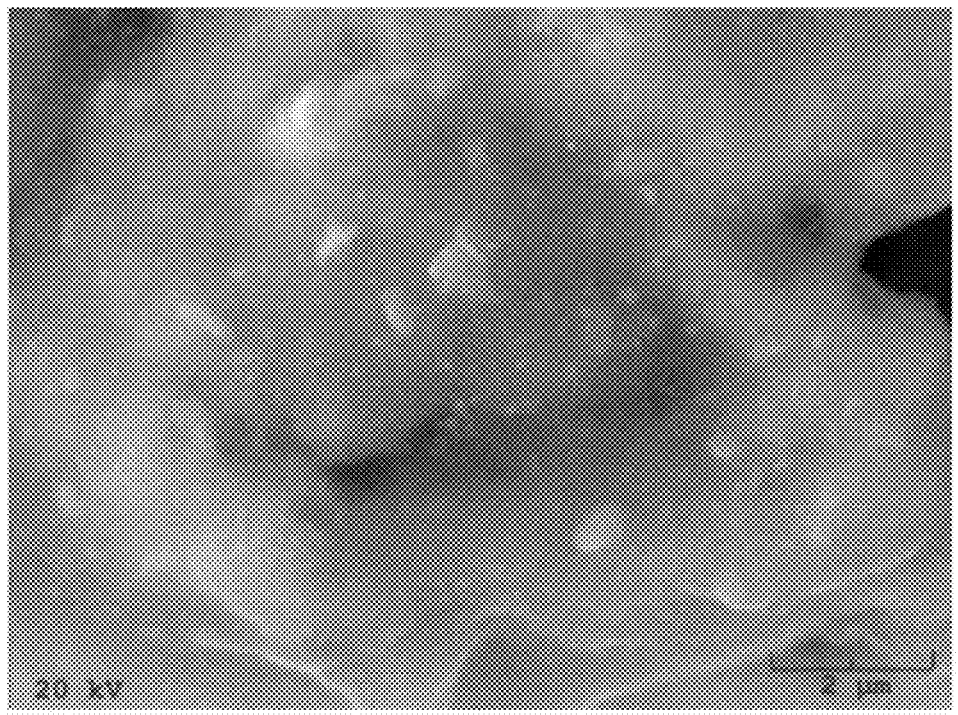
ii.
Figure 43m

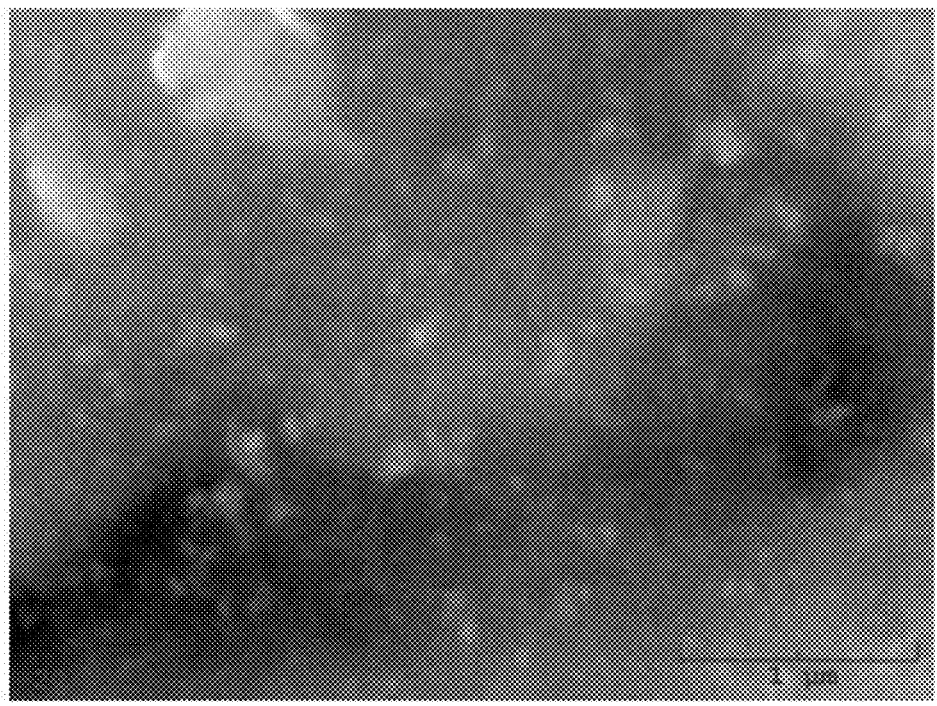
iii.
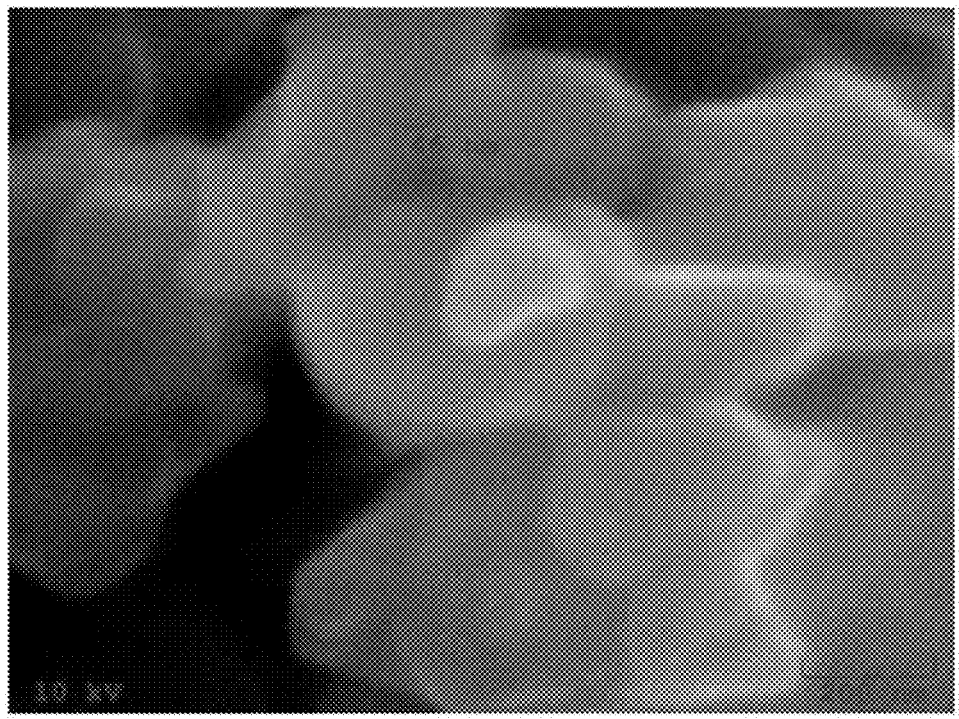
iv.
Figure 43m

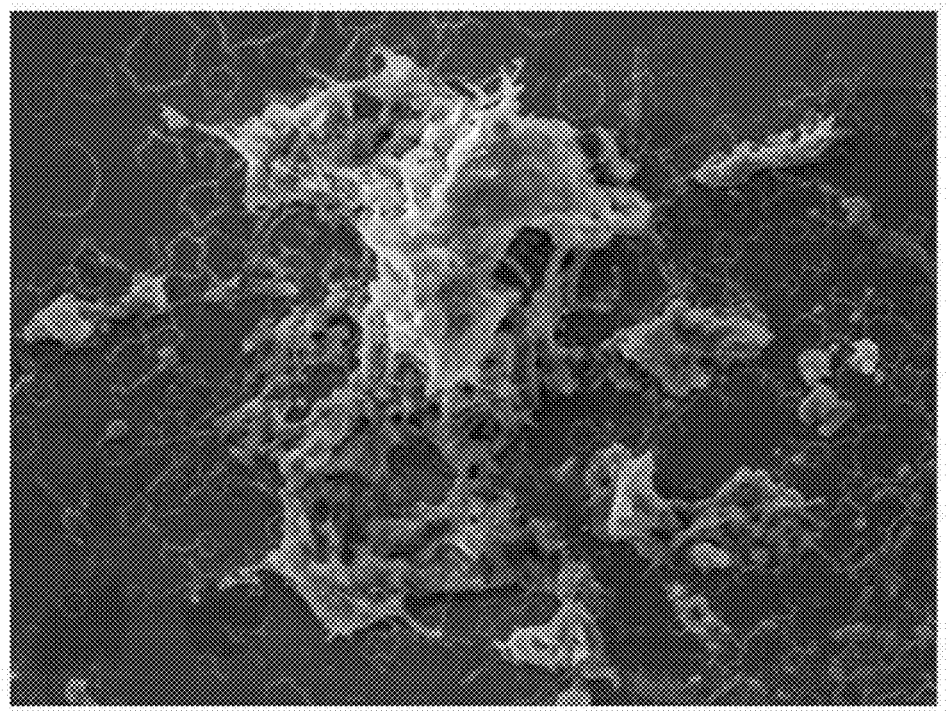
i.
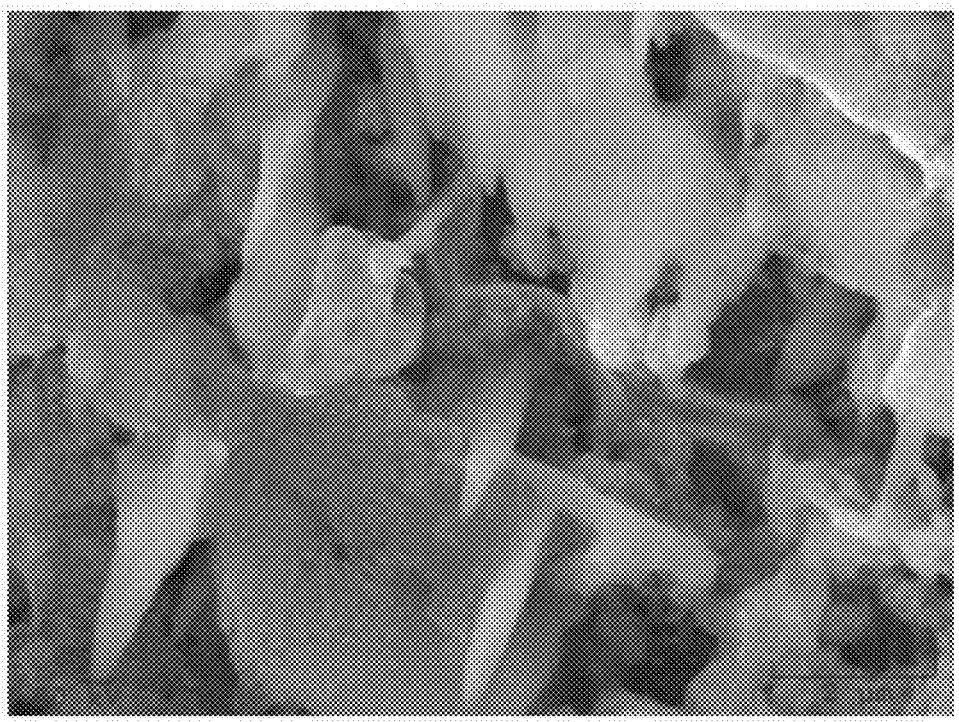
ii.
Figure 43n

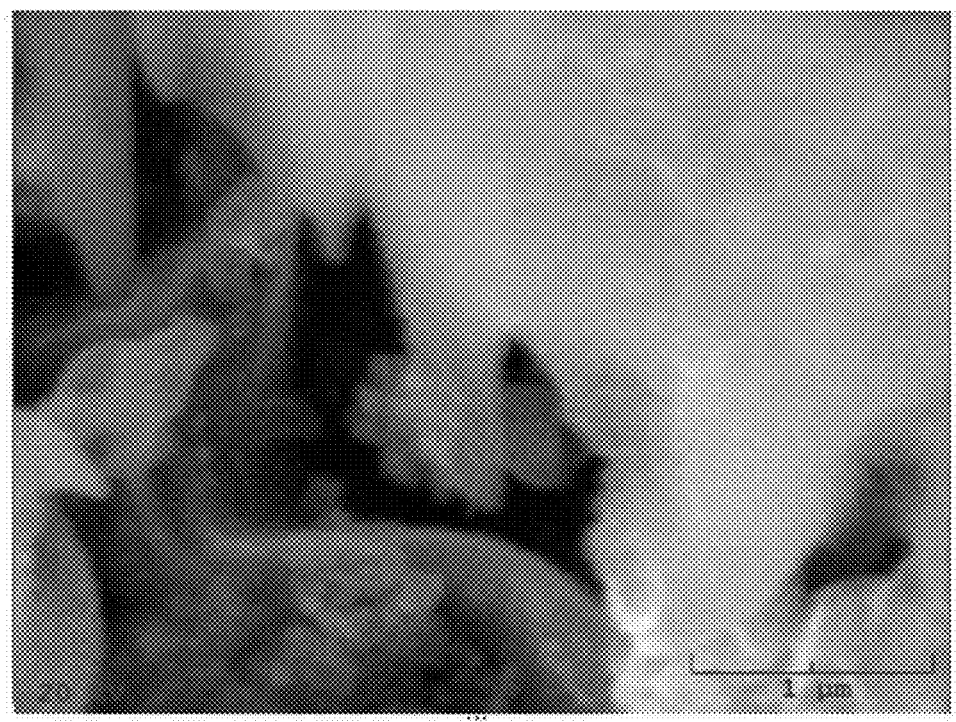
iii.
iv.
Figure 43n

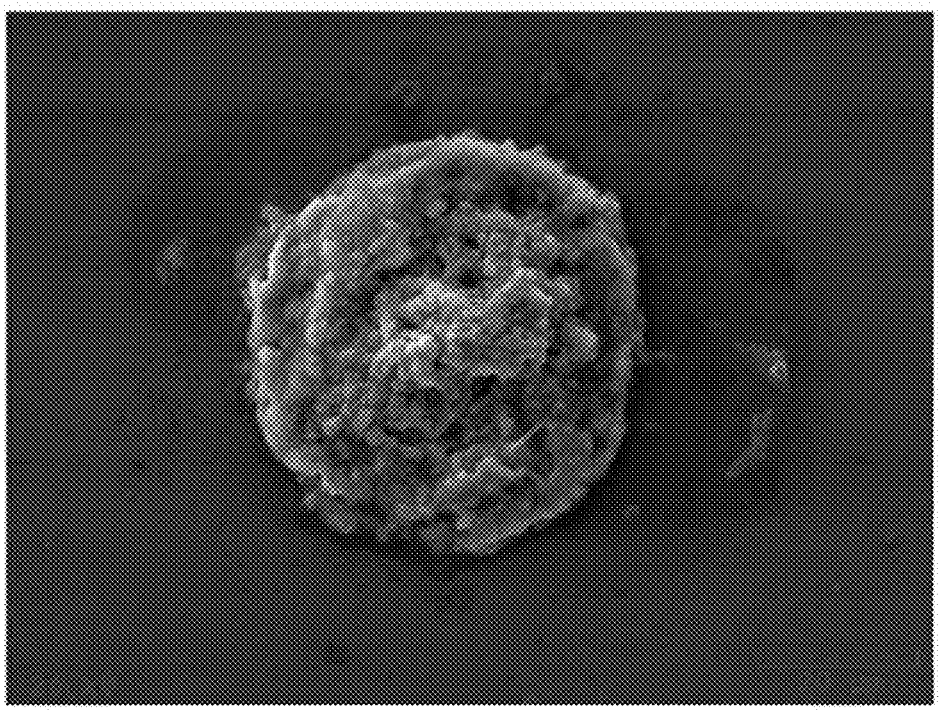
i.
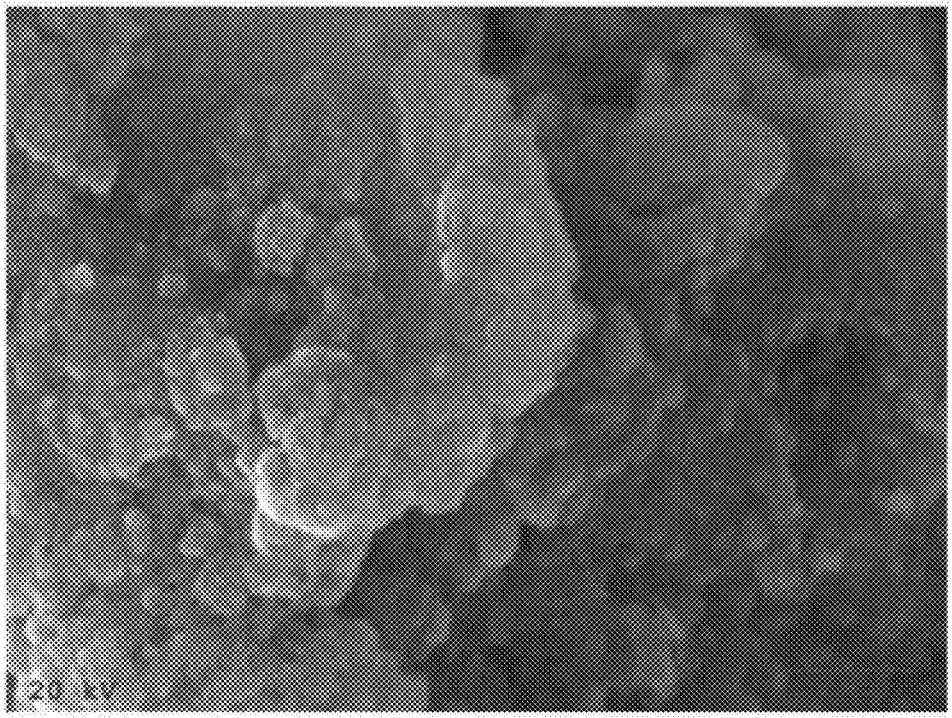
ii.
Figure 43o

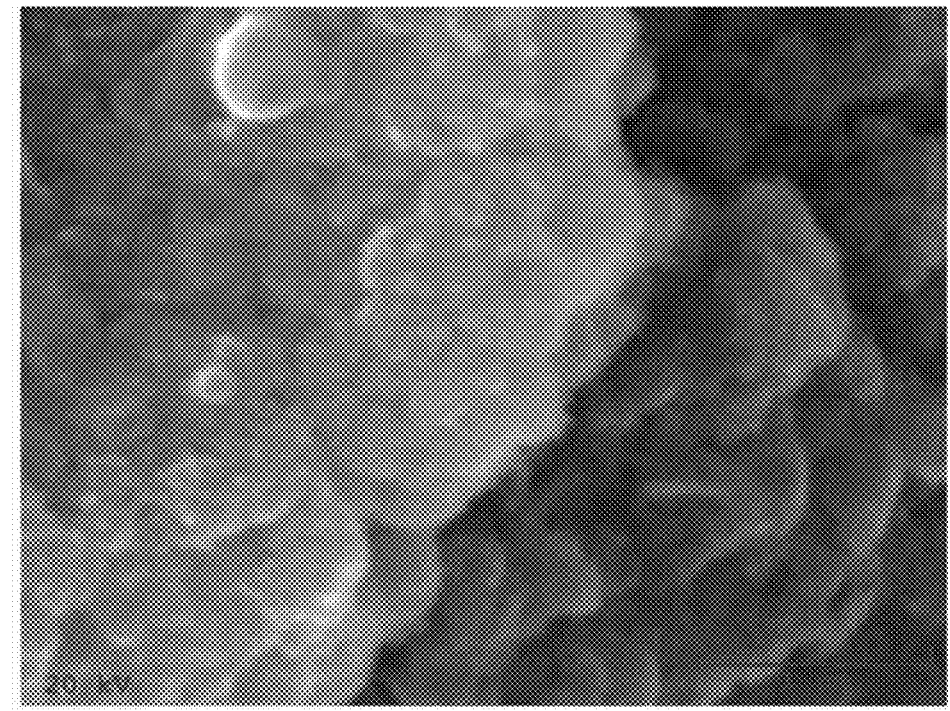
iii.
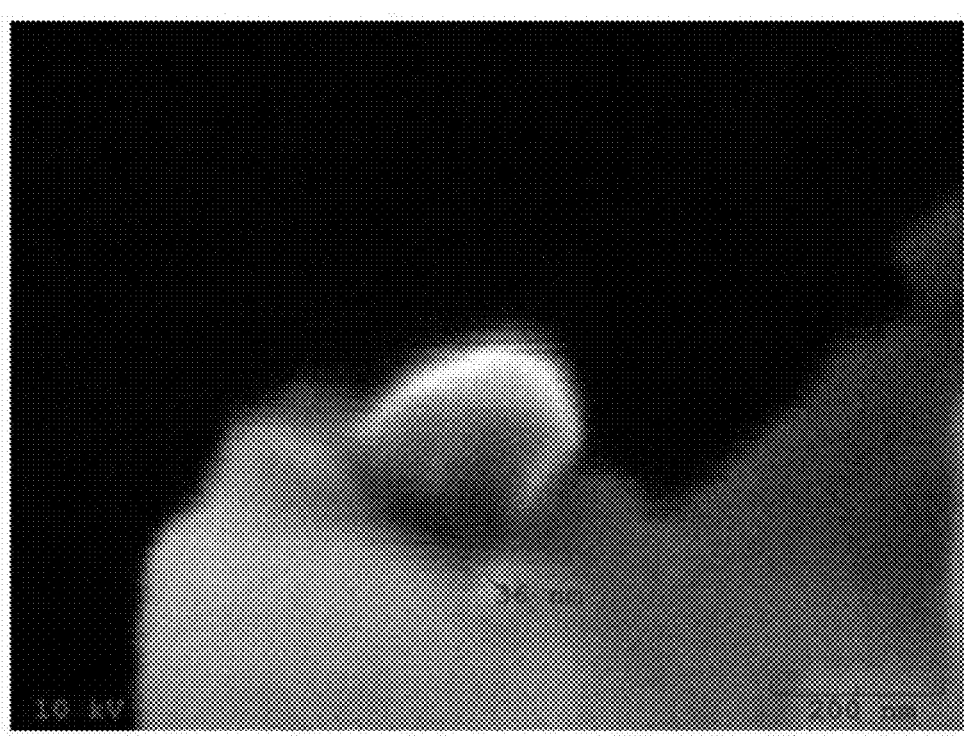
iv.
Figure 43o

UV-Vis Spectra

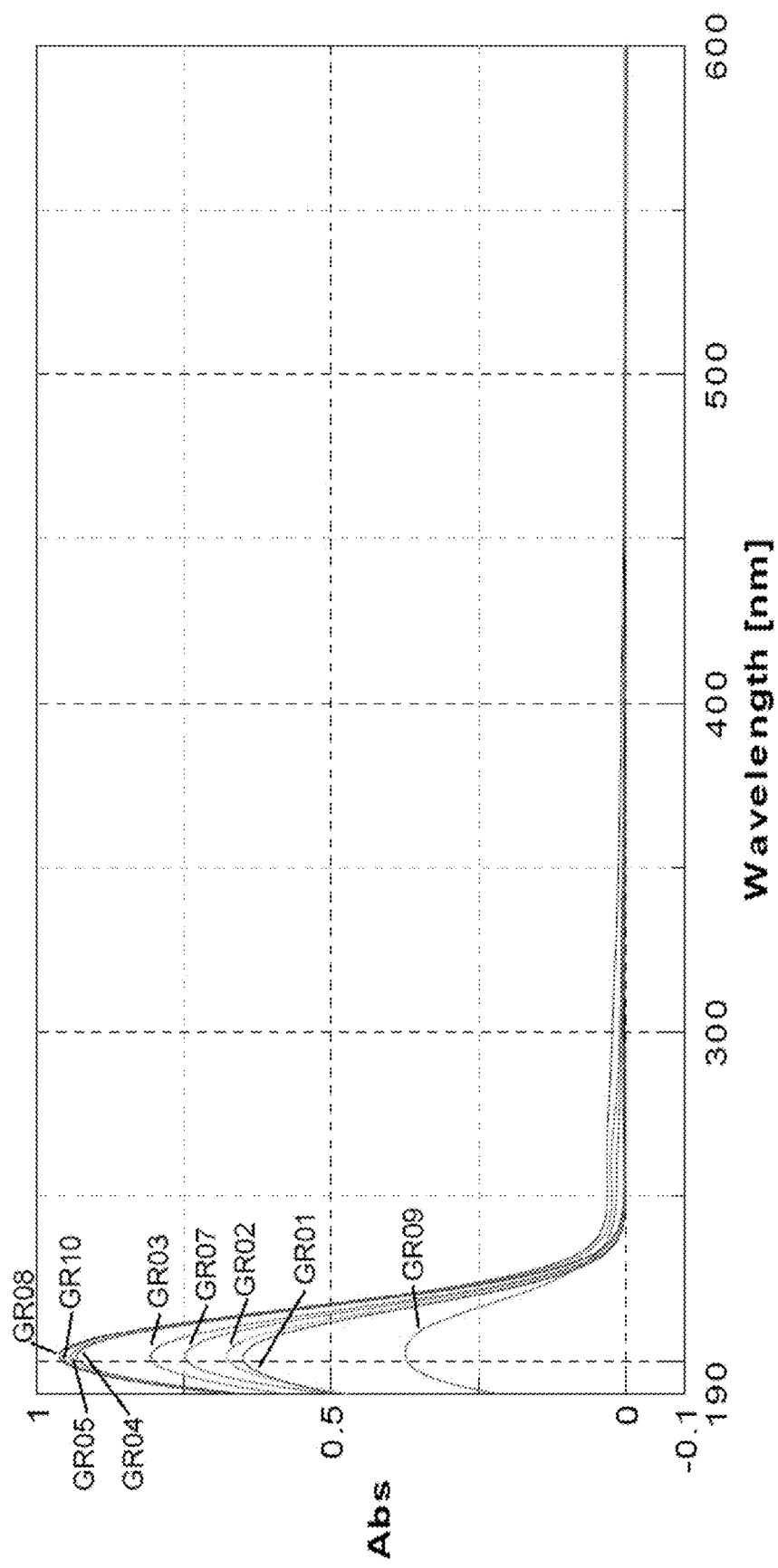

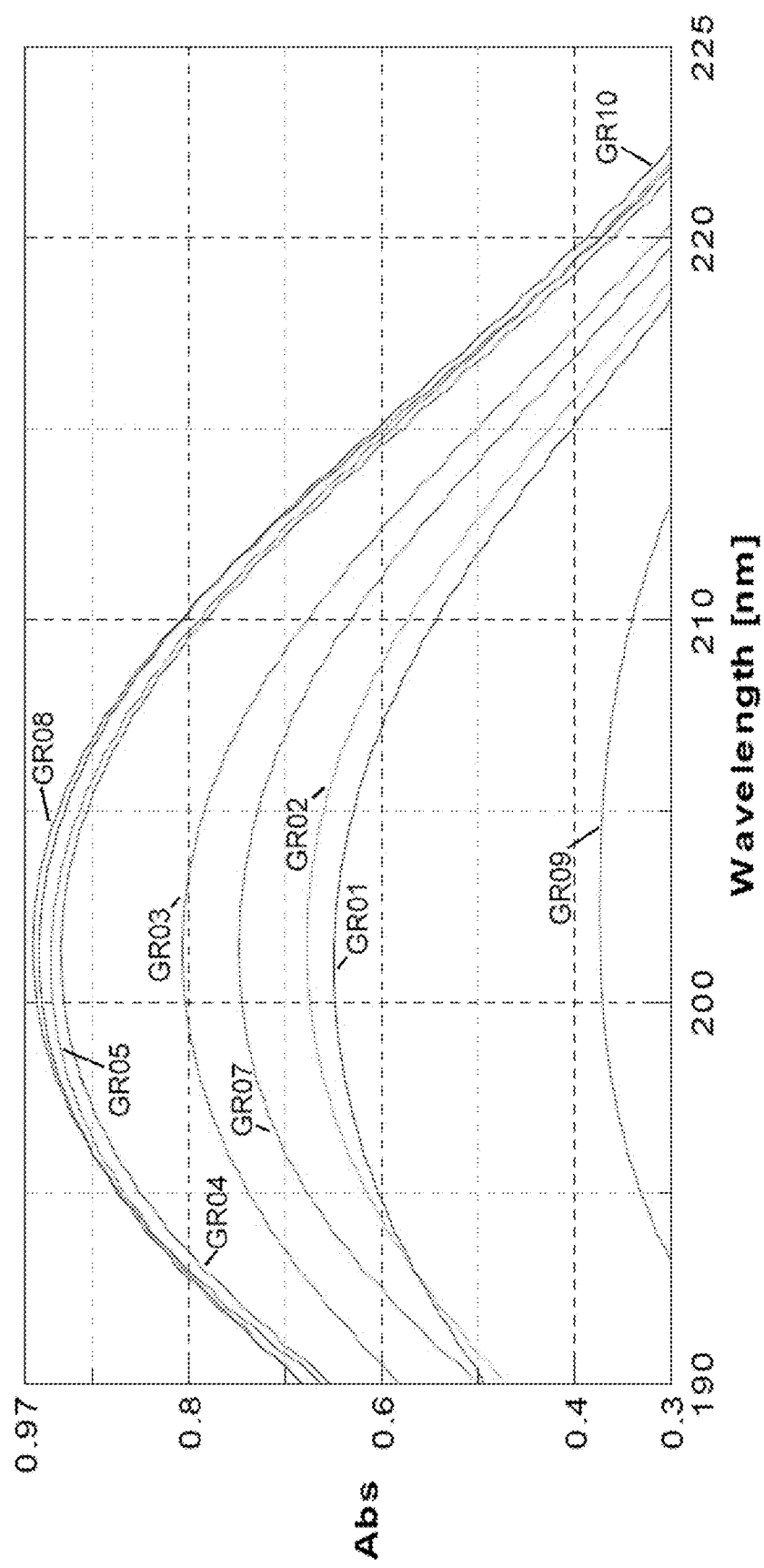

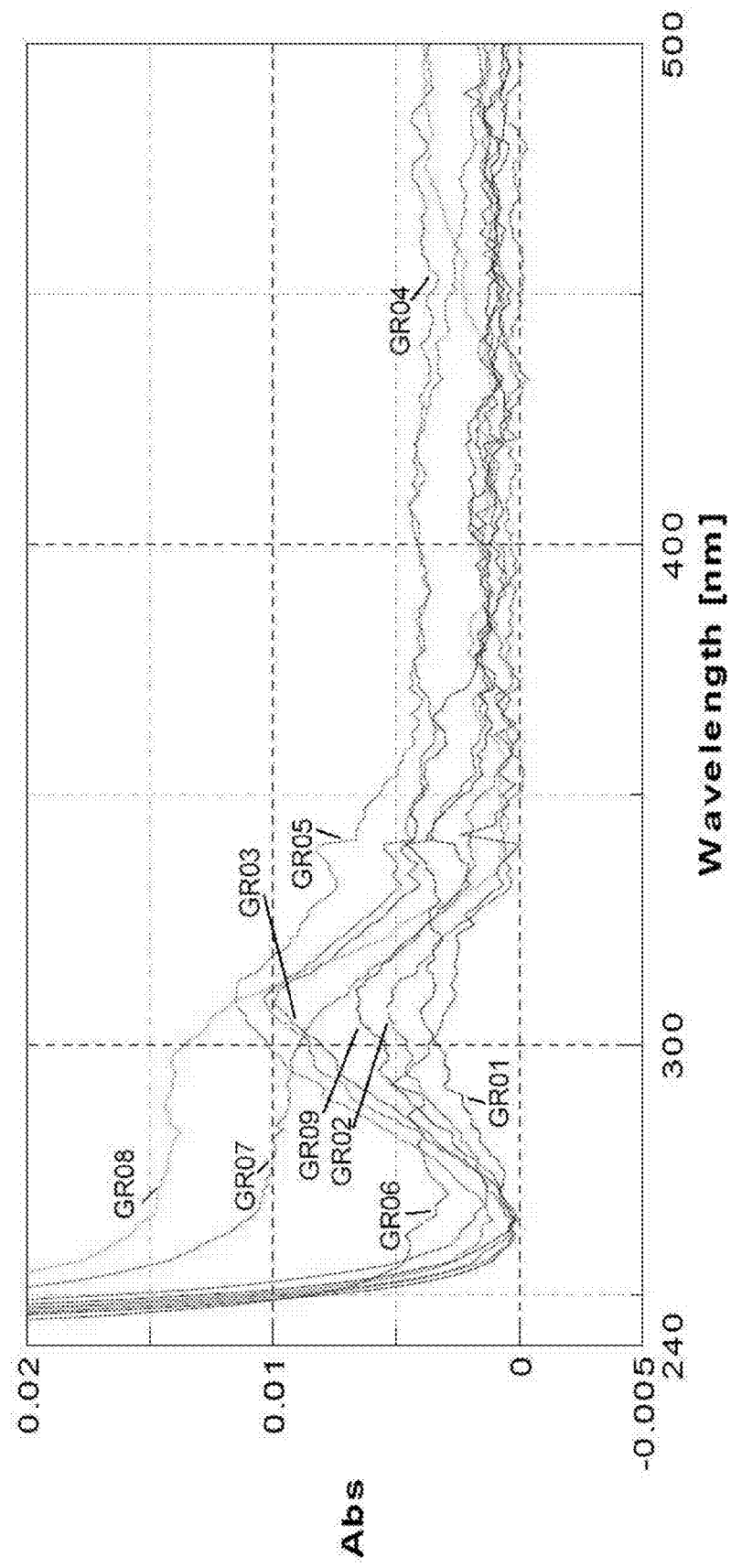

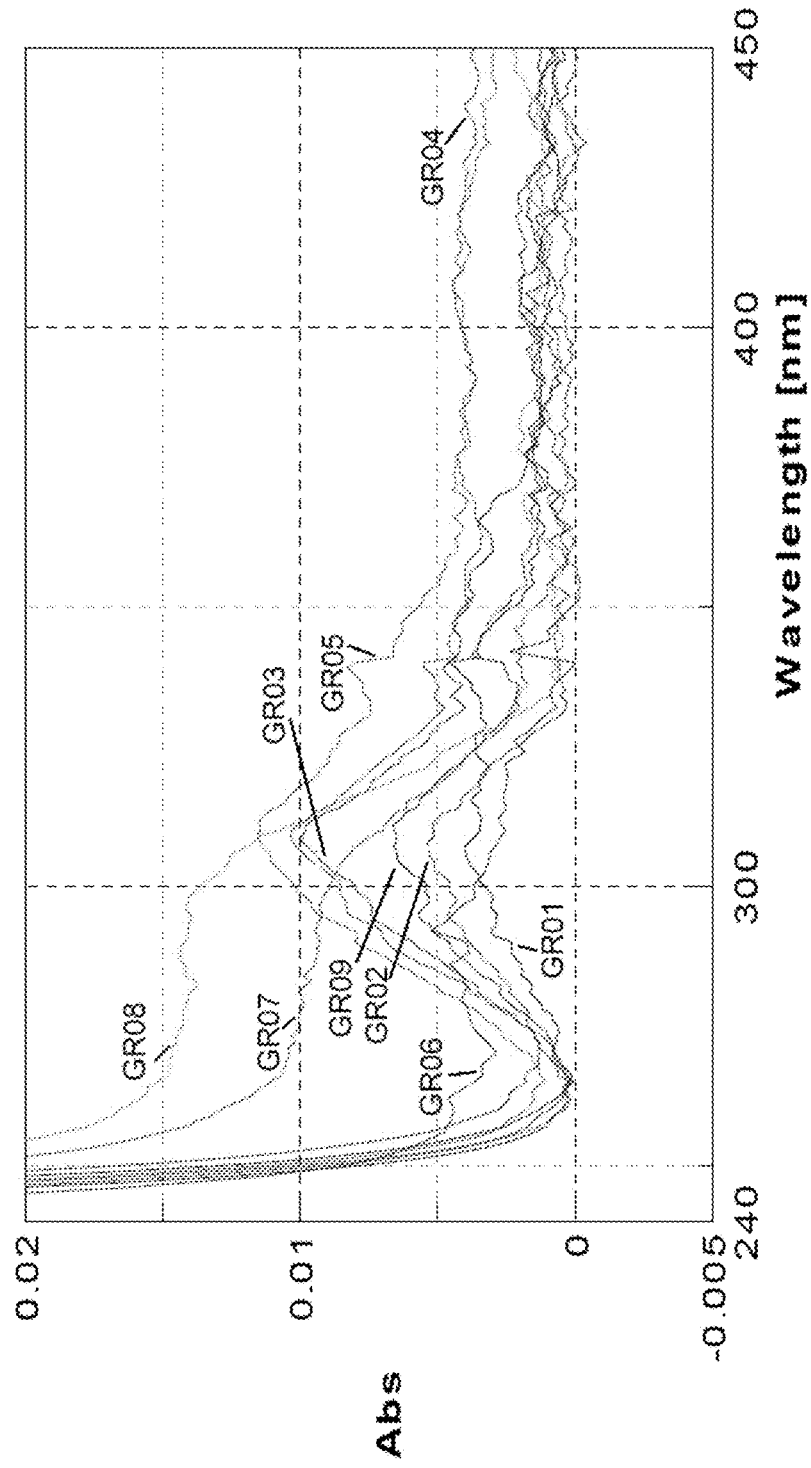

(AT086)

(AT085)

(AT084)

(AT083)

(AT082)

(AT081)

(AT080)

CONTINUOUS METHODS FOR TREATING LIQUIDS AND MANUFACTURING CERTAIN CONSTITUENTS (E.G., NANOPARTICLES) IN LIQUIDS, APPARATUSES AND NANOPARTICLES AND NANOPARTICLE/LIQUID SOLUTION(S) RESULTING THEREFROM

The present application is a divisional of U.S. application Ser. No. 12/668,181 filed on Jan. 7, 2010. The aforementioned parent application is a U.S. national phase entry of International Application No. PCT/US2008/008558 which was filed on Jul. 11, 2008. That international application claims priority to U.S. 60/949,175 filed on Jul. 11, 2007, as well as to U.S. 60/649,312, 10 filed on Jul. 12, 2007. All of the aforementioned applications are hereby expressly incorporated by reference.

FIELD OF THE INVENTION

This invention relates generally to novel methods and novel devices for the continuous manufacture of nanoparticles, microparticles and nanoparticle/liquid solution(s). The nanoparticles (and/or micron-sized particles) comprise a variety of possible compositions, sizes and shapes. The particles (e.g., nanoparticles) are caused to be present (e.g., created) in a liquid (e.g., water) by, for example, preferably utilizing at least one adjustable plasma (e.g., created by at least one AC and/or DC power source), which plasma communicates with at least a portion of a surface of the liquid. At least one subsequent and/or substantially simultaneous adjustable electrochemical processing technique is also preferred. Multiple adjustable plasmas and/or adjustable electrochemical processing techniques are preferred. The continuous process causes at least one liquid to flow into, through and out of at least one trough member, such liquid being processed, conditioned and/or effected in said trough member(s). Results include constituents formed in the liquid including micron-sized particles and/or nanoparticles (e.g., metallic-based nanoparticles) of novel size, shape, composition and properties present in a liquid.

BACKGROUND OF THE INVENTION

Many techniques exist for the production of nanoparticles including techniques set forth in "Recent Advances in the Liquid-Phase Syntheses of Inorganic Nanoparticles" written by Brian L. Cushing, Vladimire L. Kolesnichenko and Charles J. O'Connor; and published in *Chemical Reviews*, volume 104, pages 3893-3946 in 2004 by the American Chemical Society; the subject matter of which is herein expressly incorporated by reference.

Further, the article "Chemistry and Properties of Nanocrystals of Different Shapes" written by Clemens Burda, Xiaobo Chen, Radha Narayanan and Mostafa A. El-Sayed; and published in *Chemical Reviews*, volume 105, pages 1025-1102 in 2005 by the American Chemical Society; discloses additional processing techniques, the subject matter of which is herein expressly incorporated by reference.

The article "Shape Control of Silver Nanoparticles" written by Benjamin Wiley, Yugang Sun, Brian Mayers and Younan Xia; and published in *Chemistry—A European Journal*, volume 11, pages 454-463 in 2005 by Wiley-VCH; discloses additional important subject matter, the subject matter of which is herein expressly incorporated by reference.

Still further, U.S. Pat. No. 7,033,415, issued on Apr. 25, 2006 to Mirkin et al., entitled Methods of Controlling Nanoparticle Growth; and U.S. Pat. No. 7,135,055, issued on Nov. 14, 2006, to Mirkin et al., entitled Non-Alloying Core Shell Nanoparticles; both disclose additional techniques for the growth of nanoparticles; the subject matter of both are herein expressly incorporated by reference.

Moreover, U.S. Pat. No. 7,135,054, which issued on Nov. 14, 2006 to Jin et al., and entitled Nanoprisms and Method of Making Them; is also herein expressly incorporated by reference.

The present invention has been developed to overcome a variety of deficiencies/inefficiencies present in known processing techniques and to achieve a new and controllable process for making nanoparticles of a variety of shapes and sizes and/or new nanoparticle/liquid materials not before achievable.

SUMMARY OF THE INVENTION

This invention relates generally to novel methods and novel devices for the continuous manufacture of a variety of constituents in a liquid including micron-sized particles, nanoparticles and nanoparticle/liquid(s) solution(s). The nanoparticles produced can comprise a variety of possible compositions, sizes and shapes, which exhibit a variety of novel and interesting physical, catalytic, biocatalytic and/or biophysical properties. The liquid(s) used and created/modified during the process play an important role in the manufacturing of, and/or the functioning of the micron-sized particles and the nanoparticles. The particles (e.g., nanoparticles) are caused to be present (e.g., created) in at least one liquid (e.g., water) by, for example, preferably utilizing at least one adjustable plasma (e.g., created by at least one AC and/or DC power source), which adjustable plasma communicates with at least a portion of a surface of the liquid. Metal-based electrodes of various composition(s) and/or unique configurations are preferred for use in the formation of the adjustable plasma(s), but non-metallic-based electrodes can also be utilized. Utilization of at least one subsequent and/or substantially simultaneous adjustable electrochemical processing technique is also preferred. Metal-based electrodes of various composition(s) and/or unique configurations are preferred for use in the electrochemical processing technique(s). Electric fields, magnetic fields, electromagnetic fields, electrochemistry, pH, etc., are just some of the variables that can be positively effected by the adjustable plasma(s) and/or adjustable electrochemical processing technique(s). Multiple adjustable plasmas and/or adjustable electrochemical techniques are preferred to achieve many of the processing advantages of the present invention, as well as many of the novel compositions which result from practicing the teachings of the preferred embodiments. The overall process is a continuous process, having many attendant benefits, wherein at least one liquid, for example water, flows into, through and out of at least one trough member and such liquid is processed, conditioned, modified and/or effected by said at least one adjustable plasma and/or said at least one adjustable electrochemical technique. The results of the continuous processing include new constituents in the liquid, micron-sized particles, nanoparticles (e.g., metallic-based nanoparticles) of novel size, shape, composition and/or properties suspended in a liquid, such nanoparticle/liquid mixture being produced in an efficient and economical manner.

The phrase "trough member" is used throughout the text. This phrase should be understood as meaning a large variety of fluid handling devices including, pipes, half pipes, channels or grooves existing in materials or objects, conduits, ducts, tubes, chutes, hoses and/or spouts, so long as such are compatible with the process disclosed herein.

Additional processing techniques such as applying certain crystal growth techniques disclosed in copending patent application entitled Methods for Controlling Crystal Growth, Crystallization, Structures and Phases in Materials and Systems; which was filed on Mar. 21, 2003, and was published by the World Intellectual Property Organization under publication number WO 03/089692 on Oct. 30, 2003 and the U.S. National Phase application, which was filed on Jun. 6, 2005, and was published by the United States Patent and Trademark Office under publication number 20060037177 on Feb. 23, 2006 (the inventors of each being Bentley J. Blum, Juliana H. J. Brooks and Mark G. Mortenson). The subject matter of both applications is herein expressly incorporated by reference. These applications teach, for example, how to grow preferentially one or more specific crystals or crystal shapes from solution. Further, drying, concentrating and/or freeze drying can also be utilized to remove at least a portion of, or substantially all of, the suspending liquid, resulting in, for example, dehydrated nanoparticles.

An important aspect of one embodiment of the invention involves the creation of an adjustable plasma, which adjustable plasma is located between at least one electrode positioned adjacent to (e.g., above) at least a portion of the surface of a liquid and at least a portion of the surface of the liquid itself. The liquid is placed into electrical communication with at least one second electrode (or a plurality of second electrodes) causing the surface of the liquid to function as an electrode helping to form the adjustable plasma. This configuration has certain characteristics similar to a dielectric barrier discharge configuration, except that the surface of the liquid is an active electrode participant in this configuration.

Each adjustable plasma utilized can be located between the at least one electrode located above a surface of the liquid and a surface of the liquid due to at least one electrically conductive electrode being located somewhere within (e.g., at least partially within) the liquid. At least one power source (in a preferred embodiment, at least one source of volts and amps such as a transformer) is connected electrically between the at least one electrode located above the surface of the liquid and the at least one electrode contacting the surface of the liquid (e.g., located at least partially, or substantially completely, within the liquid). The electrode(s) may be of any suitable composition and suitable physical configuration (e.g., size and shape) which results in the creation of a desirable plasma between the electrode(s) located above the surface of the liquid and at least a portion of the surface of the liquid itself.

The applied power (e.g., voltage and amperage) between the electrode(s) (e.g., including the surface of the liquid functioning as at least one electrode for forming the plasma) can be generated by any suitable source (e.g., voltage from a transformer) including both AC and DC sources and variants and combinations thereof. Generally, the electrode or electrode combination located within (e.g., at least partially below the surface of the liquid) takes part in the creation of a plasma by providing voltage and current to the liquid or solution, however, the adjustable plasma is actually located between at least a portion of the electrode(s) located above the surface of the liquid (e.g., at a tip or point thereof) and one or more portions or areas of the liquid surface itself. In this regard, the adjustable plasma can be created between the aforementioned electrodes (i.e., those located above at least a portion of the surface of the liquid and a portion of the liquid surface itself) when a breakdown voltage of the gas or vapor around and/or between the electrode(s) and the surface of the liquid is achieved or maintained.

In one preferred embodiment of the invention, the liquid comprises water, and the gas between the surface of the water and the electrode(s) above the surface of the water (i.e., that gas or atmosphere that takes part in the formation of the adjustable plasma) comprises air. The air can be controlled to contain various different water content(s) or a desired humidity which can result in different compositions, sizes and/or shapes of nanoparticles being produced according to the present invention (e.g., different amounts of certain constituents in the adjustable plasma and/or in the solution can be a function of the water content in the air located above the surface of the liquid) as well as different processing times, etc.

The breakdown electric field at standard pressures and temperatures for dry air is about 3 MV/m or about 30 kV/cm. Thus, when the local electric field around, for example, a metallic point exceeds about 30 kV/cm, a plasma can be generated in dry air. Equation (1) gives the empirical relationship between the breakdown electric field "$E_c$" and the distance "d" (in meters) between two electrodes:

$$E_c = 3000 + \frac{1.35}{d} \text{kV/m} \qquad \text{Equation 1}$$

Of course, the breakdown electric field "$E_c$" will vary as a function of the properties and composition of the gas located between electrodes. In this regard, in one preferred embodiment where water is the liquid, significant amounts of water vapor can be inherently present in the air between the "electrodes" (i.e., between the at least one electrode located above the surface of the water and the water surface itself which is functioning as one electrode for plasma formation) and such water vapor should have an effect on at least the breakdown electric field required to create a plasma therebetween. Further, a higher concentration of water vapor can be caused to be present locally in and around the created plasma due to the interaction of the adjustable plasma with the surface of the water. The amount of "humidity" present in and around the created plasma can be controlled or adjusted by a variety of techniques discussed in greater detail later herein. Likewise, certain components present in any liquid can form at least a portion of the constituents forming the adjustable plasma located between the surface of the liquid and the electrode(s) located adjacent (e.g., along) the surface of the liquid. The constituents in the adjustable plasma, as well as the physical properties of the plasma per se, can have a dramatic influence on the liquid, as well as on certain of the processing techniques (discussed in greater detail later herein).

The electric field strengths created at and near the electrodes are typically at a maximum at a surface of an electrode and typically decrease with increasing distance therefrom. In cases involving the creation of an adjustable plasma between a surface of the liquid and the at least one electrode(s) located adjacent to (e.g., above) the liquid, a portion of the volume of gas between the electrode(s) located above a surface of a liquid and at least a portion of the liquid surface itself can contain a sufficient breakdown electric field to create the adjustable plasma. These created electric fields can influence, for example, behavior of the adjustable plasma, behavior of the liquid, behavior of constituents in the liquid, etc.

In this regard, FIG. 1a shows one embodiment of a point source electrode 1 having a triangular cross-sectional shape located a distance "x" above the surface 2 of a liquid 3 flowing, for example, in the direction "F". An adjustable plasma 4 can be generated between the tip or point 9 of the electrode 1 and the surface 2 of the liquid 3 when an appropriate power source 10 is connected between the point source electrode 1 and the electrode 5, which electrode 5 communicates with the liquid 3 (e.g., is at least partially below the surface 2 of the liquid 3). It should be noted that under certain conditions the tip 9' of the electrode 5 may actually be located physically slightly above the bulk surface 2 of the liquid 3, but the liquid still communicates with the electrode through a phenomenon known as "Taylor cones". Taylor cones are discussed in U.S. Pat. No. 5,478,533, issued on Dec. 26, 1995 to Inculet, entitled Method and Apparatus for Ozone Generation and Treatment of Water, the subject matter of which is herein expressly incorporated by reference. In this regard, FIG. 1b shows an electrode configuration similar to that shown in FIG. 1a, except that a Taylor cone "T" is utilized for electrical connection between the electrode 5 and the surface 2 (or actually the effective surface 2') of the liquid 3. The creation and use of Taylor cones is discussed in greater detail elsewhere herein.

The adjustable plasma region 4, created in the embodiment shown in FIG. 1a can typically have a shape corresponding to a cone-like structure for at least a portion of the process, and in some embodiments of the invention, can maintain such cone-like shape for substantially all of the process. The volume, intensity, constituents (e.g., composition), activity, precise locations, etc., of the adjustable plasma(s) 4 will vary depending on a number of factors including, but not limited to, the distance "x", the physical and/or chemical composition of the electrode 1, the shape of the electrode 1, the power source 10 (e.g., DC, AC, rectified AC, the applied polarity of DC and/or rectified AC, RF, etc.), the power applied by the power source (e.g., the volts applied, the amps applied, electron velocity, etc.) the frequency and/or magnitude of the electric and/or magnetic fields created by the power source applied or ambient, electric, magnetic or electromagnetic fields, acoustic fields, the composition of the naturally occurring or supplied gas or atmosphere (e.g., air, nitrogen, helium, oxygen, ozone, reducing atmospheres, etc.) between and/or around the electrode 1 and the surface 2 of the liquid 3, temperature, pressure, volume, flow rate of the liquid 3 in the direction "F", spectral characteristics, composition of the liquid 3, conductivity of the liquid 3, cross-sectional area (e.g., volume) of the liquid near and around the electrodes 1 and 5, (e.g., the amount of time the liquid 3 is permitted to interact with the adjustable plasma 4 and the intensity of such interactions), the presence of atmosphere flow (e.g., air flow) at or near the surface 2 of the liquid 3 (e.g., fan(s) or atmospheric movement means provided) etc., (discussed in more detail later herein).

The composition of the electrode(s) 1 involved in the creation of the adjustable plasma(s) 4 of FIG. 1a, in one preferred embodiment of the invention, are metal-based compositions (e.g., metals such as platinum, gold, silver, zinc, copper, titanium, and/or alloys or mixtures thereof, etc.), but the electrodes 1 and 5 may be made out of any suitable material compatible with the various aspects (e.g., processing parameters) of the inventions disclosed herein. In this regard, while the creation of a plasma 4 in, for example, air above the surface 2 of a liquid 3 (e.g., water) will, typically, produce at least some ozone, as well as amounts of nitrogen oxide and other components (discussed in greater detail elsewhere herein). These produced components can be controlled and may be helpful or harmful to the formation and/or performance of the resultant nanoparticles and/or nanoparticle/solutions produced and may need to be controlled by a variety of different techniques, discussed in more detail later herein. Further, the emission spectrum of each plasma 4 is also a function of similar factors (discussed in greater detail later herein). As shown in FIG. 1a, the adjustable plasma 4 actually contacts the surface 2 of the liquid 3. In this embodiment of the invention, material (e.g., metal) from the electrode 1 may comprise a portion of the adjustable plasma 4 (e.g., and thus be part of the emission spectrum of the plasma) and may be caused, for example, to be "sputtered" onto and/or into the liquid 3 (e.g., water). Accordingly, when metal(s) are used as the electrode(s) 1, elementary metal(s), metal ions, Lewis acids, Bronsted-Lowry acids, metal oxides, metal nitrides, metal hydrides, metal hydrates and/or metal carbides, etc., can be found in the liquid 3 (e.g., for at least a portion of the process), depending upon the particular set of operating conditions associated with the adjustable plasma 4. Such constituents may be transiently present or may be semi-permanent or permanent. Further, depending on, for example, electric, magnetic and/or electromagnetic field strength in and around the liquid 3 and the volume of liquid 3 (discussed in greater detail elsewhere herein), the physical and chemical construction of the electrode(s) 1 and 5, atmosphere (naturally occurring or supplied), liquid composition, greater or lesser amounts of electrode(s) materials(s) (e.g., metal(s) or derivatives of metals) may be found in the liquid 3. In certain situations, the material(s) (e.g., metal(s) or metal(s) composite(s)) or constituents (e.g., Lewis acids, Bronsted-Lowry acids, etc.) found in the liquid 3, or in the plasma 4, may have very desirable effects, in which case relatively large amounts of such materials will be desirable; whereas in other cases, certain materials found in the liquid 3 (e.g., by-products) may have undesirable effects, and thus minimal amounts of such materials may be desired in the liquid-based final product. Accordingly, electrode composition can play an important role in the material that is formed according to the embodiments disclosed herein. The interplay between these components of the invention are discussed in greater detail later herein.

Still further, the electrode(s) 1 and 5 may be of similar chemical composition and/or mechanical configuration or completely different compositions in order to achieve various compositions and/or structures of liquids and/or specific effects discussed later herein.

The distance between the electrode(s) 1 and 5; or 1 and 1 (shown later herein) or 5 and 5 (shown later herein) is one important aspect of the invention. In general, the location of the smallest distance "y" between the closest portions of the electrode(s) used in the present invention should be greater than the distance "x" in order to prevent an undesirable arc or formation of an unwanted corona or plasma occurring between the electrode (e.g., the electrode(s) 1 and the electrode(s) 5). Features of the invention relating to electrode design, electrode location and electrode interactions between a variety of electrodes are discussed in greater detail later herein.

The power applied through the power source 10 may be any suitable power which creates a desirable adjustable plasma 4 under all of the process conditions of the present invention. In one preferred mode of the invention, an alternating current from a step-up transformer (discussed in greater detail later herein) is utilized. In another preferred embodiment, a rectified AC source creates a positively charged electrode 1 and a negatively charged surface 2 of the liquid 3. In another preferred embodiment, a rectified AC source creates a negatively charged electrode 1 and a positively charged surface 2 of the liquid 3. Further, other power sources such as RF power sources are also useable with the present invention. In general, the combination of electrode(s) components 1 and 5, physical size and shape of the electrode(s) 1 and 5, electrode manufacturing process, mass of electrodes 1 and/or 5, the distance "x" between the tip 9 of electrode 1 above the surface 2 of the liquid 3, the composition of the gas between the electrode tip 9 and the surface 2, the flow rate and/or flow direction "F" of the liquid 3, the amount of liquid 3 provided, type of power source 10, all contribute to the design, and thus power requirements (e.g., breakdown electric field) required to obtain a controlled or adjustable plasma 4 between the surface 2 of the liquid 3 and the electrode tip 9.

In further reference to the configurations shown in FIG. 1a, electrode holders 6a and 6b are capable of being lowered and raised by any suitable means (and thus the electrodes are capable of being lowered and raised). For example, the electrode holders 6a and 6b are capable of being lowered and raised in and through an insulating member 8 (shown in cross-section). The mechanical embodiment shown here include male/female screw threads. The portions 6a and 6b can be covered by, for example, additional electrical insulating portions 7a and 7b. The electrical insulating portions 7a and 7b can be any suitable material (e.g., plastic, polycarbonate, poly(methyl methacrylate), polystyrene, acrylics, polyvinylchloride (PVC), nylon, rubber, fibrous materials, etc.) which prevent undesirable currents, voltage, arcing, etc., that could occur when an individual interfaces with the electrode holders 6a and 6b (e.g., attempts to adjust the height of the electrodes). Likewise, the insulating member 8 can be made of any suitable material which prevents undesirable electrical events (e.g., arcing, melting, etc.) from occurring, as well as any material which is structurally and environmentally suitable for practicing the present invention. Typical materials include structural plastics such as polycarbonates, plexiglass (poly(methyl methacrylate), polystyrene, acrylics, and the like. Additional suitable materials for use with the present invention are discussed in greater detail elsewhere herein.

FIG. 1c shows another embodiment for raising and lowering the electrodes 1, 5. In this embodiment, electrical insulating portions 7a and 7b of each electrode are held in place by a pressure fit existing between the friction mechanism 13a, 13b and 13c, and the portions 7a and 7b. The friction mechanism 13a, 13b and 13c could be made of, for example, spring steel, flexible rubber, etc., so long as sufficient contact is maintained therebetween.

Preferred techniques for automatically raising and/or lowering the electrodes 1, 5 are discussed later herein. The power source 10 can be connected in any convenient electrical manner to the electrodes 1 and 5. For example, wires 11a and 11b can be located within at least a portion of the electrode holders 6a, 6b (and/or electrical insulating portions 7a, 7b) with a primary goal being achieving electrical connections between the portions 11a, 11b and thus the electrodes 1, 5.

FIG. 2a shows another schematic of a preferred embodiment of the invention, wherein an inventive control device 20 is connected to the electrodes 1 and 5, such that the control device 20 remotely (e.g., upon command from another device) raises and/or lowers the electrodes 1, 5 relative to the surface 2 of the liquid 3. The inventive control device 20 is discussed in more detail later herein. In this one preferred aspect of the invention, the electrodes 1 and 5 can be, for example, remotely lowered and controlled, and can also be monitored and controlled by a suitable controller or computer (not shown in FIG. 2a) containing a software program (discussed in detail later herein). In this regard, FIG. 2b shows an electrode configuration similar to that shown in FIG. 2a, except that a Taylor Cone "T" is utilized for electrical connection between the electrode 5 and the surface 2 (or effective surface 2') of the liquid 3. Accordingly, the embodiments shown in FIGS. 1a, 1b and 1c should be considered to be a manually controlled apparatus for use with the techniques of the present invention, whereas the embodiments shown in FIGS. 2a and 2b should be considered to include an automatic apparatus or assembly which can remotely raise and lower the electrodes 1 and 5 in response to appropriate commands. Further, the FIG. 2a and FIG. 2b preferred embodiments of the invention can also employ computer monitoring and computer control of the distance "x" of the tips 9 of the electrodes 1 (and tips 9' of the electrodes 5) away from the surface 2 (discussed in greater detail later herein). Thus, the appropriate commands for raising and/or lowering the electrodes 1 and 5 can come from an individual operator and/or a suitable control device such as a controller or a computer (not shown in FIG. 2a).

FIG. 3a corresponds in large part to FIGS. 2a and 2b, however, FIGS. 3b, 3c and 3d show various alternative electrode configurations that can be utilized in connection with certain preferred embodiments of the invention. FIG. 3b shows essentially a mirror image electrode assembly from that electrode assembly shown in FIG. 3a. In particular, as shown in FIG. 3b, with regard to the direction "F" corresponding to the flow direction of the liquid 3, the electrode 5 is the first electrode which communicates with the fluid 3 when flowing in the longitudinal direction "F" and contact with the plasma 4 created at the electrode 1 follows. FIG. 3c shows two electrodes 5a and 5b located within the fluid 3. This particular electrode configuration corresponds to another preferred embodiment of the invention. In particular, as discussed in greater detail herein, the electrode configuration shown in FIG. 3c can be used alone, or in combination with, for example, the electrode configurations shown in FIGS. 3a and 3b. Similarly, a fourth possible electrode configuration is shown in FIG. 3d. In this FIG. 3d, no electrode(s) 5 are shown, but rather only electrodes 1a and 1b are shown. In this case, two adjustable plasmas 4a and 4b are present between the electrode tips 9a and 9b and the surface 2 of the liquid 3. The distances "xa" and "xb" can be about the same or can be substantially different, as long as each distance "xa" and "xb" does not exceed the maximum distance for which a plasma 4 can be formed between the electrodes 9a/9b and the surface 2 of the liquid 3. As discussed above, the electrode configuration shown in FIG. 3d can be used alone, or in combination with one or more of the electrode configurations shown in FIGS. 3a, 3b and 3c. The desirability of utilizing particular electrode configurations in combination with each other with regard to the fluid flow direction "F" is discussed in greater detail later herein.

Likewise, a set of manually controllable electrode configurations, corresponding generally to FIG. 1a, are shown in FIGS. 4a, 4b, 4c and 4d, all of which are shown in a partial cross-sectional view. Specifically, FIG. 4a corresponds to FIG. 1a. Moreover, FIG. 4b corresponds in electrode configuration to the electrode configuration shown in FIG. 3b; FIG. 4c corresponds to FIG. 3c and FIG. 4d corresponds to FIG. 3d. In essence, the manual electrode configurations shown in FIGS. 4a-4d can functionally result in similar materials produced according to certain inventive aspects of the invention as those materials produced corresponding to remotely adjustable (e.g., remote-controlled by computer or controller means) electrode configurations shown in FIGS. 3a-3d. The desirability of utilizing various electrode configuration combinations is discussed in greater detail later herein.

FIGS. 5a-5e show perspective views of various desirable electrode configurations for the electrode 1 shown in FIGS. 1-4 (as well as in other Figures and embodiments discussed later herein). The electrode configurations shown in FIGS. 5a-5e are representative of a number of different configurations that are useful in various embodiments of the present invention. Criteria for appropriate electrode selection for the electrode 1 include, but are not limited to the following conditions: the need for a very well defined tip or point 9, composition, mechanical limitations, the ability to make shapes from the material comprising the electrode 1, convenience, the constituents introduced into the plasma 4, the influence upon the liquid 3, etc. In this regard, a small mass of material comprising the electrodes 1 shown in, for example, FIGS. 1-4 may, upon creation of the adjustable plasmas 4 according to the present invention (discussed in greater detail later herein), rise to operating temperatures where the size and or shape of the electrode(s) 1 can be adversely affected. In this regard, for example, if the electrode 1 was of relatively small mass (e.g., if the electrode(s) 1 was made of silver and weighed about 0.5 gram or less) and included a very fine point, then it is possible that under certain sets of conditions that a fine point (e.g., a thin wire having a diameter of only a few millimeters and exposed to a few hundred to a few thousand volts; or a triangular-shaped piece of metal) would be incapable of functioning as the electrode 1, absent some type of additional interactions (e.g., a cooling means such as a fan, etc.). Accordingly, the composition of (e.g., the material comprising) the electrode(s) 1 may affect possible suitable electrode physical shape due to, for example, melting points, pressure sensitivities, environmental reactions (e.g., the local environment of the adjustable plasma 4 could cause chemical, mechanical and/or electrochemical erosion of the electrode(s)), etc.

Moreover, it should be understood that in alternative preferred embodiments of the invention, well defined sharp points are not always required. In this regard, the electrode 1 shown in FIG. 5e comprises a rounded point. It should be noted that partially rounded or arc-shaped electrodes can also function as the electrode 1 because the adjustable plasma 4, which is created in the inventive embodiments shown herein (see, for example, FIGS. 1-4), can be created from rounded electrodes or electrodes with sharper or more pointed features. During the practice of the inventive techniques of the present invention, such adjustable plasmas can be positioned or can be located along various points of the electrode 1 shown in FIG. 5e. In this regard, FIG. 6 shows a variety of points "a-g" which correspond to initiating points 9 for the plasmas 4a-4g which occur between the electrode 1 and the surface 2 of the liquid 3. Accordingly, it should be understood that a variety of sizes and shapes corresponding to electrode 1 can be utilized in accordance with the teachings of the present invention. Still further, it should be noted that the tips 9, 9' of the electrodes 1 and 5, respectively, shown in various Figures herein, may be shown as a relatively sharp point or a relatively blunt end. Unless specific aspects of these electrode tips are discussed in greater contextual detail, the actual shape of the electrode tip(s) shown in the Figures should not be given great significance.

FIG. 7a shows a cross-sectional perspective view of the electrode configuration corresponding to that shown in FIG. 2a (and FIG. 3a) contained within a trough member 30. This trough member 30 has a liquid 3 supplied into it from the back side identified as 31 of FIG. 7a and the flow direction "F" is out of the page toward the reader and toward the cross-sectioned area identified as 32. The trough member 30 is shown here as a unitary piece of one material, but could be made from a plurality of materials fitted together and, for example, fixed (e.g., glued, mechanically attached, etc.) by any acceptable means for attaching materials to each other. Further, the trough member 30 shown here is of a rectangular or square cross-sectional shape, but may comprise a variety of different cross-sectional shapes (discussed in greater detail later herein). Accordingly, the flow direction of the fluid 3 is out of the page toward the reader and the liquid 3 flows past each of the electrodes 1 and 5, which are, in this embodiment, located substantially in line with each other relative to the longitudinal flow direction "F" of the fluid 3 within the trough member 30. This causes the liquid 3 to first experience an adjustable plasma interaction with the adjustable plasma 4 (e.g., a conditioning reaction) and subsequently then the conditioned fluid 3 is permitted to interact with the electrode 5. Specific desirable aspects of these electrode/liquid interactions and electrode placement(s) are discussed in greater detail elsewhere herein.

FIG. 7b shows a cross-sectional perspective view of the electrode configuration shown in FIG. 2a (as well as in FIG. 3a), however, these electrodes 1 and 5 are rotated on the page 90 degrees relative to the electrodes 1 and 5 shown in FIGS. 2a and 3a. In this embodiment of the invention, the liquid 3 contacts the adjustable plasma 4 generated between the electrode 1 and the surface 2 of the liquid 3, and the electrode 5 at substantially the same point along the longitudinal flow direction "F" (i.e., out of the page) of the trough member 30. The direction of liquid 3 flow is longitudinally along the trough member 30 and is out of the paper toward the reader, as in FIG. 7a. Various desirable aspects of this electrode configuration are discussed in greater detail later herein.

FIG. 8a shows a cross-sectional perspective view of the same embodiment shown in FIG. 7a. In this embodiment, as in FIG. 7a, the fluid 3 firsts interacts with the adjustable plasma 4 created between the electrode 1 and the surface 2 of the liquid 3. Thereafter the plasma influenced or conditioned fluid 3, having been changed (e.g., conditioned, modified, or prepared) by the adjustable plasma 4, thereafter communicates with the electrode 5 thus permitting various electrochemical reactions to occur, such reactions being influenced by the state (e.g., chemical composition, physical or crystal structure, excited state(s), etc., of the fluid 3 (and constituents within the fluid 3)) discussed in greater detail elsewhere herein. An alternative embodiment is shown in FIG. 8b. This embodiment essentially corresponds in general arrangement to those embodiments shown in FIGS. 3b and 4b. In this embodiment, the fluid 3 first communicates with the electrode 5, and thereafter the fluid 3 communicates with the adjustable plasma 4 created between the electrode 1 and the surface 2 of the liquid 3.

FIG. 8c shows a cross-sectional perspective view of two electrodes 5a and 5b (corresponding to the embodiments shown in FIGS. 3c and 4c) wherein the longitudinal flow direction "F" of the fluid 3 contacts the first electrode 5a and thereafter contacts the second electrode 5b in the direction "F" of fluid flow.

Likewise, FIG. 8d is a cross-sectional perspective view and corresponds to the embodiments shown in FIGS. 3d and 4d. In this embodiment, the fluid 3 communicates with a first adjustable plasma 4a created by a first electrode 1a and thereafter communicates with a second adjustable plasma 4b created between a second electrode 1b and the surface 2 of the fluid 3.

FIG. 9a shows a cross-sectional perspective view and corresponds to the electrode configuration shown in FIG. 7b (and generally to the electrode configuration shown in FIGS. 3a and 4a but is rotated 90 degrees relative thereto). All of the electrode configurations shown in FIGS. 9a-9d are situated such that the electrode pairs shown are located substantially at the same longitudinal point along the trough member 30, as in FIG. 7b.

Likewise, FIG. 9b corresponds generally to the electrode configuration shown in FIGS. 3b and 4b, and is rotated 90 degrees relative to the configuration shown in FIG. 8b.

Figure 1A:
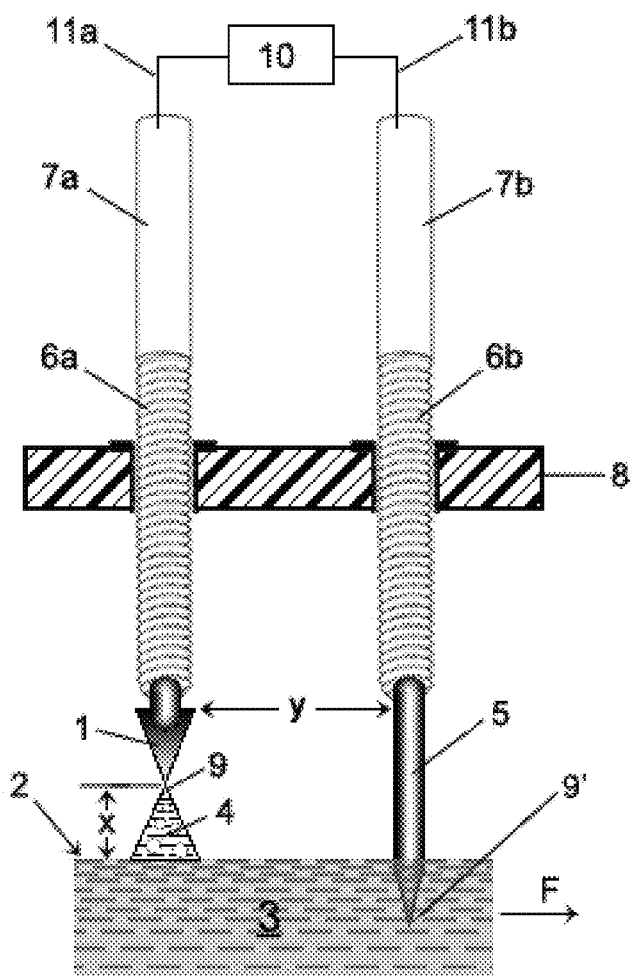

The electrode configurations shown generally in FIGS. 7, 8 and 9, all can create different results (e.g., different conditioning effects for the fluid 3, different pH's in the fluid 3, different sizes, shapes, and/or amounts of particulate matter found in the fluid 3, different functioning of the fluid/nanoparticle combination, etc.) as a function of a variety of features including the electrode orientation and position relative to the fluid flow direction "F", the number of electrode pairs provided and their positioning in the trough member 30 relative to each other. Further, the electrode compositions, size, specific shapes, number of different types of electrodes provided, voltage applied, amperage applied, AC source, DC source, RF source, electrode polarity, etc., can all influence the properties of the liquid 3 (and/or constituents contained in the liquid 3) as the liquid 3 flows past these electrodes 1, 5 and hence resultant properties of the materials (e.g., the nanoparticle solution) produced therefrom. Additionally, the liquid-containing trough member 30, in some preferred embodiments, contains a plurality of the electrode combinations shown in FIGS. 7, 8 and 9. These electrode assemblies may be all the same configuration or may be a combination of various different electrode configurations (discussed in greater detail elsewhere herein). Moreover, the electrode configurations may sequentially communicate with the fluid "F" or may simultaneously, or in parallel communicate with the fluid "F". Different exemplary and preferred electrode configurations are shown in additional figures later herein and are discussed in greater detail later herein in conjunction with different nanoparticles and nanoparticle/solutions produced therefrom.

Figure 9A:
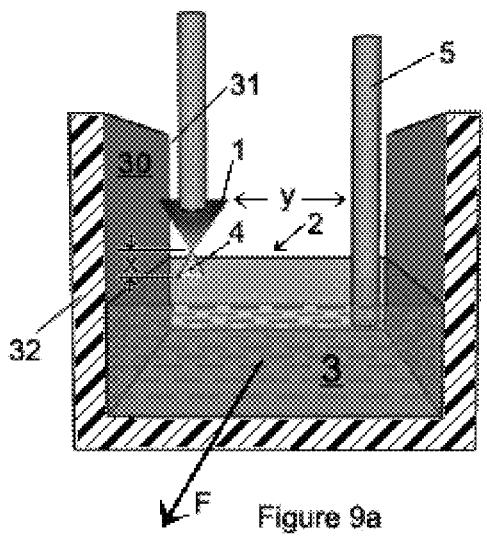
FIG. 9c shows an electrode configuration corresponding generally to FIGS. 3c and 4c, and is rotated 90 degrees relative to the electrode configuration shown in FIG. 8c.
FIG. 9d shows an electrode configuration corresponding generally to FIGS. 3d and 4d and is rotated 90 degrees relative to the electrode configuration shown in FIG. 8d.
Figure 9B:
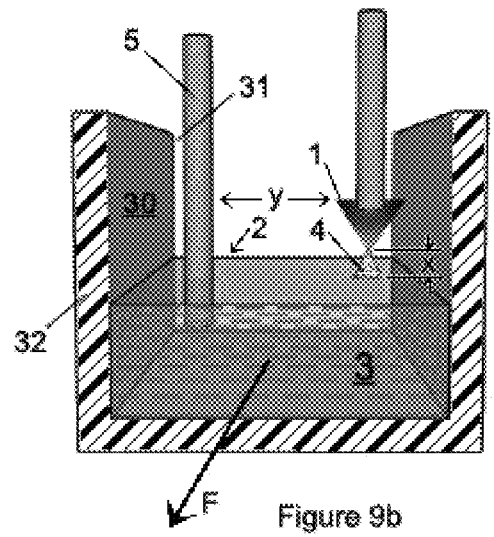
Figure 9C:
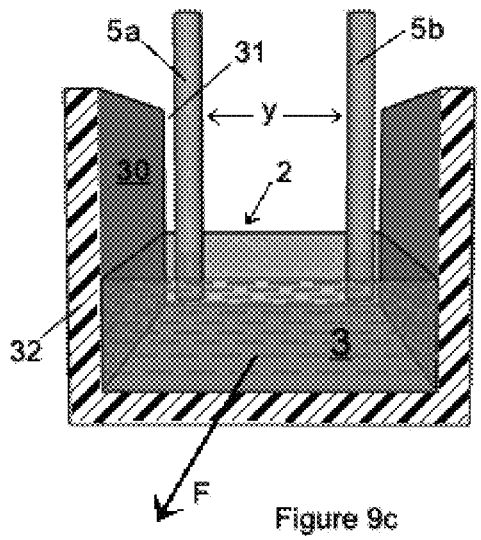
Figure 9D:
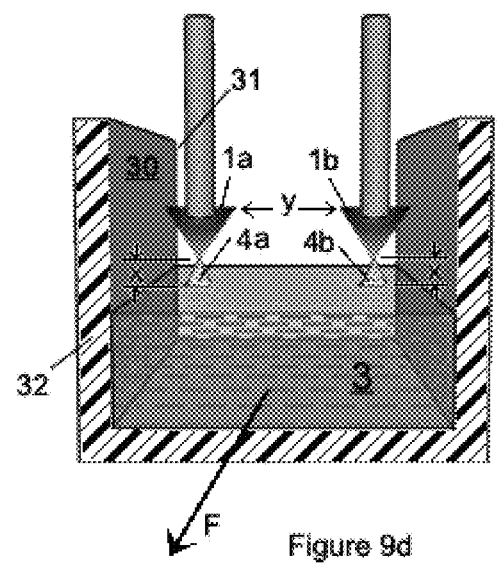
Figure 10A:
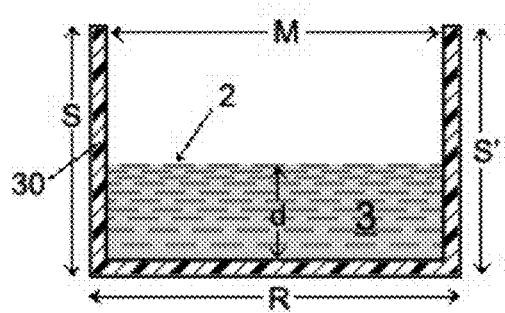

FIG. 10a shows a cross-sectional view of the liquid containing trough member 30 shown in FIGS. 7, 8 and 9. This trough member 30 has a cross-section corresponding to that of a rectangle or a square and the electrodes (not shown in FIG. 10a) can be suitably positioned therein.

Likewise, several additional alternative cross-sectional embodiments for the liquid-containing trough member 30 are shown in FIGS. 10b, 10c, 10d and 10e. The distance "S" and "S" for the preferred embodiment shown in each of FIGS. 10a-10e measures, for example, between about 1" and about 3" (about 2.5 cm-7.6 cm). The distance "M" ranges from about 2" to about 4" (about 5 cm-10 cm). The distance "R" ranges from about 1/16"-1/2" to about 3" (about 1.6 mm-3 mm to about 76 mm) All of these embodiments (as well as additional configurations that represent alternative embodiments are within the metes and bounds of this inventive disclosure) can be utilized in combination with the other inventive aspects of the invention. It should be noted that the amount of liquid 3 contained within each of the liquid containing trough members 30 is a function not only of the depth "d", but also a function of the actual cross-section. Briefly, the amount of fluid 3 present in and around the electrode(s) 1 and 5 can influence one or more effects of the adjustable plasma 4 upon the liquid 3 as well as the electrochemical interaction(s) of the electrode 5 with the liquid 3. These effects include not only adjustable plasma 4 conditioning effects (e.g., interactions of the plasma electric and magnetic fields, interactions of the electromagnetic radiation of the plasma, creation of various chemical species (e.g., Lewis acids, Bronsted-Lowry acids) within the liquid, pH changes, etc.) upon the liquid 3, but also the concentration or interaction of the adjustable plasma 4 with the liquid 3. Similarly, the influence of many aspects of the electrode 5 on the liquid 3 (e.g., electrochemical interactions) is also, at least partially, a function of the amount of liquid juxtaposed to the electrode(s) 5. Further, strong electric and magnetic field concentrations will also effect the interaction of the plasma 4 with the liquid 3 as well as effect the interaction of the electrode 5 with the liquid 3. Some important aspects of these important interactions are discussed in greater detail later herein. Further, a trough member 30 may comprise more than one cross-sectional shape along its entire longitudinal length. The incorporation of multiple cross-sectional shapes along the longitudinal length of a trough member 30 can result in, for example, varying the field or concentration or reaction effects being produced by the inventive embodiments disclosed herein (discussed in greater detail elsewhere herein). Further, a trough member 30 may not be linear or "I-shaped", but rather may be "Y-shaped" or "Ψ-shaped", with each portion of the "Y" (or "Ψ") having a different (or similar) cross-sectional shape and/or set of dimensions.

Figure 10B:
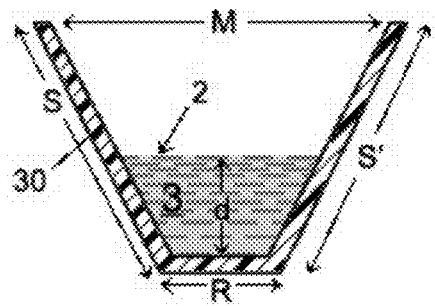
Figure 10C:
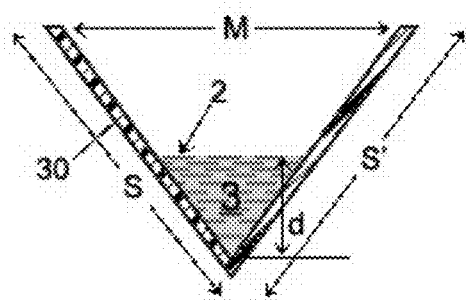
Figure 10D:
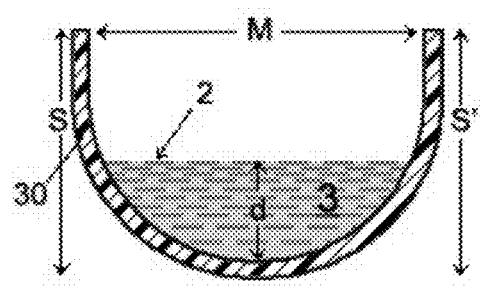
Figure 10E:
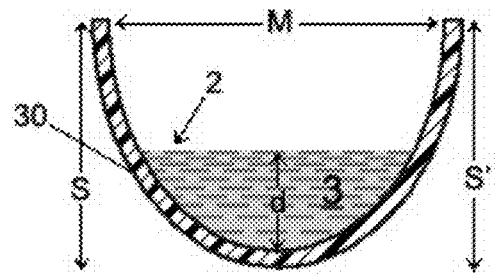

FIG. 11a shows a perspective view of one embodiment of substantially all of the trough member 30 shown in FIG. 10b including an inlet portion or inlet end 31 and an outlet portion or outlet end 32. The flow direction "F" discussed in other figures herein corresponds to a liquid entering at or near the end 31 (e.g., utilizing an appropriate means for delivering fluid into the trough member 30 at or near the inlet portion 31) and exiting the trough member 30 through the end 32. FIG. 11b shows the trough member 30 of FIG. 11a containing three control devices 20a, 20b and 20c removably attached to the trough member 30. The interaction and operations of the control devices 20a, 20b and 20c containing the electrodes 1 and/or 5 are discussed in greater detail later herein. However, in a preferred embodiment of the invention, the control devices 20, can be removably attached to a top portion of the trough member 30 so that the control devices 20 are capable of being positioned at different positions along the trough member 30, thereby affecting certain processing parameters, constituents produced, reactivity of constituents produced, as well as nanoparticle(s)/fluid(s) produced therefrom.

FIG. 11c shows a perspective view of an atmosphere control device cover 35'. The atmosphere control device or cover 35' has attached thereto a plurality of control devices 20a, 20b and 20c controllably attached to electrode(s) 1 and/or 5. The cover 35' is intended to provide the ability to control the atmosphere within and/or along a substantial portion of (e.g., greater than 50% of) the longitudinal direction of the trough member 30, such that any adjustable plasma(s) 4 created between any electrode(s) 1 and surface 2 of the liquid 3 can be a function of voltage, current, current density, polarity, etc. (as discussed in more detail elsewhere herein) as well as a controlled atmosphere (also discussed in more detail elsewhere herein).

FIG. 11d shows the apparatus of FIG. 11c including an additional support means 34 for supporting the trough member 30 (e.g., on an exterior portion thereof), as well as supporting (at least partially) the control devices 20 (not shown in FIG. 11d). It should be understood by the reader that various details can be changed regarding, for example, the cross-sectional shapes shown for the trough member 30, atmosphere control(s) (e.g., the cover 35') and external support means (e.g., the support means 34) which are within the metes and bounds of this disclosure, some of which are discussed in greater detail later herein.

Figure 11E:
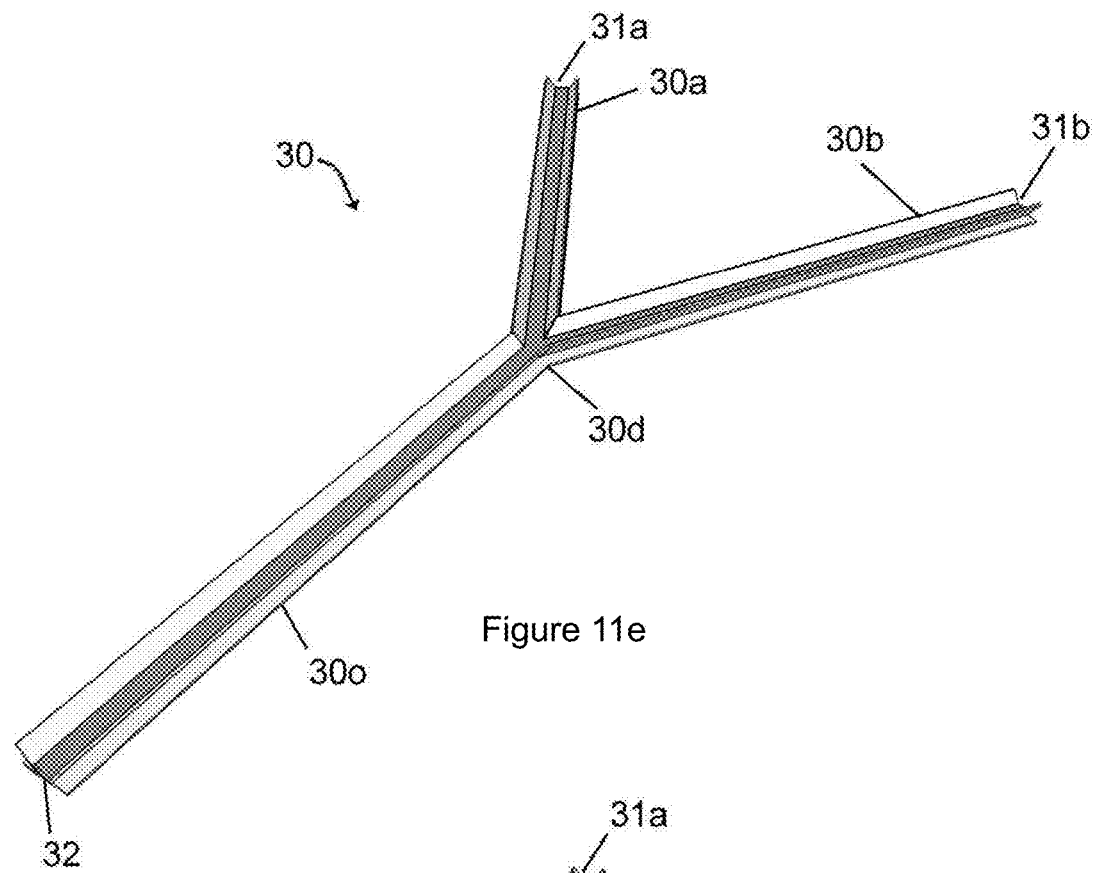

FIG. 11e shows an alternative configuration for the trough member 30. Specifically, the trough member 30 is shown in perspective view and is "Y-shaped". Specifically, the trough member 30 comprises top portions 30a and 30b and a bottom portion 30o. Likewise, inlets 31a and 31b are provided along with outlet 32. A portion 30d corresponds to the point where 30a and 30b meet 30o.

Figure 11F:
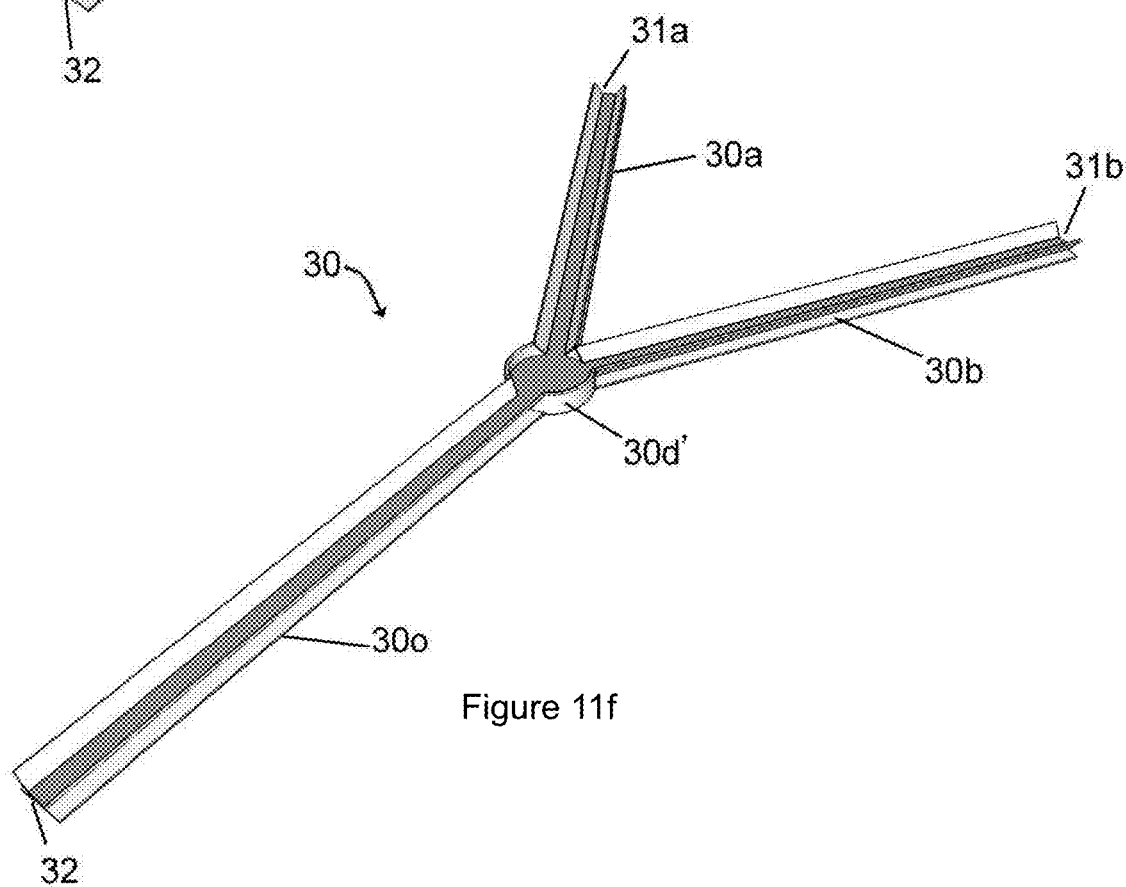

FIG. 11f shows the same "Y-shaped" trough member shown in FIG. 11e, except that the portion 30d of FIG. 11e is now shown as a mixing section 30d'. In this regard, certain constituents manufactured or produced in the liquid 3 in one or all of, for example, the portions 30a, 30b and/or 30c, may be desirable to be mixed together at the point 30d (or 30d'). Such mixing may occur naturally at the intersection 30d shown in FIG. 11e (i.e., no specific or special section 30d' may be needed), or may be more specifically controlled at the portion 30d'. It should be understood that the portion 30d' could be shaped in any effective shape, such as square, circular, rectangular, etc., and be of the same or different depth relative to other portions of the trough member 30. In this regard, the area 30d could be a mixing zone or subsequent reaction zone.

Figure 11G:
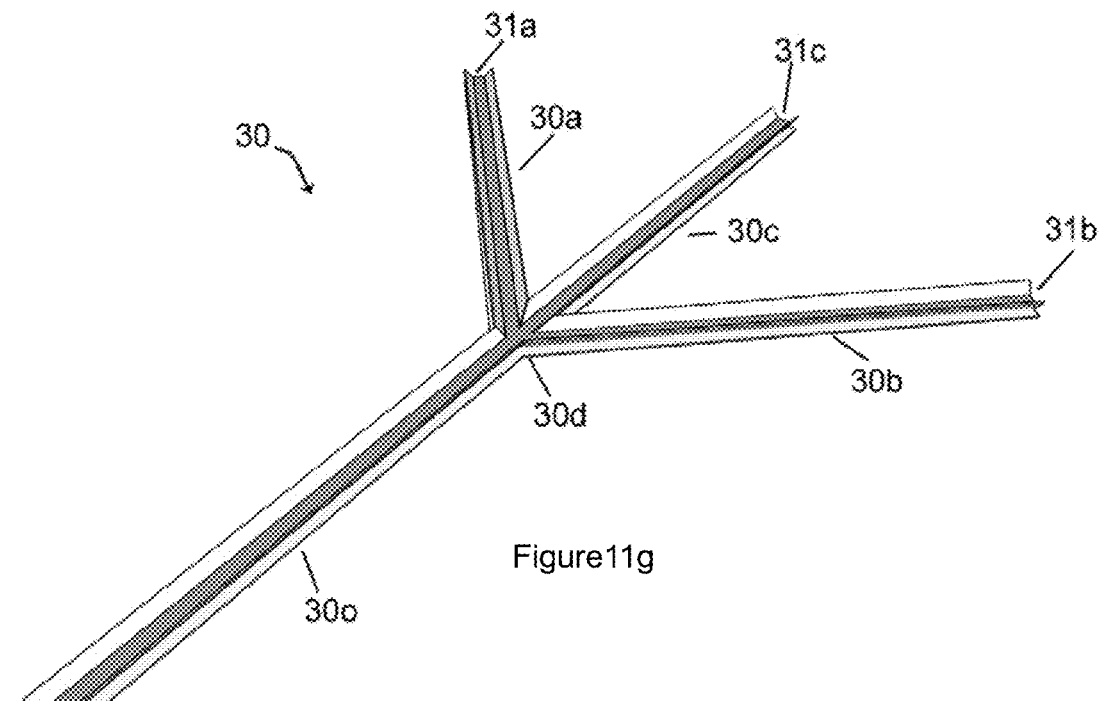
Figure 11H:
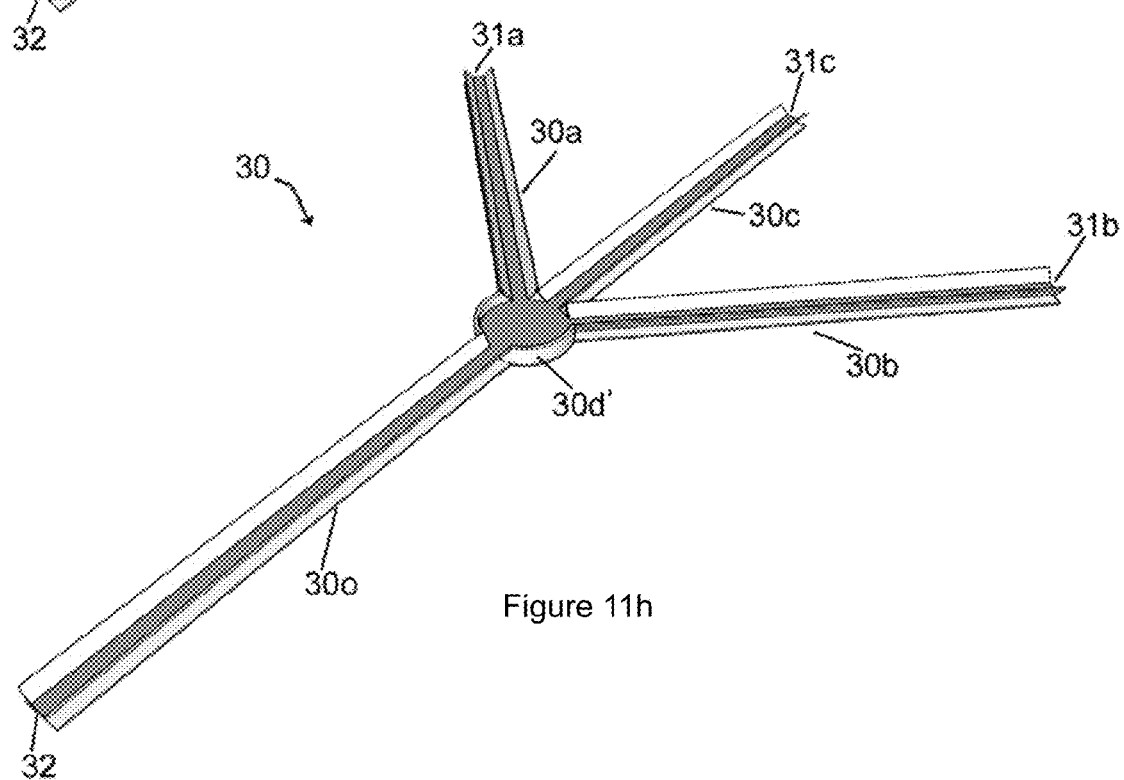

FIGS. 11g and 11h show a "Ψ-shaped" trough member 30. Specifically, a new portion 30c has been added. Other features of FIGS. 11g and 11h are similar to those features shown in 11e and 11f.

It should be understood that a variety of different shapes can exist for the trough member 30, any one of which can produce desirable results.

Figure 12A:

FIG. 12a shows a perspective view of a local atmosphere control apparatus 35 which functions as a means for controlling a local atmosphere around the electrode sets 1 and/or 5 so that various localized gases can be utilized to, for example, control and/or effect certain components in the adjustable plasma 4 between electrode 1 and surface 2 of the liquid 3, as well as influence adjustable electrochemical reactions at and/or around the electrode(s) 5. The throughholes 36 and 37 shown in the atmosphere control apparatus 35 are provided to permit external communication in and through a portion of the apparatus 35. In particular, the hole or inlet 37 is provided as an inlet connection for any gaseous species to be introduced to the inside of the apparatus 35. The hole 36 is provided as a communication port for the electrodes 1 and/or 5 extending therethrough which electrodes are connected to, for example, the control device 20 located above the apparatus 35. Gasses introduced through the inlet 37 can simply be provided at a positive pressure relative to the local external atmosphere and may be allowed to escape by any suitable means or pathway including, but not limited to, bubbling out around the portions 39a and/or 39b of the apparatus 35, when such portions are caused, for example, to be at least partially submerged beneath the surface 2 of the liquid 3 (discussed in greater detail later herein). Alternatively, a second hole or outlet (not shown) can be provided elsewhere in the atmosphere control apparatus 35. Generally, the portions 39a and 39b can break the surface 2 of the liquid 3 effectively causing the surface 2 to act as part of the seal to form a localized atmosphere around electrode sets 1 and/or 5. When a positive pressure of a desired gas enters through the inlet port 37, small bubbles can be caused to bubble past, for example, the portions 39a and/or 39b. Alternatively, gas may exit through an appropriate outlet in the atmosphere control apparatus 35.

Figure 12B:

FIG. 12b shows a perspective view of first atmosphere control apparatus 35a in the foreground of the trough member 30 contained within the support housing 34. A second atmosphere control apparatus 35b is included and shows a control device 20 located thereon. "F" denotes the longitudinal direction of flow of liquid through the trough member 30. The desirability of locally controlled atmosphere(s) (e.g., of substantially the same chemical constituents, such as air or nitrogen, or substantially different chemical constituents, such as helium and nitrogen) around different electrode sets 1 and/or 5 is discussed in greater detail later herein.

Figure 13:
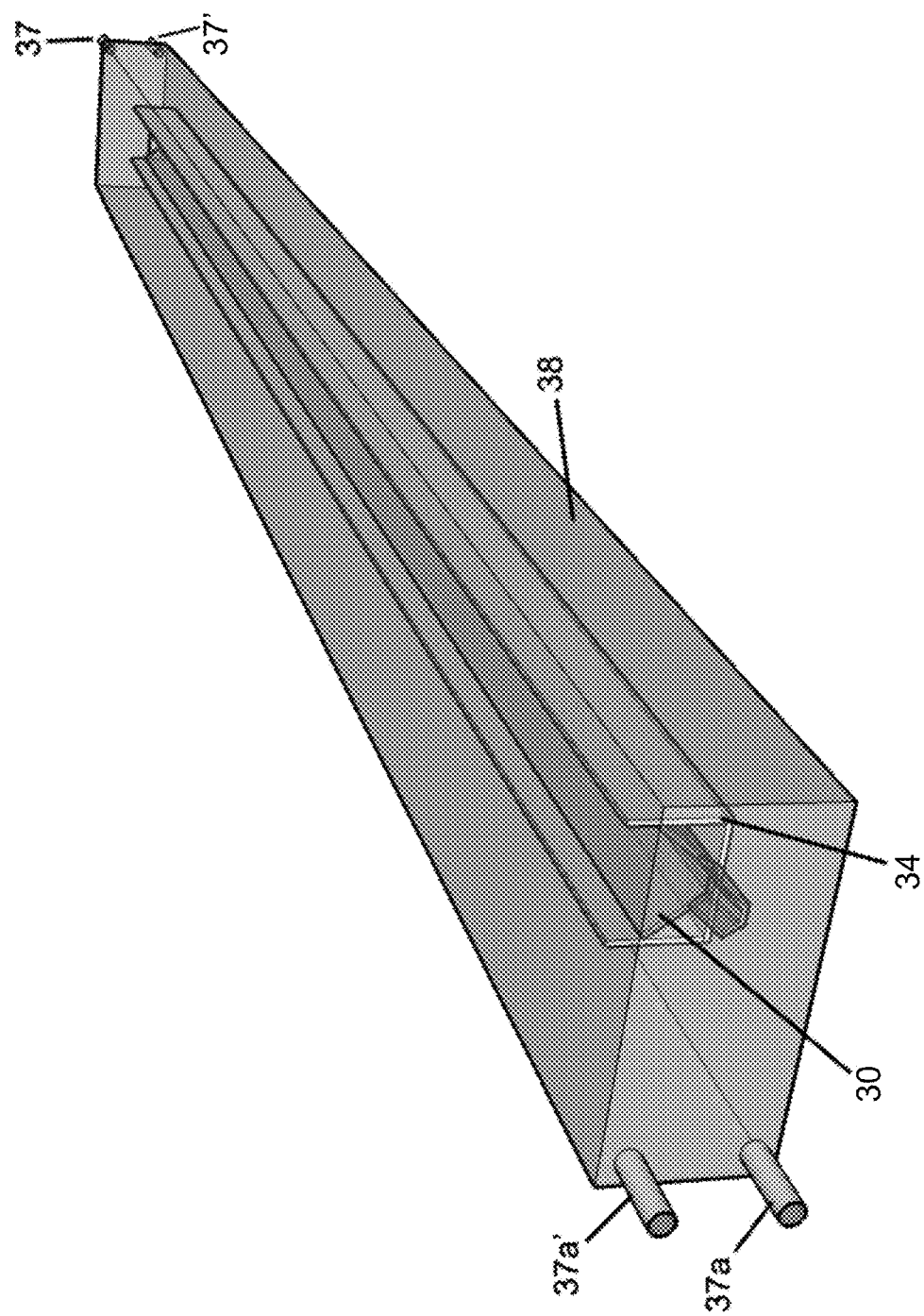

FIG. 13 shows a perspective view of an alternative atmosphere control apparatus 38 wherein the entire trough member 30 and support means 34 are contained within the atmosphere control apparatus 38. In this case, for example, gas inlet 37 (37') can be provided along with a gas outlet(s) 37a (37a'). The exact positioning of the gas inlet(s) 37 (37') and gas outlet(s) 37a (37a') on the atmosphere control apparatus 38 is a matter of convenience, as well as a matter of the composition of the atmosphere contained therein. In this regard, if the gas is heavier than air or lighter than air, inlet and outlet locations can be adjusted accordingly. Aspects of these factors are discussed in greater detail later herein.

Figure 14:
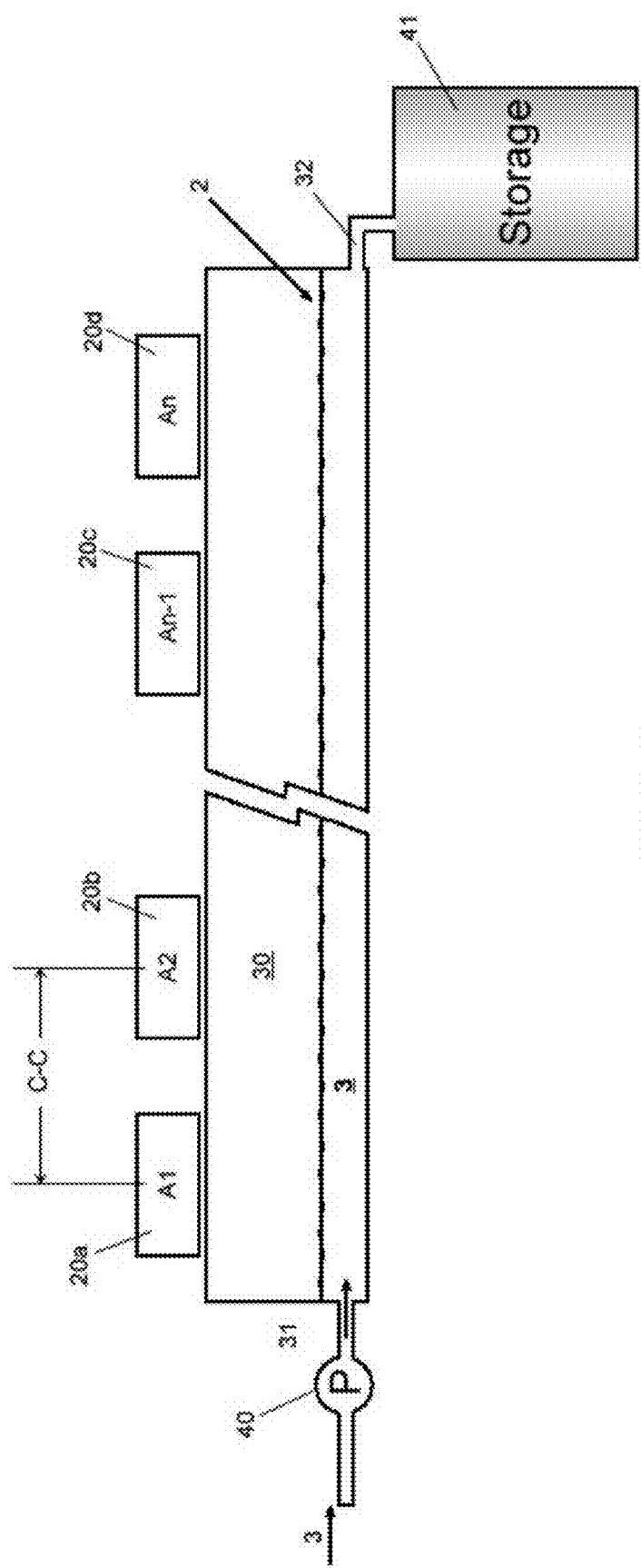

FIG. 14 shows a schematic view of the general apparatus utilized in accordance with the teachings of some of the preferred embodiments of the present invention. In particular, this FIG. 14 shows a side schematic view of the trough member 30 containing a liquid 3 therein. On the top of the trough member 30 rests a plurality of control devices 20a-20d which are, in this embodiment, removably attached thereto. The control devices 20a-20d may of course be permanently fixed in position when practicing various embodiments of the invention. The precise number of control devices 20 (and corresponding electrode(s) 1 and/or 5 as well as the configuration(s) of such electrodes) and the positioning or location of the control devices 20 (and corresponding electrodes 1 and/or 5) are a function of various preferred embodiments of the invention discussed in greater detail later herein. However, in general, an input liquid 3 (for example water or purified water) is provided to a liquid transport means 40 (e.g., a liquid pump, gravity or liquid pumping means for pumping the liquid 3) such as a peristaltic pump for pumping the liquid water 3 into the trough member 30 at a first-end 31 thereof. Exactly how the liquid 3 is introduced is discussed in greater detail later herein. The liquid transport means 40 may include any means for moving liquids 3 including, but not limited to a gravity-fed or hydrostatic means, a pumping means, a regulating or valve means, etc. However, the liquid transport means 40 should be capable of reliably and/or controllably introducing known amounts of the liquid 3 into the trough member 30. Once the liquid 3 is provided into the trough member 30, means for continually moving the liquid 3 within the trough member 30 may or may not be required. However, a simple means for continually moving the liquid 3 includes the trough member 30 being situated on a slight angle θ (e.g., less than a degree to a few degrees for a low viscosity fluid 3 such as water) relative to the support surface upon which the trough member 30 is located. For example, a difference in vertical height of less than one inch between an inlet portion 31 and an outlet portion 32, spaced apart by about 6 feet (about 1.8 meters) relative to the support surface may be all that is required, so long as the viscosity of the liquid 3 is not too high (e.g., any viscosity around the viscosity of water can be controlled by gravity flow once such fluids are contained or located within the trough member 30). In this regard, FIGS. 15a and 15b show two acceptable angles θ1 and θ2, respectively, for trough member 30 that can process various viscosities, including low viscosity fluids such as water. The need for a greater angle θ could be a result of processing a liquid 3 having a viscosity higher than water; the need for the liquid 3 to transit the trough 30 at a fast rate, etc. Further, when viscosities of the liquid 3 increase such that gravity alone is insufficient, other phenomena such as specific uses of hydrostatic head pressure or hydrostatic pressure can also be utilized to achieve desirable fluid flow. Further, additional means for moving the liquid 3 along the trough member 30 could also be provided inside the trough member 30. Such means for moving the fluid include mechanical means such as paddles, fans, propellers, augers, etc., acoustic means such as transducers, thermal means such as heaters (which may have additional processing benefits), etc., are also desirable for use with the present invention.

FIG. 14 also shows a storage tank or storage vessel 41 at the end 32 of the trough member 30. Such storage vessel 41 can be any acceptable vessel and/or pumping means made of one or more materials which, for example, do not negatively interact with the liquid 3 produced within the trough member 30. Acceptable materials include, but are not limited to plastics such as high density polyethylene (HDPE), glass, metal(s) (such a certain grades of stainless steel), etc. Moreover, while a storage tank 41 is shown in this embodiment, the tank 41 should be understood as including a means for distributing or directly bottling or packaging the fluid 3 processed in the trough member 30.

Figure 16C:
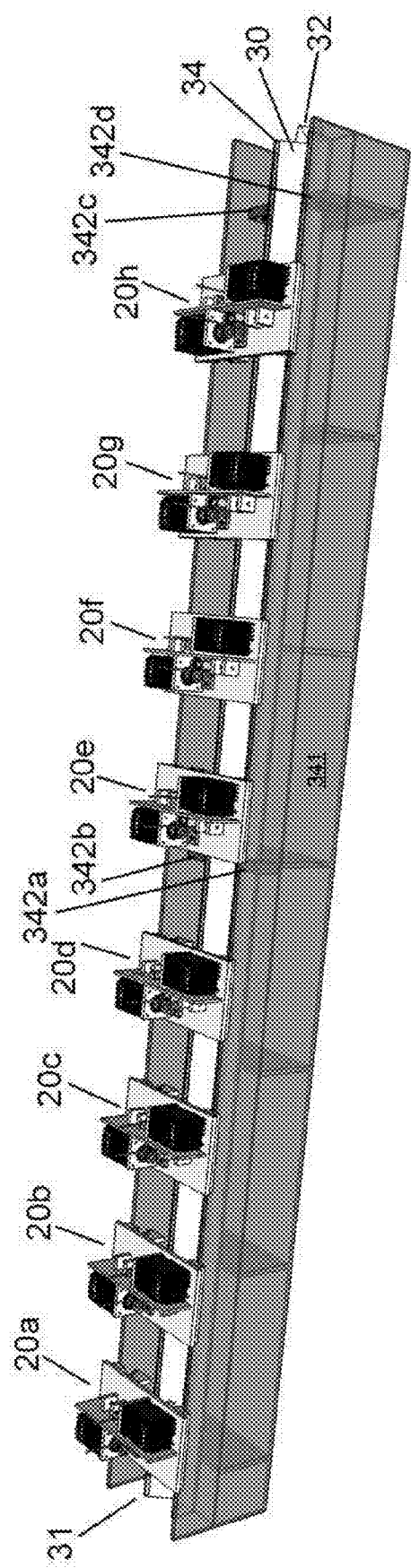

FIGS. 16a, 16b and 16c show a perspective view of one preferred embodiment of the invention. In these FIGS. 16a, 16b and 16c, eight separate control devices 20a-h are shown in more detail. Such control devices 20 can utilize one or more of the electrode configurations shown in, for example, FIGS. 8a, 8b, 8c and 8d. The precise positioning and operation of the control devices 20 (and the corresponding electrodes 1 and/or 5) are discussed in greater detail elsewhere herein. FIG. 16b includes use of two air distributing or air handling devices (e.g., fans 342a and 342b). Similarly, FIG. 16c includes the use of two alternative air distributing or air handling devices 342c and 342d.

Figure 17:
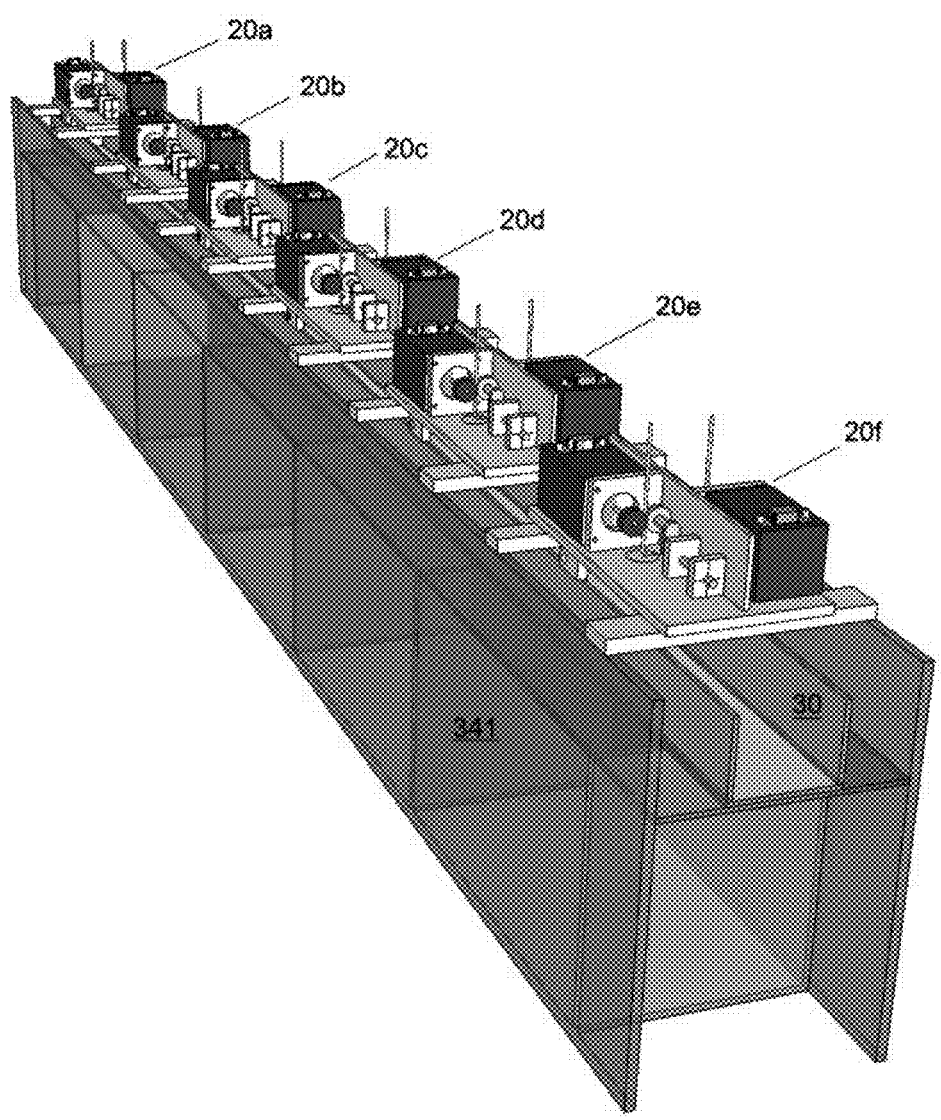

FIG. 17 shows another perspective view of another embodiment of the apparatus according to the present invention wherein six control devices 20a-20f are rotated approximately 90 degrees relative to the eight control devices 20a-20h shown in FIGS. 16a, 16b and 16c. The precise location and operation of the control devices 20 and the associated electrodes 1 and/or 5 are discussed in greater detail elsewhere herein.

Figure 18:
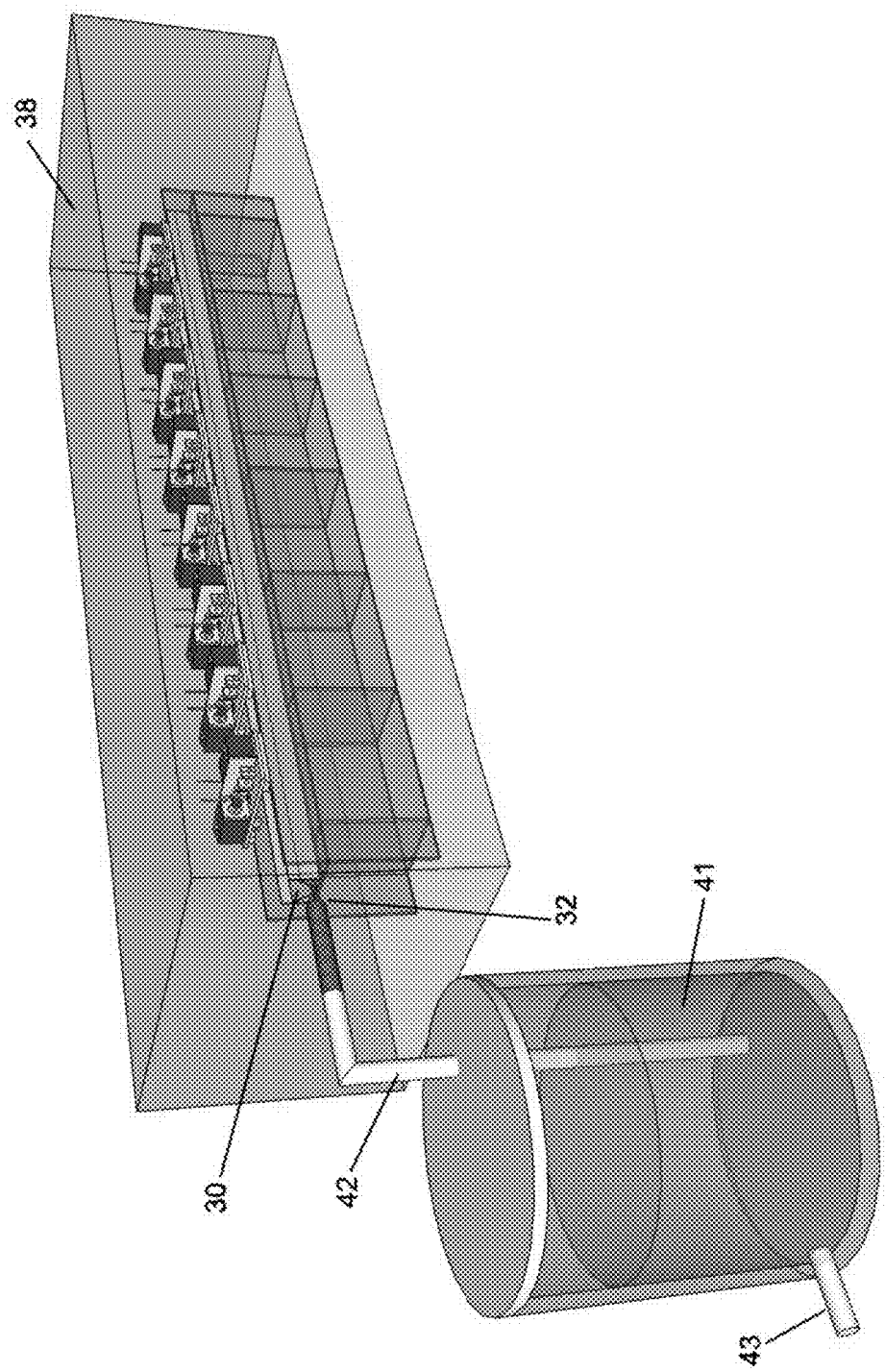

FIG. 18 shows a perspective view of the apparatus shown in FIG. 16a, but such apparatus is now shown as being substantially completely enclosed by an atmosphere control apparatus 38. Such apparatus 38 is a means for controlling the atmosphere around the trough member 30, or can be used to isolate external and undesirable material from entering into the trough member 30 and negatively interacting therewith. Further, the exit 32 of the trough member 30 is shown as communicating with a storage vessel 41 through an exit pipe 42. Moreover, an exit 43 on the storage tank 41 is also shown. Such exit pipe 43 can be directed toward any other suitable means for storage, packing and/or handling the liquid 3 (discussed in greater detail herein).

FIGS. 19a, 19b, 19c and 19d show additional cross-sectional perspective views of additional electrode configuration embodiments which can be used according to the present invention.

In particular, FIG. 19a shows two sets of electrodes 5 (i.e., 4 total electrodes 5a, 5b, 5c and 5d) located approximately parallel to each other along a longitudinal direction of the trough member 30 and substantially perpendicular (i.e., 60°-90°) to the flow direction "F" of the liquid 3 through the trough member 30. In contrast, FIG. 19b shows two sets of electrodes 5 (i.e, 5a, 5b, 5c and 5d) located adjacent to each other along the longitudinal direction of the trough member 30.

In contrast, FIG. 19c shows one set of electrodes 5 (5a, 5b) located substantially perpendicular to the direction of fluid flow "F" and another set of electrodes 5 (5c, 5d) located substantially parallel to the direction of the fluid flow "F". FIG. 19d shows a mirror image of the electrode configuration shown in FIG. 19c. While each of FIGS. 19a, 19b, 19c and 19d show only electrode(s) 5 it is clear that electrode(s) 1 could be substituted for some or all of those electrode(s) 5 shown in each of FIGS. 19a-19d, and/or intermixed therein (e.g., similar to the electrode configurations disclosed in FIGS. 8a-8d and 9a-9d). These alternative electrode configurations, and some of their associated advantages, are discussed in greater detail herein.

Figure 20A:
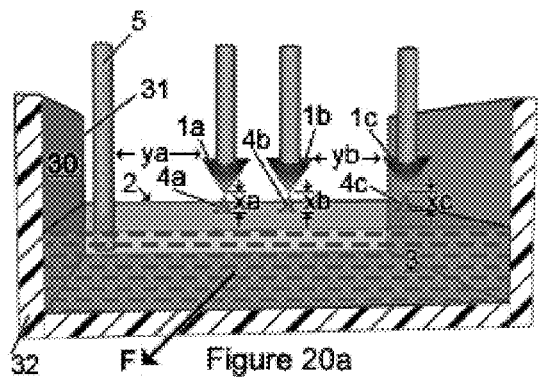
Figure 20B:
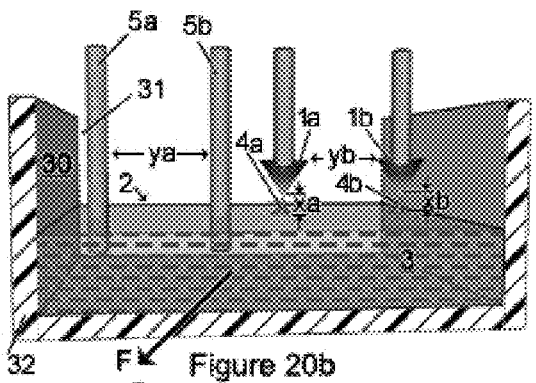
Figure 20C:
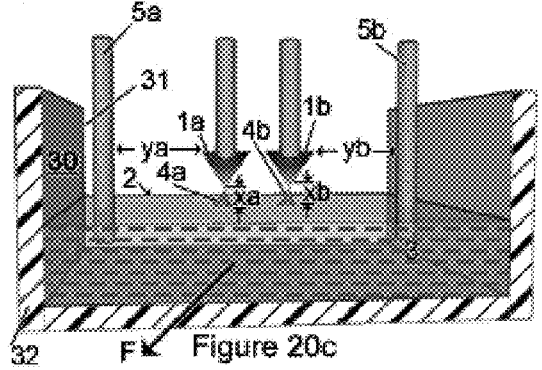
Figure 20D:
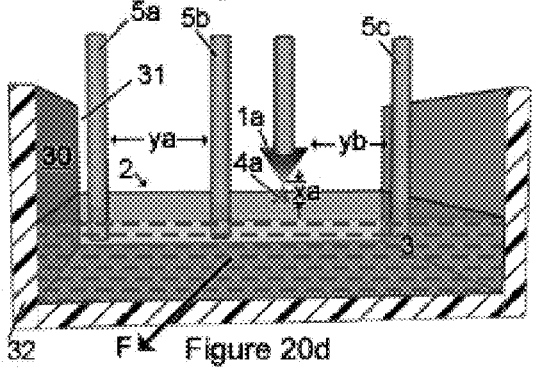
Figure 20E:
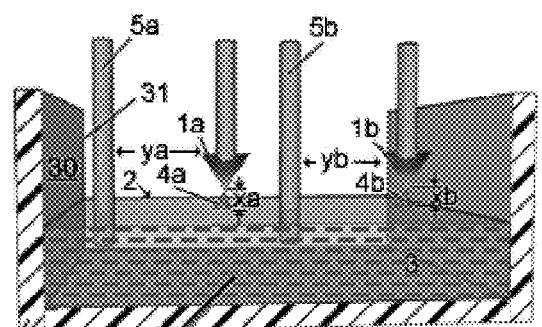
Figure 20F:
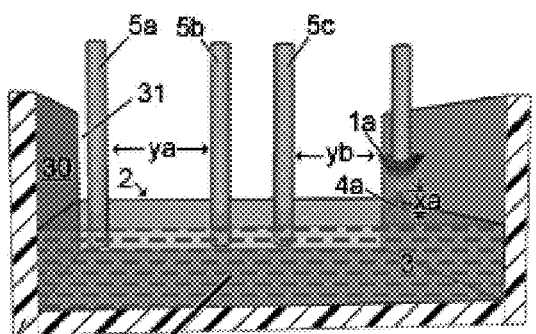
Figure 20G:
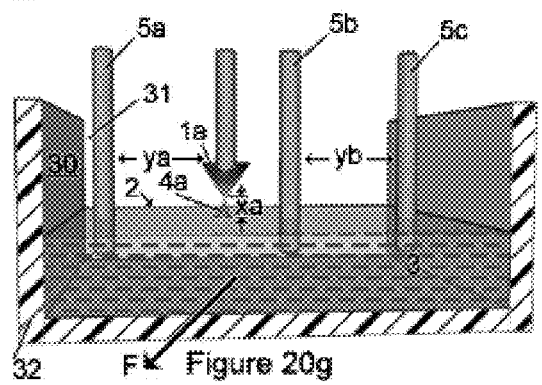
Figure 20H:
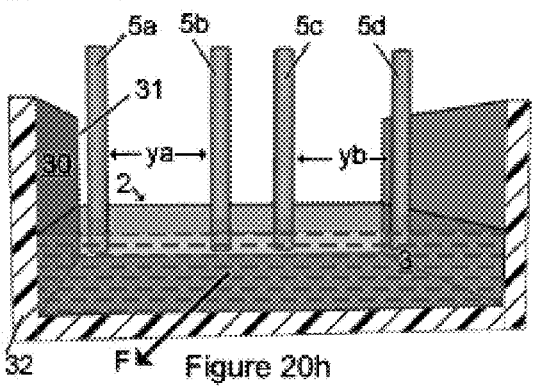
Figure 24A:
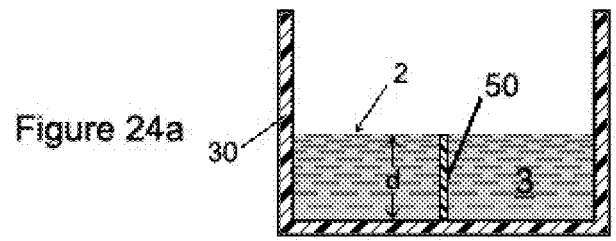
Figure 24B:
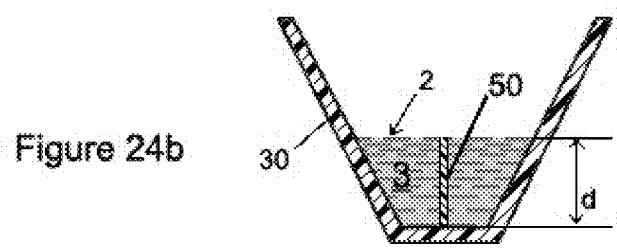
Figure 24C:
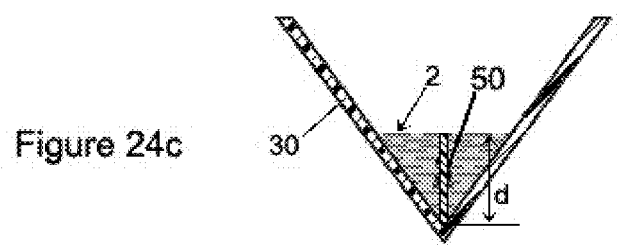
Figure 24D:
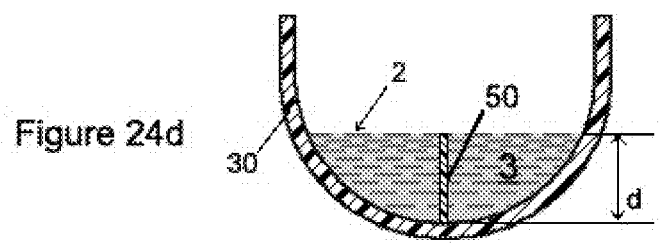
Figure 24E:
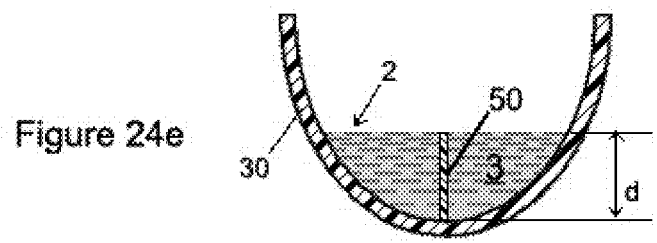
Figure 25A:
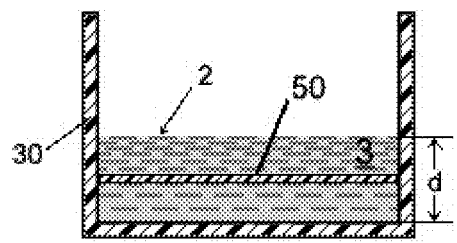
Figure 25B:
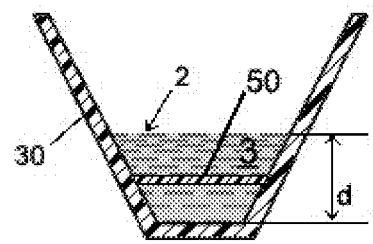
Figure 25C:
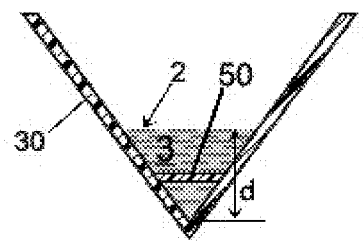
Figure 25D:
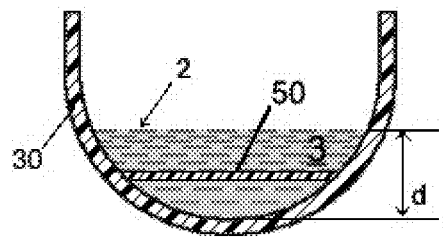
Figure 25E:
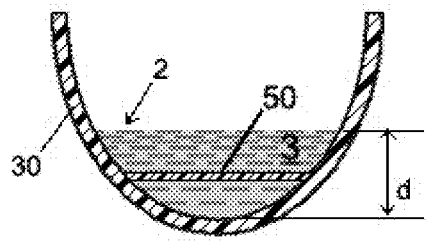
Figure 26A:
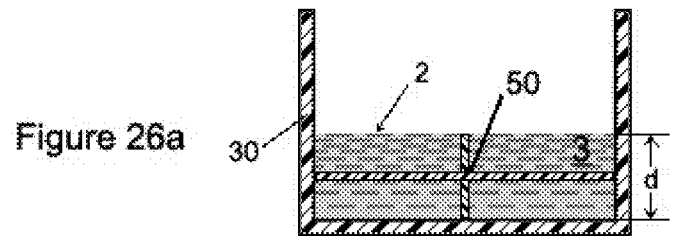
Figure 26B:
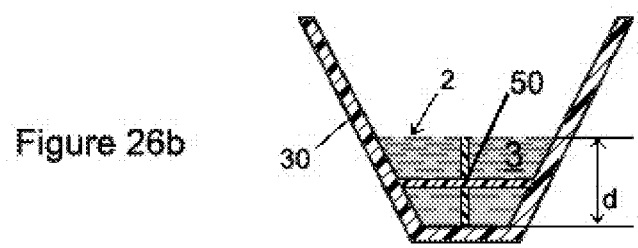
Figure 26C:
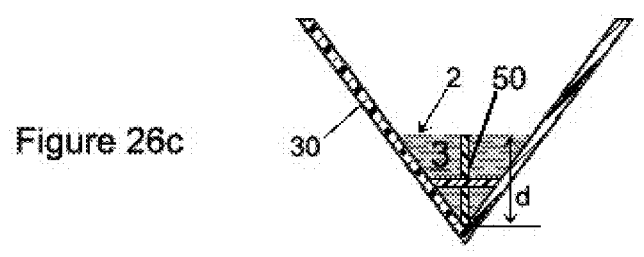
Figure 26D:
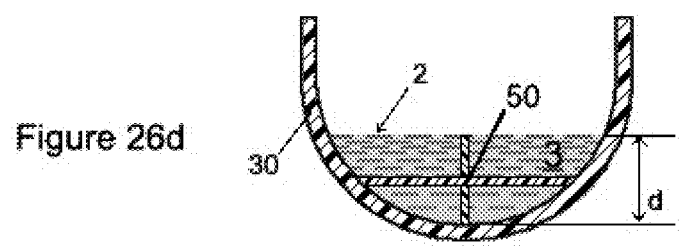
Figure 26E:
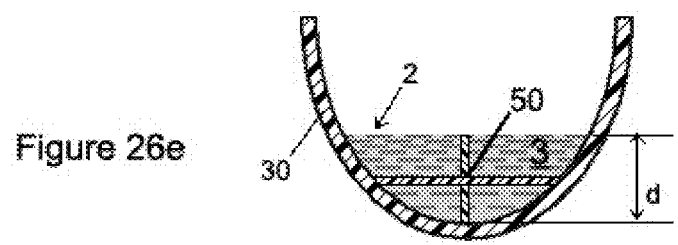

FIGS. 20a-20p show a variety of cross-sectional perspective views of the various electrode configuration embodiments possible and usable for all those configurations of electrodes 1 and 5 corresponding only to the embodiment shown in FIG. 19a. In particular, for example, the number of electrodes 1 or 5 varies in these FIGS. 20a-20p, as well as the specific locations of such electrode(s) 1 and 5 relative to each other. Of course, these electrode combinations 1 and 5 shown in FIGS. 20a-20p could also be configured according to each of the alternative electrode configurations shown in FIGS. 19b, 19c and 19d (i.e., sixteen additional figures corresponding to each of FIGS. 19b, 19c and 19d) but additional figures have not been included herein for the sake of brevity. Specific advantages of these electrode assemblies, and others, are disclosed in greater detail elsewhere herein.

Each of the electrode configurations shown in FIGS. 20a-20p, depending on the particular run conditions, can result in different products coming from the mechanisms, apparatuses and processes of the present invention. A more detailed discussion of these various configurations and advantages thereof are discussed in greater detail elsewhere herein.

FIGS. 21a, 21b, 21c and 21d show cross sectional perspective views of additional embodiments of the present invention. The electrode arrangements shown in these FIGS. 21a-21d are similar in arrangement to those electrode arrangements shown in FIGS. 19a, 19b, 19c and 19d, respectively. However, in these FIGS. 21a-21d a membrane or barrier assembly 50 is also included. In these embodiments of the invention, a membrane 50 is provided as a means for separating different products made at or near different electrode sets so that some or all of the products made by the set of electrodes 1 and/or 5 on one side of the membrane 50 can be at least partially isolated, or segregated, or substantially completely isolated from certain products made at or near electrodes 1 and/or 5 on the other side of the membrane 50. This membrane means 50 may act as a mechanical barrier, physical barrier, mechano-physical barrier, chemical barrier, electrical barrier, etc. Accordingly, certain products made from a first set of electrodes 1 and/or 5 can be at least partially, or substantially completely, isolated from certain products made from a second set of electrodes 1 and/or 5. Likewise, additional serially located electrode sets can also be similarly situated. In other words, different membrane(s) 50 can be utilized at or near each set of electrodes 1 and/or 5 and certain products produced therefrom can be controlled and selectively delivered to additional electrode sets 1 and/or 5 longitudinally downstream therefrom. Such membranes 50 can result in a variety of different compositions of the liquid 3 and/or nanoparticles or ions or constituents present in the liquid 3 produced in the trough member 30 (discussed in greater detail herein). For example, different formed compositions in the liquid 3 can be isolated from each other.

FIG. 22a shows a perspective cross-sectional view of an electrode assembly which corresponds to the electrode assembly 5a, 5b shown in FIG. 9c. This electrode assembly can also utilize a membrane 50 for chemical, physical, chemo-physical and/or mechanical separation. In this regard, FIG. 22b shows a membrane 50 located between the electrodes 5a, 5b. It should be understood that the electrodes 5a, 5b could be interchanged with the electrodes 1 in any of the multiple configurations shown, for example, in FIGS. 9a-9c. In the case of FIG. 22b, the membrane assembly 50 has the capability of isolating partially or substantially completely, some or all of the products formed at electrode 5a, from some or all of those products formed at electrode 5b. Accordingly, various species formed at either of the electrodes 5a and 5b can be controlled so that they can sequentially react with additional electrode assembly sets 5a, 5b and/or combinations of electrode sets 5 and electrode sets 1 in the longitudinal flow direction "F" that the liquid 3 undertakes along the longitudinal length of the trough member 30. Accordingly, by appropriate selection of membrane 50, which products located at which electrode (or subsequent or downstream electrode set) can be controlled, manipulated and/or adjusted. In a preferred embodiment where the polarity of the electrodes 5a and 5b are opposite, a variety of different products may be formed at the electrode 5a relative to the electrode 5b.

FIG. 22c shows another different embodiment of the invention in a cross-sectional schematic view of a completely different alternative electrode configuration for electrodes 5a and 5b. In this case, electrode(s) 5a (or of course electrode(s) 1a) are located above a membrane 50 and electrode(s) 5b are located below a membrane 50 (e.g., are substantially completely submerged in the liquid 3). In this regard, the electrode(s), 5b can comprise a plurality of electrodes or may be a single electrode running along at least some or the entire longitudinal length of the trough member 30. In this embodiment, certain species created at electrode(s) 5 above the membrane 50 can be different from certain species created below the membrane 50 and such species can react differently along the longitudinal length of the trough member 30. In this regard, the membrane 50 need not run the entire length of the trough member 30, but may be present for only a portion of such length and thereafter sequential assemblies of electrodes 1 and/or 5 can react with the products produced therefrom. It should be clear to the reader that a variety of additional embodiments beyond those expressly mentioned here would fall within the spirit of the embodiments expressly disclosed.

FIG. 22d shows another alternative embodiment of the invention whereby a configuration of electrodes 5a (and of course electrodes 1) shown in FIG. 22c are located above a portion of a membrane 50 which extends at least a portion along the length of a trough member 30 and a second electrode (or plurality of electrodes) 5b (similar to electrode(s) 5b in FIG. 22c) run for at least a portion of the longitudinal length along the bottom of the trough member 30. In this embodiment of utilizing multiple electrodes 5a, additional operational flexibility can be achieved. For example, by splitting the voltage and current into at least two electrodes 5a, the reactions at the multiple electrodes 5a can be different from those reactions which occur at a single electrode 5a of similar size, shape and/or composition. Of course this multiple electrode configuration can be utilized in many of the embodiments disclosed herein, but have not been expressly discussed for the sake of brevity. However, in general, multiple electrodes 1 and/or 5 (i.e., instead of a single electrode 1 and/or 5) can add great flexibility in products produced according to the present invention. Details of certain of these advantages are discussed elsewhere herein.

FIG. 23a is a cross-sectional perspective view of another embodiment of the invention which shows a set of electrodes 5 corresponding generally to that set of electrodes 5 shown in FIG. 19a however, the difference between the embodiment of FIG. 23a is a third set of electrode(s) 5e, 5f have been provided in addition to those two sets of electrodes 5a, 5b, 5c and 5d shown in FIG. 19a. Of course, the sets of electrodes 5a, 5b, 5c, 5d, 5e and 5f can also be rotated 90 degrees so they would correspond roughly to those two sets of electrodes shown in FIG. 19b. Additional figures showing additional embodiments of those sets of electrode configurations have not been included here for the sake of brevity.

FIG. 23b shows another embodiment of the invention which also permutates into many additional embodiments, wherein membrane assemblies 50a and 50b have been inserted between the three sets of electrodes 5a,5b-5c,5d and 5e,5f. It is of course apparent that the combination of electrode configuration(s), number of electrode(s) and precise membrane(s) means 50 used to achieve separation includes many embodiments, each of which can produce different products when subjected to the teachings of the present invention. More detailed discussion of such products and operations of these embodiments are discussed elsewhere herein.

FIGS. 24a-24e; 25a-25e; and 26a-26e show cross-sectional views of a variety of membrane means 50 designs and/or locations that can be utilized according to various embodiments disclosed herein. In each of these embodiments, the membrane means 50 provide a means for separating one or more products made at one or more electrode assemblies 1/5.

DETAILED DESCRIPTION OF THE DRAWINGS

Figure 1B:
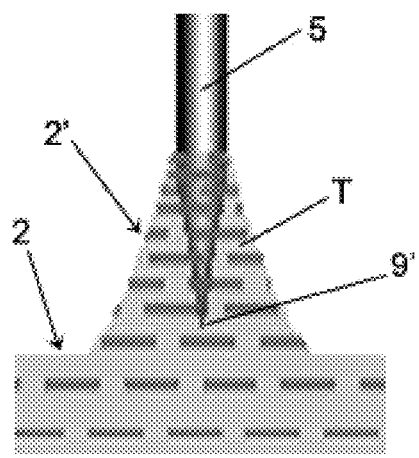
Figure 1C:
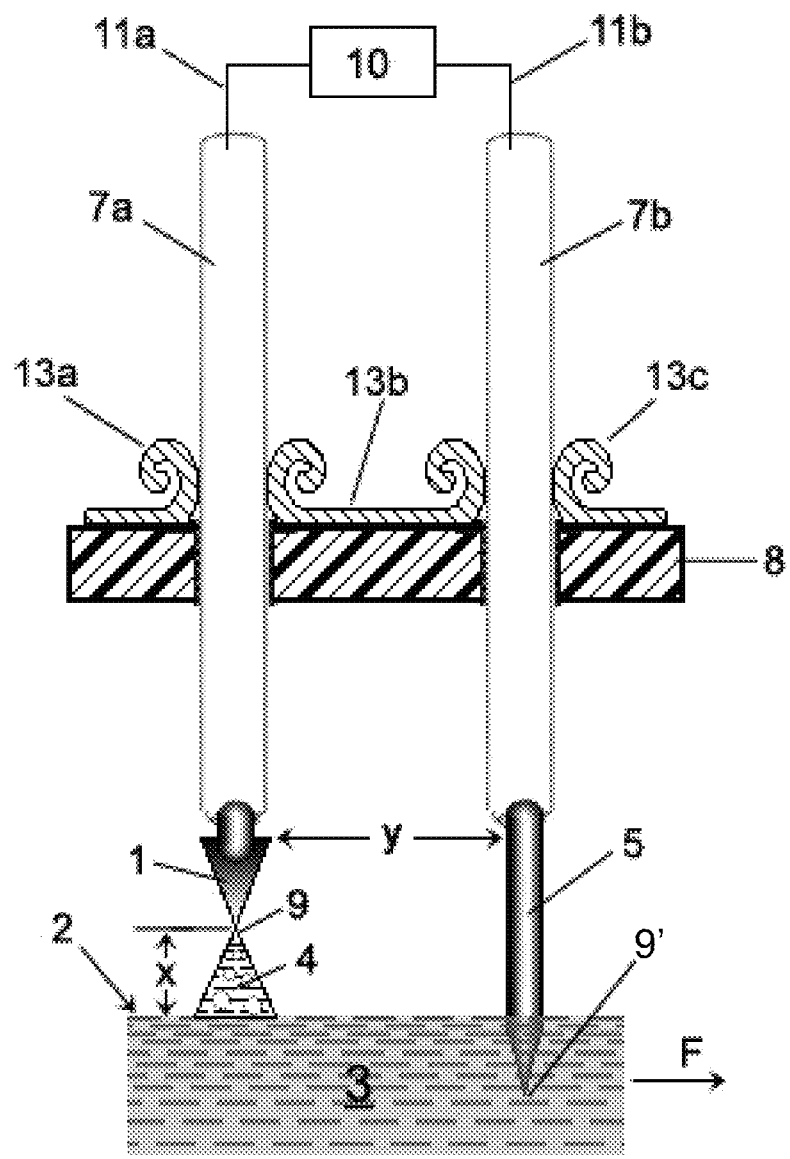

FIGS. 1a, 1b and 1c show schematic cross-sectional views of a manual electrode assembly according to the present invention.

Figure 2A:
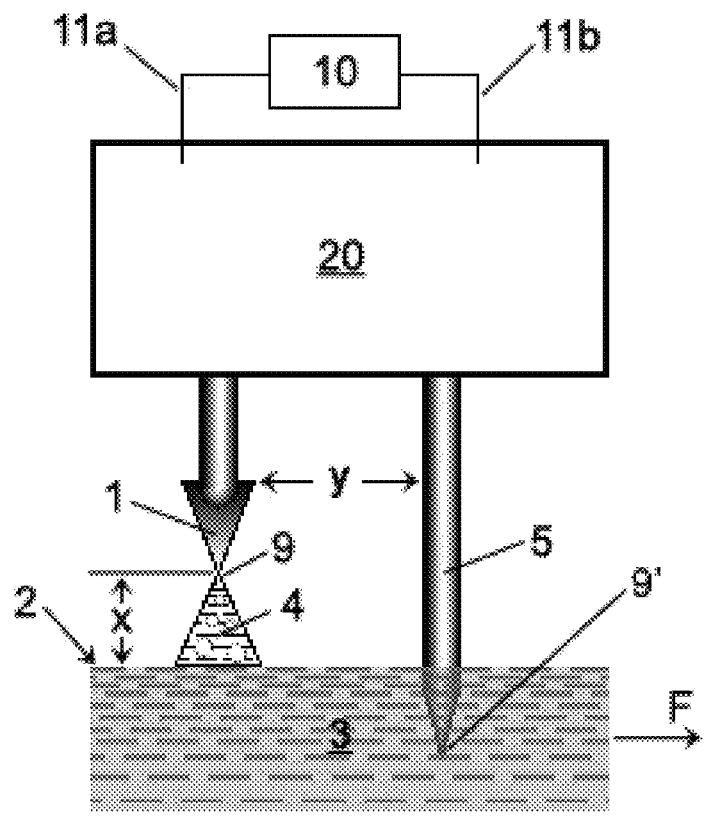
Figure 2B:
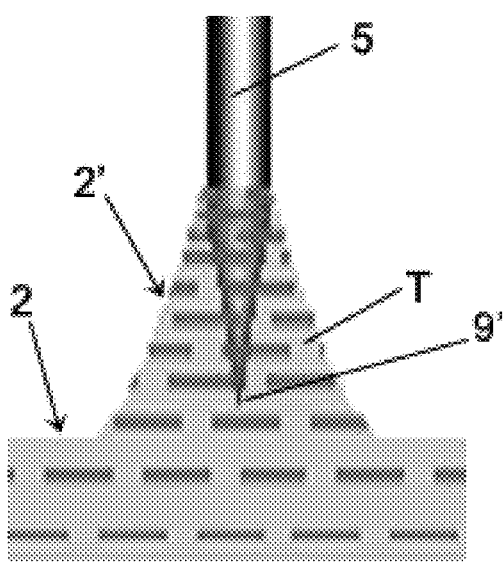

FIGS. 2a and 2b show schematic cross-sectional views of an automatic electrode assembly according to the present invention.

FIGS. 3a-3d show four alternative electrode configurations for the electrodes 1 and 5 controlled by an automatic device.

FIGS. 4a-4d show four alternative electrode configurations for the electrodes 1 and 5 which are manually controlled.

FIGS. 5a-5e show five different representative embodiments of configurations for the electrode 1.

Figure 6:
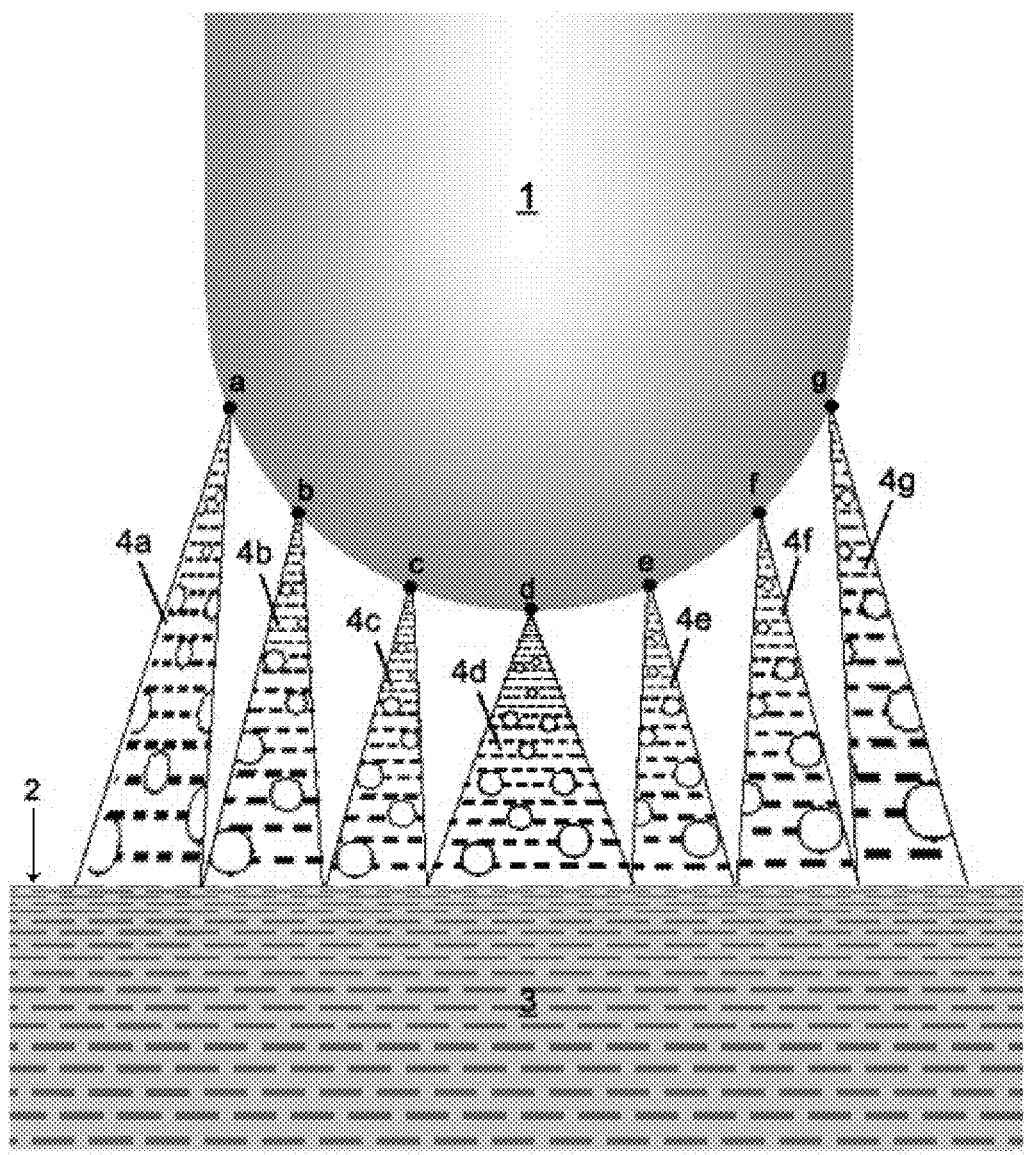

FIG. 6 shows a cross-sectional schematic view of plasmas produced utilizing one specific configuration of electrode 1.

Figure 7A:
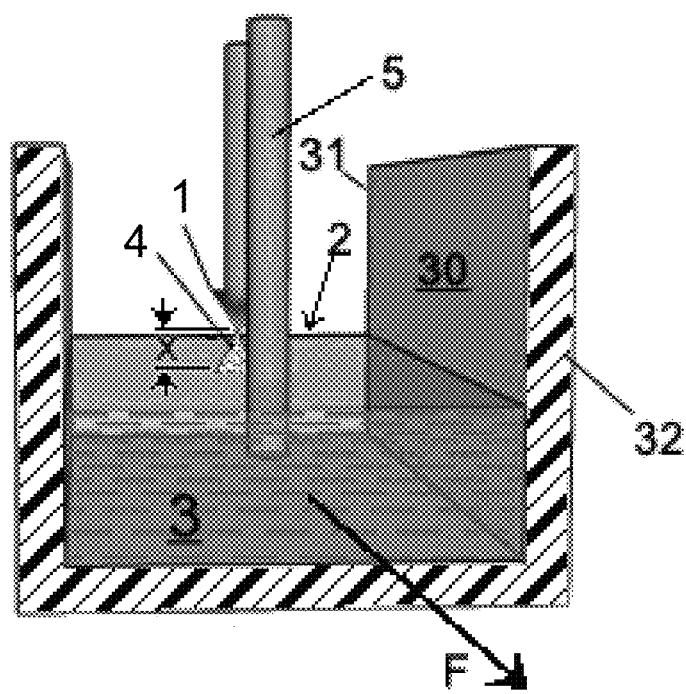
Figure 7B:
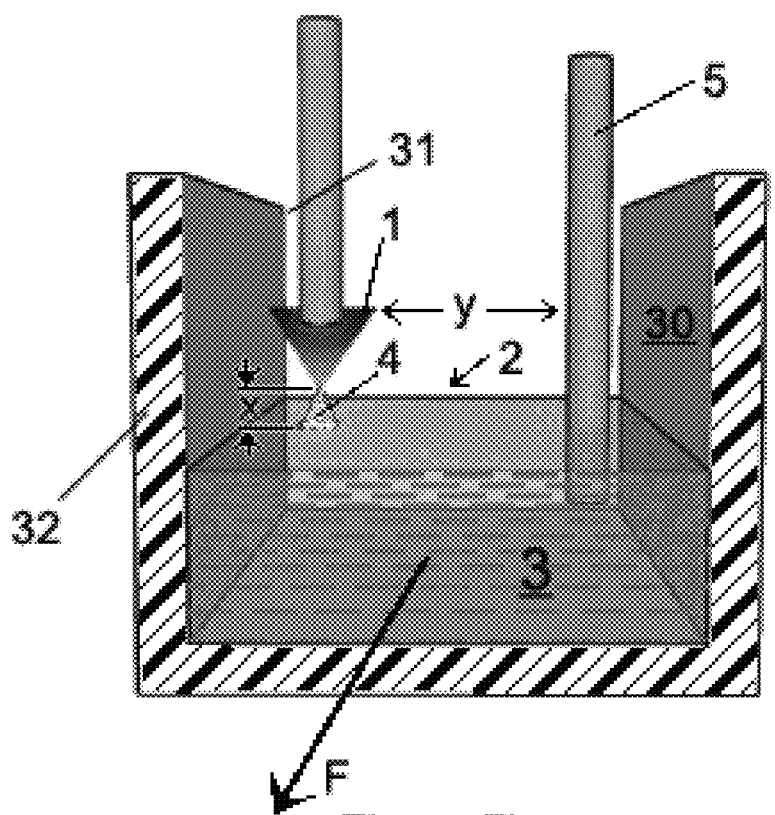

FIGS. 7a and 7b show a cross-sectional perspective view of two electrode assemblies utilized.

FIGS. 8a-8d show schematic perspective views of four different electrode assemblies corresponding to those electrode assemblies shown in FIGS. 3a-3d, respectively.

FIGS. 9a-9d show schematic perspective views of four different electrode assemblies corresponding to those electrode assemblies shown in FIGS. 4a-4d, respectively.

FIGS. 10a-10e show cross-sectional views of various trough members 30.

FIGS. 11a-11h show perspective views of various trough members and atmosphere control and support devices.

FIGS. 12a and 12b show various atmosphere control devices for locally controlling atmosphere around electrode sets 1 and/or 5.

FIG. 13 shows an atmosphere control device for controlling atmosphere around the entire trough member 30.

FIG. 14 shows a schematic cross-sectional view of a set of control devices 20 located on a trough member 30 with a liquid 3 flowing therethrough.

FIGS. 15a and 15b show schematic cross-sectional views of various angles $\theta_1$ and $\theta_2$ for the trough member 30.

FIGS. 16a, 16b and 16c show perspective views of various control devices 20 containing electrode assemblies 1 and/or 5 thereon located on top of a trough member 30.

FIG. 17 shows a perspective view of various control devices 20 containing electrode assemblies 1 and/or 5 thereon located on top of a trough member 30.

FIG. 18 shows a perspective view of various control devices 20 containing electrode assemblies 1 and/or 5 thereon located on top of a trough member 30 and including an enclosure 38 which controls the environment around the entire device and further including a holding tank 41.

FIGS. 19a-19d are perspective schematic views of multiple electrode sets contained within a trough member 30.

FIGS. 20a-20p show perspective views of multiple electrode sets 1/5 in 16 different possible combinations.

FIGS. 21a-21d show four perspective schematic views of possible electrode configurations separated by a membrane 50.

FIGS. 22a-22d show a perspective schematic views of four different electrode combinations separated by a membrane 50.

FIGS. 23a and 23b show a perspective schematic view of three sets of electrodes and three sets of electrodes separated by two membranes 50a and 50b, respectively.

FIGS. 24a-24e show various membranes 50 located in various cross-sections of a trough member 30.

FIGS. 25a-25e show various membranes 50 located in various cross-sections of a trough member 30.

FIGS. 26a-26e show various membranes 50 located in various cross-sections of a trough member 30.

Figure 27:
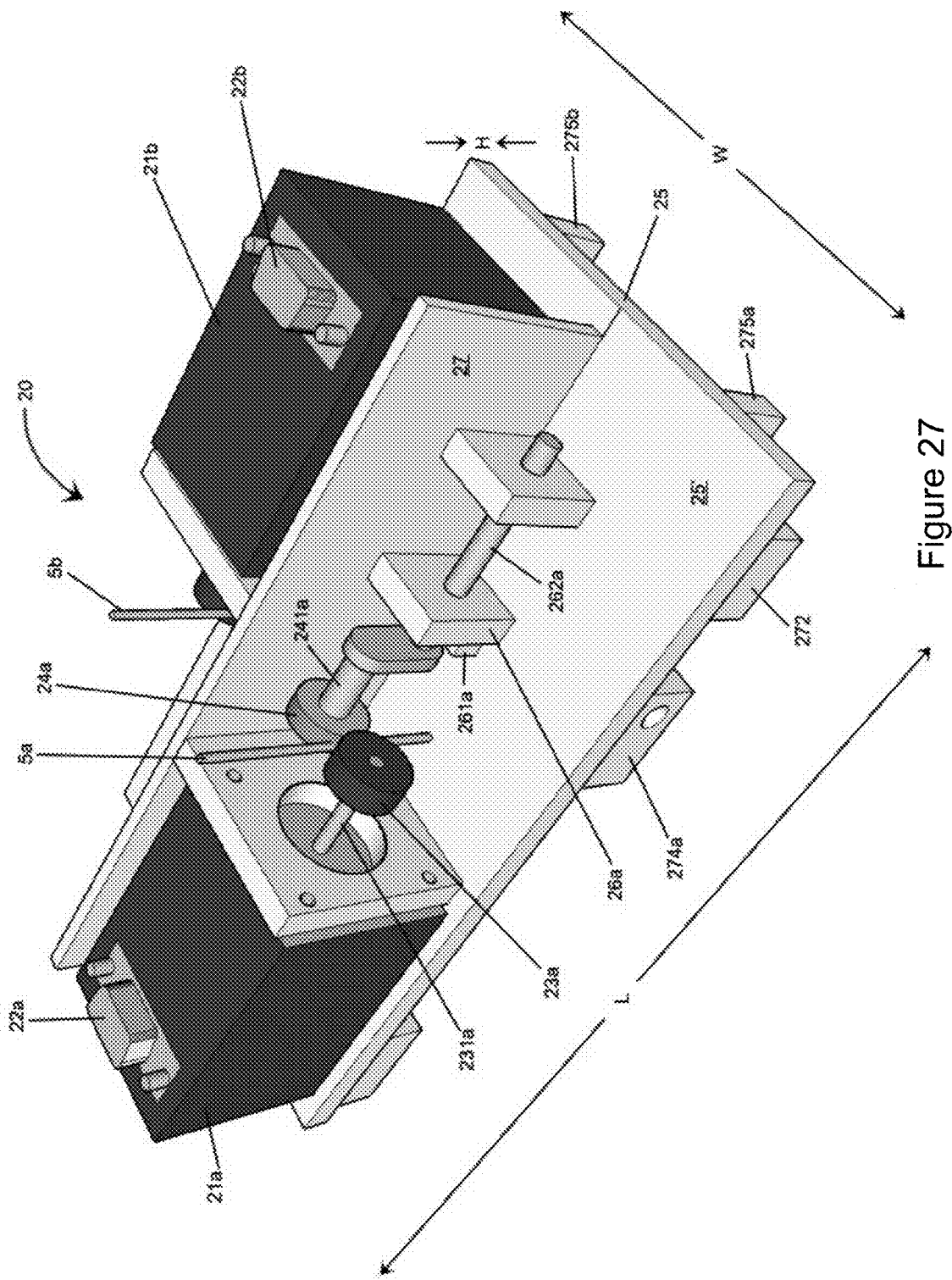

FIG. 27 shows a perspective view of a control device 20.

Figure 28A:
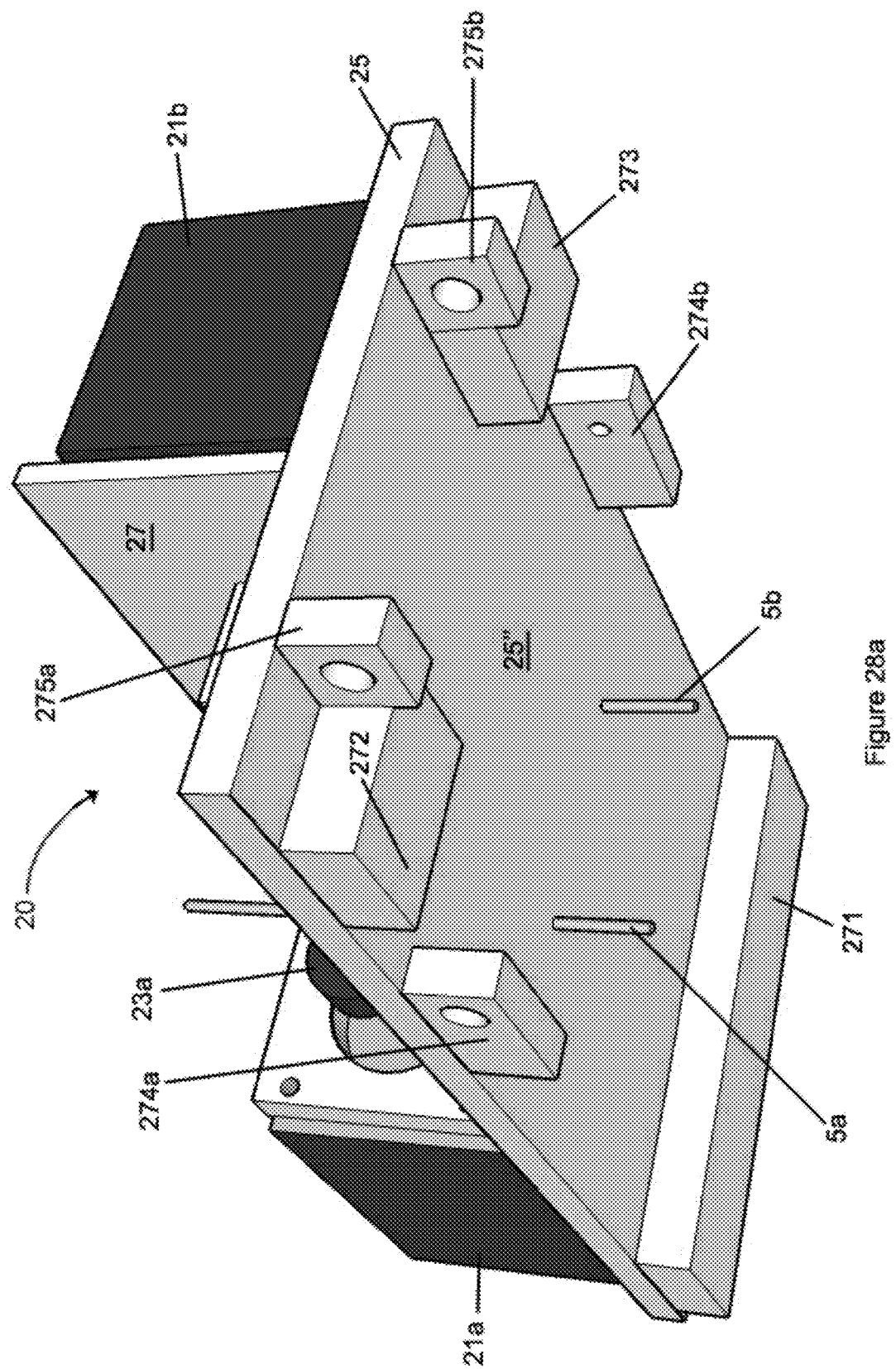
Figure 28B:
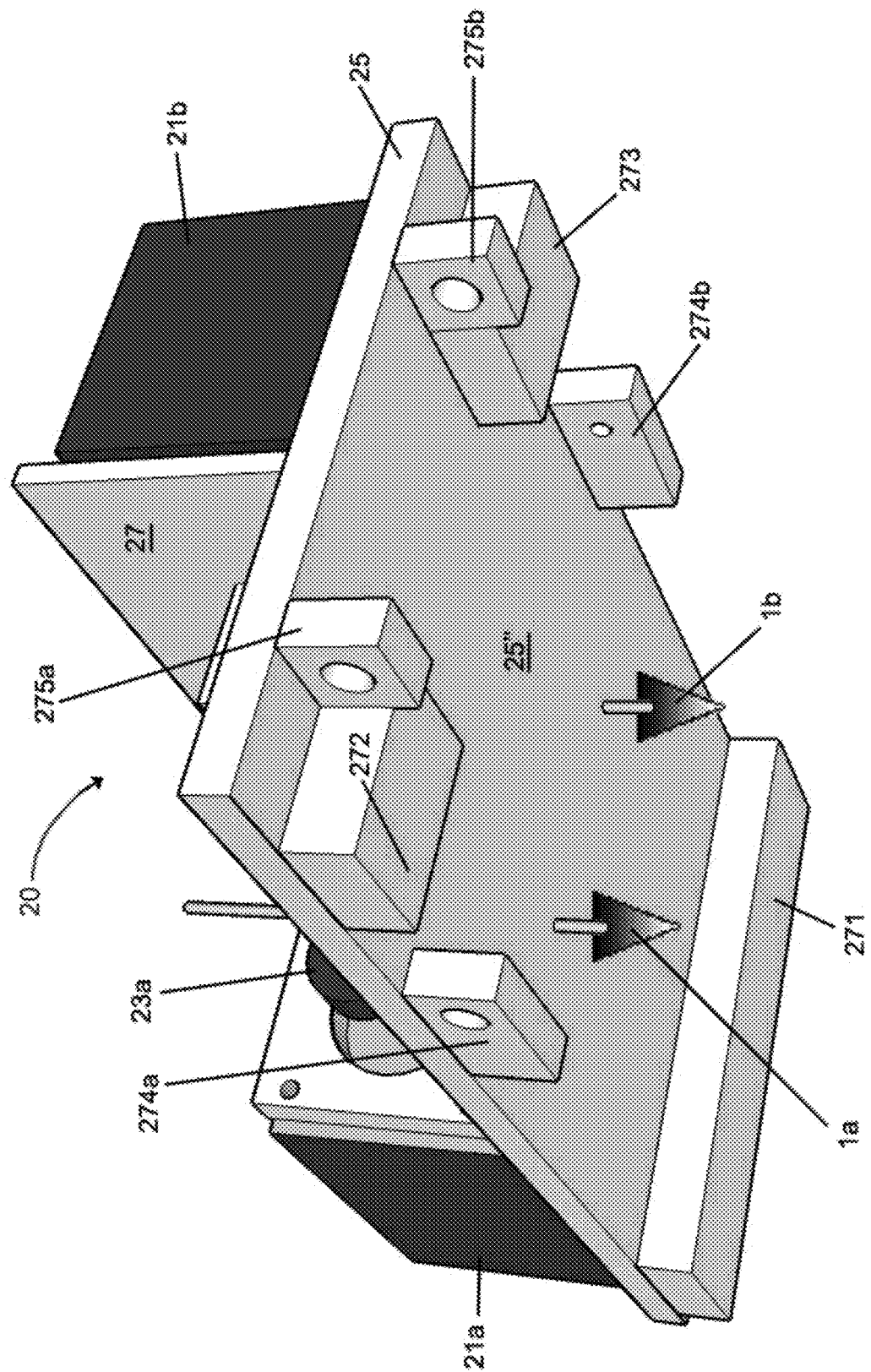

FIGS. 28a and 28b show a perspective view of a control device 20.

Figure 28C:
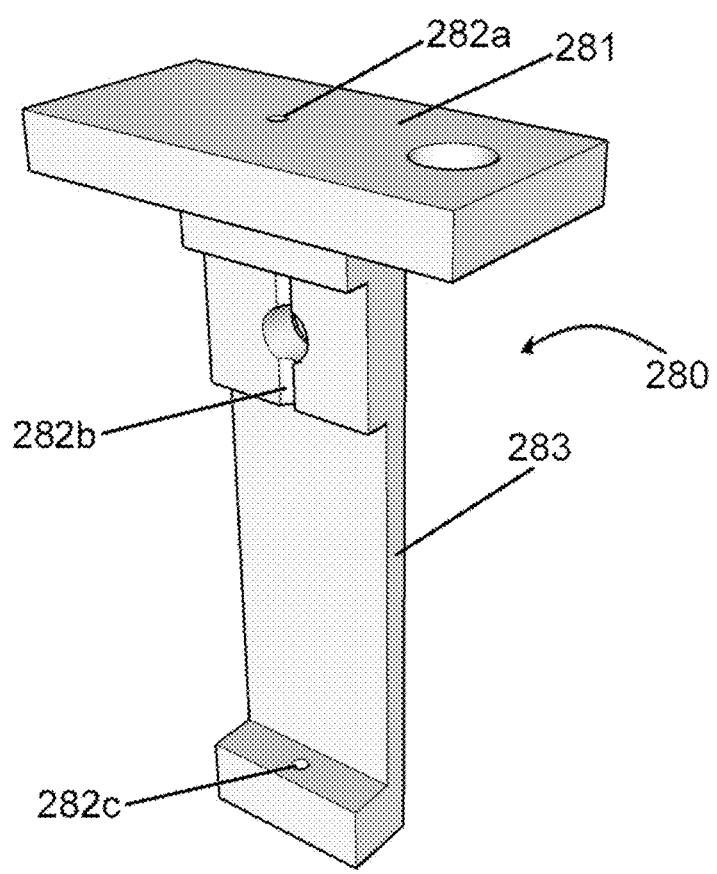

FIG. 28c shows a perspective view of an electrode holder.

FIGS. 28d-28l show a variety of perspective views of different control devices 20, with and without localized atmospheric control devices.

Figure 29:
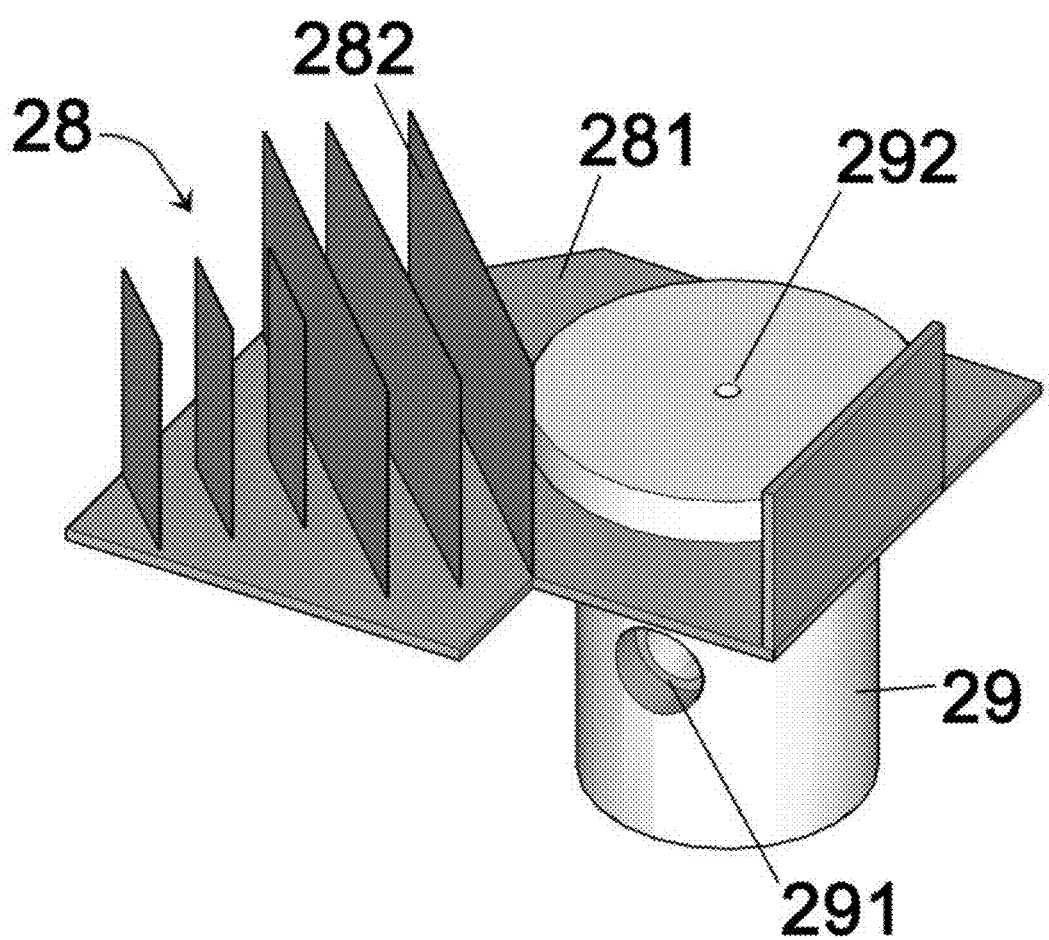

FIG. 29 shows a perspective view of a thermal management device including a refractory member 29 and a heat sink 28.

Figure 30:
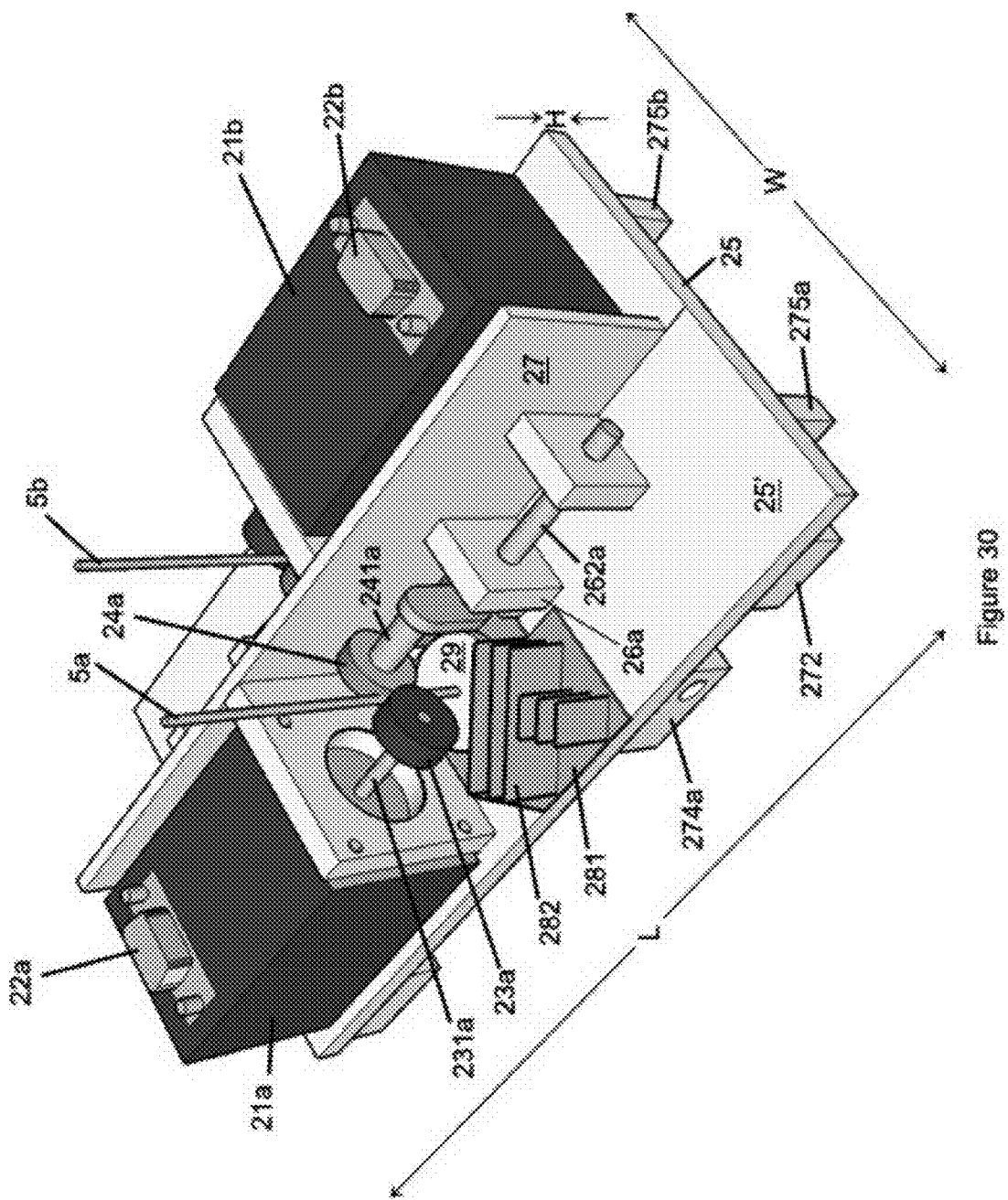

FIG. 30 shows a perspective view of a control device 20.

Figure 31:
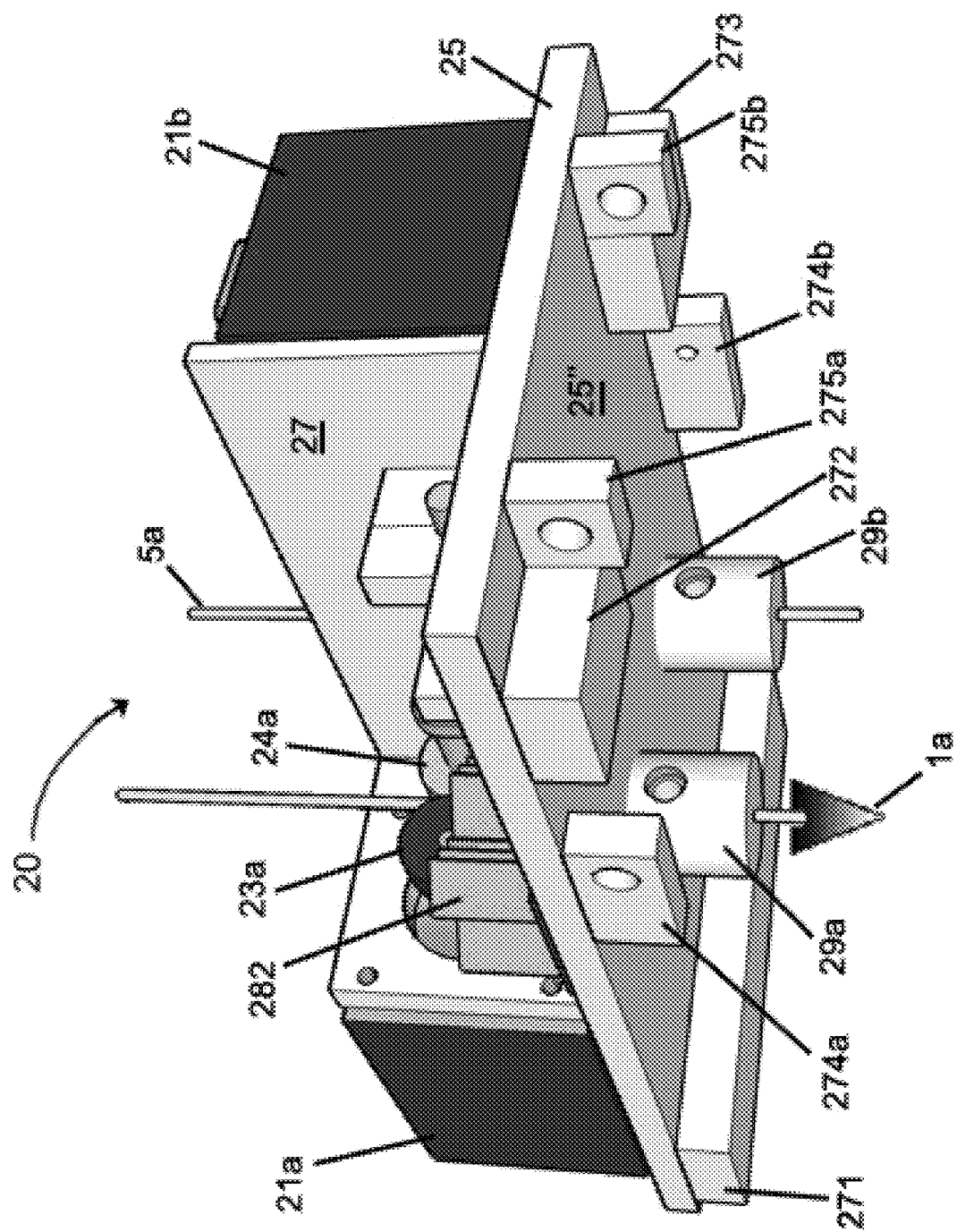

FIG. 31 shows a perspective view of a control device 20.

Figure 32A:
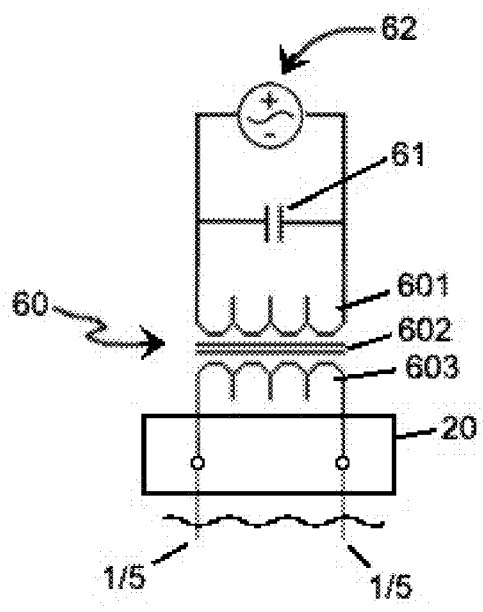
Figure 32B:
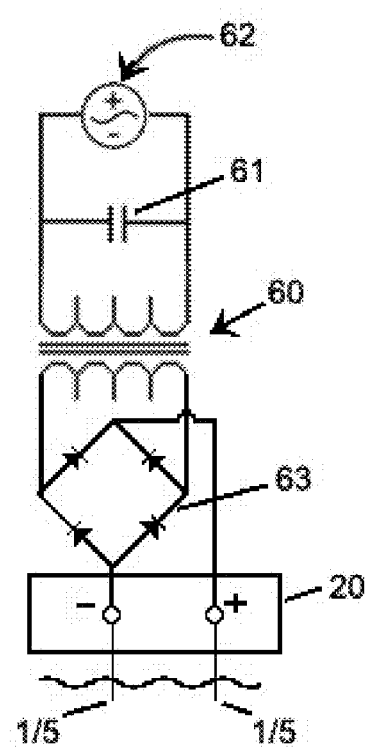
Figure 32C:
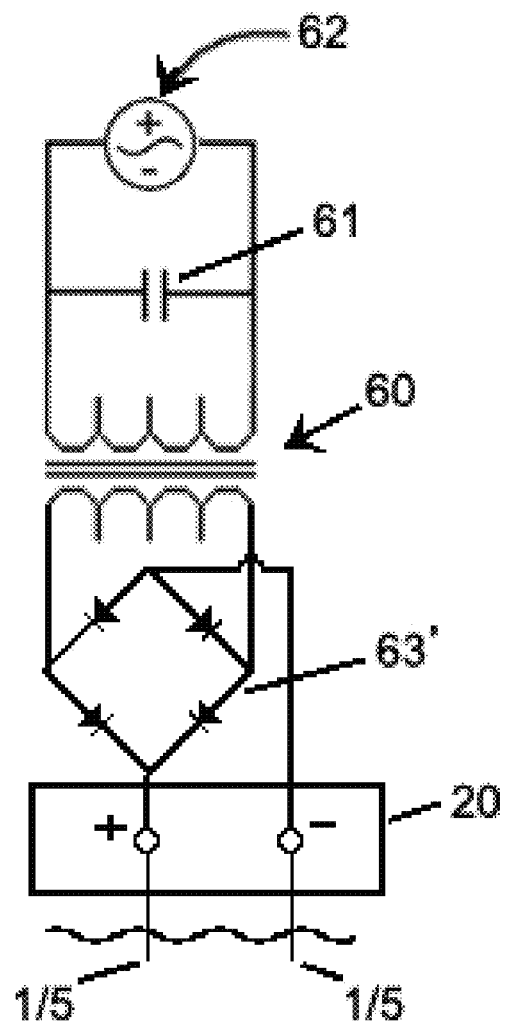

FIGS. 32a, 32b and 32c show AC transformer electrical wiring diagrams for use with different embodiments of the invention.

Figure 33A:
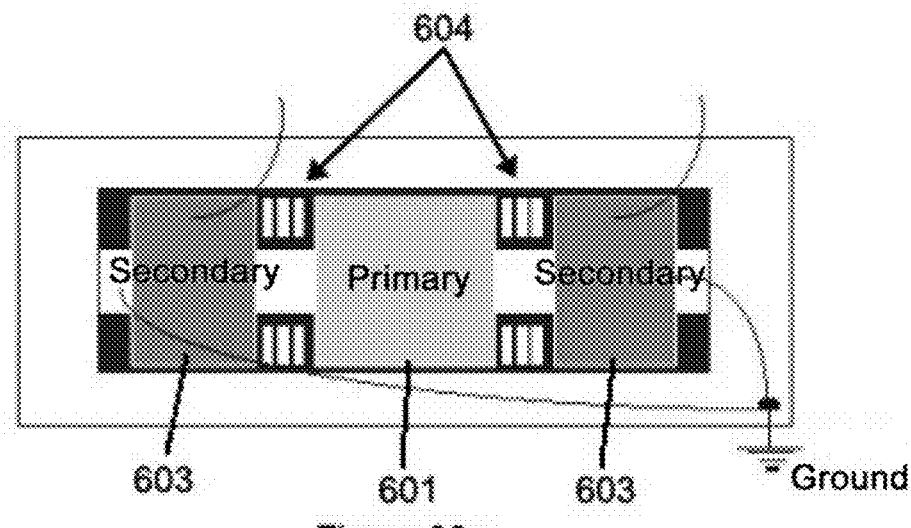
Figure 33B:
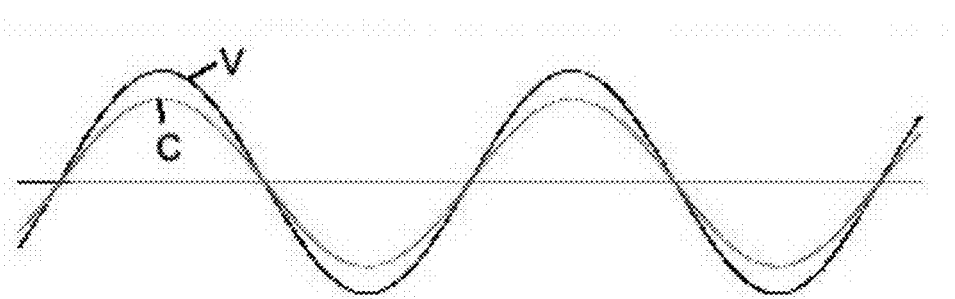
Figure 33C:
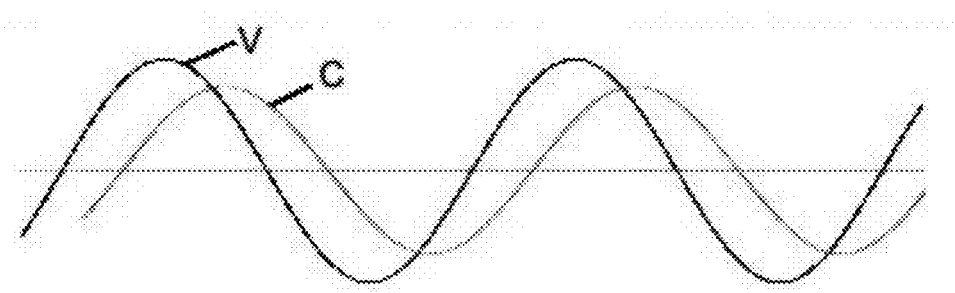

FIG. 33a shows a schematic view of a transformer and FIGS. 33b and 33c show schematic representations of two sine waves in phase and out of phase, respectively.

Figure 34A:
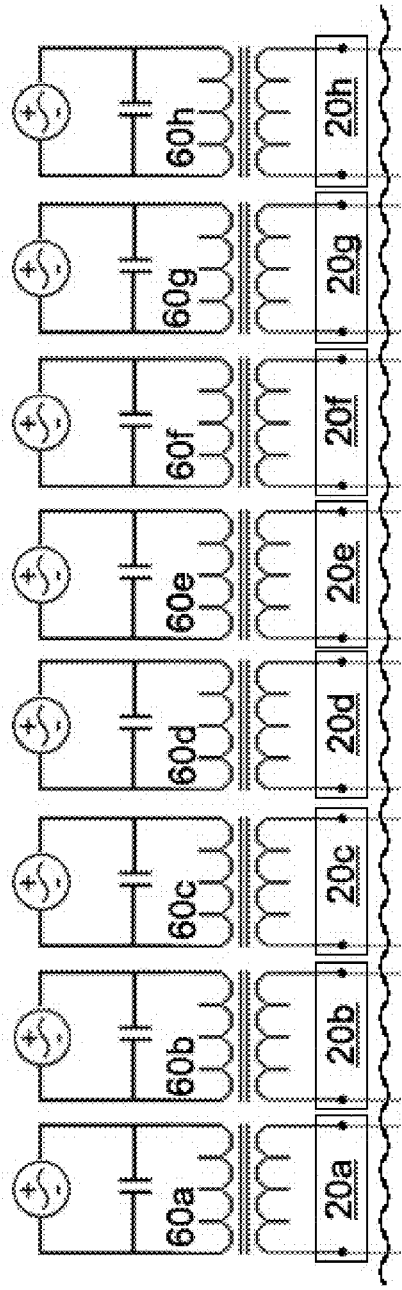
Figure 34B:
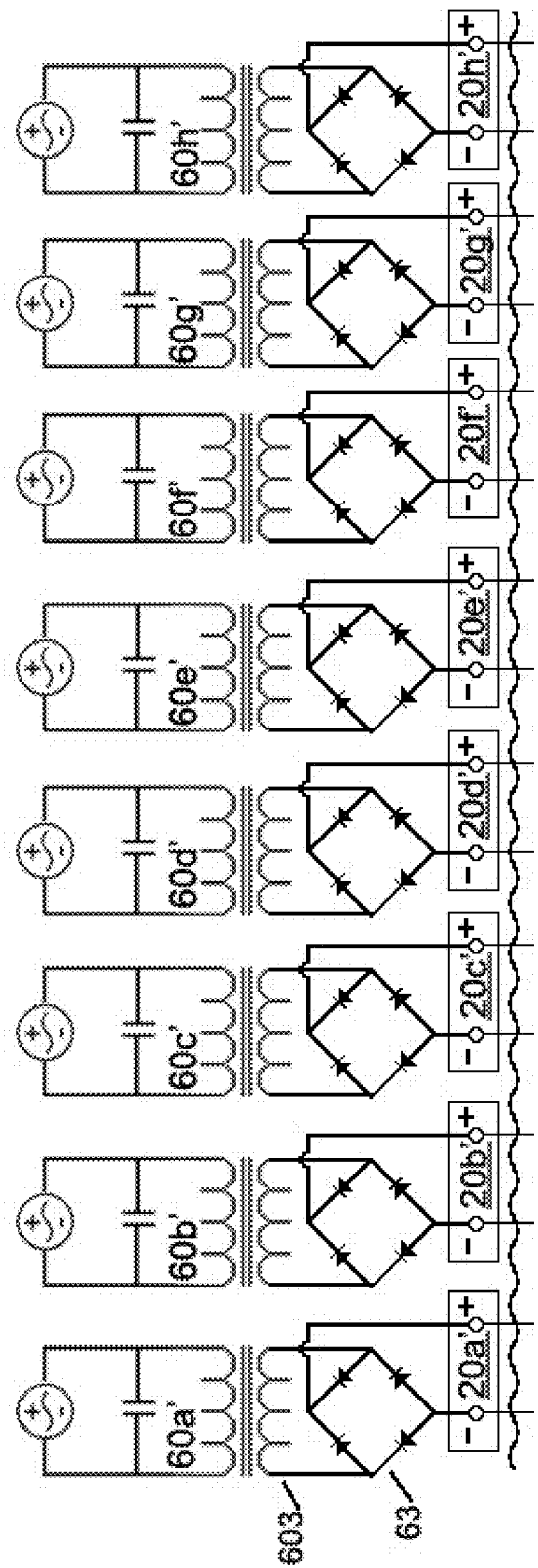
Figure 34C:
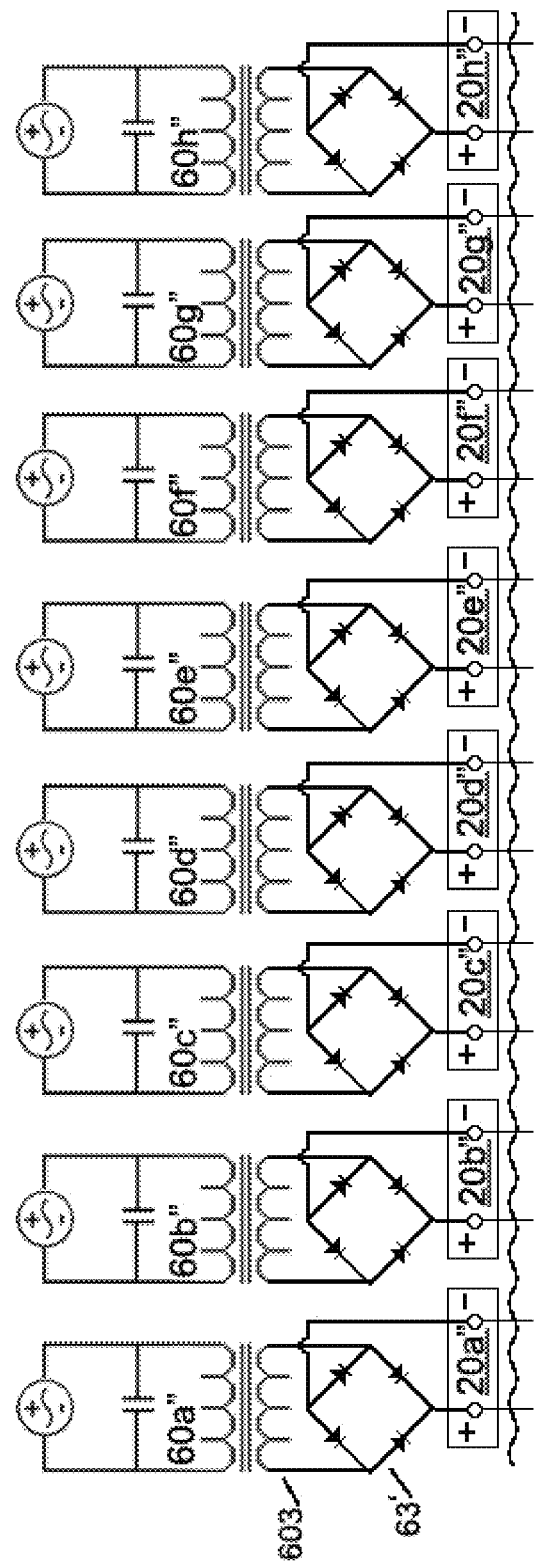

FIGS. 34a, 34b and 34c each show schematic views of eight electrical wiring diagrams for use with 8 sets of electrodes.

Figure 35:
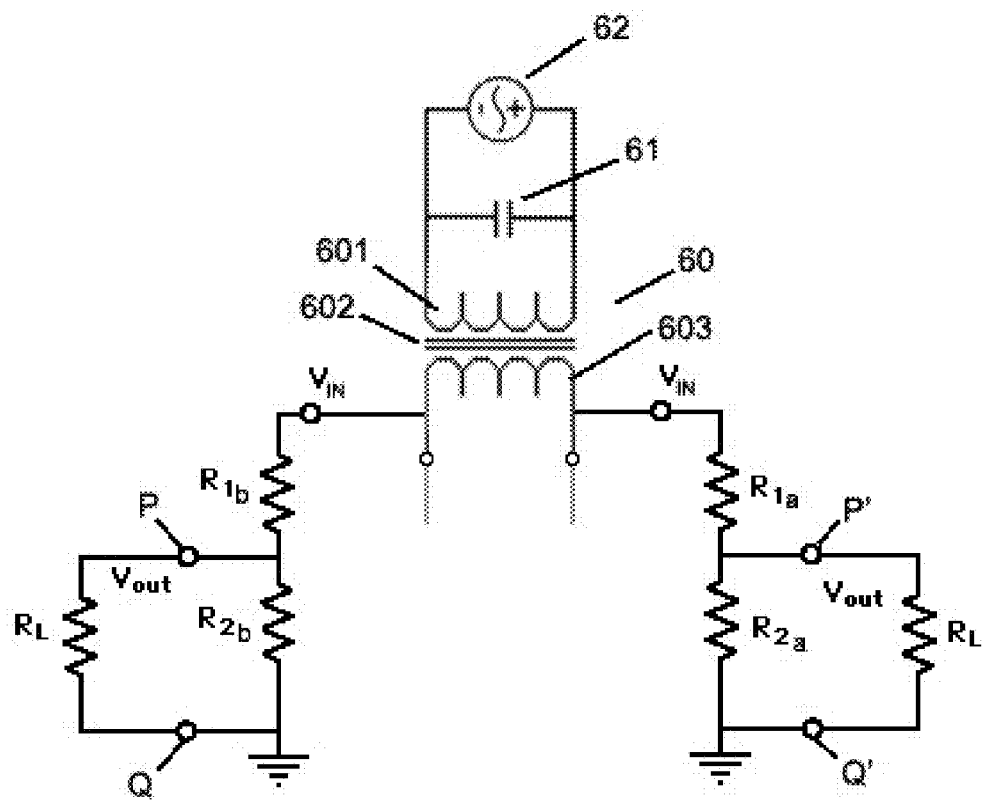

FIG. 35 shows a schematic view of an electrical wiring diagram utilized to monitor voltages from the outputs of a secondary coil of a transformer.

Figure 36A:
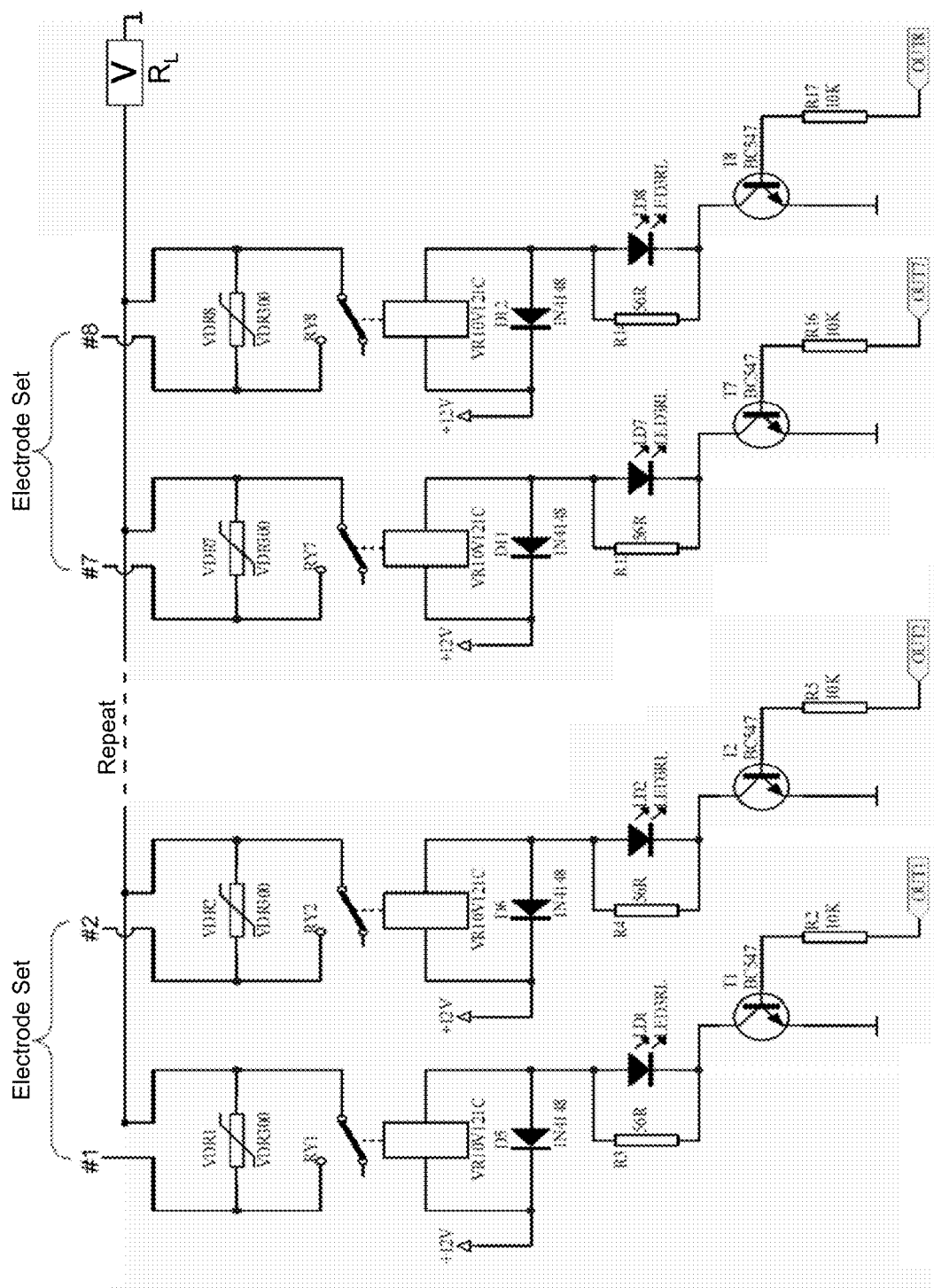
Figures 36B, 36C:
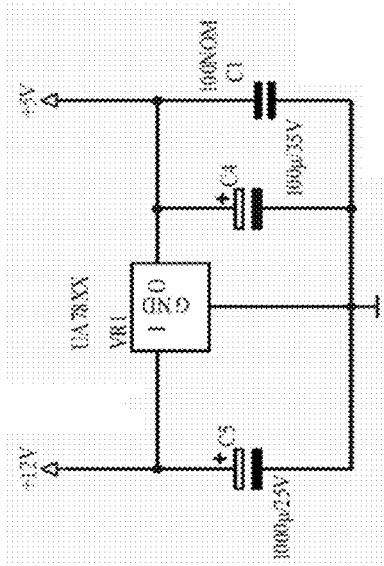

FIGS. 36a, 36b and 36c show schematic views of wiring diagrams associated with a Velleman K8056 circuit relay board.

Figure 37A:
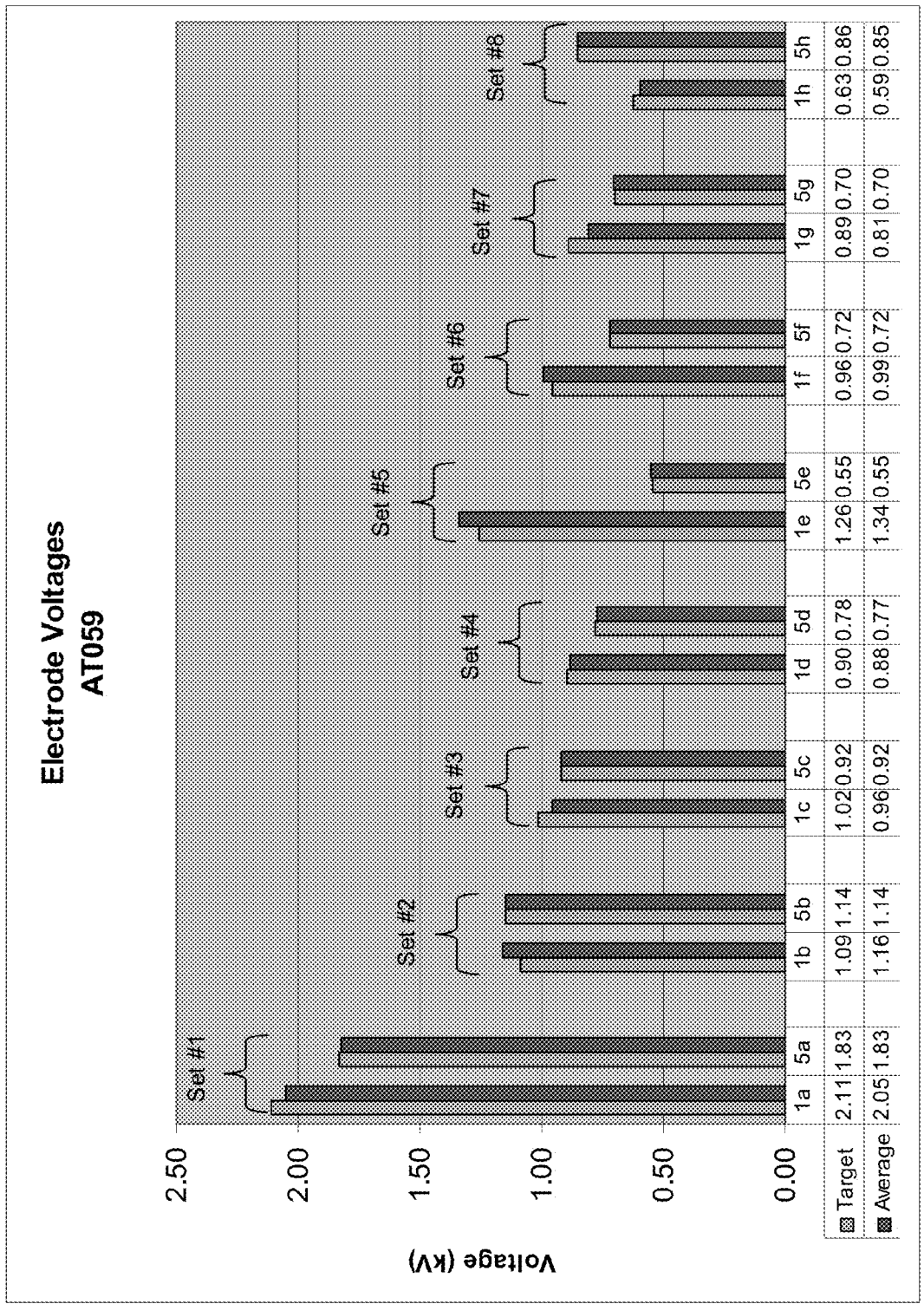
Figure 37B:
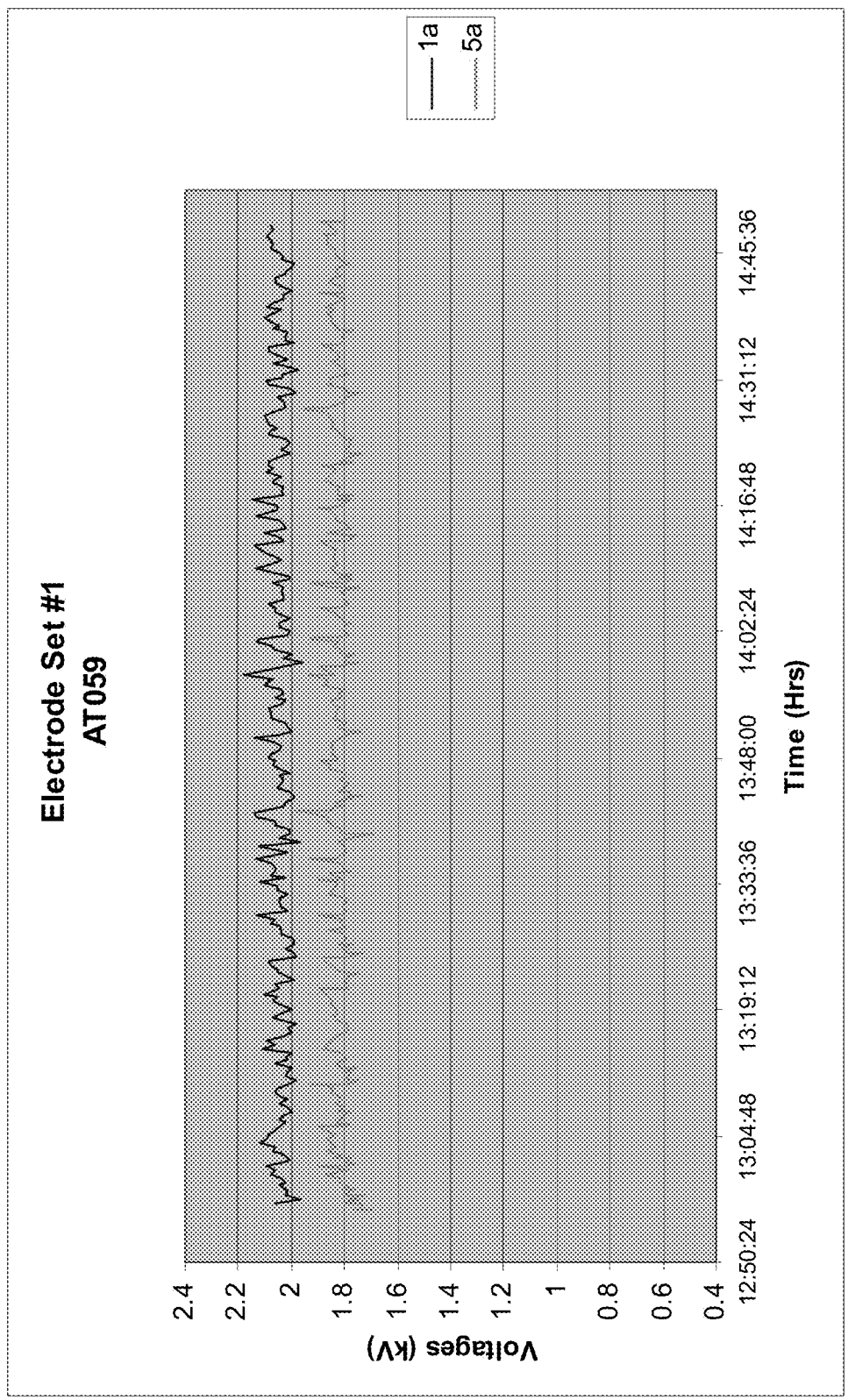
Figure 37C:
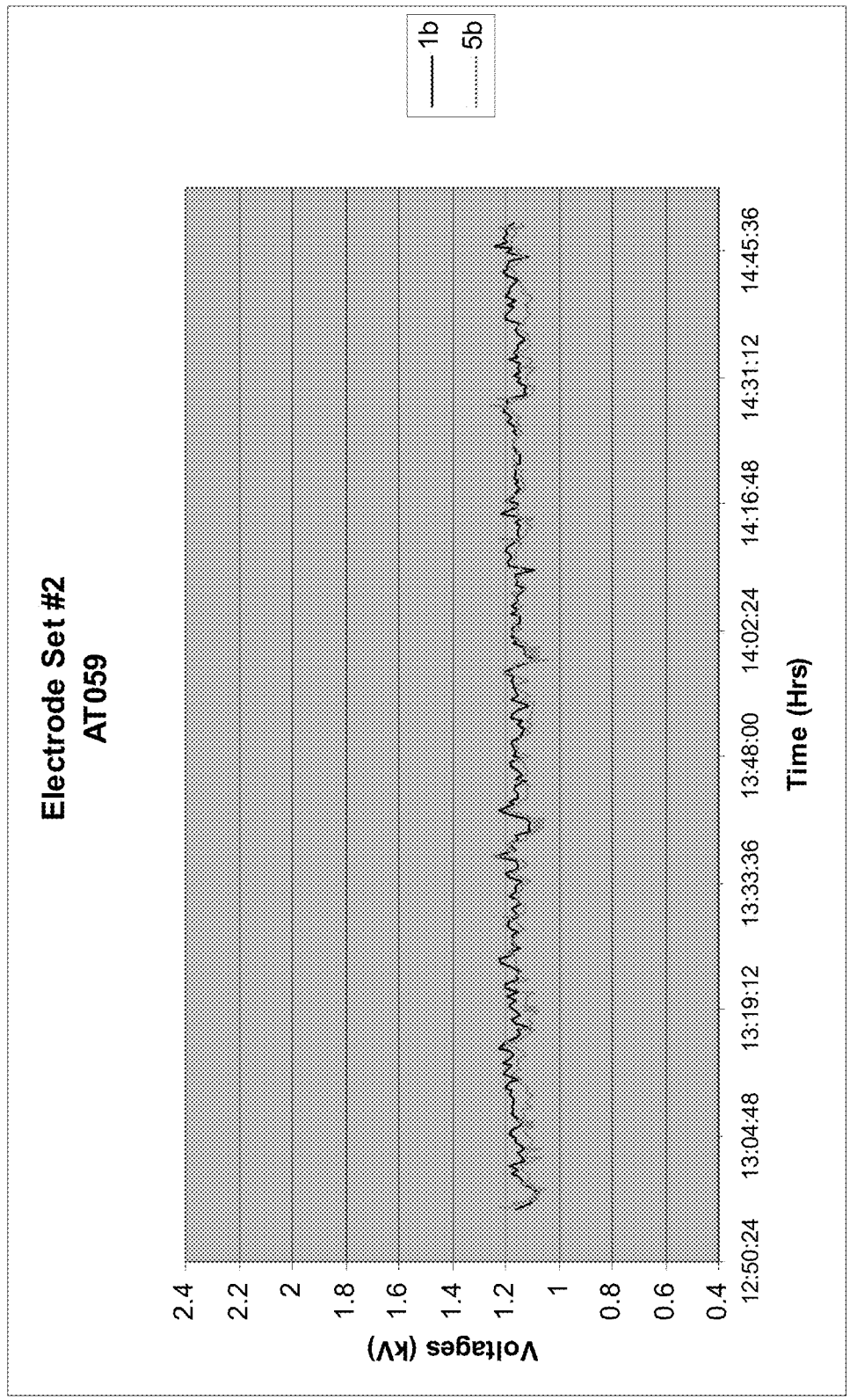
Figure 37D:
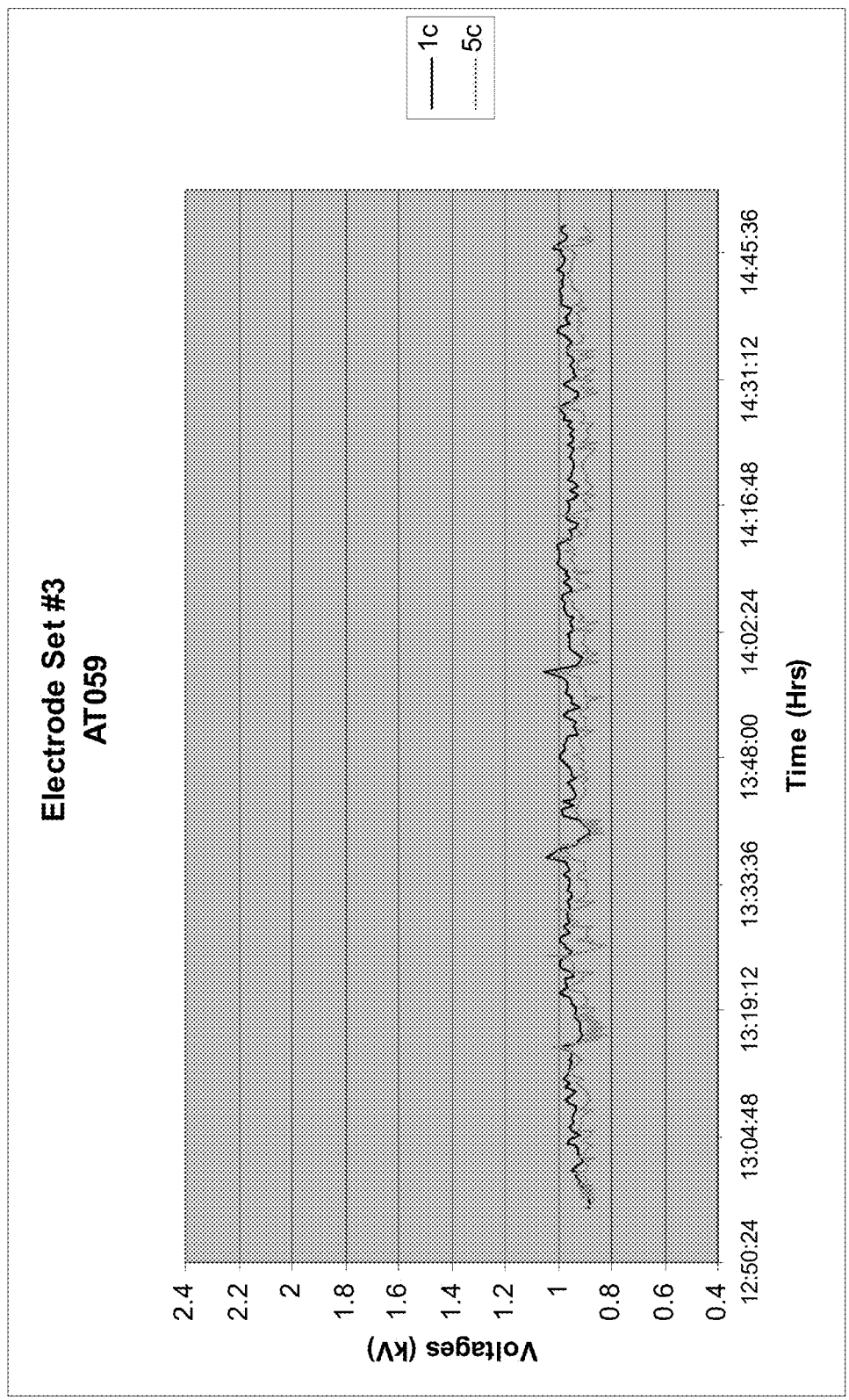
Figure 37E:
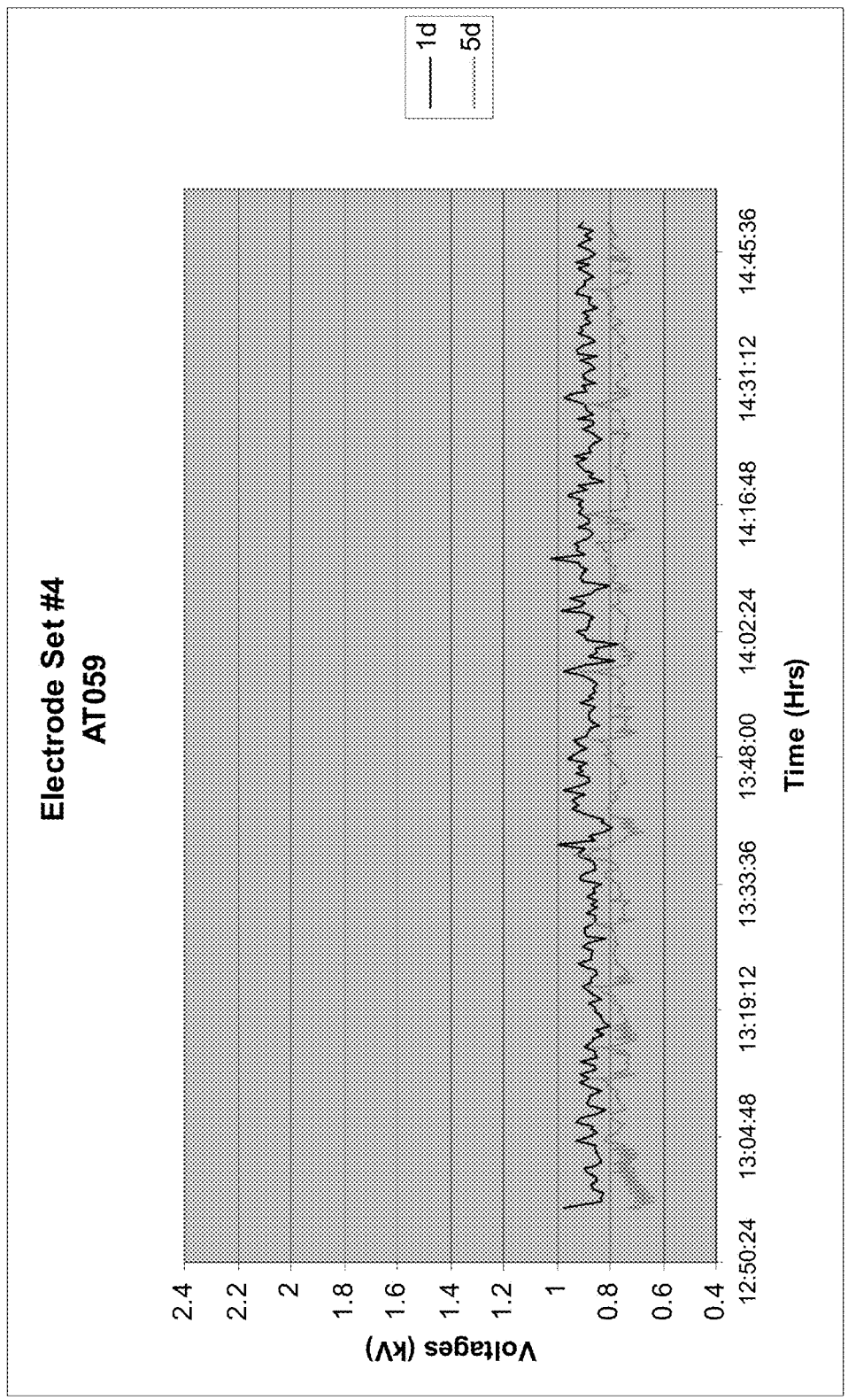
Figure 37F:
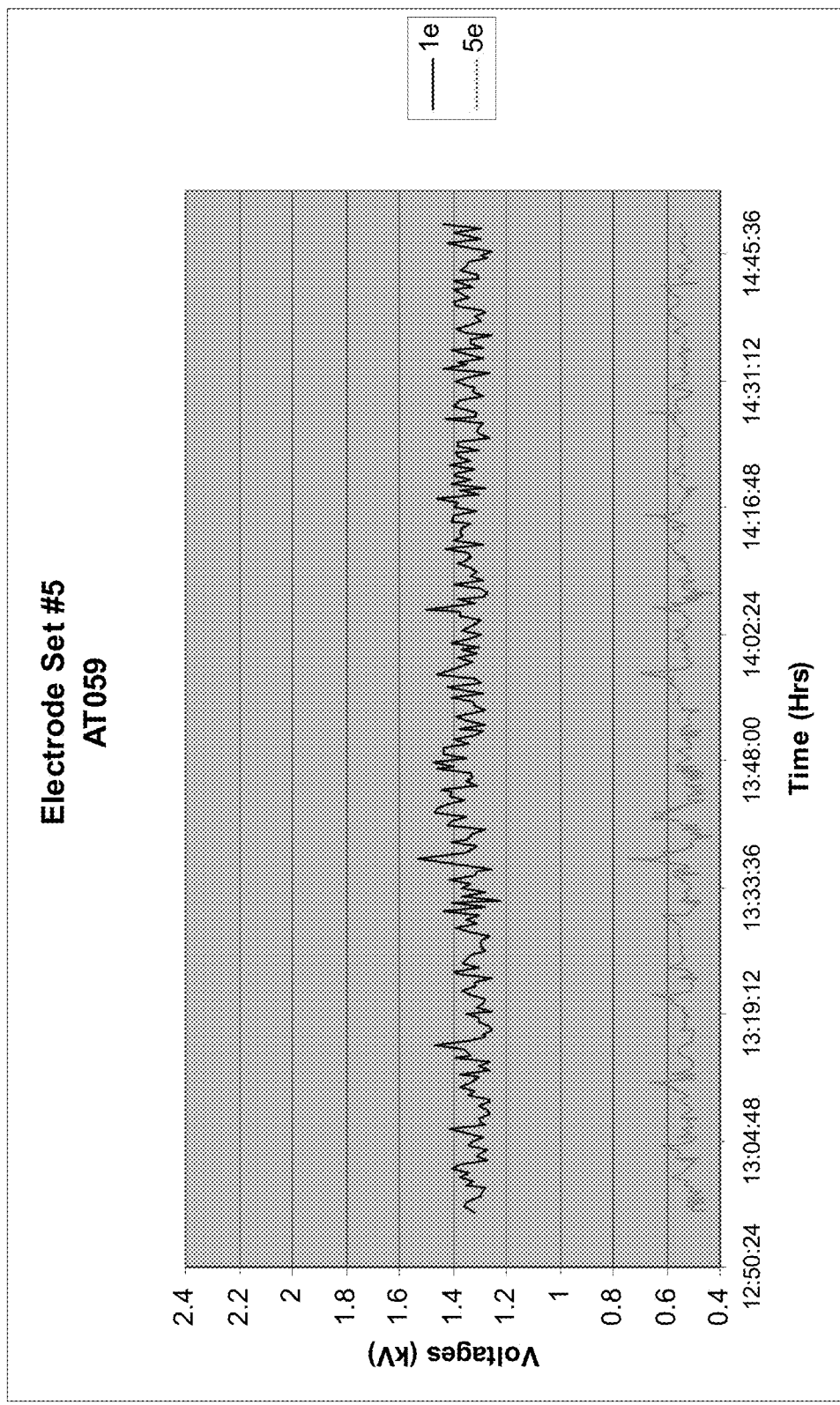
Figure 37G:
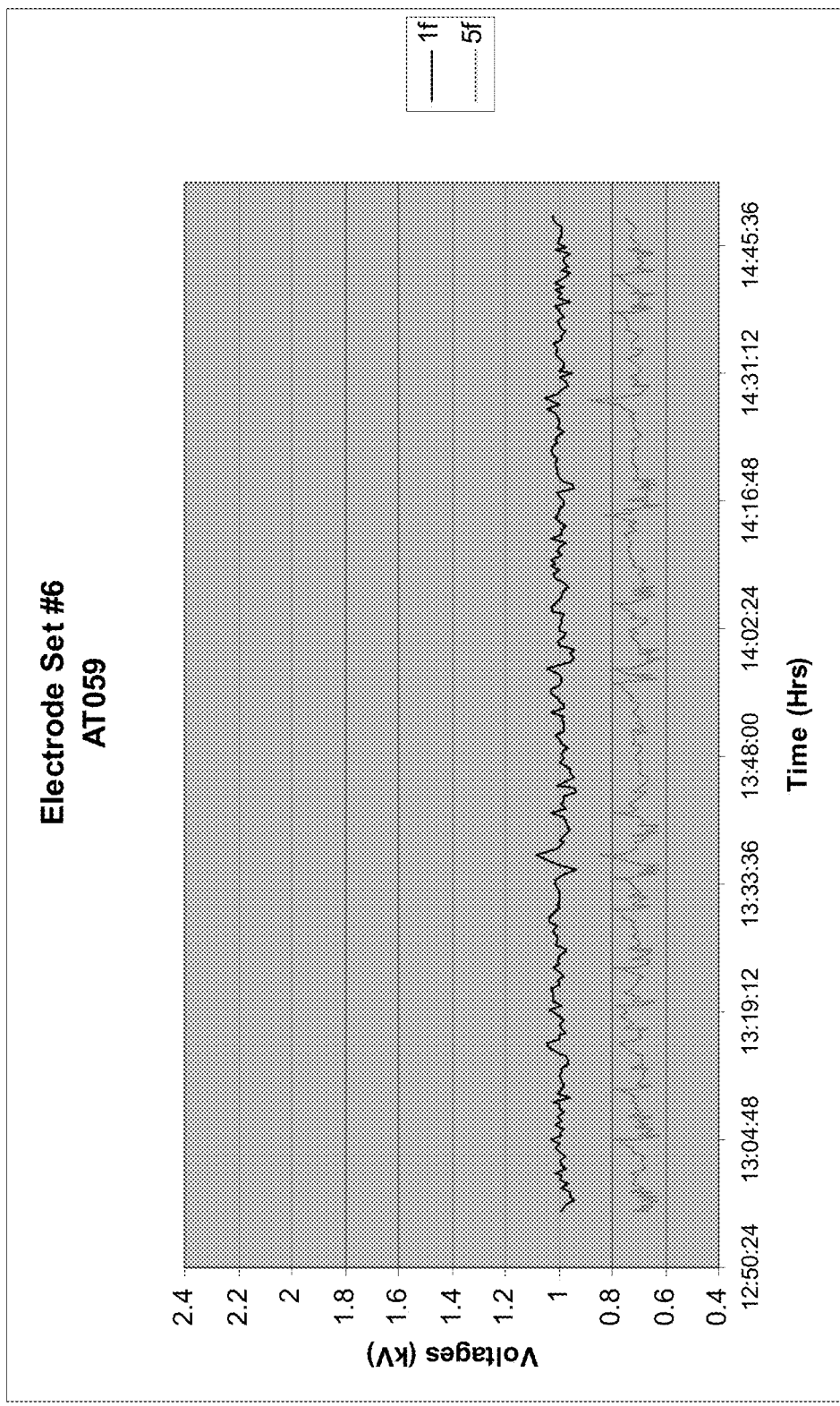
Figure 37H:
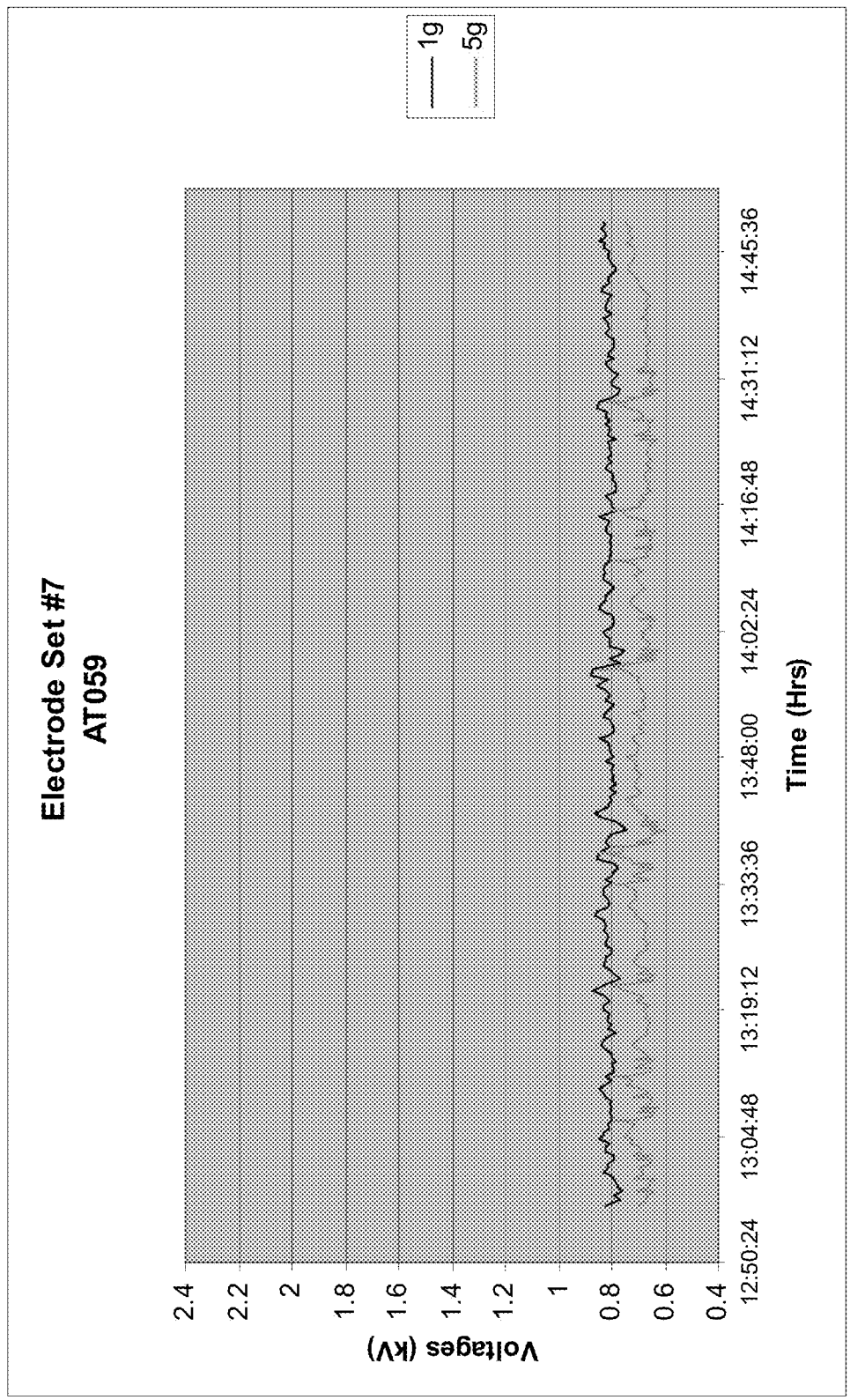
Figure 37I:
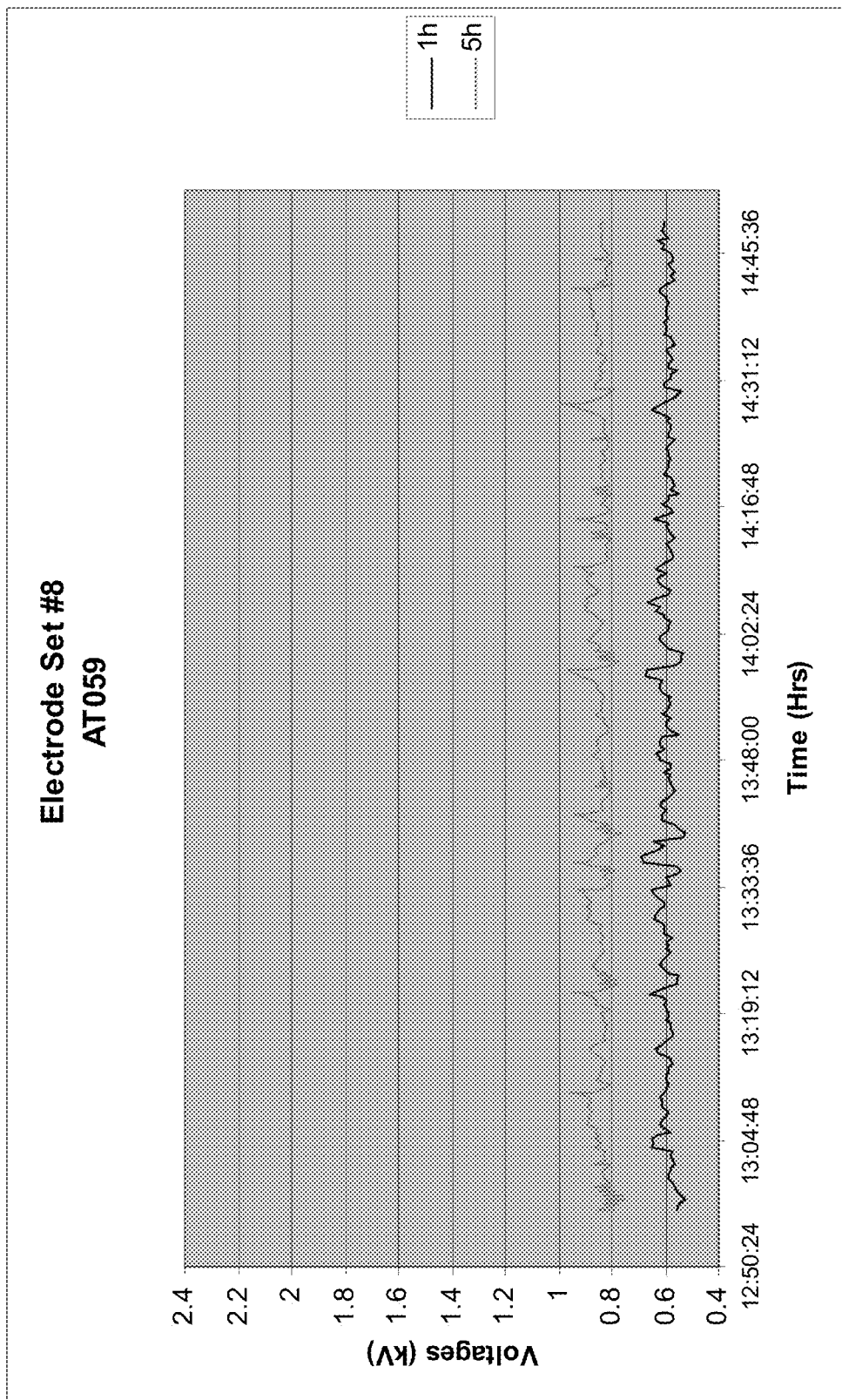

FIG. 37a shows a bar chart of various target and actual average voltages applied to 16 different electrodes in an 8 electrode set used in Example 1 to manufacture silver-based nanoparticles and nanoparticle solutions.

FIGS. 37b-37i show actual voltages applied as a function of time for the 16 different electrodes used in Example 1.

Figure 38A:
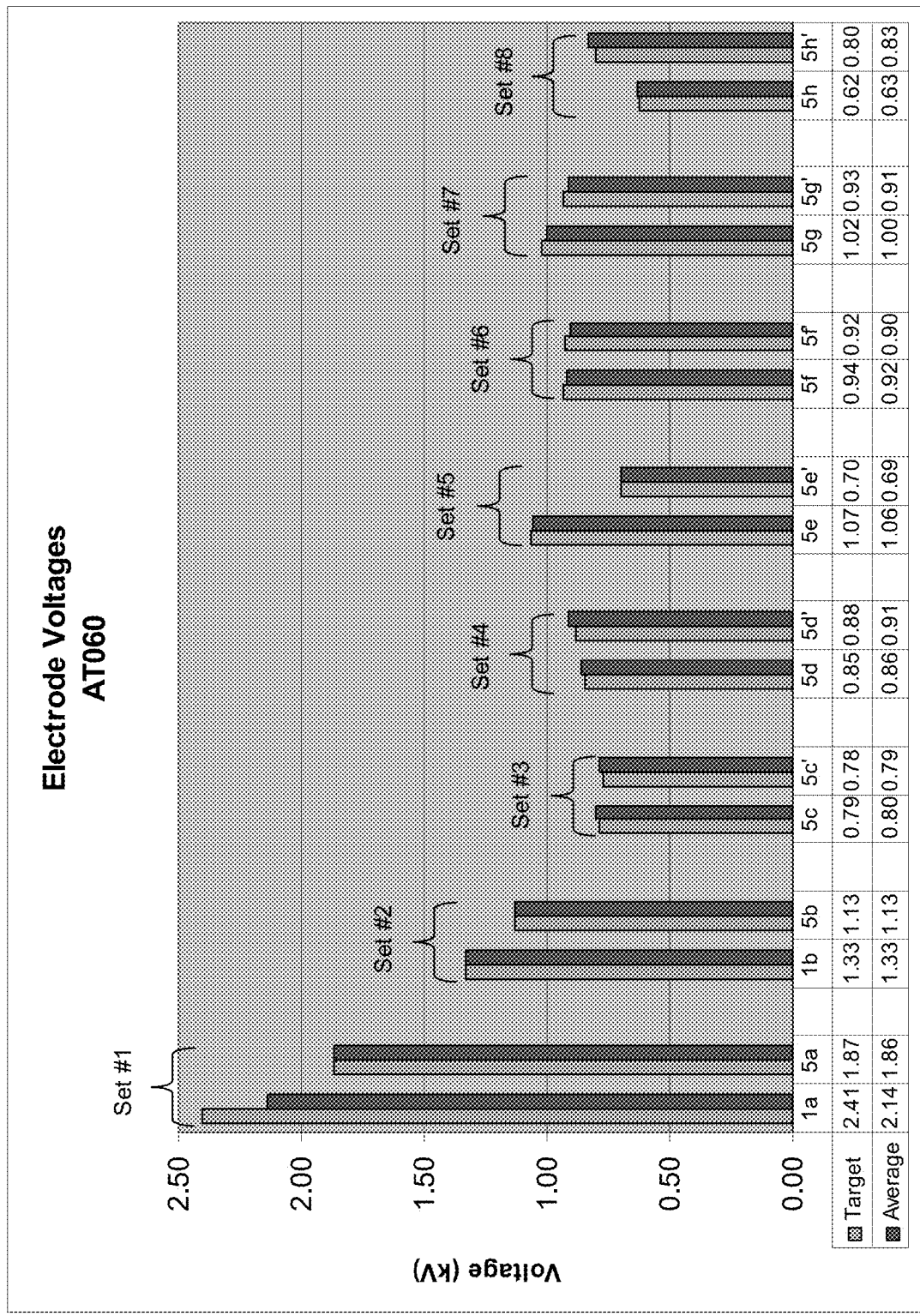
Figure 38B:
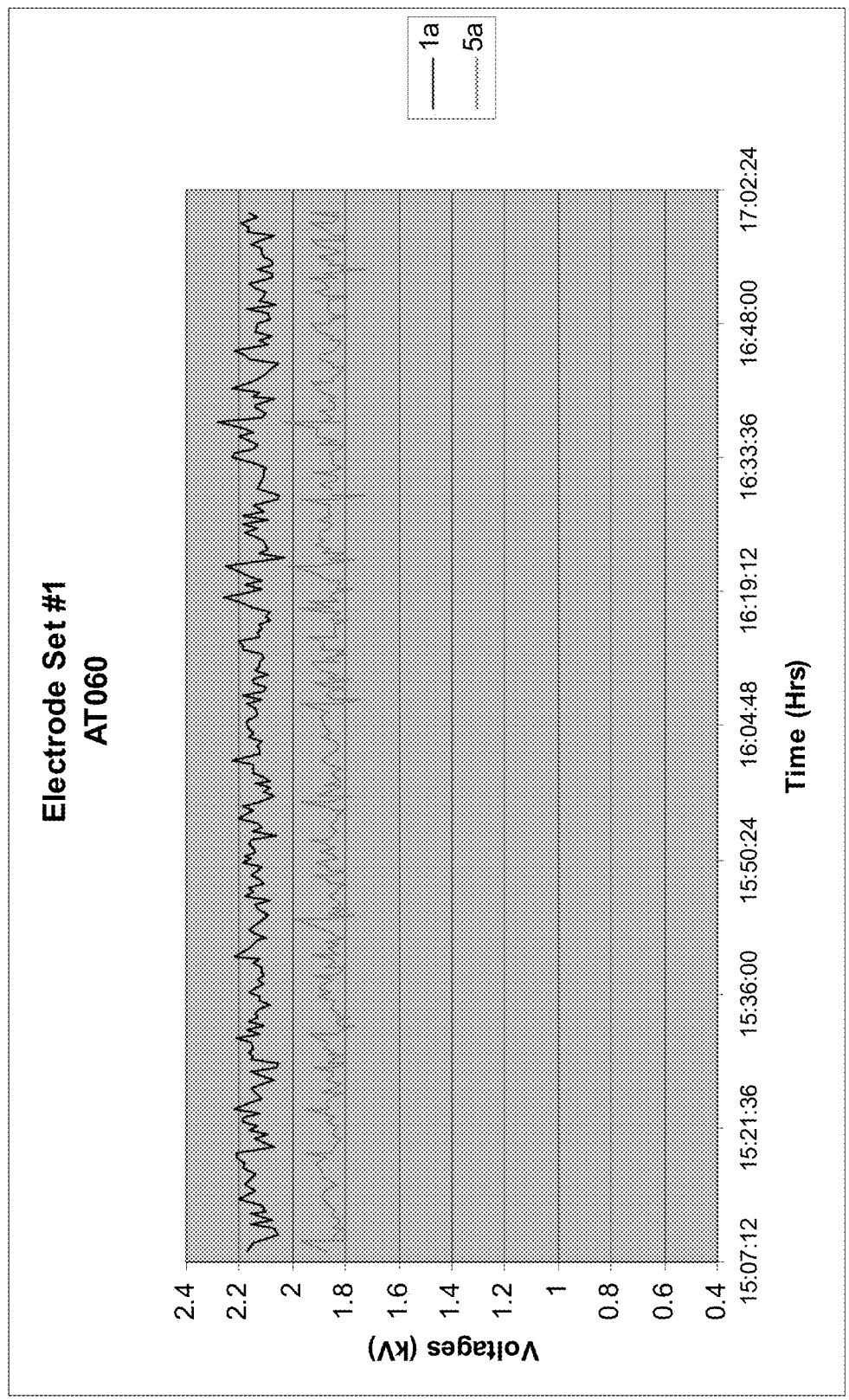
Figure 38C:
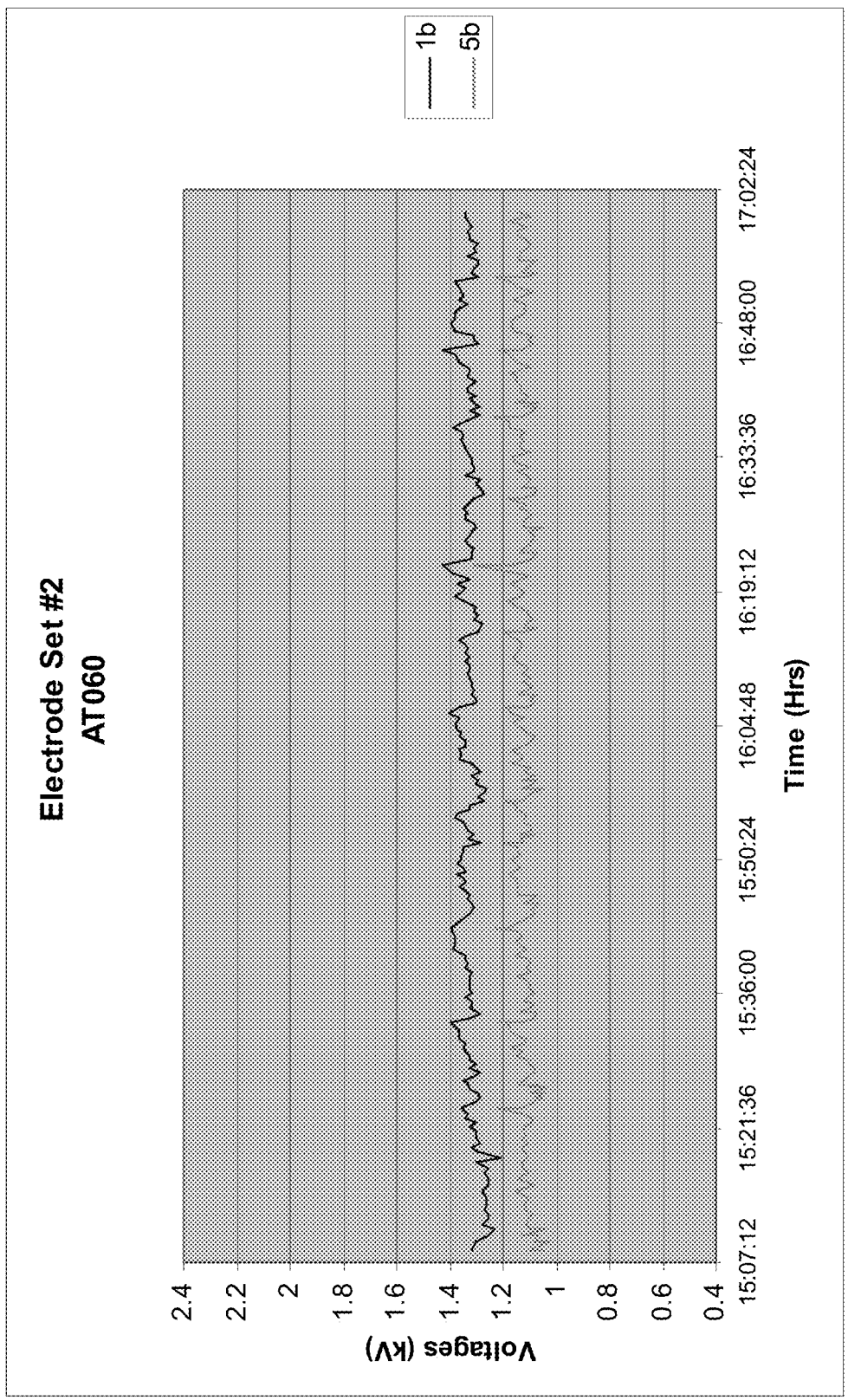
Figure 38D:
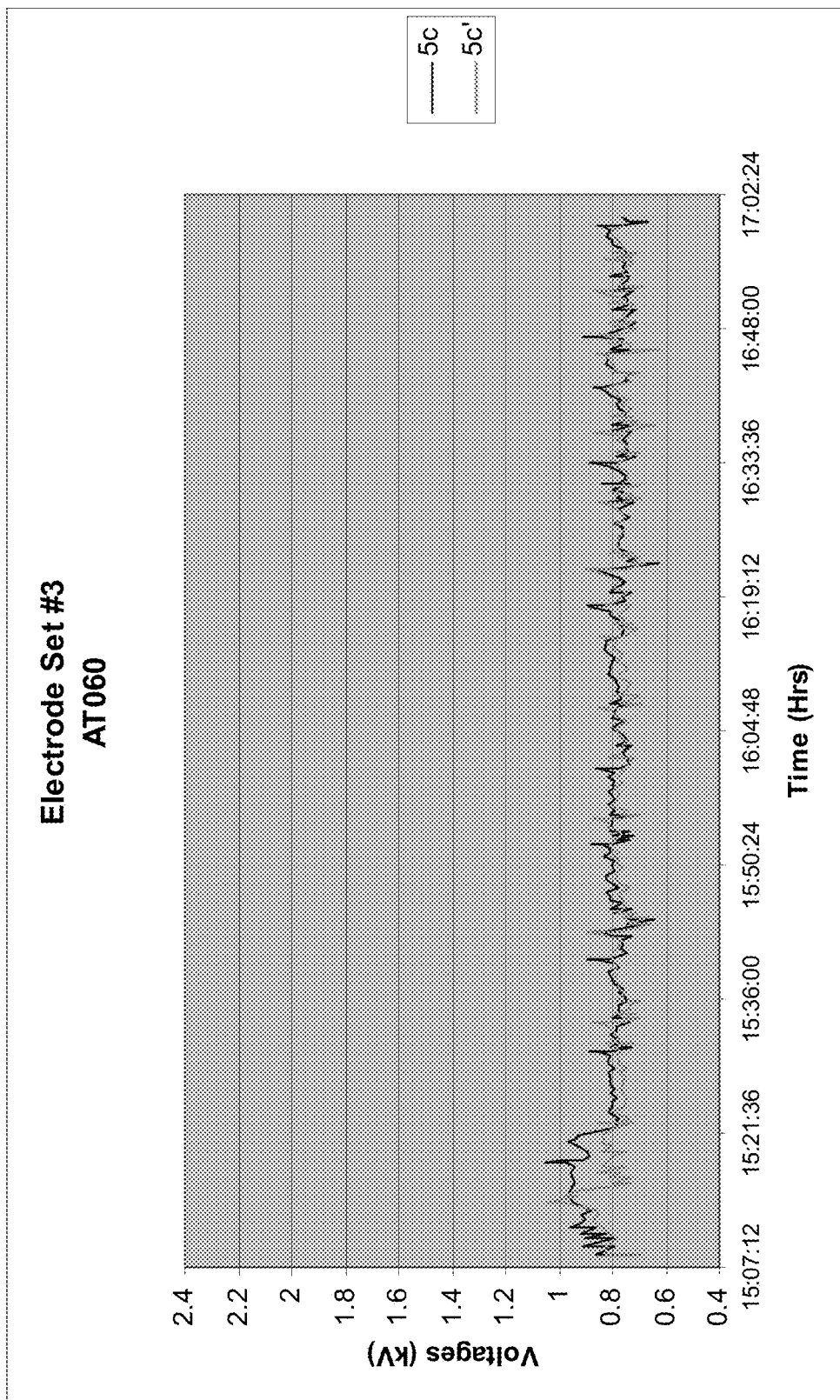
Figure 38E:
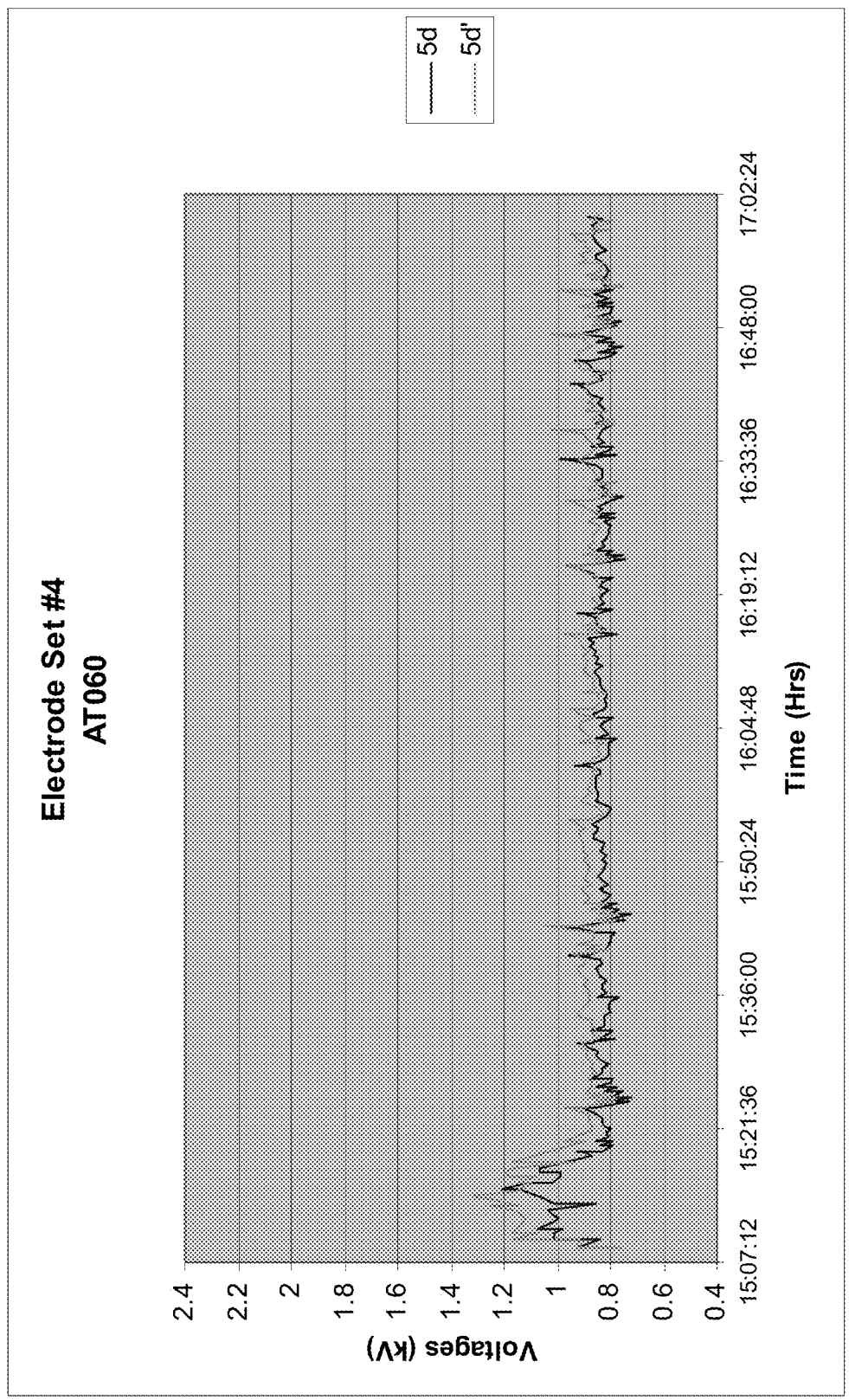
Figure 38F:
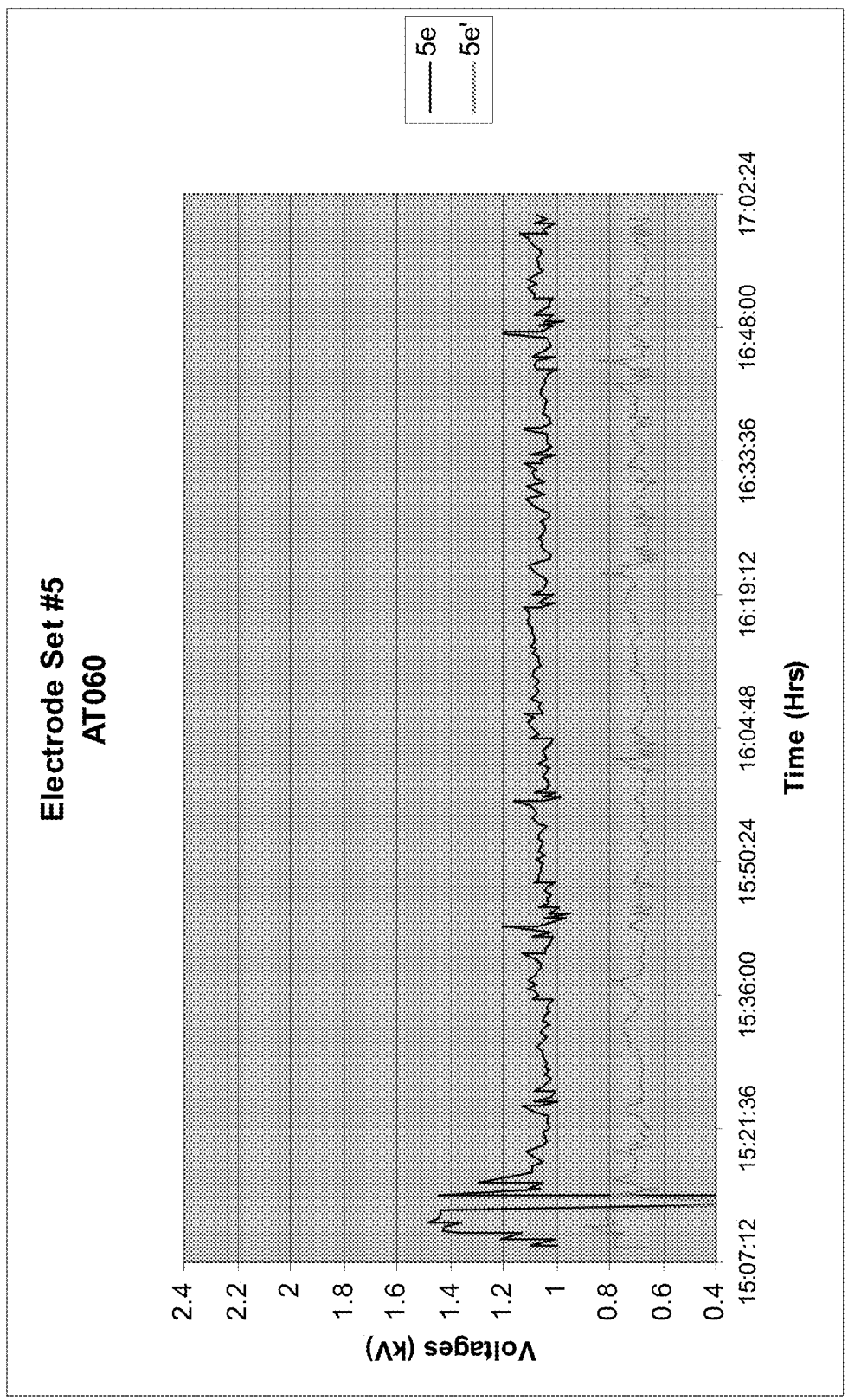
Figure 38G:
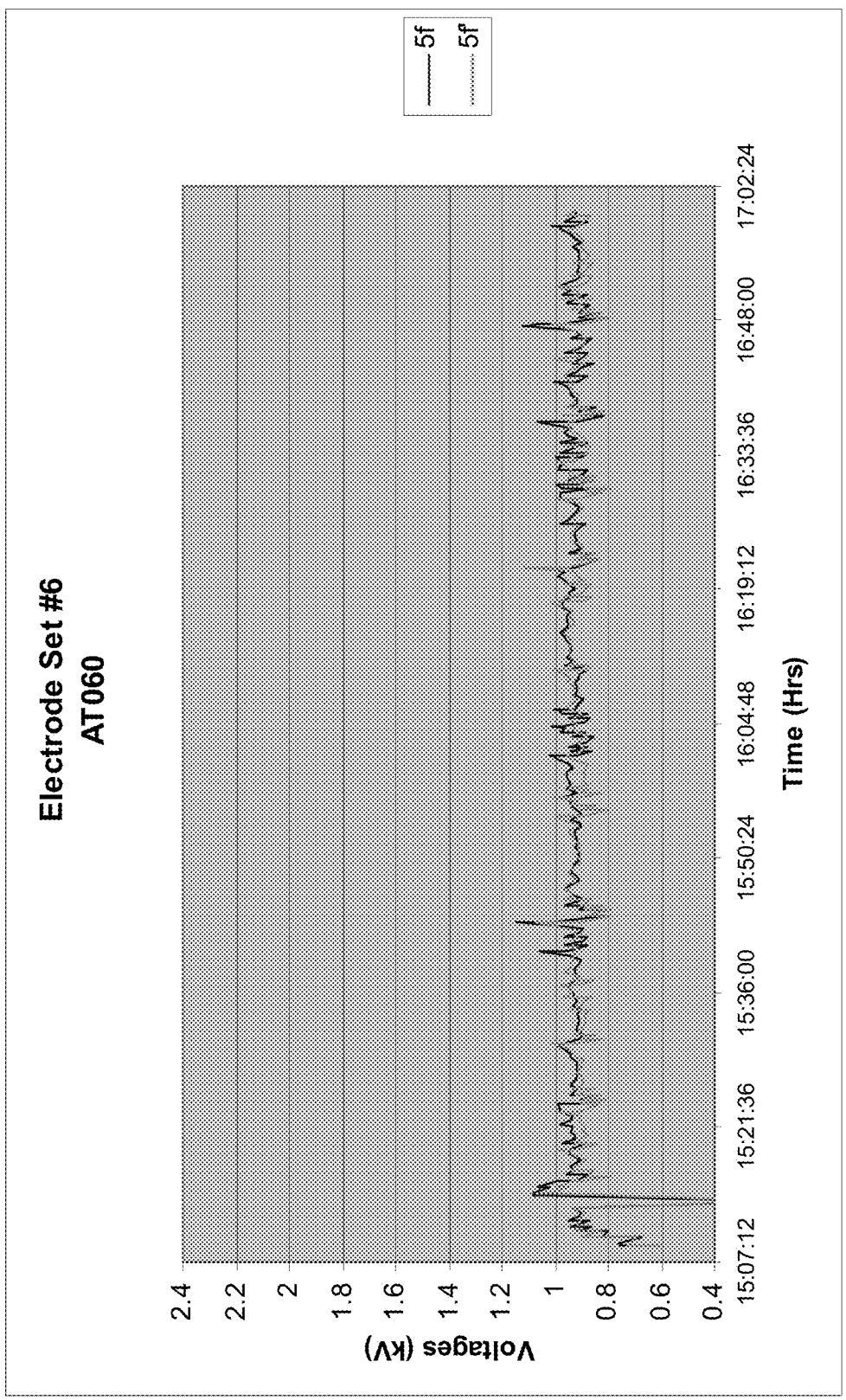
Figure 38H:
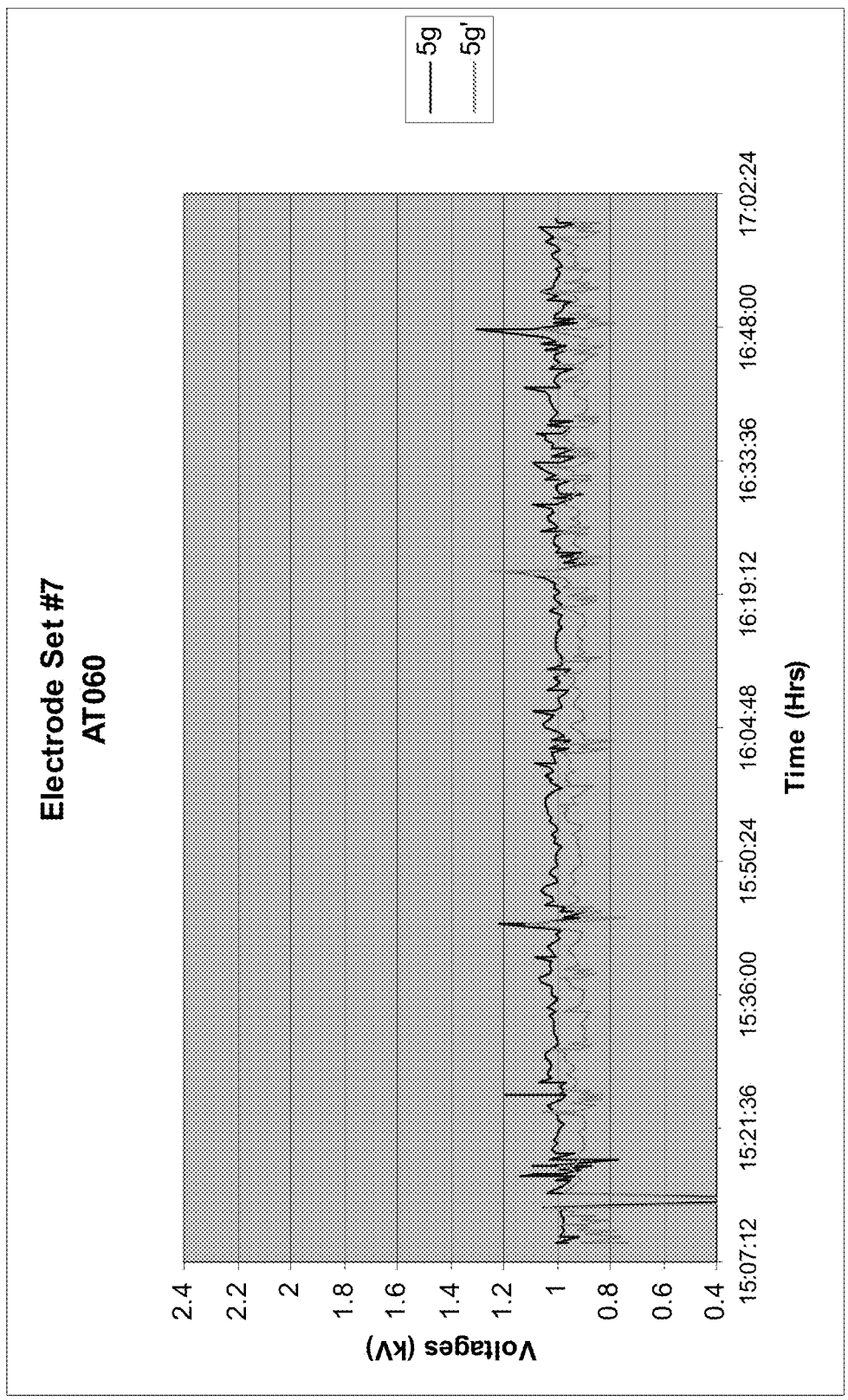
Figure 38I:
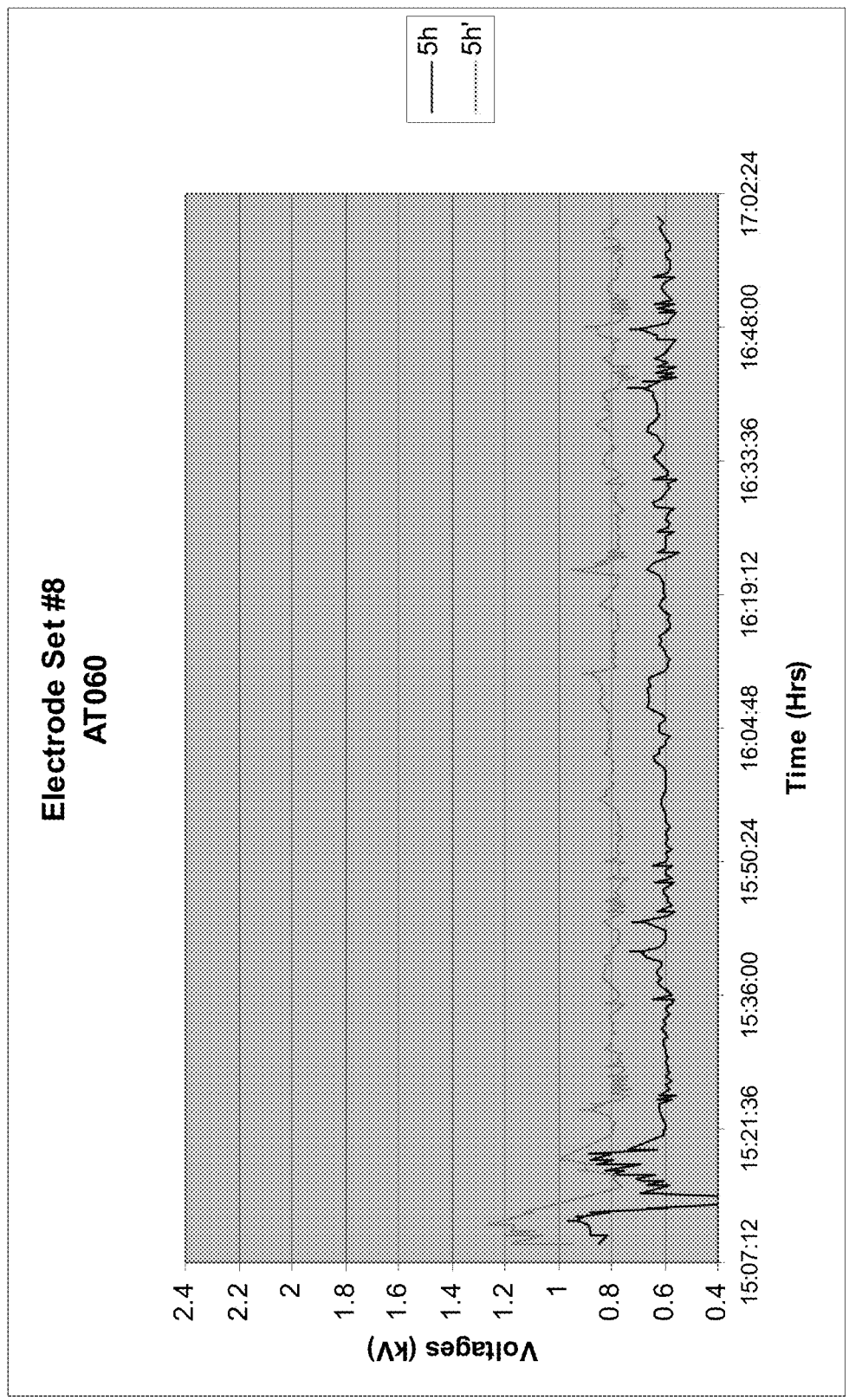

FIG. 38a shows a bar chart of various target and actual average voltages applied to 16 different electrodes in an 8 electrode set used in Example 2 to manufacture silver-based nanoparticles and nanoparticle solutions.

FIGS. 38b-38i show actual voltages applied as a function of time for the 16 different electrodes used in Example 2.

Figure 39A:
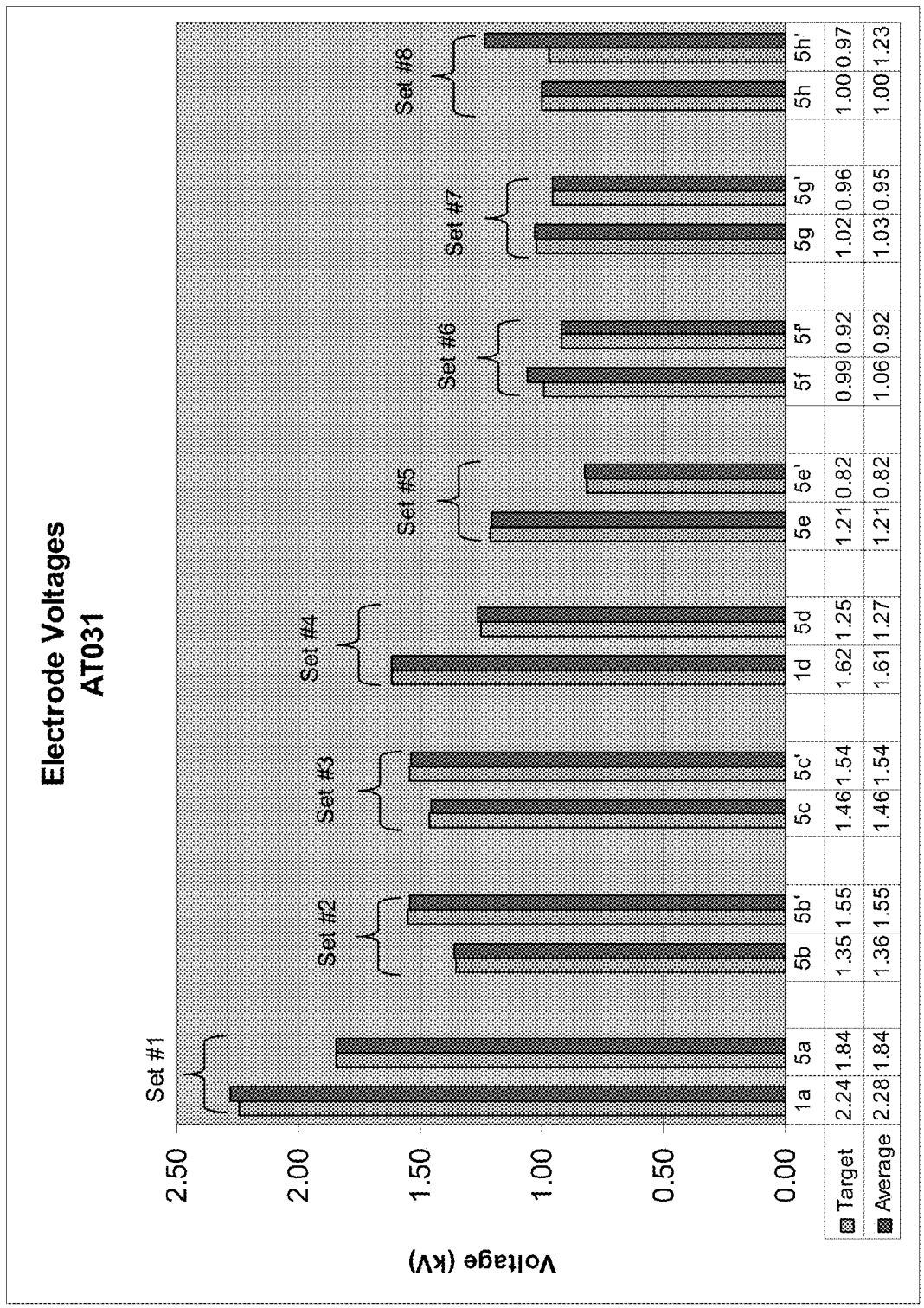
Figure 39B:
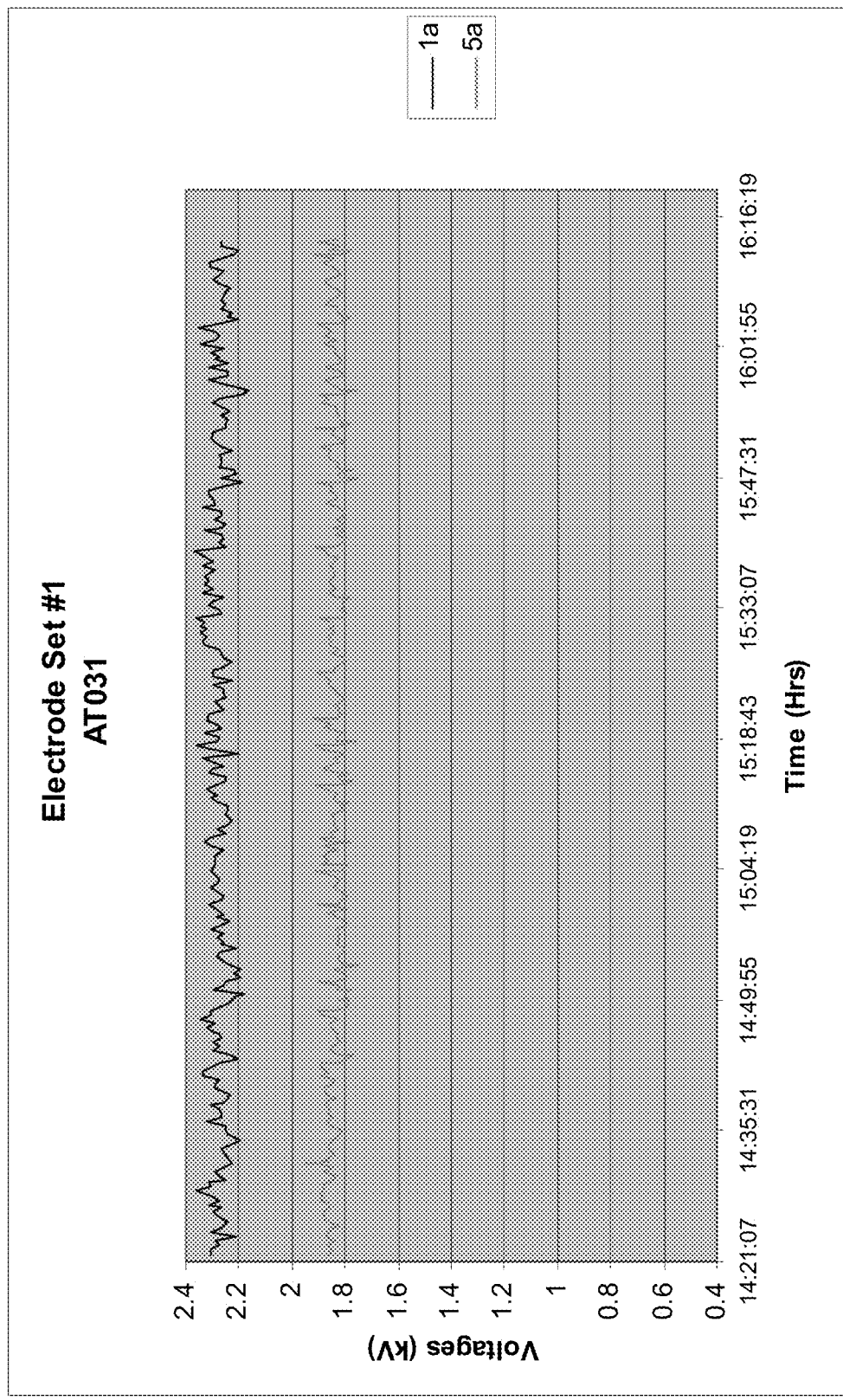
Figure 39C:
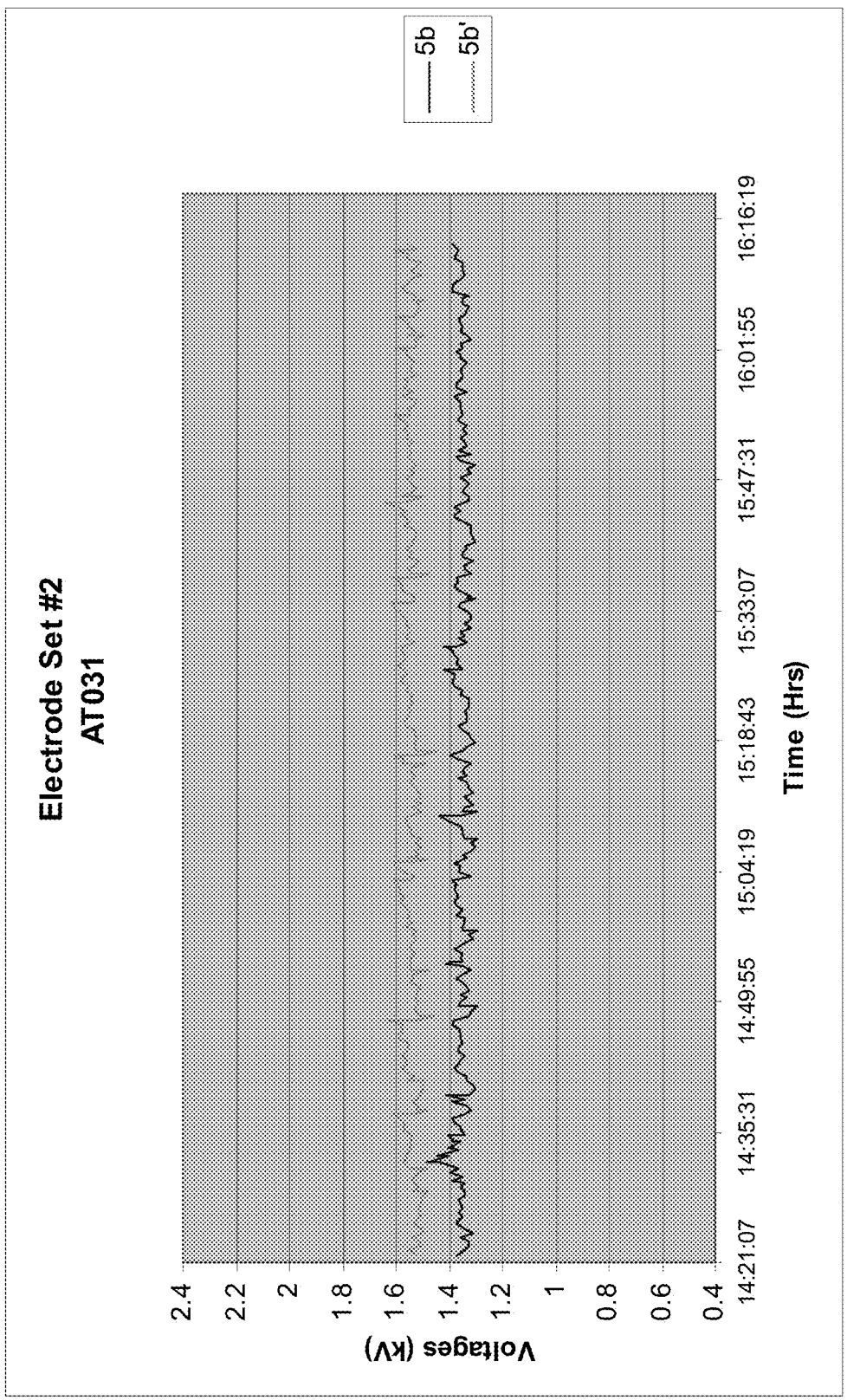
Figure 39D:
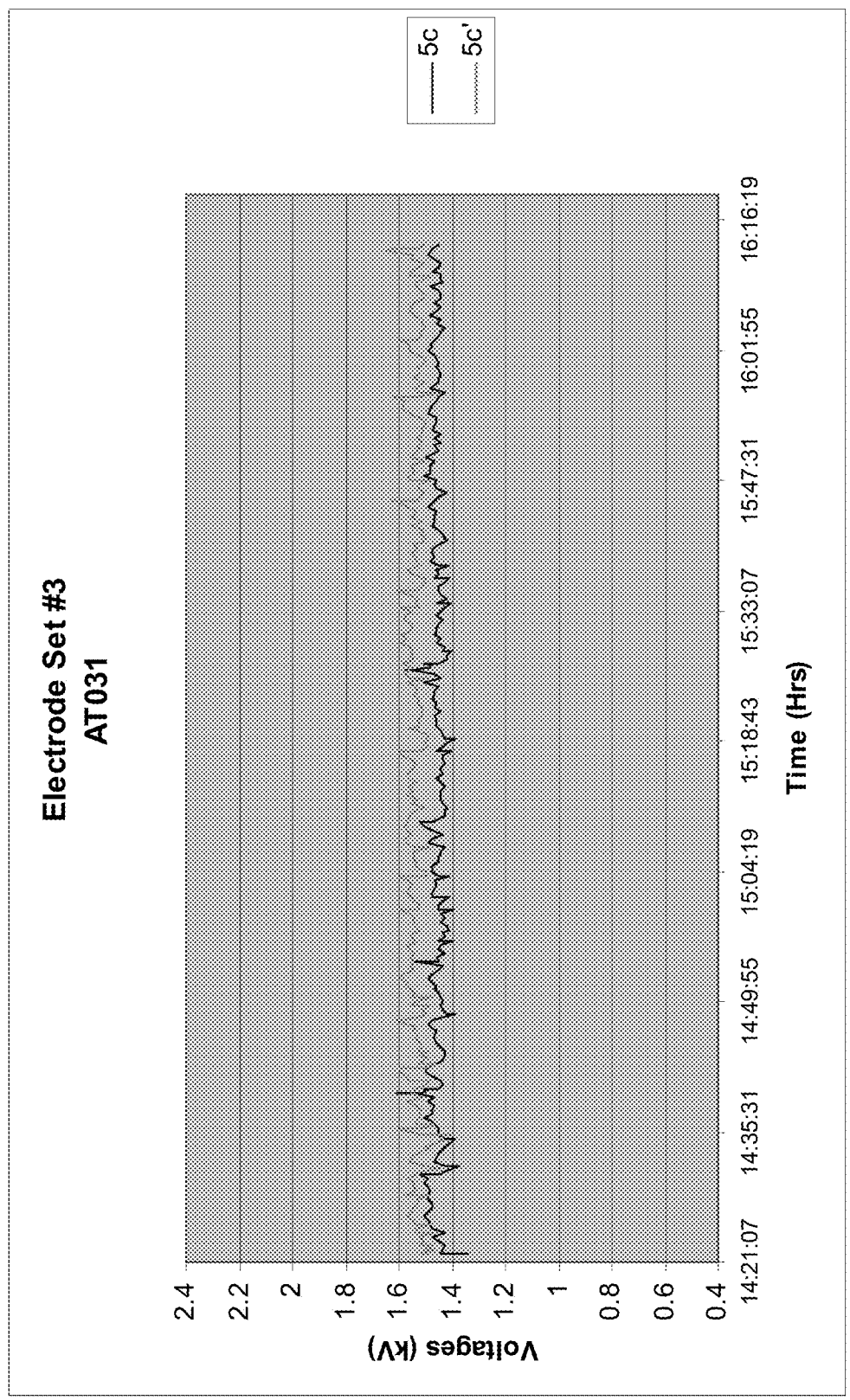
Figure 39E:
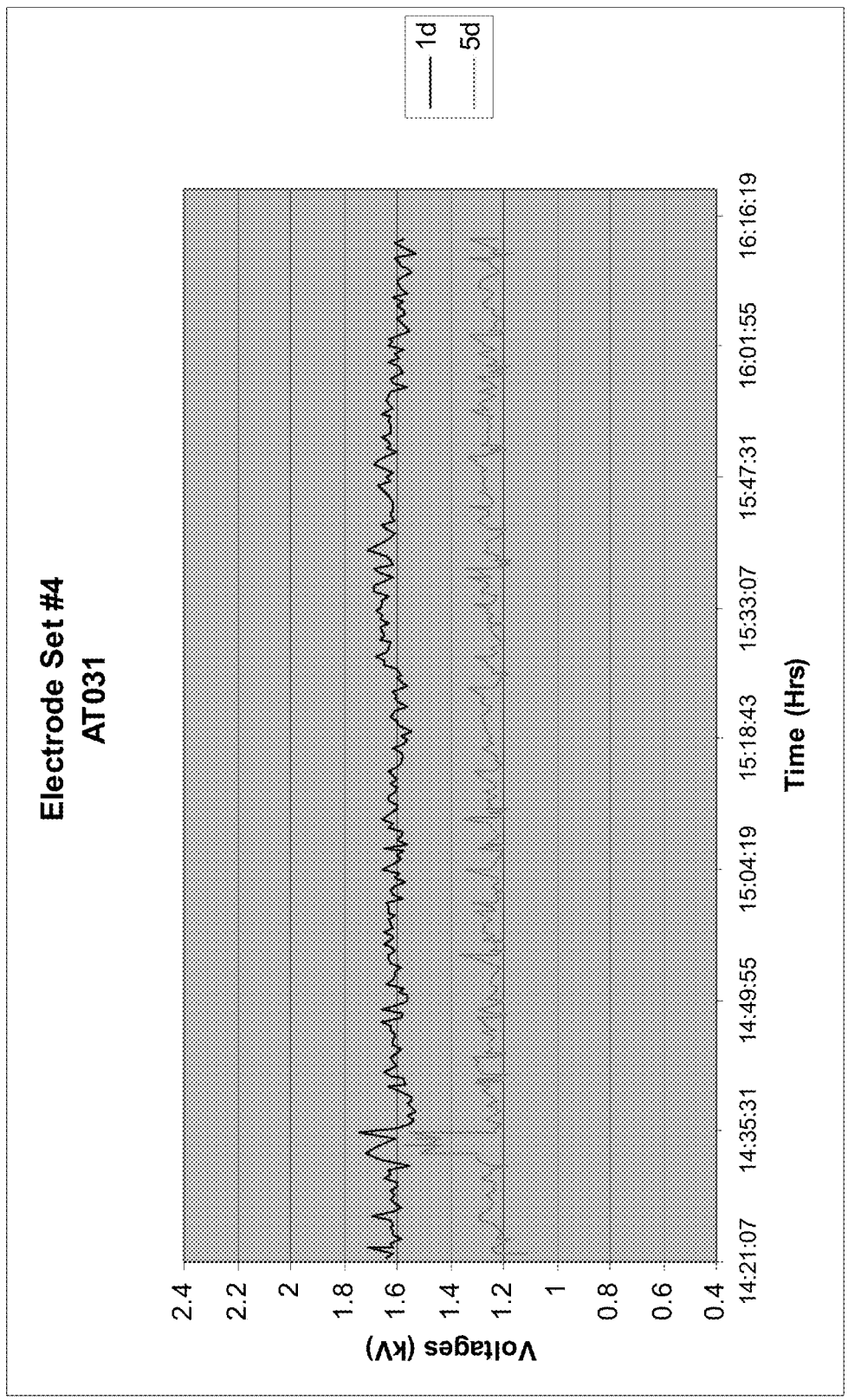
Figure 39F:
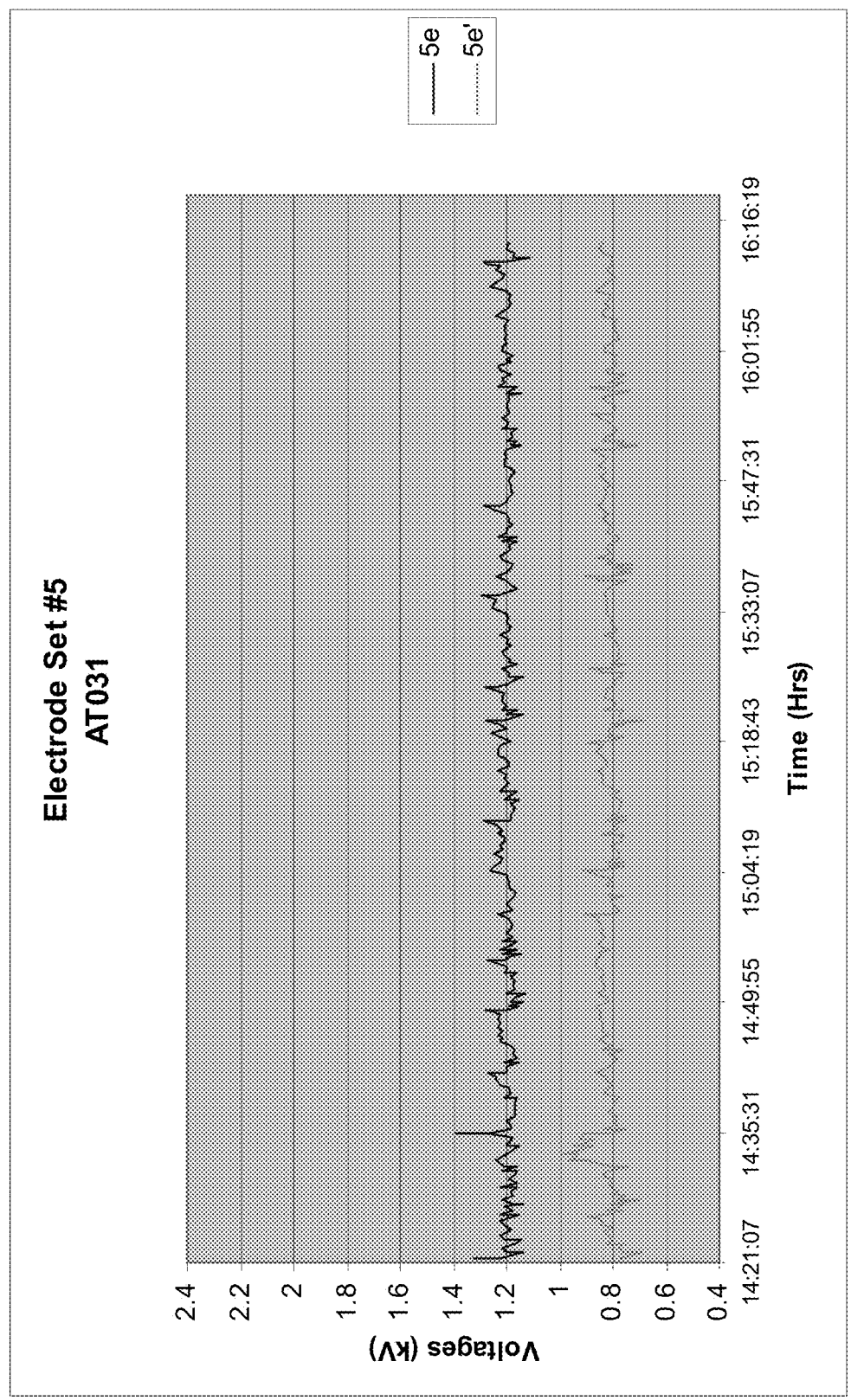
Figure 39G:
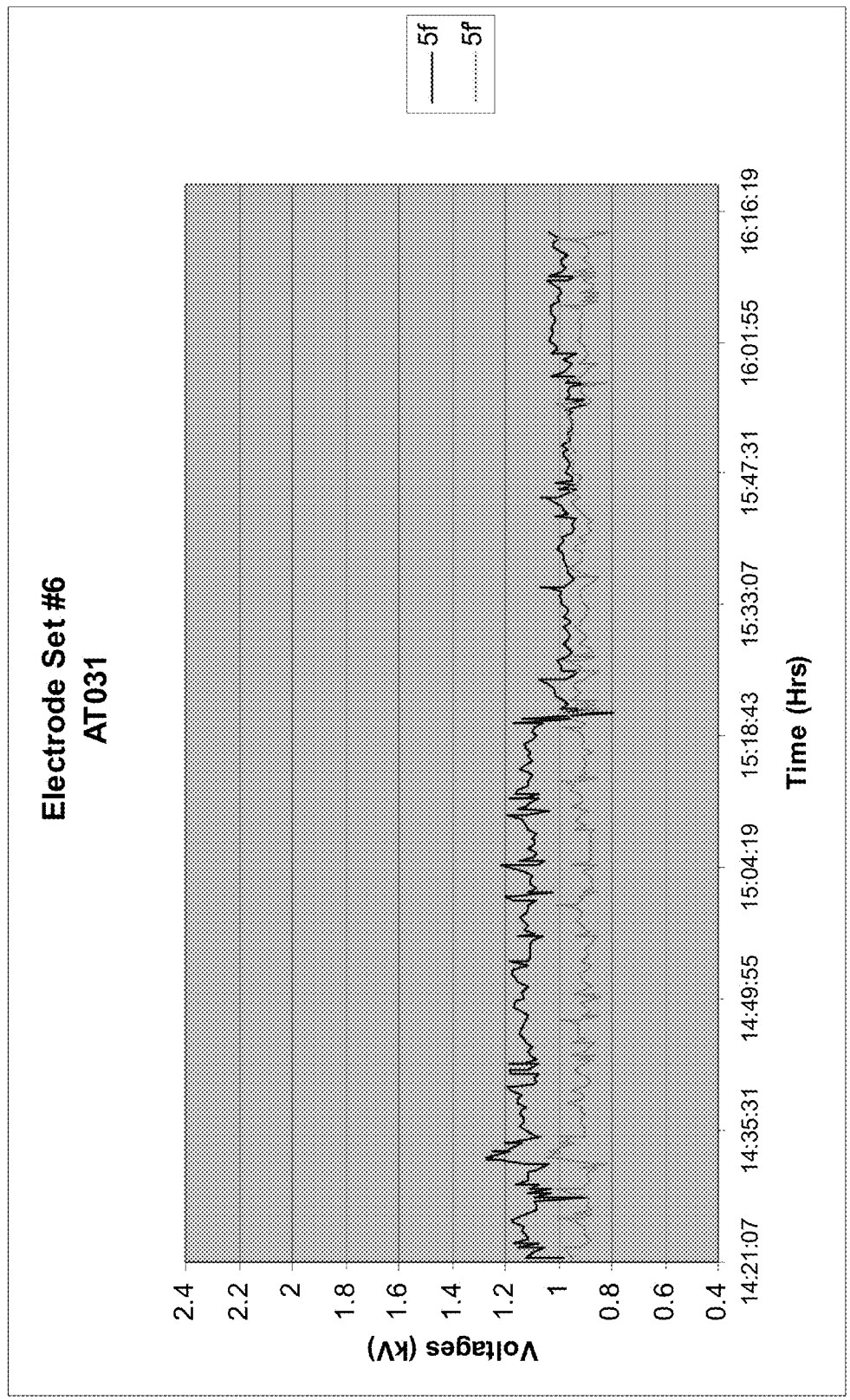
Figure 39H:
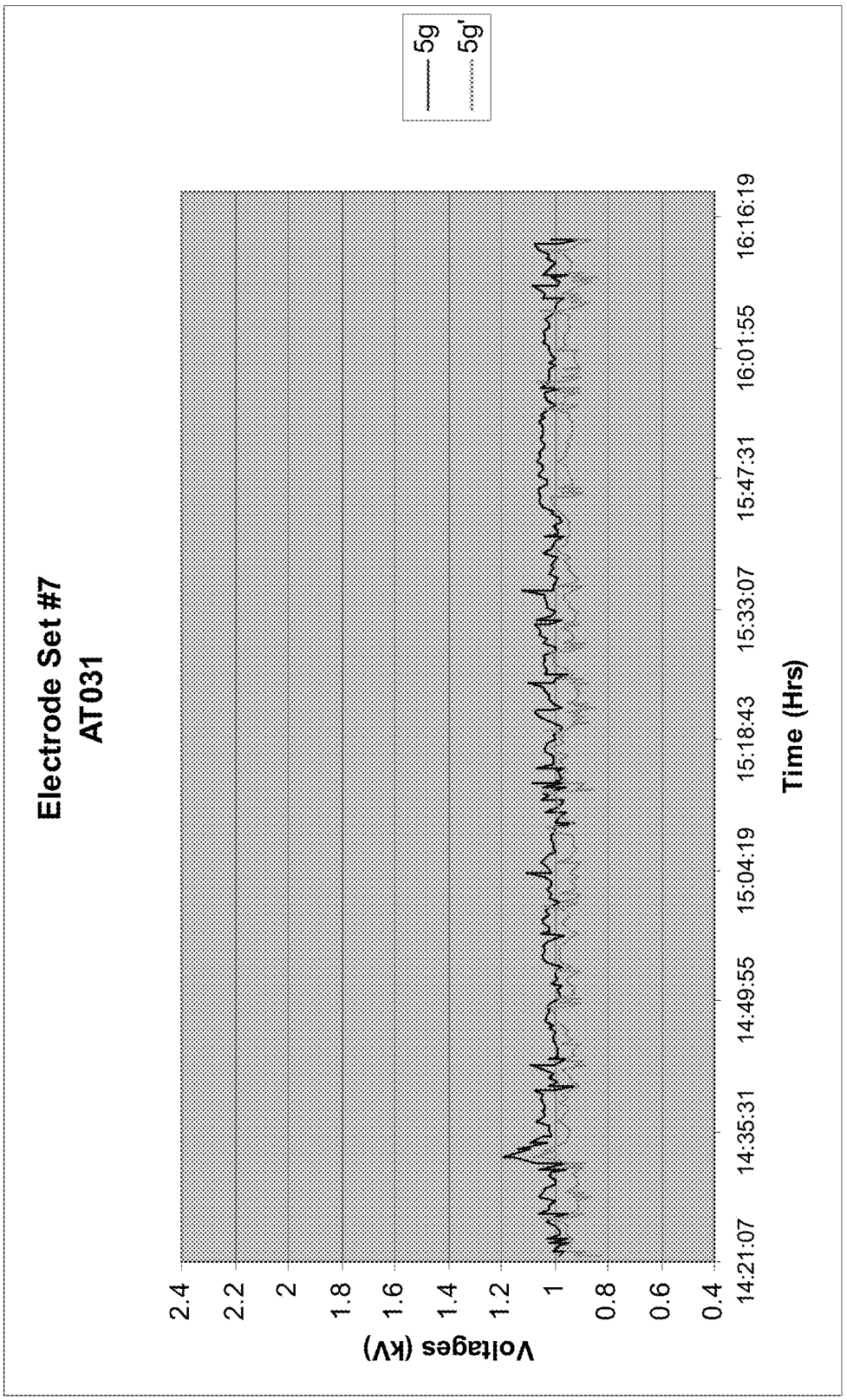
Figure 39I:
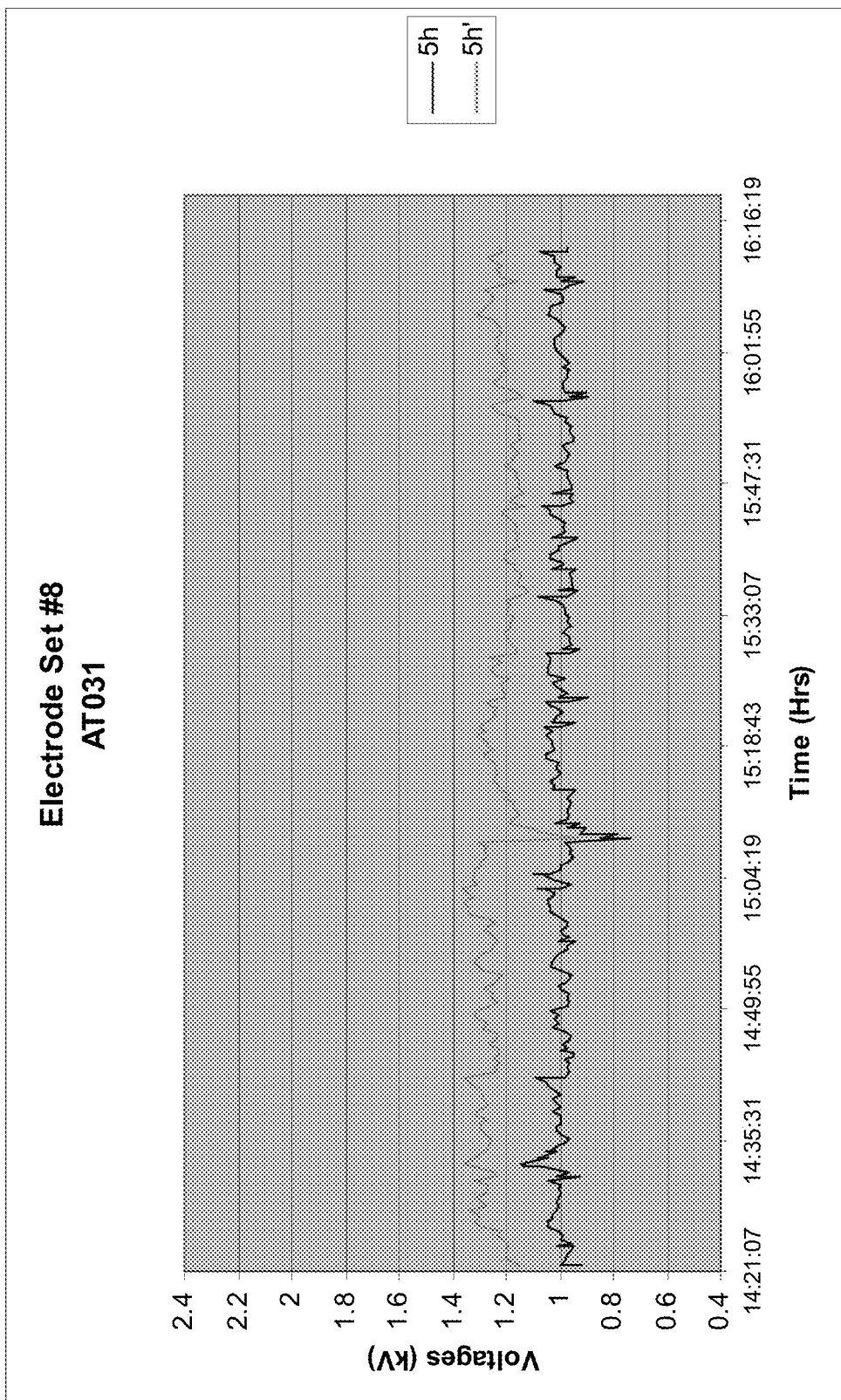

FIG. 39a shows a bar chart of various target and actual average voltages applied to 16 different electrodes in an 8 electrode set used in Example 3 to manufacture silver-based nanoparticles and nanoparticle solutions.

FIGS. 39b-39i show actual voltages applied as a function of time for 16 different electrodes used in Example 3.

Figure 40A:
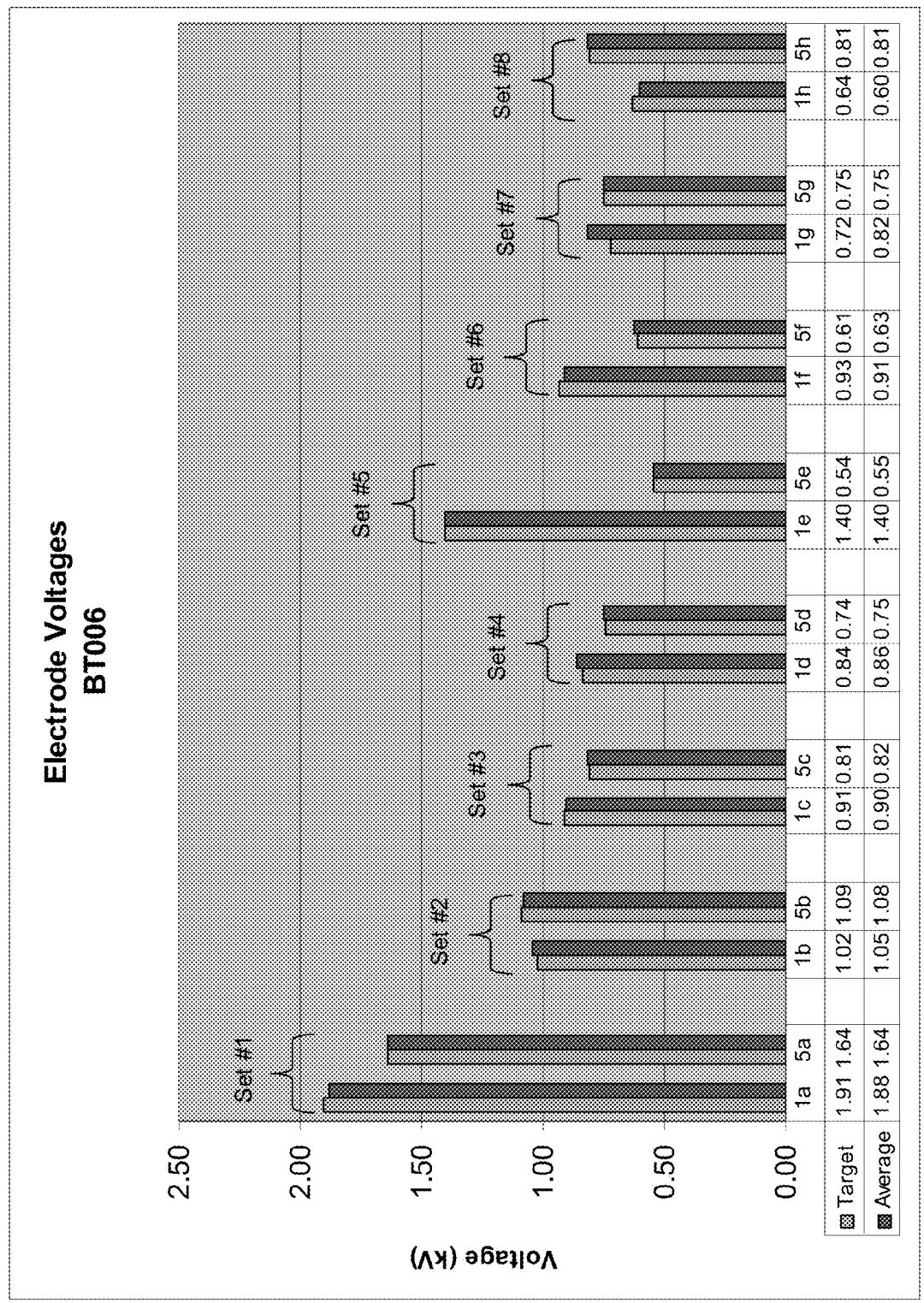
Figure 40B:
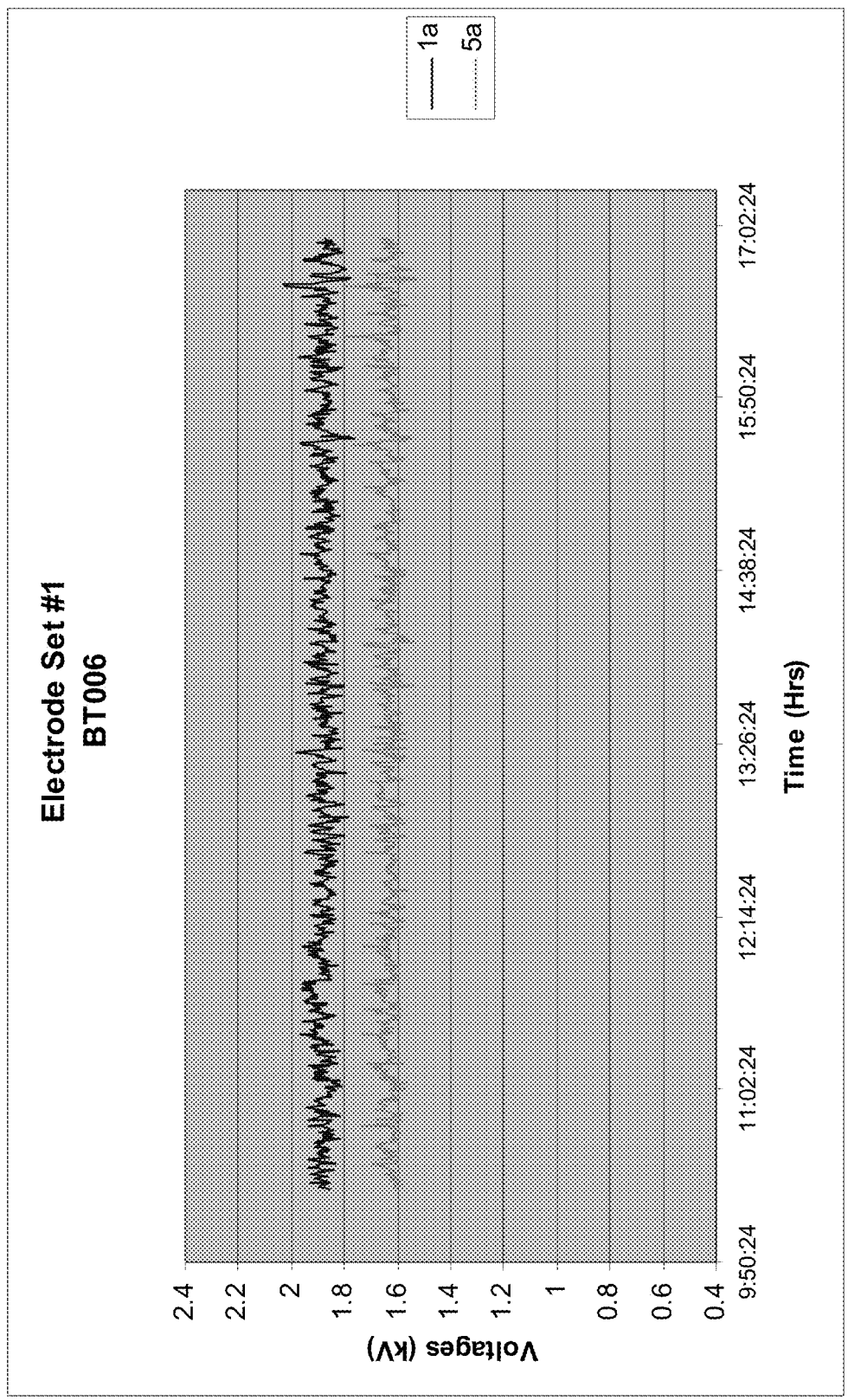
Figure 40C:
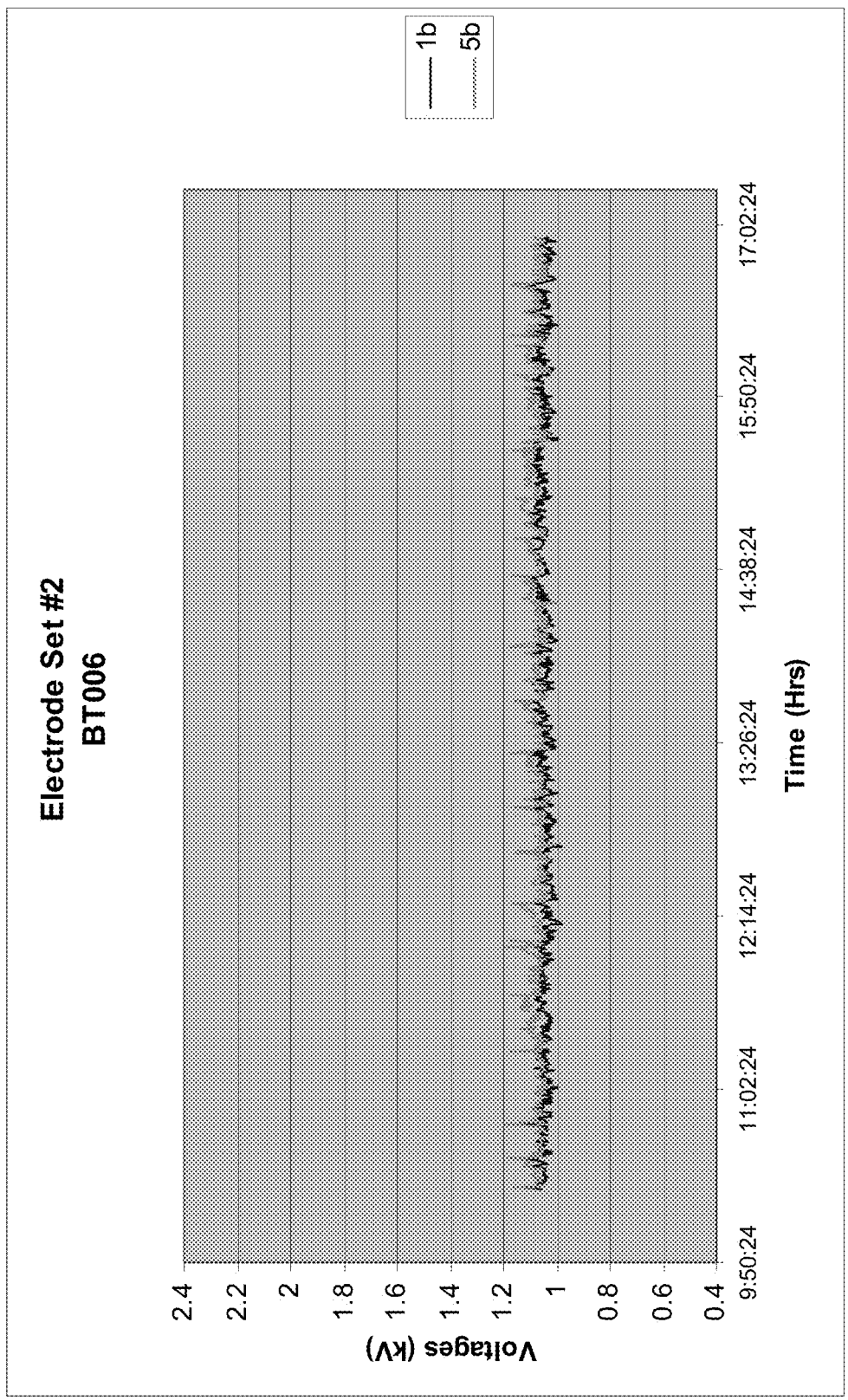
Figure 40D:
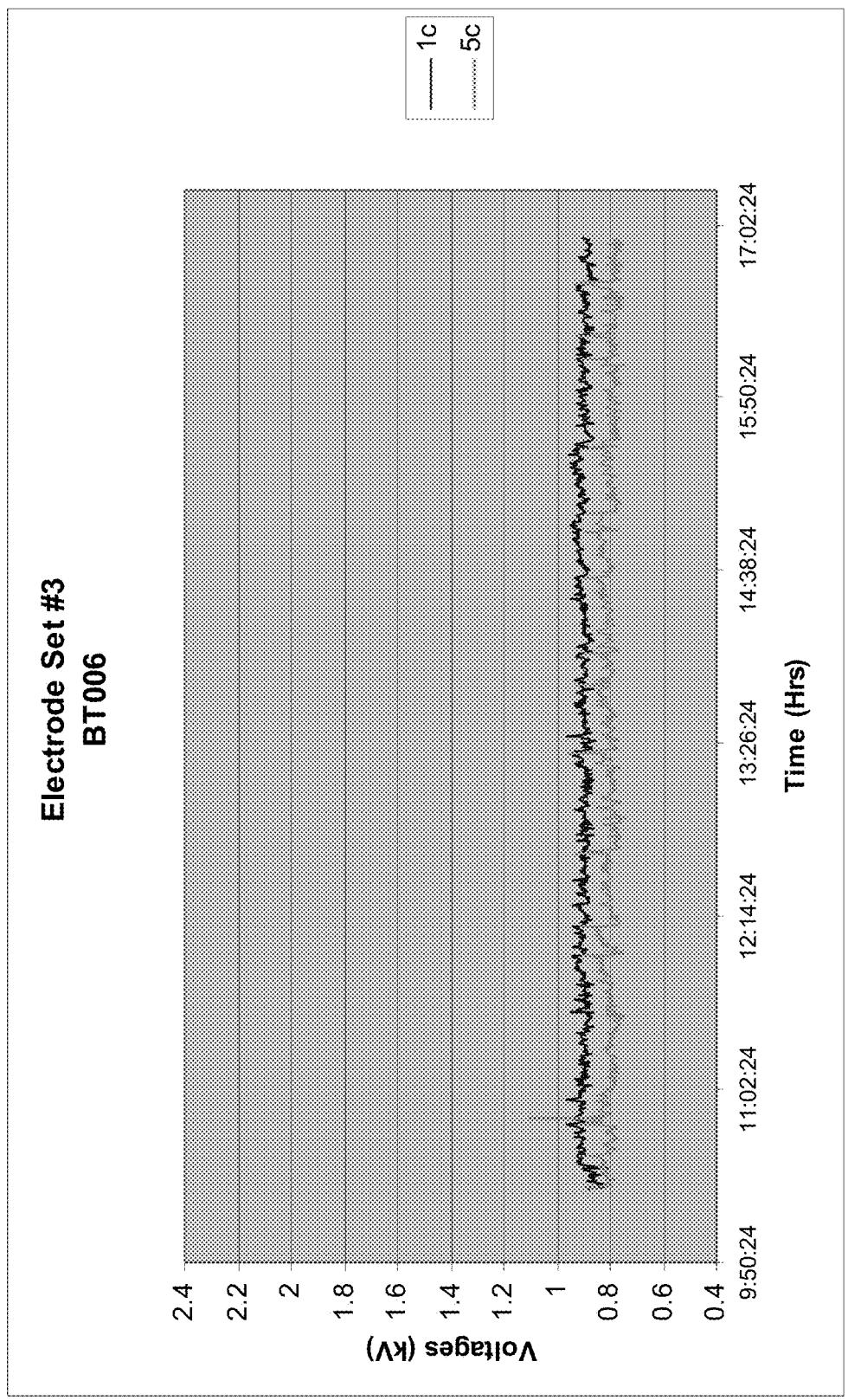
Figure 40E:
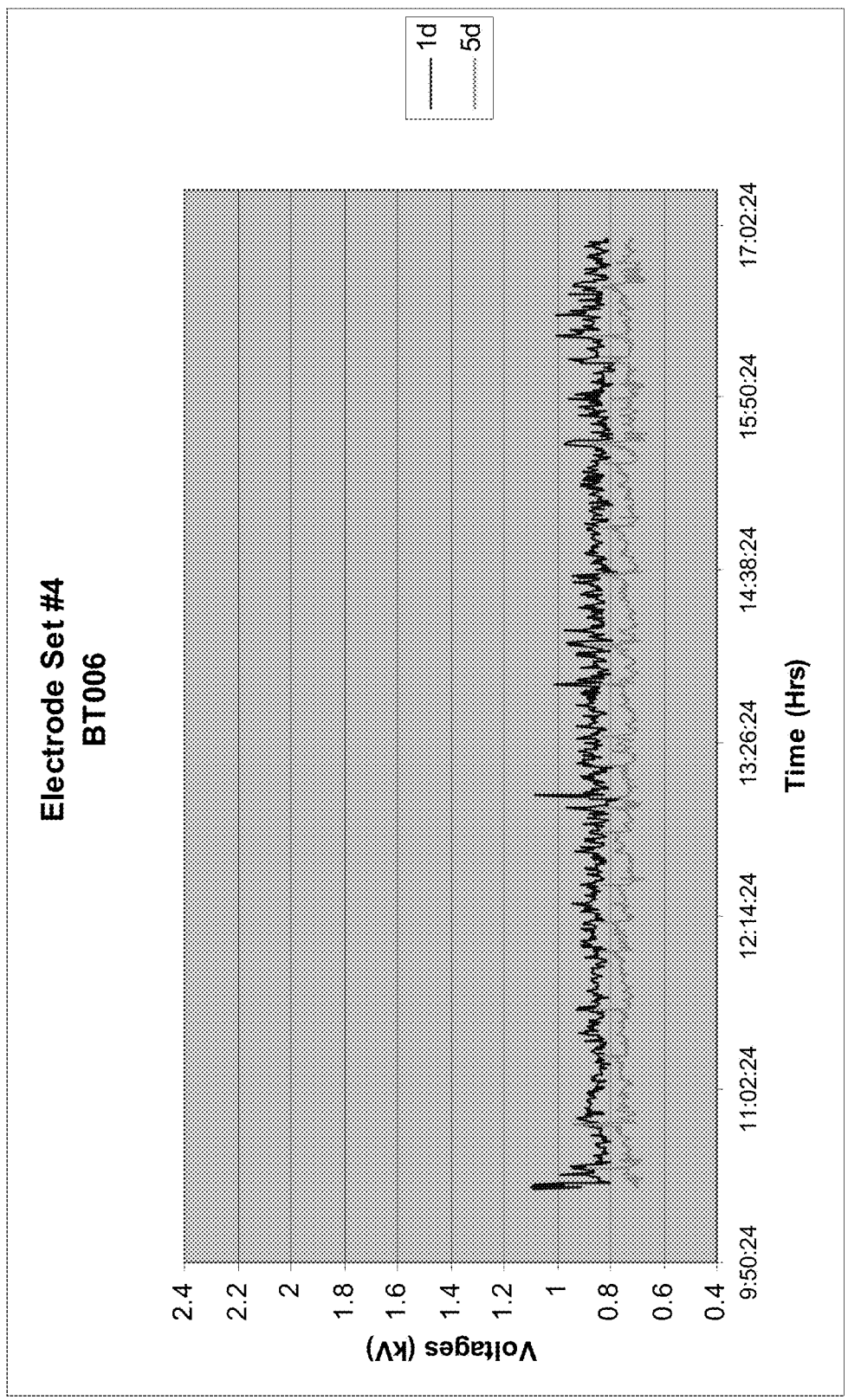
Figure 40F:
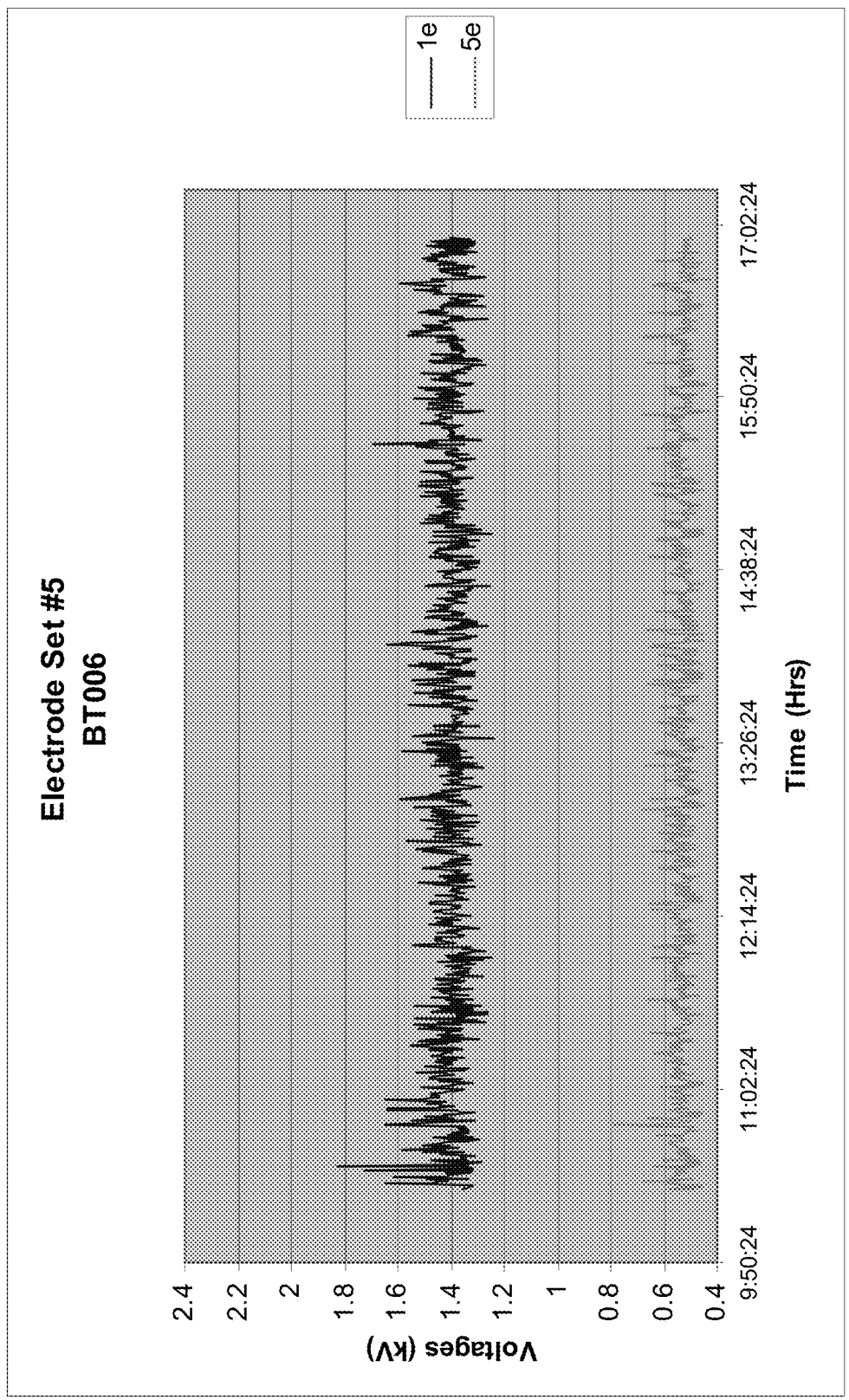
Figure 40G:
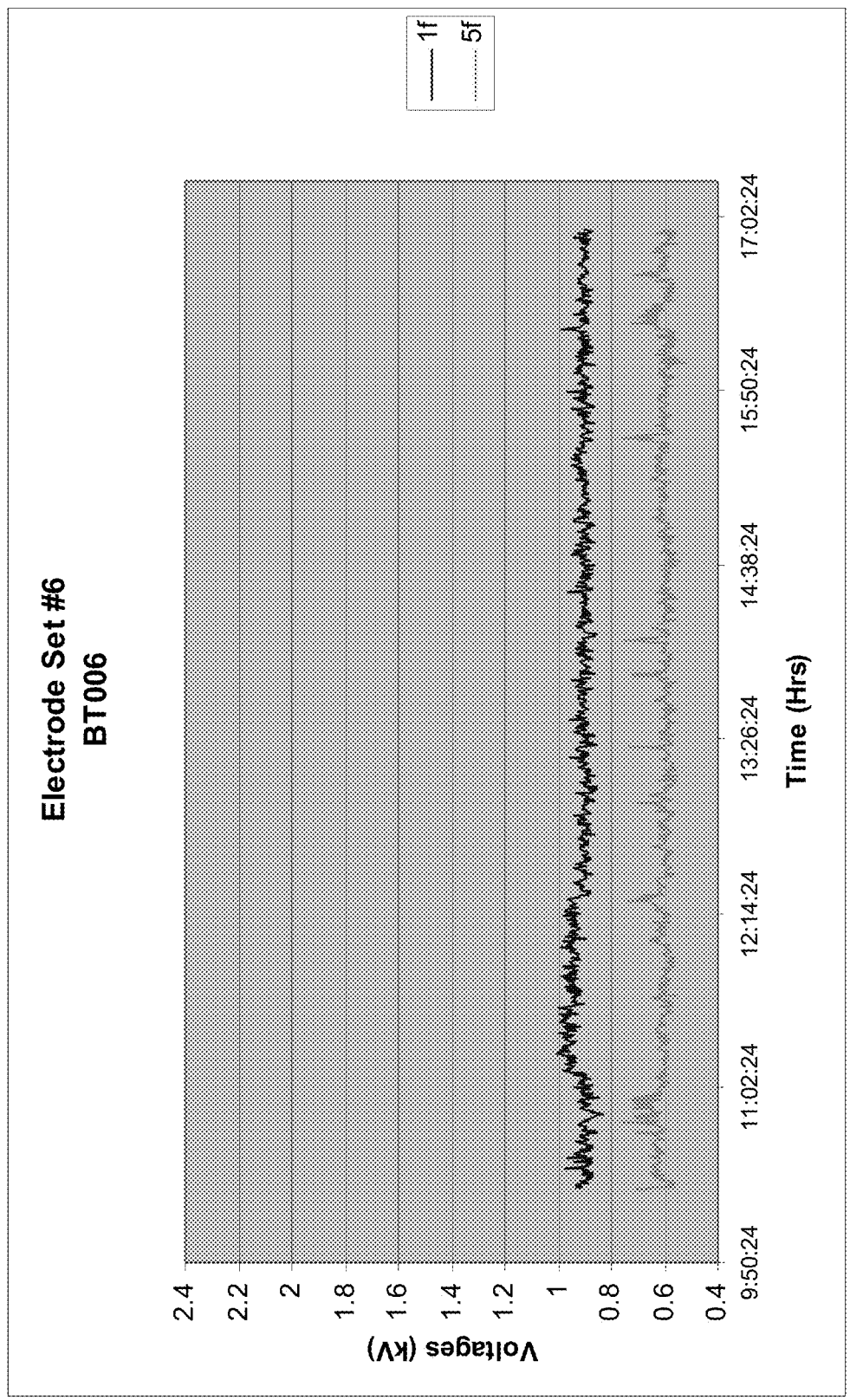
Figure 40H:
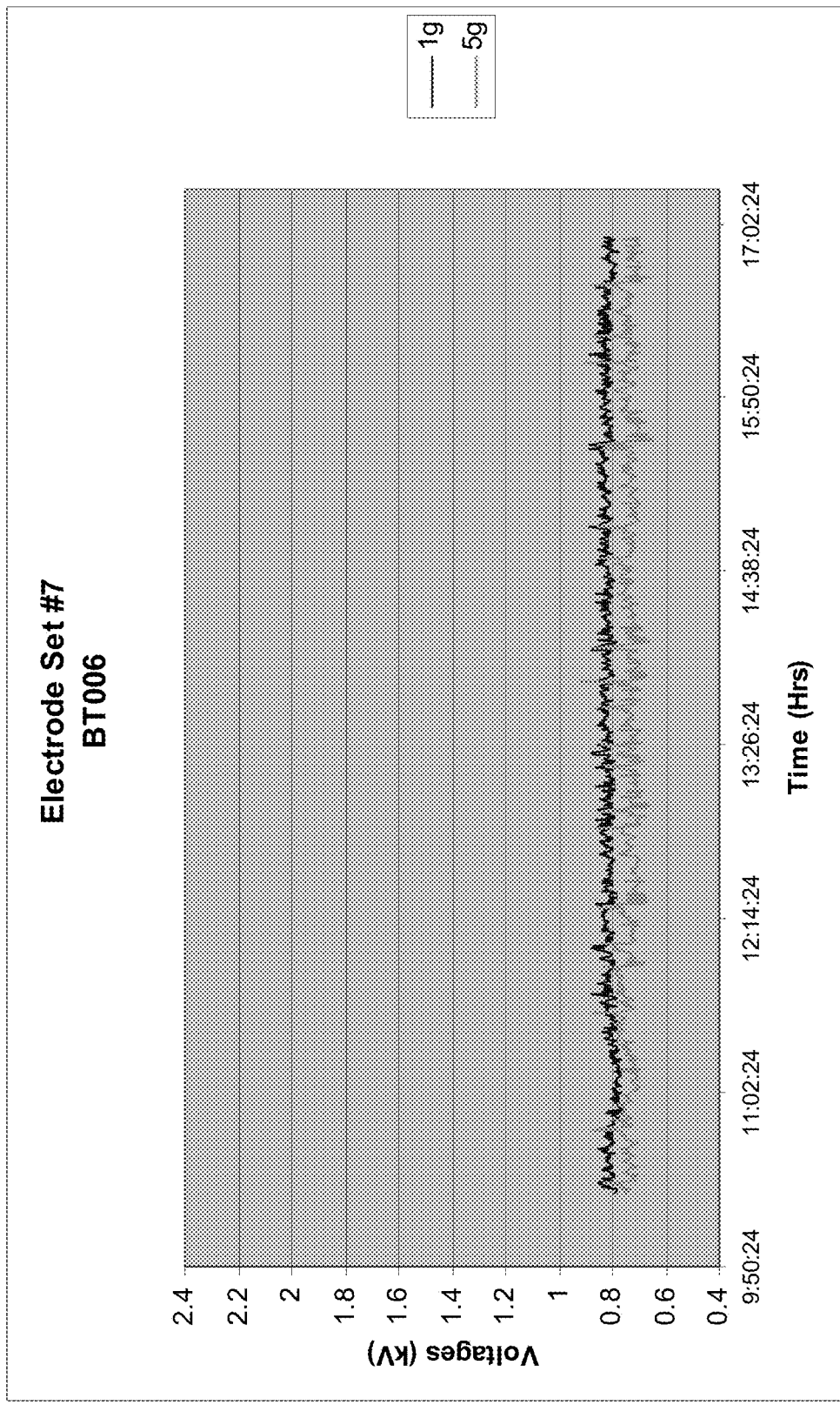
Figure 40I:
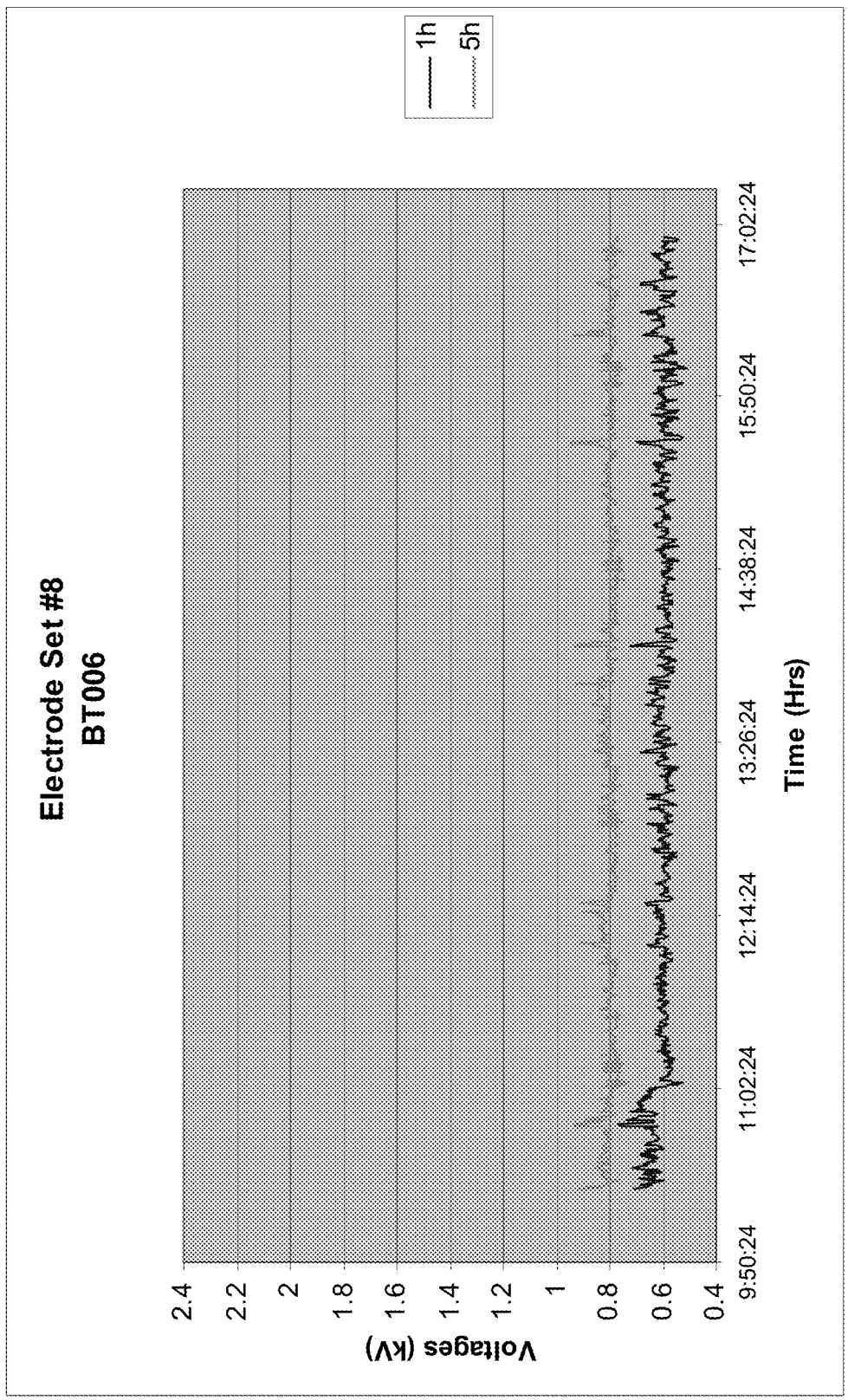

FIG. 40a shows a bar chart of various target and actual average voltages applied to 16 different electrodes in an 8 electrode set used in Example 4 to manufacture zinc-based nanoparticles and nanoparticle solutions.

FIGS. 40b-40i show actual voltages applied as a function of time for the 16 different electrodes used in Example 4.

Figure 41A:
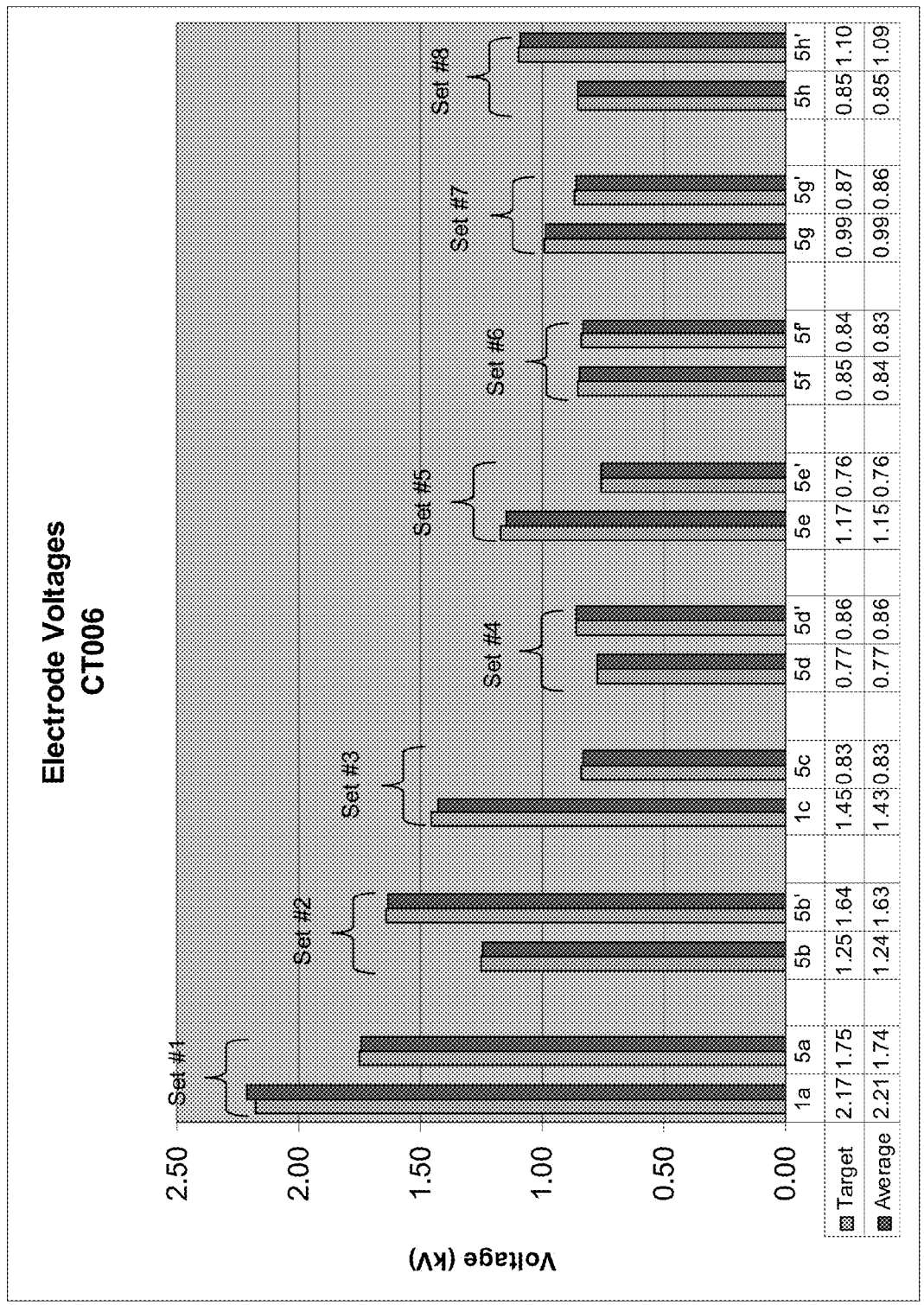
Figure 41B:
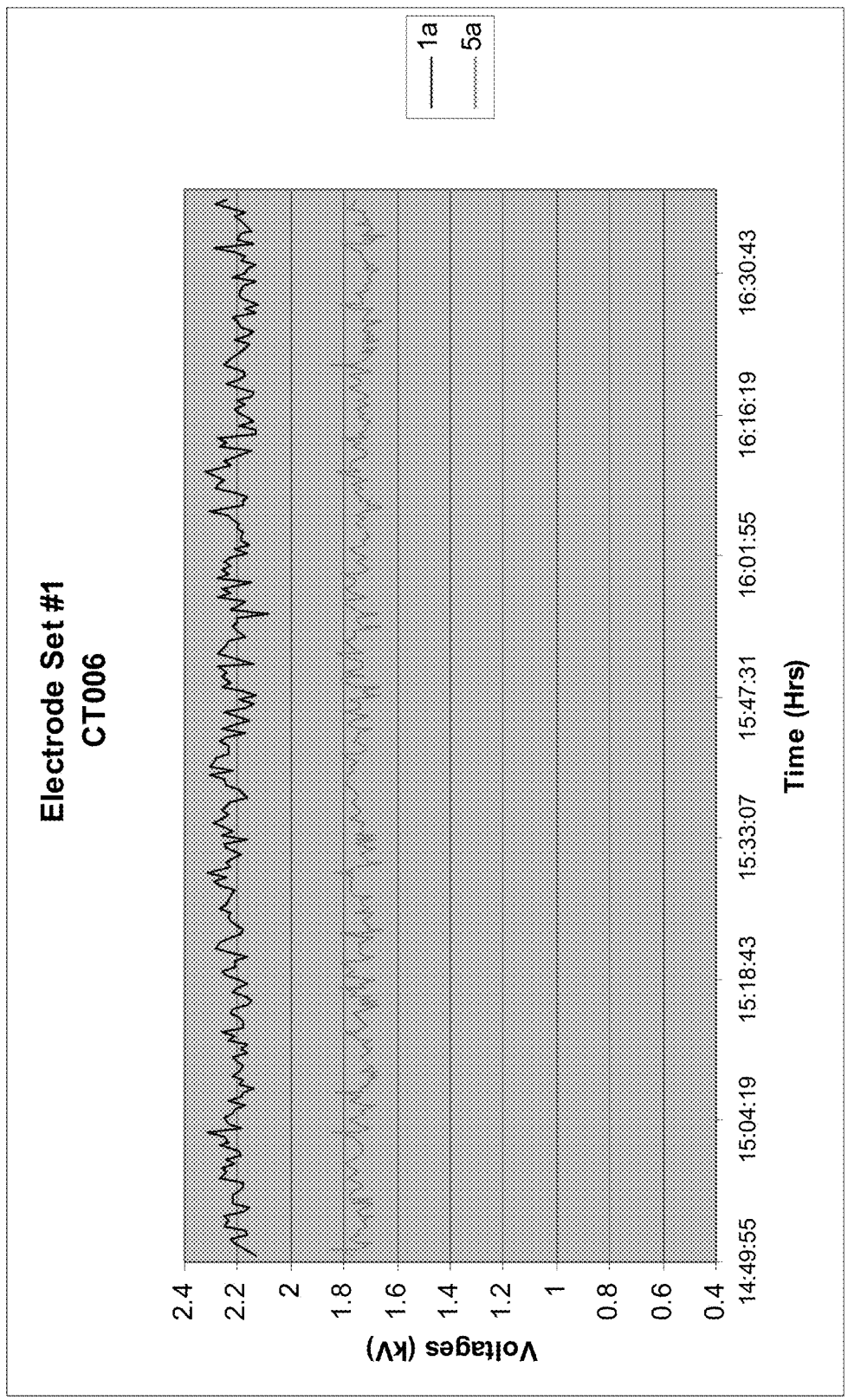
Figure 41C:
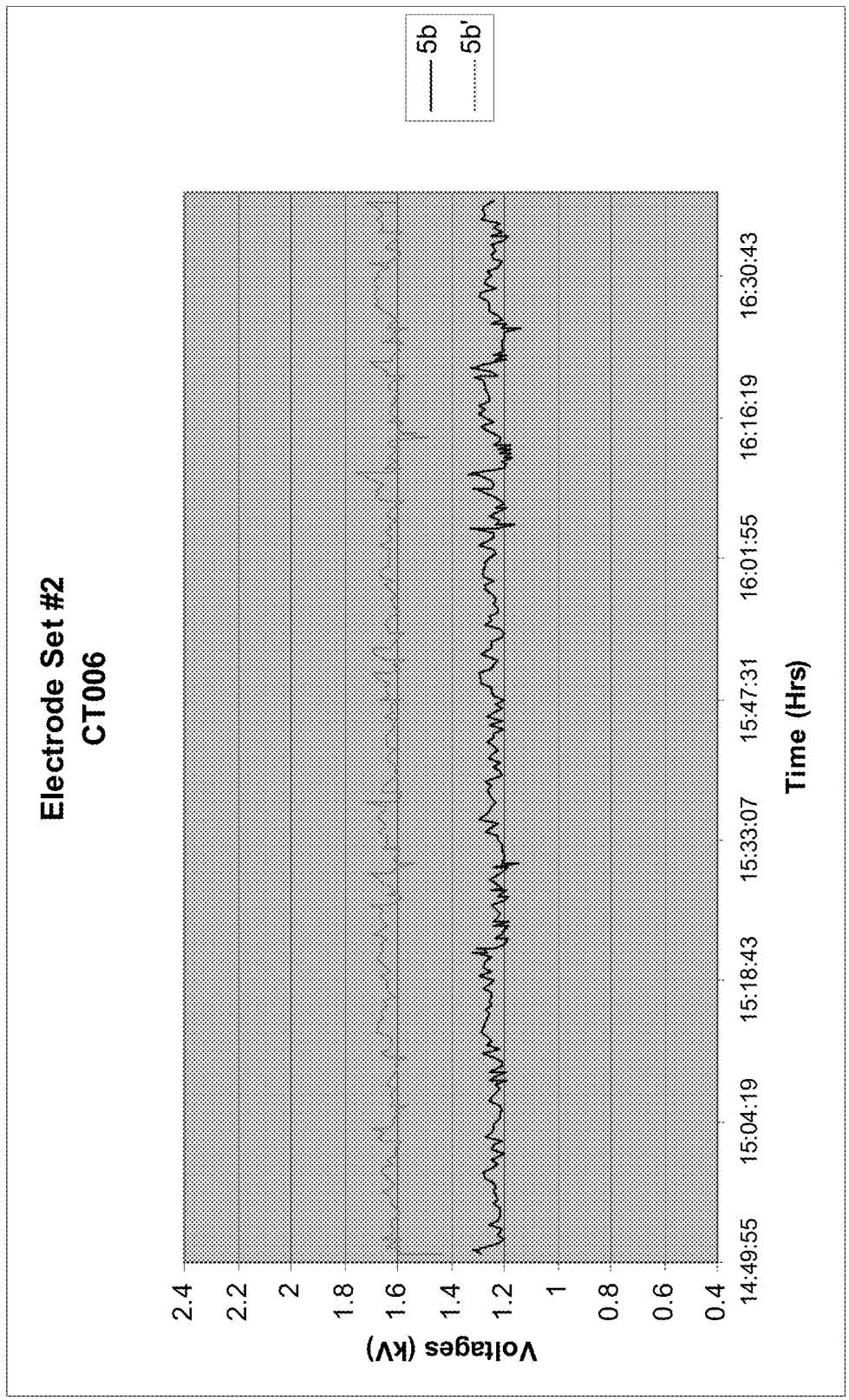
Figure 41D:
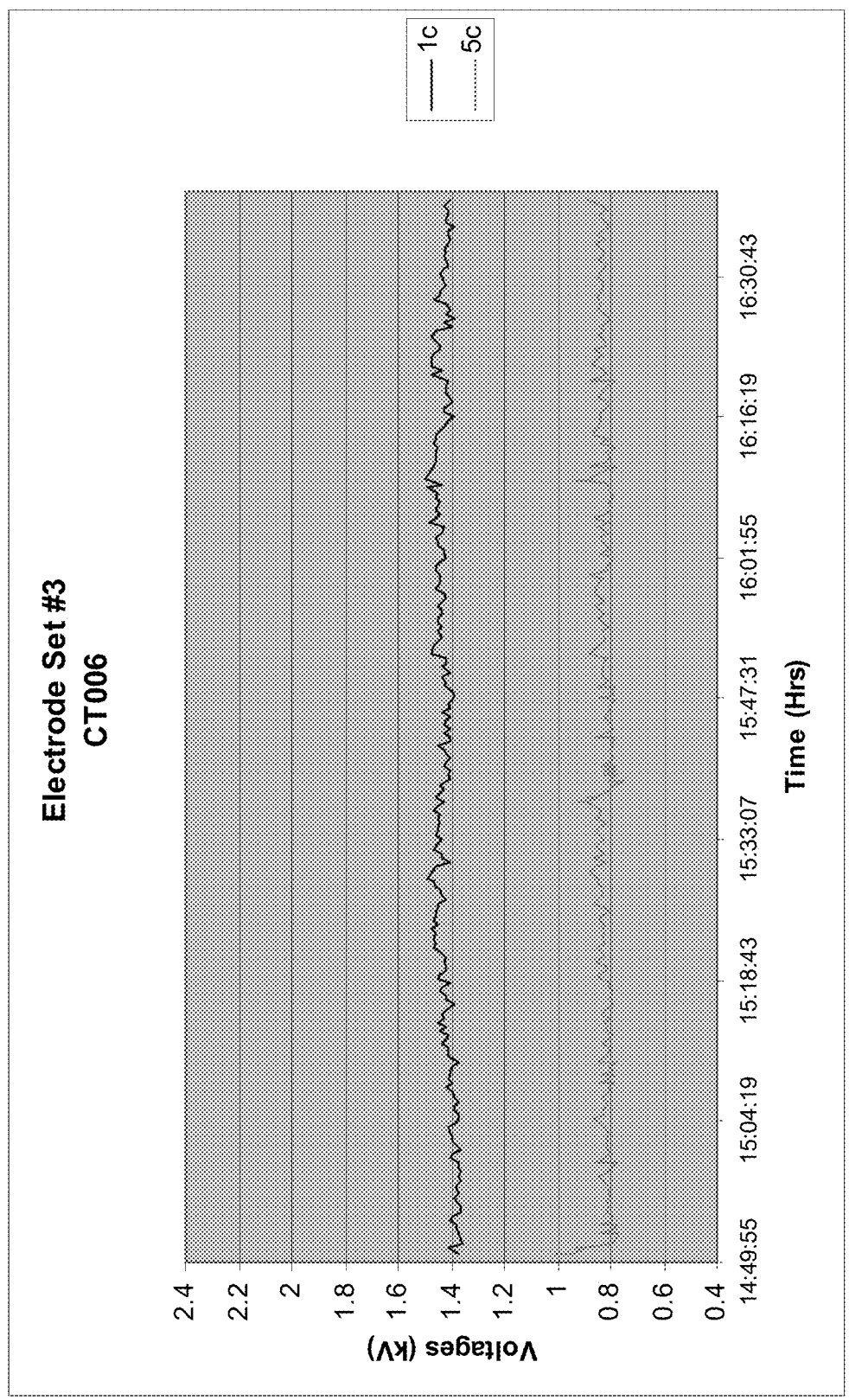
Figure 41E:
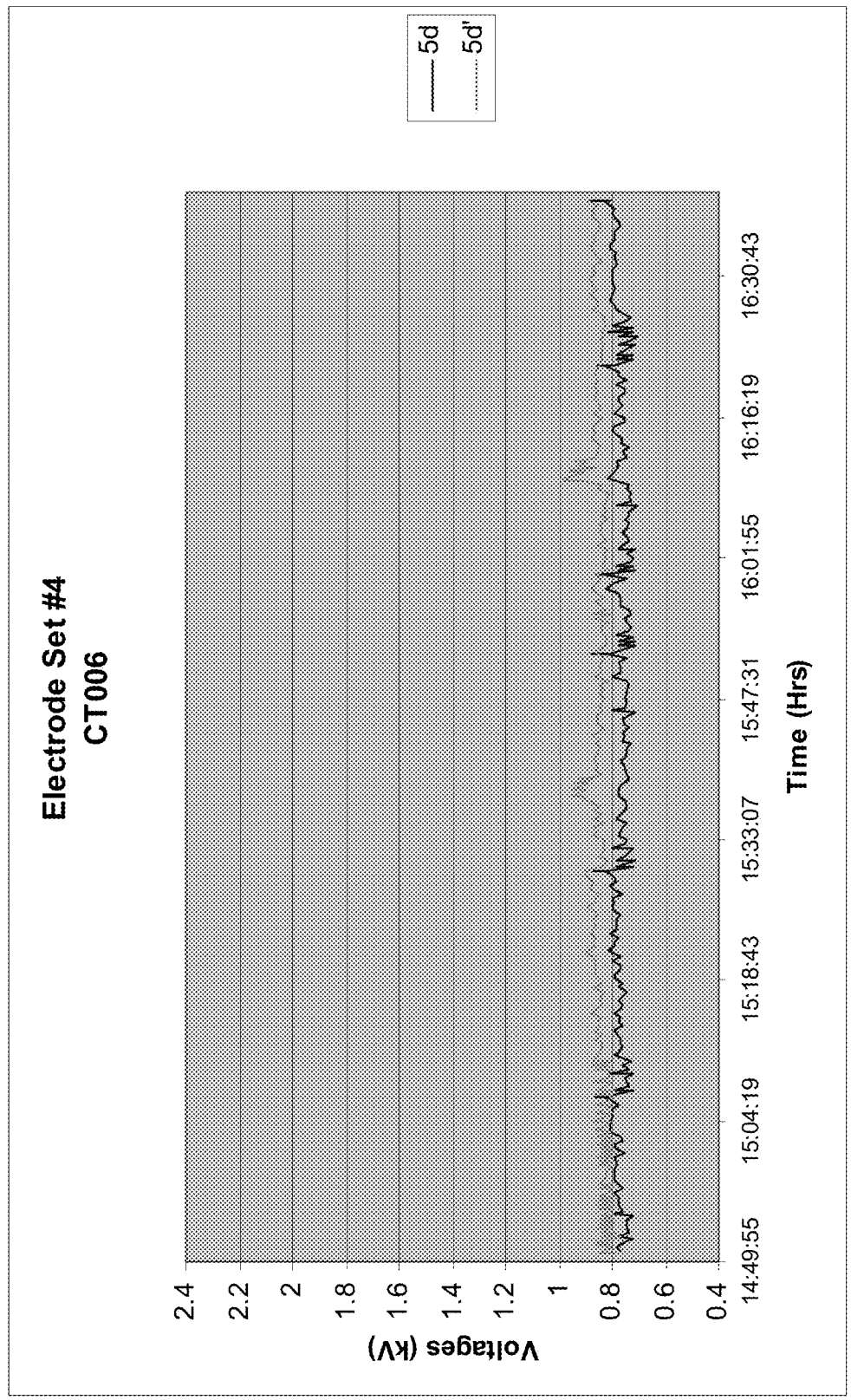
Figure 41F:
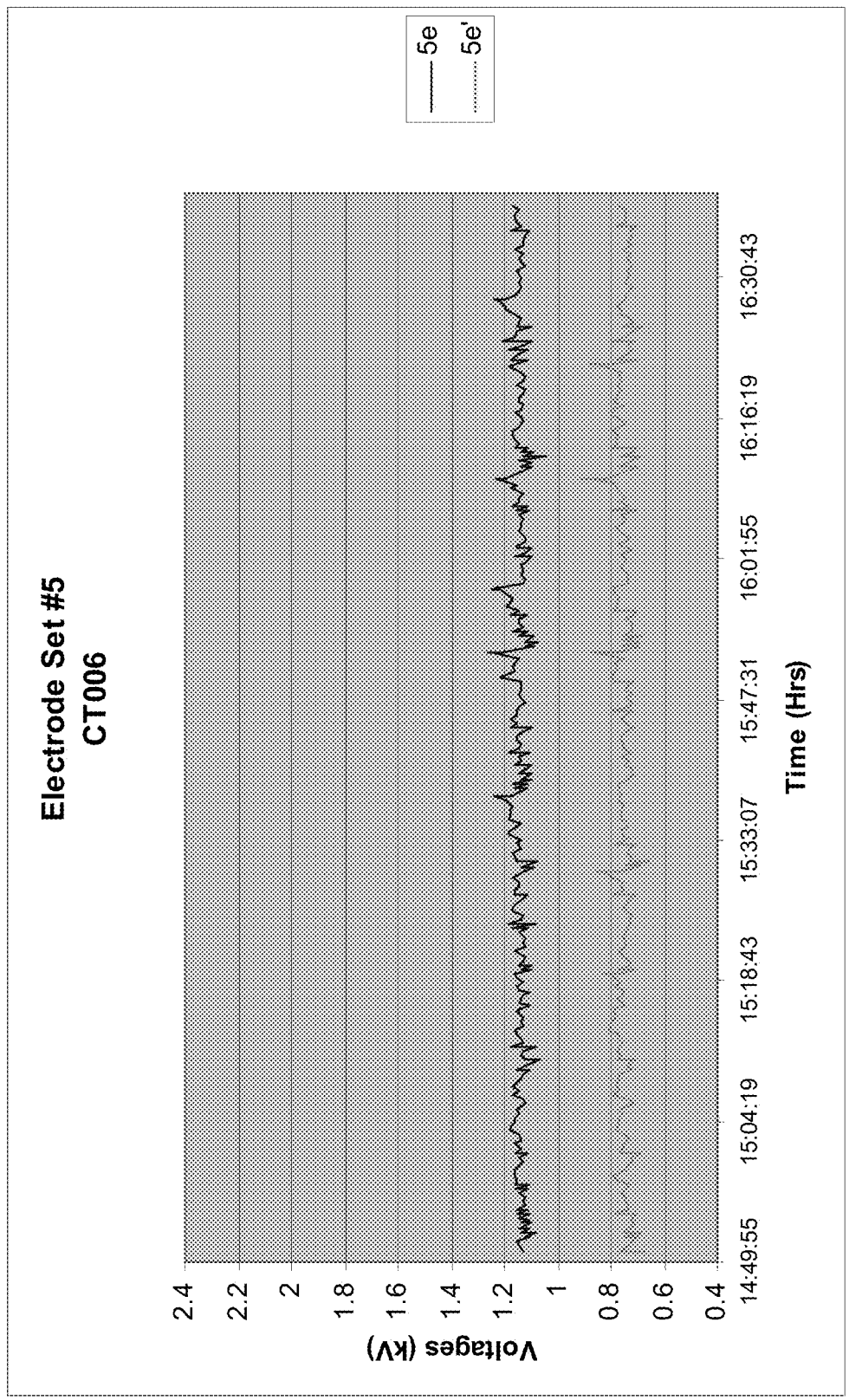
Figure 41G:
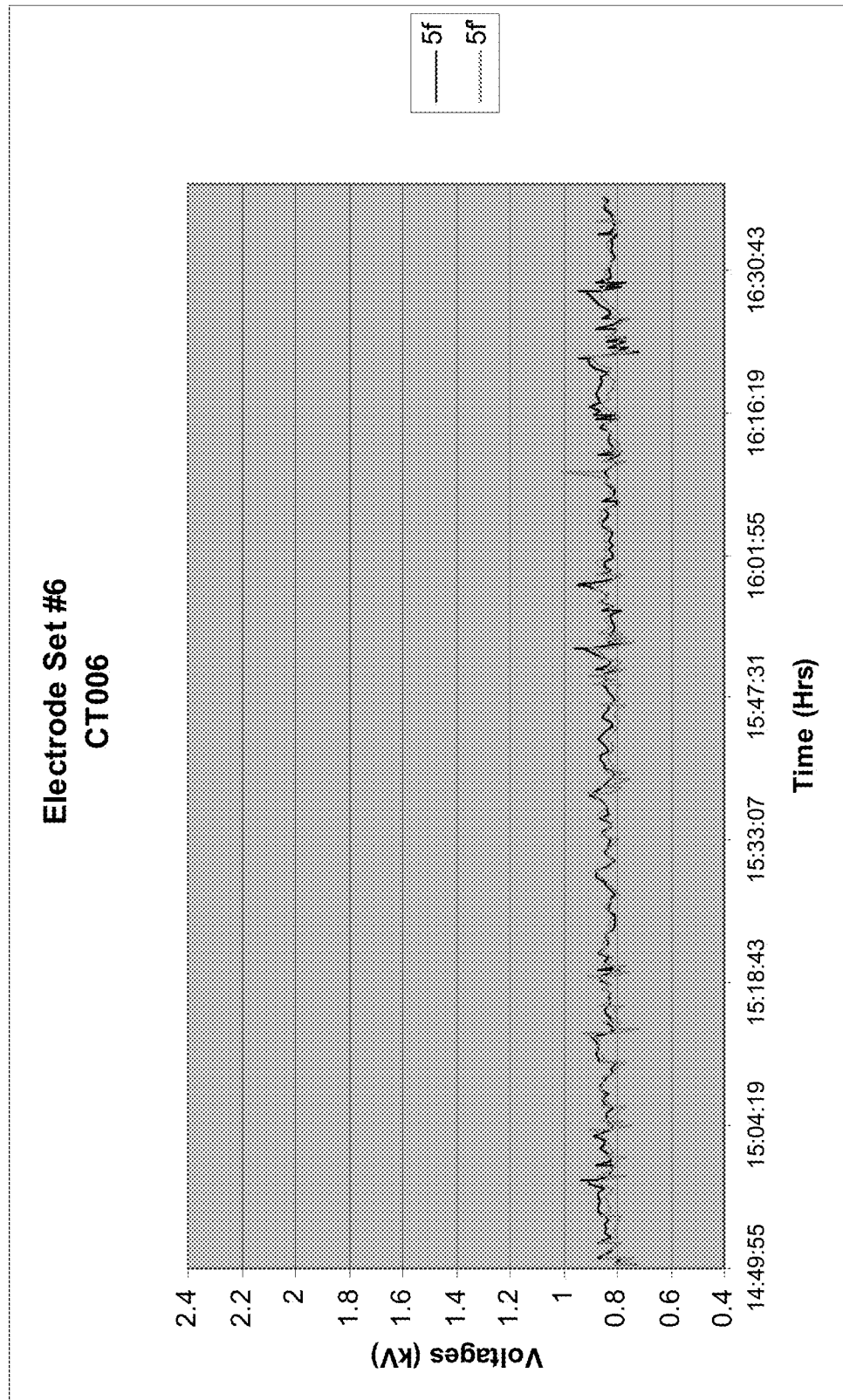
Figure 41H:
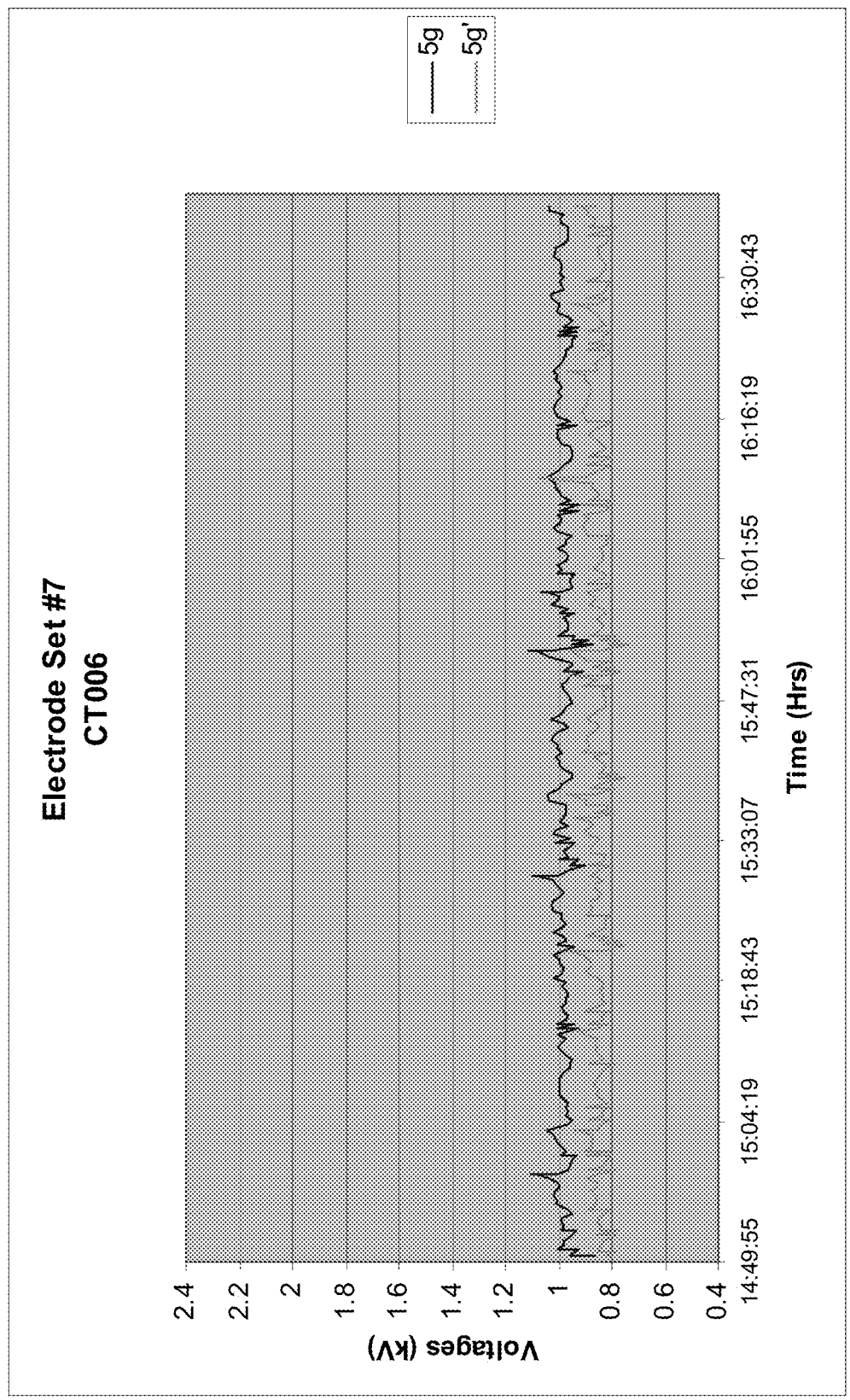
Figure 41I:
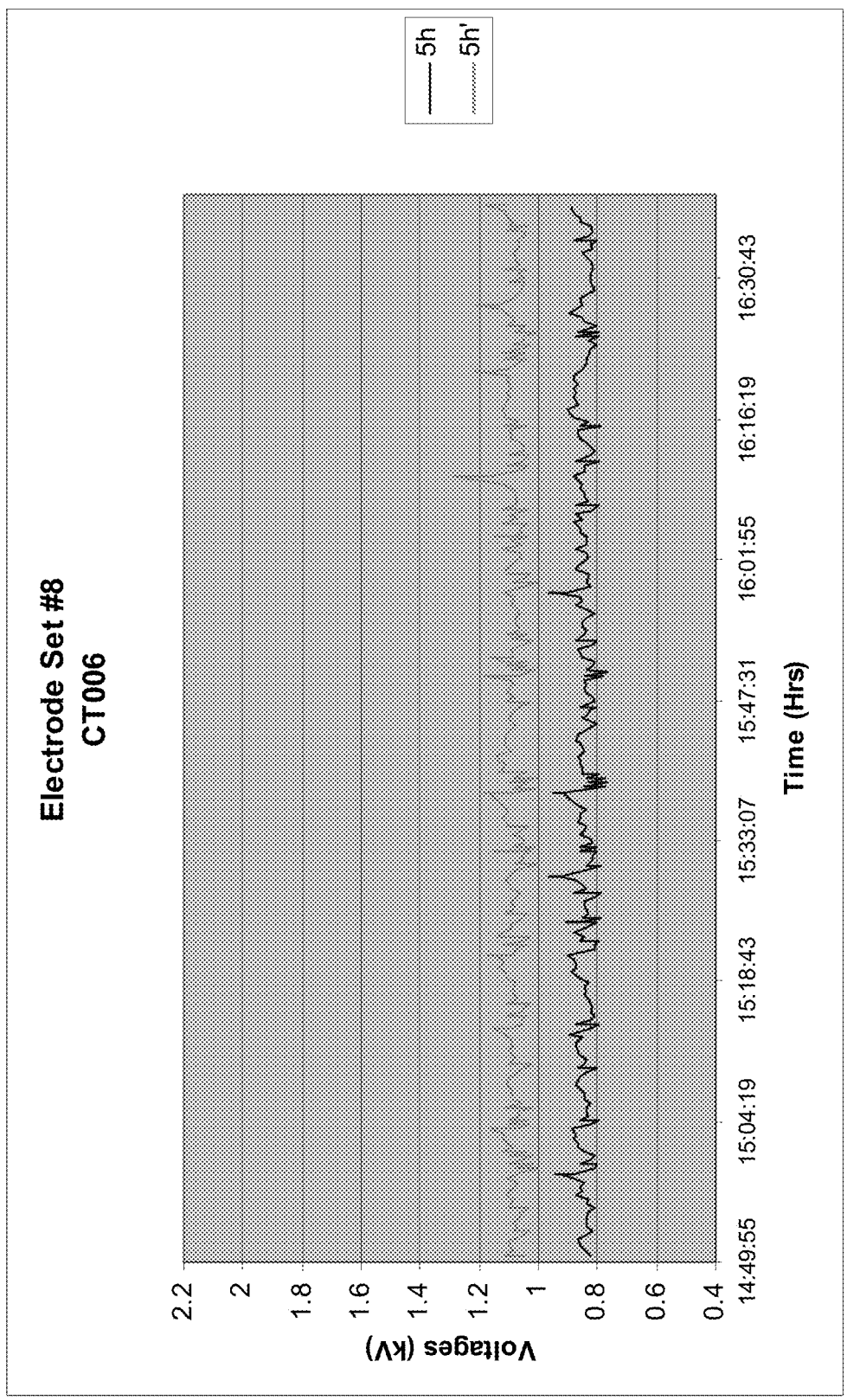
Figure 42A:
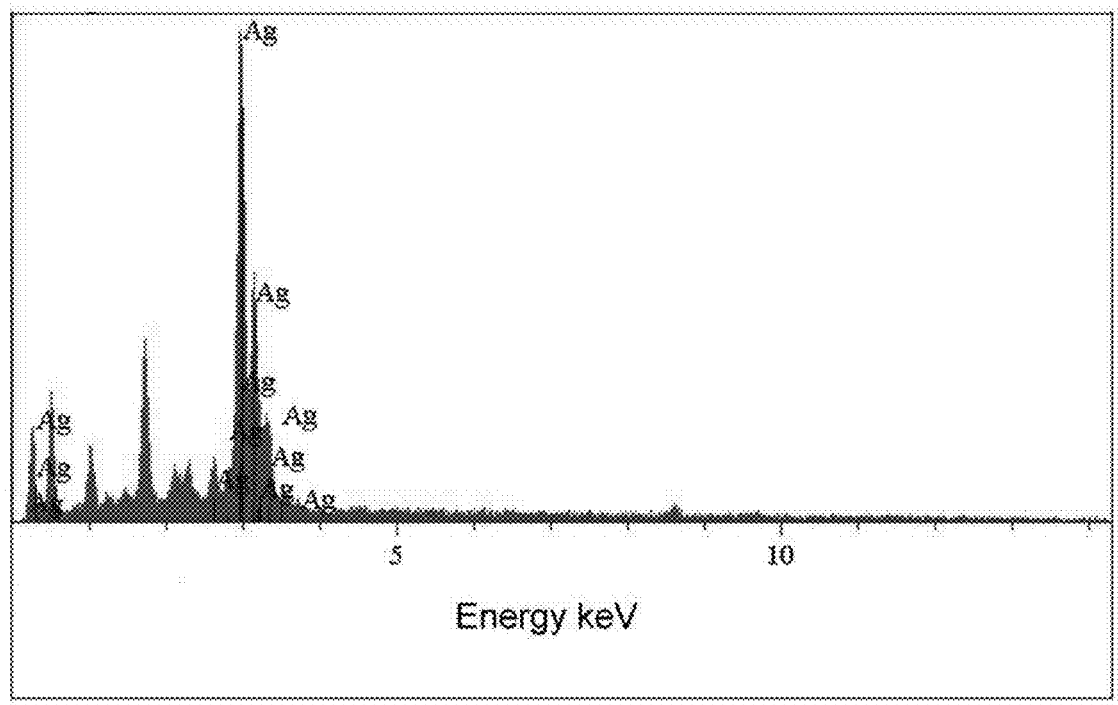
Figure 42B:
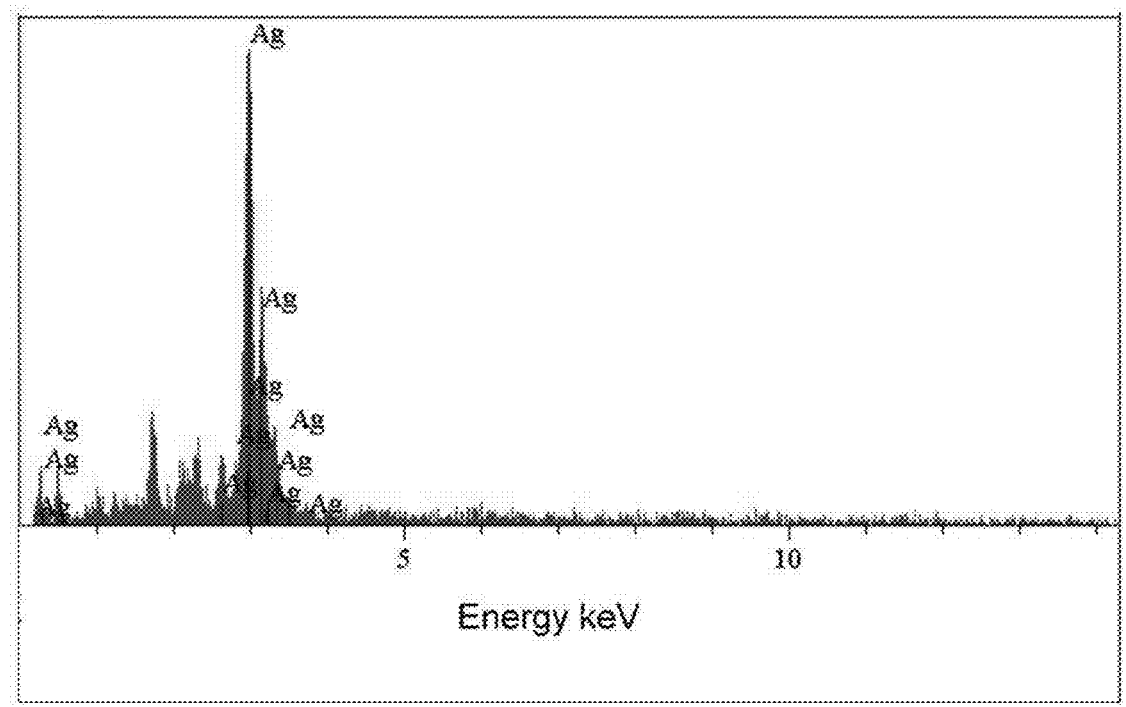
Figure 42C:
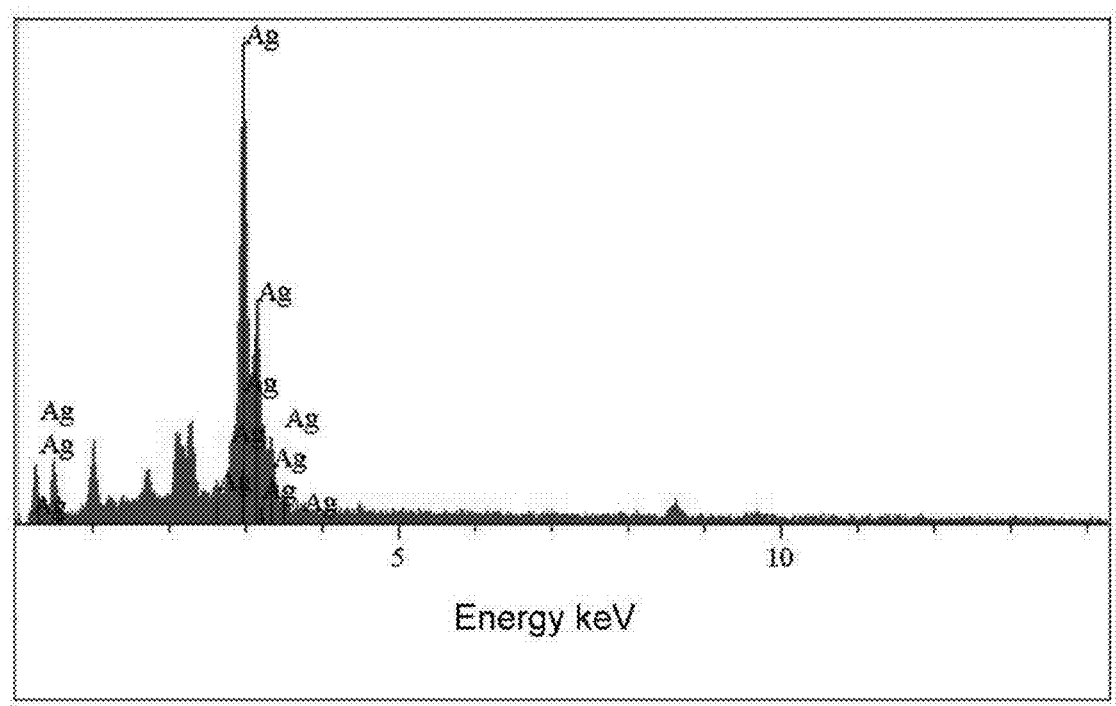
Figure 42D:
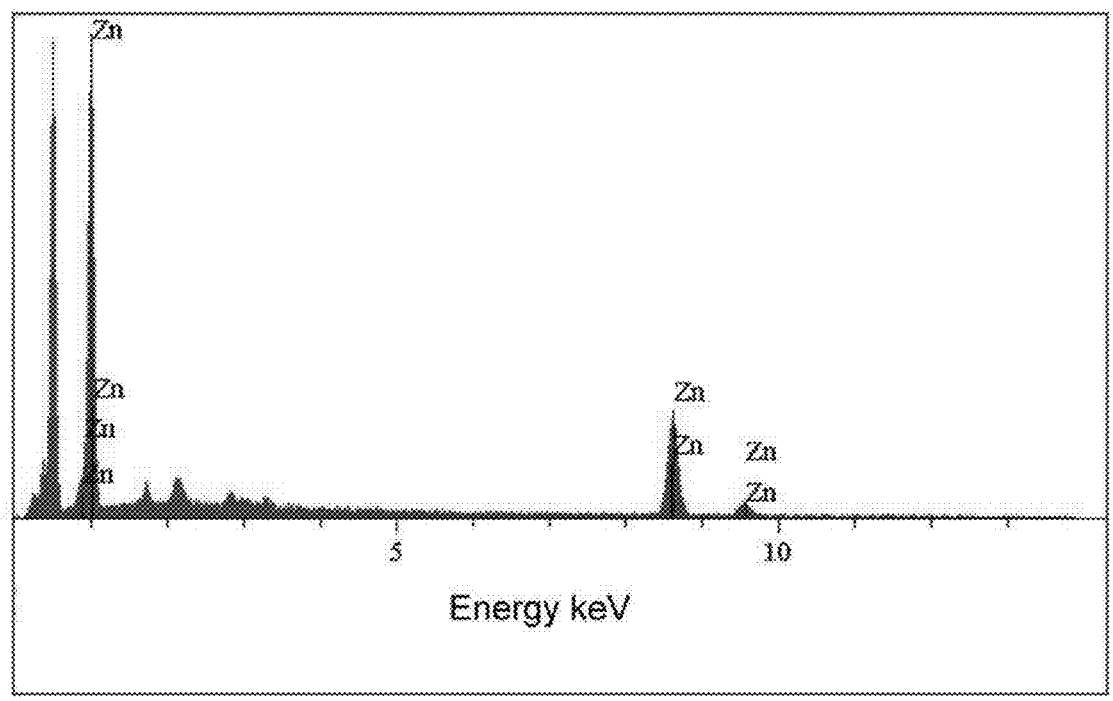
Figure 42E:
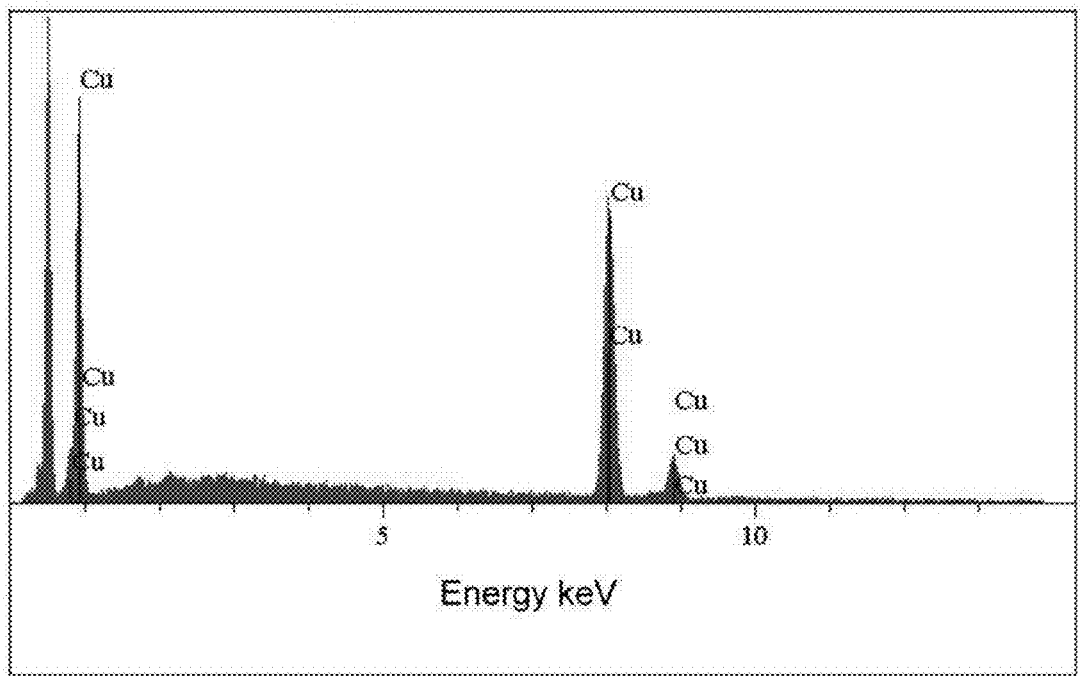
Figure 42F:
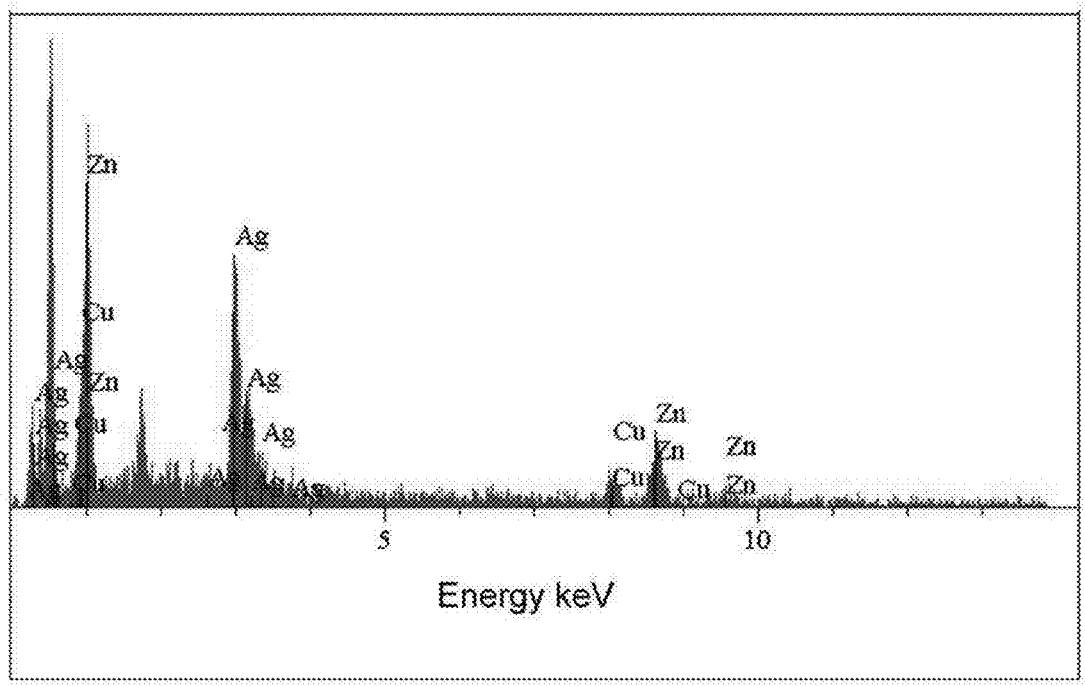
Figure 42G:
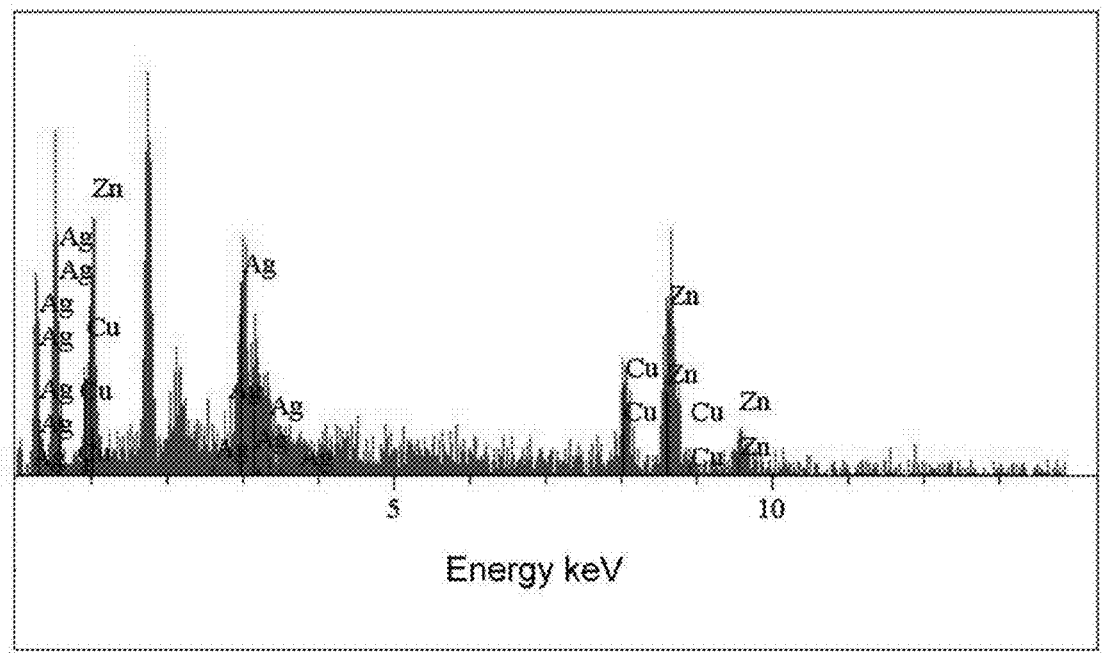
Figure 42H:
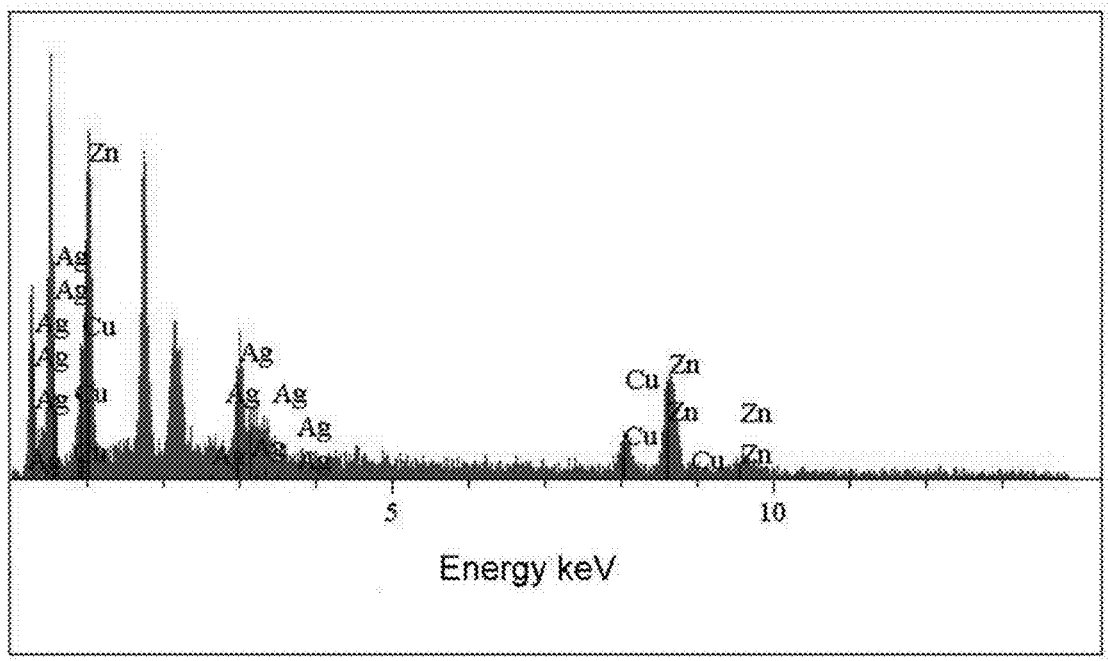
Figure 42I:
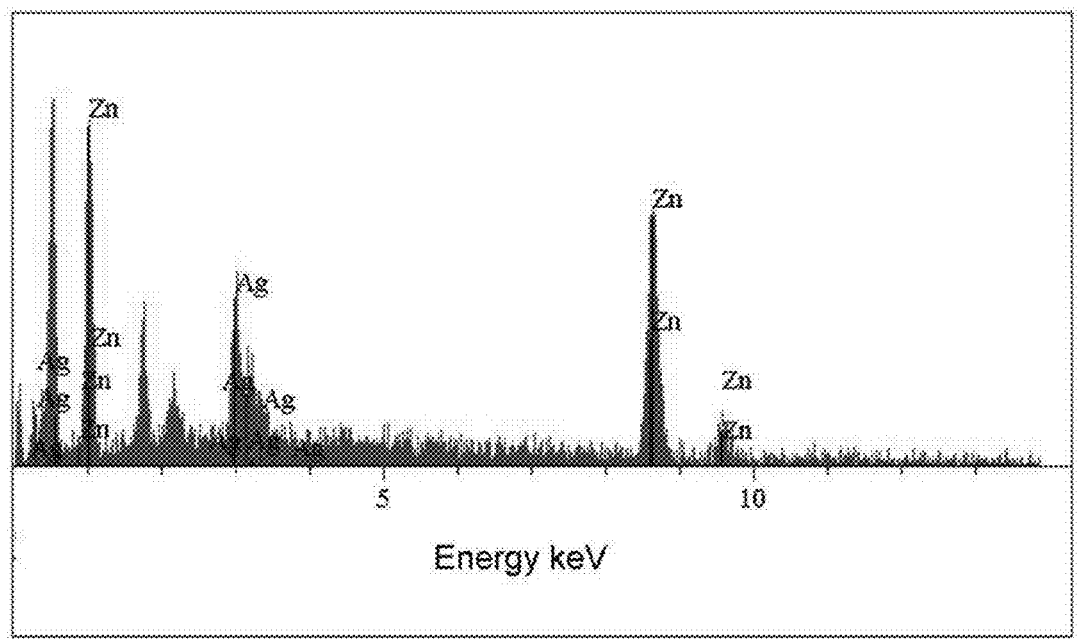
Figure 42J:
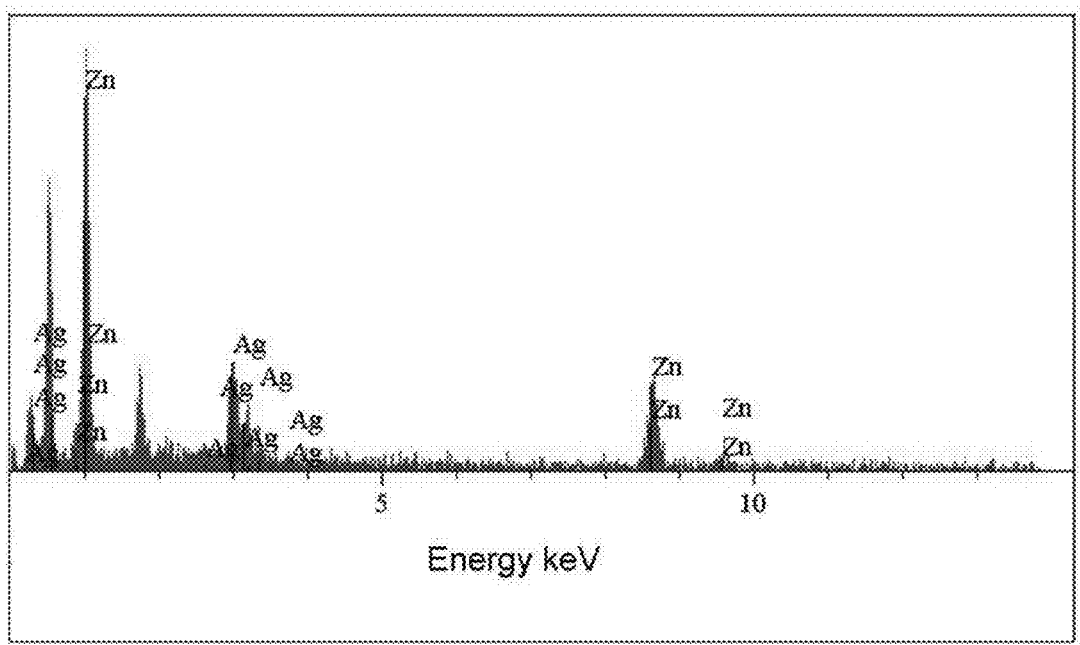
Figure 42K:
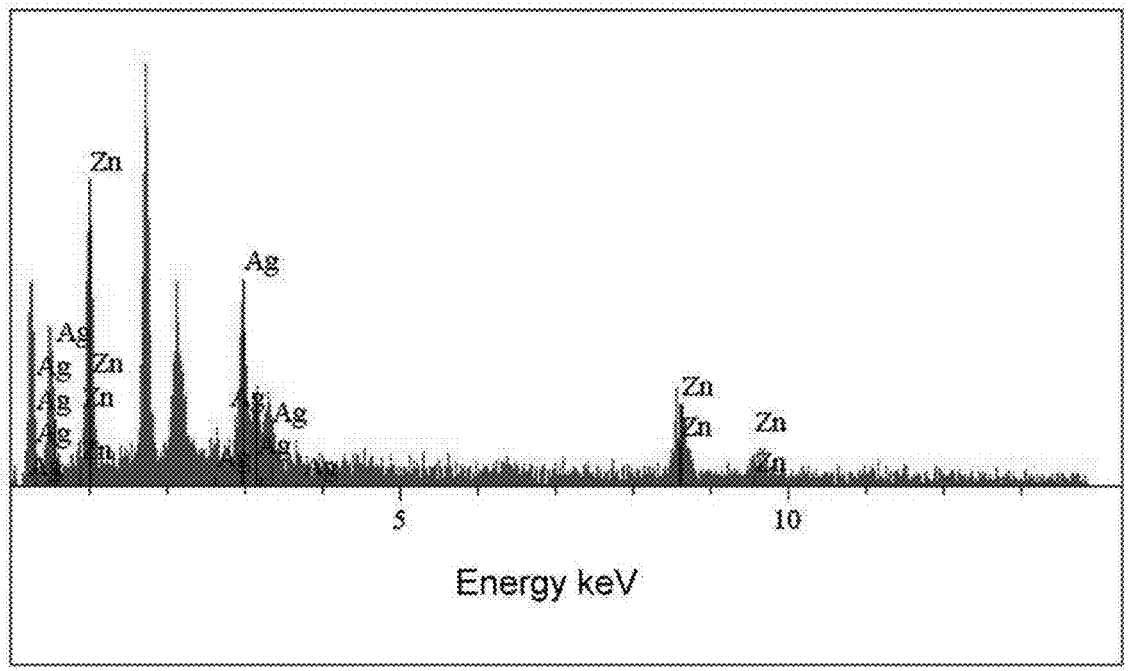
Figure 42L:
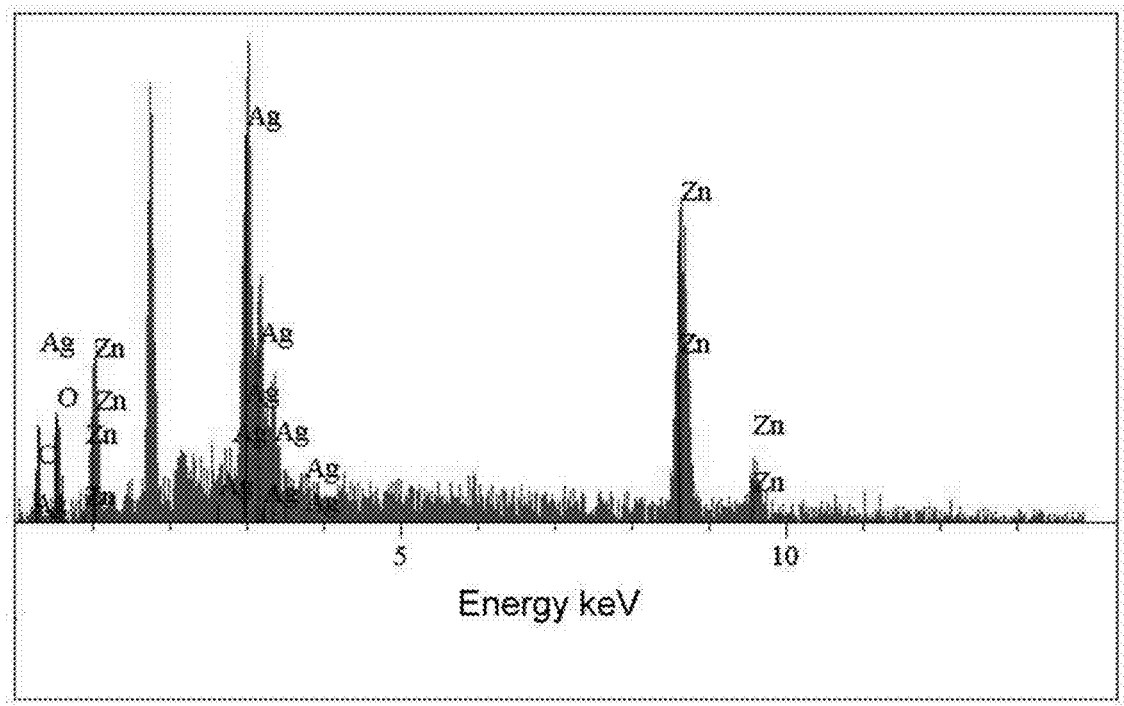
Figure 42M:
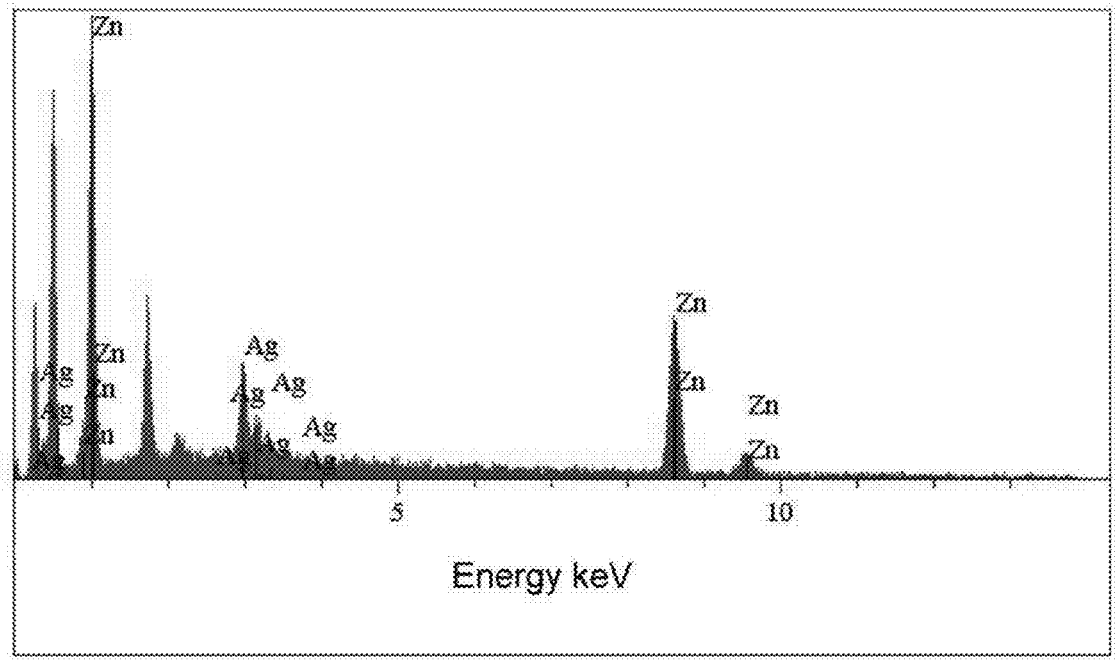
Figure 42N:
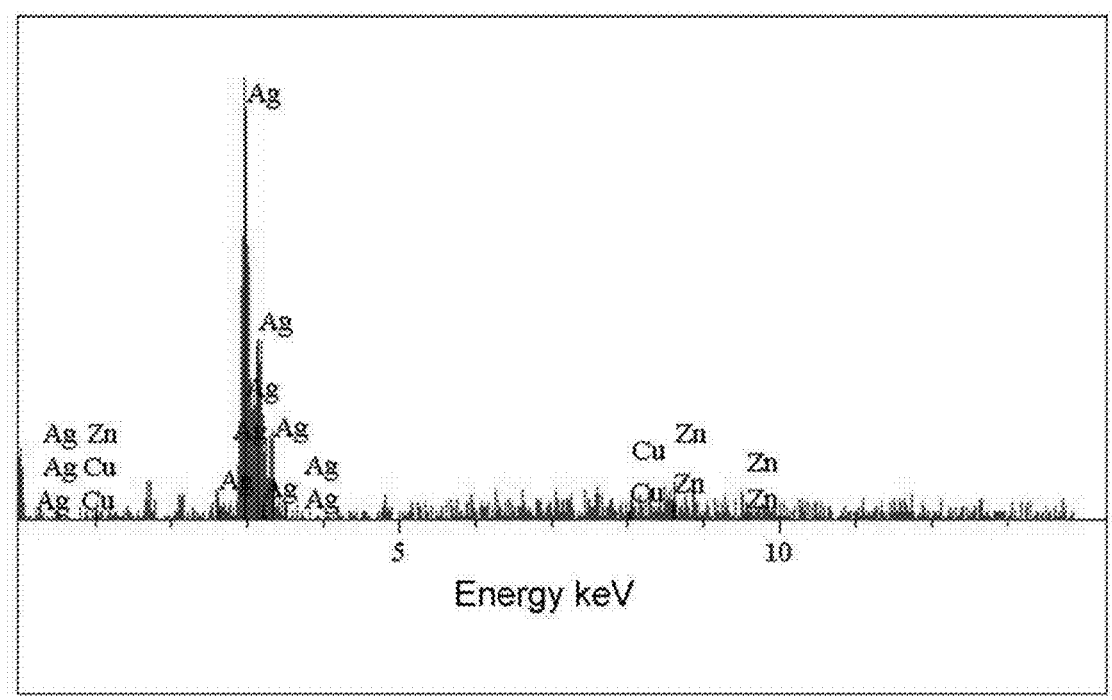
Figure 42O:
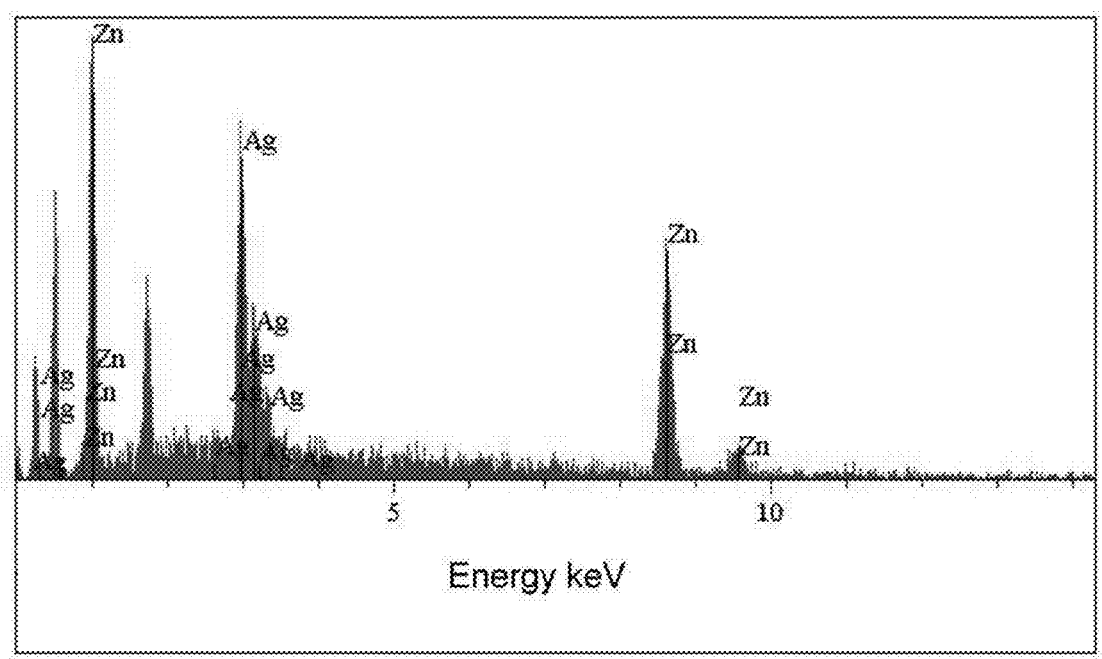

FIG. 41a shows a bar chart of various target and actual average voltages applied to 16 different electrodes in an 8 electrode set used in Example 5 to manufacture copper-based nanoparticles and nanoparticle solutions.

FIGS. 41b-41i show actual voltages applied as a function of time for the 16 different electrodes used in Example 5.

FIGS. 42a-e are SEM-EDS plots of the materials made in each of Examples 1-5, respectively.

FIGS. 42f-o correspond to 10 different solutions GR1-GR10 made utilizing the raw materials of Examples 1-5 (i.e., made according to Table 8 and Table 9).

FIGS. 43a(i-iv)-43e(i-iv) are SEM photomicrographs at 4 different magnifications in each Figure corresponding to the raw materials of Examples 1-5, respectively.

Figure 43F:
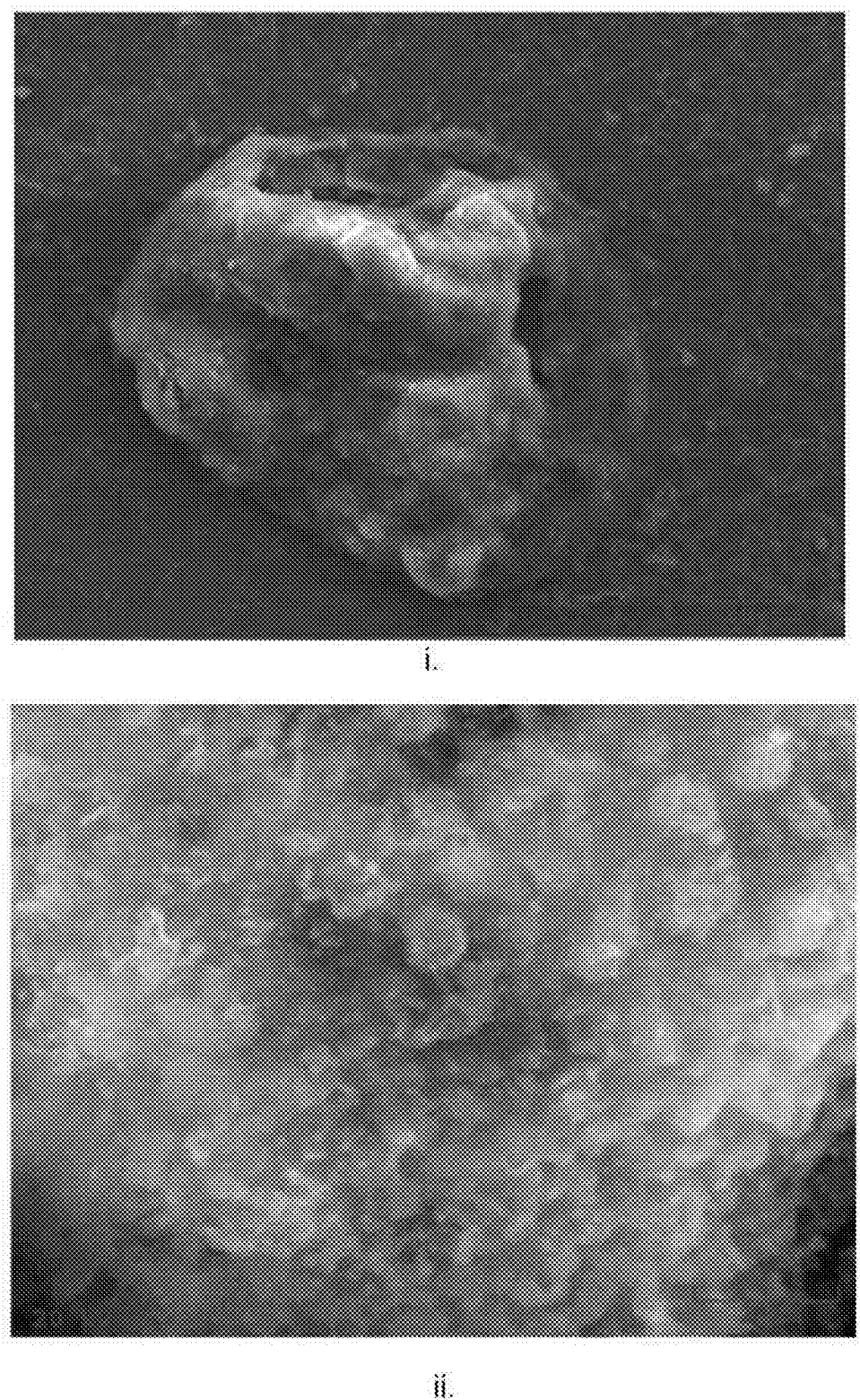
Figure 43H:
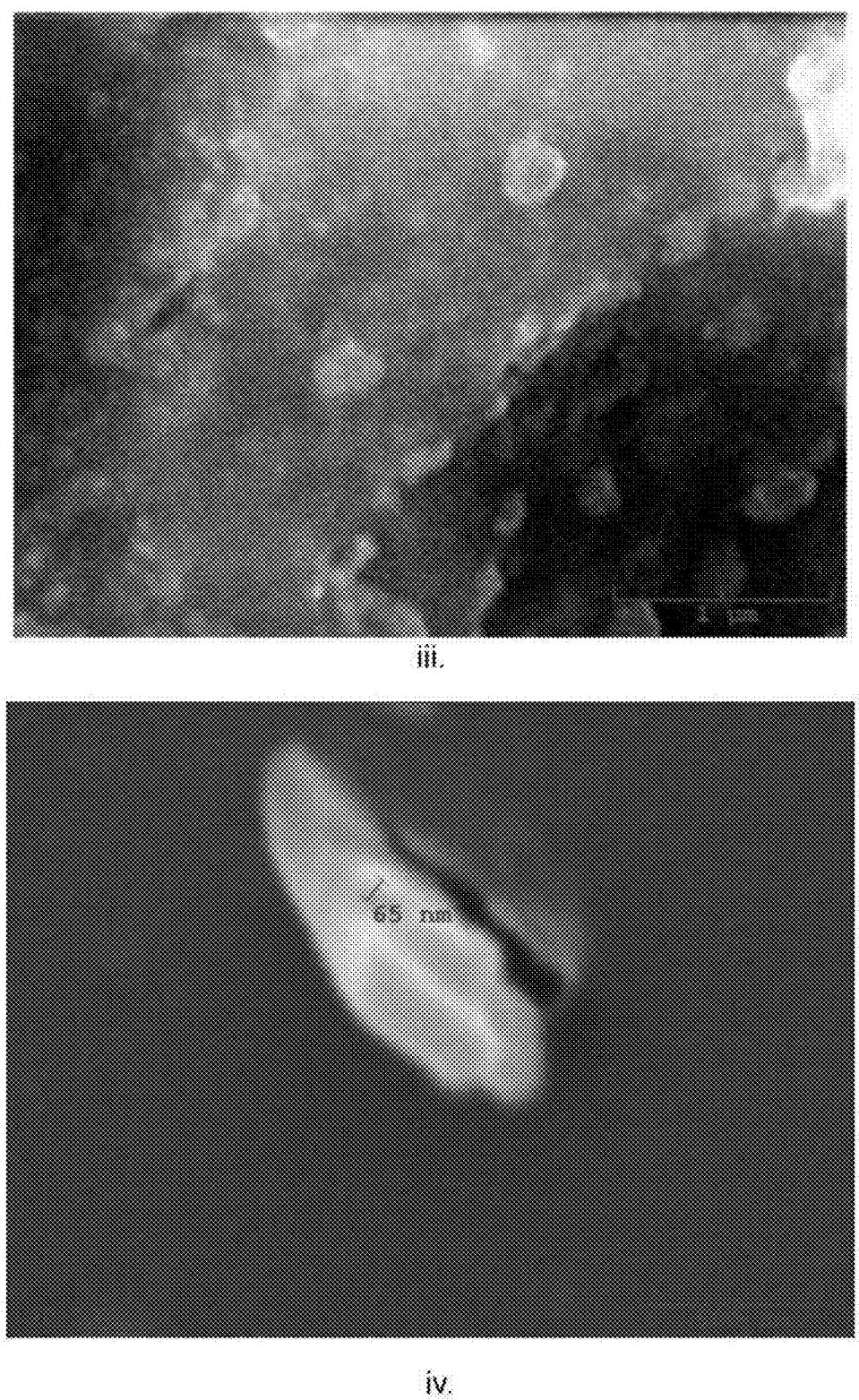
Figure 43I:
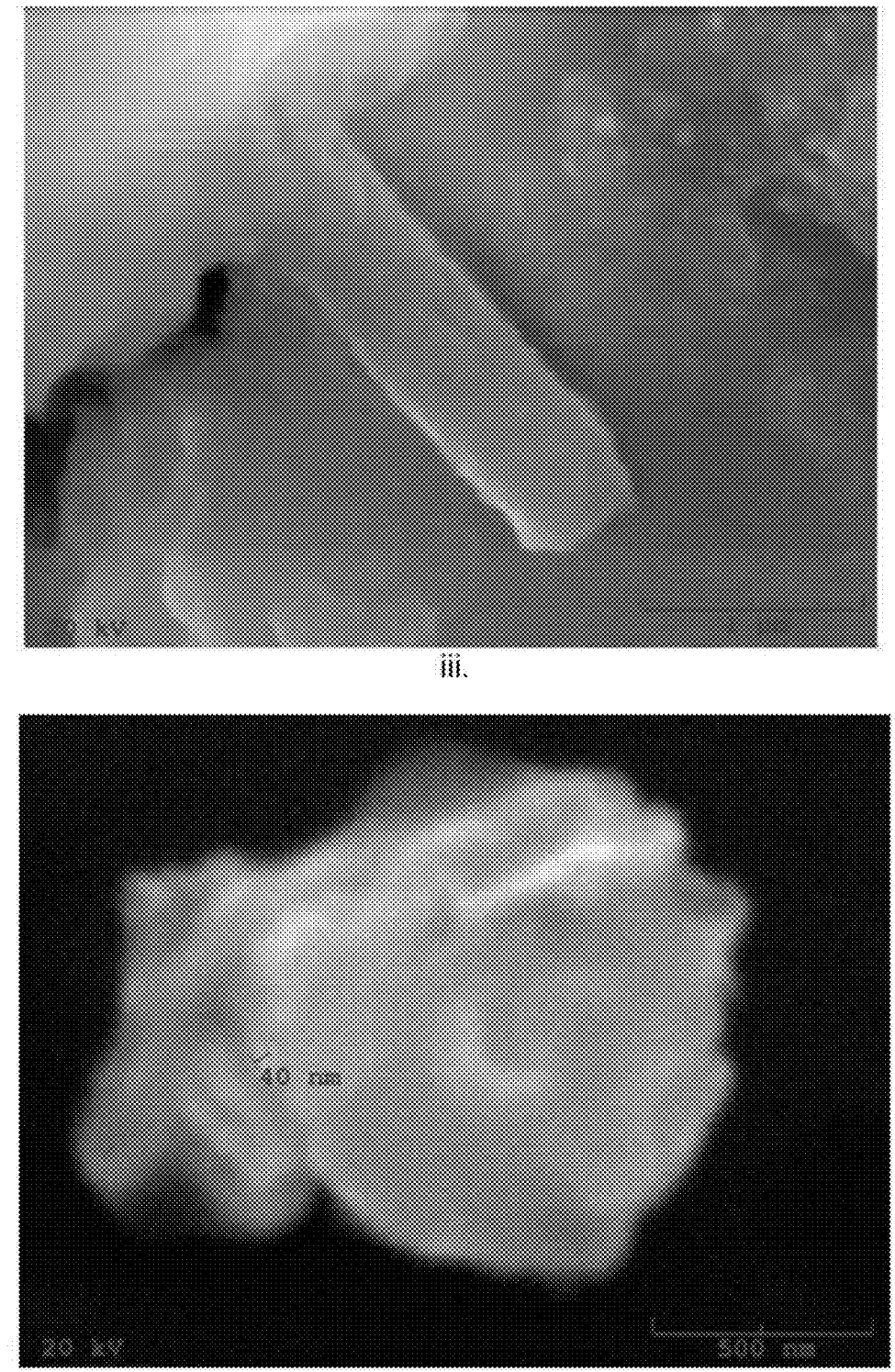

FIGS. 43f(i-iv)-43o(i-iv) are SEM photomicrographs at 4 different magnifications in each Figure corresponding to the solutions GR1-GR10 disclosed in Table 8 and Table 9.

Figure 43P:
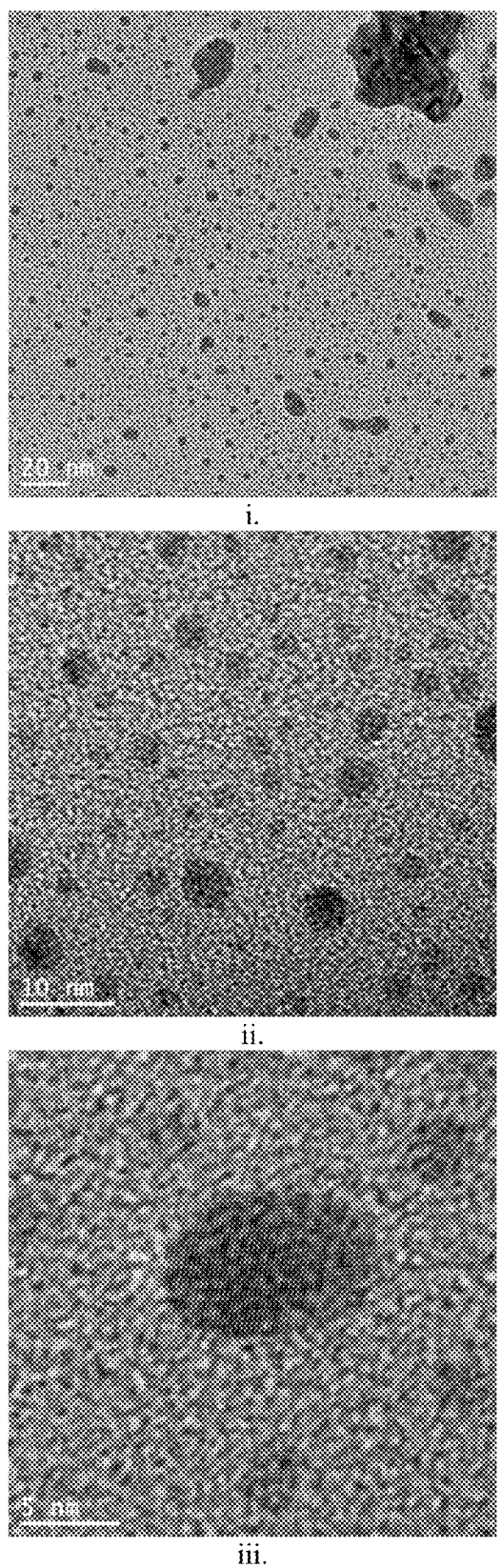

FIGS. 43p(i)-43p(iii) disclose three different magnification TEM photomicrographs of a silver constituent made corresponding to the production parameters used to manufacture AT031.

Figure 43Q:
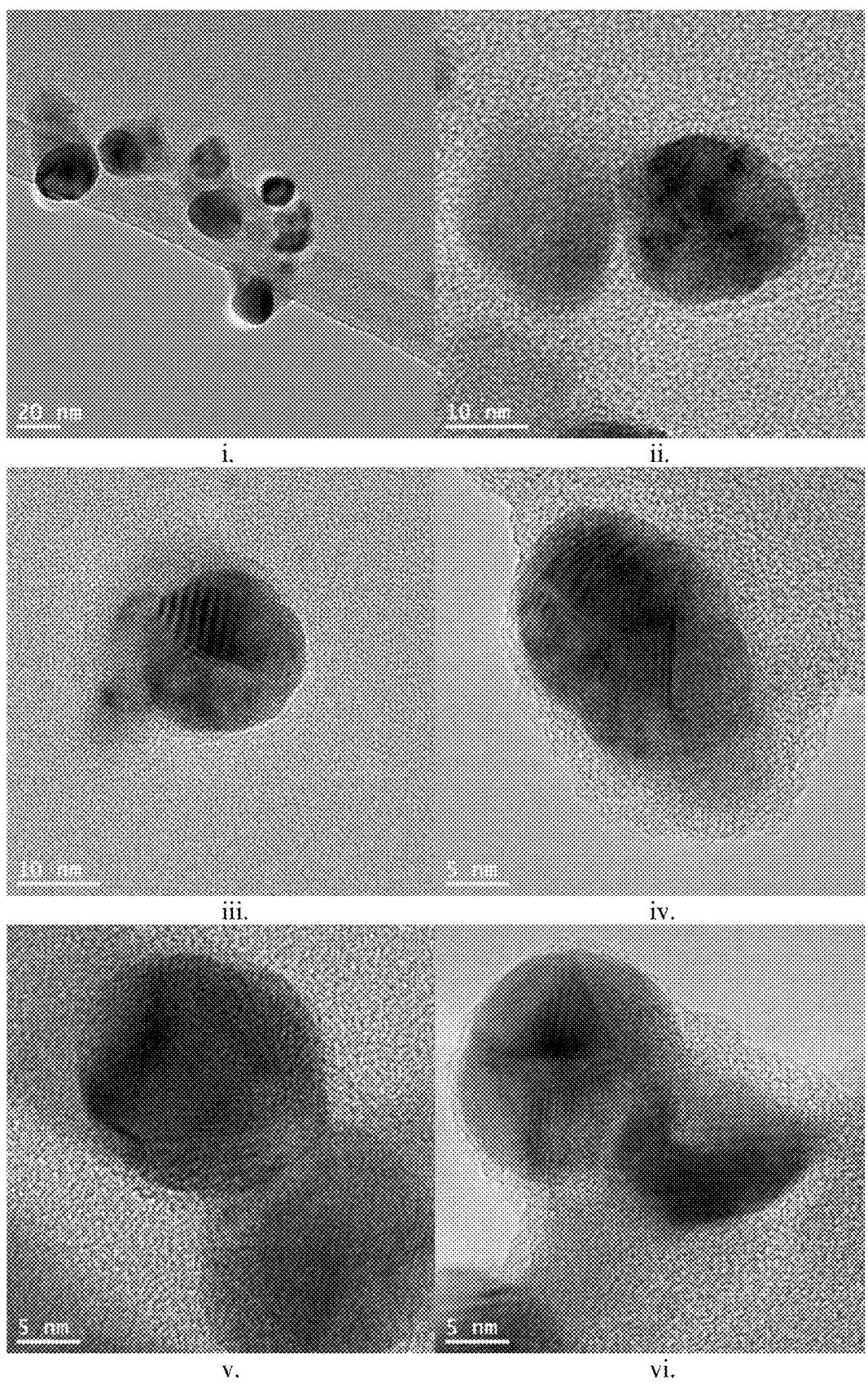

FIGS. 43q(i)-43q(vi) disclose six different TEM photomicrographs taken at three different magnifications of a silver constituent made corresponding to the production parameters used to manufacture AT060.

Figure 43R:
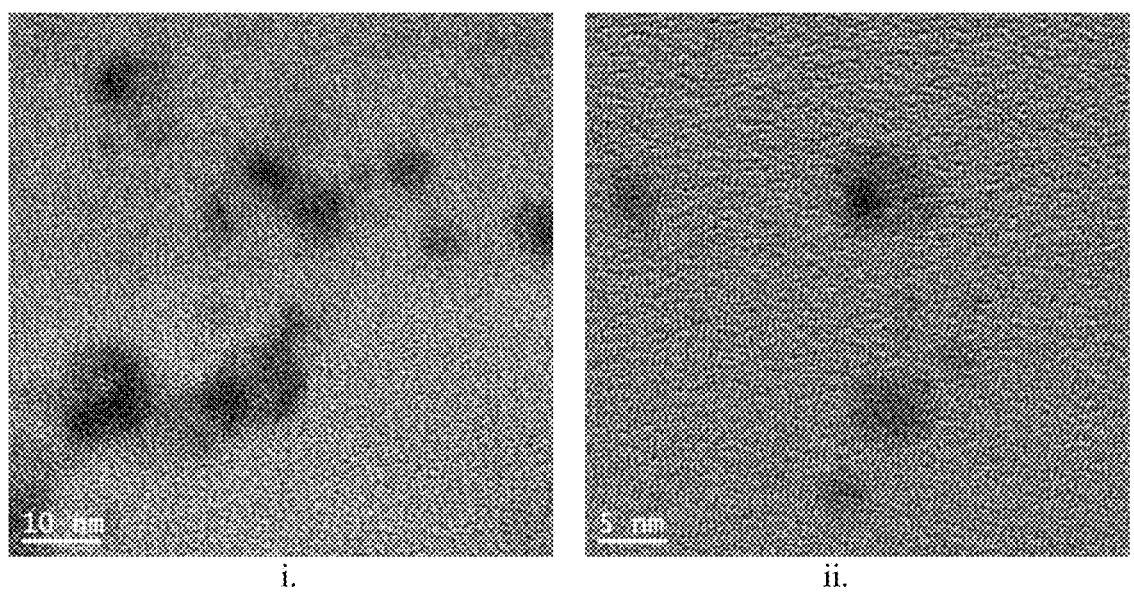

FIGS. 43r(i)-43r(ii) disclose two different TEM photomicrographs taken at two different magnifications of a zinc constituent made according to the production parameters used to manufacture BT006.

Figure 43S:
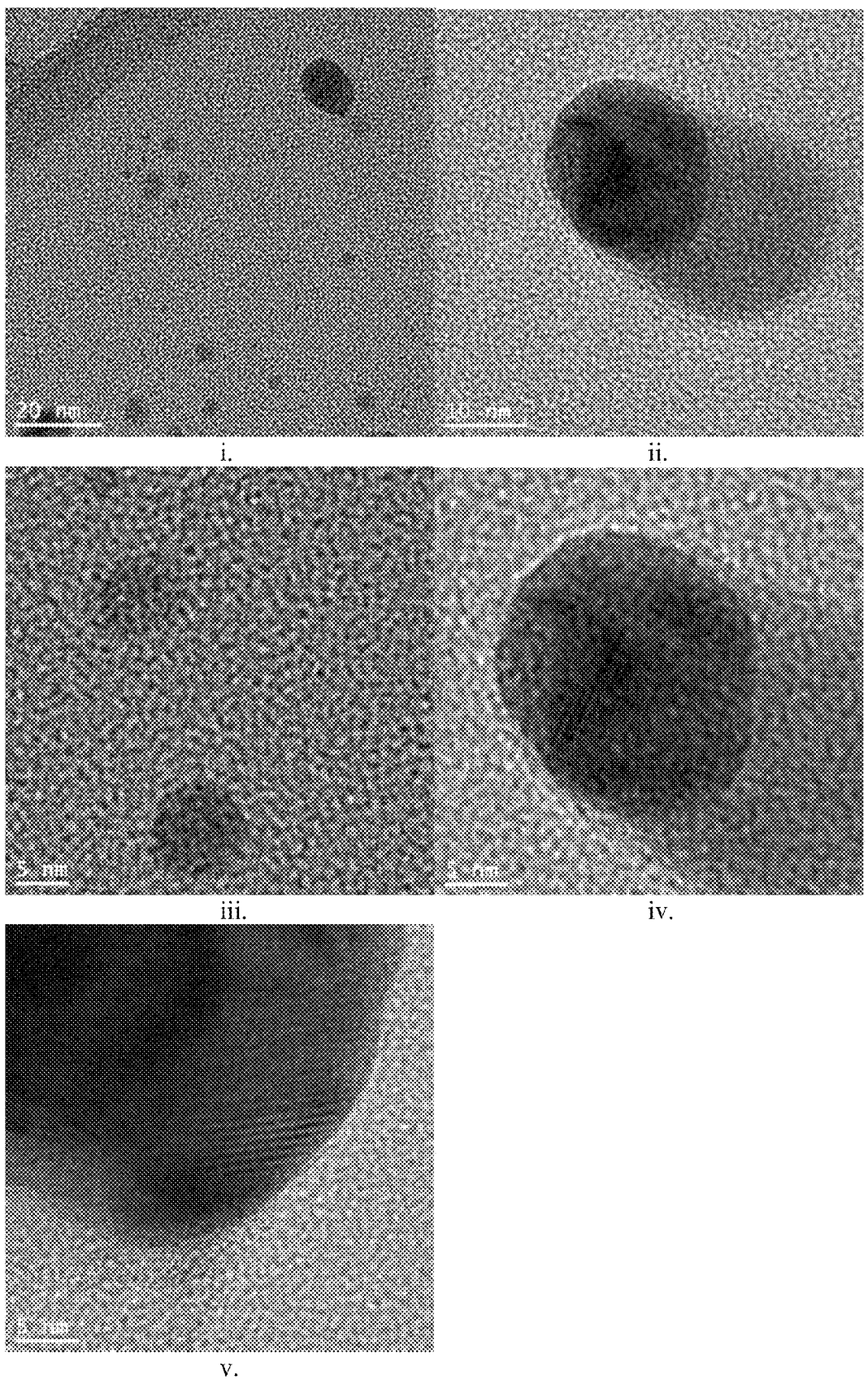

FIGS. 43s(i)-43s(v) disclose five different TEM photomicrographs taken at three different magnifications of a solution GR5.

Figure 43T:
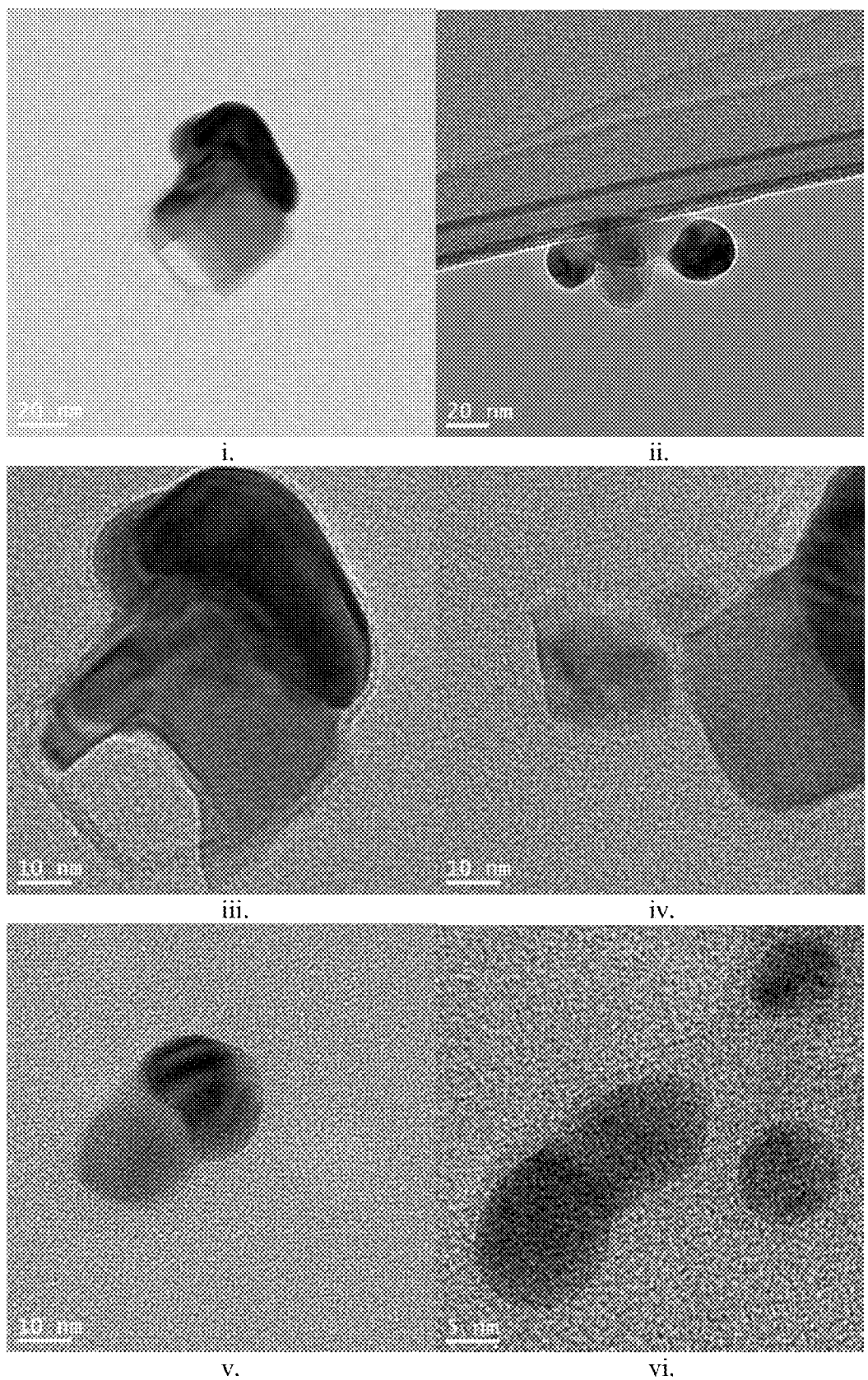
Figure 43T:
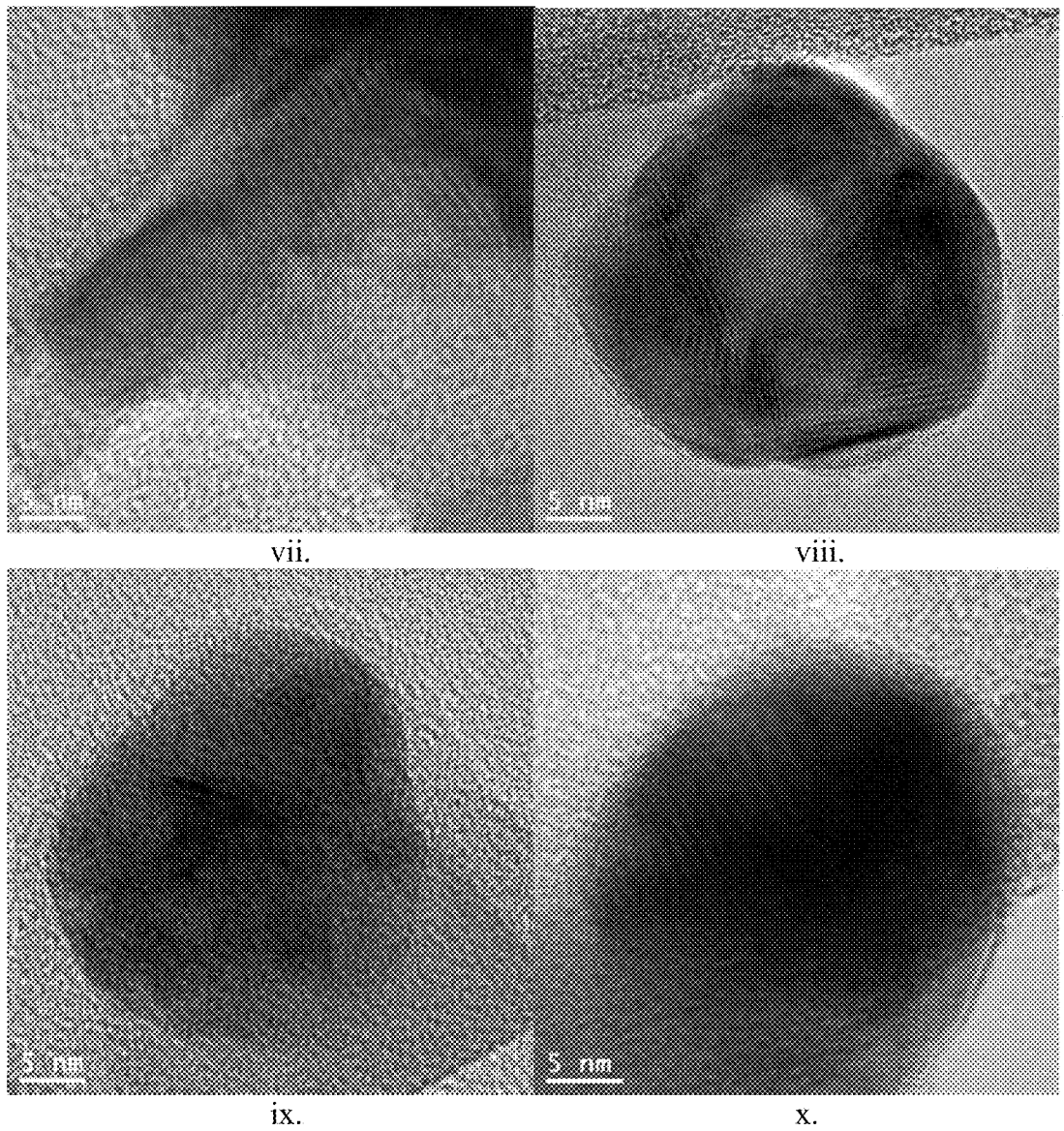

FIGS. 43t(i)-43t(x) disclose ten different TEM photomicrographs taken at three different magnifications of a solution GR8.

Figure 44A:
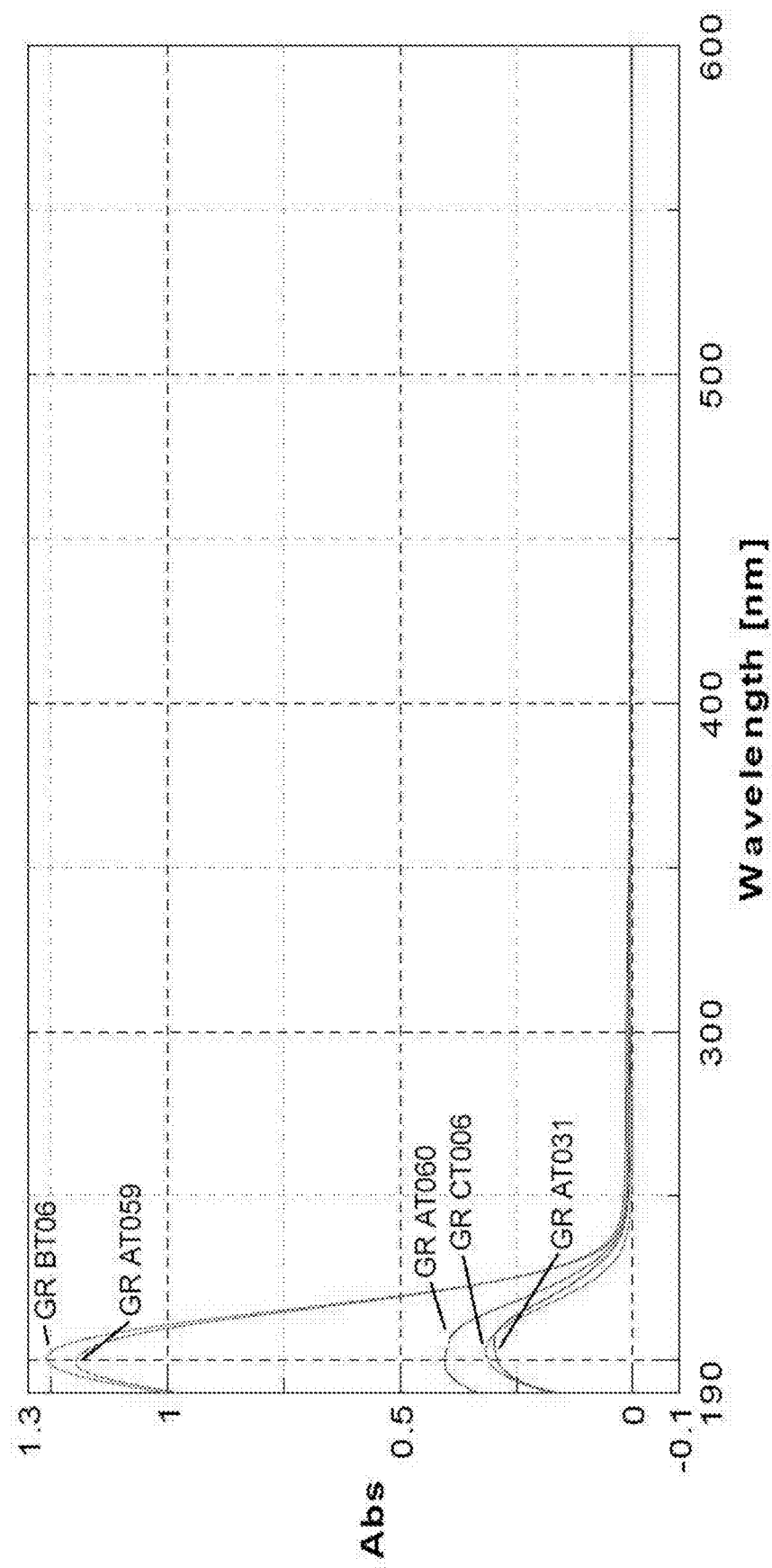

FIG. 44a shows 5 UV-Vis spectra of the raw materials made according to Examples 1-5.

FIGS. 44b-44e show UV-Vis spectra of the 10 different solutions GR1-GR10 shown in Table 8 and Table 9 made with the raw materials according to Examples 1-5.

Figure 45:
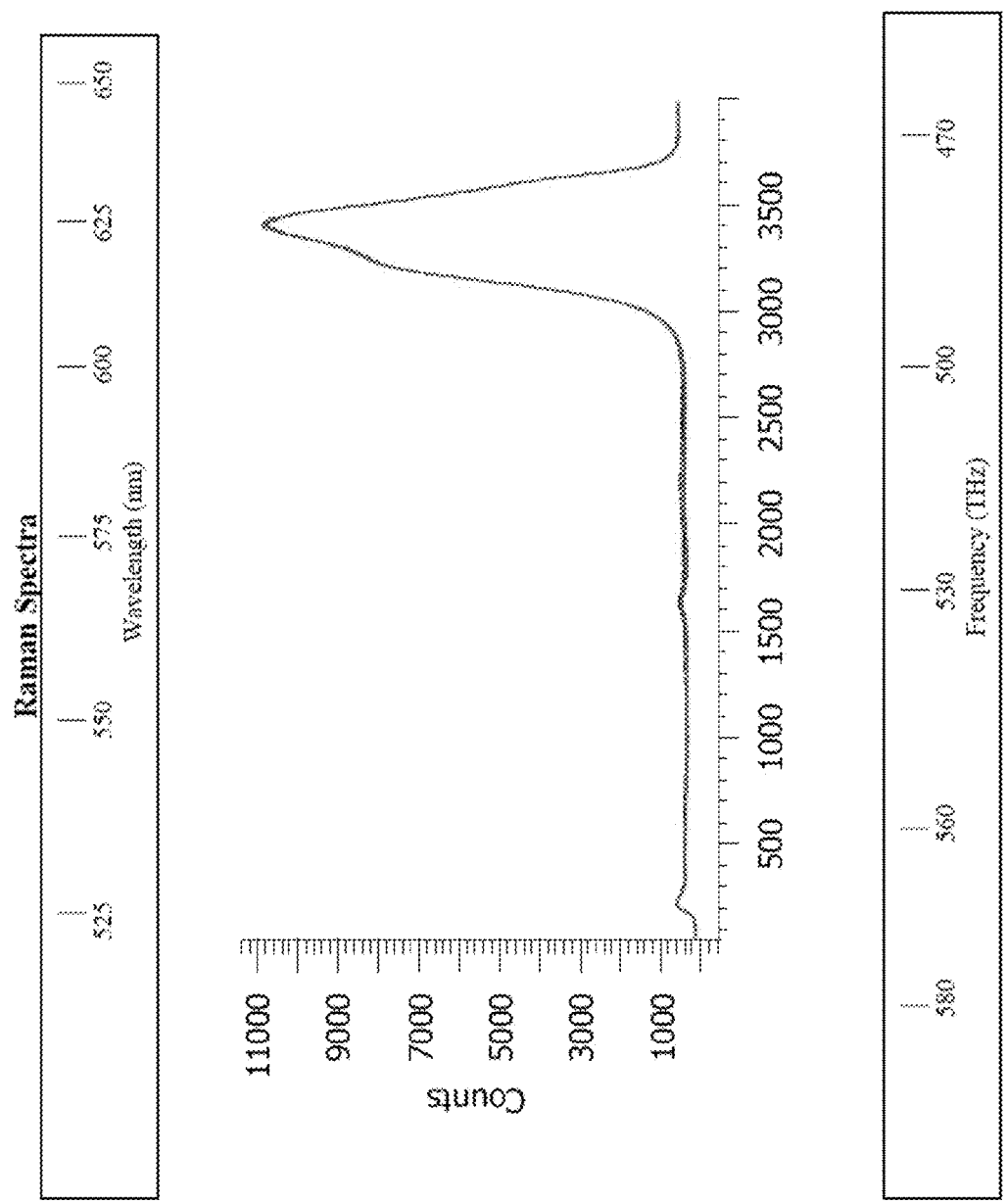

FIG. 45 shows a raman spectra of each of the 10 solutions GR1-GR10 shown in Table 8 and Table 9.

Figure 46:
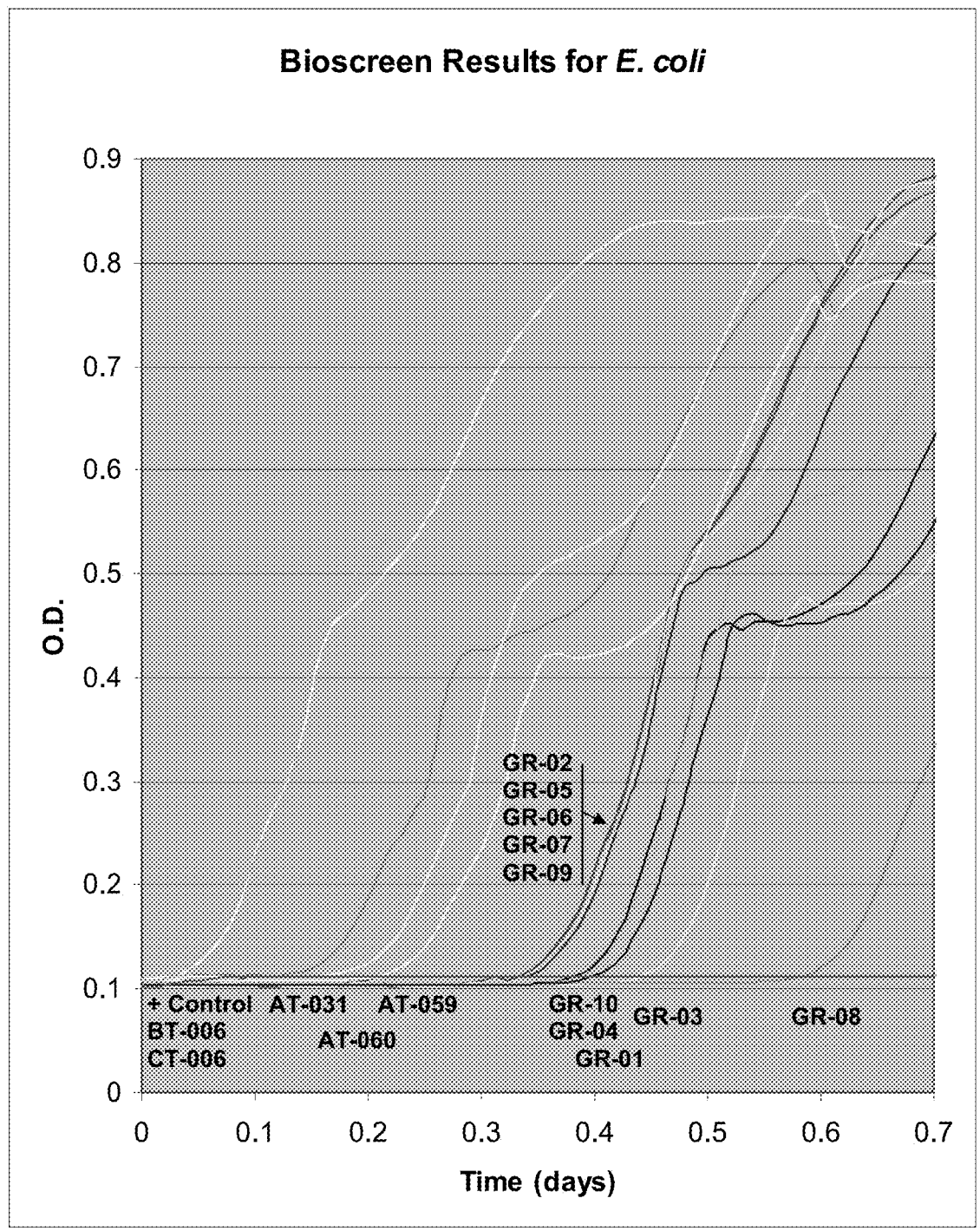

FIG. 46 shows biological Bioscreen results for E. coli against the raw materials of Examples 1-5 and the solutions GR1-GR10 shown in Table 8 and Table 9.

Figure 47:
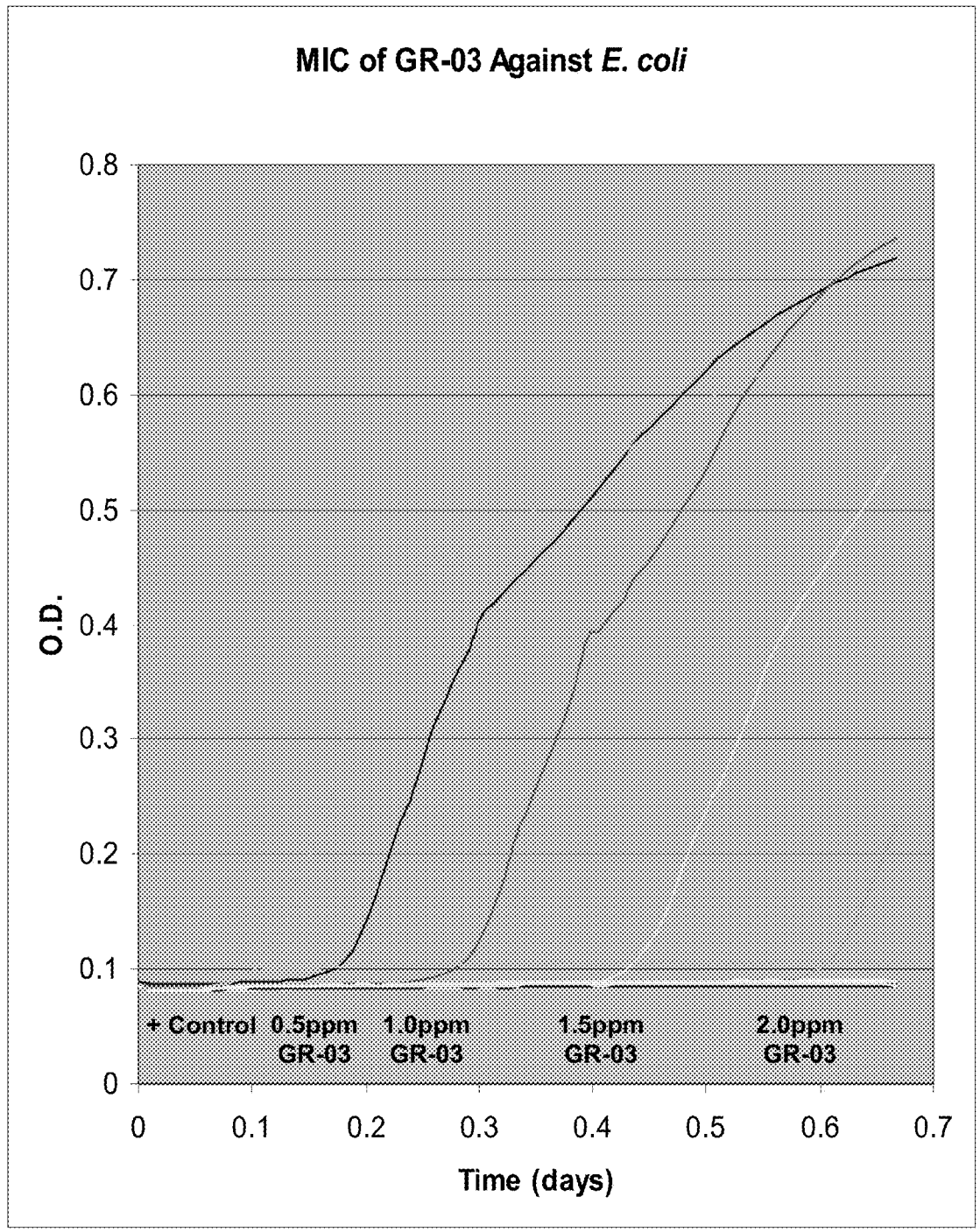

FIG. 47 shows biological minimum inhibitory concentration ("MIC") results obtained with a Bioscreen device utilizing GR3 against e. coli; optimal density is plotted as a function of time.

Figure 48:
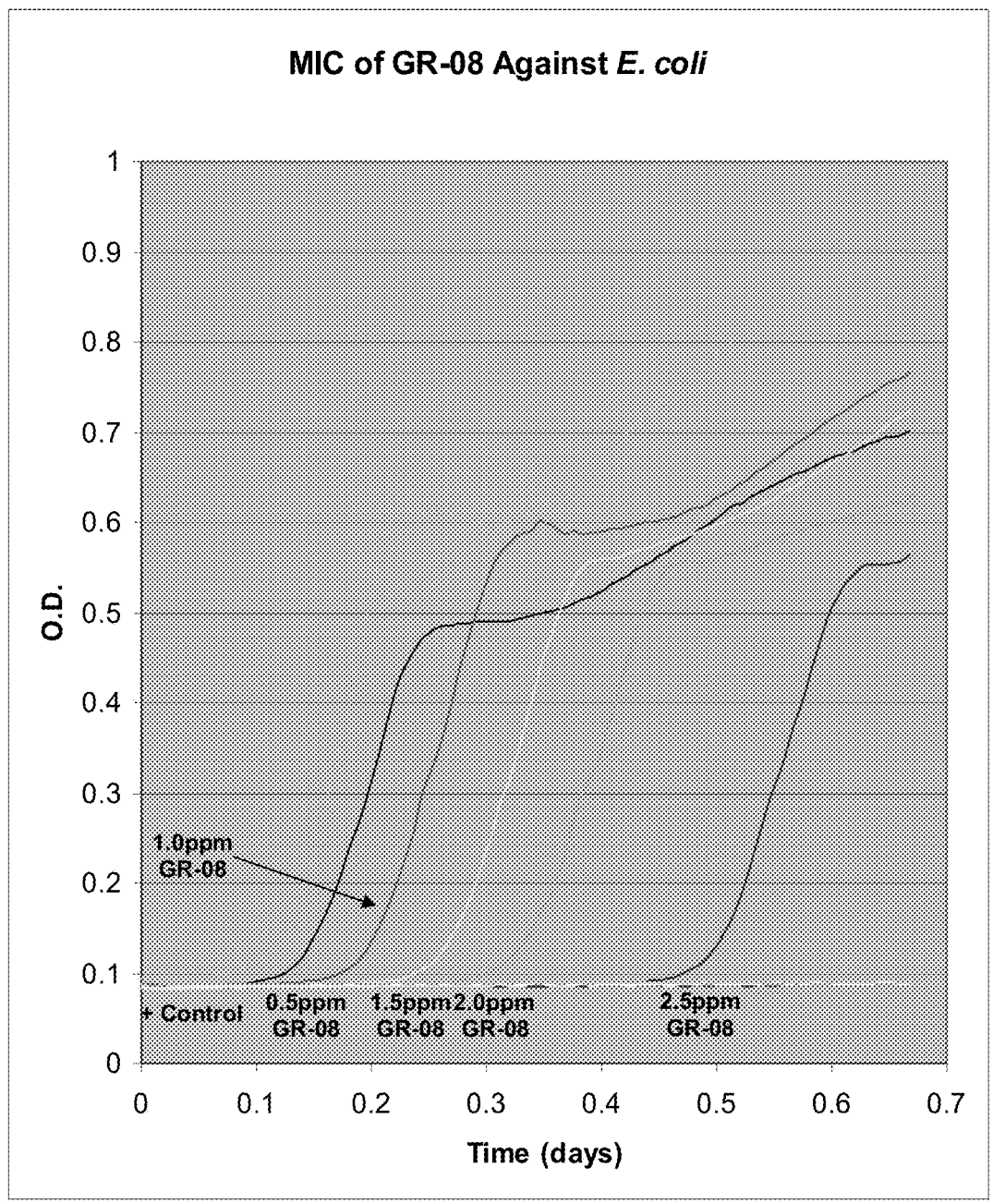

FIG. 48 shows biological minimum inhibitory concentration ("MIC") results obtained with a Bioscreen device utilizing GR8 against e. coli; optimal density is plotted as a function of time.

Figure 49:
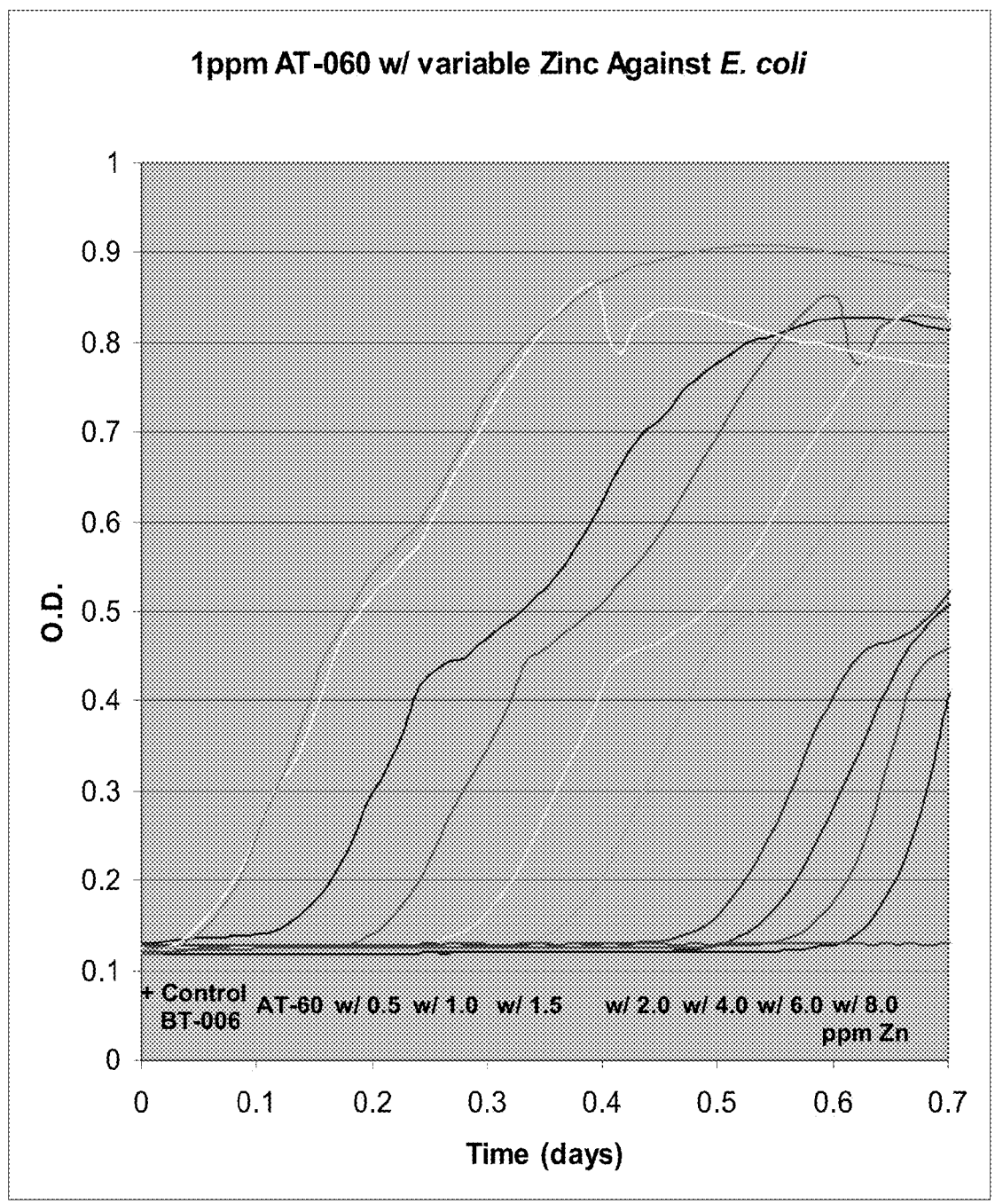
Figure 50A:
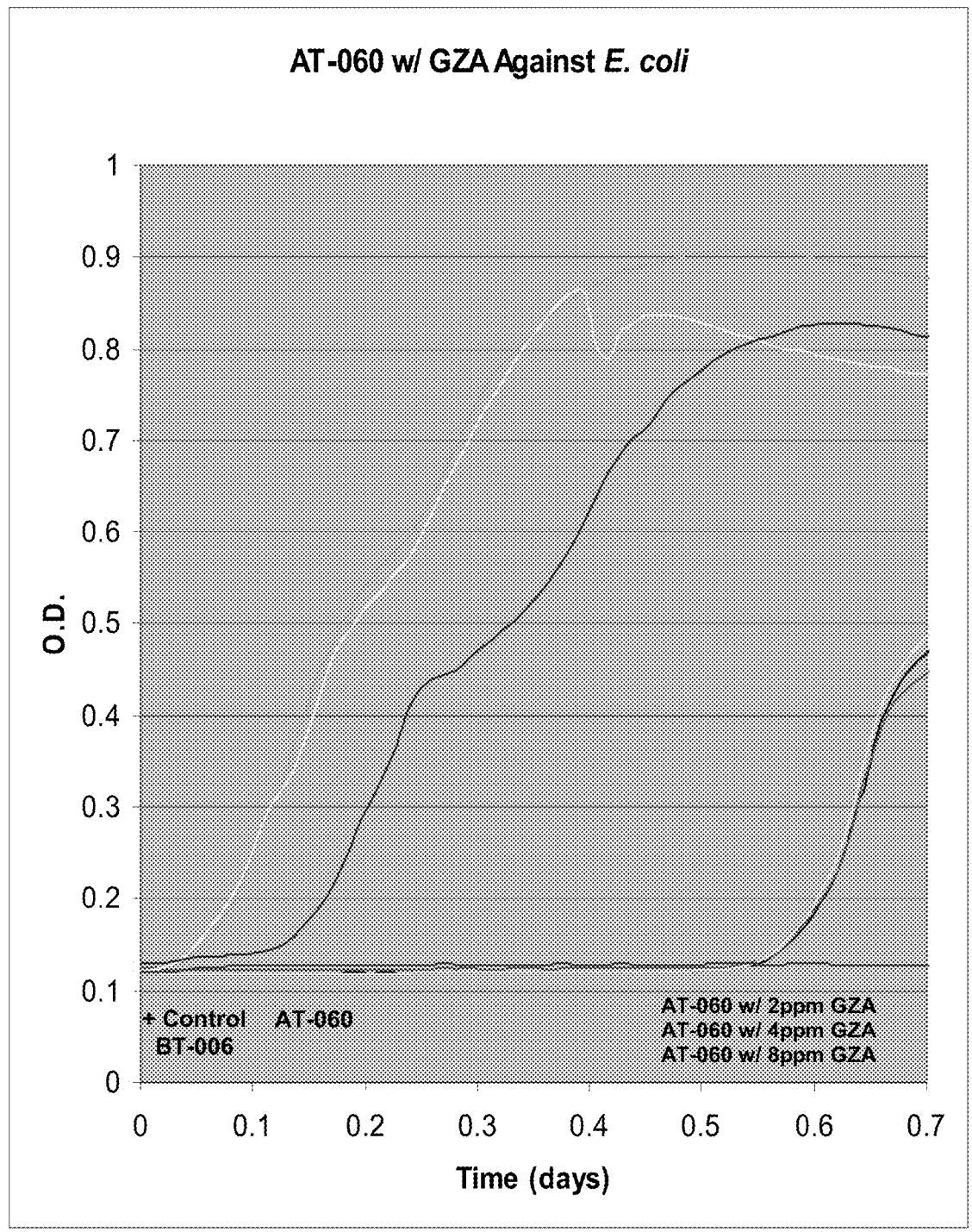
Figure 50B:
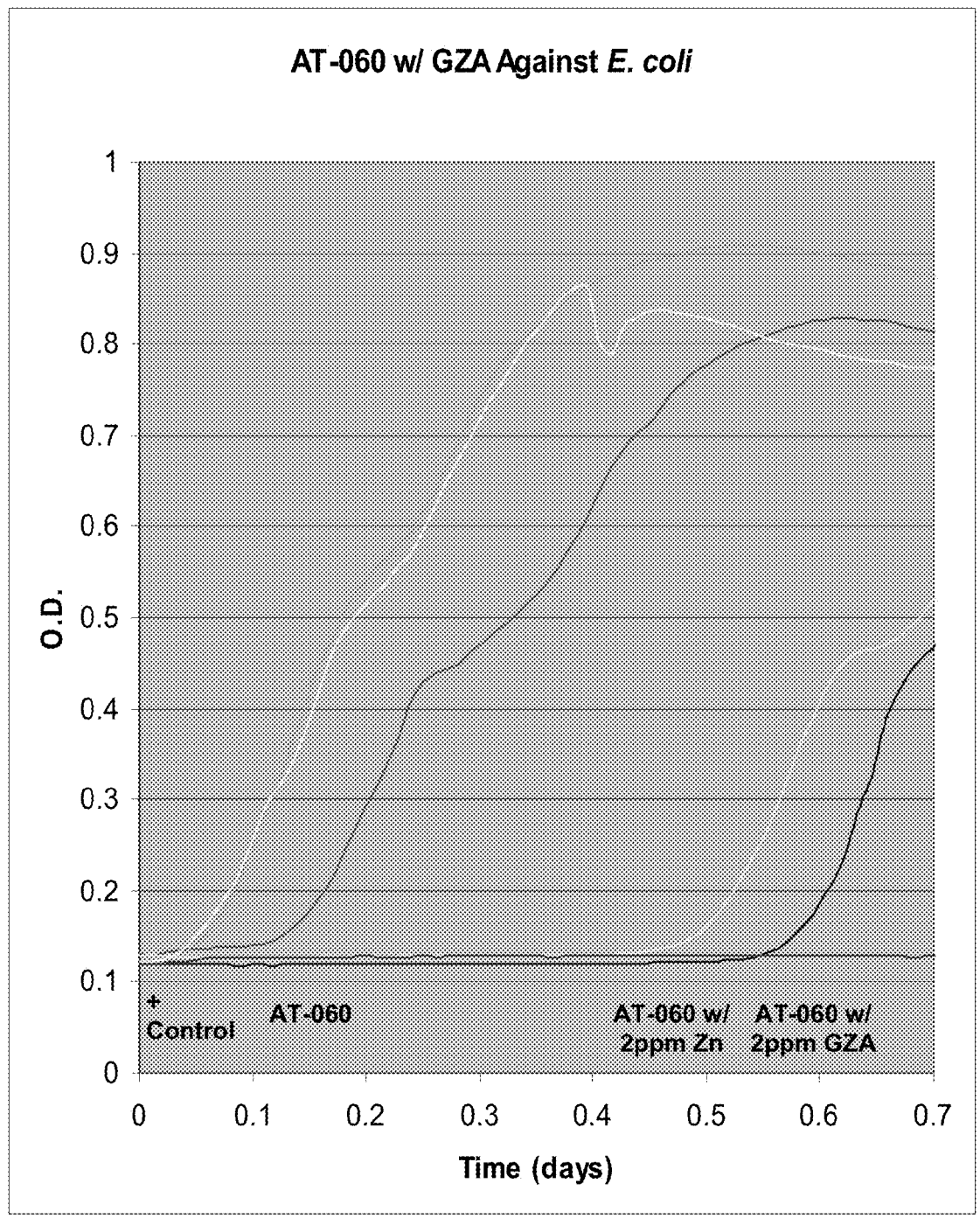
Figure 50C:
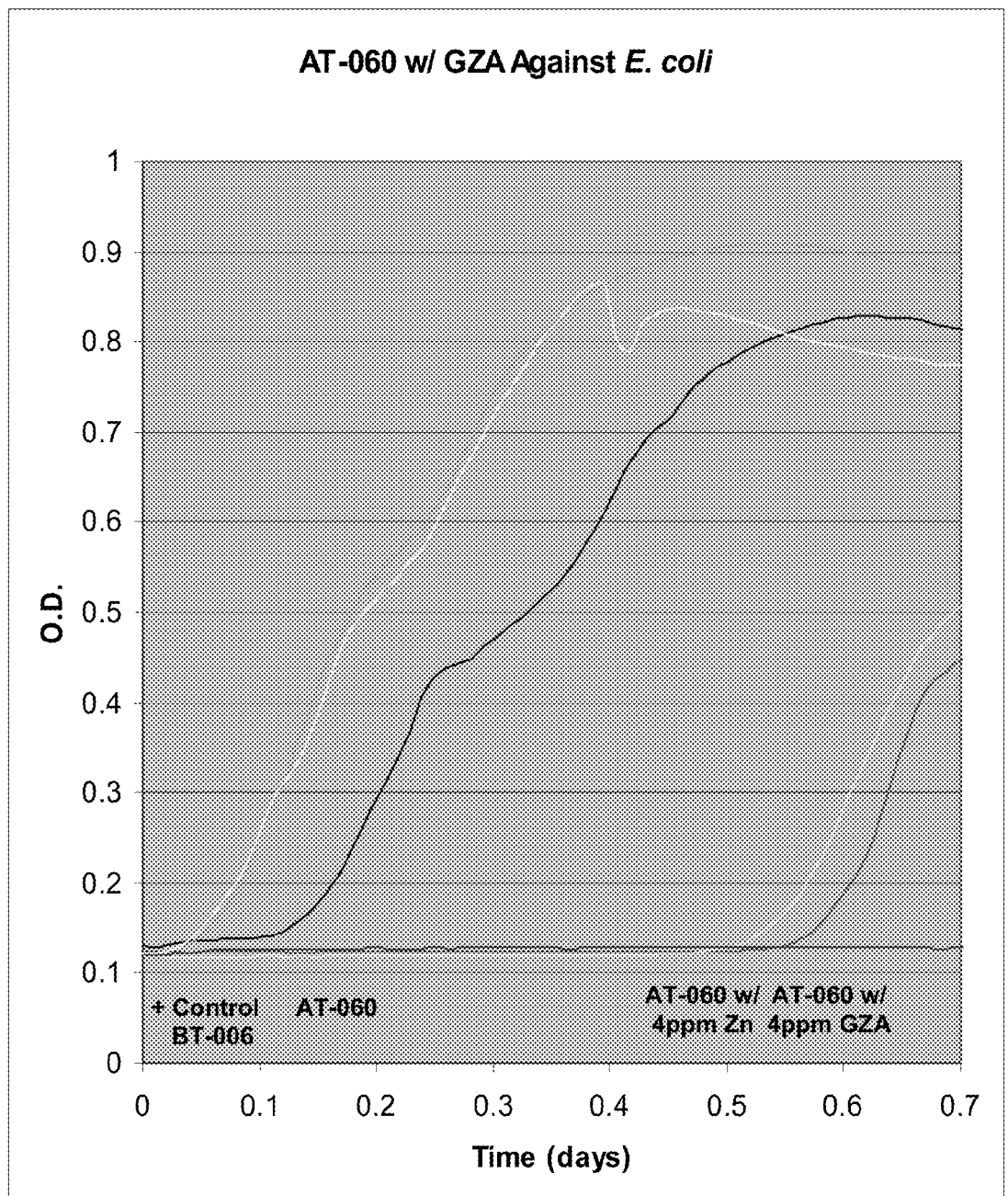
Figure 50D:
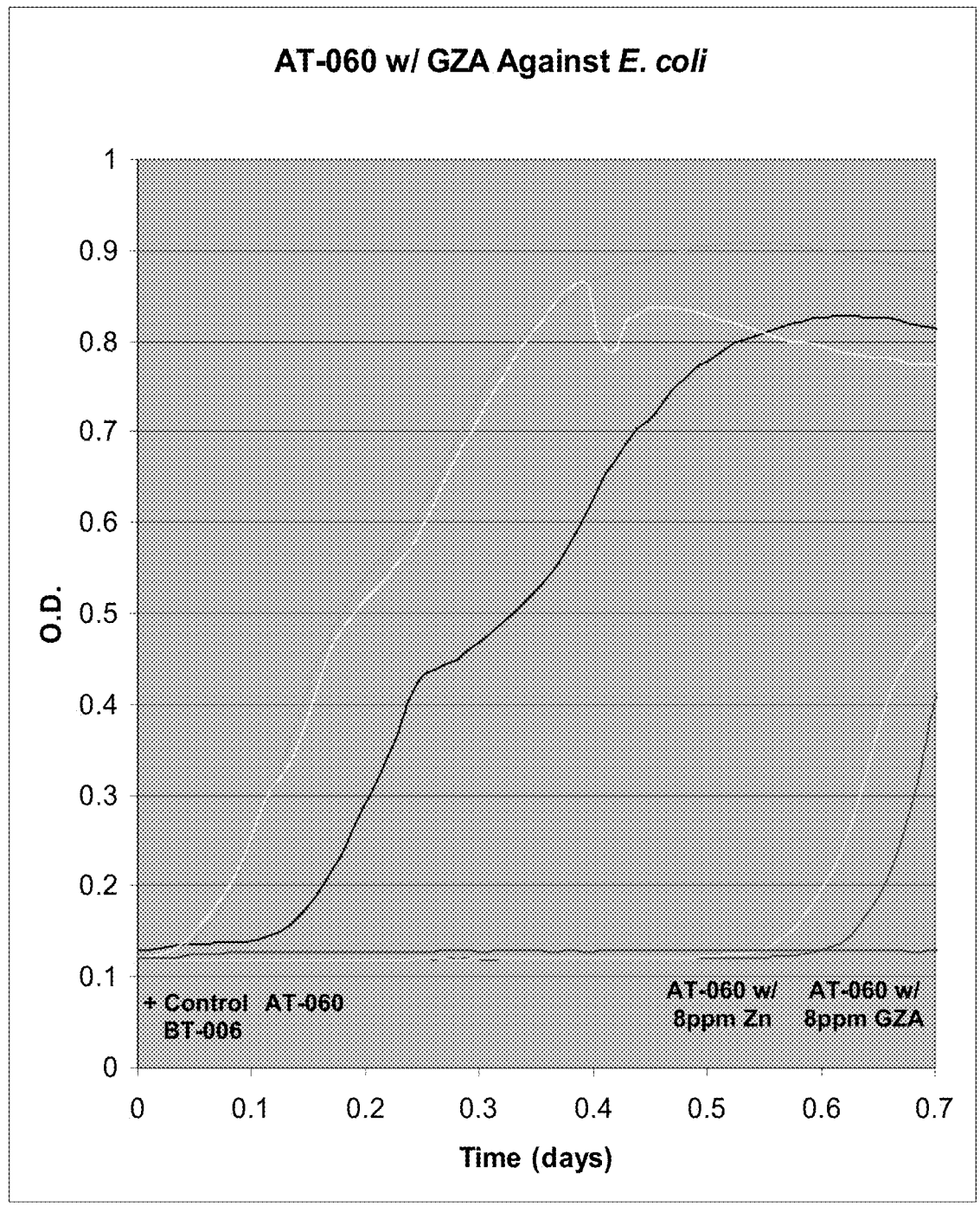

FIG. 49 shows biological results from a Bioscreen device utilizing the raw material made from Example 2 combined with various varying amounts of the raw materials made in Example 4; optimal density is plotted as a function of time.

FIGS. 50a-50d show biological results of the raw material made in Example 2 obtained with a Bioscreen device with various amounts of treated water added thereto; optimal density is plotted as a function of time.

FIGS. 51a-51h show various cellular growth and cytotoxicity curves for solutions GR3, GR5, GR8 and GR9 against both mini-pig kidney fibroblast cells and murine liver epithelial cells; the amount of fluorescence relative to control (100%) cells is plotted against increasing amounts of nanoparticles.

FIGS. 52a-52f show cytotoxicity ($LD_{50}$) results (curves) for GR3, GR5 and GR8 against murine liver epithelial cells; the amount of fluorescence relative to control (100%) cells is plotted against increasing amounts of nanoparticles.

FIGS. 53a-53h show $LD_{50}$ results (curves) for GR3, GR5, GR8 and GR9 against mini-pig kidney fibroblast cells; the amount of fluorescence relative to control (100%) cells is plotted against increasing amounts of nanoparticles.

Figure 54:
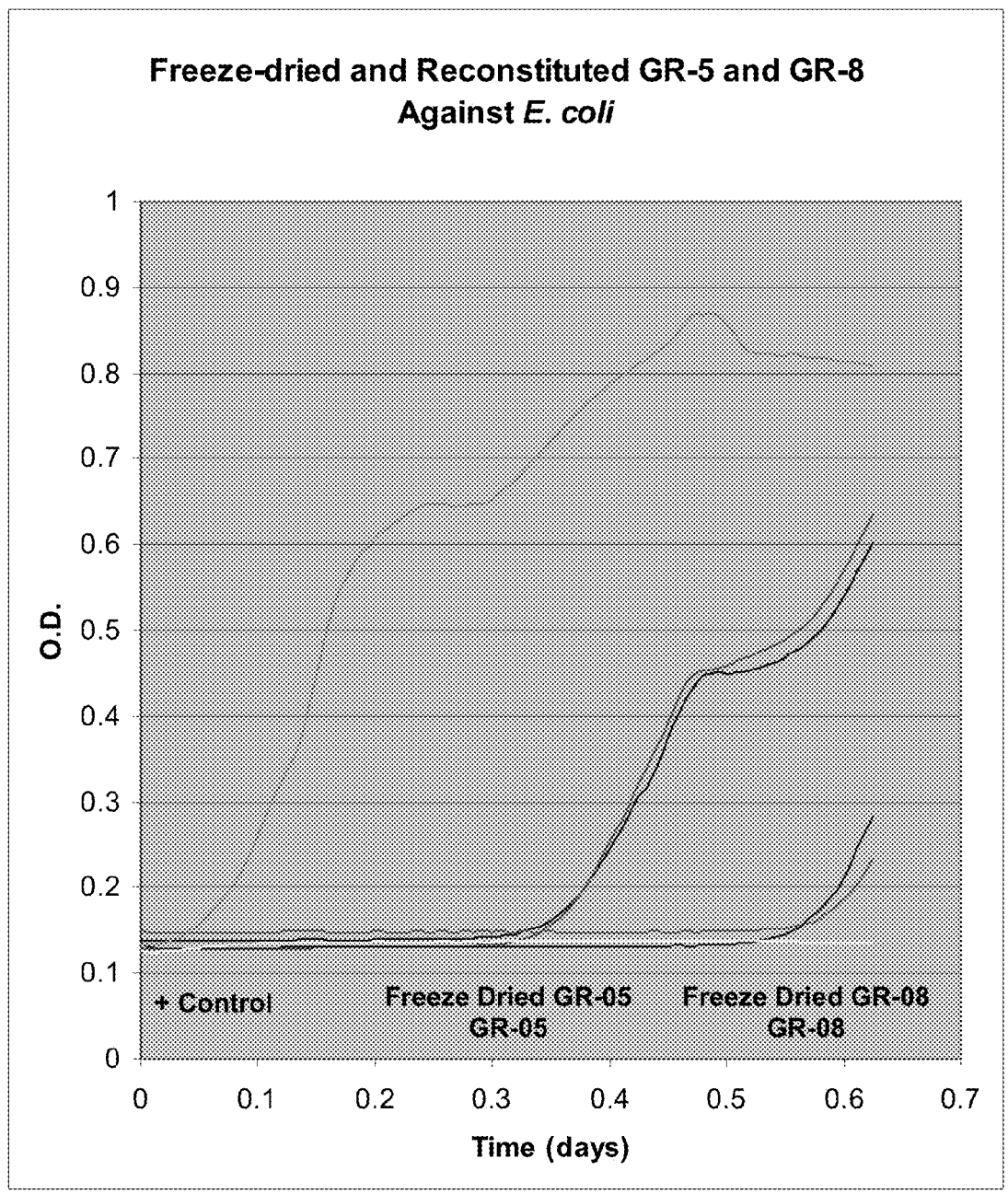

FIG. 54 shows biological results from a Bioscreen device for the performance of solution GR5, as formed in Table 8 and, compared to a freeze-dried and rehydrated GR5; optimal density is plotted as a function of time.

Figure 55A:
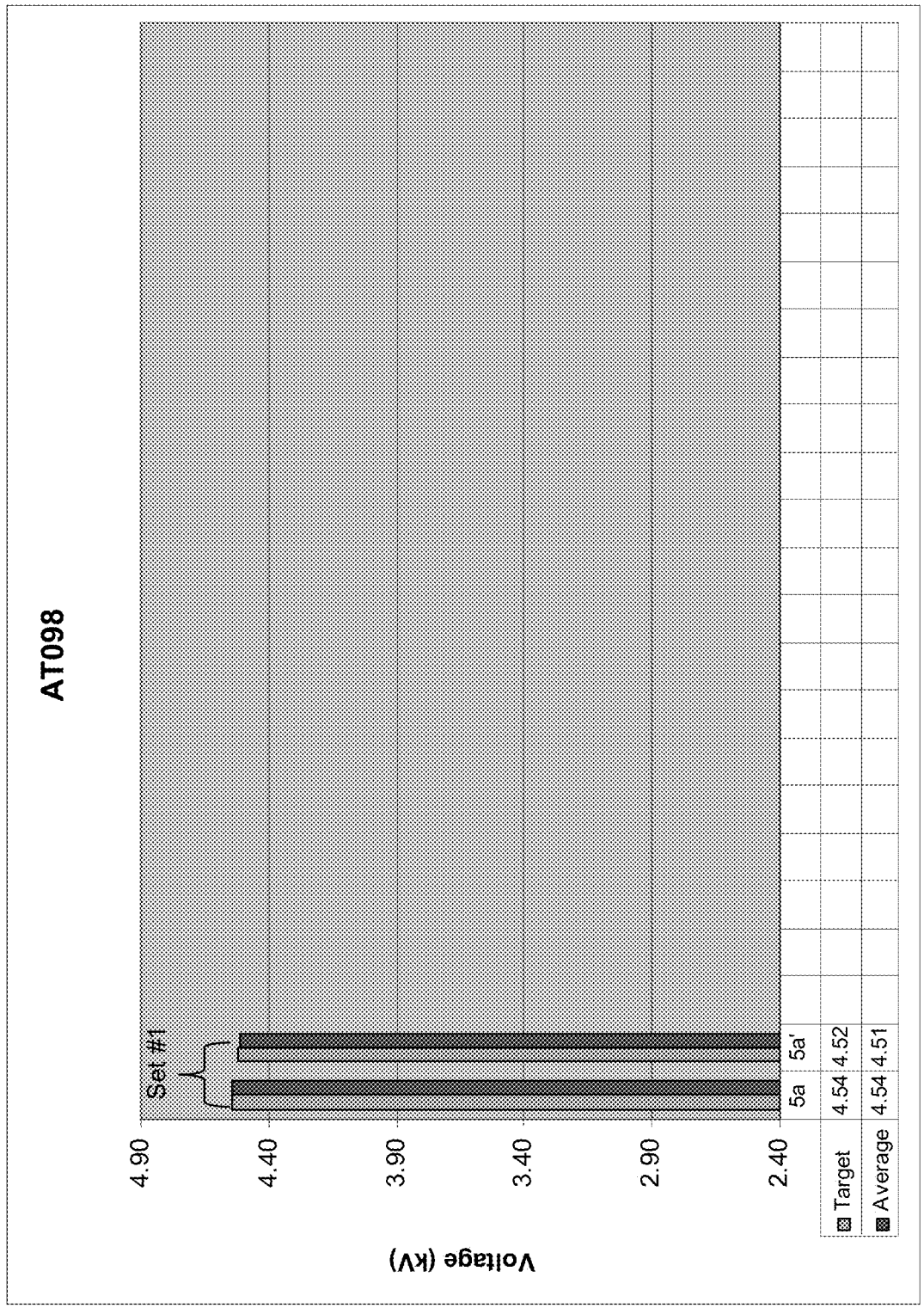
Figure 55B:
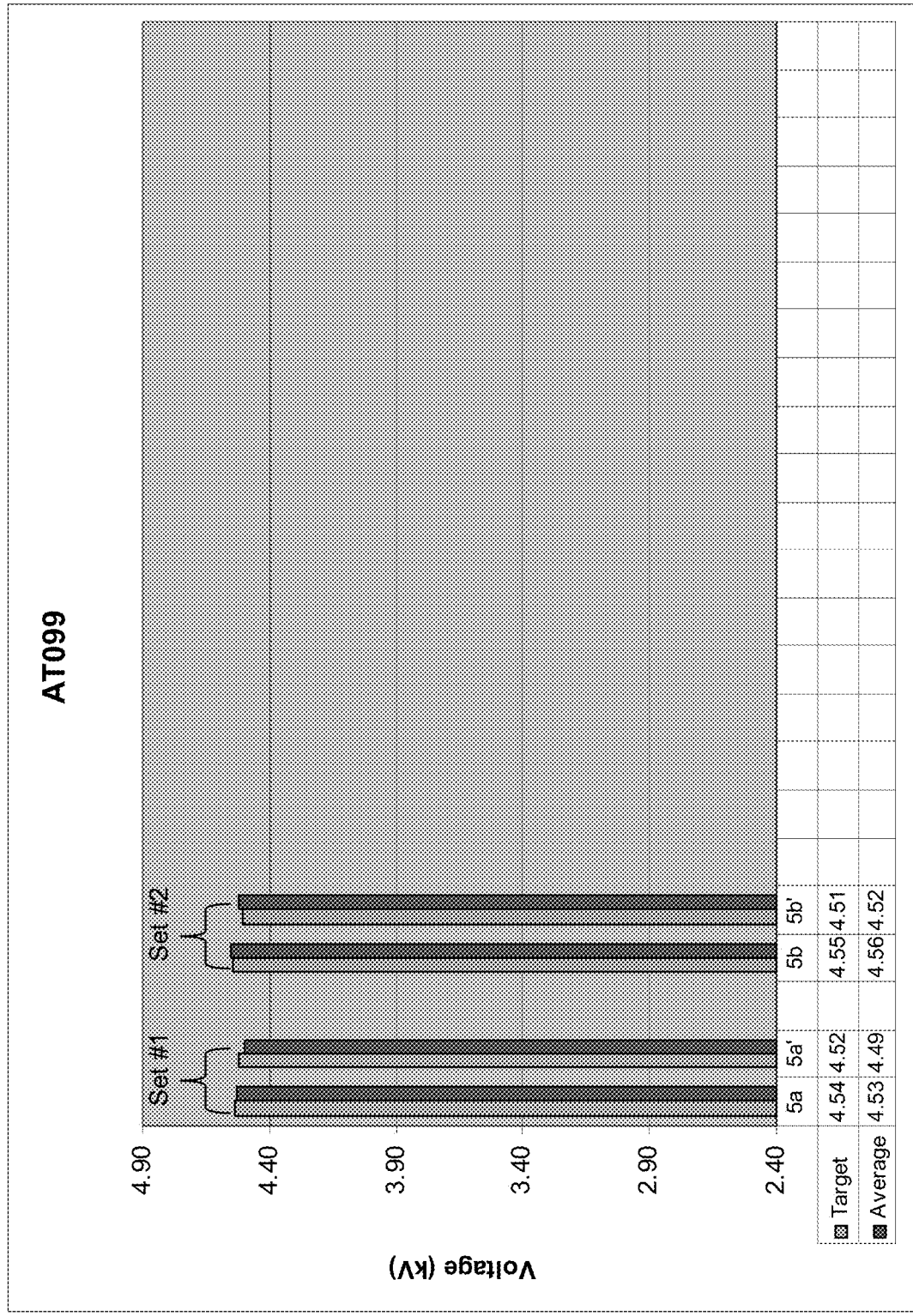
Figure 55C:
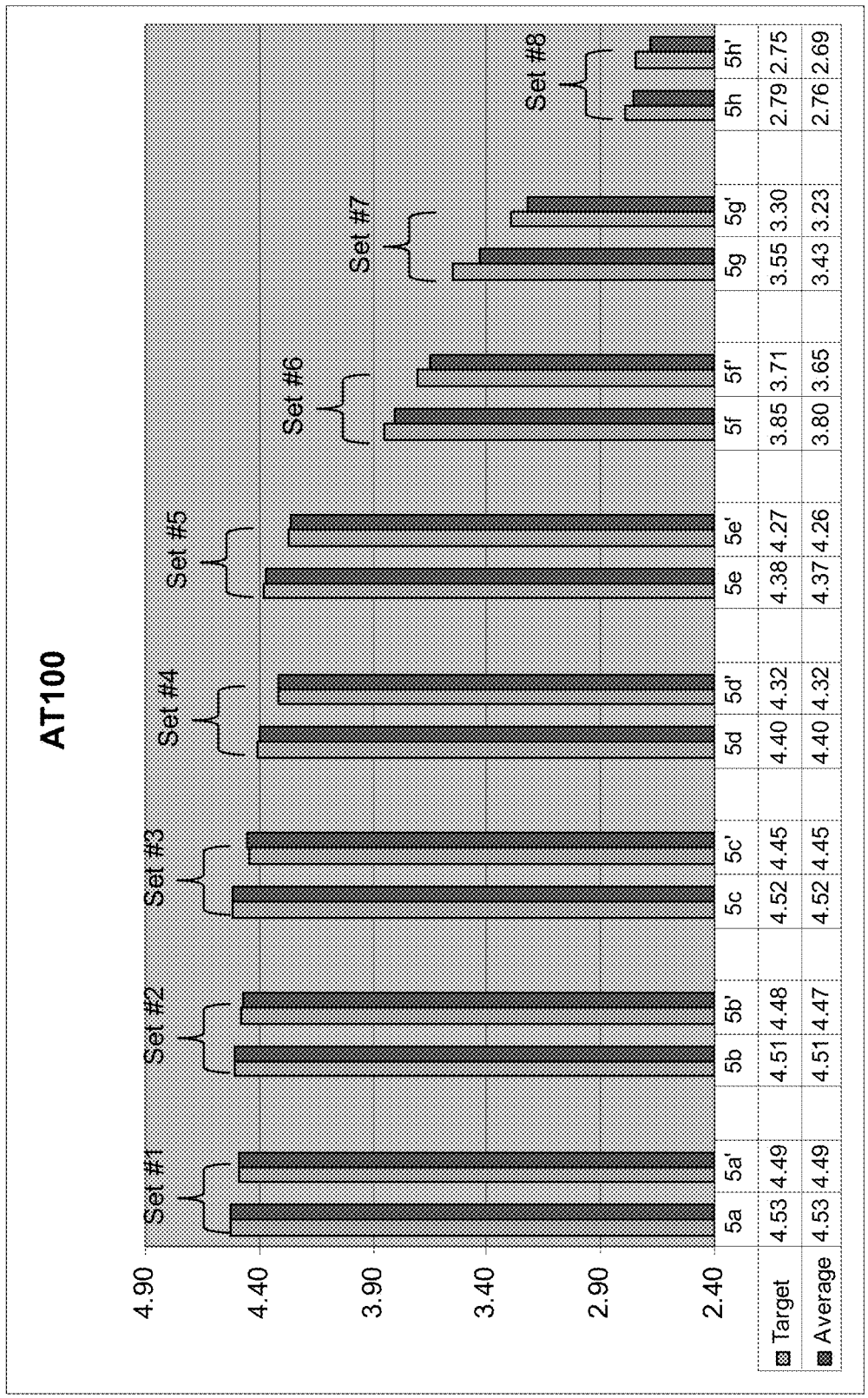
Figure 56A:
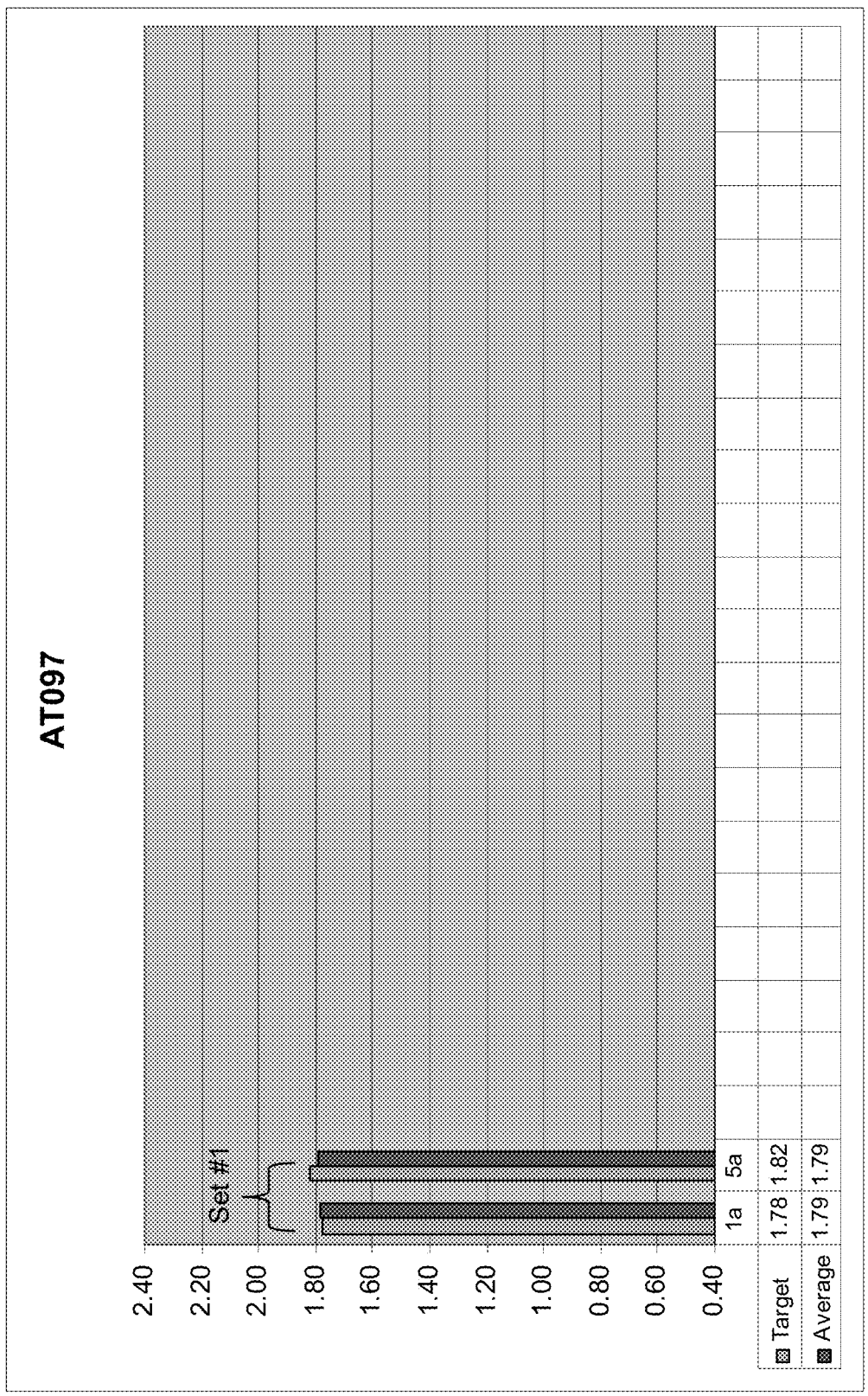
Figure 56B:
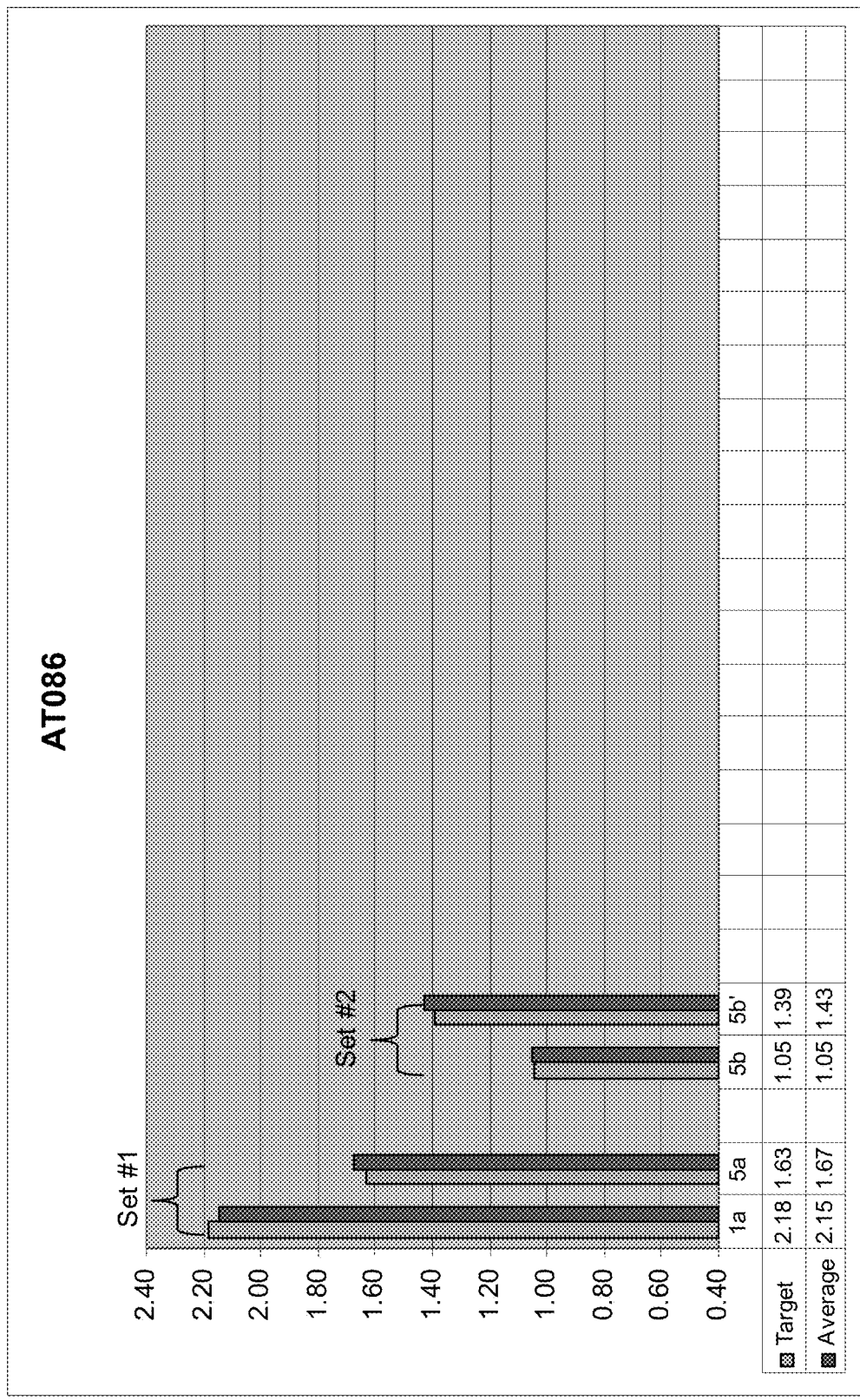
Figure 56C:
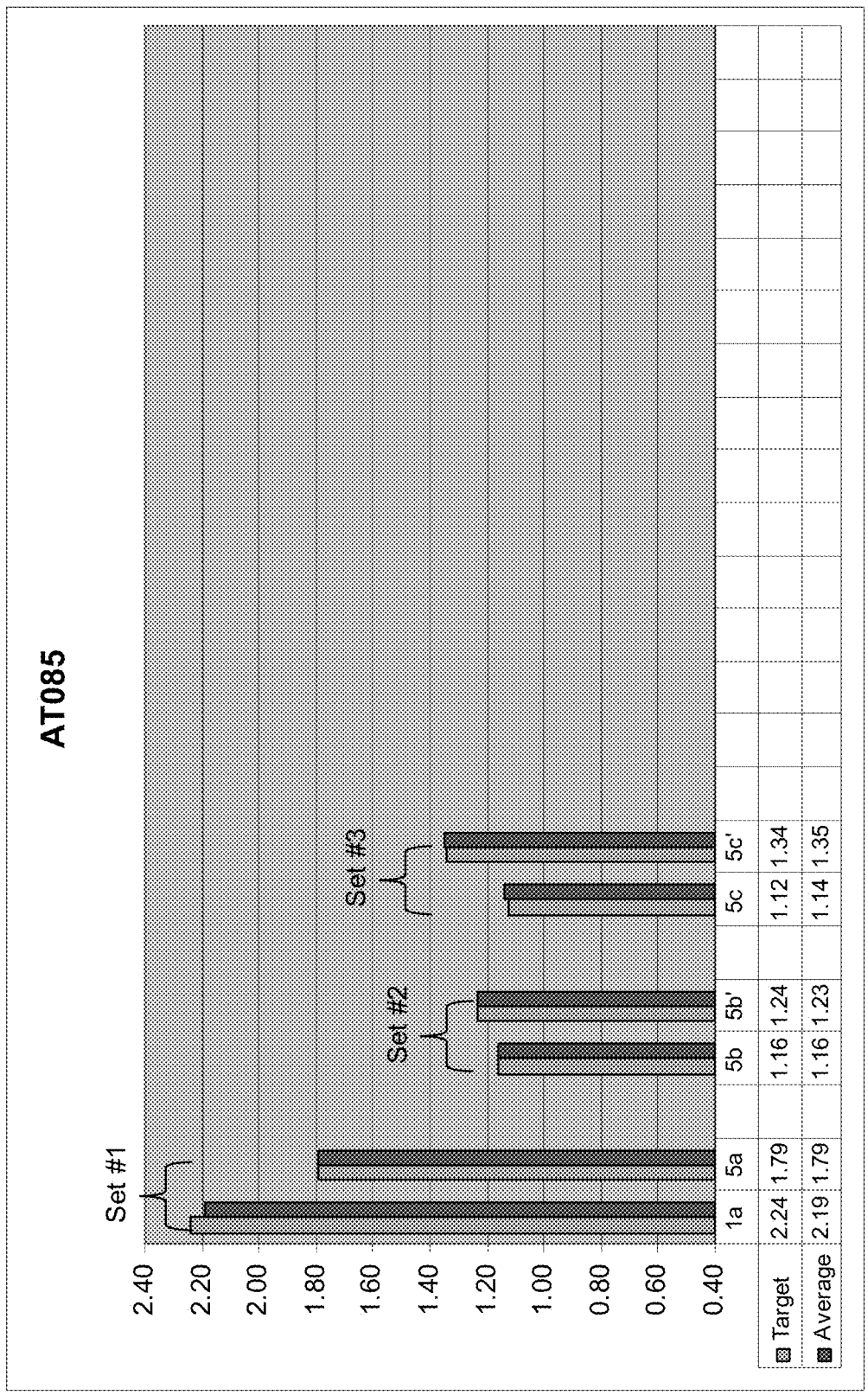
Figure 56D:
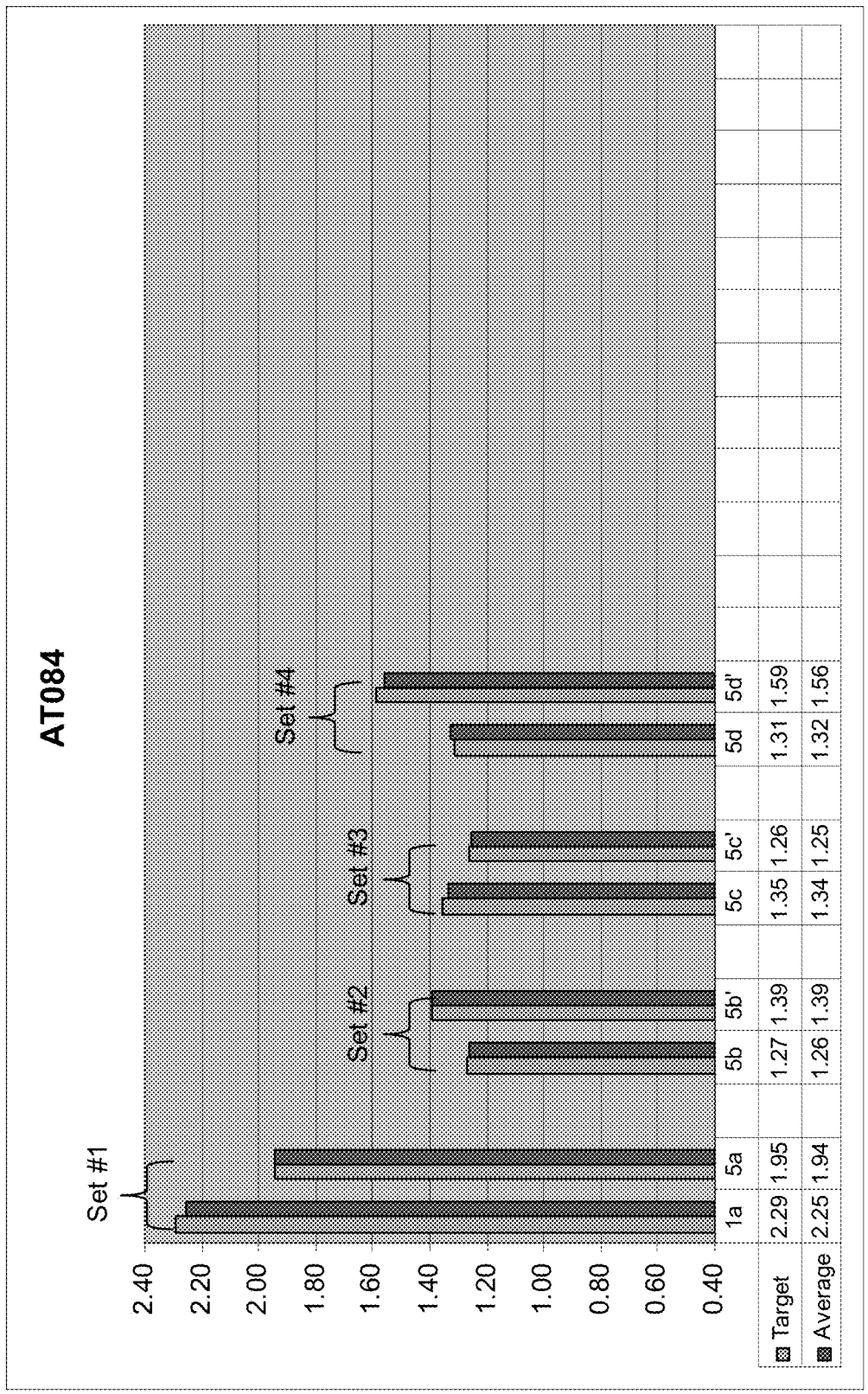
Figure 56E:
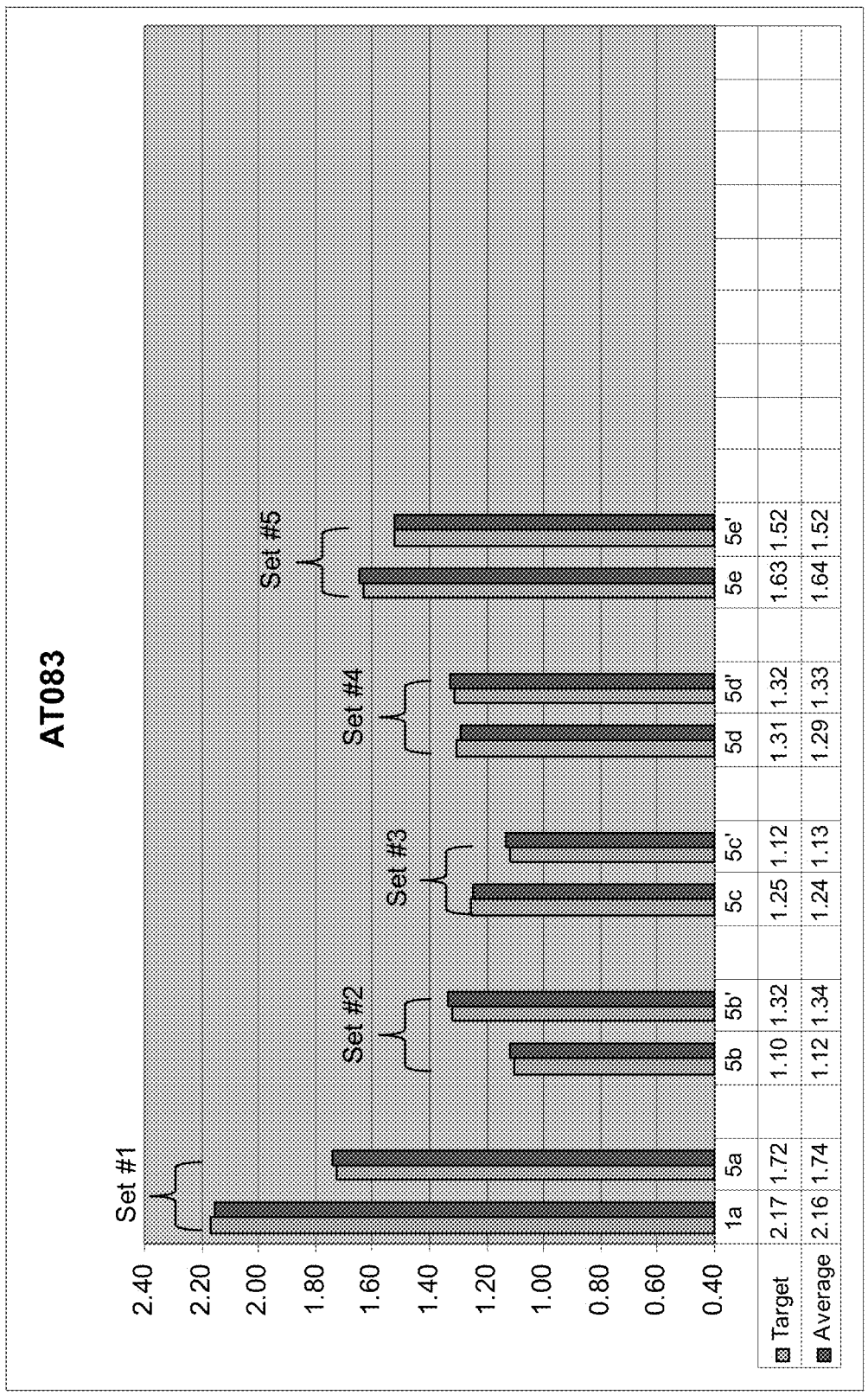
Figure 56F:
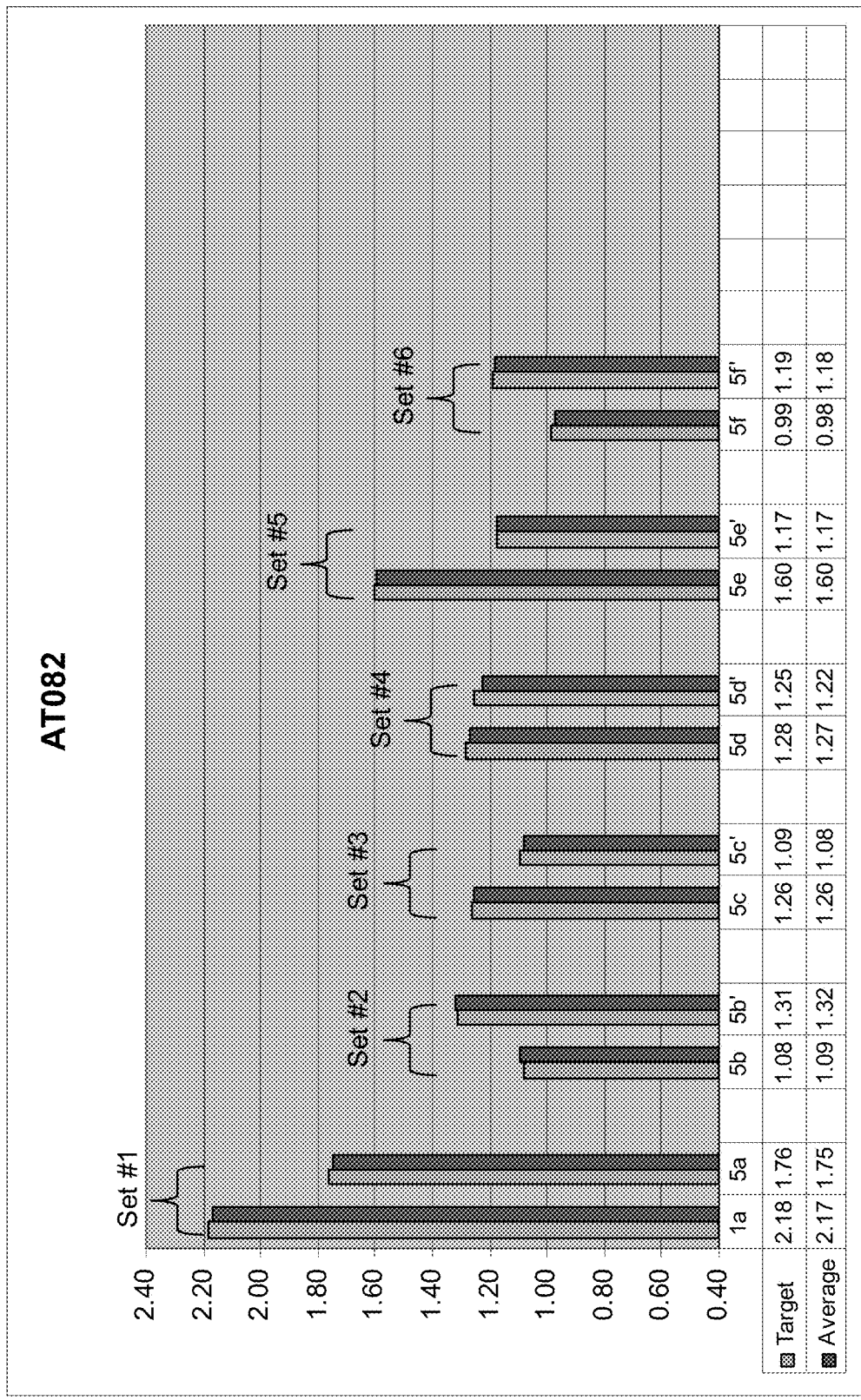
Figure 56G:
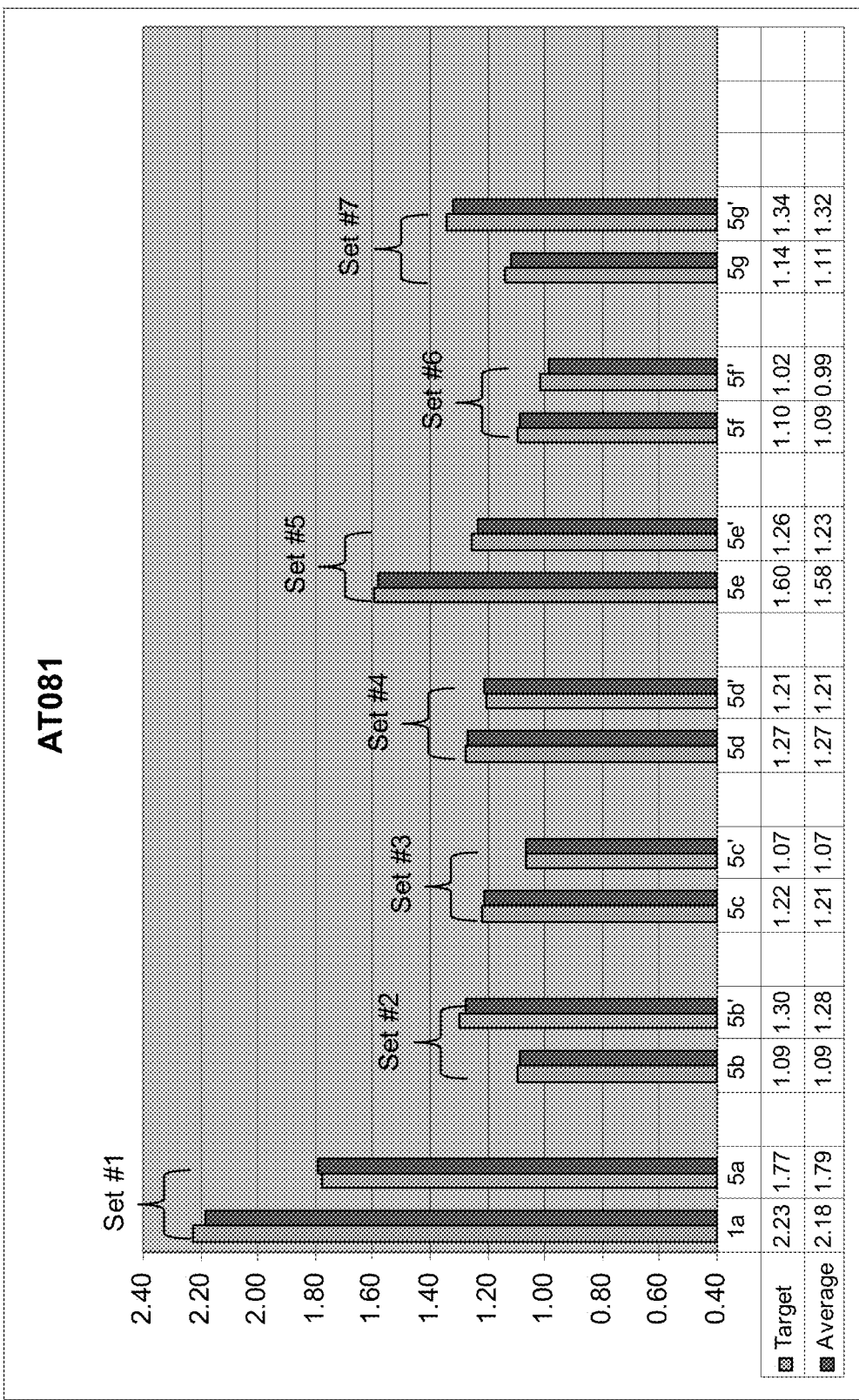
Figure 56H:
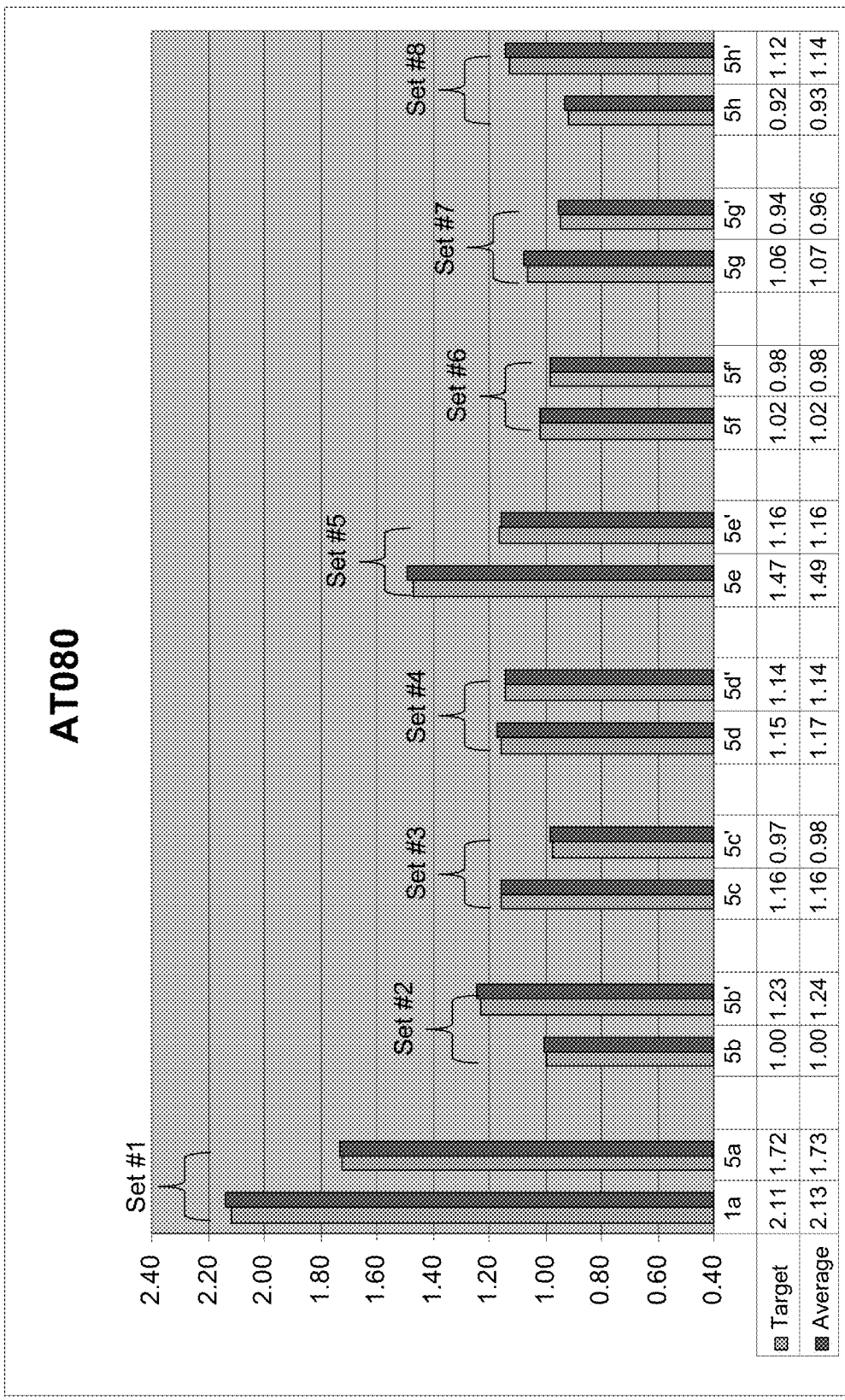

FIGS. 55a-55c show bar charts of various target and actual average voltages applied to different electrodes used in Example 6 to manufacture silver-based nanoparticles and nanoparticle solutions.

FIGS. 56a-56h show bar charts of various target and actual average voltages applied to different electrodes used in Example 7 to manufacture silver-based nanoparticles and nanoparticle solutions.

Figure 57A:
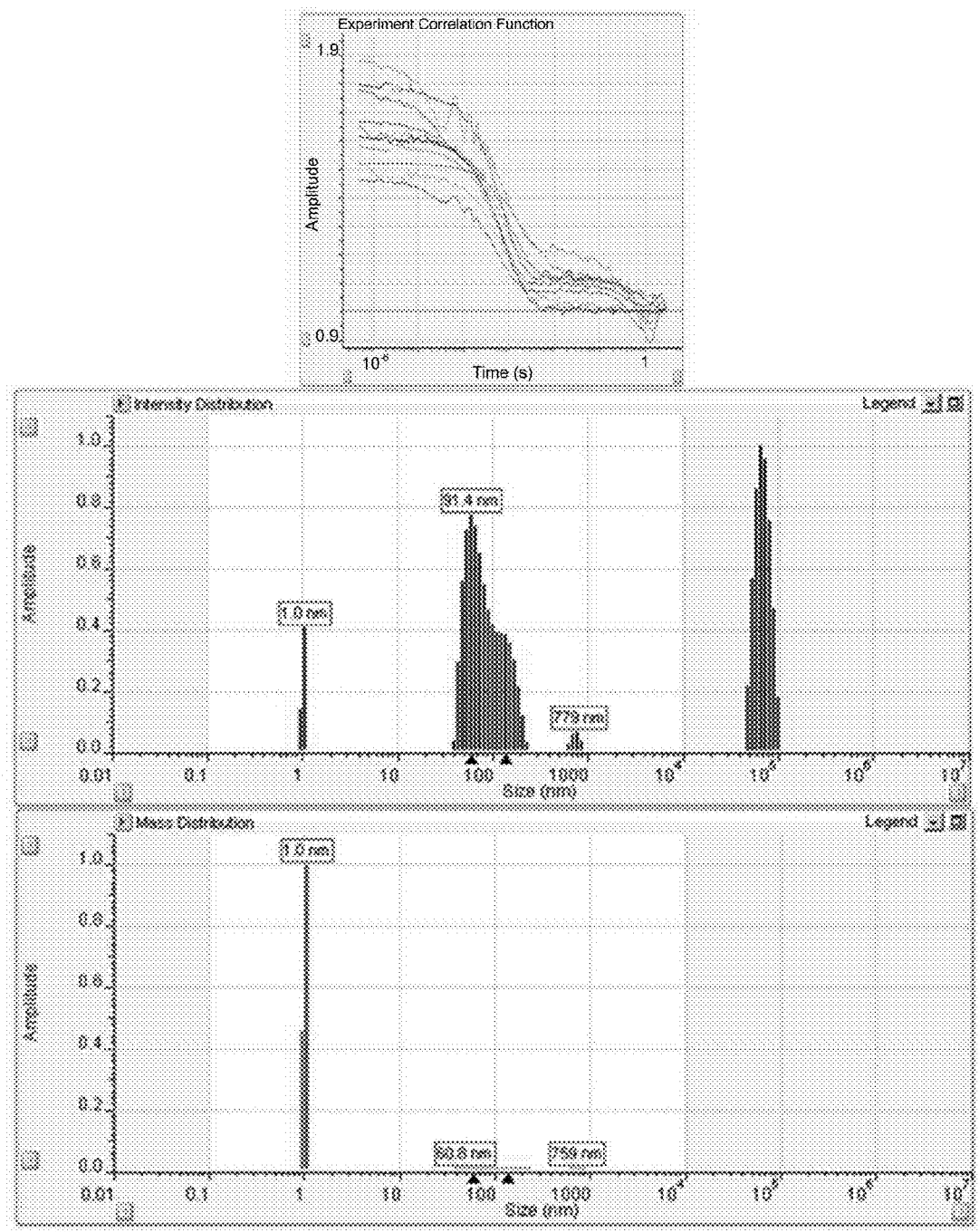
Figure 57B:
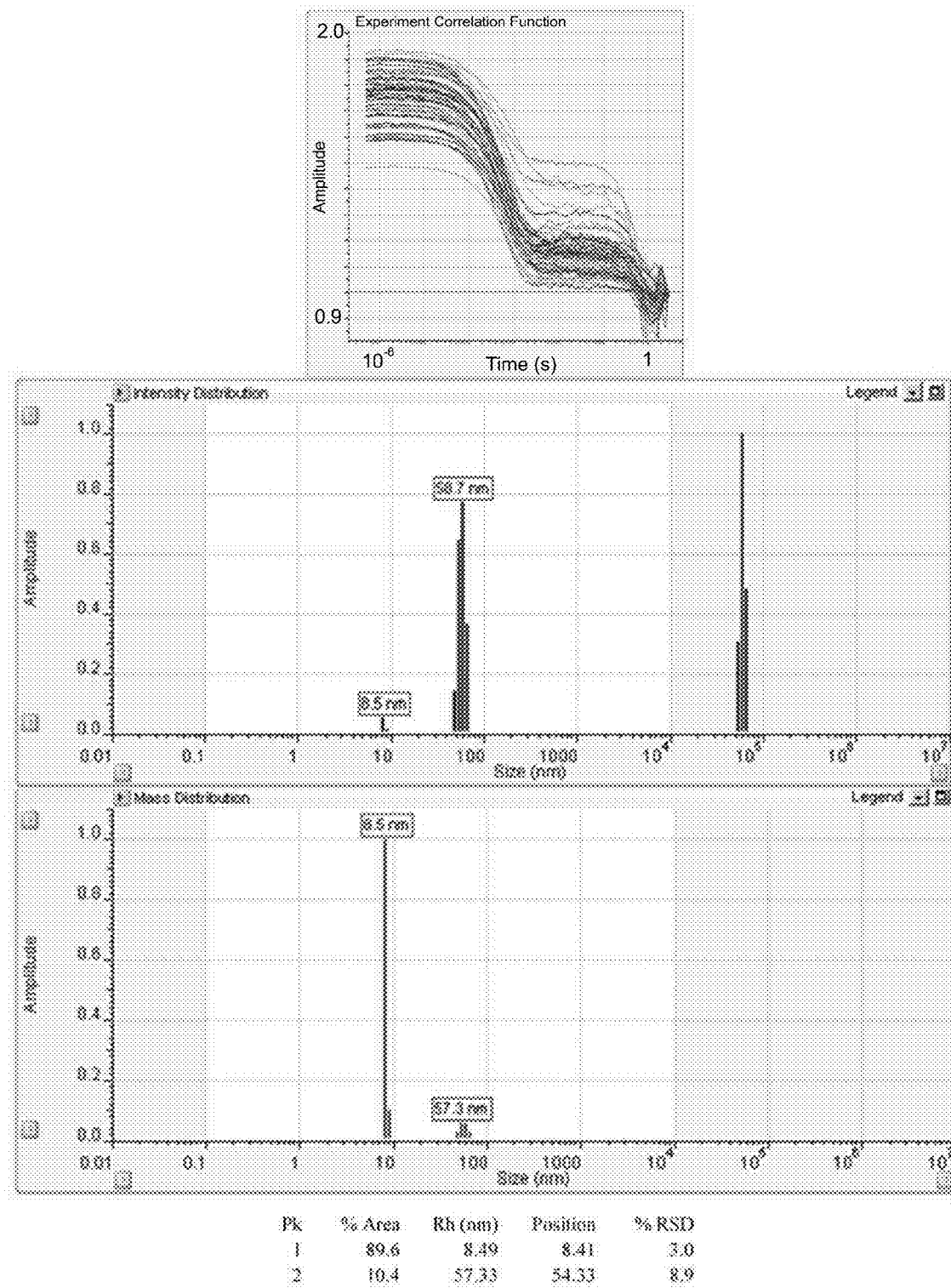

FIGS. 57a-57b show Dynamic Light Scattering measurements for Example 7.

FIGS. 58a-58g are SEM photomicrographs of dried samples made according to Example 7.

Figure 59A:
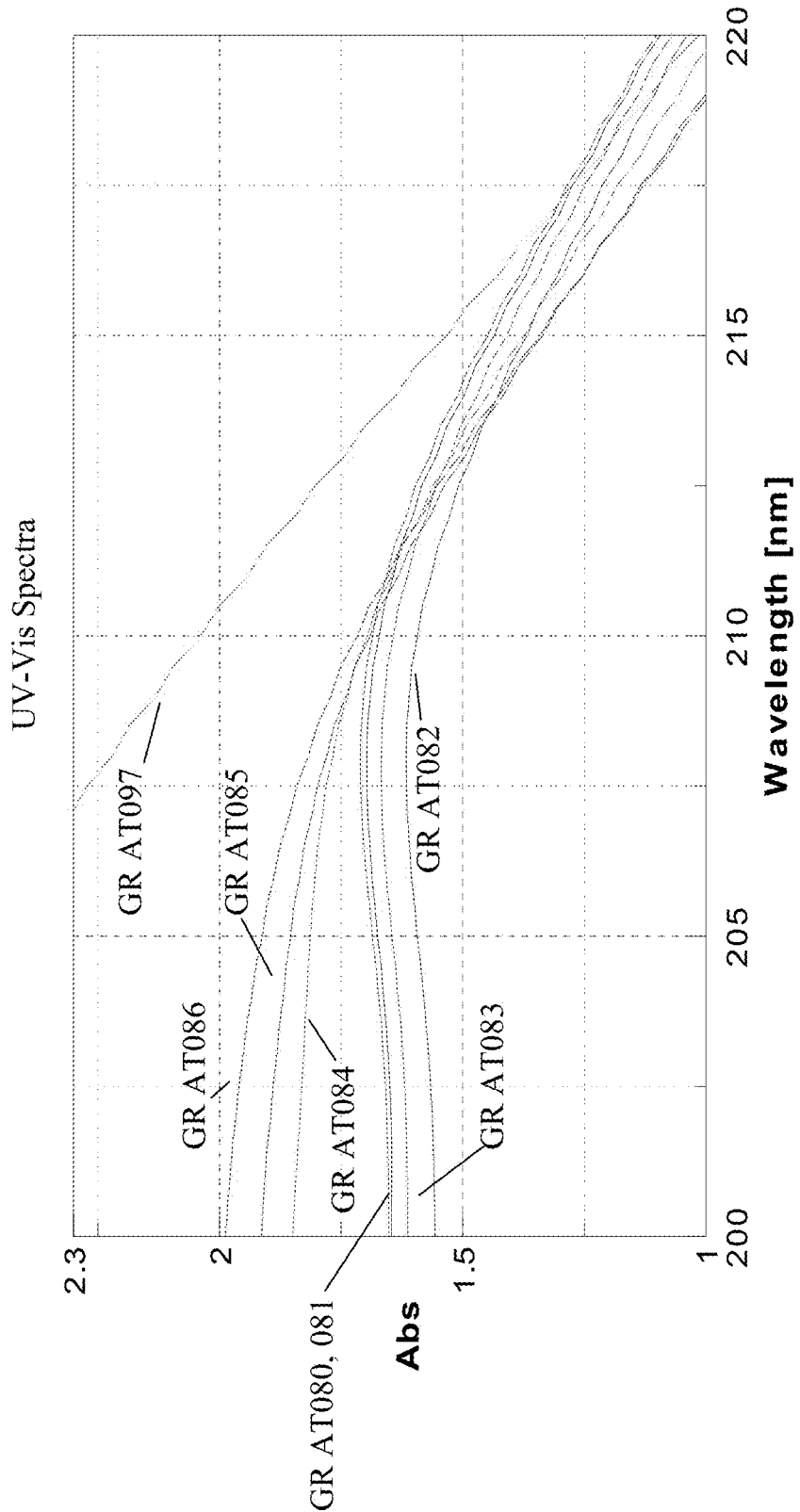
Figure 59B:
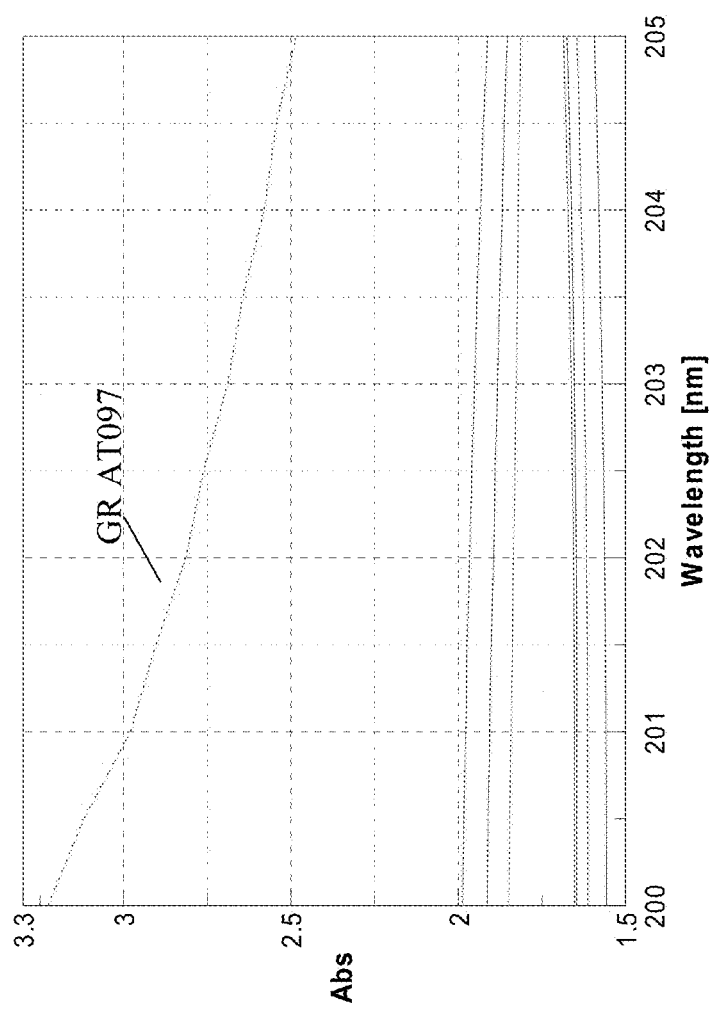
Figure 59C:
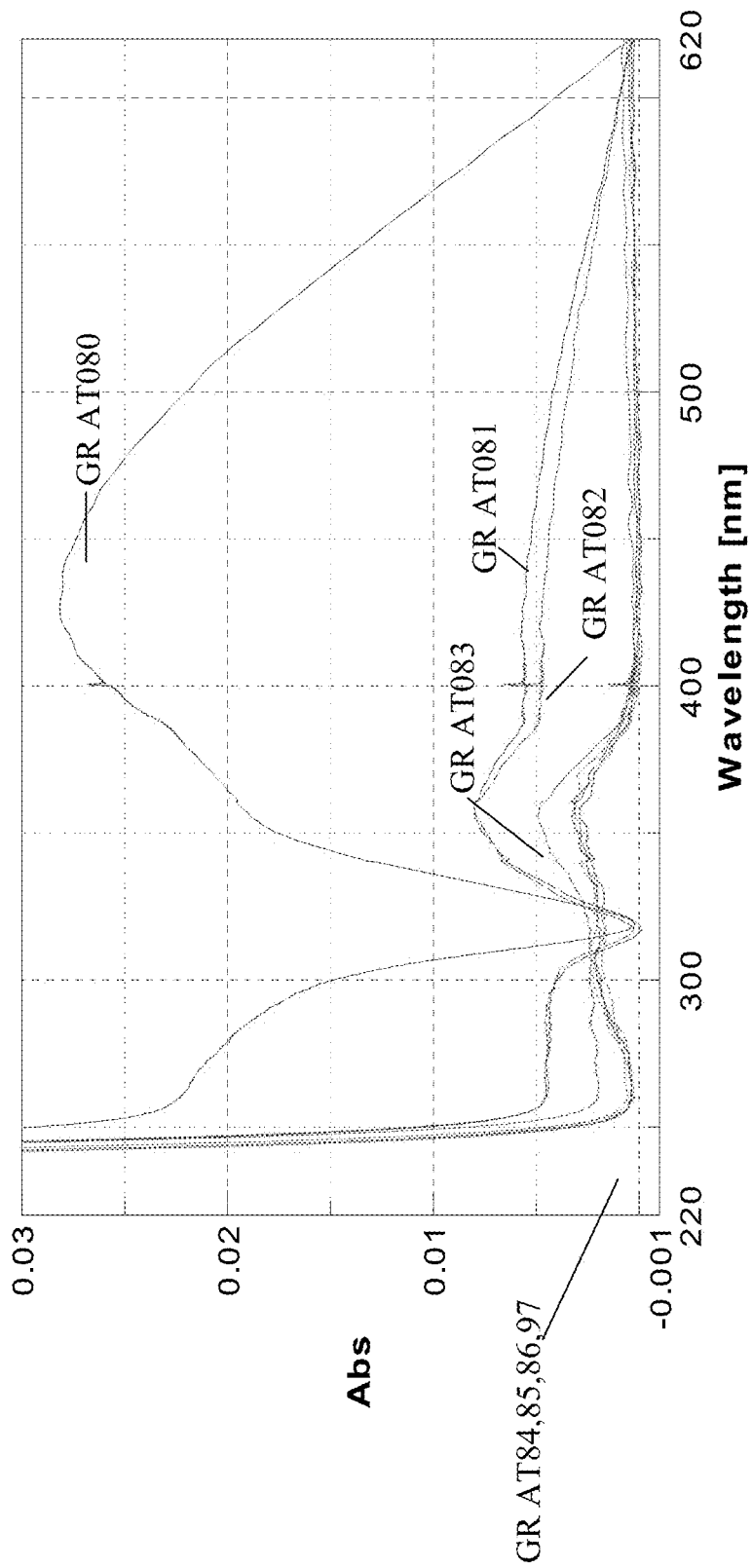

FIGS. 59a-59c are UV-Vis Spectra taken of the liquid samples made according to Example 7.

Figure 60:
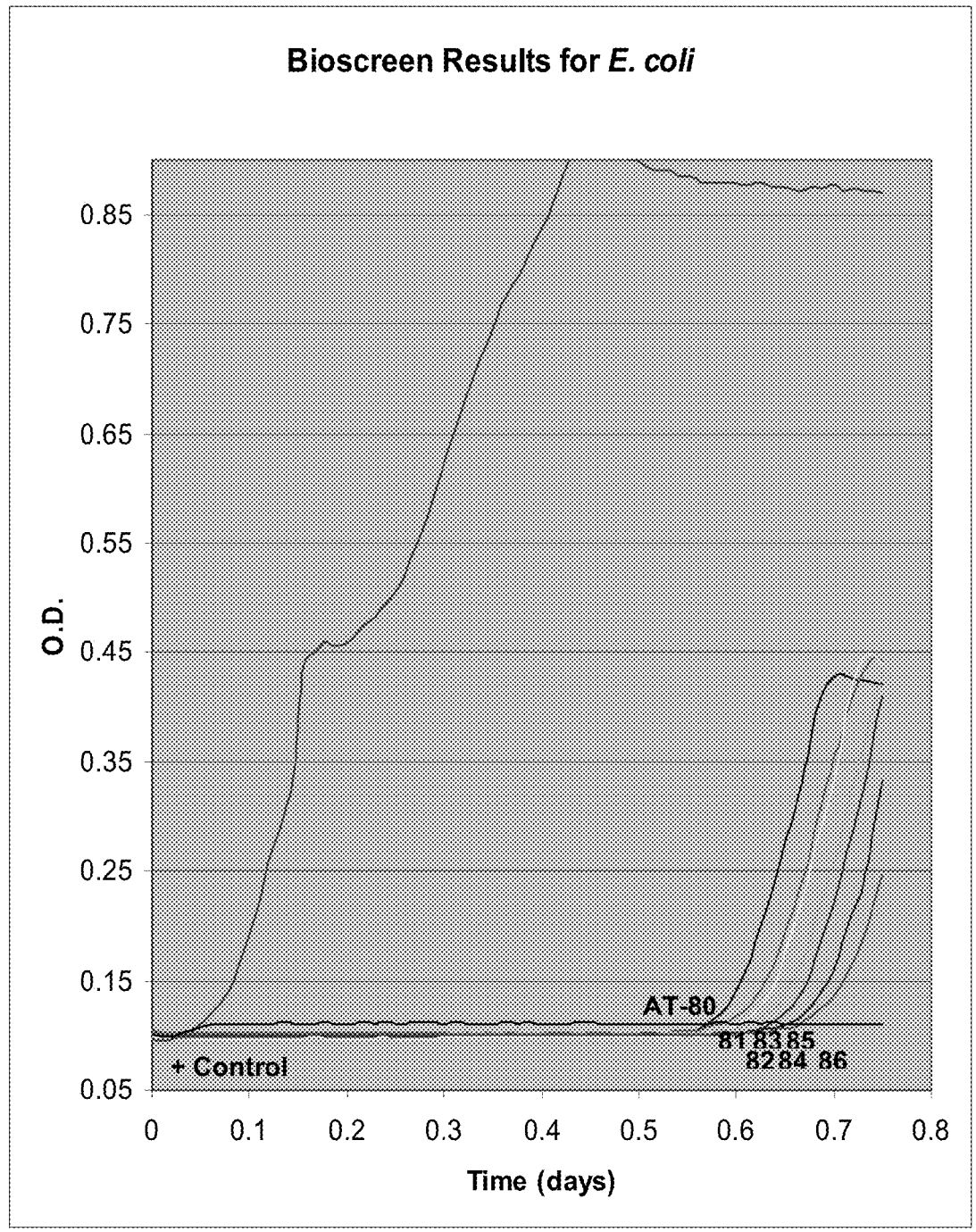

FIG. 60 shows biological Bioscreen results for the samples made according to Example 7.

Figure 61A:
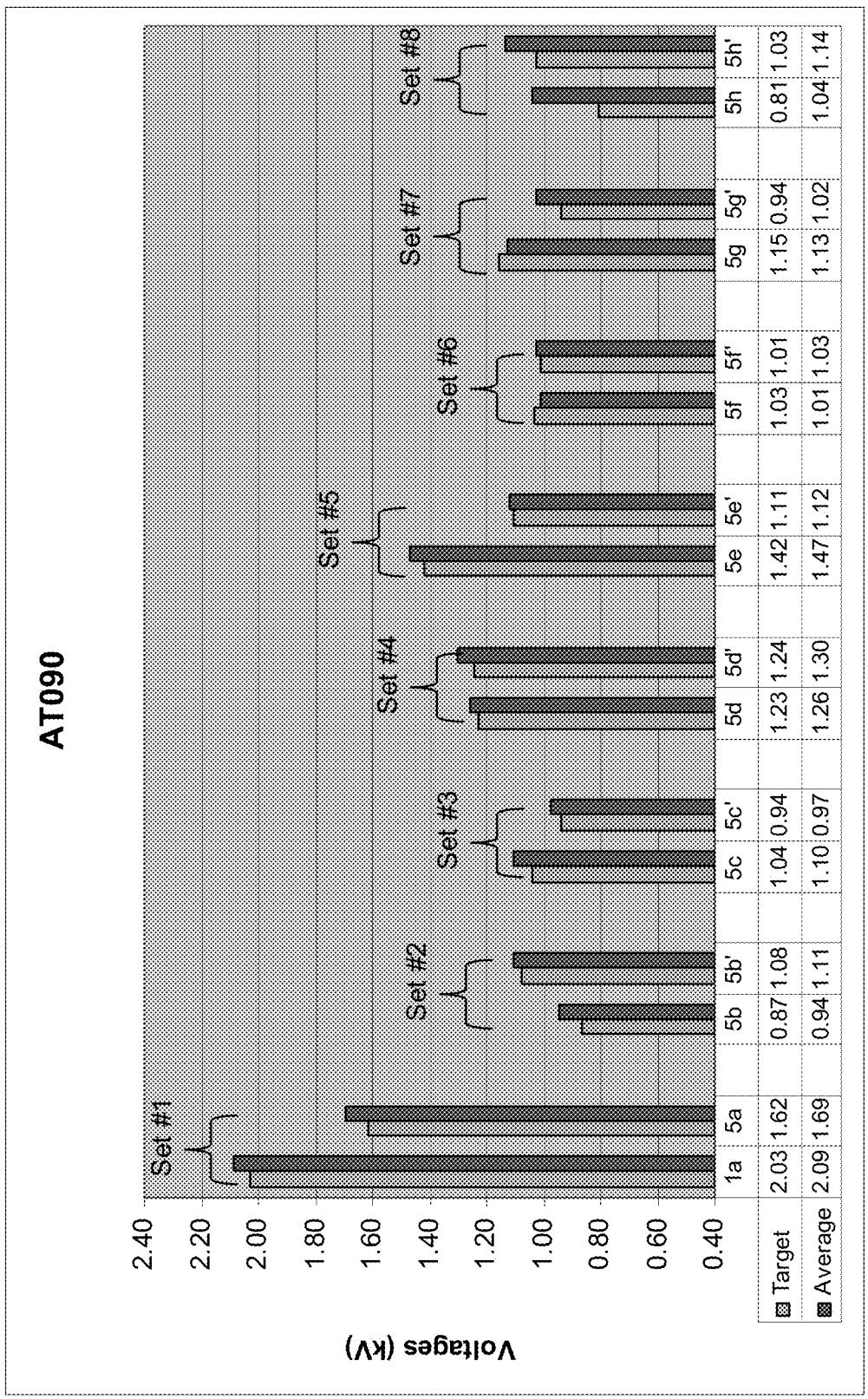
Figure 61B:
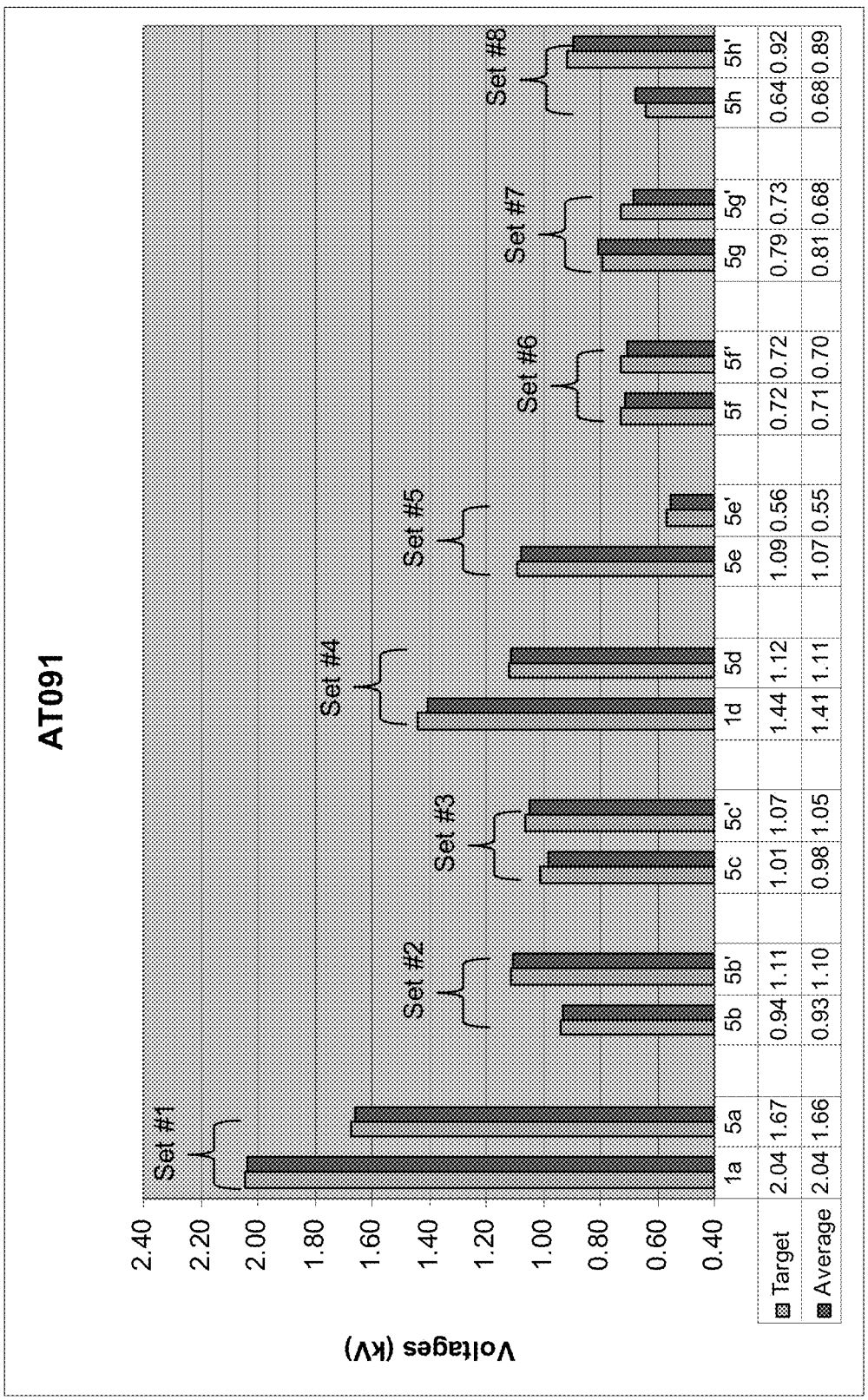
Figure 61C:
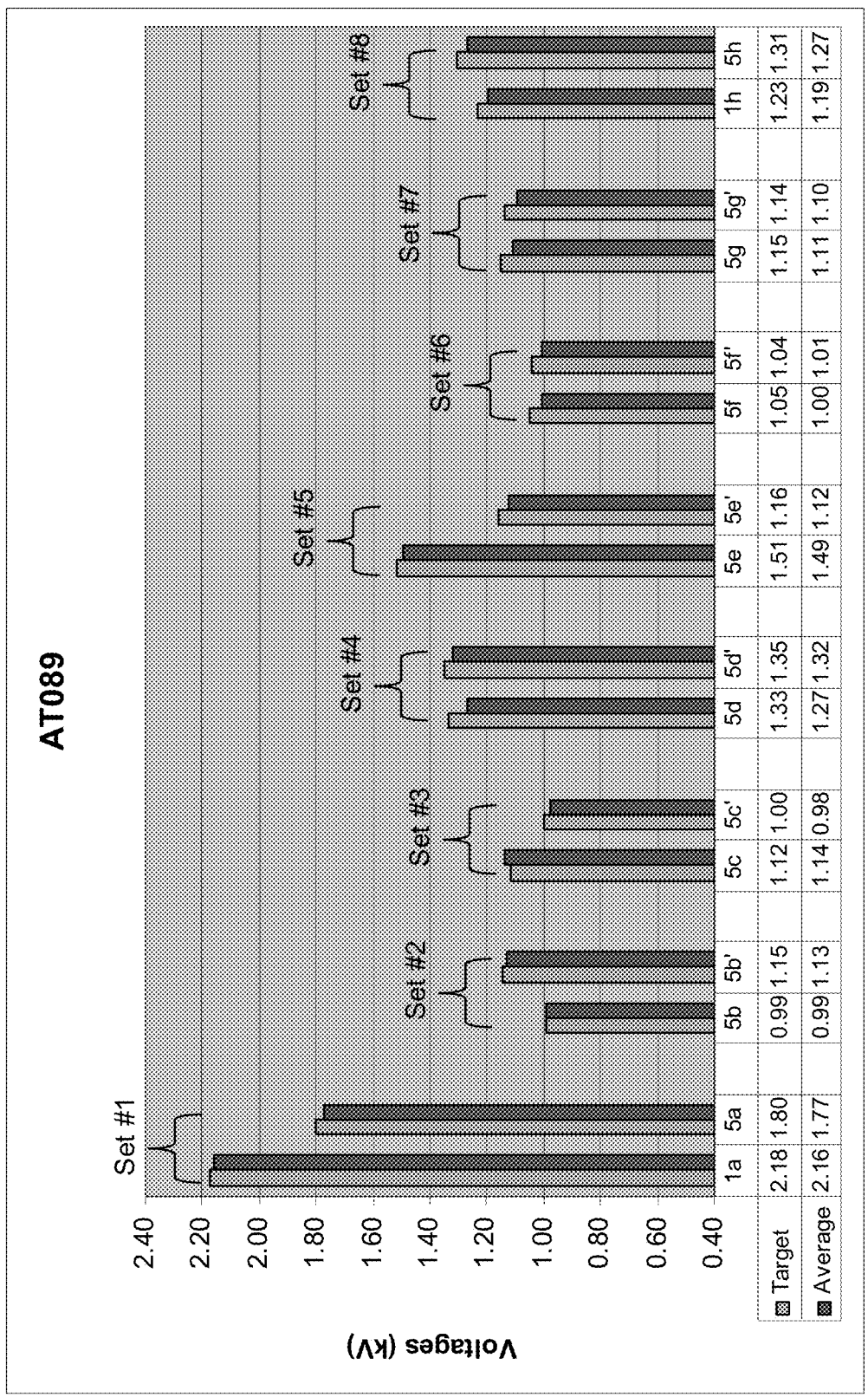

FIGS. 61a-61c show bar charts of various target and actual average voltages applied to different electrodes used in Example 8 to manufacture silver-based nanoparticles and nanoparticle solutions.

Figure 62A:
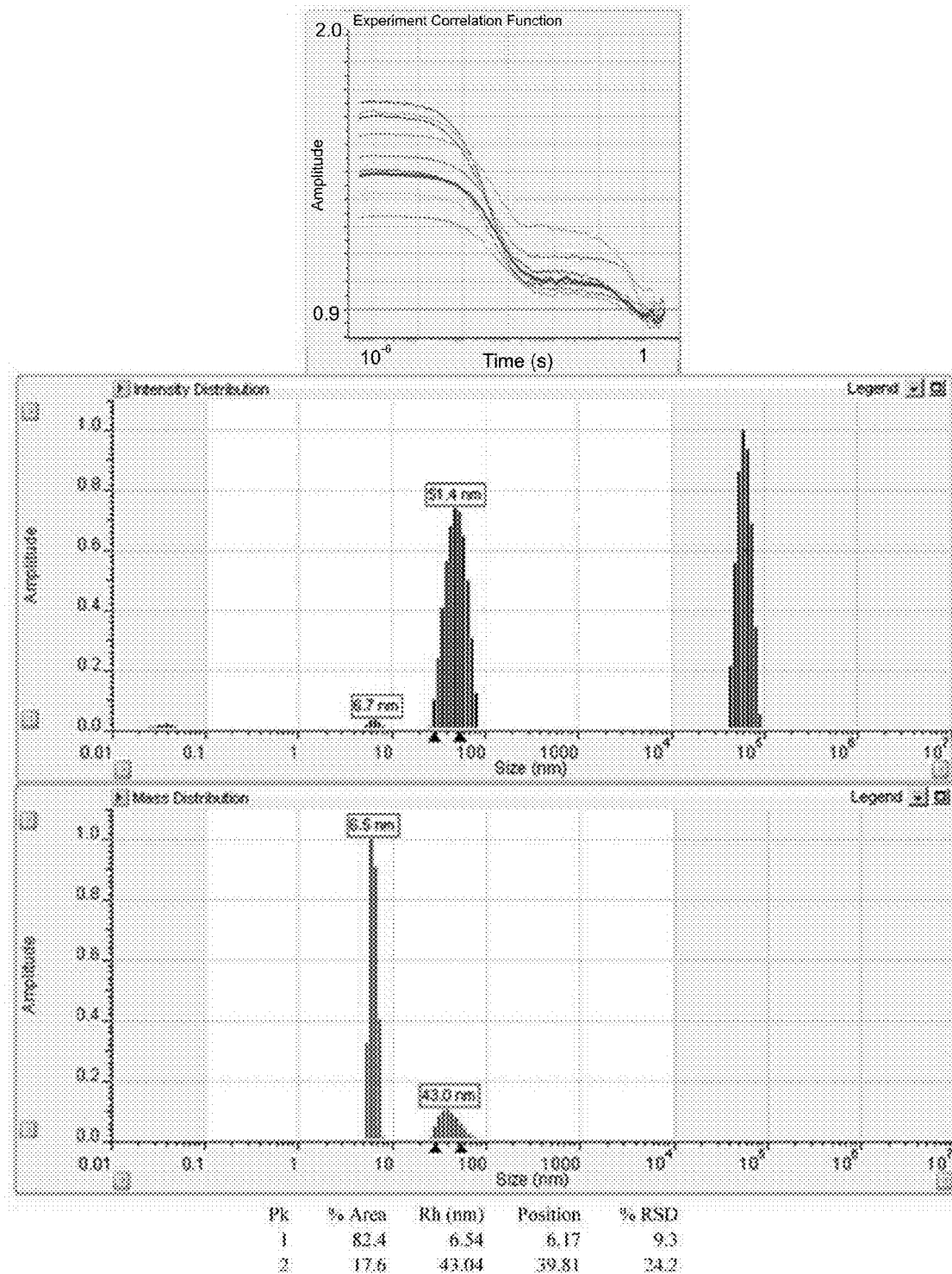
Figure 62B:
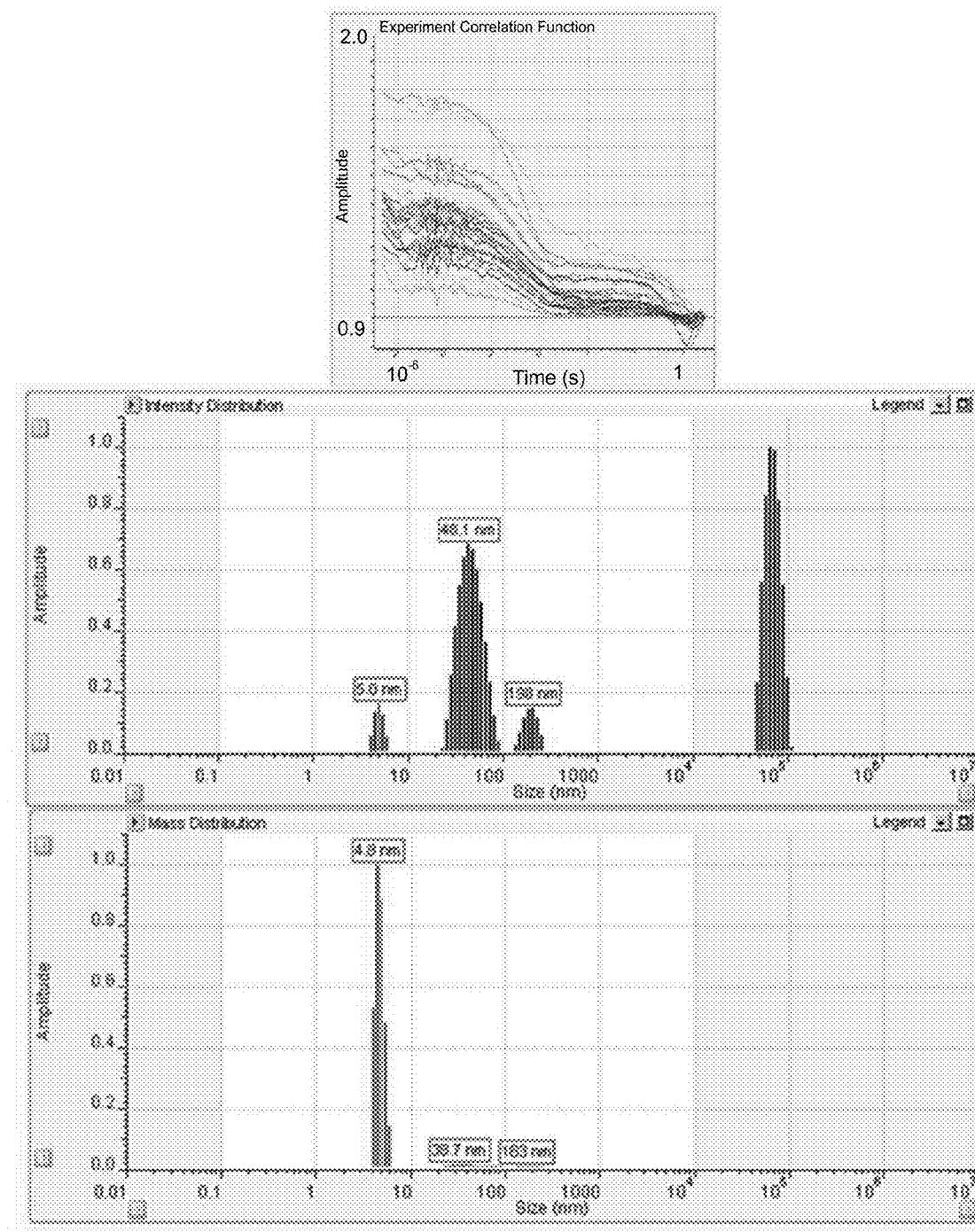
Figure 62C:
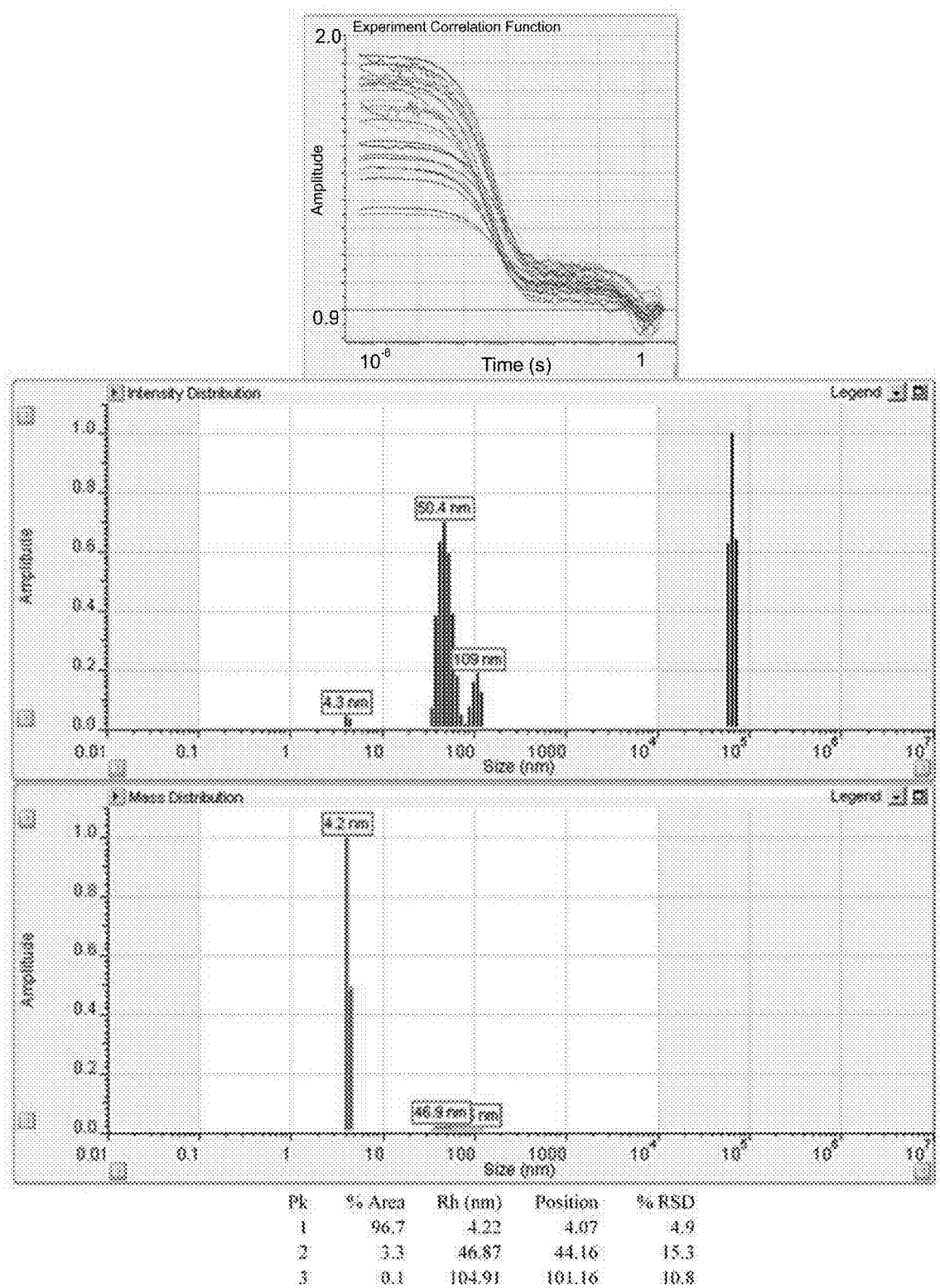

FIGS. 62a-62c show Dynamic Light Scattering measurements for Example 8.

Figure 63:
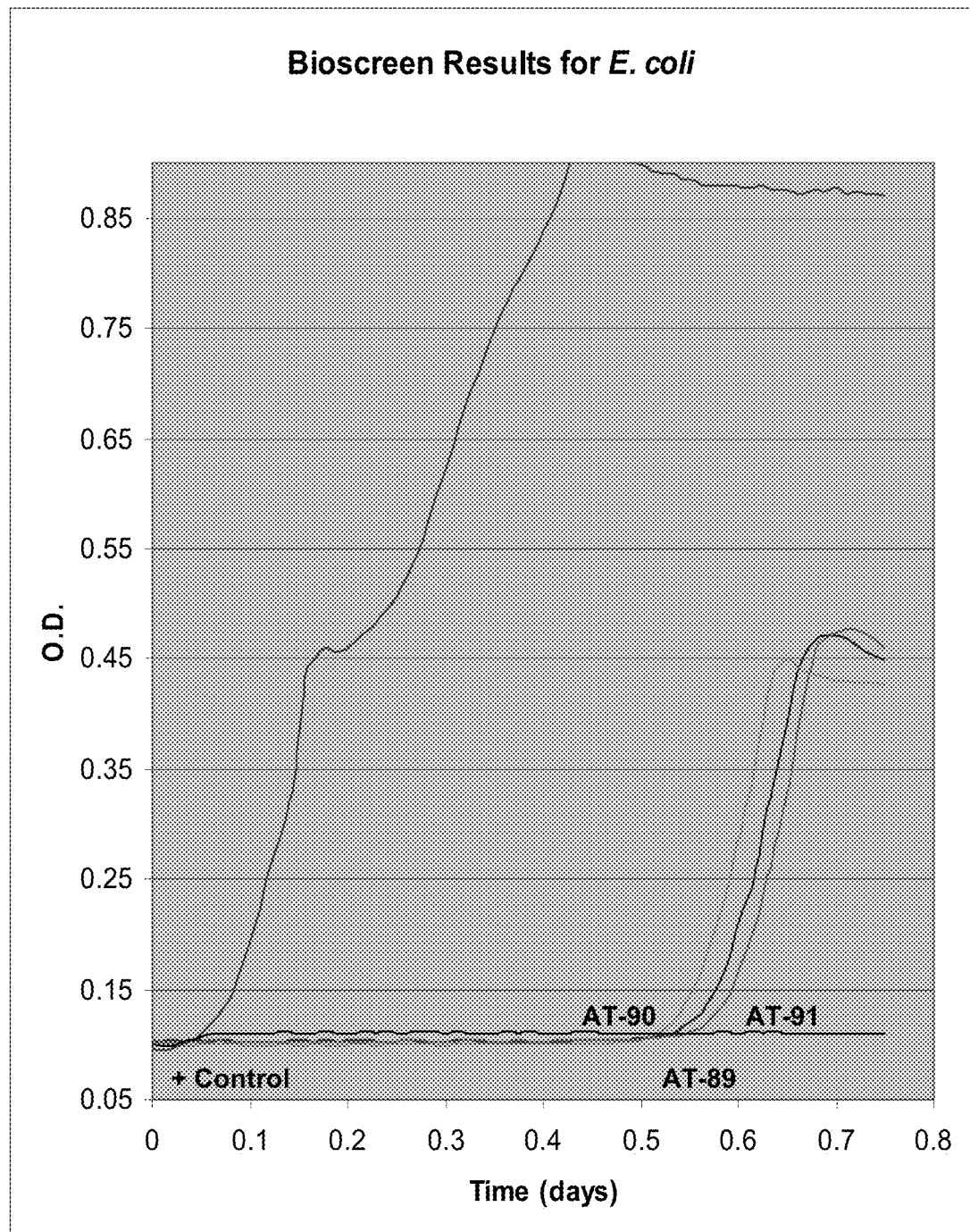
Figure 64A:
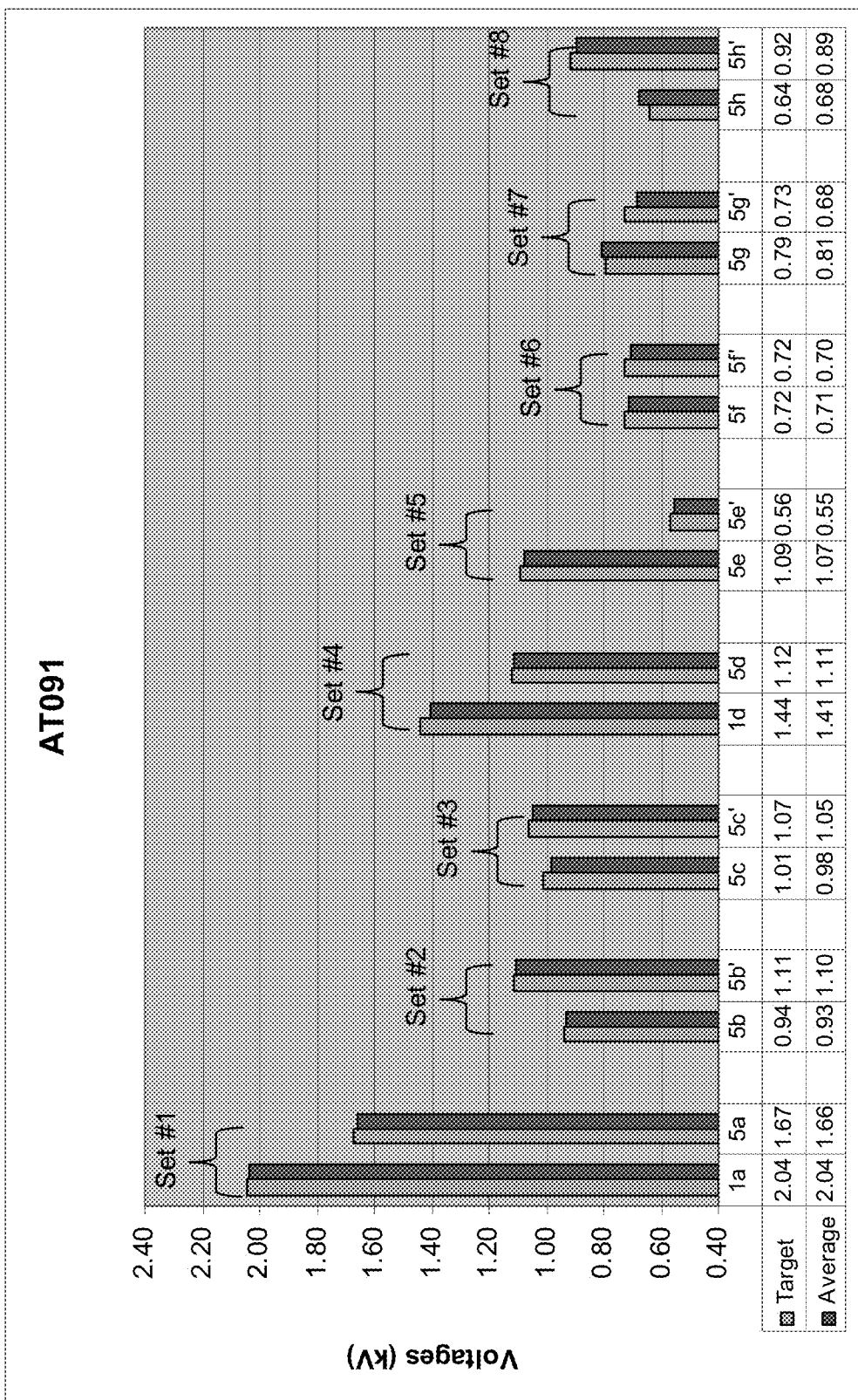
Figure 64B:
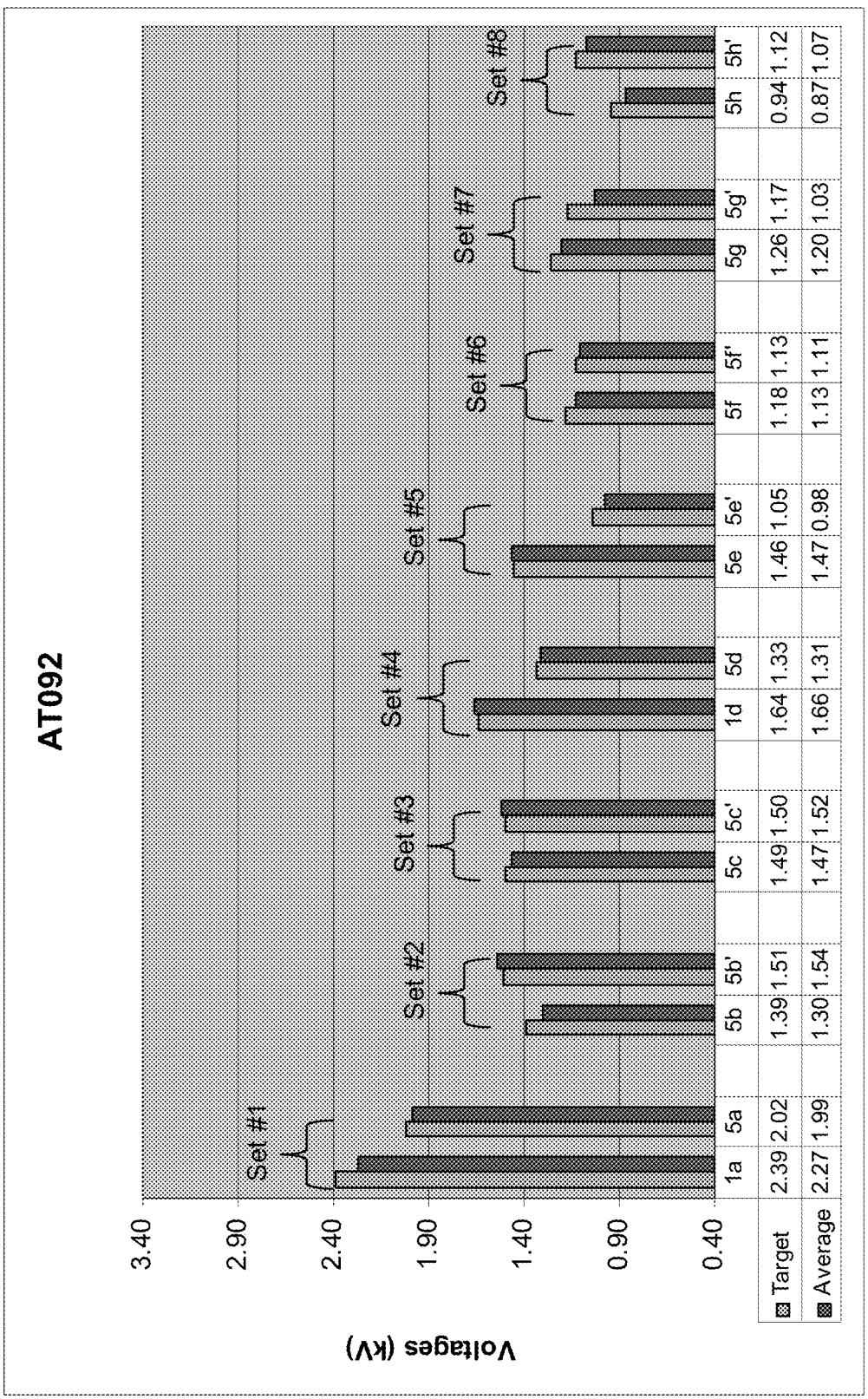
Figure 64C:
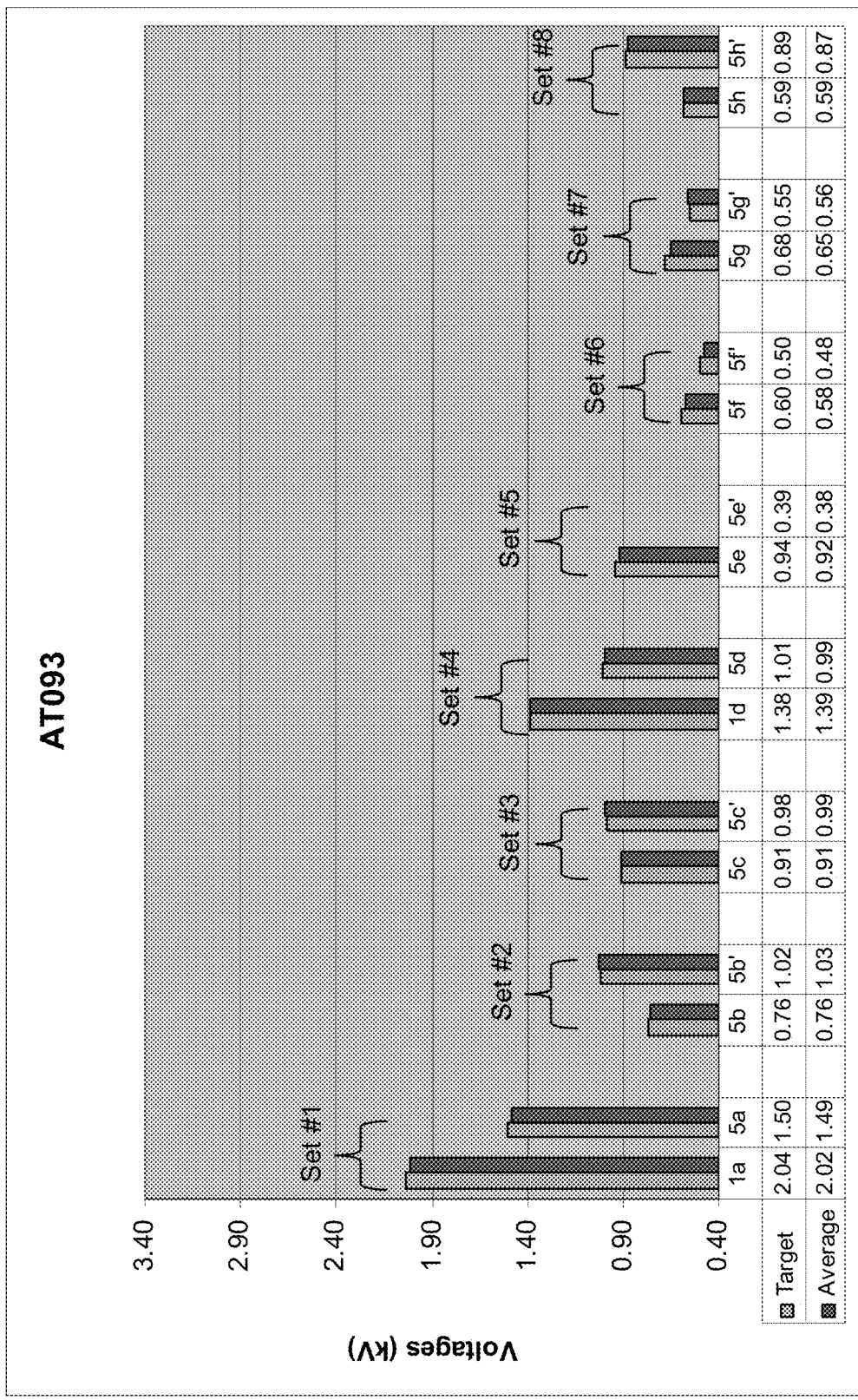
Figure 64D:
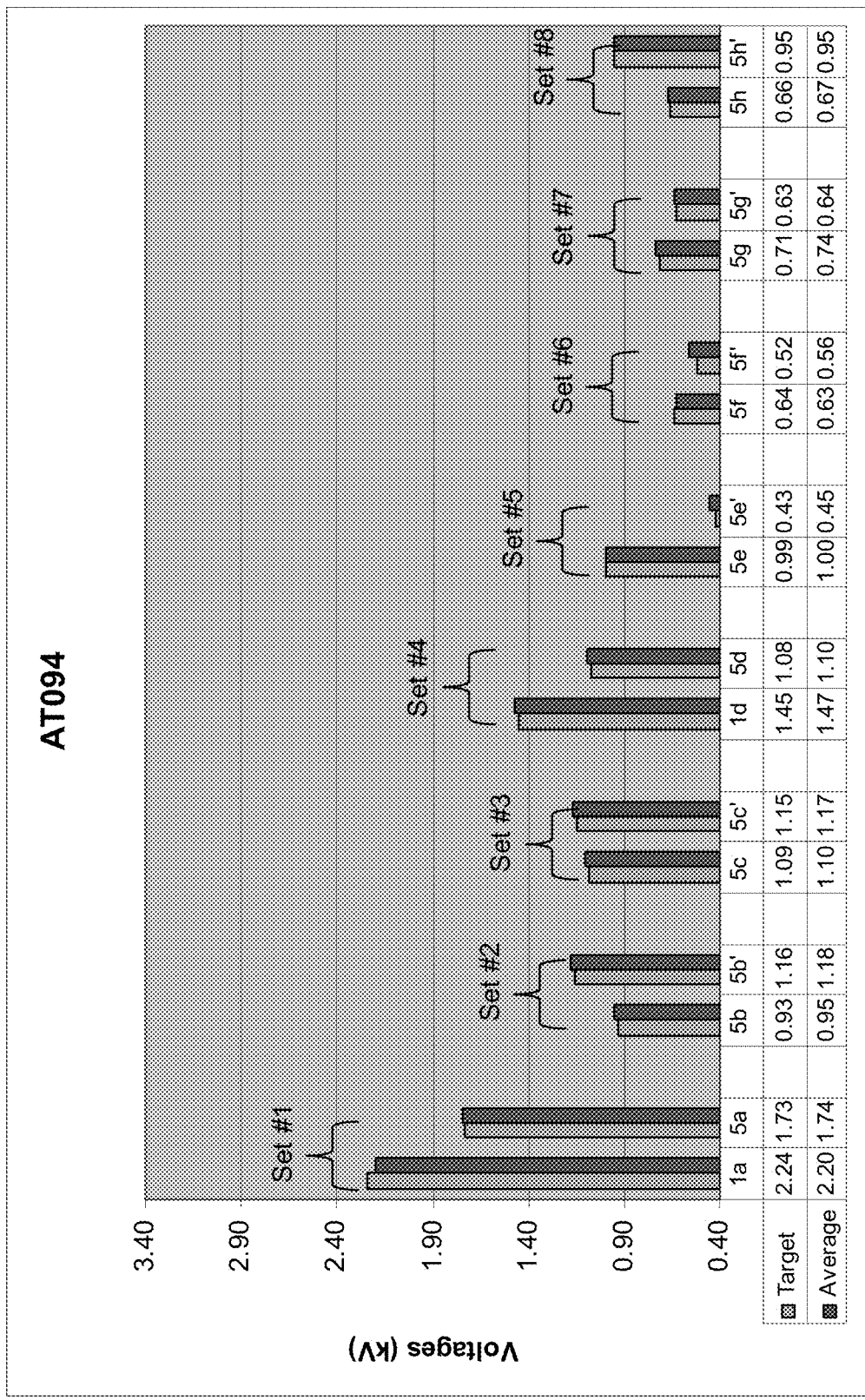
Figure 64E:
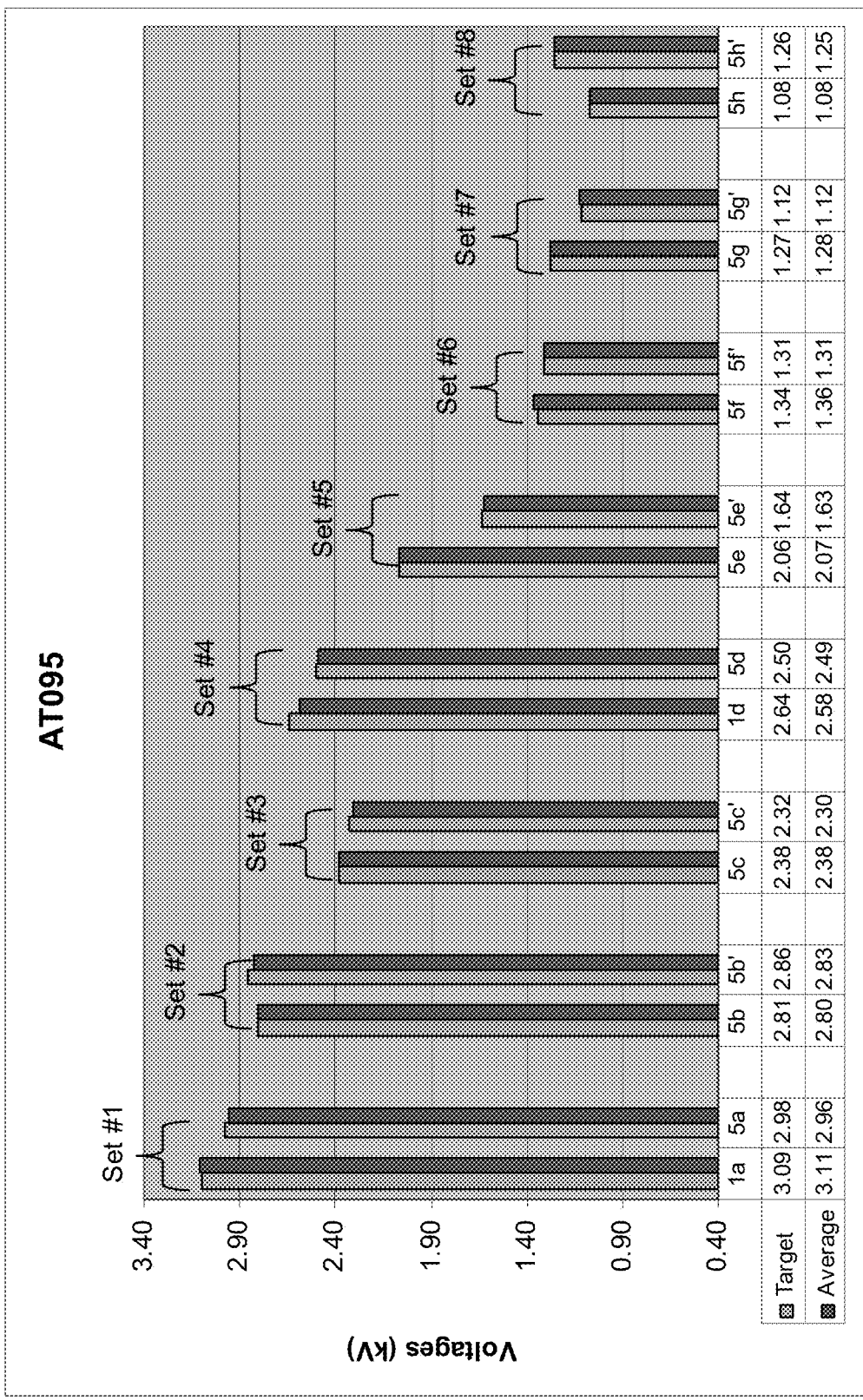

FIG. 63 shows biological Bioscreen results for the Example 8.

FIGS. 64a-64e show bar charts of various target and actual average voltages applied to different electrodes used in Example 9 to manufacture silver-based nanoparticles and nanoparticle solutions.

Figure 65A:
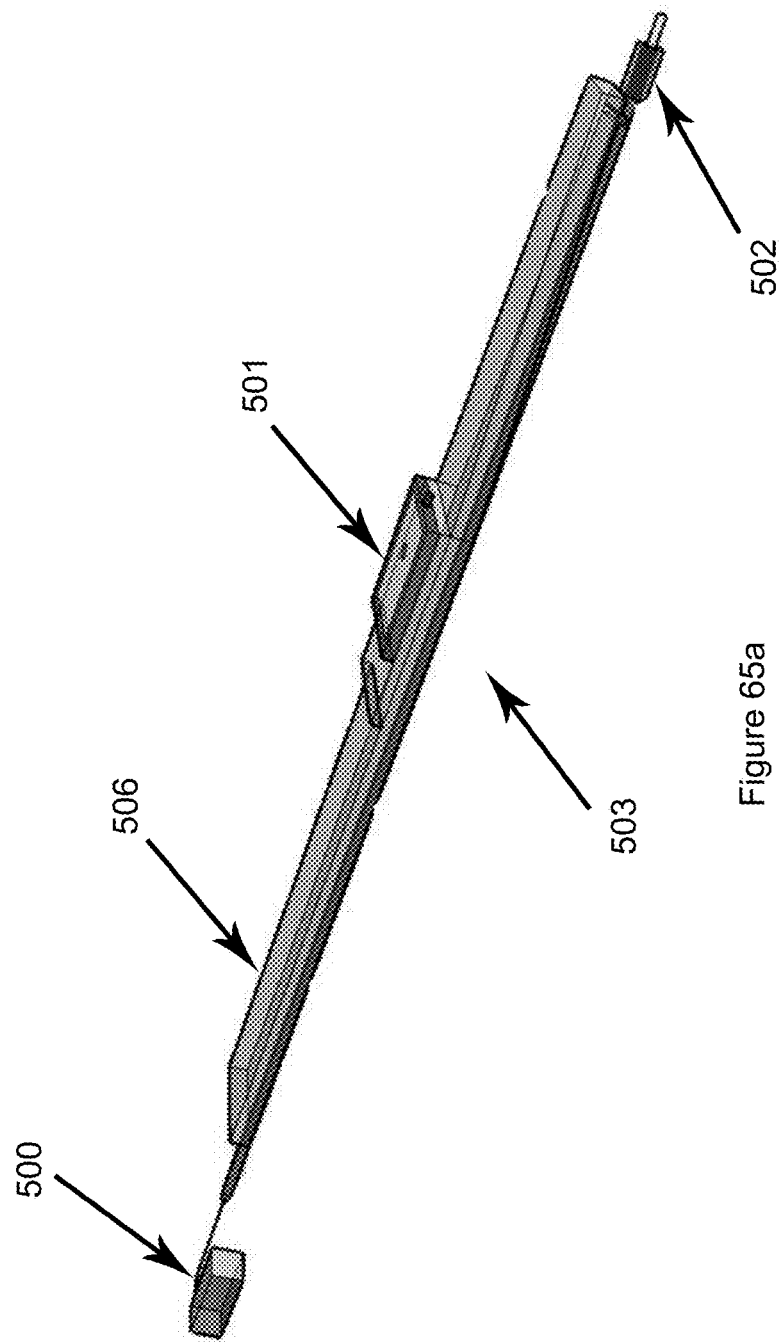
Figure 65B:
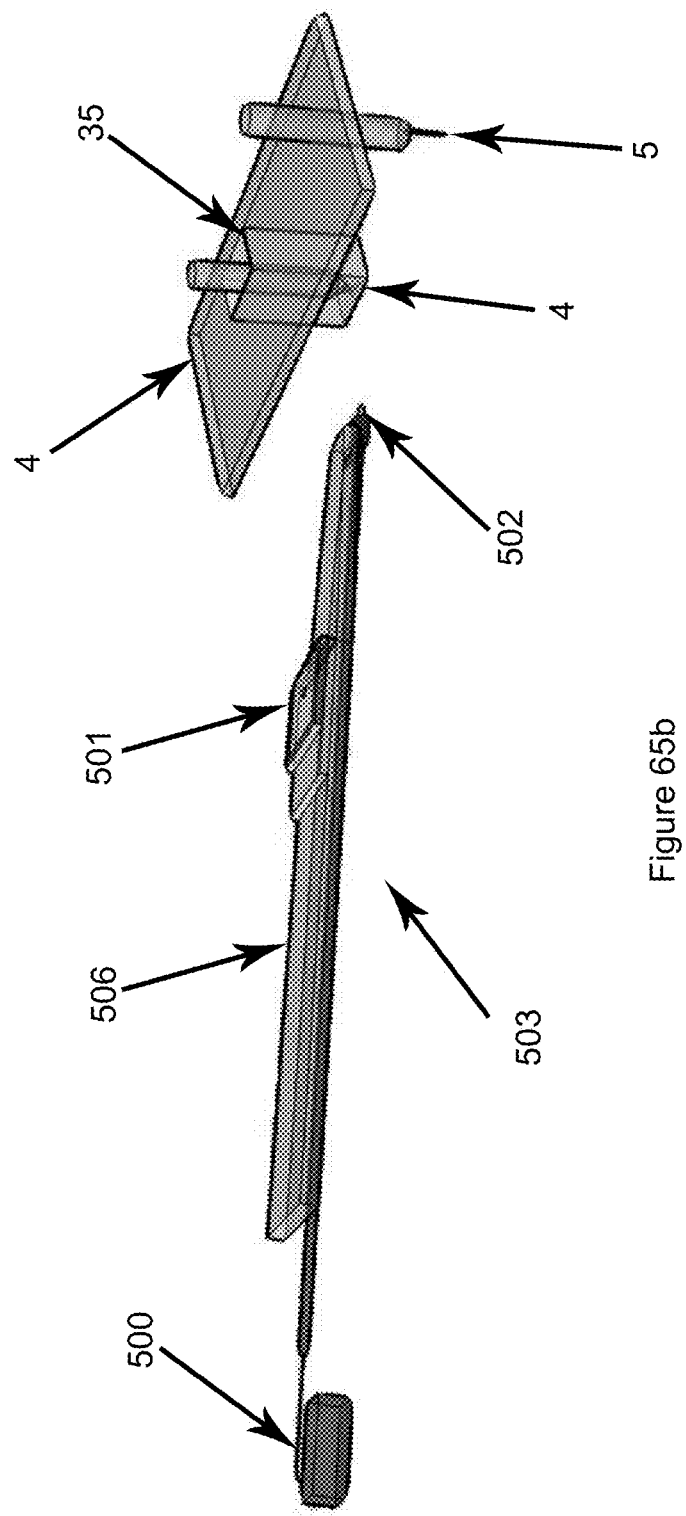

FIGS. 65a-65b show a perspective view of a spectra collection apparatus used in Example 9.

FIGS. 66a-66e show spectra collected from Example 9.

FIGS. 67a-67f show representative spectra known in the art.

Figure 68:
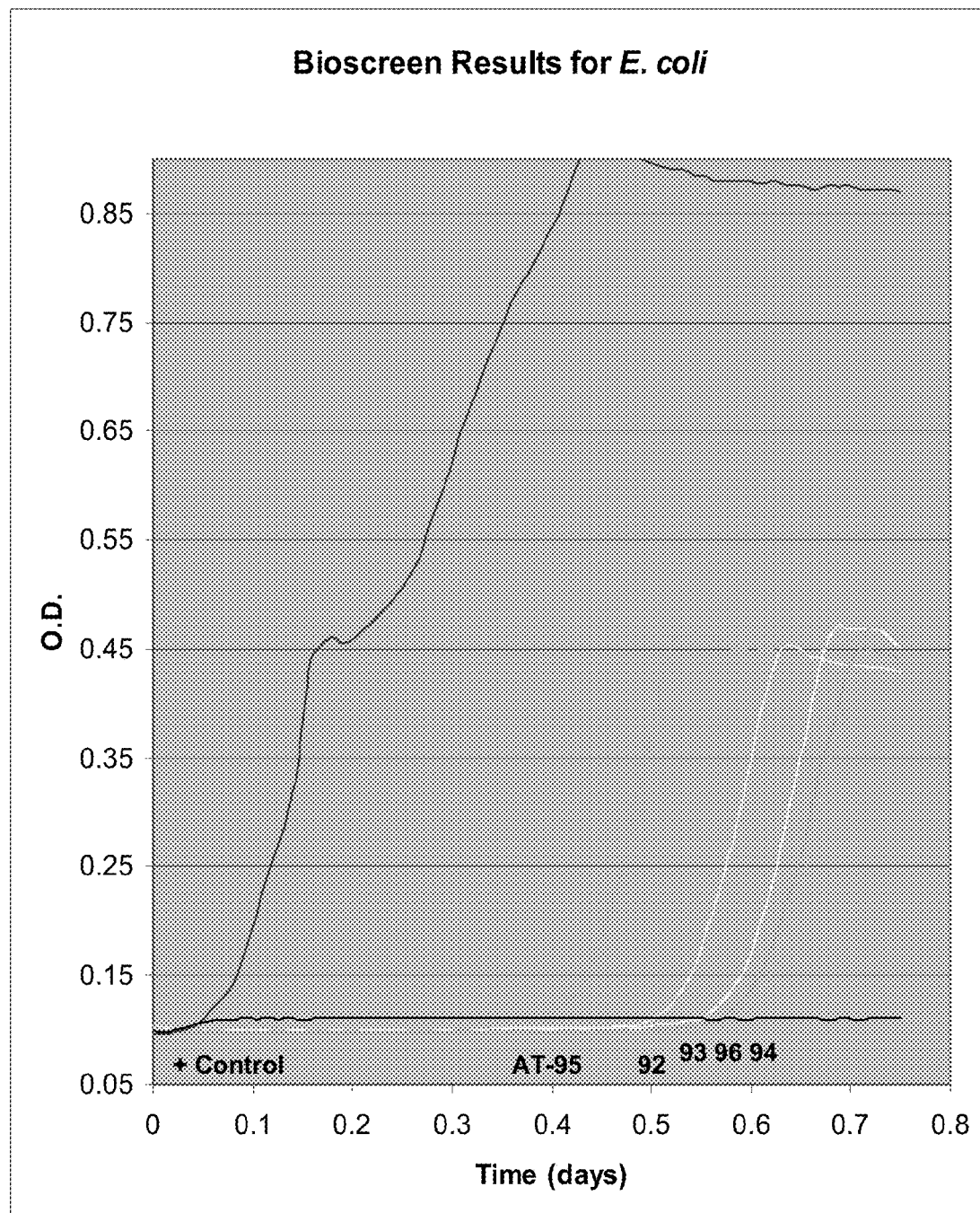

FIG. 68 shows biological Bioscreen results for the Example 9.

Figure 69:
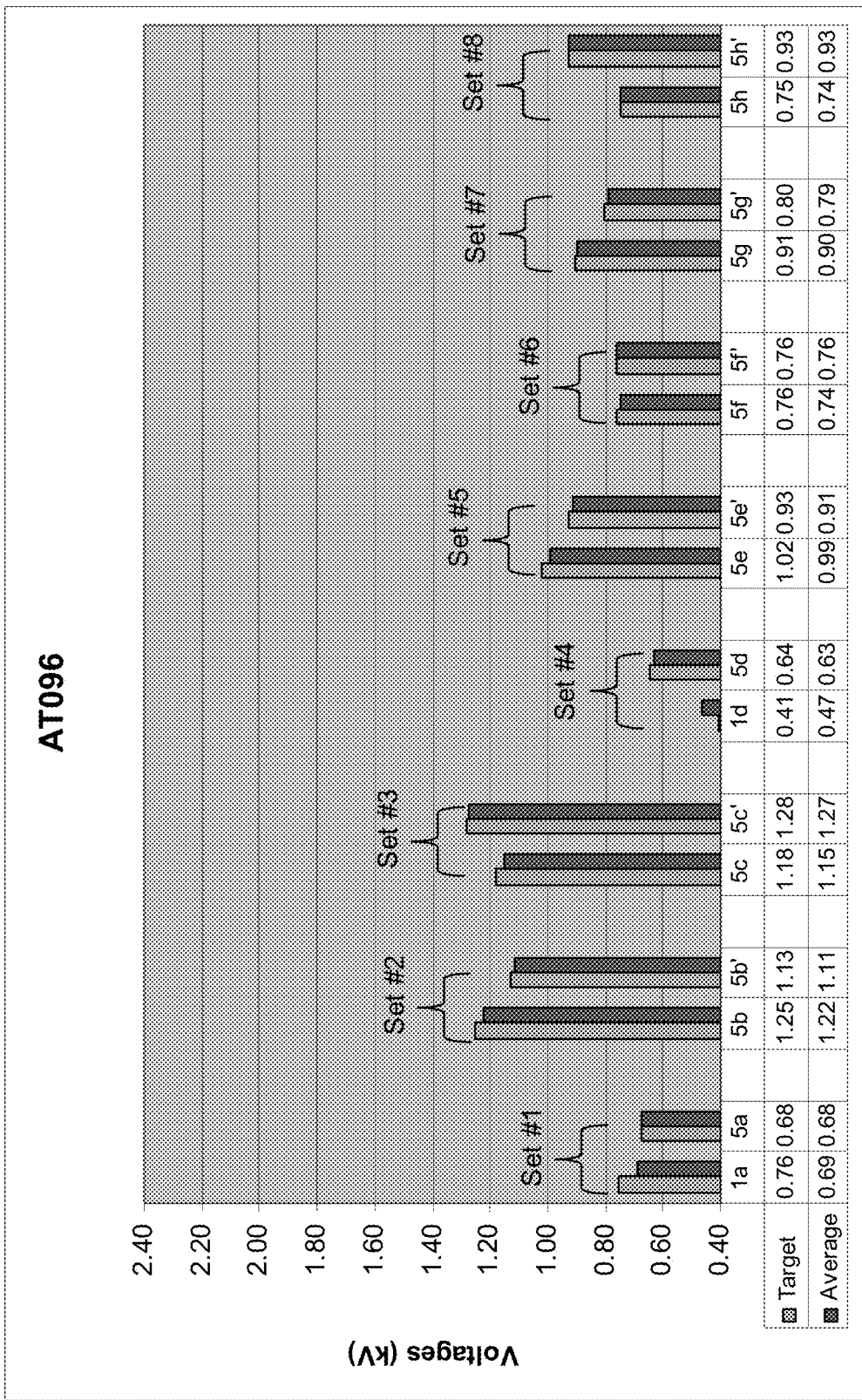

FIG. 69 show bar charts of various target and actual average voltages applied to different electrodes used in Example 10 to manufacture silver-based nanoparticles and nanoparticle solutions.

Figure 70A:
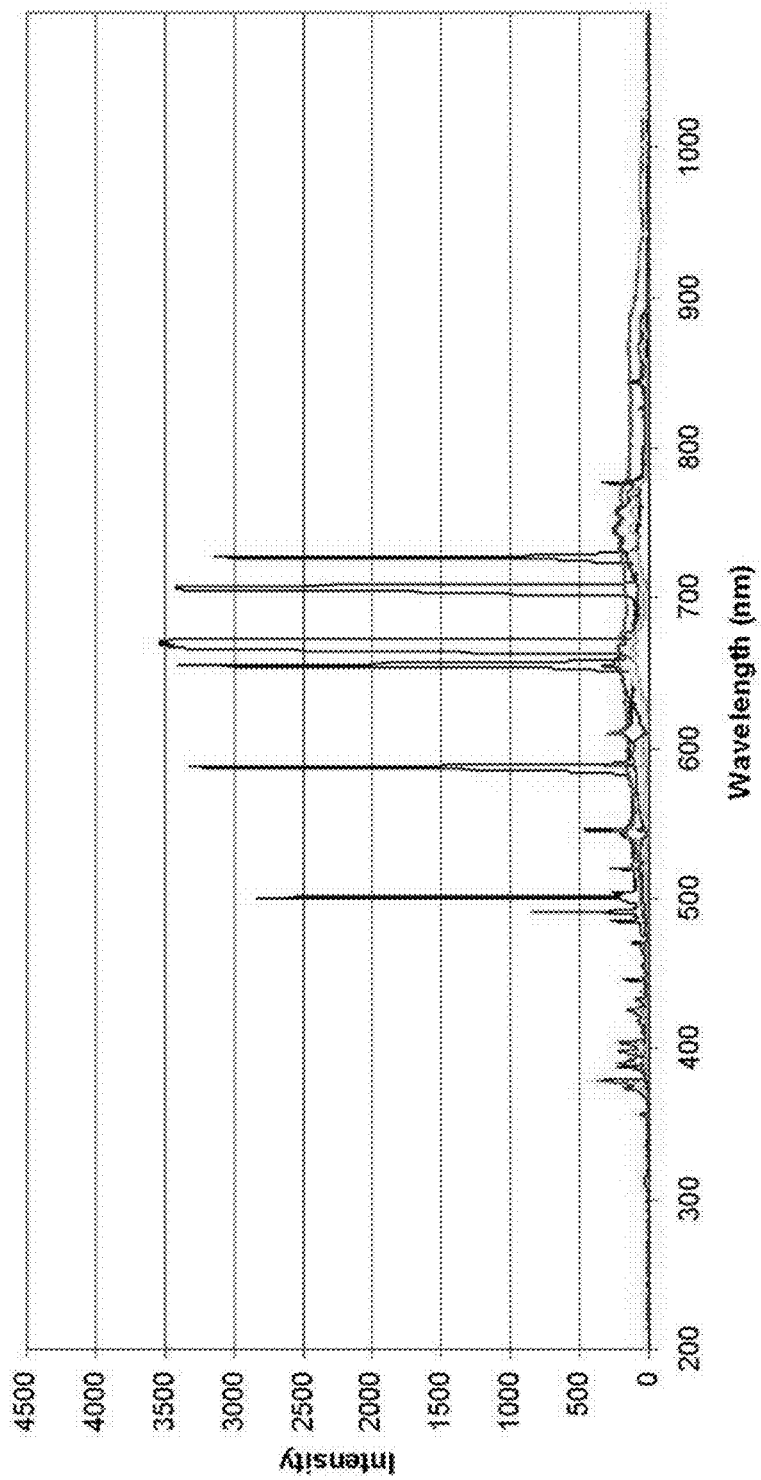
Figure 70B:
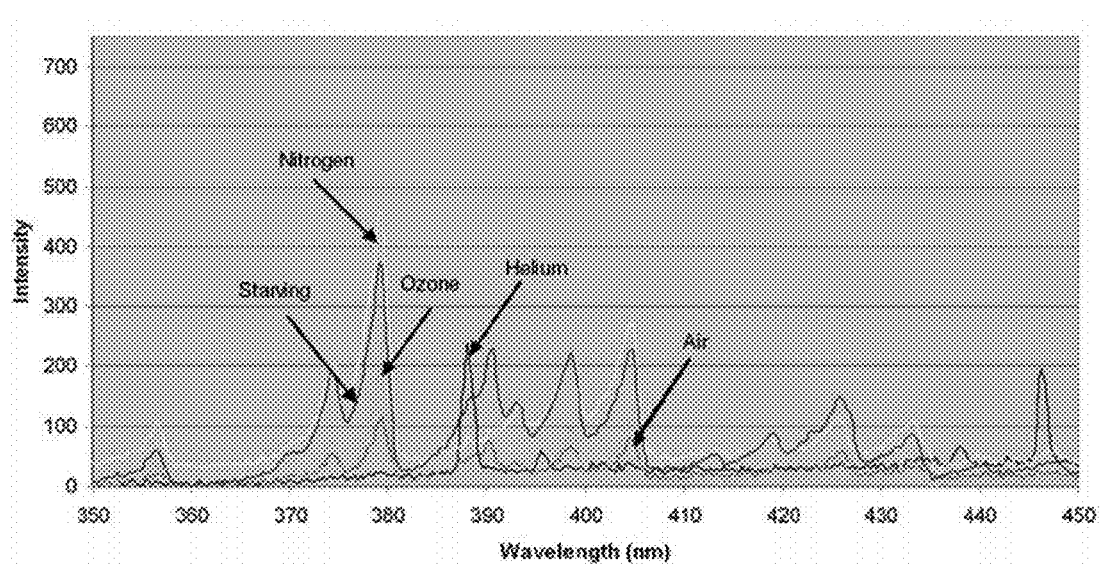
Figure 70C:
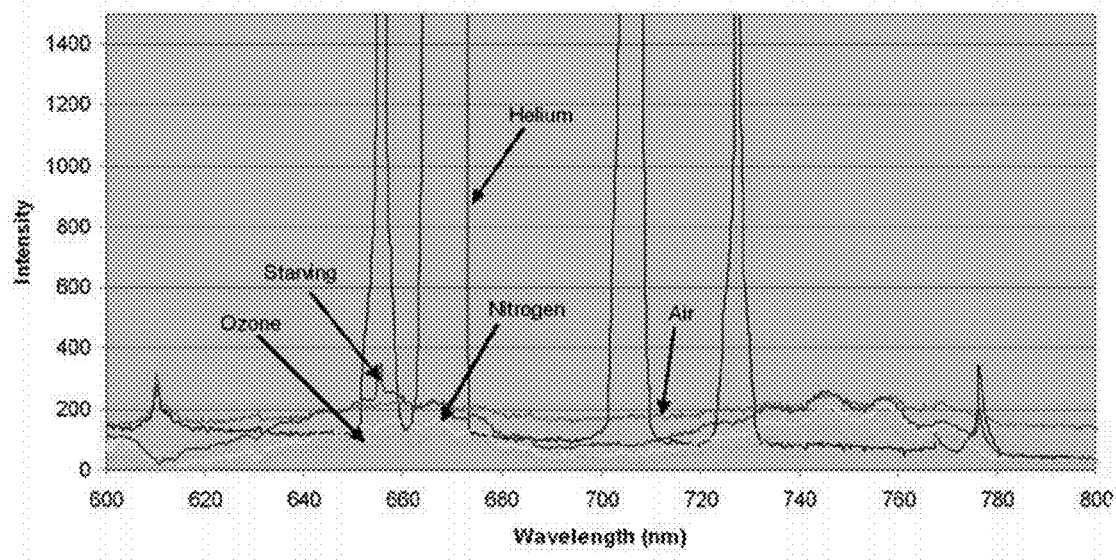

FIGS. 70a-70c show spectra collected from Example 10.

Figure 71A:
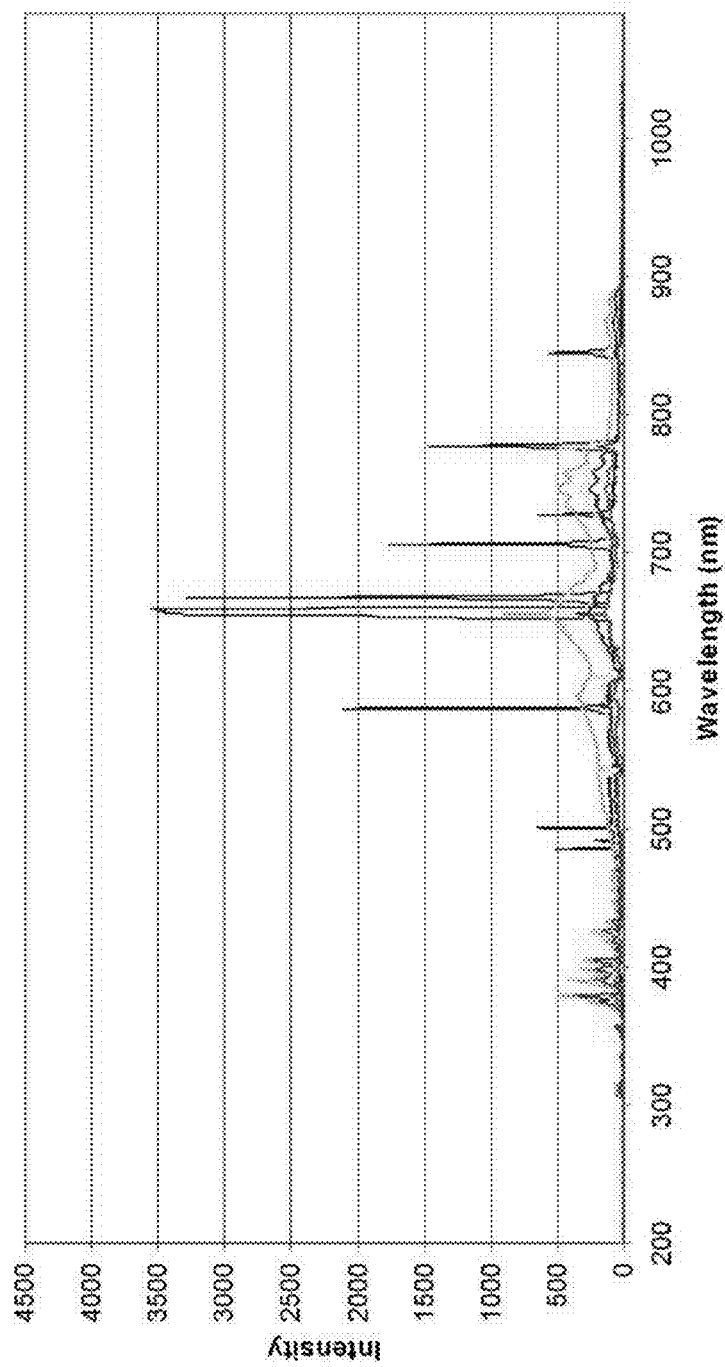
Figure 71B:
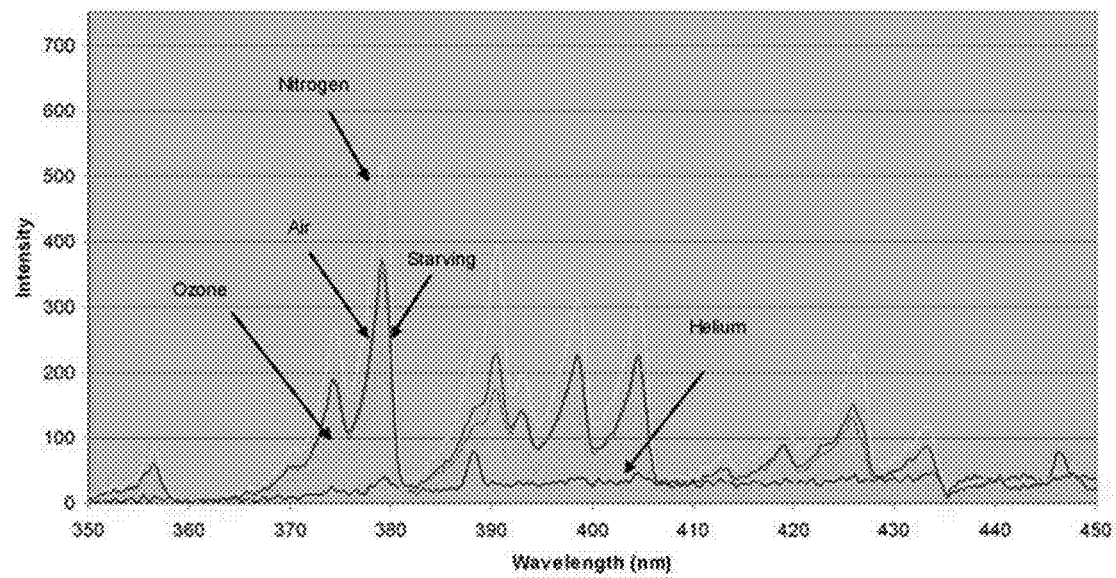
Figure 71C:
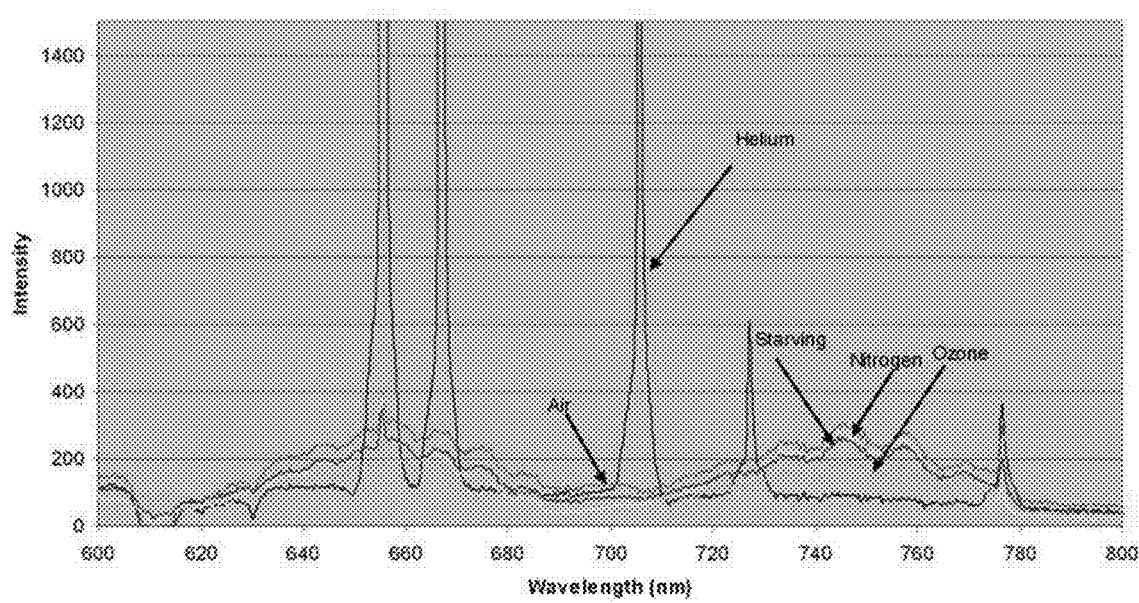

FIGS. 71a-71c show spectra collected from Example 10.

Figure 72A:
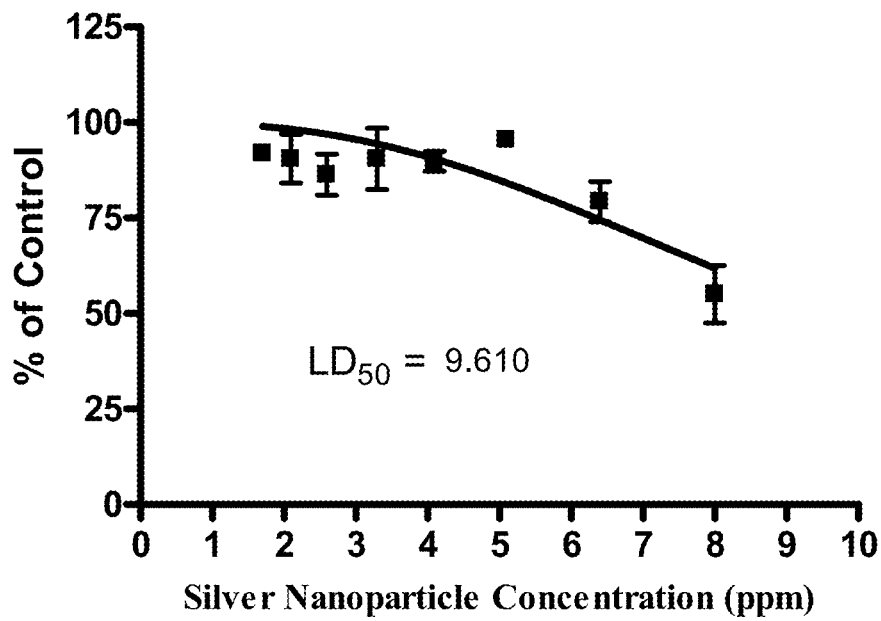
Figure 72B:
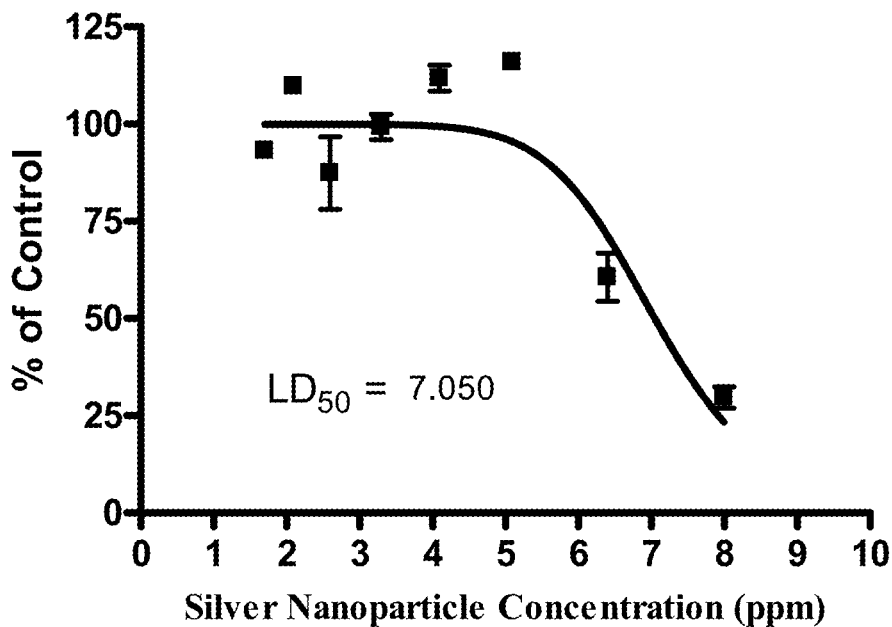
Figure 72C:
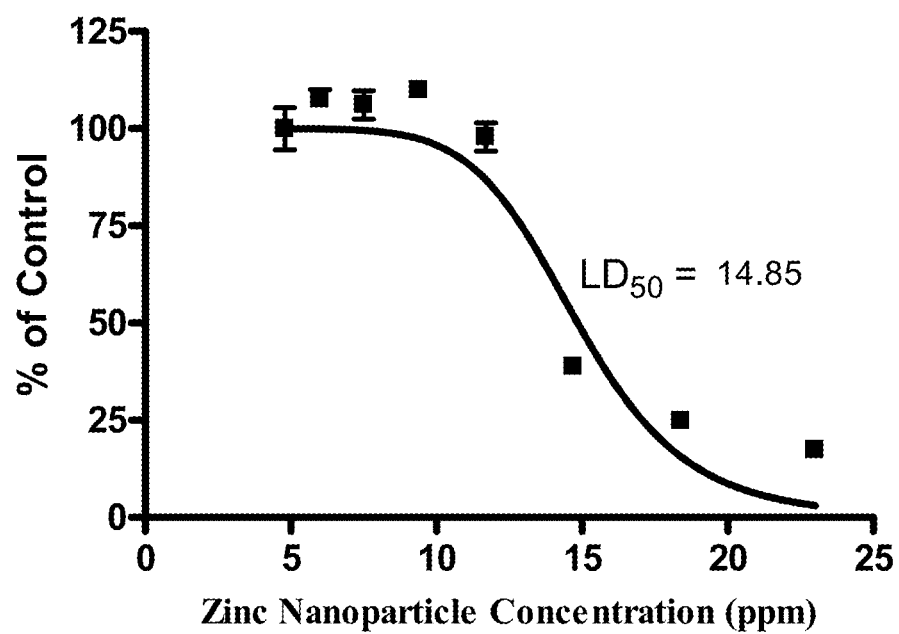

FIGS. 72a-72c show various cytotoxicity curves for solutions used in Example 11 against murine liver epithelial cells; the amount of fluorescence relative to control (100%) cells is plotted against increasing amounts of nanoparticles.

Figure 73A:
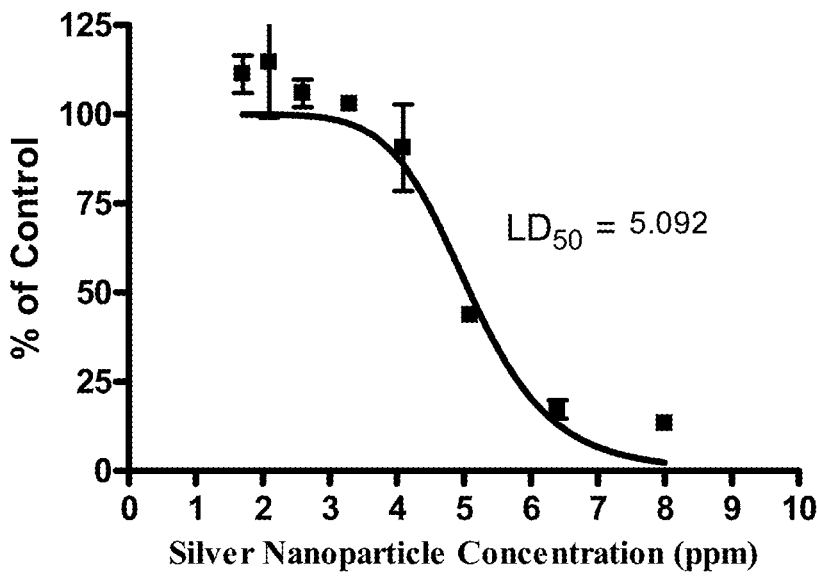
Figure 73B:
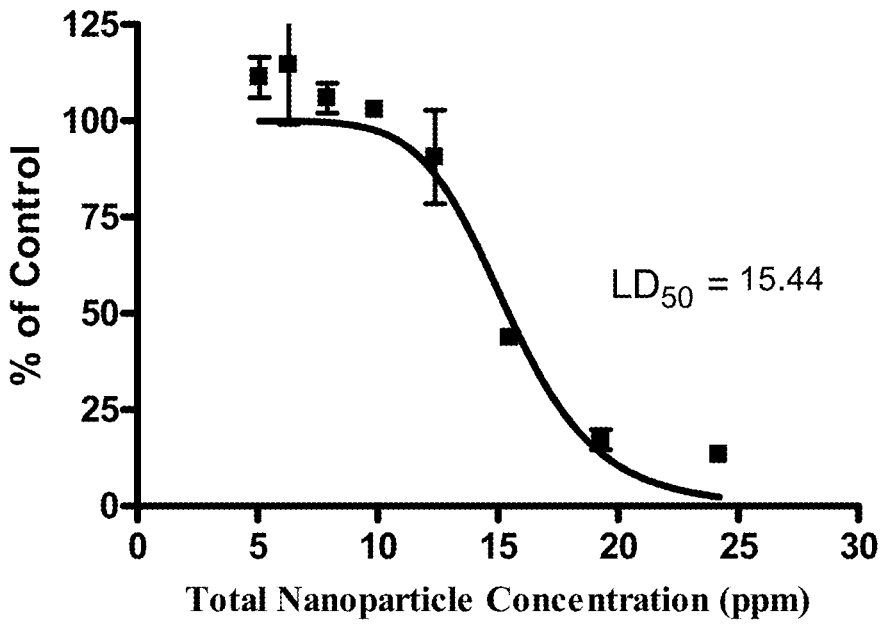

FIGS. 73a-73b show various cytotoxicity curves for solutions used in Example 11 against murine liver epithelial cells; the amount of fluorescence relative to control (100%) cells is plotted against increasing amounts of nanoparticles.

Figure 74A:
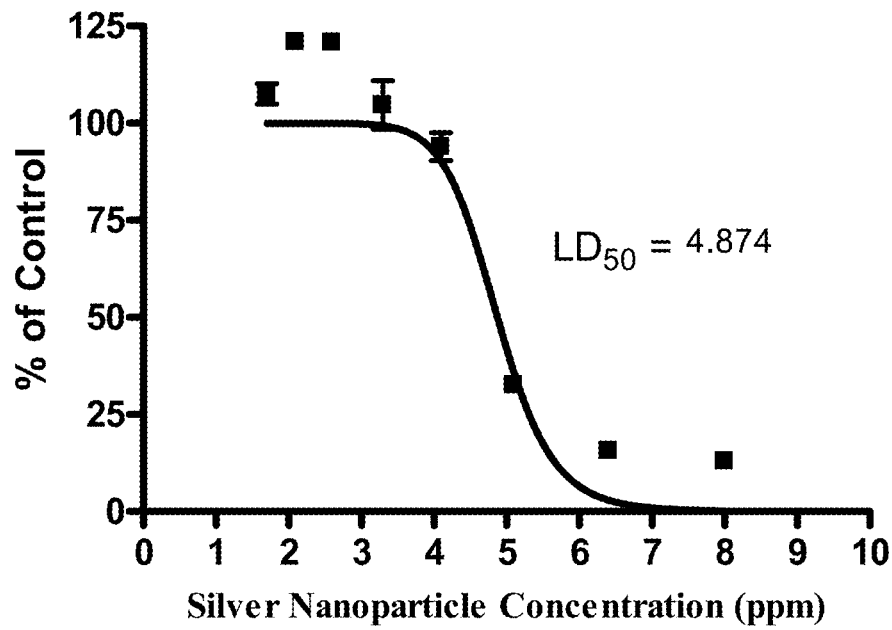
Figure 74B:
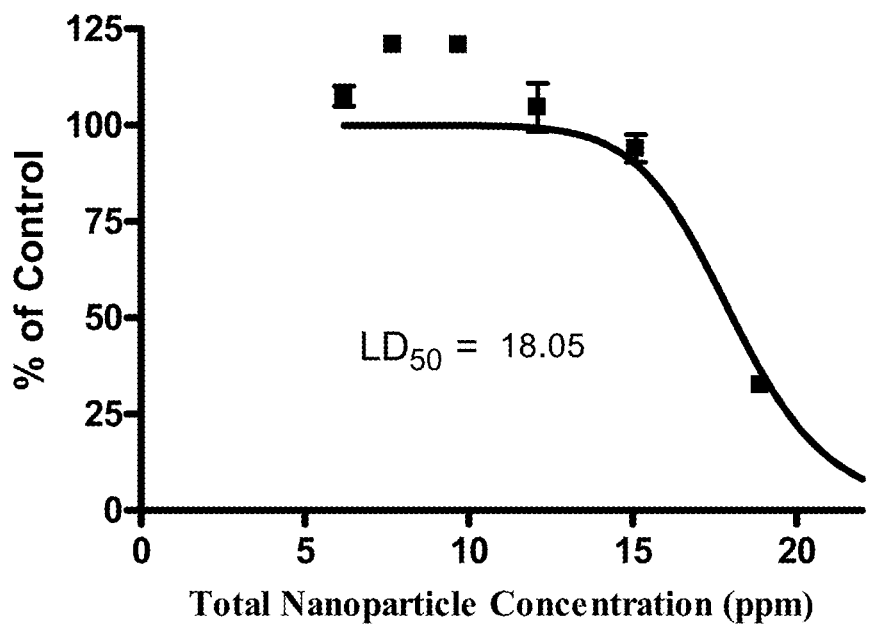

FIG. 74a-74b show various cytotoxicity curves for solutions used in Example 11 against murine liver epithelial cells; the amount of fluorescence relative to control (100%) cells is plotted against increasing amounts of nanoparticles.

Figure 75:
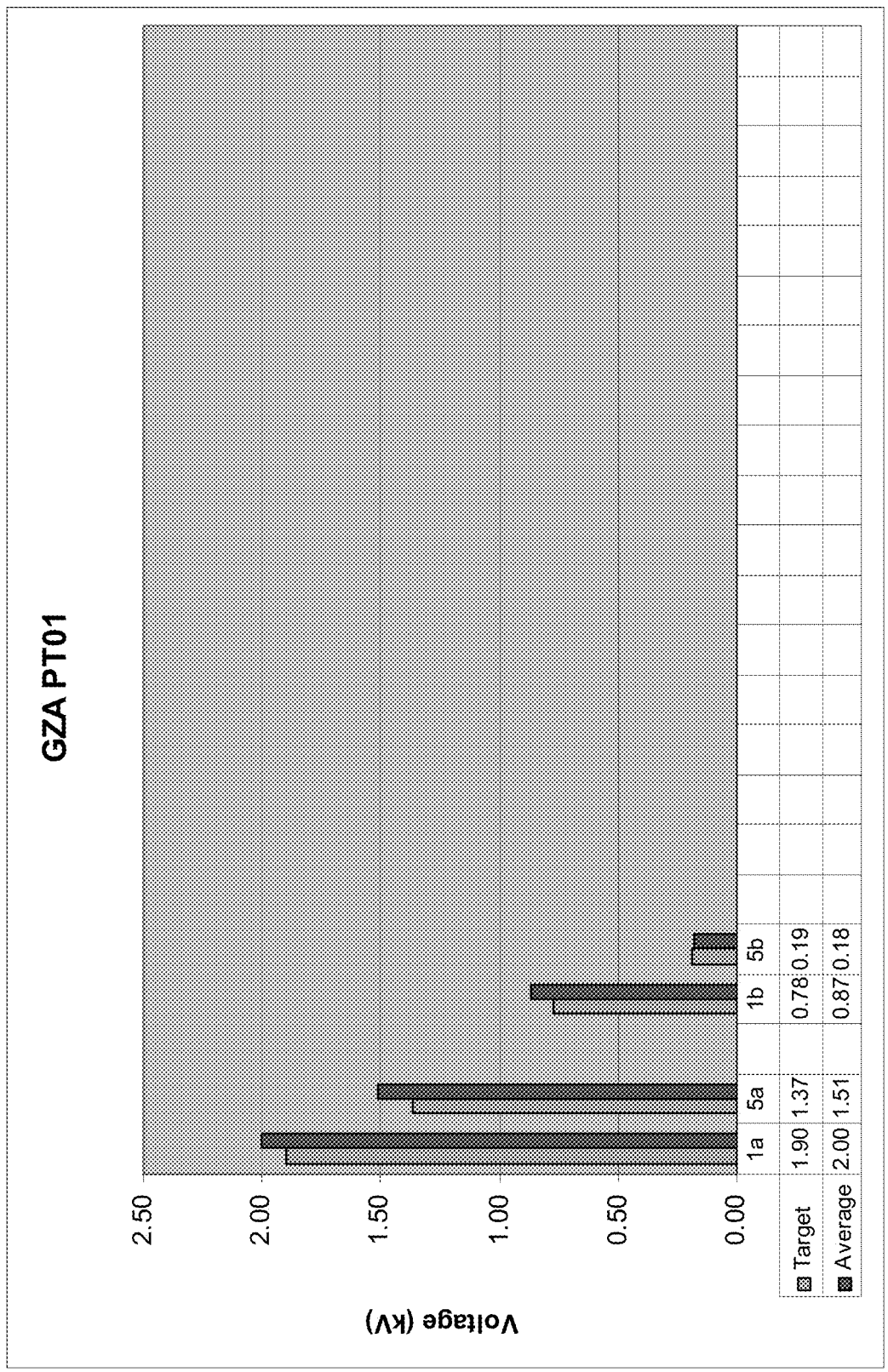

FIG. 75 shows a bar chart of various target and actual average voltages applied to different electrodes used in Example 11 to manufacture silver-based nanoparticles and nanoparticle solutions.

Figure 76A:
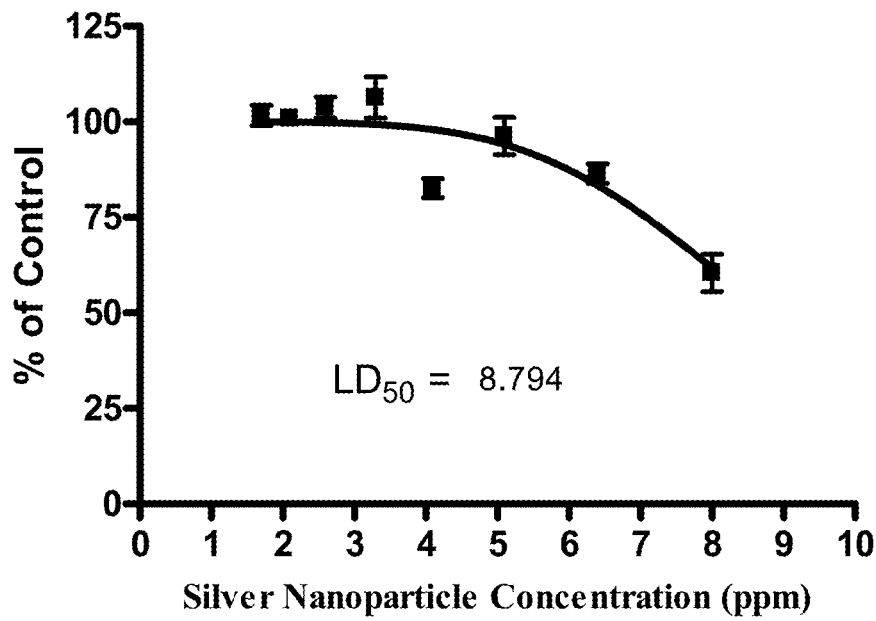
Figure 76B:
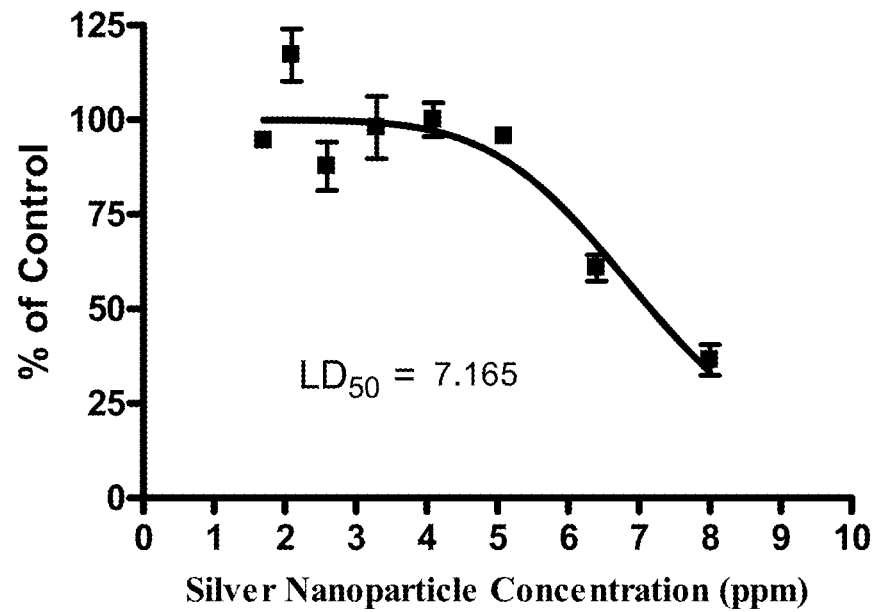

FIGS. 76a-76b show various cytotoxicity curves for solutions used in Example 11 against murine liver epithelial cells; the amount of fluorescence relative to control (100%) cells is plotted against increasing amounts of nanoparticles.

Figure 77A:
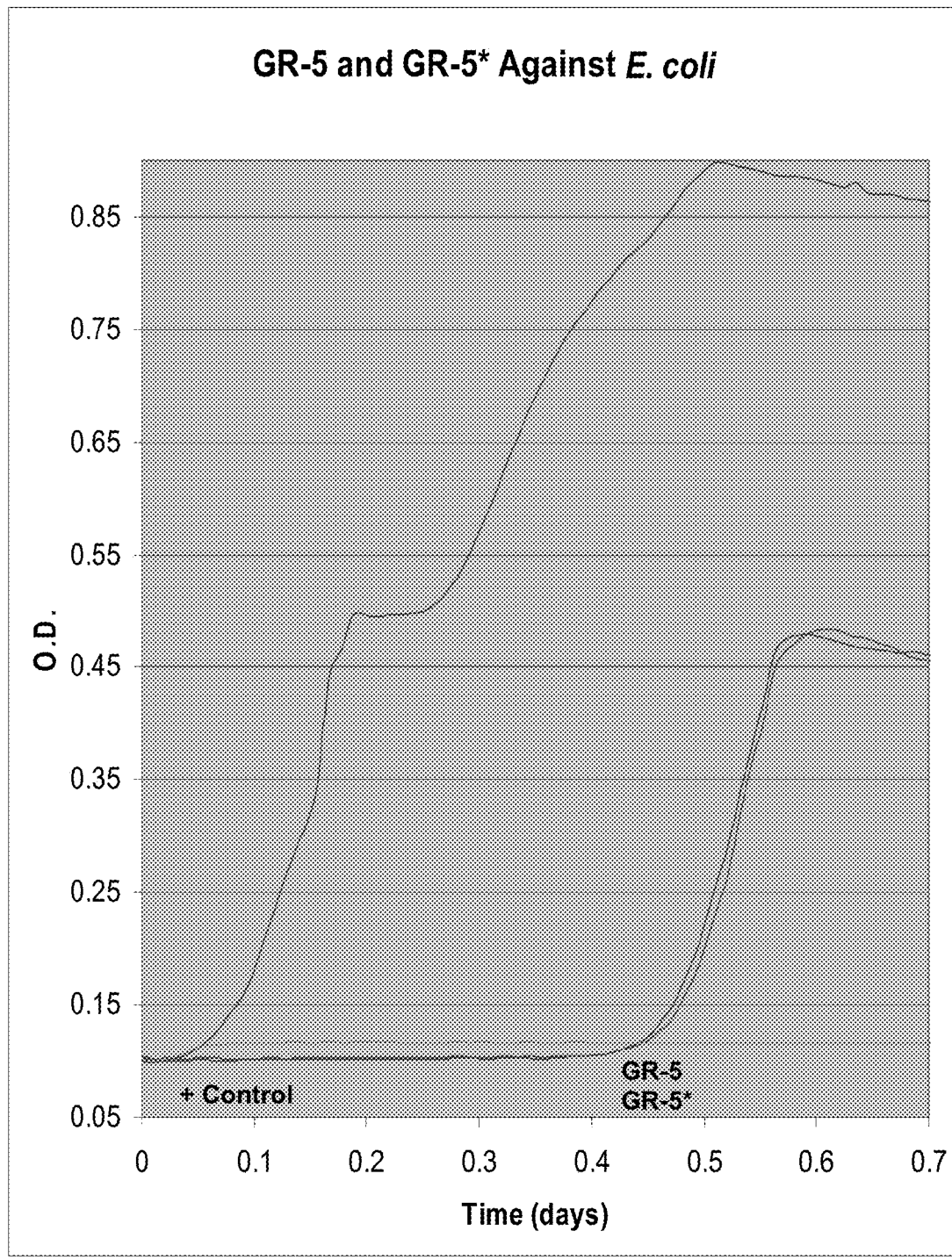
Figure 77B:
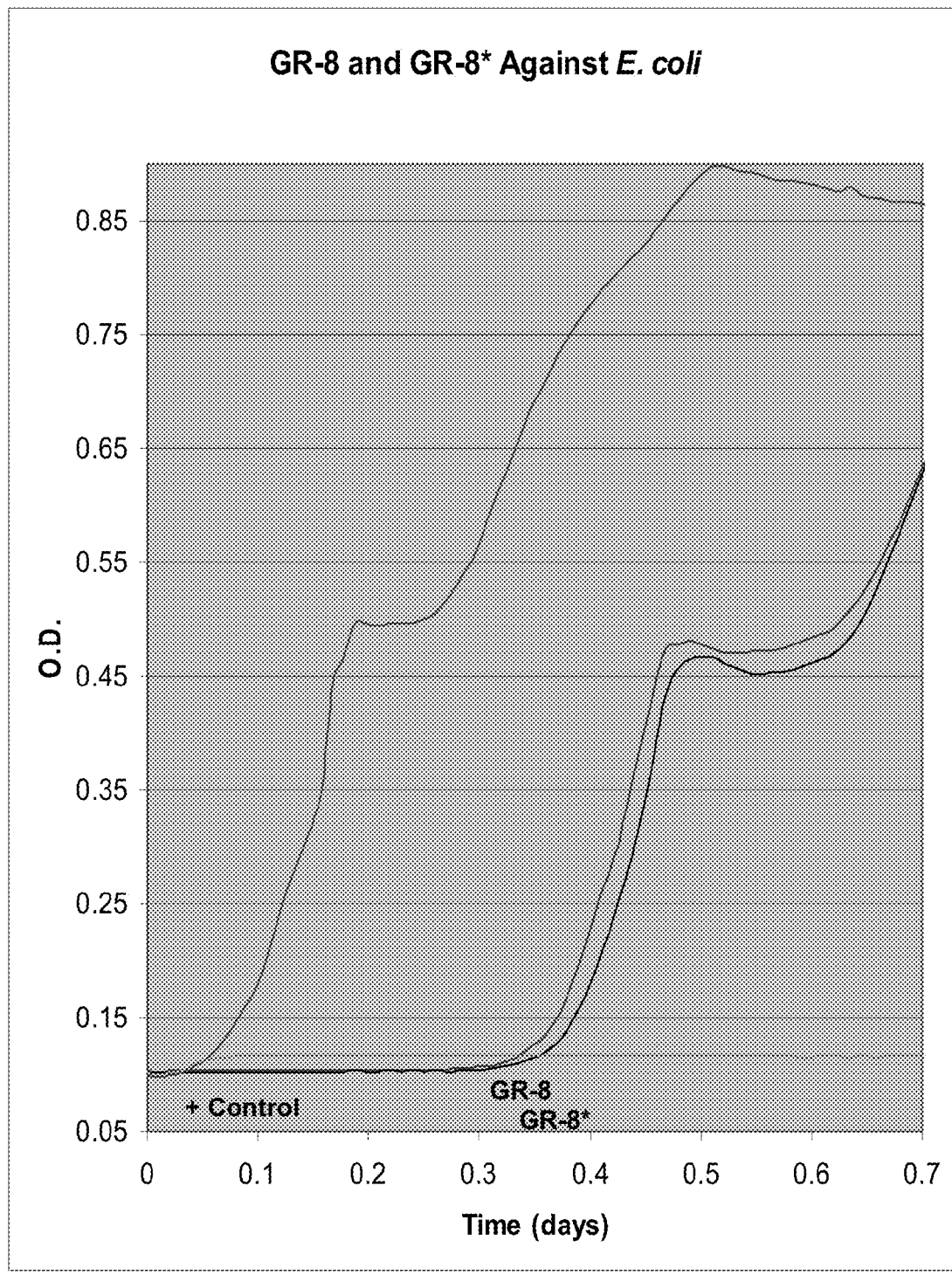

FIGS. 77a-77b show biological Bioscreen results for Example 11.

Figure 78A:
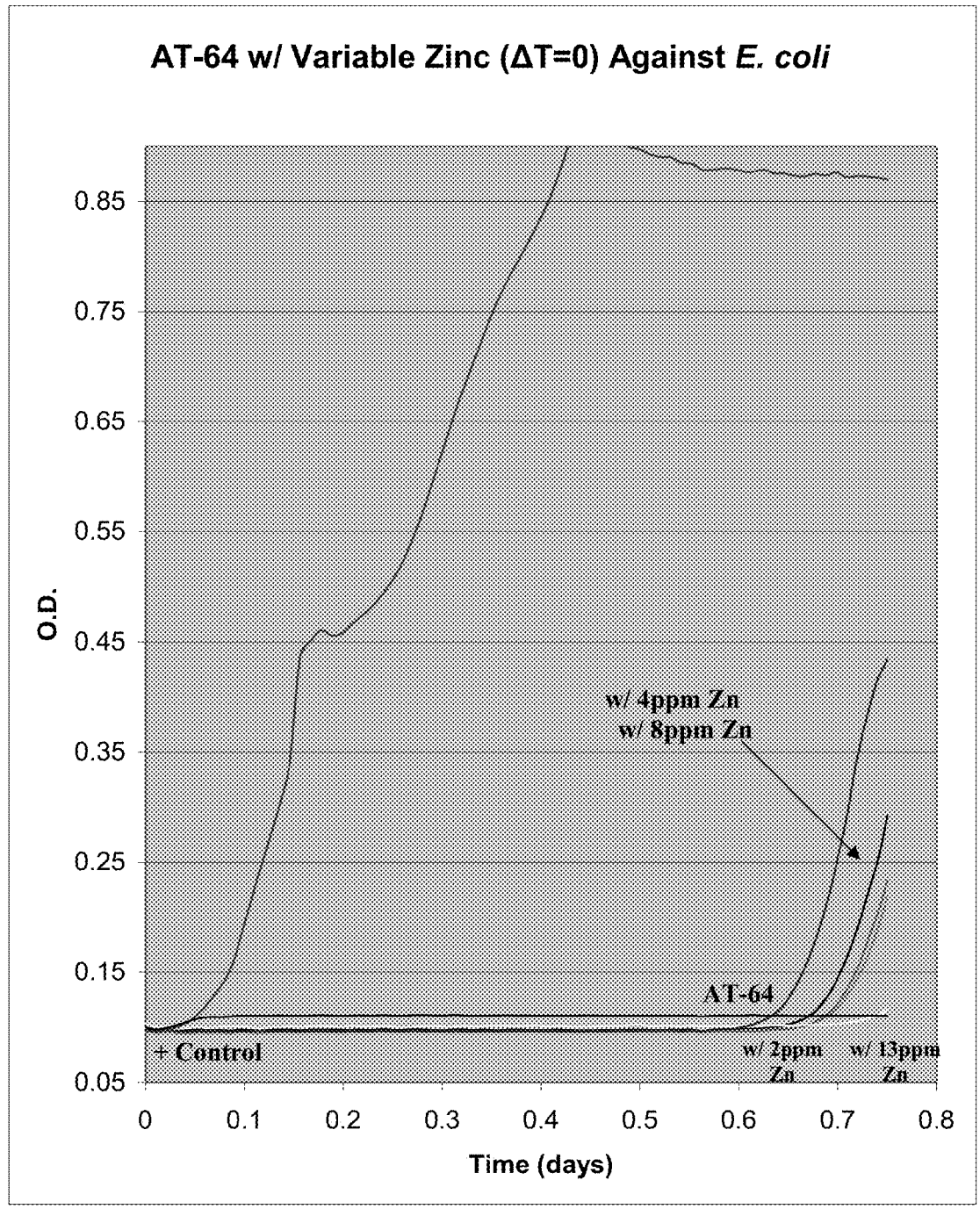
Figure 78B:
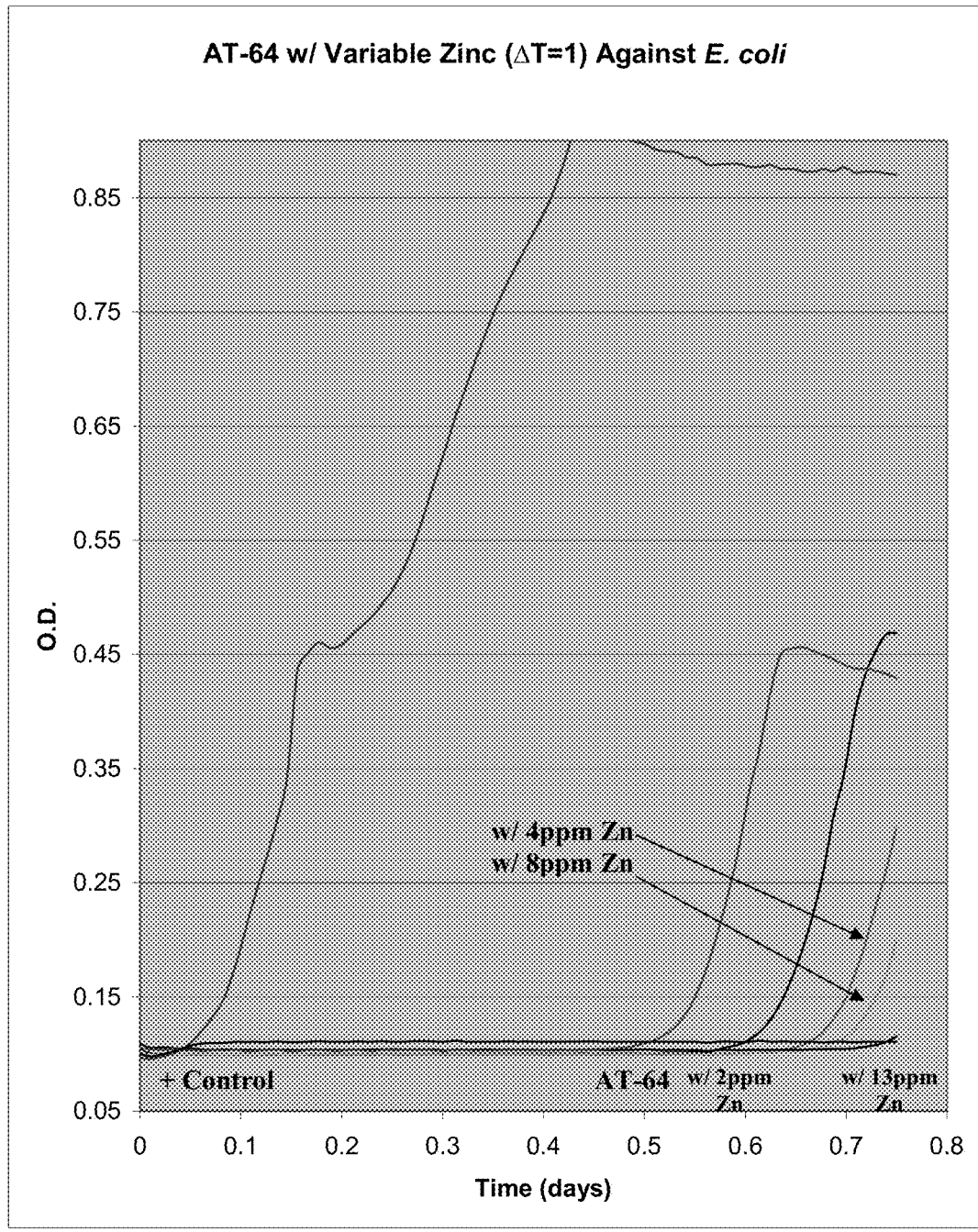

FIGS. 78a-78b show biological Bioscreen results for the Example 12.

Figure 79A:
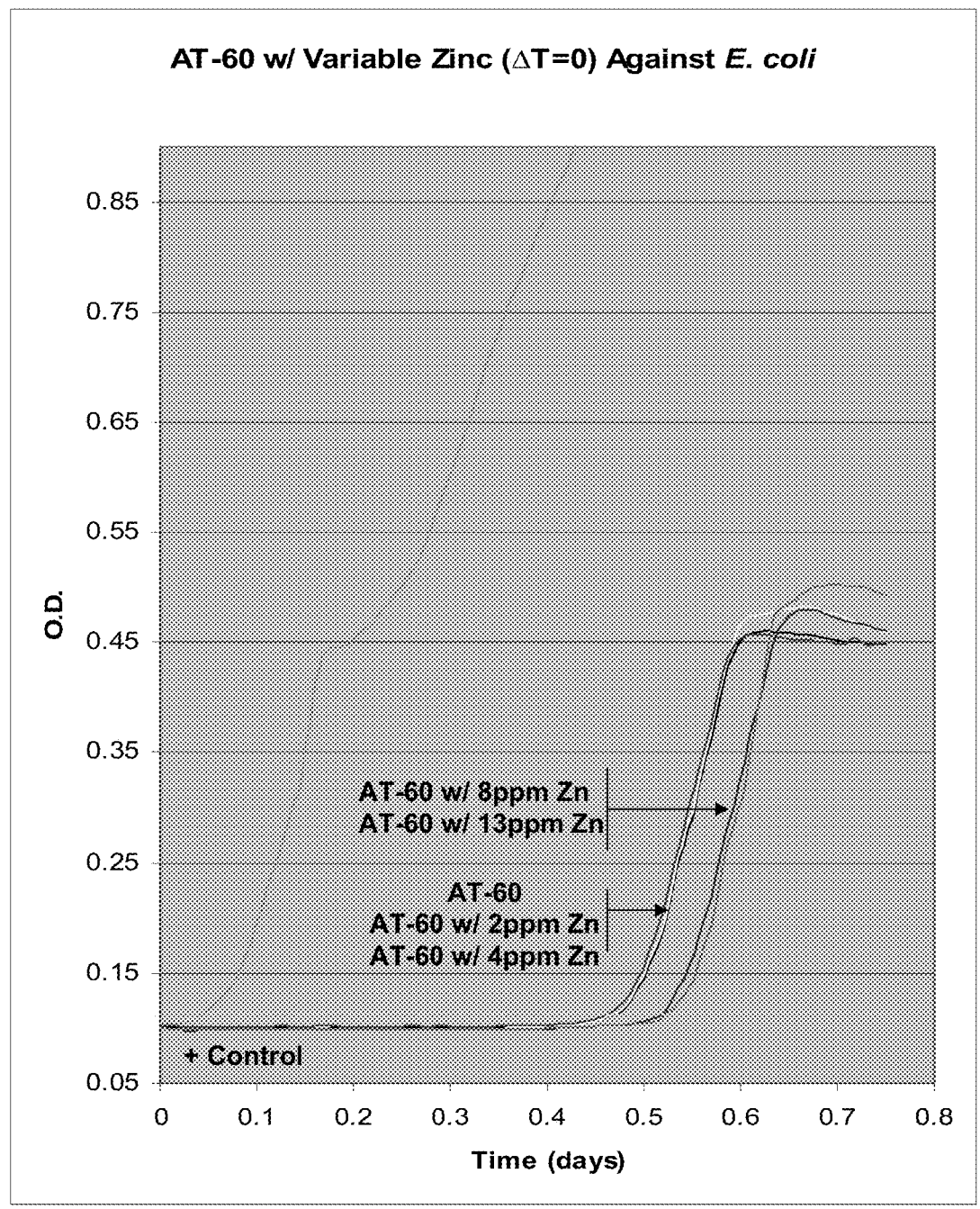
Figure 79B:
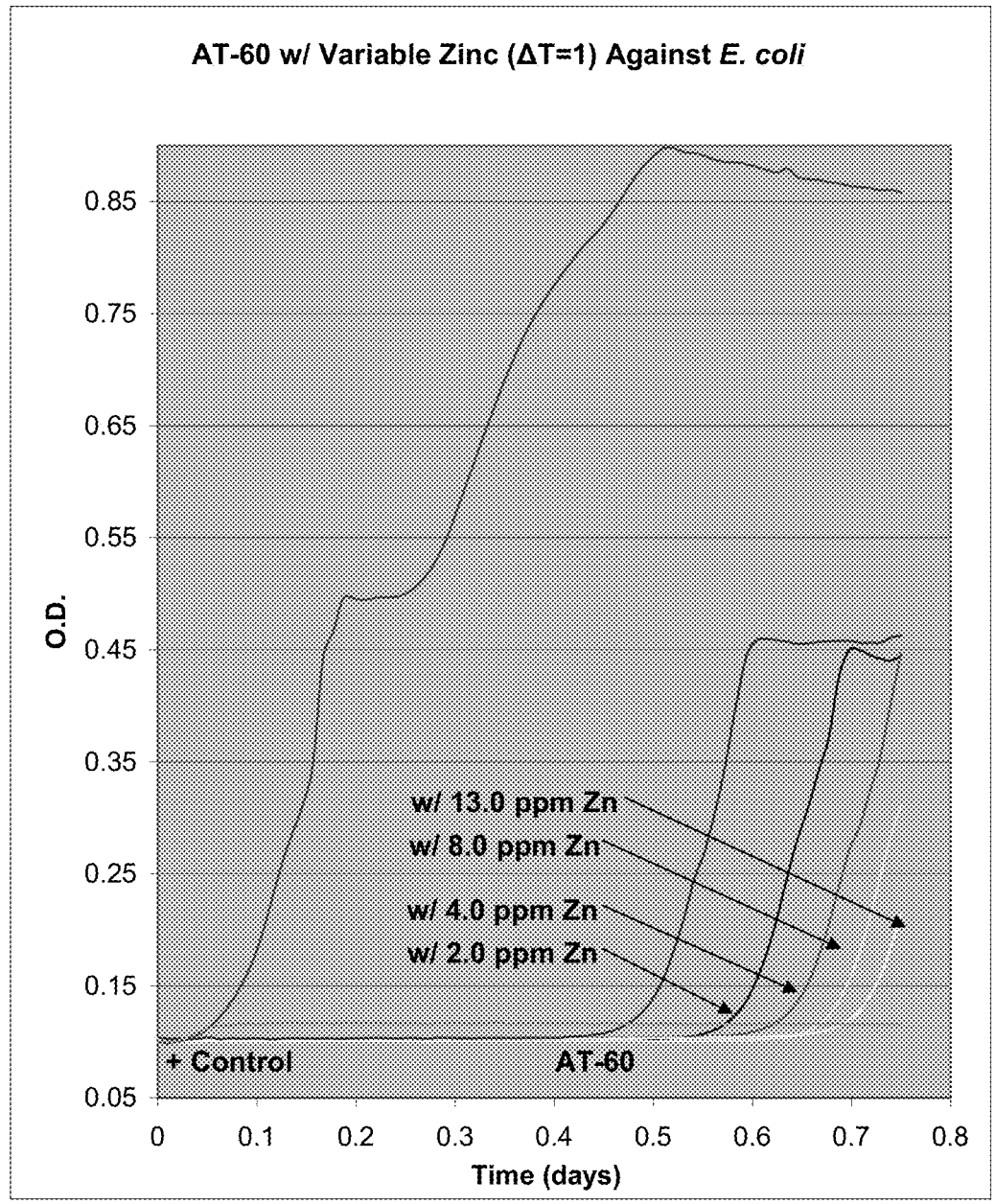
Figure 79C:
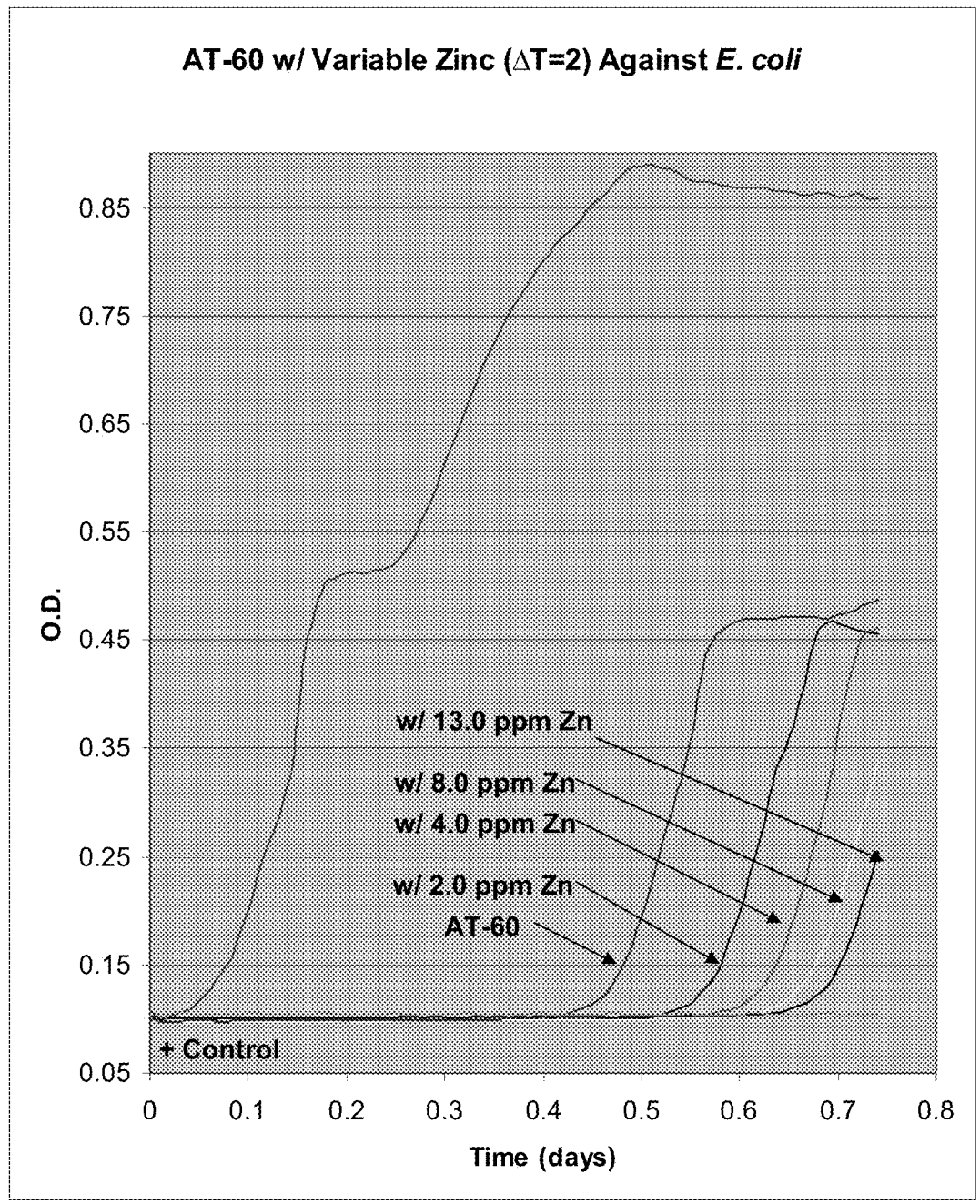
Figure 80A:
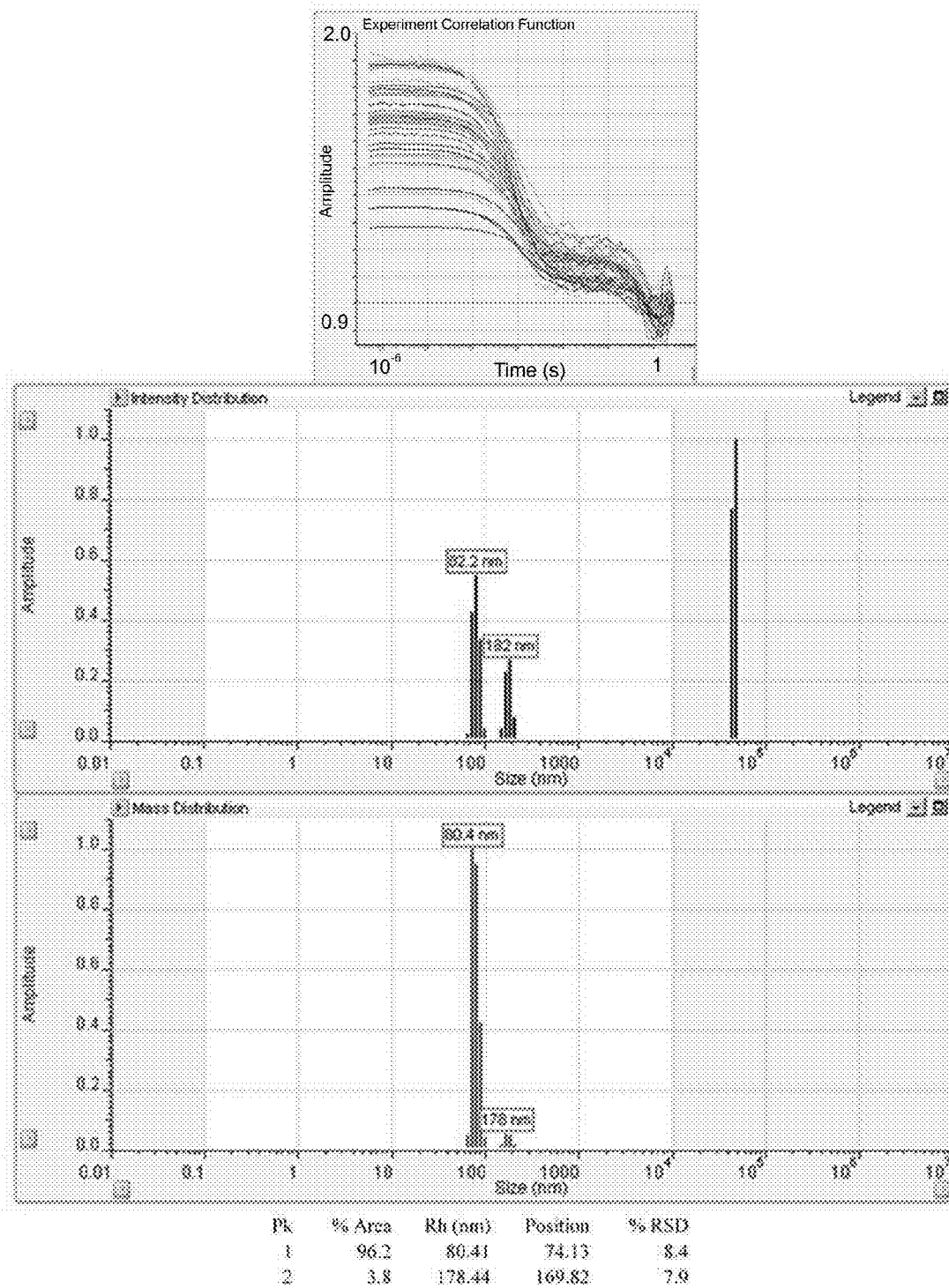
Figure 80B:
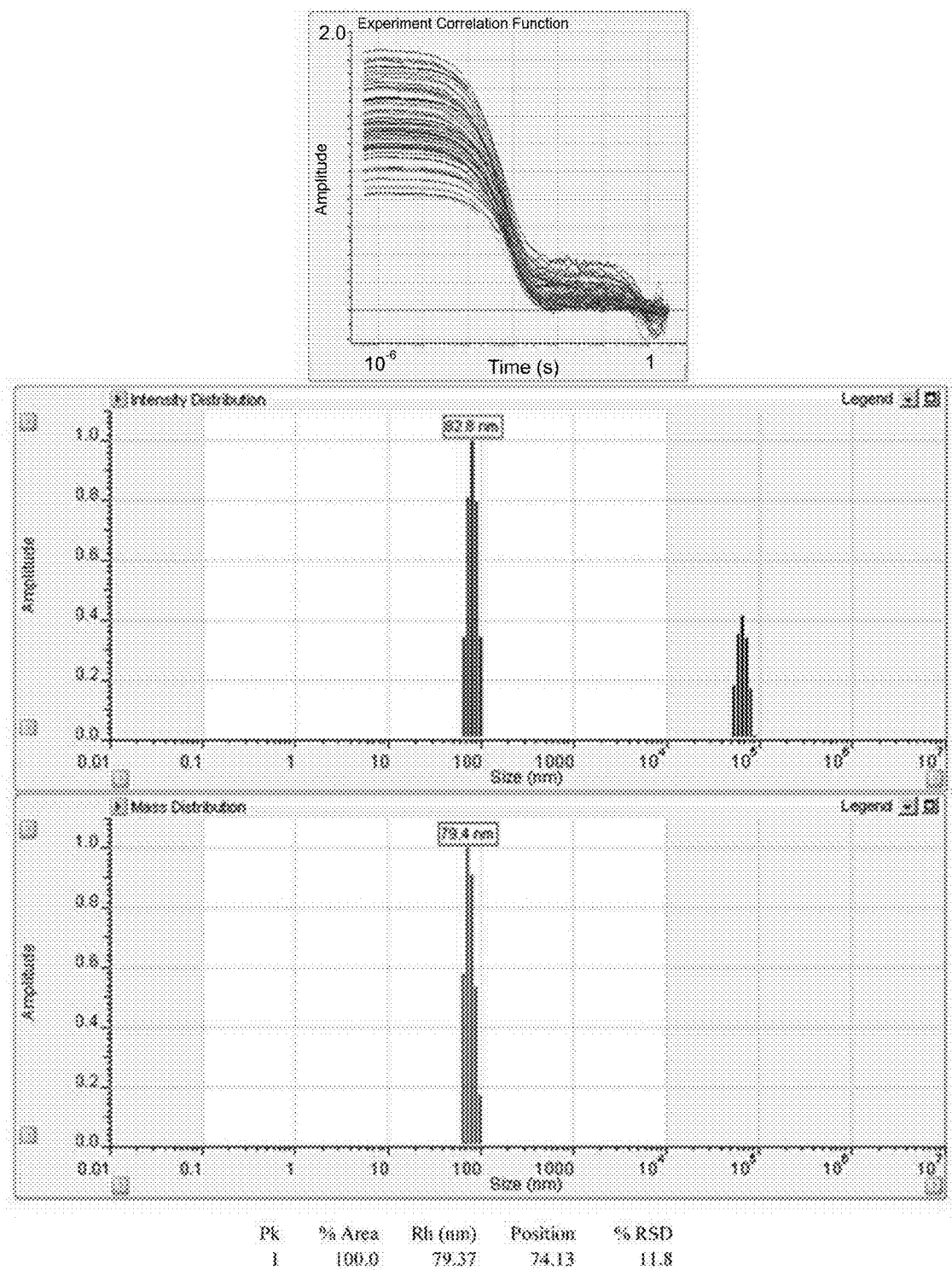
Figure 80C:
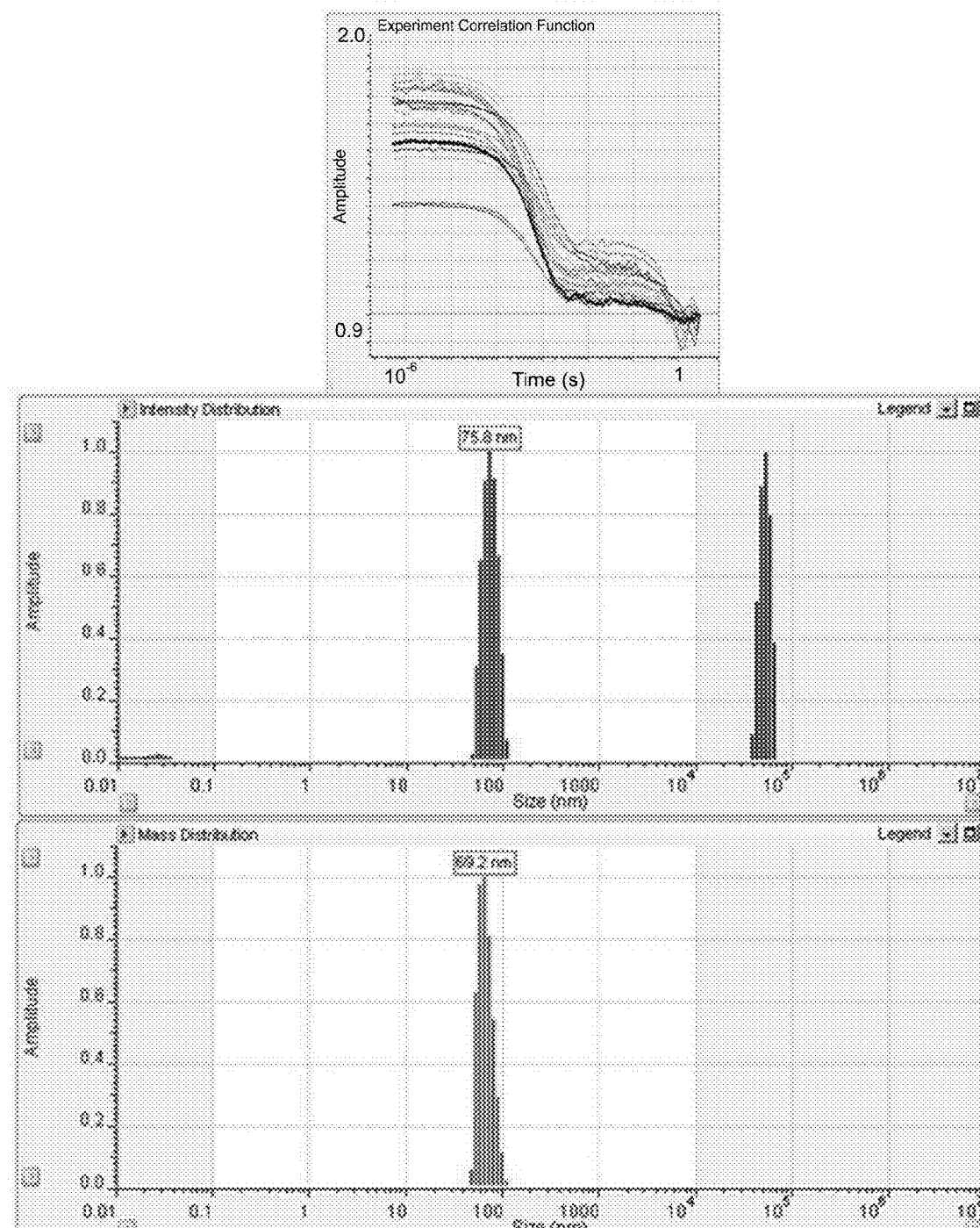
Figure 80D:
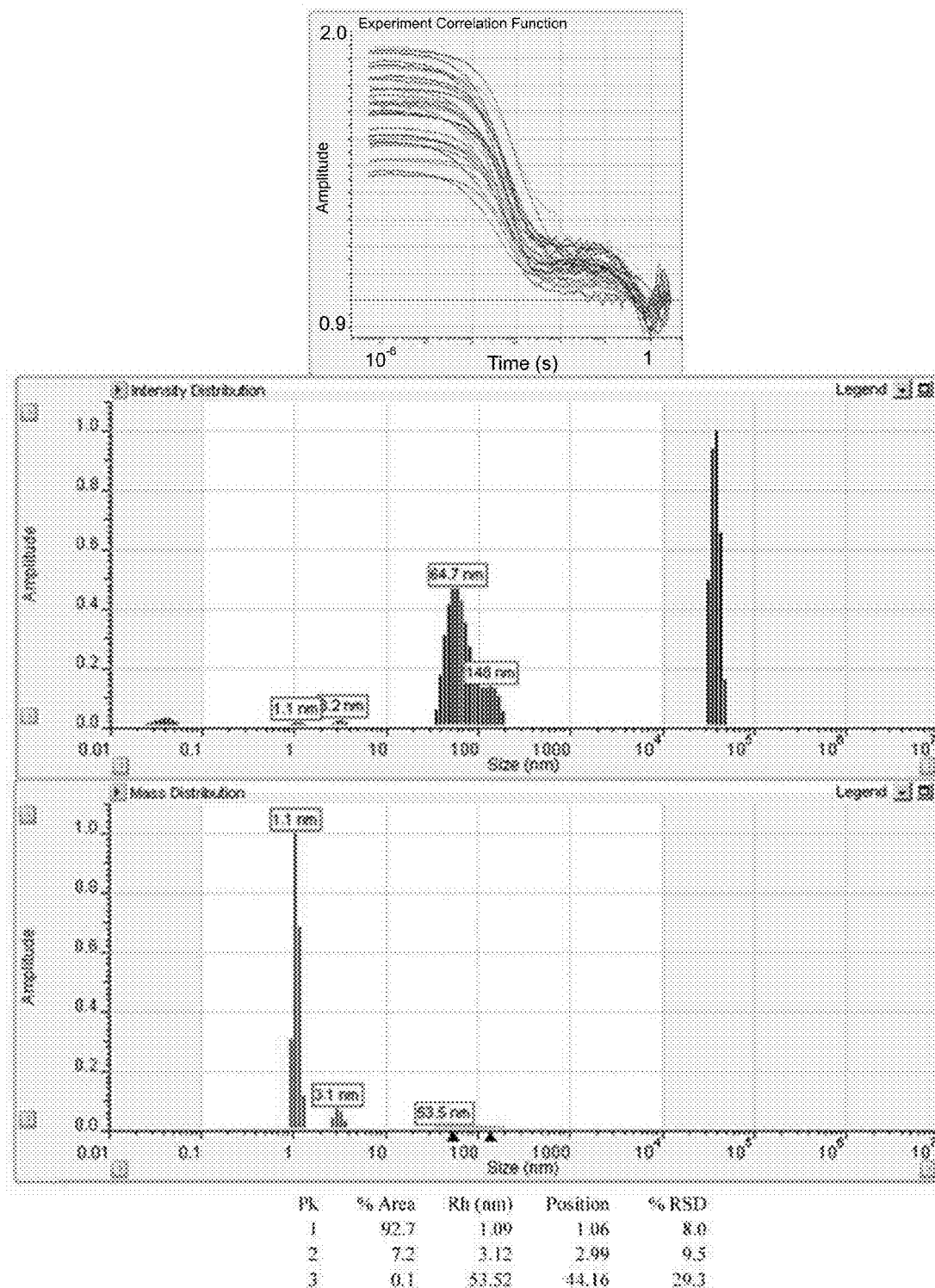
Figure 80E:
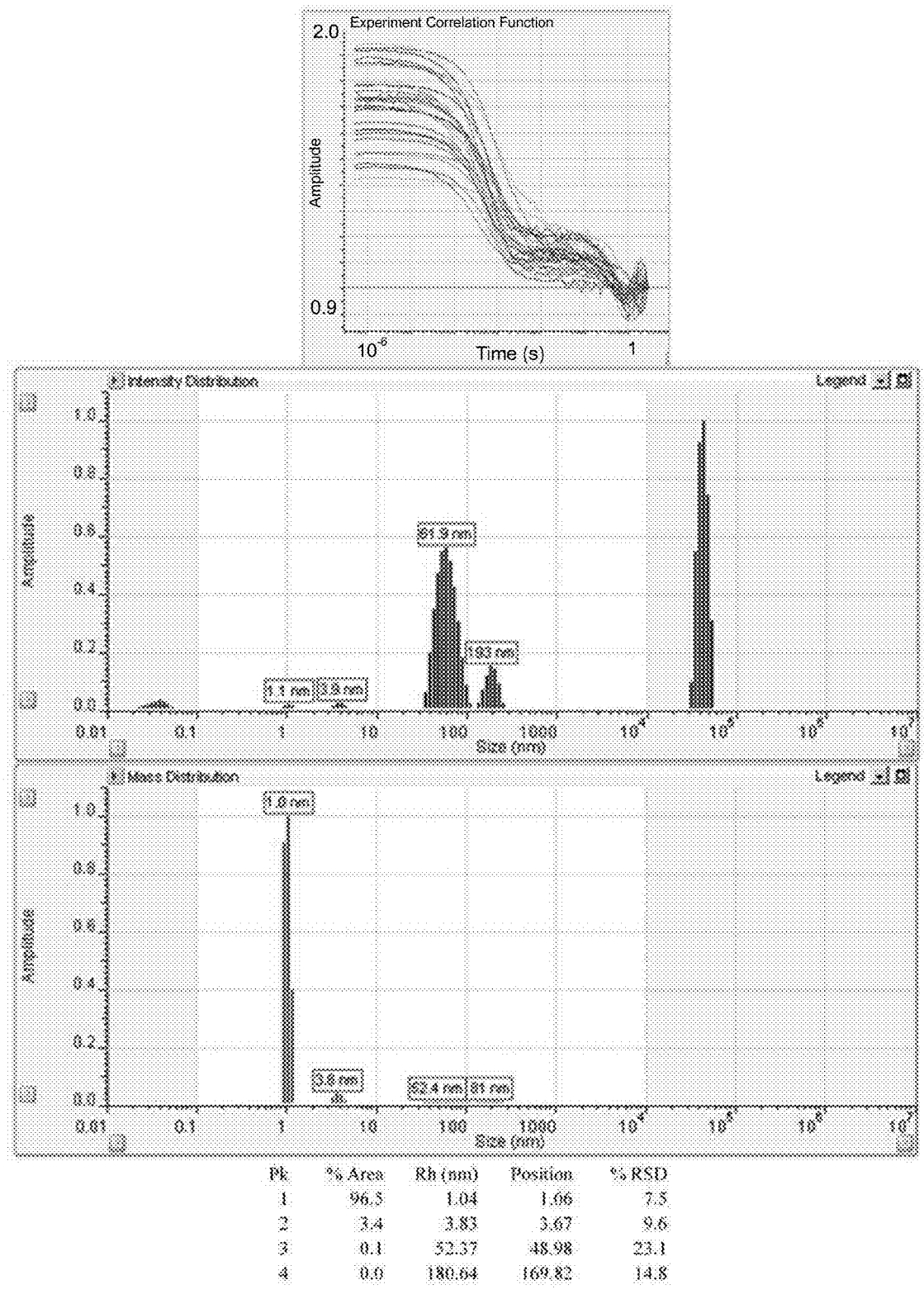
Figure 80F:
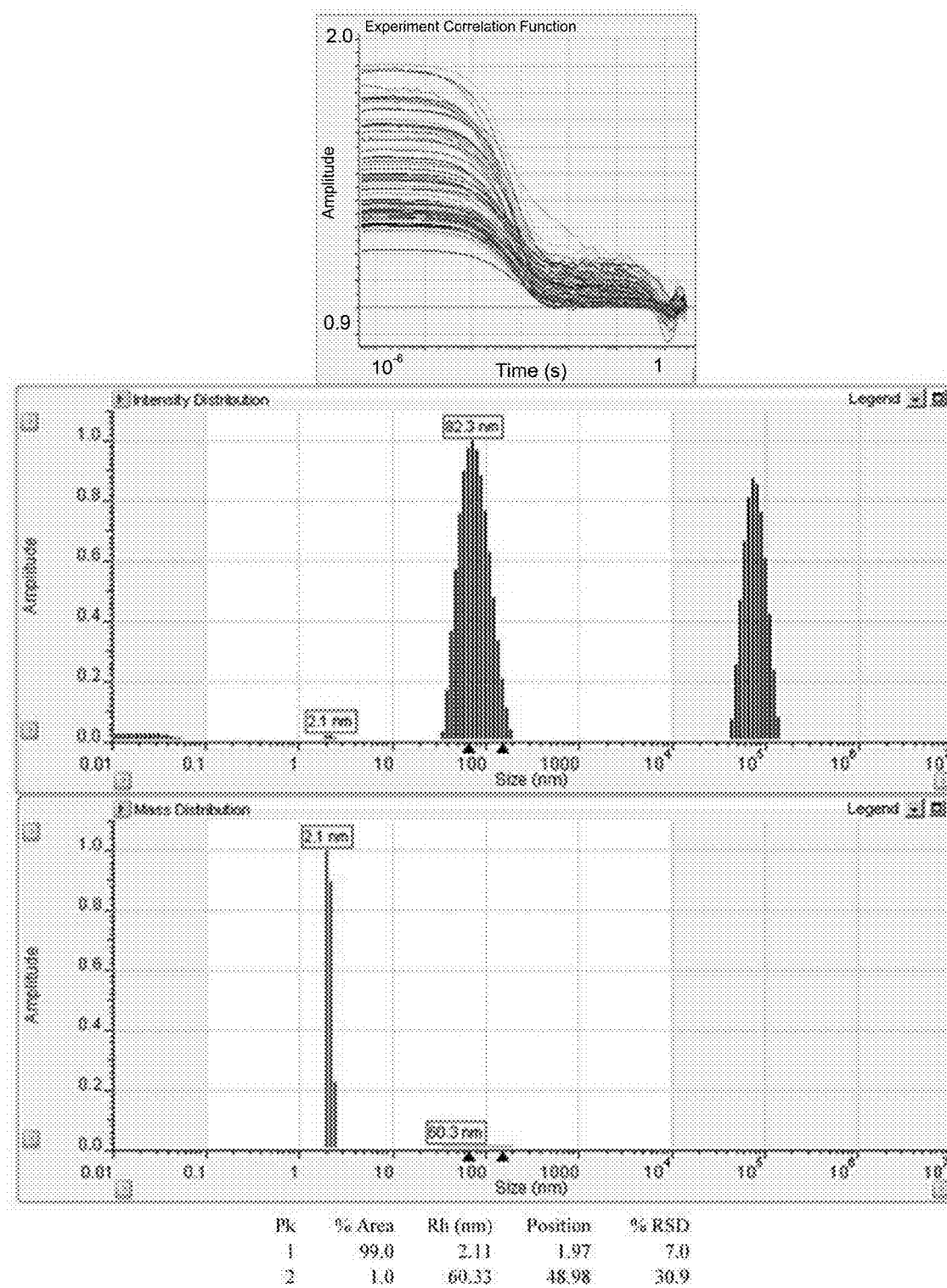
Figure 81A:
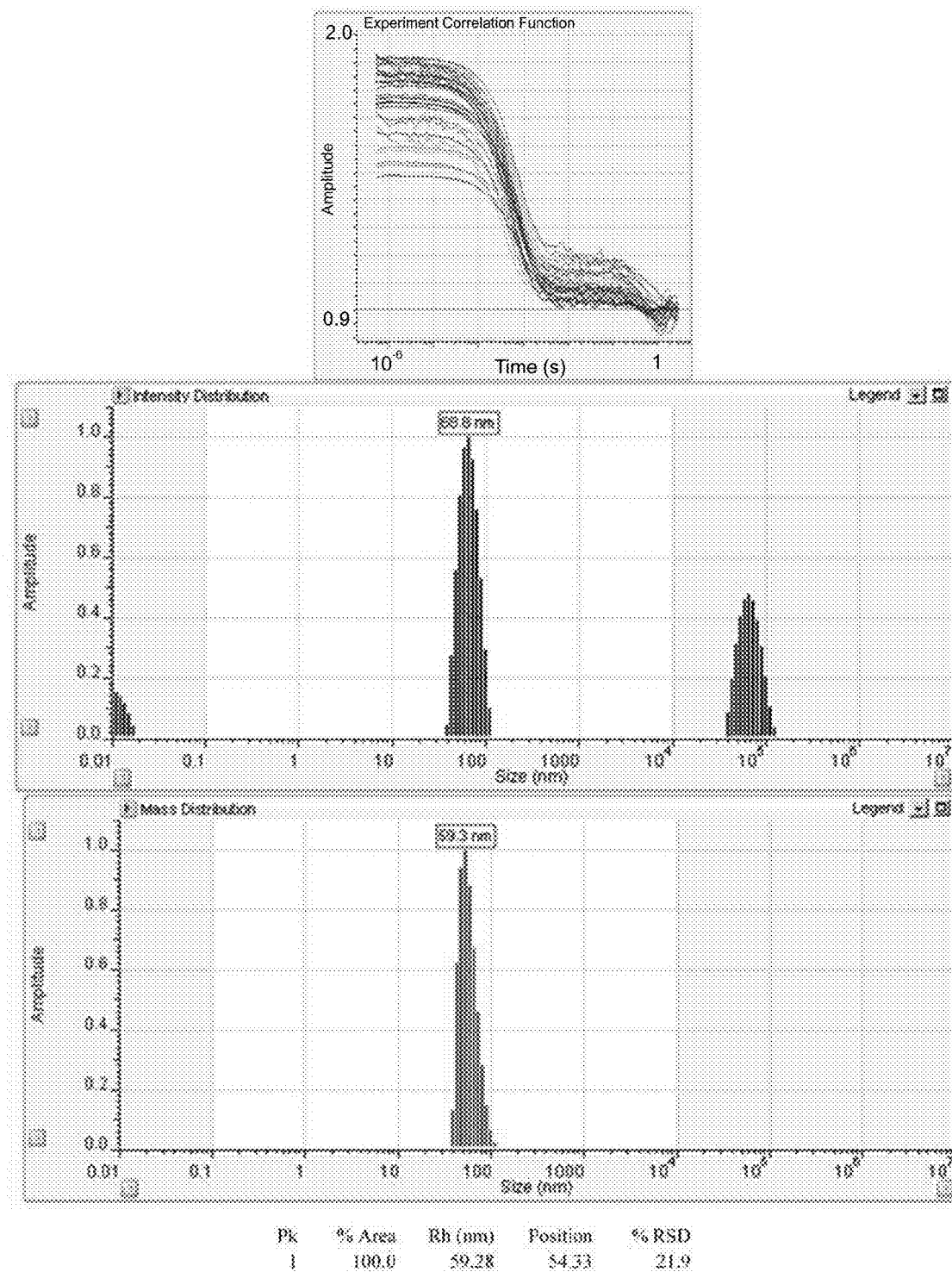
Figure 81B:
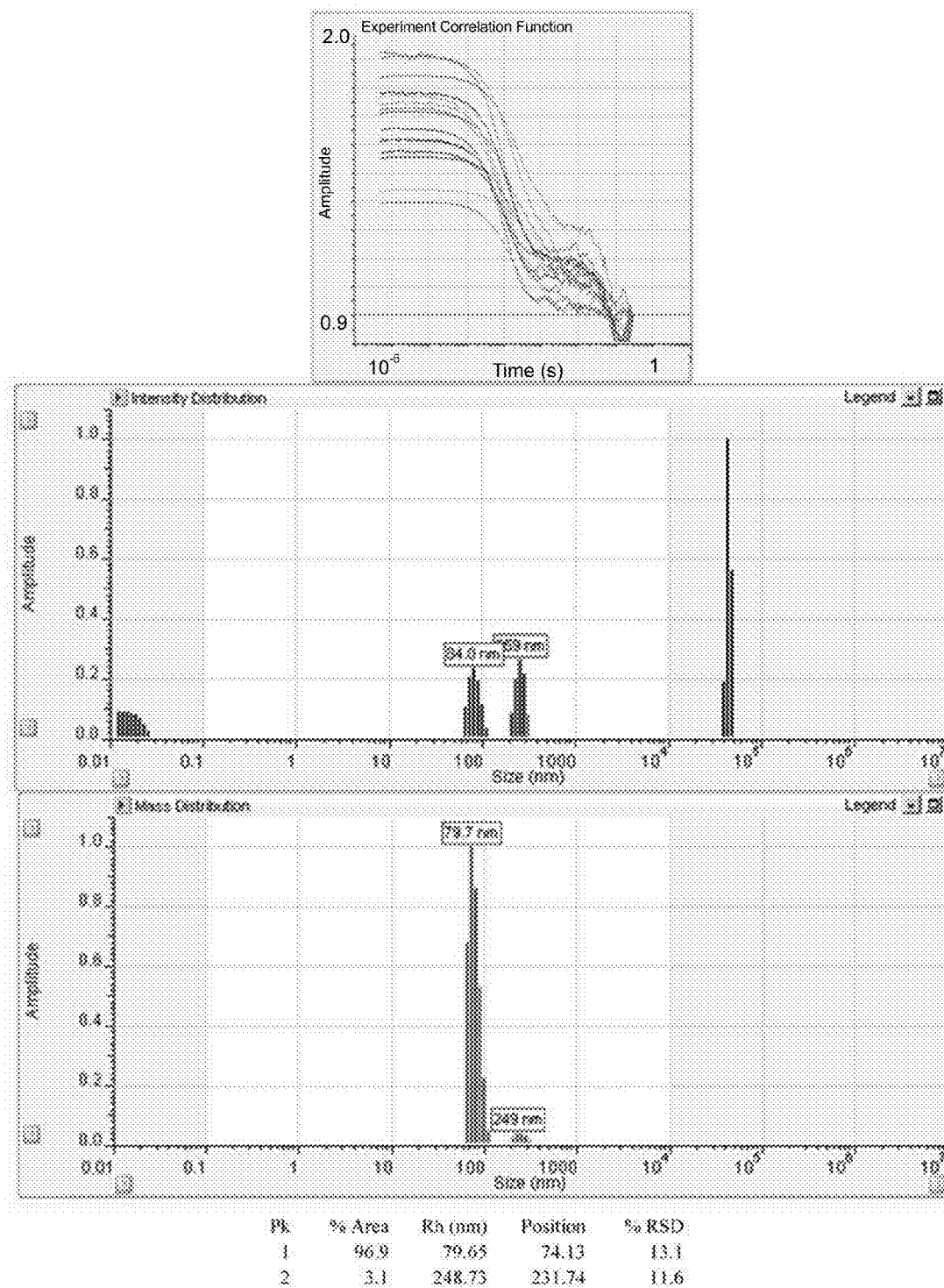
Figure 81C:
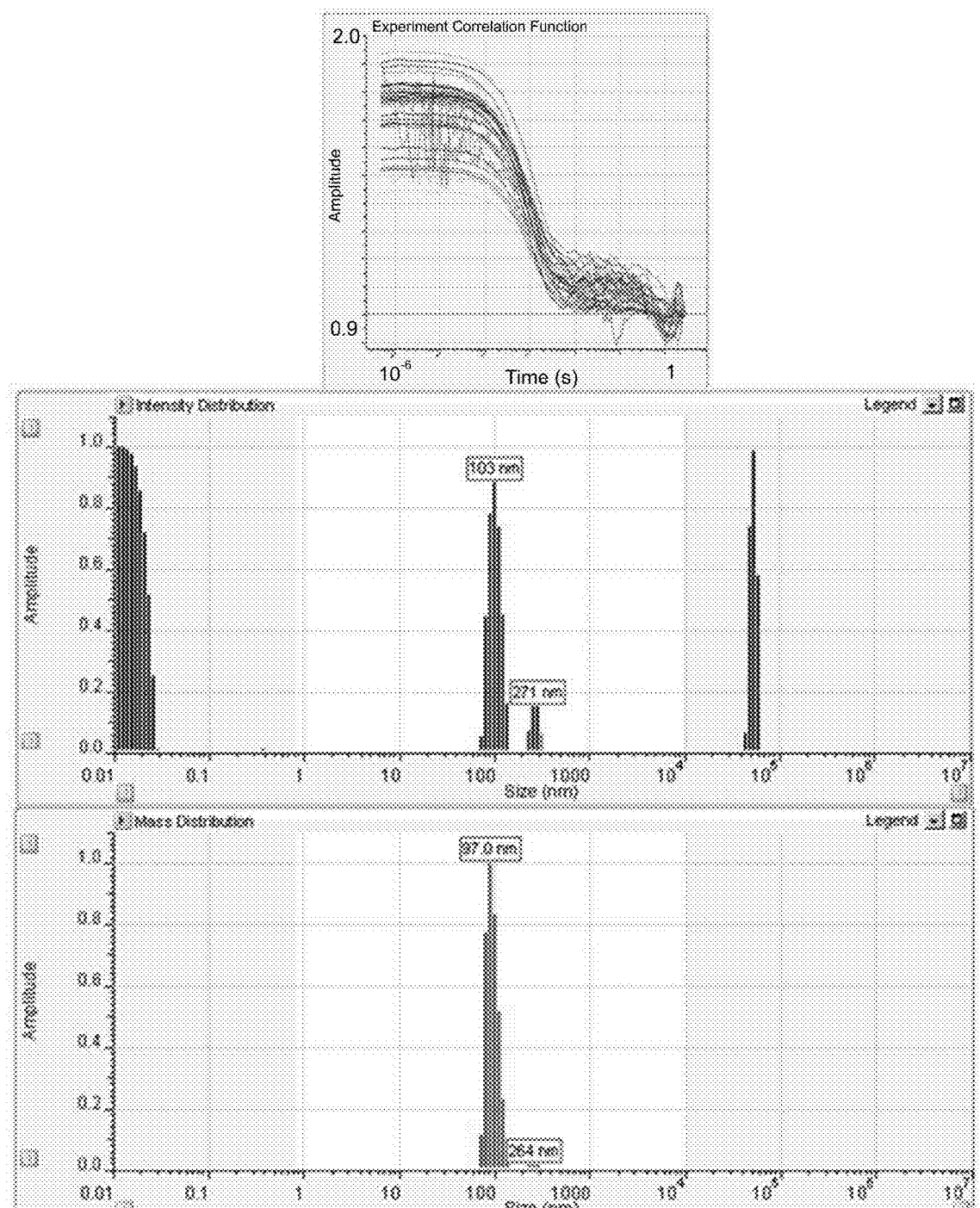
Figure 81D:
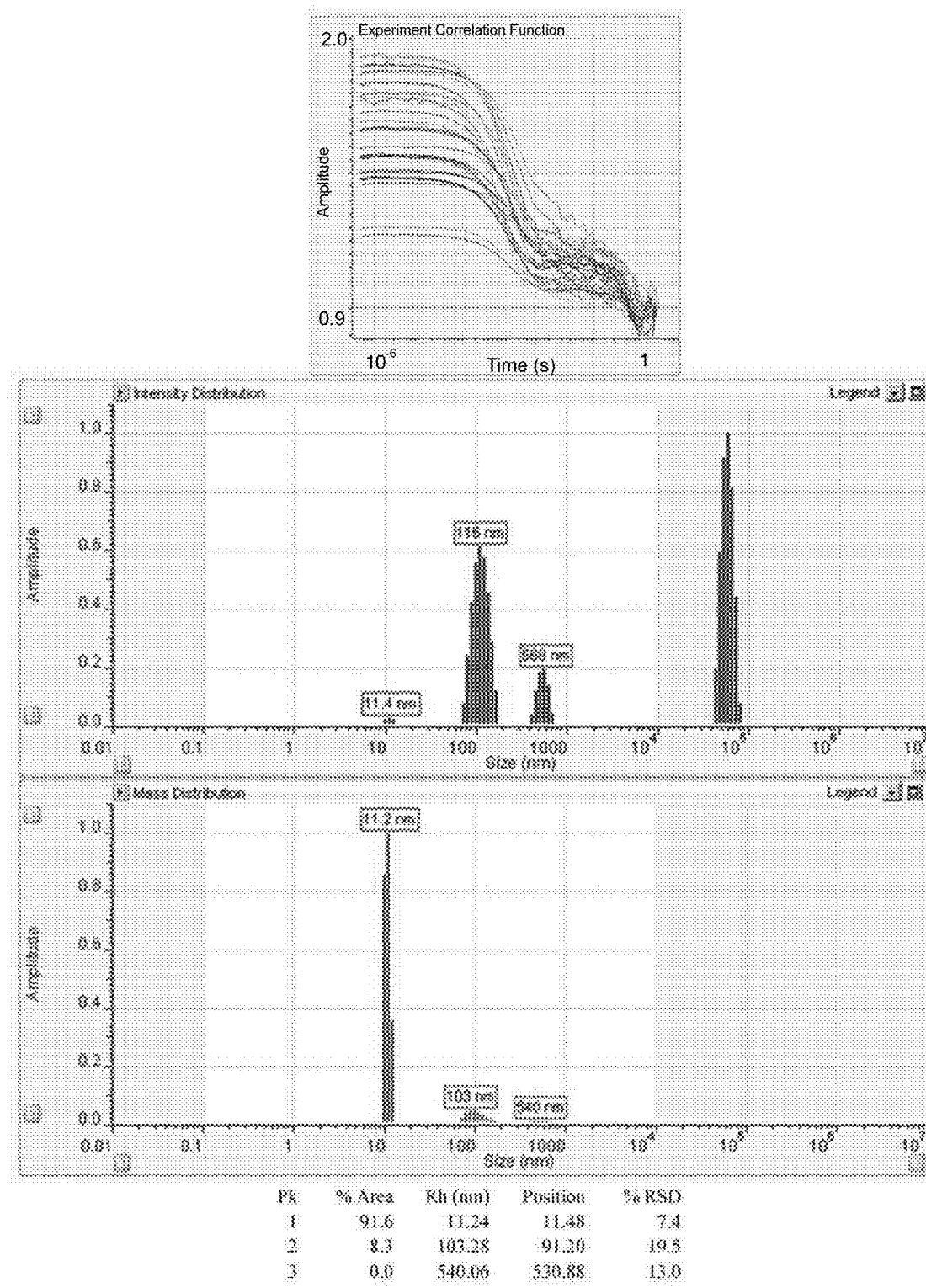
Figure 81E:
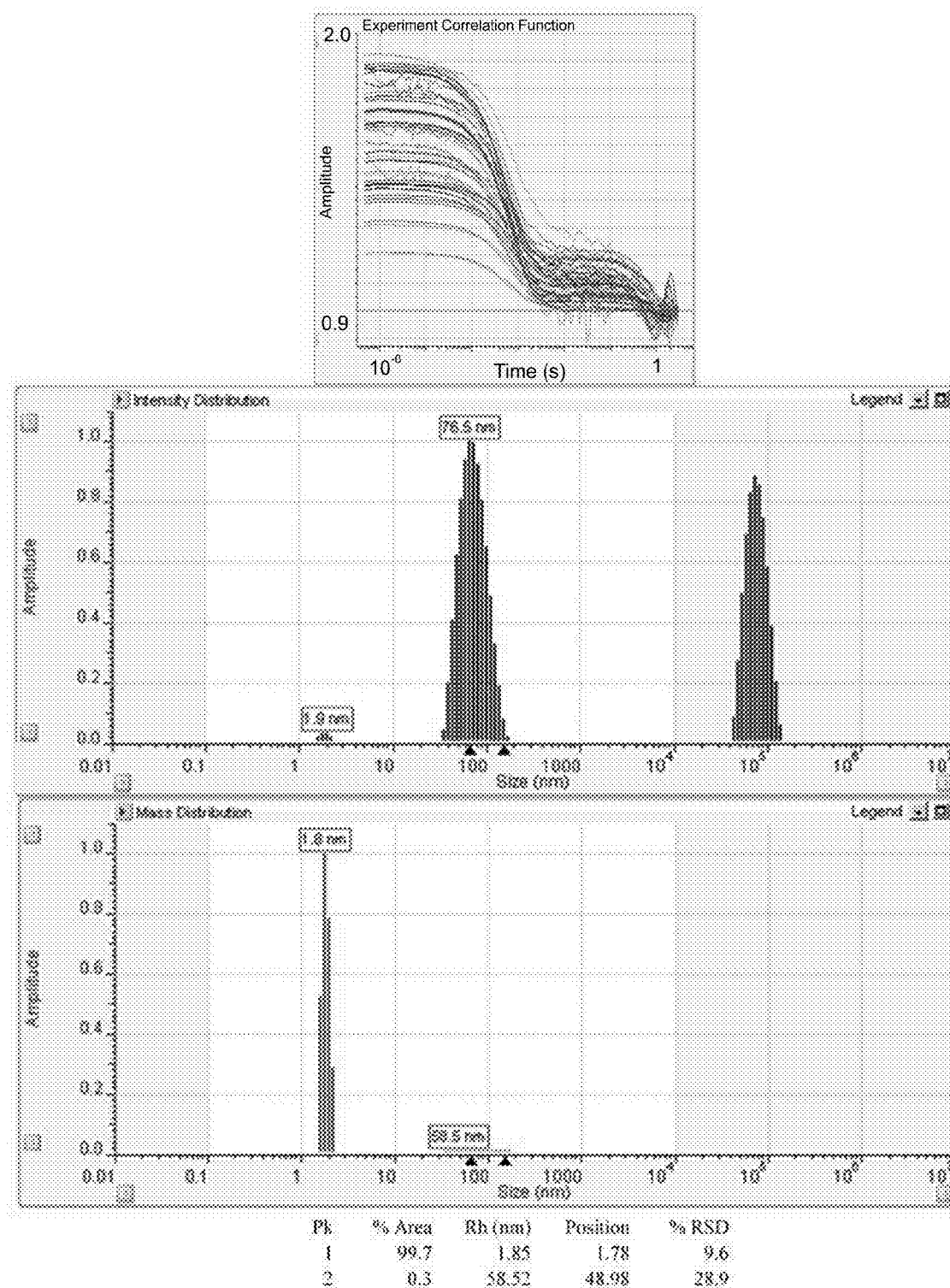

FIGS. 79a-79c show biological Bioscreen results for the Example 12.

FIGS. 80a-80f show Dynamic Light Scattering measurements for Example 12.

FIGS. 81a-81e show Dynamic Light Scattering measurements for Example 12.

DETAILED DESCRIPTION OF THE PREFERRED EMBODIMENTS

The embodiments disclosed herein relate generally to novel methods and novel devices for the continuous manufacture of a variety of constituents in a liquid including nanoparticles, and nanoparticle/liquid(s) solution(s). The nanoparticles produced in the various liquids can comprise a variety of possible compositions, sizes and shapes, conglomerates, composites and/or surface morphologies which exhibit a variety of novel and interesting physical, catalytic, biocatalytic and/or biophysical properties. The liquid(s) used and/or created/modified during the process play an important role in the manufacturing of and/or the functioning of the nanoparticles and/or nanoparticle/liquid(s) solutions(s). The atmosphere(s) used play an important role in the manufacturing and/or functioning of the nanoparticle and/or nanoparticle/liquid(s) solution(s). The nanoparticles are caused to be present (e.g., created) in at least one liquid (e.g., water) by, for example, preferably utilizing at least one adjustable plasma (e.g., formed in one or more atmosphere(s)), which adjustable plasma communicates with at least a portion of a surface of the liquid. The power source(s) used to create the plasma(s) play(s) an important role in the manufacturing of and/or functioning of the nanoparticles and/or nanoparticle/liquid(s) solution(s). For example, the voltage, amperage, polarity, etc., all can influence processing and/or final properties of produced products. Metal-based electrodes of various composition(s) and/or unique configurations are preferred for use in the formation of the adjustable plasma(s), but non-metallic-based electrodes can also be utilized. Utilization of at least one subsequent and/or substantially simultaneous adjustable electrochemical processing technique is also preferred. Metal-based electrodes of various composition(s) and/or unique configurations are preferred for use in the adjustable electrochemical processing technique(s).

Adjustable Plasma Electrodes and Adjustable Electrochemical Electrodes

An important aspect of one embodiment of the invention involves the creation of an adjustable plasma, which adjustable plasma is located between at least one electrode (or plurality of electrodes) positioned above at least a portion of the surface of a liquid and at least a portion of the surface of the liquid itself. The surface of the liquid is in electrical communication with at least one second electrode (or a plurality of second electrodes). This configuration has certain characteristics similar to a dielectric barrier discharge configuration, except that the surface of the liquid is an active participant in this configuration.

FIG. 1a shows a partial cross-sectional view of one embodiment of a electrode 1 having a triangular shape located a distance "x" above the surface 2 of a liquid 3 flowing, for example, in the direction "F". The electrode 1 shown is an isosceles triangle, but may be shaped as a right angle or equilateral triangle as well. An adjustable plasma 4 is generated between the tip or point 9 of the electrode 1 and the surface 2 of the liquid 3 when an appropriate power source 10 is connected between the point source electrode 1 and the electrode 5, which electrode 5 communicates with the liquid 3 (e.g., is at least partially below the surface 2 (e.g., bulk surface or effective surface) of the liquid 3). It should be noted that under certain conditions the tip 9' of the electrode 5 may actually be located physically slightly above the bulk surface 2 of the liquid 3, but the liquid still communicates with the electrode through a phenomena known as "Taylor cones" thereby creating an effective surface 2'. Taylor cones are discussed in U.S. Pat. No. 5,478,533, issued on Dec. 26, 1995 to Inculet, entitled Method and Apparatus for Ozone Generation and Treatment of Water; the subject matter of which is herein expressly incorporated by reference. In this regard, FIG. 1b shows an electrode configuration similar to that shown in FIG. 1a, except that a Taylor cone "T" is utilized to create an effective surface 2' to achieve electrical connection between the electrode 5 and the surface 2 (2') of the liquid 3. Taylor cones are referenced in the Inculet patent as being created by an "impressed field". In particular, Taylor cones were first analyzed by Sir Geoffrey Taylor in the early 1960's wherein Taylor reported that the application of an electrical field of sufficient intensity will cause a water droplet to assume a conical formation. It should be noted that Taylor cones, while a function of the electric field, are also a function of the conductivity of the fluid. Accordingly, as conductivity changes, the shape and or intensity of a Taylor cone can also change. Accordingly, Taylor cones of various intensity can be observed near tips 9' at electrode(s) 5 of the present invention as a function of not only the electric field which is generated around the electrode(s) 5, but also is a function of constituents in the liquid 3 (e.g., conductive constituents provided by, for example, the adjustable plasma 4) and others. Further, electric field changes are also proportional to the amount of current applied.

The adjustable plasma region 4, created in the embodiment shown in FIG. 1a, can typically have a shape corresponding to a cone-like structure for at least a portion of the process, and in some embodiments of the invention, can maintain such cone-like shape for substantially all of the process. In other embodiments, the shape of the adjustable plasma region 4 may be shaped more like lightning bolts. The volume, intensity, constituents (e.g., composition), activity, precise locations, etc., of the adjustable plasma(s) 4 will vary depending on a number of factors including, but not limited to, the distance "x", the physical and/or chemical composition of the electrode 1, the shape of the electrode 1, the location of the electrode 1 relative to other electrode(s) 1 located upstream from the electrode 1, the power source 10 (e.g., DC, AC, rectified AC, polarity of DC and/or rectified AC, RF, etc.), the power applied by the power source (e.g., the volts applied, the amps applied, etc.) the electric and/or magnetic fields created at or near the plasma 4, the composition of the naturally occurring or supplied gas or atmosphere between and/or around the electrode 1 and the surface 2 of the liquid 3, temperature, pressure, flow rate of the liquid 3 in the direction "F", composition of the liquid 3, conductivity of the liquid 3, cross-sectional area (e.g., volume) of the liquid near and around the electrodes 1 and 5 (e.g., the amount of time the liquid 3 is permitted to interact with the adjustable plasma 4 and the intensity of such interactions), the presence of atmosphere flow (e.g., air flow) at or near the surface 2 of the liquid 3 (e.g., cooling fan(s) or atmosphere movement means provided), etc. Specifically, for example, the maximum distance "x" that can be utilized for the adjustable plasma 4 is where such distance "x" corresponds to, for example, the breakdown electric field "$E_c$" shown in Equation 1. In other words, achieving breakdown of the gas or atmosphere provided between the tip 9 of the electrode 1 and the surface 2 of the liquid 3. If the distance "x" exceeds the maximum distance required to achieve electric breakdown ("$E_c$"), then no plasma 4 will be observed absent the use of additional techniques or interactions. However, whenever the distance "x" is equal to or less than the maximum distance required to achieve the formation of the adjustable plasma 4, then various physical and/or chemical adjustments of the plasma 4 can be made. Such changes will include diameter of the plasma 4 at the surface 2 of the liquid 3, intensity (e.g., brightness and/or strength and/or reactivity) of the plasma 4, the strength of the electric wind created by the plasma 4 and blowing toward the surface 2 of the liquid 3, etc.

The composition of the electrode 1 can also play an important role in the formation of the adjustable plasma 4. For example, a variety of known materials are suitable for use as the electrode(s) 1 of the embodiments disclosed herein. These materials include metals such as platinum, gold, silver, zinc, copper, titanium, and/or alloys or mixtures thereof, etc. However, the electrode(s) 1 (and 5) can be made of any suitable material which may comprise metal(s) (e.g., including appropriate oxides, carbides, nitrides, carbon, silicon and mixtures or composites thereof, etc.). Still further, alloys of various metals are also desirable for use with the present invention. Specifically, alloys can provide chemical constituents of different amounts, intensities and/or reactivities in the adjustable plasma 4 resulting in, for example, different properties in and/or around the plasma 4 and/or different constituents within the liquid 3. For example, different spectra can be emitted from the plasma 4, different fields can be emitted from the plasma 4, etc. Thus, the plasma 4 can be involved in the formation of a variety of different nanoparticles and/or nanoparticle/solutions and/or desirable constituents, or intermediate(s) present in the liquid 3 required to achieve desirable end products. Still further, it is not only the chemical composition and shape factor(s) of the electrode(s) 1, 5 that play a role in the formation of the adjustable plasma 4, but also the manor in which any electrode(s) 1, 5 have been manufactured can also influence the performance of the electrode(s) 1, 5. In this regard, the precise shaping technique(s) including forging, drawing and/or casting technique(s) utilized to from the electrode(s) 1, 5 can have an influence on the chemical and/or physical activity of the electrode(s) 1, 5, including thermodynamic and/or kinetic issues.

The creation of an adjustable plasma 4 in, for example, air above the surface 2 of a liquid 3 (e.g., water) will, typically, produce at least some ozone, as well as certain amounts of a variety of nitrogen-based compounds and other components. Various exemplary materials can be produced in the adjustable plasma 4 and include a variety of materials that are dependent on a number of factors including the atmosphere between the electrode 1 and the surface 2 of the liquid 3. To assist in understanding the variety of species that are possibly present in the plasma 4 and/or in the liquid 3 (when the liquid comprises water), reference is made to a 15 Jun. 2000 thesis by Wilhelmus Frederik Laurens Maria Hoeben, entitled "Pulsed corona-induced degradation of organic materials in water", the subject matter of which is expressly herein incorporated by reference. The work in the aforementioned thesis is directed primarily to the creation of corona-induced degradation of undesirable materials present in water, wherein such corona is referred to as a pulsed DC corona. However, many of the chemical species referenced therein, can also be present in the adjustable plasma 4 of the embodiments disclosed herein, especially when the atmosphere assisting in the creation of the adjustable plasma 4 comprises humid air and the liquid 3 comprises water. In this regard, many radicals, ions and meta-stable elements can be present in the adjustable plasma 4 due to the dissociation and/or ionization of any gas phase molecules or atoms present between the electrode 1 and the surface 2. When humidity in air is present and such humid air is at least a major component of the atmosphere "feeding" the adjustable plasma 4, then oxidizing species such as hydroxyl radicals, ozone, atomic oxygen, singlet oxygen and hydropereoxyl radicals can be formed. Still further, amounts of nitrogen oxides like $NO_x$ and $N_2O$ can also be formed. Accordingly, Table 1 lists some of the reactants that could be expected to be present in the adjustable plasma 4 when the liquid 3 comprises water and the atmosphere feeding or assisting in providing raw materials to the adjustable plasma 4 comprises humid air.

TABLE 1

| Reaction/Species | | Equation |
|---|---|---|
| $H_2O + e_- \rightarrow OH + H + e_-$ | dissociation | 2 |
| $H_2O + e_- \rightarrow H_2O_+ + 2e_-$ | ionization | 3 |
| $H_2O_+ + H_2O \rightarrow H_3O_+ + OH$ | dissociation | 4 |
| $N_2 + e_- \rightarrow N_2^* + e_-$ | excitation | 5 |
| $O_2 + e_- \rightarrow O_2^* + e_-$ | excitation | 6 |
| $N_2 + e_- \rightarrow 2N + e_-$ | dissociation | 7 |
| $O_2 + e_- \rightarrow 2O + e_-$ | dissociation | 8 |
| $N_2 + e_- \rightarrow N_{2+} + 2e_-$ | ionization | 9 |
| $O_2 + e_- \rightarrow O_{2+} + 2e_-$ | ionization | 10 |
| $O_2 + e_- \rightarrow O_{2-}$ | attachment | 11 |
| $O_2 + e_- \rightarrow O_- + O$ | dissociative attachment | 12 |
| $O_2 + O \rightarrow O_3$ | association | 13 |
| $H + O_2 \rightarrow HO_2$ | association | 14 |
| $H + O_3 \rightarrow HO_3$ | association | 15 |
| $N + O \rightarrow NO$ | association | 16 |
| $NO + O \rightarrow NO_2$ | association | 17 |
| $N_{2+} + O_{2-} \rightarrow 2NO$ | recombination | 18 |
| $N_2 + O \rightarrow N_2O$ | association | 19 |

An April, 1995 article, entitled "Electrolysis Processes in D.C. Corona Discharges in Humid Air", written by J. Lelievre, N. Dubreuil and J.-L. Brisset, and published in the *J. Phys. III France* 5 on pages 447-457 therein (the subject matter of which is herein expressly incorporated by reference) was primarily focused on DC corona discharges and noted that according to the polarity of the active electrode, anions such as nitrites and nitrates, carbonates and oxygen anions were the prominent ions at a negative discharge; while protons, oxygen and $NO_x$ cations were the major cationic species created in a positive discharge. Concentrations of nitrites and/or nitrates could vary with current intensity. The article also disclosed in Table I therein (i.e., Table 2 reproduced herein) a variety of species and standard electrode potentials which are capable of being present in the DC plasmas created therein. Accordingly, one would expect such species as being capable of being present in the adjustable plasma(s) 4 of the present invention depending on the specific operating conditions utilized to create the adjustable plasma(s) 4.

TABLE 2

| $O_3/O_2$ | [2.07] | $NO_3^-/N_2$ | [1.24] | $HO_2^-/OH^-$ | [0.88] |
|---|---|---|---|---|---|
| $N_2/NH_4^+$ | [0.27] | $HN_3/NH_4^+$ | [1.96] | $O_2/H_2O$ | [1.23] |
| $NO_3^-/N_2O_4$ | [0.81] | $O_2/HO_2^-$ | [-0.08] | $H_2O_2/H_2O$ | [1.77] |
| $NO_3^-/N_2O$ | [1.11] | $NO_3^-/NO_2$ | [0.81] | $CO_2/CO$ | [-0.12] |

TABLE 2-continued

| | | | | | |
|---|---|---|---|---|---|
| $N_2O/N_2$ | [1.77] | $N_2O_4/HNO_2$ | [1.07] | $NO/H_2N_2O_2$ | [0.71] |
| $CO_2/HCO_2H$ | [−0.2] | $NO/N_2O$ | [1.59] | $HNO_2/NO$ | [0.98] |
| $O_2/H_2O_2$ | [0.69] | $N_2/N_2H_5^+$ | [−0.23] | $NO^+/NO$ | [1.46] |
| $HO_3^-/NO$ | [0.96] | $NO_3^-/NO_2^-$ | [0.49] | $CO_2/H_2C_2O_4$ | [−0.49] |
| $H_3NOH^+/N_2H_5^+$ | [1.42] | $NO_3^-/HNO_2$ | [0.94] | $O_2/OH^-$ | [0.41] |
| $H_2O/e_{aq.}$ | [−2.07] | $N_2H_5/NH_4^+$ | [1.27] | | |

An article published 15 Oct. 2003, entitled, "Optical and electrical diagnostics of a non-equilibrium air plasma", authored by XinPei Lu, Frank Leipold and Mounir Laroussi, and published in the *Journal of Physics D: Applied Physics*, on pages 2662-2666 therein (the subject matter of which is herein expressly incorporated by reference) focused on the application of AC (60 Hz) high voltage (<20 kV) to a pair of parallel electrodes separated by an air gap. One of the electrodes was a metal disc, while the other electrode was a surface of water. Spectroscopic measurements performed showed that light emission from the plasma was dominated by OH (A-X, $N_2$ (C-B) and $N_2^+$ (B-X) transitions. The spectra from FIG. 4a therefrom have been reproduced herein as FIG. 67a.

An article by Z. Machala, et al., entitled, "Emission spectroscopy of atmospheric pressure plasmas for bio-medical and environmental applications", published in 2007 in the *Journal of Molecular Spectroscopy*, discloses additional emission spectra of atmospheric pressure plasmas. The spectra from FIGS. 3 and 4 therefrom have been reproduced as FIGS. 67b and 67c.

An article by M. Laroussi and X. Lu, entitled, "Room-temperature atmospheric pressure plasma plume for biomedical applications", published in 2005 in *Applied Physics Letters*, discloses emission spectra from OH, $N_2$, $N_2^+$, He and O. The spectra from FIG. 4 therein has been reproduced as FIGS. 67d, 67e and 67f.

Also known in the art is the generation of ozone by pulsed-corona discharge over a water surface as disclosed by Petr Lukes, et al, in the article, "Generation of ozone by pulsed corona discharge over water surface in hybrid gas-liquid electrical discharge reactor", published in *J. Phys. D: Appl. Phys.* 38 (2005) 409-416 (the subject matter of which is herein expressly incorporated by reference). Lukes, et al, disclose the formation of ozone by pulse-positive corona discharge generated in a gas phase between a planar high voltage electrode (made from reticulated vitreous carbon) and a water surface, said water having an immersed ground stainless steel "point" mechanically-shaped electrode located within the water and being powered by a separate electrical source. Various desirable species are disclosed as being formed in the liquid, some of which species, depending on the specific operating conditions of the embodiments disclosed herein, could also be expected to be present.

Further, U.S. Pat. No. 6,749,759 issued on Jun. 15, 2004 to Denes, et al, and entitled Method for Disinfecting a Dense Fluid Medium in a Dense Medium Plasma Reactor (the subject matter of which is herein expressly incorporated by reference), discloses a method for disinfecting a dense fluid medium in a dense medium plasma reactor. Denes, et al, disclose decontamination and disinfection of potable water for a variety of purposes. Denes, et al, disclose various atmospheric pressure plasma environments, as well as gas phase discharges, pulsed high voltage discharges, etc. Denes, et al, use a first electrode comprising a first conductive material immersed within the dense fluid medium and a second electrode comprising a second conductive material, also immersed within the dense fluid medium. Denes, et al then apply an electric potential between the first and second electrodes to create a discharge zone between the electrodes to produce reactive species in the dense fluid medium.

All of the constituents discussed above, if present, can be at least partially (or substantially completely) managed, controlled, adjusted, maximized, minimized, eliminated, etc., as a function of such species being helpful or harmful to the resultant nanoparticles and/or nanoparticle/solutions produced, and then may need to be controlled by a variety of different techniques (discussed in more detail later herein). As shown in FIG. 1a, the adjustable plasma 4 contacts the actual surface 2 of the liquid 3. In this embodiment of the invention, material (e.g., metal) from the electrode 1 may comprise a portion of the adjustable plasma 4 and may be caused, for example, to be "sputtered" onto and/or into the liquid (e.g., water). Accordingly, when metal(s) are used as the electrode(s) 1, elementary metal(s), metal ions, Lewis acids, Bronsted-Lowry acids, metal oxides, metal nitrides, metal hydrides, metal hydrates, metal carbides, and/or mixtures thereof etc., can be found in the liquid (e.g., for at least a portion of the process), depending upon the particular set of operating conditions associated with the adjustable plasma 4 (as well as other operating conditions).

Further, depending on, for example, electric, magnetic and/or electromagnetic field strength, polarity, etc., in and around the liquid 3, as well as the volume of liquid 3 present (e.g., a function of, for example, the cross-sectional size and shape of the trough member 30 and/or flow rate of the liquid 3) discussed in greater detail elsewhere herein), the physical and chemical construction of the electrode(s) 1 and 5, atmosphere (naturally occurring or supplied), liquid 3 composition, greater or lesser amounts of electrode(s) materials(s) (e.g., metal(s) or derivatives of metals) may be found in the liquid 3. Additional important information is disclosed in copending patent application entitled Methods for Controlling Crystal Growth, Crystallization, Structures and Phases in Materials and Systems; which was filed on Mar. 21, 2003, and was published by the World Intellectual Property Organization under publication number WO 03/089692 on Oct. 30, 2003 and the U.S. National Phase application, which was filed on Jun. 6, 2005, and was published by the United States Patent and Trademark Office under publication number 20060037177 on Feb. 23, 2006 (the inventors of each being Bentley J. Blum, Juliana H. J. Brooks and Mark G. Mortenson). The subject matter of both applications is herein expressly incorporated by reference. These published applications disclose (among other things) that the influence of, for example, electric fields, magnetic fields, electromagnetic energy, etc., have proven to be very important in the formation and/or control of various structures in a variety of solids, liquids, gases and/or plasmas. Such disclosed effects are also relevant in the embodiments disclosed herein. Further, the observation of extreme variations of, for example, pH in and around electrodes having a potential applied thereto (and current flow therethrough) also controls reaction products and/or reaction rates. Thus, a complex set of reactions are likely to be occurring at each electrode 1, 5 and electrode assemblies or electrode sets (e.g., 1, 5; 1, 1; 5, 5; etc.).

In certain situations, the material(s) (e.g., metal(s), metal ion(s), metal composite(s) or constituents (e.g., Lewis acids, Bronsted-Lowry acids, etc.) and/or inorganics found in the liquid 3 (e.g., after processing thereof) may have very desirable effects, in which case relatively large amounts of such material(s) will be desirable; whereas in other cases, certain materials found in the liquid (e.g., undesirable by-products) may have undesirable effects, and thus minimal amounts of such material(s) may be desired in the final product. Further, the structure/composition of the liquid 3 per se may also be beneficially or negatively affected by the processing conditions of the present invention. Accordingly, electrode composition can play an important role in the ultimate material(s) (e.g., nanoparticles and/or nanoparticle/solutions) that are formed according to the embodiments disclosed herein. As discussed above herein, the atmosphere involved with the reactions occurring at the electrode(s) 1 (and 5) plays an important role. However, electrode composition also plays an important role in that the electrodes 1 and 5 themselves can become part of, at least partially, intermediate and/or final products formed. Alternatively, electrodes may have a substantial role in the final products. In other words, the composition of the electrodes may be found in large part in the final products of the invention or may comprise only a small chemical part of products produced according to the embodiments disclosed herein. In this regard, when electrode(s) 1, 5 are found to be somewhat reactive according to the process conditions of the various embodiments disclosed herein, it can be expected that ions and/or physical particles (e.g., metal-based particles of single or multiple crystals) from the electrodes can become part of a final product. Such ions and/or physical components may be present as a predominant part of a particle in a final product, may exist for only a portion of the process, or may be part of a core in a core-shell arrangement present in a final product. Further, the core-shell arrangement need not include complete shells. For example, partial shells and/or surface irregularities or specific desirable surface shapes on a formed nanoparticle can have large influence on the ultimate performance of such nanoparticles in their intended use. It should be clear to an artisan of ordinary skill that slight adjustments of chemical composition, reactive atmospheres, power intensities, etc., can cause a variety of different chemical compounds (both semi-permanent and transient) nanoparticles (and nanoparticle components) to be formed, as well as different nanoparticle/solutions (e.g., including modifying the structures of the liquid 3 (such as water) per se).

Still further, the electrode(s) 1 and 5 may be of similar chemical composition or completely different chemical compositions and/or made by similar or completely different forming processes in order to achieve various compositions of ions, compounds, and/or physical particles in liquid and/or structures of liquids per se and/or specific effects from final resultant products. For example, it may be desirable that electrode pairs, shown in the various embodiments herein, be of the same or substantially similar composition, or it may be desirable for the electrode pairs, shown in the various embodiments herein, to be of different chemical composition(s). Different chemical compositions may result in, of course, different constituents being present for possible reaction in the various plasma and/or electrochemical embodiments disclosed herein. Further, a single electrode 1 or 5 (or electrode pair) can be made of at least two different metals, such that components of each of the metals, under the process conditions of the disclosed embodiments, can interact with each other, as well as with other constituents in the plasma(s) 4 and or liquid(s) 3, fields, etc., present in, for example, the plasma 4 and/or the liquid 3.

Further, the distance between the electrode(s) 1 and 5; or 1 and 1 (e.g., see FIGS. 3d, 4d, 8d and 9d) or 5 and 5 (e.g., see FIGS. 3c, 4c, 8c and 9c) is one important aspect of the invention. In general, the location of the smallest distance "y" between the closest portions of the electrode(s) used in the present invention should be greater than the distance "x" in order to prevent an undesirable arc or formation of an unwanted corona or plasma occurring between the electrode (e.g., the electrode(s) 1 and the electrode(s) 5). Various electrode design(s), electrode location(s) and electrode interaction(s) are discussed in more detail in the Examples section herein.

The power applied through the power source 10 may be any suitable power which creates a desirable adjustable plasma 4 and desirable adjustable electrochemical reaction under all of the process conditions of the present invention. In one preferred mode of the invention, an alternating current from a step-up transformer (discussed in the "Power Sources" section and the "Examples" section) is utilized. In other preferred embodiments of the invention, polarity of an alternating current power source is modified by diode bridges to result in a positive electrode 1 and a negative electrode 5; as well as a positive electrode 5 and a negative electrode 1. In general, the combination of electrode(s) components 1 and 5, physical size and shape of the electrode(s) 1 and 5, electrode manufacturing process, mass of electrodes 1 and/or 5, the distance "x" between the tip 9 of electrode 1 above the surface 2 of the liquid 3, the composition of the gas between the electrode tip 9 and the surface 2, the flow rate and/or flow direction "F" of the liquid 3, compositions of the liquid 3, conductivity of the liquid 3, voltage, amperage, polarity of the electrodes, etc., all contribute to the design, and thus power requirements (e.g., breakdown electric field or "$E_c$" of Equation 1) all influence the formation of a controlled or adjustable plasma 4 between the surface 2 of the liquid 3 and the electrode tip 9.

In further reference to the configurations shown in FIGS. 1a and 1b, electrode holders 6a and 6b are capable of being lowered and raised (and thus the electrodes are capable of being lowered and raised) in and through an insulating member 8 (shown in cross-section). The embodiment shown here are male/female screw threads. However, the electrode holders 6a and 6b can be configured in any suitable means which allows the electrode holders 6a and 6b to be raised and/or lowered reliably. Such means include pressure fits between the insulating member 8 and the electrode holders 6a and 6b, notches, mechanical hanging means, movable annulus rings, etc. In other words, any means for reliably fixing the height of the electrode holders 6a and 6b should be considered as being within the metes and bounds of the embodiments disclosed herein.

For example, FIG. 1c shows another embodiment for raising and lowering the electrodes 1, 5. In this embodiment, electrical insulating portions 7a and 7b of each electrode are held in place by a pressure fit existing between the friction mechanism 13a, 13b and 13c, and the portions 7a and 7b. The friction mechanism 13a, 13b and 13c could be made of, for example, spring steel, flexible rubber, etc., so long as sufficient contact is maintained thereafter.

The portions 6a and 6b can be covered by, for example, additional electrical insulating portions 7a and 7b. The electrical insulating portions 7a and 7b can be any suitable electrically insulating material (e.g., plastic, rubber, fibrous materials, etc.) which prevent undesirable currents, voltage, arcing, etc., that could occur when an individual interfaces with the electrode holders 6a and 6b (e.g., attempts to adjust the height of the electrodes). Moreover, rather than the electrical insulating portion 7a and 7b simply being a cover over the electrode holder 6a and 6b, such insulating portions 7a and 7b can be substantially completely made of an electrical insulating material. In this regard, a longitudinal interface may exist between the electrical insulating portions 7a/7b and the electrode holder 6a/6b respectively (e.g., the electrode holder 6a/6b may be made of a completely different material than the insulating portion 7a/7b and mechanically or chemically (e.g., adhesively) attached thereto.

Likewise, the insulating member 8 can be made of any suitable material which prevents undesirable electrical events (e.g., arcing, melting, etc.) from occurring, as well as any material which is structurally and environmentally suitable for practicing the present invention. Typical materials include structural plastics such as polycarbonate plexiglass (poly(methyl methacrylate), polystyrene, acrylics, and the like. Certain criteria for selecting structural plastics and the like include, but are not limited to, the ability to maintain a shape and/or rigidity, while experiencing the electrical, temperature and environmental conditions of the process. Preferred materials include acrylics, plexiglass, and other polymer materials of known chemical, electrical and electrical resistance as well as relatively high mechanical stiffness. In this regard, desirable thicknesses for the member 8 are on the order of about $\frac{1}{16}"$-$\frac{3}{4}"$ (1.6 mm-19.1 mm).

The power source 10 can be connected in any convenient electrical manner to the electrodes 1 and 5. For example, wires 11a and 11b can be located within at least a portion of the electrode holders 6a, 6b with a primary goal being achieving electrical connections between the portions 11a, 11b and thus the electrodes 1, 5. Specific details of preferred electrical connections are discussed elsewhere herein.

FIG. 2a shows another schematic view of a preferred embodiment of the invention, wherein an inventive control device 20 is connected to the electrodes 1 and 5, such that the control device 20 remotely (e.g., upon command from another device) raises and/or lowers the electrodes 1, 5 relative to the surface 2 of the liquid 3. The inventive control device 20 is discussed in more detail later herein. In this preferred embodiment of the invention, the electrodes 1 and 5 can be, for example, remotely lowered and controlled, and can also be monitored and controlled by a suitable controller or computer (not shown in FIG. 2a) containing a software program (discussed in detail later herein). In this regard, FIG. 2b shows an electrode configuration similar to that shown in FIG. 2a, except that a Taylor cone "T" is utilized for electrical connection between the electrode 5 and the effective surface 2' of the liquid 3. Accordingly, the embodiments shown in FIGS. 1a, 1b and 1c should be considered to be a manually controlled apparatus for use with the teachings of the present invention, whereas the embodiments shown in FIGS. 2a and 2b should be considered to include an automatic apparatus or assembly which can remotely raise and lower the electrodes 1 and 5 in response to appropriate commands. Further, the FIG. 2a and FIG. 2b preferred embodiments of the invention can also employ computer monitoring and computer control of the distance "x" of the tips 9 of the electrode(s) 1 (and tips 9' of the electrodes 5) away from the surface 2 (discussed in greater detail later herein). Thus, the appropriate commands for raising and/or lowering the electrodes 1 and 5 can come from an individual operator and/or a suitable control device such as a controller or a computer (not shown in FIG. 2a).

Figure 3A:
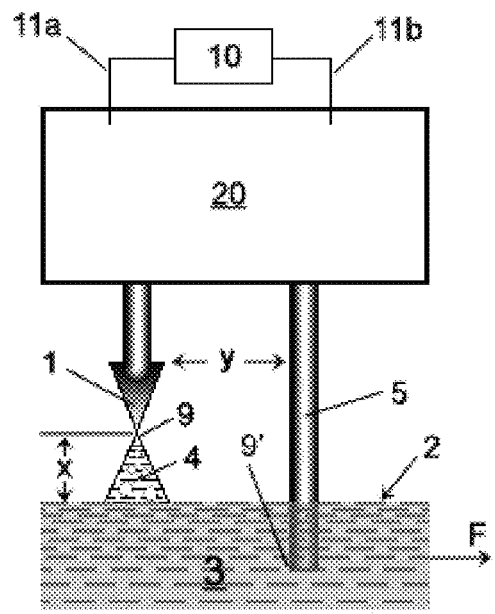
Figure 3B:
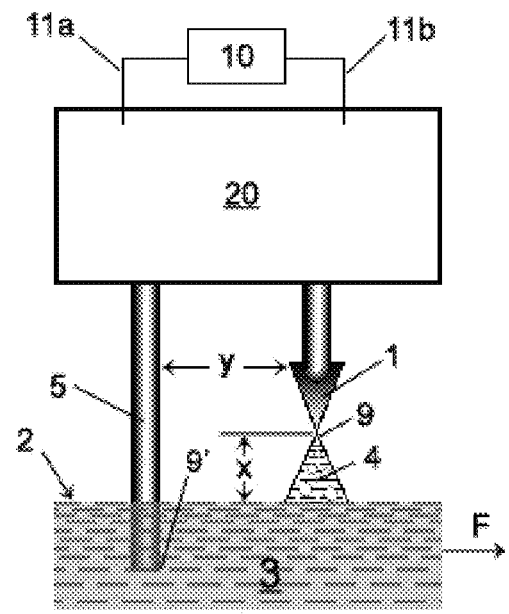
Figure 3C:
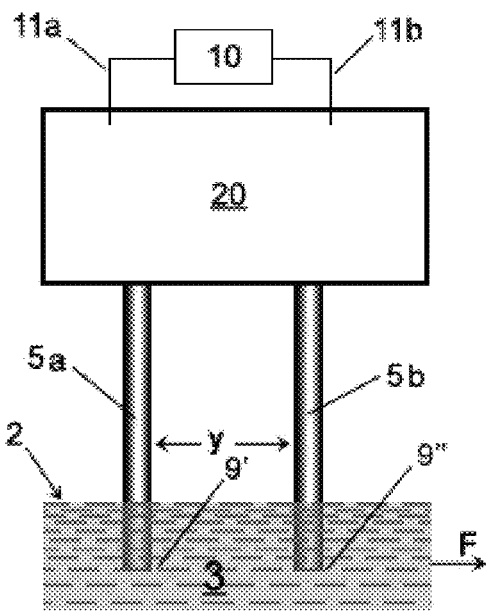
Figure 3D:
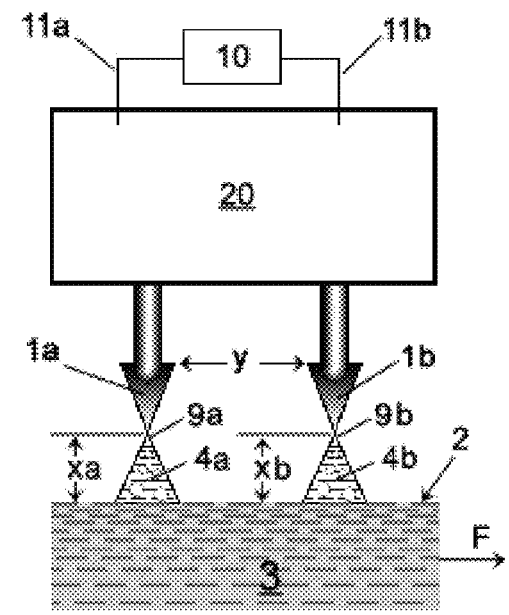

FIG. 3a corresponds in large part to FIGS. 2a and 2b, however, FIGS. 3b, 3c and 3d show various alternative electrode configurations that can be utilized in connection with certain preferred embodiments of the invention. FIG. 3b shows essentially a mirror image electrode assembly from that electrode assembly shown in FIG. 3a. In particular, as shown in FIG. 3b, with regard to the direction "F" corresponding to the flow direction of the liquid 3 in FIG. 3b, the electrode 5 is the first electrode which communicates with the fluid 3 when flowing in the longitudinal direction "F" and the electrode 1 subsequently contacts the fluid 3 already modified by the electrode 5. FIG. 3c shows two electrodes 5a and 5b located within the fluid 3. This particular electrode configuration corresponds to another preferred embodiment of the invention. In particular, any of the electrode configurations shown in FIGS. 3a-3d, can be used in combination with each other. For example, the electrode configuration (i.e., the electrode set) shown in FIG. 3a can be the first electrode set or configuration that a liquid 3 flowing in the direction "F" encounters. Thereafter, the liquid 3 could encounter a second electrode set or configuration 3a; or alternatively, the liquid 3 could encounter a second electrode set or configuration 3b; or, alternatively, the liquid 3 flowing in the direction "F" could encounter a second electrode set like that shown in FIG. 3c; or, alternatively, the liquid 3 flowing in the direction "F" could encounter a second electrode set similar to that shown in FIG. 3d. Alternatively, if the first electrode configuration or electrode set encountered by a liquid 3 flowing in the direction "F" is the electrode configuration shown in FIG. 3a, a second electrode set or configuration could be similar to that shown in FIG. 3c and a third electrode set or electrode configuration that a liquid 3 flowing in the direction "F" could encounter could thereafter be any of the electrode configurations shown in FIGS. 3a-3d. Alternatively, a first electrode set or configuration that a liquid 3 flowing in the direction "F" could encounter could be that electrode configuration shown in FIG. 3d; and thereafter a second electrode set or configuration that a liquid 3 flowing in the direction "F" could encounter could be that electrode configuration shown in FIG. 3c; and thereafter any of the electrode sets or configurations shown in FIGS. 3a-3d could comprise the configuration for a third set of electrodes. Still further, a first electrode configuration that a liquid 3 flowing in the direction "F" may encounter could be the electrode configuration shown in FIG. 3a; and a second electrode configuration could be an electrode configuration also shown in FIG. 3a; and thereafter a plurality of electrode configurations similar to that shown in FIG. 3c could be utilized. In another embodiment, all of the electrode configurations could be similar to that of FIG. 3a. In this regard, a variety of electrode configurations (including number of electrode sets utilized) are possible and each electrode configuration results in either very different resultant constituents in the liquid 3 (e.g., nanoparticle or nanoparticle/solution mixtures) or only slightly different constituents (e.g., nanoparticle/nanoparticle solution mixtures) all of which may exhibit different properties (e.g., different chemical properties, different reactive properties, different catalytic properties, etc.). In order to determine the desired number of electrode sets and desired electrode configurations and more particularly a desirable sequence of electrode sets, many factors need to be considered including all of those discussed herein such as electrode composition, plasma composition (and atmosphere composition) and intensity, power source, electrode polarity, voltage, amperage, liquid flow rate, liquid composition, liquid conductivity, cross-section (and volume of fluid treated), magnetic, electromagnetic and/or electric fields created in and around each of the electrodes in each electrode assembly, whether any field intensifiers are included, additional desired processing steps (e.g., electromagnetic radiation treatment) the desired amount of certain constituents in an intermediate product and in the final product, etc. Some specific examples of electrode assembly combinations are included in the "Examples" section later herein. However, it should be understood that the embodiments of the present invention allow a plethora of electrode combinations and numbers of electrode sets, any of which can result in very desirable nanoparticles/solutions for different specific chemical, catalytic, biological and/or physical applications.

With regard to the adjustable plasmas 4 shown in FIGS. 3a, 3b and 3d, the distance "x" (or in FIG. 3d "xa" and "xb") are one means for controlling certain aspects of the adjustable plasma 4. In this regard, if nothing else in FIG. 3a, 3b or 3d was changed except for the distance "x", then different intensity adjustable plasmas 4 can be achieved. In other words, one adjustment means for adjusting plasma 4 (e.g., the intensity) is adjusting the distance "x" between the tip 9 of the electrode 1 and the surface 2 of the fluid 3. Changing of such distance can be accomplished up to a maximum distance "x" where the combined voltage and amperage are no longer are sufficient to cause a breakdown of the atmosphere between the tip 9 and the surface 2 according to Equation 1. Accordingly, the maximum preferable distances "x" are just slightly within or below the range where "$E_c$" breakdown of the atmosphere begins to occur. Alternatively, the minimum distances "x" are those distances where an adjustable plasma 4 forms in contrast to the other phenomena discussed earlier herein where a Taylor cone forms. In this regard, if the distance "x" becomes so small that the liquid 3 tends to wick or contact the tip 9 of the electrode 1, then no visually absorbable plasma will be formed. Accordingly, the minimum and maximum distances "x" are a function of all of the factors discussed elsewhere herein including amount of power applied to the system, composition of the atmosphere, composition (e.g., electrical conductivity) of the liquid, etc. Further, intensity changes in the plasma(s) 4 may also result in certain species becoming active, relative to other processing conditions. This may result in, for example, different spectral emissions as well as changes in amplitude of various spectral lines in the plasma(s) 4. Certain preferred distances "x" for a variety of electrode configurations and compositions are discussed in the "Examples" section later herein.

Still further, with regard to FIG. 3d, the distances "xa" and "xb" can be about the same or can be substantially different. In this regard, in one preferred embodiment of the invention, for a liquid 3 flowing in the direction "F", it is desirable that the adjustable plasma 4a have different properties than the adjustable plasma 4b. In this regard, it is possible that different atmospheres can be provided so that the composition of the plasmas 4a and 4b are different from each other, and it is also possible that the height "xa" and "xb" are different from each other. In the case of differing heights, the intensity or power associated with each of the plasmas 4a and 4b can be different (e.g., different voltages can be achieved). In this regard, because the electrodes 1a and 1b are electrically connected, the total amount of power in the system will remain substantially constant, and the amount of power thus provided to one electrode 1a or 1b will increase at the expense of the power decreasing in the other electrode 1a or 1b. Accordingly, this is another inventive embodiment for controlling constituents and/or intensity and/or presence or absence of spectral peaks in the plasmas 4a and 4b and thus adjusting their interactions with the liquid 3 flowing in the direction "F".

Figure 4A:
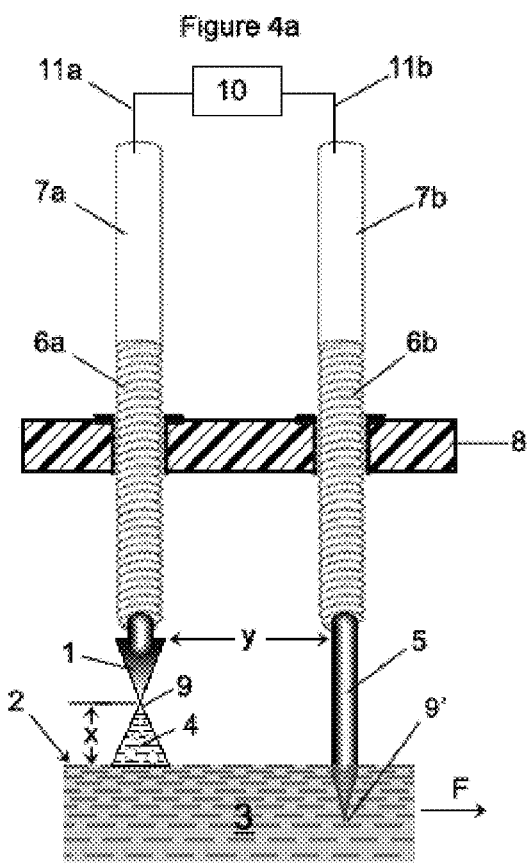
Figure 4B:
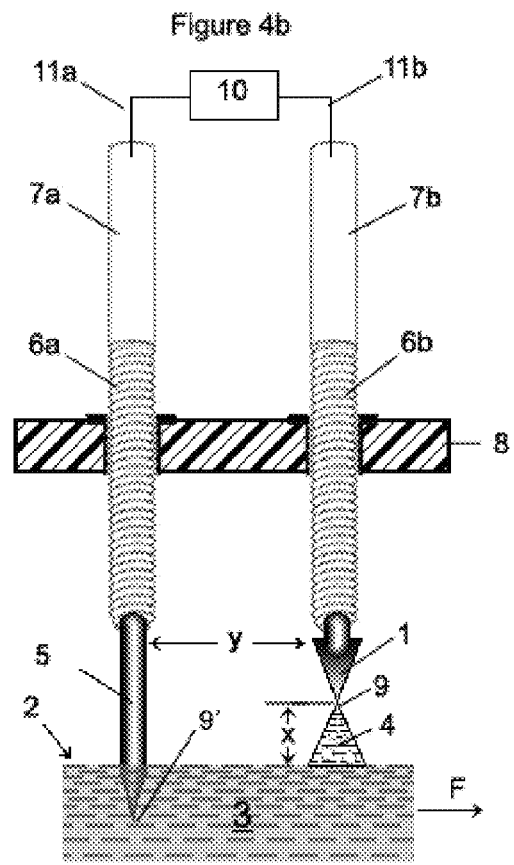
Figure 4C:
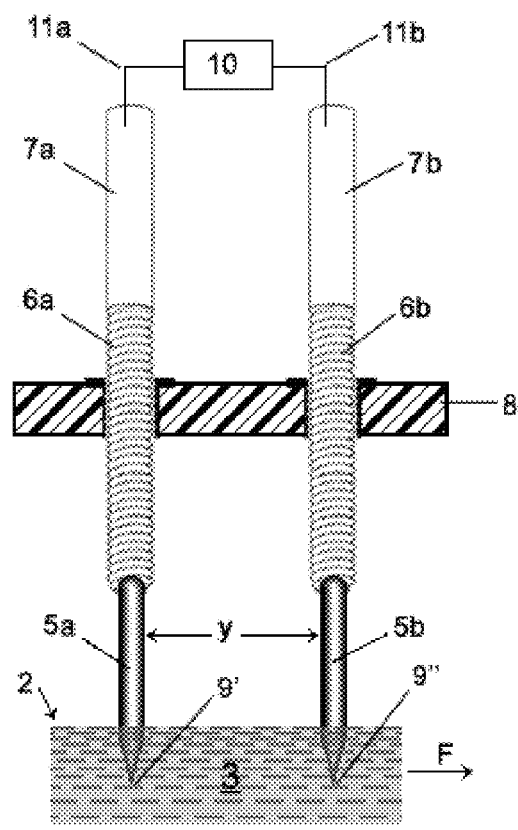

Likewise, a set of manually controllable electrode configurations are shown in FIGS. 4a, 4b, 4c and 4d which are shown in a partial cross-sectional view. Specifically, FIG. 4a corresponds substantially to FIG. 1a. Moreover, FIG. 4b corresponds in electrode configuration to the electrode configuration shown in FIG. 3b; FIG. 4c corresponds to FIG. 3c and FIG. 4d corresponds to FIG. 3d. In essence, the manual electrode configurations shown in FIGS. 4a-4d can functionally result in similar materials produced according to the inventive aspects of the invention as those materials and compositions produced corresponding to remotely adjustable (e.g., remote-controlled) electrode configurations shown in FIGS. 3a-3d. However, one or more operators will be required to adjust manually those electrode configurations. Still further, in certain embodiments, a combination of manually controlled and remotely controlled electrode(s) and/or electrode sets may be desirable.

FIGS. 5a-5e show perspective views of various desirable electrode configurations for the electrode(s) 1 shown in the Figures herein. The electrode configurations shown in FIGS. 5a-5e are representative of a number of different configurations that are useful in various embodiments of the present invention. Criteria for appropriate electrode selection for the electrode 1 include, but are not limited to the following conditions: the need for a very well defined tip or point 9, composition of the electrode 1, mechanical limitations encountered when forming the compositions comprising the electrode 1 into various shapes, shape making capabilities associated with forging techniques, wire drawing and/or casting processes utilized to make shapes, convenience, etc. In this regard, a small mass of material comprising the electrodes 1 shown in, for example, FIGS. 1-4 may, upon creation of the adjustable plasmas 4 according to the present invention, rise to operation temperatures where the size and or shape of the electrode(s) 1 can be adversely affected. The use of the phrase "small mass" should be understood as being a relative description of an amount of material used in an electrode 1, which will vary in amount as a function of composition, forming means, process conditions experienced in the trough member 30, etc. For example, if an electrode 1, comprises silver, and is shaped similar to the electrode shown in FIG. 5a, in certain preferred embodiments shown in the Examples section herein, its mass would be about 0.5 grams-8 grams with a preferred mass of about 1 gram-3 grams; whereas if an electrode 1, comprises copper, and is shaped similar to the electrode shown in FIG. 5a, in certain preferred embodiments shown in the Examples section herein, its mass would be about 0.5 grams-6 grams with a preferred mass of about 1 gram-3 grams; whereas if an electrode 1, comprises zinc, and is shaped similar to the electrode shown in FIG. 5a, in certain preferred embodiments shown in the Examples section herein, its mass would be about 0.5 grams-4 grams with a preferred mass of about 1 gram-3 grams; whereas if the electrode 1 comprises gold and is shaped similar to the electrode shown in FIG. 5e, its mass would be about 1.5 grams-20 grams with a preferred mass of about 5 grams-10 grams. In this regard, for example, when the electrode 1 comprises a relatively small mass, then certain power limitations may be associated with utilizing a small mass electrode 1. In this regard, if a large amount of power is applied to a relatively small mass and such power results in the creation of an adjustable plasma 4, then a large amount of thermal energy can be concentrated in the small mass electrode 1. If the small mass electrode 1 has a very high melting point, then such electrode may be capable of functioning as an electrode 1 in the present invention. However, if the electrode 1 is made of a composition which has a relatively low melting point (e.g., such as silver, aluminum, or the like) then under some (but not all) embodiments of the invention, the thermal energy transferred to the small mass electrode 1 could cause one or more undesirable effects including melting, cracking, or disintegration of the small mass electrode 1. Accordingly, one choice for utilizing lower melting point metals is to use larger masses of such metals so that thermal energy can be dissipated throughout such larger mass. Alternatively, if a small mass electrode 1 with low melting point is desired, then some type of cooling means could be required. Such cooling means include, for example, simple fans blowing ambient or applied atmosphere past the electrode 1, or other such means as appropriate. However, one potential undesirable aspect for providing a cooling fan juxtaposed a small mass electrode 1 is that the atmosphere involved with forming the adjustable plasma 4 could be adversely affected. For example, the plasma could be found to move or gyrate undesirably if, for example, the atmosphere flow around or between the tip 9 and the surface 2 of the liquid 3 was vigorous. Accordingly, the composition of (e.g., the material comprising) the electrode(s) 1 may affect possible suitable electrode physical shape(s) due to, for example, melting points, pressure sensitivities, environmental reactions (e.g., the local environment of the adjustable plasma 4 could cause chemical, mechanical and/or electrochemical erosion of the electrode(s)), etc.

Moreover, it should be understood that in alternative preferred embodiments of the invention, well defined sharp points for the tip 9 are not always required. In this regard, the electrode 1 shown in FIG. 5e (which is a perspective drawing) comprises a rounded point. It should be noted that partially rounded or arc-shaped electrodes can also function as the electrode 1 because often times the adjustable plasma 4, can be positioned or be located along various points of the electrode 1 shown in FIG. 5e. In this regard, FIG. 6 shows a variety of points "a-g" which correspond to initiating points 9 for the plasmas 4a-4g which occur between the electrode 1 and the surface 2 of the liquid 3. For example, in practicing certain preferred embodiments of the invention, the precise location of the adjustable plasma 4 will vary as a function of time. Specifically, a first plasma 4d may be formed at the point d on the tip 9 of the electrode 1. Thereafter, the exact location of the plasma contact point on the tip 9 may change to, for example, any of the other points 4a-4g. It should be noted that the schematic shown in FIG. 6 is greatly enlarged relative to the actual arrangement in the inventive embodiments, in order to make the point that the tip 9 on the electrode 1 may permit a variety of precise points a-g as being the initiating or contact point on tip 9 on the electrode 1. Essentially, the location of the adjustable plasma 4 can vary in position as a function of time and can be governed by electric breakdown of the atmosphere (according to Equation 1 herein) located between the electrode 1 and the surface 2 of the liquid 3. Further, while the plasmas 4a-4g are represented as being cone-shaped, it should be understood that the plasmas 4, formed in connection with any of the electrodes 1, shown in FIGS. 5a-5e, may comprise shapes other than cones for a portion of, or substantially all of, the process conditions. For example, shapes best described as lightning bolts or glowing cylinders can also be present. Further, the colors emitted by such plasmas 4 (e.g., in the visible spectrum) can vary wildly from reddish in color, bluish in color, yellow in color, orangish in color, violet in color, white in color, etc., which colors are a function of atmosphere present, voltage, amperage, electrode composition, liquid composition, etc.

Accordingly, it should be understood that a variety of sizes and shapes corresponding to electrode 1 can be utilized in accordance with the teachings of the present invention. Still further, it should be noted that the tips 9 of the electrodes 1 shown in various figures herein may be shown as a relatively sharp point or a relatively blunt end. Unless specific aspects of these electrode tips are discussed in greater contextual detail, the actual shape of the electrode tip(s) shown in the Figures should not be given great significance.

FIG. 7a shows a cross-sectional perspective view of the electrode configuration corresponding to that shown in FIG. 2a (and FIG. 3a) contained within a trough member 30. This trough member 30 has a liquid 3 supplied into it from the back side 31 of FIG. 7a and the flow direction "F" is out of the page toward the reader and toward the cross-sectional area identified as 32. The trough member 30 is shown here as a unitary of piece of one material, but could be made from a plurality of materials fitted together and, for example, fixed (e.g., glued, mechanically attached, etc.) by any acceptable means for attaching materials to each other. Further, the trough member 30 shown here is of a rectangular or square cross-sectional shape, but may comprise a variety of different cross-sectional shapes. Further, the trough member 30 does not necessarily need to be made of a single cross-sectional shape, but in another preferred embodiment herein, comprises a plurality of different cross-sectional shapes. In a first preferred embodiment the cross-sectional shape is roughly the same throughout the longitudinal dimension of the trough member 30 but the size dimensions of the cross-sectional shape change in coordination with different plasma and/or electrochemical reactions. Further, more than two cross-sectional shapes can be utilized in a unitary trough member 30. The advantages of the different cross-sectional shapes include, but are not limited to, different power, electric field, magnetic field, electromagnetic interactions, electrochemical, effects, different chemical reactions in different portions, etc., which are capable of being achieved in different longitudinal portions of the same unitary trough member 30. Still further, some of the different cross-sectional shapes can be utilized in conjunction with, for example, different atmospheres being provided locally or globally such that at least one of the adjustable plasma(s) 4 and/or at least one of the electrochemical reactions occurring at the electrode(s) 5 are a function of different possible atmospheres and/or atmospheric concentrations of constituents therein. Further, the amount or intensity of applied and/or created fluids can be enhanced by, for example, cross-sectional shape, as well as by providing, for example, various field concentrators at, near, adjacent to or juxtaposed against various electrode sets or electrode configurations to enhance or diminish one or more reactions occurring there. Accordingly, the cross-sectional shape of the trough member 30 can influence both liquid 3 interactions with the electrode(s) as well as adjustable plasma 4 interactions with the liquid 3.

Still further, it should be understood that a trough member need not be only linear or "I-shaped", but rather, may be shaped like a "Y" or like a "Ψ", each portion of which may have similar or dissimilar cross-sections. One reason for a "Y" or "Ψ"-shaped trough member 30 is that two different sets of processing conditions can exist in the two upper portions of the "Y"-shaped trough member 30. Further, a third set of processing conditions can exist in the bottom portion of the "Y"-shaped trough member 30. Thus, two different fluids 3, of different compositions and/or different reactants, could be brought together into the bottom portion of the "Y"-shaped trough member 30 and processed together to from a large variety of final products.

FIG. 11e shows an alternative configuration for the trough member 30. Specifically, the trough member 30 is shown in perspective view and is "Y-shaped". Specifically, the trough member 30 comprises top portions 30a and 30b and a bottom portion 30o. Likewise, inlets 31a and 31b are provided along with outlet 32. A portion 30d corresponds to the point where 30a and 30b meet 30o.

FIG. 11f shows the same "Y-shaped" trough member shown in FIG. 11e, except that the portion 30d of FIG. 11e is now shown as a mixing section 30d'. In this regard, certain constituents manufactured or produced in the liquid 3 in one or all of, for example, the portions 30a, 30b and/or 30c, may be desirable to be mixed together at the point 30d (or 30d'). Such mixing may occur naturally at the intersection 30d shown in FIG. 11e (i.e., no specific or special section 30d' may be needed), or may be more specifically controlled at the portion 30d'. It should be understood that the portion 30d' could be shaped in any effective shape, such as square, circular, rectangular, etc., and be of the same or different depth relative to other portions of the trough member 30. In this regard, the area 30d could be a mixing zone or subsequent reaction zone.

FIGS. 11g and 11h show a "Ψ-shaped" trough member 30. Specifically, a new portion 30c has been added. Other features of FIGS. 11g and 11h are similar to those features shown in 11e and 11f.

It should be understood that a variety of different shapes can exist for the trough member 30, any one of which can produce desirable results.

Again with regard to FIG. 7a, the flow direction of the liquid 3 is out of the page toward the reader and the liquid 3 flows past each of the electrode(s) 1 and 5, sequentially, which are, in this embodiment, located substantially in line with each other relative to the longitudinal flow direction "F" of the liquid 3 within the trough member 30 (e.g., their arrangement is parallel to each other and the longitudinal dimensions of the trough member 30). This causes the liquid 3 to first experience an adjustable plasma 4 interaction with the liquid 3 (e.g., a conditioning reaction) and subsequently then the conditioned liquid 3 can thereafter interact with the electrode 5. As discussed earlier herein, a variety of constituents can be expected to be present in the adjustable plasma 4 and at least a portion of such constituents or components (e.g., chemical, physical and/or fluid components) will interact with at least of the portion of the liquid 3 and change the liquid 3. Accordingly, subsequent reactions (e.g., electrochemical) can occur at electrode(s) 5 after such components or constituents or alternative liquid structure(s) have been caused to be present in the liquid 3. Thus, it should be apparent from the disclosure of the various embodiments herein, that the type, amount and activity of constituents or components in the adjustable plasma 4 are a function of a variety of conditions associated with practicing the preferred embodiments of the present invention. Such constituents (whether transient or semi permanent), once present and/or having at least partially modified the liquid 3, can favorably influence subsequent reactions along the longitudinal direction of the trough member 30 as the liquid 3 flows in the direction "F" therethrough. By adjusting the types of reactions (e.g., electrode assemblies and reactions associated therewith) and sequentially providing additional similar or different electrode sets or assemblies (such as those shown in FIGS. 3a-3d) a variety of compounds, nanoparticles and nanoparticle/solution(s) can be achieved. For example, nanoparticles may experience growth (e.g., apparent or actual) within the liquid 3 as constituents within the liquid 3 pass by and interact with various electrode sets (e.g., 5, 5) along the longitudinal length of the trough member 30 (discussed in greater detail in the Examples section). Such growth, observed at, for example, electrode sets 5, 5, seems to be greatly accelerated when the liquid 3 has previously been contacted with an electrode set 1, 5 and/or 1, 1 and/or 5, 1. Depending on the particular final uses of the liquid 3 produced according to the invention, certain nanoparticles, some constituents in the liquid 3, etc., could be considered to be very desirable; whereas other constituents could be considered to be undesirable. However, due to the versatility of the electrode design, number of electrode sets, electrode set configuration, fluid composition, processing conditions at each electrode in each electrode assembly or set, sequencing of different electrode assemblies or sets along the longitudinal direction of the trough member 30, shape of the trough member 30, cross-sectional size and shape of the trough member 30, all such conditions can contribute to more or less of desirable or undesirable constituents or components (transient or semi-permanent) present in the liquid 3 and/or differing structures of the liquid per se during at least a portion of the processes disclosed herein.

FIG. 7b shows a cross-sectional perspective view of the electrode configuration shown in FIG. 2a (as well as in FIG. 3a), however, these electrodes 1 and 5 are rotated on the page 90 degrees relative to the electrodes 1 and 5 shown in FIGS. 2a and 3a. In this embodiment of the invention, the liquid 3 contacts the adjustable plasma 4 generated between the electrode 1 and the surface 2 of the liquid 3, and the electrode 5 at substantially the same point along the longitudinal flow direction "F" (i.e., out of the page) of the trough member 30. The direction of liquid 3 flow is longitudinally along the trough member 30 and is out of the paper toward the reader, as in FIG. 7a. Accordingly, as discussed immediately above herein, it becomes clear that the electrode assembly shown in FIG. 7b can be utilized with one or more of the electrode assemblies or sets discussed above herein as well as later herein. For example, one use for the assembly shown in FIG. 7b is that when the constituents created in the adjustable plasma 4 (or resultant products in the liquid 3) flow downstream from the contact point with the surface 2 of the liquid 3, a variety of subsequent processing steps can occur. For example, the distance "y" between the electrode 1 and the electrode 5 (as shown, for example, in FIG. 7b) is limited to certain minimum distances as well as certain maximum distances. The minimum distance "y" is that distance where the distance slightly exceeds the electric breakdown "$E_c$" of the atmosphere provided between the closest points between the electrodes 1 and 5. Whereas the maximum distance "y" corresponds to the distance at a maximum which at least some conductivity of the fluid permits there to be an electrical connection from the power source 10 into and through each of the electrode(s) 1 and 5 as well as through the liquid 3. The maximum distance "y" will vary as a function of, for example, constituents within the liquid 3 (e.g., conductivity of the liquid 3). Accordingly, some of those highly energized constituents comprising the adjustable plasma 4 could be very reactive and could create compounds (reactive or otherwise) within the liquid 3 and a subsequent processing step could be enhanced by the presence of such constituents or such very reactive components or constituents could become less reactive as a function of, for example, time. Moreover, certain desirable or undesirable reactions could be minimized or maximized by locations and/or processing conditions associated with additional electrode sets downstream from that electrode set shown in, for example, FIG. 7b.

Figure 8A:
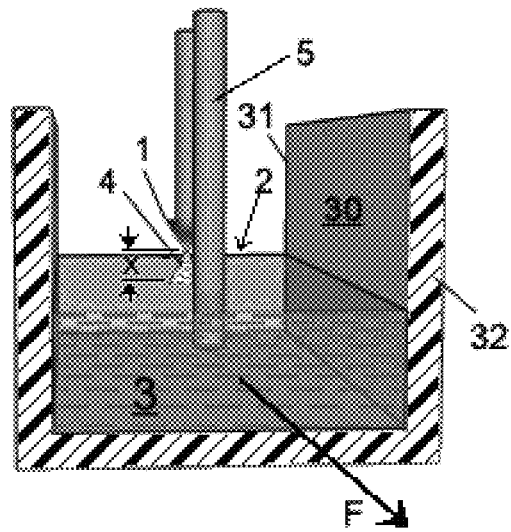
Figure 8B:
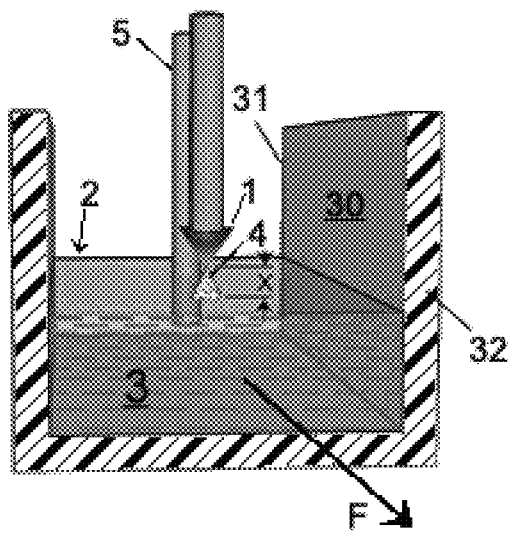

FIG. 8a shows a cross-sectional perspective view of the same embodiment shown in FIG. 7a. In this embodiment, as in the embodiment shown in FIG. 7a, the fluid 3 firsts interacts with the adjustable plasma 4 created between the electrode 1 and the surface 2 of the liquid 3. Thereafter the plasma influenced or conditioned fluid 3, having been changed (e.g., conditioned, or modified or prepared) by the adjustable plasma 4, thereafter communicates with the electrode 5 thus permitting various electrochemical reactions to occur, such reactions being influenced by the state (e.g., chemical composition, physical or crystal structure, excited state(s), etc., of the fluid 3 (and constituents or components in the fluid 3)). An alternative embodiment is shown in FIG. 8b. This embodiment essentially corresponds in general to those embodiments shown in FIGS. 3b and 4b. In this embodiment, the fluid 3 first communicates with the electrode 5, and thereafter the fluid 3 communicates with the adjustable plasma 4 created between the electrode 1 and the surface 2 of the liquid 3.

Figure 8C:
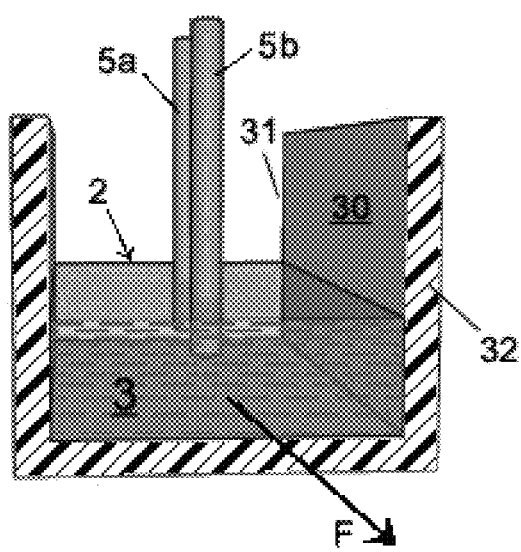

FIG. 8c shows a cross-sectional perspective view of two electrodes 5a and 5b (corresponding to the embodiments shown in FIGS. 3c and 4c) wherein the longitudinal flow direction "F" of the fluid 3 contacts the first electrode 5a and thereafter contacts the second electrode 5b in the direction "F" of fluid flow.

Figure 4D:
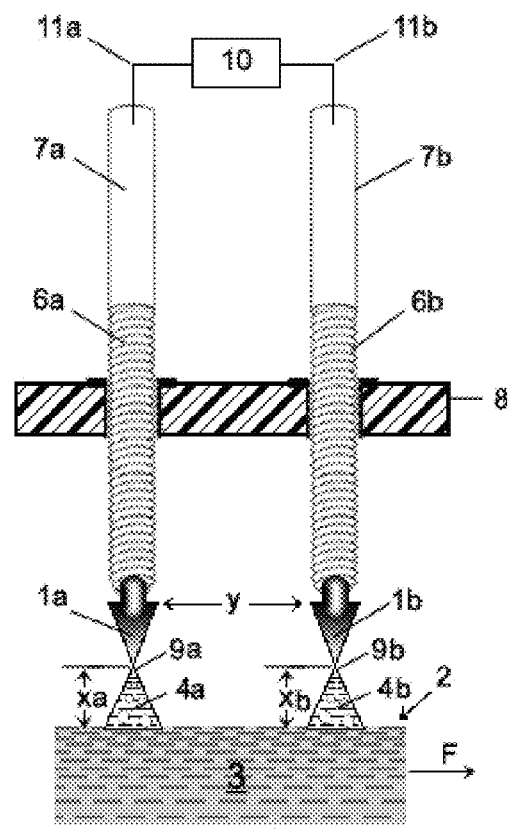
Figure 5A:
Figure 5B:
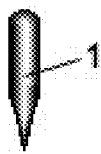
Figure 5C:
Figure 5D:
Figure 5E:
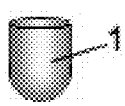
Figure 8D:
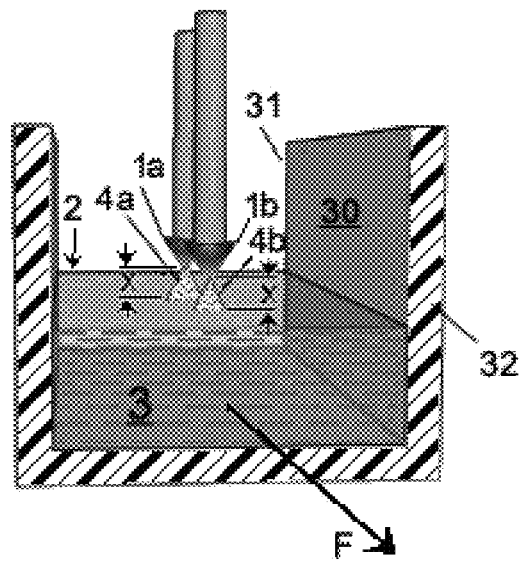

Likewise, FIG. 8d is a cross-sectional perspective view and corresponds to the embodiments shown in FIGS. 3d and 4d. In this embodiment, the fluid 3 communicates with a first adjustable plasma 4a created by a first electrode 1a and thereafter communicates with a second adjustable plasma 4b created between a second electrode 1b and the surface 2 of the fluid 3.

Accordingly, it should be clear from the disclosed embodiments that the various electrode configurations or sets shown in FIGS. 8a-8d can be used alone or in combination with each other in a variety of different configurations. A number of factors direct choices for which electrode configurations are best to be used to achieve various desirable results. As well, the number of such electrode configurations and the location of such electrode configurations relative to each other all influence resultant constituents within the liquid 3, nanoparticles and/or nanoparticle/liquid solutions resulting therefrom. Some specific examples of electrode configuration dependency are included in the "Examples" section herein. However, it should be apparent to the reader a variety of differing products and desirable set-ups are possible according to the teachings (both expressly and inherently) present herein, which differing set-ups can result in very different products (discussed further in the "Examples" section herein).

FIG. 9a shows a cross-sectional perspective view and corresponds to the electrode configuration shown in FIG. 7b (and generally to the electrode configuration shown in FIGS. 3a and 4a but is rotated 90 degrees relative thereto). All of the electrode configurations shown in FIGS. 9a-9d are situated such that the electrode pairs shown are located substantially at the same longitudinal point along the trough member 30, as in FIG. 7b.

Likewise, FIG. 9b corresponds generally to the electrode configuration shown in FIGS. 3b and 4b, and is rotated 90 degrees relative to the configuration shown in FIG. 8b.

FIG. 9c shows an electrode configuration corresponding generally to FIGS. 3c and 4c, and is rotated 90 degrees relative to the electrode configuration shown in FIG. 8c.

FIG. 9d shows an electrode configuration corresponding generally to FIGS. 3d and 4d and is rotated 90 degrees relative to the electrode configuration shown in FIG. 8d.

As discussed herein, the electrode configurations or sets shown generally in FIGS. 7, 8 and 9, all can create different results (e.g., different sizes, shapes, amounts, compounds, constituents, functioning of nanoparticles present in a liquid, different liquid structures, different pH's, etc.) as a function of their orientation and position relative to the fluid flow direction "F" and relative to their positioning in the trough member 30, relative to each other. Further, the electrode number, compositions, size, specific shapes, voltages applied, amperages applied, fields created, distance between electrodes in each electrode set, distance between electrode sets, etc., can all influence the properties of the liquid 3 as it flows past these electrodes and hence resultant properties of the materials (e.g., the constituents in the fluid 3, the nanoparticles and/or the nanoparticle/solution) produced therefrom. Additionally, the liquid-containing trough member 30, in some preferred embodiments, contains a plurality of the electrode combinations shown in FIGS. 7, 8 and 9. These electrode assemblies may be all the same or may be a combination of various different electrode configurations. Moreover, the electrode configurations may sequentially communicate with the fluid "F" or may simultaneously, or in parallel communicate with the fluid "F". Different exemplary electrode configurations are shown in additional figures later herein and are discussed in greater detail later herein (e.g., in the "Examples" section) in conjunction with different constituents produced in the liquid 3, nanoparticles and/or different nanoparticle/solutions produced therefrom.

FIG. 10a shows a cross-sectional view of the liquid containing trough member 30 shown in FIGS. 7, 8 and 9. This trough member 30 has a cross-section corresponding to that of a rectangle or a square and the electrodes (not shown in FIG. 10a) can be suitably positioned therein.

Likewise, several additional alternative cross-sectional embodiments for the liquid-containing trough member 30 are shown in FIGS. 10b, 10c, 10d and 10e. The distance "S" and "S'" for the preferred embodiments shown in each of FIGS. 10a-10e measures, for example, between about 1" and about 3" (about 2.5 cm-7.6 cm). The distance "M" ranges from about 2" to about 4" (about 5 cm-10 cm). The distance "R" ranges from about $\frac{1}{16}$"-$\frac{1}{2}$" to about 3" (about 1.6 mm-13 mm to about 76 mm) All of these embodiments (as well as additional configurations that represent alternative embodiments are within the metes and bounds of this inventive disclosure) can be utilized in combination with the other inventive aspects of the invention. It should be noted that the amount of liquid 3 contained within each of the liquid containing trough members 30 is a function not only of the depth "d", but also a function of the actual cross-section. Briefly, the amount or volume of liquid 3 present in and around the electrode(s) 1 and 5 can influence one or more effect(s) (e.g., fluid or concentration effects including field concentration effects) of the adjustable plasma 4 upon the liquid 3 as well as one or more chemical or electrochemical interaction(s) of the electrode 5 with the liquid 3. These effects include not only adjustable plasma 4 conditioning effects (e.g., interactions of the plasma electric and magnetic fields, interactions of the electromagnetic radiation of the plasma, creation of various chemical species (e.g., Lewis acids, Bronsted-Lowry acids, etc.) within the liquid, pH changes, etc.) upon the liquid 3, but also the concentration or interaction of the adjustable plasma 4 with the liquid 3 and electrochemical interactions of the electrode 5 with the liquid 3. Different effects are possible due to, for example, the actual volume of liquid present around a longitudinal portion of each electrode assembly 1 and/or 5. In other words, for a given length along the longitudinal direction of the trough member 30, different amounts or volume of liquid 3 will be present as a function of cross-sectional shape. As a specific example, reference is made to FIGS. 10a and 10c. In the case of FIG. 10a, the rectangular shape shown therein has a top portion about the same distance apart as the top portion shown in FIG. 10c. However, the amount of fluid along the same given longitudinal amount (i.e., into the page) will be significantly different in each of FIGS. 10a and 10c.

Similarly, the influence of many aspects of the electrode 5 on the liquid 3 (e.g., electrochemical interactions) is also, at least partially, a function of the amount of fluid juxtaposed to the electrode(s) 5, as discussed immediately above herein.

Further, electric and magnetic field concentrations can also significantly affect the interaction of the plasma 4 with the liquid 3, as well as affect the interactions of the electrode(s) 5 with the liquid 3. For example, without wishing to be bound by any particular theory or explanation, when the liquid 3 comprises water, a variety of electric field, magnetic field and/or electromagnetic field influences can occur. Specifically, water is a known dipolar molecule which can be at least partially aligned by an electric field. Having partial alignment of water molecules with an electric field can, for example, cause previously existing hydrogen bonding and bonding angles to be oriented at an angle different than prior to electric field exposure, cause different vibrational activity, or such bonds may actually be broken. Such changing in water structure can result in the water having a different (e.g., higher) reactivity. Further, the presence of electric and magnetic fields can have opposite effects on ordering or structuring of water and/or nanoparticles present in the water. It is possible that unstructured or small structured water having relatively fewer hydrogen bonds relative to, for example, very structured water, can result in a more reactive (e.g., chemically more reactive) environment. This is in contrast to open or higher hydrogen-bonded networks which can slow reactions due to, for example, increased viscosity, reduced diffusivities and a smaller activity of water molecules. Accordingly, factors which apparently reduce hydrogen bonding and hydrogen bond strength (e.g., electric fields) and/or increase vibrational activity, can encourage reactivity and kinetics of various reactions.

Further, electromagnetic radiation can also have direct and indirect effects on water and it is possible that the electromagnetic radiation per se (e.g., that radiation emitted from the plasma 4), rather than the individual electric or magnetic fields alone can have such effects, as disclosed in the aforementioned published patent application entitled Methods for Controlling Crystal Growth, Crystallization, Structures and Phases in Materials and Systems which has been incorporated by reference herein. Different spectra associated with different plasmas 4 are discussed in the "Examples" section herein.

Further, by passing an electric current through the electrode(s) 1 and/or 5 disclosed herein, the voltages present on, for example, the electrode(s) 5 can have an orientation effect (i.e., temporary, semi-permanent or longer) on the water molecules. The presence of other constituents (i.e., charged species) in the water may enhance such orientation effects. Such orientation effects may cause, for example, hydrogen bond breakage and localized density changes (i.e., decreases). Further, electric fields are also known to lower the dielectric constant of water due to the changing (e.g., reduction of) the hydrogen bonding network. Such changing of networks should change the solubility properties of water and may assist in the concentration or dissolution of a variety of gases and/or constituents or reactive species in the liquid 3 (e.g., water) within the trough member 30. Still further, it is possible that the changing or breaking of hydrogen bonds from application of electromagnetic radiation (and/or electric and magnetic fields) can perturb gas/liquid interfaces and result in more reactive species. Still further, changes in hydrogen bonding can affect carbon dioxide hydration resulting in, among other things, pH changes. Thus, when localized pH changes occur around, for example, at least one or more of the electrode(s) 5 (or electrode(s) 1), many of the possible reactants (discussed elsewhere herein) will react differently with themselves and/or the atmosphere and/or the adjustable plasma(s) 4 as well as the electrode(s) 1 and/or 5, per se. The presence of Lewis acids and/or Bronsted-Lowry acids, can also greatly influence reactions.

Further, a trough member 30 may comprise more than one cross-sectional shapes along its entire longitudinal length. The incorporation of multiple cross-sectional shapes along the longitudinal length of a trough member 30 can result in, for example, a varying field or concentration or reaction effects being produced by the inventive embodiments disclosed herein. Additionally, various modifications can be added at points along the longitudinal length of the trough member 30 which can enhance and/or diminish various of the field effects discussed above herein. In this regard, compositions of materials in and/or around the trough (e.g., metals located outside or within at least a portion of the trough member 30) can act as concentrators or enhancers of various of the fields present in and around the electrode(s) 1 and/or 5. Additionally, applications of externally-applied fields (e.g., electric, magnetic, electromagnetic, etc.) and/or the placement of certain reactive materials within the trough member 30 (e.g., at least partially contacting a portion of the liquid 3 flowing thereby) can also result in: (1) a gathering, collecting or filtering of undesirable species; or (2) placement of desirable species onto, for example, at least a portion of an outer surface of nanoparticles already formed upstream therefrom. Further, it should be understood that a trough member 30 may not be linear or "I-shaped", but rather may be "Y-shaped" or "Ψ-shaped", with each portion of the "Y" or "Ψ" having a different (or similar) cross-section. One reason for a "Y" or "Ψ-shaped" trough member 30 is that two (or more) different sets of processing conditions can exist in the two (or more) upper portions of the "Y-shaped" or "Ψ-shaped" trough member 30. Further, another additional set of processing conditions can exist in the bottom portion of the "Y-shaped" trough member 30. Thus, different fluids 3, of different compositions and/or different reactants, could be brought together into the bottom portion of the "Y-shaped" trough member 30 and processed together to from a large variety of final products.

FIG. 11a shows a perspective view of one embodiment of substantially all of the trough member 30 shown in FIG. 10b including an inlet portion or inlet end 31 and an outlet portion or outlet end 32. The flow direction "F" discussed in other figures herein corresponds to a liquid entering at or near the end 31 (e.g., utilizing an appropriate means for delivering fluid into the trough member 30 at or near the inlet portion 31) and exiting the trough member 30 through the outlet end 32. Additionally, while a single inlet end 31 is shown in FIG. 11*a*, multiple inlet(s) 31 could be present near that shown in FIG. 11*a*, or could be located at various positions along the longitudinal length of the trough member 30 (e.g., immediately upstream from one or more of the electrode sets positioned along the trough member 30). Thus, the plurality of inlet(s) 31 can permit the introduction of more than one liquid 3 at a first longitudinal end 31 thereof; or the introduction of multiple liquids 3 at the longitudinal end 31; and/or the introduction of different liquids 3 at different positions along the longitudinal length of the trough member 30.

FIG. 11*b* shows the trough member 30 of FIG. 11*a* containing three control devices 20 removably attached to a top portion of the trough member 30. The interaction and operations of the control devices 20 containing the electrodes 1 and/or 5 are discussed in greater detail later herein.

FIG. 11*c* shows a perspective view of the trough member 30 incorporating an atmosphere control device cover 35'. The atmosphere control device or cover 35' has attached thereto a plurality of control devices 20 (in FIG. 11*c*, three control devices 20*a*, 20*b* and 20*c* are shown) containing electrode(s) 1 and/or 5. The cover 35' is intended to provide the ability to control the atmosphere within and/or along a substantial portion of (e.g., greater than 50% of) the longitudinal direction of the trough member 30, such that any adjustable plasma(s) 4 created at any electrode(s) 1 can be a function of voltage, current, current density, etc., as well as any controlled atmosphere provided. The atmosphere control device 35' can be constructed such that one or more electrode sets can be contained within. For example, a localized atmosphere can be created between the end portions 39*a* and 39*b* along substantially all or a portion of the longitudinal length of the trough member 30 and a top portion of the atmosphere control device 35'. An atmosphere can be caused to flow into at least one inlet port (not shown) incorporated into the atmosphere control device 35' and can exit through at least one outlet port (not shown), or be permitted to enter/exit along or near, for example, the portions 39*a* and 39*b*. In this regard, so long as a positive pressure is provided to an interior portion of the atmosphere control device 35' (i.e., positive relative to an external atmosphere) then any such gas can be caused to bubble out around the portions 39*a* and/or 39*b*. Further, depending on, for example, if one portion of 39*a* or 39*b* is higher relative to the other, an internal atmosphere may also be appropriately controlled. A variety of atmospheres suitable for use within the atmosphere control device 35' include conventionally regarded non-reactive atmospheres like noble gases (e.g., argon or helium) or conventionally regarded reactive atmospheres like, for example, oxygen, nitrogen, ozone, controlled air, etc. The precise composition of the atmosphere within the atmosphere control device 35' is a function of desired processing techniques and/or desired constituents to be present in the plasma 4 and/or the liquid 3, desired nanoparticles/composite nanoparticles and/or desired nanoparticles/solutions.

FIG. 11*d* shows the apparatus of FIG. 11*c* including an additional support means 34 for supporting the trough member 30 (e.g., on an exterior portion thereof), as well as supporting (at least partially) the control devices 20 (not shown in this FIG. 11*c*). It should be understood that various details can be changed regarding, for example, the cross-sectional shapes shown for the trough member 30, atmosphere control(s) (e.g., the atmosphere control device 35') and external support means (e.g., the support means 34) all of which should be considered to be within the metes and bounds of this inventive disclosure. The material(s) comprising the additional support means 34 for supporting the trough member 30 can be any material which is convenient, structurally sound and non-reactive under the process conditions practiced for the present inventive disclosure. Acceptable materials include polyvinyls, acrylics, plexiglass, structural plastics, nylons, teflons, etc., as discussed elsewhere herein.

FIG. 11*e* shows an alternative configuration for the trough member 30. Specifically, the trough member 30 is shown in perspective view and is "Y-shaped". Specifically, the trough member 30 comprises top portions 30*a* and 30*b* and a bottom portion 30*o*. Likewise, inlets 31*a* and 31*b* are provided along with outlet 32. A portion 30*d* corresponds to the point where 30*a* and 30*b* meet 30*o*.

FIG. 11*f* shows the same "Y-shaped" trough member shown in FIG. 11*e*, except that the portion 30*d* of FIG. 11*e* is now shown as a mixing section 30*d'*. In this regard, certain constituents manufactured or produced in the liquid 3 in one or all of, for example, the portions 30*a*, 30*b* and/or 30*c*, may be desirable to be mixed together at the point 30*d* (or 30*d'*). Such mixing may occur naturally at the intersection 30*d* shown in FIG. 11*e* (i.e., no specific or special section 30*d'* may be needed), or may be more specifically controlled at the portion 30*d'*. It should be understood that the portion 30*d'* could be shaped in any effective shape, such as square, circular, rectangular, etc., and be of the same or different depth relative to other portions of the trough member 30. In this regard, the area 30*d* could be a mixing zone or subsequent reaction zone.

FIGS. 11*g* and 11*h* show a "Ψ-shaped" trough member 30. Specifically, a new portion 30*c* has been added. Other features of FIGS. 11*g* and 11*h* are similar to those features shown in 11*e* and 11*f*.

It should be understood that a variety of different shapes can exist for the trough member 30, any one of which can produce desirable results.

FIG. 12*a* shows a perspective view of a local atmosphere control apparatus 35 which functions as a means for controlling a local atmosphere around at least one electrode set 1 and/or 5 so that various localized gases can be utilized to, for example, control and/or effect certain parameters of the adjustable plasma 4 between electrode 1 and surface 2 of the liquid 3, as well as influence certain constituents within the liquid 3 and/or adjustable electrochemical reactions at and/or around the electrode(s) 5. The through-holes 36 and 37 shown in the atmosphere control apparatus 35 are provided to permit external communication in and through a portion of the apparatus 35. In particular, the hole or inlet 37 is provided as an inlet connection for any gaseous species to be introduced to the inside of the apparatus 35. The hole 36 is provided as a communication port for the electrodes 1 and/or 5 extending therethrough which electrodes are connected to, for example, the control device 20 above the apparatus 35. Gasses introduced through the inlet 37 can simply be provided at a positive pressure relative to the local external atmosphere and may be allowed to escape by any suitable means or pathway including, but not limited to, bubbling out around the portions 39*a* and/or 39*b* of the apparatus 35, when such portions are caused, for example, to be at least partially submerged beneath the surface 2 of the liquid 3. Generally, the portions 39*a* and 39*b* can break the surface 2 of the liquid 3 effectively causing the surface 2 to act as part of the seal to form a localized atmosphere around electrode sets 1 and/or 5. When a positive pressure of a desired gas enters through the inlet port 37, small bubbles can be caused to bubble past, for example, the portions 39a and/or 39b. Additionally, the precise location of the inlet 37 can also be a function of the gas flowing therethrough. Specifically, if a gas providing at least a portion of a localized atmosphere is heavier than air, then an inlet portion above the surface 2 of the liquid 3 should be adequate. However, it should be understood that the inlet 37 could also be located in, for example, 39a or 39b and could be bubbled through the liquid 3 and trapped within an interior portion of the localized atmosphere control apparatus 35. Accordingly, precise locations of inlets and/or outlets in the atmosphere control device 35 are a function of several factors.

FIG. 12b shows a perspective view of first atmospheric control apparatus 35a in the foreground of the trough member 30 contained within the support housing 34. A second atmospheric control apparatus 35b is included and shows a control device 20 located thereon. "F" denotes the longitudinal direction of flow of liquid 3 through the trough member 30. A plurality of atmospheric control apparatuses 35a, 35b (as well as 35c, 35d, etc. not shown in drawings) can be utilized instead of a single atmosphere control device such as that shown in FIG. 11c. The reason for a plurality of localized atmosphere control devices 35a-35x is that different atmospheres can be present around each electrode assembly, if desired. Accordingly, specific aspects of the adjustable plasma(s) 4 as well as specific constituents present in the liquid 3 and specific aspects of the adjustable electrochemical reactions occurring at, for example, electrode(s) 5, will be a function of, among other things, the localized atmosphere. Accordingly, the use of one or more localized atmosphere control device 35a provides tremendous flexibility in the formation of desired constituents, nanoparticles, and nanoparticle solution mixtures.

FIG. 13 shows a perspective view of an alternative atmosphere control apparatus 38 wherein the entire trough member 30 and support means 34 are contained within the atmospheric control apparatus 38. In this case, for example, one or more gas inlets 37, 37' can be provided along with one or more gas outlets 37a, 37a'. The exact positioning of the gas inlets 37, 37' and gas outlets 37a, 37a' on the atmospheric control apparatus 38 is a matter of convenience, as well as a matter of the composition of the atmosphere. In this regard, if, for example, the atmosphere provided is heavier than air or lighter than air, inlet and outlet locations can be adjusted accordingly. As discussed elsewhere herein, the gas inlet and gas outlet portions could be provided above or below the surface 2 of the liquid 3. Of course, when gas inlet portions are provided below the surface 2 of the liquid 3 (not specifically shown in this Figure), it should be understood that bubbled (e.g., nanobubbles and/or microbubbles) of the gas inserted through the gas inlet 37 could be incorporated into the liquid 3, for at least a portion of the processing time. Such bubbles could be desirable reaction constituents (i.e., reactive with) the liquid 3 and/or constituents within the liquid 3 and/or the electrode(s) 5, etc. Accordingly, the flexibility of introducing a localized atmosphere below the surface 2 of the liquid 3 can provide additional processing control and/or processing enhancements.

FIG. 14 shows a schematic view of the general apparatus utilized in accordance with the teachings of some of the preferred embodiments of the present invention. In particular, this FIG. 14 shows a side schematic view of the trough member 30 containing a liquid 3 therein. On the top of the trough member 30 rests a plurality of control devices 20a-20d (i.e., four of which are shown) which are, in this embodiment, removably attached thereto. The control devices 20 may of course be permanently fixed in position when practicing various embodiments of the invention. The precise number of control devices 20 (and corresponding electrode(s) 1 and/or 5 as well as the configuration(s) of such electrodes) and the positioning or location of the control devices 20 (and corresponding electrodes 1 and/or 5) are a function of various preferred embodiments of the invention some of which are discussed in greater detail in the "Examples" section herein. However, in general, an input liquid 3 (for example water) is provided to a liquid transport means 40 (e.g., a liquid peristaltic pump or a liquid pumping means for pumping liquid 3) for pumping the liquid water 3 into the trough member 30 at a first-end 31 thereof. For example, the input liquid 3 (e.g., water) could be introduced calmly or could be introduced in an agitated manner. Agitation includes, typically, the introduction of nanobubbles or microbubbles, which may or may not be desirable. If a gentle introduction is desired, then such input liquid 3 (e.g., water) could be gently provided (e.g., flow into a bottom portion of the trough). Alternatively, a reservoir (not shown) could be provided above the trough member 30 and liquid 3 could be pumped into such reservoir. The reservoir could then be drained from a lower portion thereof, a middle portion thereof or an upper portion thereof as fluid levels provided thereto reached an appropriate level. The precise means for delivering an input liquid 3 into the trough member 30 at a first end 31 thereof is a function of a variety of design choices. Further, as mentioned above herein, it should be understood that additional input portions 31 could exist longitudinally along different portions of the trough member 30. The distance "c-c" is also shown in FIG. 14. In general, the distance "c-c" (which corresponds to center-to-center longitudinal measurement between each control device 20) can be any amount or distance which permits desired functioning of the embodiments disclosed herein. The distance "c-c" should not be less than the distance "y" (e.g., ¼"-2"; 6 mm-51 mm) and in a preferred embodiment about 1.5" (about 38 mm) shown in, for example, FIGS. 1-4 and 7-9. The Examples show various distances "c-c", however, to give a general understanding of the distance "c-c", approximate distances vary from about 4" to about 8" (about 102 mm to about 203 mm) apart, however, more or less separation is of course possible (or required) as a function of application of all of the previous embodiments disclosed herein. In the Examples disclosed later herein, preferred distances "c-c" in many of the Examples are about 7"-8" (about 177-203 mm)

In general, the liquid transport means 40 may include any means for moving liquids 3 including, but not limited to a gravity-fed or hydrostatic means, a pumping means, a peristaltic pumping means, a regulating or valve means, etc. However, the liquid transport means 40 should be capable of reliably and/or controllably introducing known amounts of the liquid 3 into the trough member 30. Once the liquid 3 is provided into the trough member 30, means for continually moving the liquid 3 within the trough member 30 may or may not be required. However, a simple means includes the trough member 30 being situated on a slight angle θ (e.g., less than one degree to a few degrees) relative to the support surface upon which the trough member 30 is located. For example, the difference in vertical height between an inlet portion 31 and an outlet portion 32 relative to the support surface may be all that is required, so long as the viscosity of the liquid 3 is not too high (e.g., any viscosity around the viscosity of water can be controlled by gravity flow once such fluids are contained or located within the trough member 30). In this regard, FIG. 15a shows cross-sectional views of the trough member 30 forming an angle $\theta_1$; and FIG. 15b shows a cross-sectional view of the trough member 30 forming an angle θ₂; and a variety of acceptable angles for trough member 30 that handle various viscosities, including low viscosity fluids such as water. The angles that are desirable for different cross-sections of the trough member 30 and low viscosity fluids typically range between a minimum of about 0.1-5 degrees for low viscosity fluids and a maximum of 5-10 degrees for higher viscosity fluids. However, such angles are a function of a variety of factors already mentioned, as well as, for example, whether a specific fluid interruption means or a dam 80 is included along a bottom portion or interface where the liquid 3 contacts the trough member 30. Such flow interruption means could include, for example, partial mechanical dams or barriers along the longitudinal flow direction of the trough member 30. In this regard, θ₁ is approximately 5-10° and θ₂ is approximately 0.1-5°. FIGS. 15a and 15b show a dam 80 near an outlet portion 32 of the trough member 30. Multiple dam 80 devices can be located at various portions along the longitudinal length of the trough member 30. The dimension "j" can be, for example, about ⅛"-½" (about 3-13 mm) and the dimension "k" can be, for example, about ¼-¾" (about 6-19 mm) The cross-sectional shape (i.e., "j-k" shape) of the dam 80 can include sharp corners, rounded corners, triangular shapes, cylindrical shapes, and the like, all of which can influence liquid 3 flowing through various portions of the trough member 30.

Further, when viscosities of the liquid 3 increase such that gravity alone is insufficient, other phenomena such as specific uses of hydrostatic head pressure or hydrostatic pressure can also be utilized to achieve desirable fluid flow. Further, additional means for moving the liquid 3 along the trough member 30 could also be provided inside the trough member 30, Such means for moving the liquid 3 include mechanical means such as paddles, fans, propellers, augers, etc., acoustic means such as transducers, thermal means such as heaters (which may have additional processing benefits), etc. The additional means for moving the liquid 3 can cause liquid 3 to flow in differing amounts in different portions along the longitudinal length of the trough member 30. In this regard, for example, if liquid 3 initially flowed slowly through a first longitudinal portion of the trough member 30, the liquid 3 could be made to flow more quickly further downstream thereof by, for example, as discussed earlier herein, changing the cross-sectional shape of the trough member 30. Additionally, cross-sectional shapes of the trough member 30 could also contain therein additional fluid handling means which could speed up or slow down the rate the liquid 3 flows through the trough member 30. Accordingly, great flexibility can be achieved by the addition of such means for moving the fluid 3.

FIG. 14 also shows a storage tank or storage vessel 41 at the end 32 of the trough member 30. Such storage vessel 41 can be any acceptable vessel and/or pumping means made of one or more materials which, for example, do not negatively interact with the liquid 3 introduced into the trough member 30 and/or products produced within the trough member 30. Acceptable materials include, but are not limited to plastics such as high density polyethylene (HDPE), glass, metal(s) (such a certain grades of stainless steel), etc. Moreover, while a storage tank 41 is shown in this embodiment, the tank 41 should be understood as including a means for distributing or directly bottling or packaging the liquid 3 processed in the trough member 30.

FIGS. 16a, 16b and 16c show perspective views of one preferred embodiment of the invention. In these FIGS. 16a, 16b and 16c, eight separate control devices 20a-20h are shown in more detail. Such control devices 20 can utilize one or more of the electrode configurations shown in, for example, FIGS. 8a, 8b, 8c and 8d. The precise positioning and operation of the control devices 20 are discussed in greater detail elsewhere herein. However, each of the control devices 20 are separated by a distance "c-c" (see FIG. 14) which, in some of the preferred embodiments discussed herein, measures about 8" (about 203 mm) FIG. 16b includes use of two air distributing or air handling devices (e.g., fans 342a and 342b); and FIG. 16c includes use of two alternative or desirable air handling devices 342c and 342d. The fans 342a, 342b, 342c and/or 342d can be any suitable fan. For example a Dynatron DF124020BA, DC brushless, 9000 RPM, ball bearing fan measuring about 40 mm×40 mm×20 mm works well. Specifically, this fan has an air flow of approximately 10 cubic feet per minute.

FIG. 17 shows another perspective view of another embodiment of the apparatus according to another preferred embodiment wherein six control devices 20a-20f (i.e., six electrode sets) are rotated approximately 90 degrees relative to the eight control devices 20a-20h shown in FIGS. 16a and 16b. Accordingly, the embodiment corresponds generally to the electrode assembly embodiments shown in, for example, FIGS. 9a-9d.

FIG. 18 shows a perspective view of the apparatus shown in FIG. 16a, but such apparatus is now shown as being substantially completely enclosed by an atmosphere control apparatus 38. Such apparatus 38 is a means for controlling the atmosphere around the trough member 30, or can be used to isolate external and undesirable material from entering into the trough member 30 and negatively interacting therewith. Further, the exit 32 of the trough member 30 is shown as communicating with a storage vessel 41 through an exit pipe 42. Moreover, an exit 43 on the storage tank 41 is also shown. Such exit pipe 43 can be directed toward any other suitable means for storage, packing and/or handling the liquid 3. For example, the exit pipe 43 could communicate with any suitable means for bottling or packaging the liquid product 3 produced in the trough member 30. Alternatively, the storage tank 41 could be removed and the exit pipe 42 could be connected directly to a suitable means for handling, bottling or packaging the liquid product 3.

FIGS. 19a, 19b, 19c and 19d show additional cross-sectional perspective views of additional electrode configuration embodiments which can be used according to the present invention.

In particular, FIG. 19a shows two sets of electrodes 5 (i.e., 4 total electrodes 5a, 5b, 5c and 5d) located approximately parallel to each other along a longitudinal direction of the trough member 30 and substantially perpendicular to the flow direction "F" of the liquid 3 through the trough member 30. In contrast, FIG. 19b shows two sets of electrodes 5 (i.e., 5a, 5b, 5c and 5d) located adjacent to each other along the longitudinal direction of the trough member 30.

In contrast, FIG. 19c shows one set of electrodes 5 (i.e., 5a, 5b) located substantially perpendicular to the direction of fluid flow "F" and another set of electrodes 5 (i.e., 5c, 5d) located substantially parallel to the direction of the fluid flow "F". FIG. 19d shows a mirror image of the electrode configuration shown in FIG. 19c. While each of FIGS. 19a, 19b, 19c and 19d show only electrode(s) 5 it is clear that electrode(s) 1 could be substituted for some or all of those electrode(s) 5 shown in each of FIGS. 19a-19d, and/or intermixed therein (e.g., similar to the electrode configurations disclosed in FIGS. 8a-8d and 9a-9d). These alternative electrode configurations provide a variety of alternative electrode configuration possibilities all of which can result in different desirable nanoparticle or nanoparticle/solutions. It should now be clear to the reader that electrode assemblies located upstream of other electrode assemblies can provide raw materials, pH changes, ingredients and/or conditioning or crystal or structural changes to at least a portion of the liquid 3 such that reactions occurring at electrode(s) 1 and/or 5 downstream from a first set of electrode(s) 1 and/or 5 can result in, for example, growth of nanoparticles, shrinking (e.g., partial or complete dissolution) of nanoparticles, placing of different composition(s) on existing nanoparticles (e.g., surface feature comprising a variety of sizes and/or shapes and/or compositions which modify the performance of the nanoparticles), removing existing surface features or coatings on nanoparticles, etc. In other words, by providing multiple electrode sets of multiple configurations and one or more atmosphere control devices along with multiple adjustable electrochemical reactions and/or adjustable plasmas 4, the variety of constituents produced, nanoparticles, composite nanoparticles, thicknesses of shell layers (e.g., partial or complete) coatings or surface features on substrate nanoparticles, are numerous, and the structure and/or composition of the liquid 3 can also be reliably controlled.

FIGS. 20a-20p show a variety of cross-sectional perspective views of the various electrode configuration embodiments possible and usable for all those configurations of electrodes 1 and 5 corresponding only to the embodiment shown in FIG. 19a. In particular, for example, the number of electrodes 1 or 5 varies in these FIGS. 20a-20p, as well as the specific locations of such electrode(s) 1 and 5 relative to each other. Of course, these electrode combinations 1 and 5 shown in FIGS. 20a-20p could also be configured according to each of the alternative electrode configurations shown in FIGS. 19b, 19c and 19d (i.e., sixteen additional figures corresponding to each of FIGS. 19b, 19c and 19d) but additional figures have not been included herein for the sake of brevity. Specific advantages of these electrode assemblies, and others, are disclosed in greater detail elsewhere herein.

As disclosed herein, each of the electrode configurations shown in FIGS. 20a-20p, depending on the particular run conditions, can result in different products coming from the mechanisms, apparatuses and processes of the inventive disclosures herein.

FIGS. 21a, 21b, 21c and 21d show cross sectional perspective views of additional embodiments of the present invention. The electrode arrangements shown in these FIGS. 21a-21d are similar in arrangement to those electrode arrangements shown in FIGS. 19a, 19b, 19c and 19d, respectively. However, in these FIGS. 21a-21d a membrane or barrier assembly 50 is also included. In these embodiments of the invention, a membrane 50 is provided as a means for separating different products made at different electrode sets so that any products made by the set of electrodes 1 and/or 5 on one side of the membrane 50 can be at least partially isolated, or segregated, or substantially completely isolated from certain products made from electrodes 1 and/or 5 on the other side of the membrane 50. This membrane means 50 for separating or isolating different products may act as a mechanical barrier, physical barrier, mechano-physical barrier, chemical barrier, electrical barrier, etc. Accordingly, certain products made from a first set of electrodes 1 and/or 5 can be at least partially, or substantially completely, isolated from certain products made from a second set of electrodes 1 and/or 5. Likewise, additional serially located electrode sets can also be similarly situated. In other words, different membrane(s) 50 can be utilized at or near each set of electrodes 1 and/or 5 and certain products produced therefrom can be controlled and selectively delivered to additional electrode sets 1 and/or 5 longitudinally downstream therefrom. Such membranes 50 can result in a variety of different compositions of the liquid 3 and/or nanoparticles or ions present in the liquid 3 produced in the trough member 30.

Possible ion exchange membranes 50 which function as a means for separating for use with the present invention include Anionic membranes and Cationic membranes. These membranes can be homogenous, heterogeneous or microporous, symmetric or asymmetric in structure, solid or liquid, can carry a positive or negative charge or be neutral or bipolar. Membrane thickness may vary from as small as 100 micron to several mm.

Some specific ionic membranes for use with certain embodiments of the present invention include, but are not limited to:
Homogeneous polymerization type membranes such as sulfonated and aminated styrene-divinylbenzene copolymers
condensation and heterogeneous membranes
perfluorocarbon cation exchange membranes
membrane chlor-alkali technology
Most of cation and anion exchange membranes used in the industrial area are composed of derivatives of styrene-divinylbenzene copolymer, chloromethylstyrene-divinylbenzene copolymer or vinylpyridines-divinylbenzene copolymer.
The films used that are the basis of the membrane are generally polyethylene, polypropylene (ref. 'U, polytetrafluoroethylene, PFA, FEP and so on.
Trifluoroacrylate and styrene are used in some cases.
Conventional polymers such as polyethersulfone, polyphenylene oxide, polyvinyl chloride, polyvinylidene fluoride and so on. Especially, sulfonation or chloromethylation and amination of polyethersulfone or polyphenylene oxide.
Hydrocarbon ion exchange membranes are generally composed of derivatives of styrene-divinylbenzene copolymer and other inert polymers such as polyethylene, polyvinyl chloride and so on.

FIG. 22a shows a perspective cross-sectional view of an electrode assembly which corresponds to the electrode assembly 5a, 5b shown in FIG. 9c. This electrode assembly can also utilize a membrane 50 for chemical, physical, chemo-physical and/or mechanical separation. In this regard, FIG. 22b shows a membrane 50 located between the electrodes 5a, 5b. It should be understood that the electrodes 5a, 5b could be interchanged with the electrodes 1 in any of the multiple configurations shown, for example, in FIGS. 9a-9c. In the case of FIG. 22b, the membrane assembly 50 has the capability of isolating partially or substantially completely, some or all of the products formed at electrode 5a, from some or all of those products formed at electrode 5b. Accordingly, various species formed at either of the electrodes 5a and 5b can be controlled so that they can sequentially react with additional electrode assembly sets 5a, 5b and/or combinations of electrode sets 5 and electrode sets 1 in the longitudinal flow direction "F" that the liquid 3 undertakes along the longitudinal length of the trough member 30. Accordingly, by appropriate selection of the membrane 50, which products located at which electrode (or subsequent or downstream electrode set) can be controlled. In a preferred embodiment where the polarity of the electrodes 5a and 5b are opposite, a variety of different products may be formed at the electrode 5a relative to the electrode 5b.

FIG. 22c shows another different embodiment of the invention in a cross-sectional schematic view of a completely different alternative electrode configuration for electrodes 5a and 5b. In this case, electrode(s) 5a (or of course electrode(s) 1a) are located above a membrane 50 and electrode(s) 5b are located below a membrane 50 (e.g., are substantially completely submerged in the liquid 3). In this regard, the electrode, 5b can comprise a plurality of electrodes or may be a single electrode running along at least some or the entire longitudinal length of the trough member 30. In this embodiment, certain species created at electrodes above the membrane 50 can be different from certain species created below the membrane 50 and such species can react differently along the longitudinal length of the trough member 30. In this regard, the membrane 50 need not run the entire length of the trough member 30, but may be present for only a portion of such length and thereafter sequential assemblies of electrodes 1 and/or 5 can react with the products produced therefrom. It should be clear to the reader that a variety of additional embodiments beyond those expressly mentioned here would fall within the spirit of the embodiments expressly disclosed.

FIG. 22d shows another alternative embodiment of the invention whereby a configuration of electrodes 5a (and of course electrodes 1) shown in FIG. 22c are located above a portion of a membrane 50 which extends at least a portion along the length of a trough member 30 and a second electrode (or plurality of electrodes) 5b (similar to electrode(s) 5b in FIG. 22c) run for at least a portion of the longitudinal length along the bottom of the trough member 30. In this embodiment of utilizing multiple electrodes 5a, additional operational flexibility can be achieved. For example, by splitting the voltage and current into at least two electrodes 5a, the reactions at the multiple electrodes 5a can be different from those reactions which occur at a single electrode 5a of similar size, shape and/or composition. Of course this multiple electrode configuration can be utilized in many of the embodiments disclosed herein, but have not been expressly discussed for the sake of brevity. However, in general, multiple electrodes 1 and/or 5 (i.e., instead of a single electrode 1 and/or 5) can add great flexibility in products produced according to the present invention. Details of certain of these advantages are discussed elsewhere herein.

FIG. 23a is a cross-sectional perspective view of another embodiment of the invention which shows a set of electrodes 5 corresponding generally to that set of electrodes 5 shown in FIG. 19a, however, the difference between the embodiment of FIG. 23a is that a third set of electrode(s) 5e, 5f have been provided in addition to those two sets of electrodes 5a, 5b, 5c and 5d shown in FIG. 19a. Of course, the sets of electrodes 5a, 5b, 5c, 5d, 5d and 5f can also be rotated 90 degrees so they would correspond roughly to those two sets of electrodes shown in FIG. 19b. Additional figures showing additional embodiments of those sets of electrode configurations have not been included here for the sake of brevity.

FIG. 23b shows another embodiment of the invention which also permutates into many additional embodiments, wherein membrane assemblies 50a and 50b have been inserted between the three sets of electrodes 5a, 5b; 5c, 5d; and 5e, 5f. It is of course apparent that the combination of electrode configuration(s), number of electrode(s) and precise membrane(s) means 50 used to achieve separation includes many embodiments, each of which can produce different products when subjected to the teachings of the present invention. More detailed discussion of such products and operations of the present invention are discussed elsewhere herein.

FIGS. 24a-24e; 25a-25e; and 26a-26e show cross-sectional views of a variety of membrane 50 locations that can be utilized according to the present invention. Each of these membrane 50 configurations can result in different nanoparticles and/or nanoparticle/solution mixtures. The desirability of utilizing particular membranes in combination with various electrode assemblies add a variety of processing advantages to the present invention. This additional flexibility results in a variety of novel nanoparticle/nanoparticle solution mixtures.

Electrode Control Devices

The electrode control devices shown generally in, for example, FIGS. 2, 3, 11, 12, 14, 16, 17 and 18 are shown in greater detail in FIG. 27 and FIGS. 28a-28l. In particular, FIG. 27 shows a perspective view of one embodiment of an inventive control device 20. Further, FIGS. 28a-28l show perspective views of a variety of embodiments of control devices 20.

FIG. 28b shows the same control device 20 shown in FIGS. 28a, except that two electrode(s) 1a/1b are substituted for the two electrode(s) 5a/5b.

First, specific reference is made to FIGS. 27, 28a and 28b. In each of these three Figures, a base portion 25 is provided, said base portion having a top portion 25' and a bottom portion 25". The base portion 25 is made of a suitable rigid plastic material including, but not limited to, materials made from structural plastics, resins, polyurethane, polypropylene, nylon, teflon, polyvinyl, etc. A dividing wall 27 is provided between two electrode adjustment assemblies. The dividing wall 27 can be made of similar or different material from that material comprising the base portion 25. Two servo-step motors 21a and 21b are fixed to the surface 25' of the base portion 25. The step motors 21a, 21b could be any step motor capable of slightly moving (e.g., on a 360 degree basis, slightly less than or slightly more than 1 degree) such that a circumferential movement of the step motors 21a/21b results in a vertical raising or lowering of an electrode 1 or 5 communicating therewith. In this regard, a first wheel-shaped component 23a is the drivewheel connected to the output shaft 231a of the drive motor 21a such that when the drive shaft 231a rotates, circumferential movement of the wheel 23a is created. Further, a slave wheel 24a is caused to press against and toward the drivewheel 23a such that frictional contact exists therebetween. The drivewheel 23a and/or slavewheel 24a may include a notch or groove on an outer portion thereof to assist in accommodating the electrodes 1,5. The slavewheel 24a is caused to be pressed toward the drivewheel 23a by a spring 285 located between the portions 241a and 261a attached to the slave wheel 24a. In particular, a coiled spring 285 can be located around the portion of the axis 262a that extends out from the block 261a. Springs should be of sufficient tension so as to result in a reasonable frictional force between the drivewheel 24a and the slavewheel 24a such that when the shaft 231a rotates a determined amount, the electrode assemblies 5a, 5b, 1a, 1b, etc., will move in a vertical direction relative to the base portion 25. Such rotational or circumferential movement of the drivewheel 23a results in a direct transfer of vertical directional changes in the electrodes 1,5 shown herein. At least a portion of the drivewheel 23a should be made from an electrically insulating material; whereas the slavewheel 24a can be made from an electrically conductive material or an electrically insulating material, but preferably, an electrically insulating material.

The drive motors 21a/21b can be any suitable drive motor which is capable of small rotations (e.g., slightly below 1°/360° or slightly above 1°/360°) such that small rotational changes in the drive shaft 231a are translated into small vertical changes in the electrode assemblies. A preferred drive motor includes a drive motor manufactured by RMS Technologies model 1MC17-504 step motor, which is a DC-powered step motor. This step motors 21a/21b include an RS-232 connection 22a/22b, respectively, which permits the step motors to be driven by a remote control apparatus such as a computer or a controller.

With reference to FIGS. 27, 28a and 28b, the portions 271, 272 and 273 are primarily height adjustments which adjust the height of the base portion 25 relative to the trough member 30. The portions 271, 272 and 273 can be made of same, similar or different materials from the base portion 25. The portions 274a/274b and 275a/275b can also be made of the same, similar or different material from the base portion 25. However, these portions should be electrically insulating in that they house various wire components associated with delivering voltage and current to the electrode assemblies 1a/1b, 5a/5b, etc.

The electrode assembly specifically shown in FIG. 28a comprises electrodes 5a and 5b (corresponding to, for example, the electrode assembly shown in FIG. 3c). However, that electrode assembly could comprise electrode(s) 1 only, electrode(s) 1 and 5, electrode(s) 5 and 1, or electrode(s) 5 only. In this regard, FIG. 28b shows an assembly where two electrodes 1a/1b are provided instead of the two electrode(s) 5a/5b shown in FIG. 28a. All other elements shown in FIG. 28b are similar to those shown in FIG. 28a.

With regard to the size of the control device 20 shown in FIGS. 27, 28a and 28b, the dimensions "L" and "W" can be any dimension which accommodates the size of the step motors 21a/21b, and the width of the trough member 30. In this regard, the dimension "L" shown in FIG. 27 needs to be sufficient such that the dimension "L" is at least as long as the trough member 30 is wide, and preferably slightly longer (e.g., 10-30%). The dimension "W" shown in FIG. 27 needs to be wide enough to house the step motors 21a/21b and not be so wide as to unnecessarily underutilize longitudinal space along the length of the trough member 30. In one preferred embodiment of the invention, the dimension "L" is about 7 inches (about 19 millimeters) and the dimension "W" is about 4 inches (about 10.5 millimeters). The thickness "H" of the base member 25 is any thickness sufficient which provides structural, electrical and mechanical rigidity for the base member 25 and should be of the order of about ¼"-¾" (about 6 mm-19 mm) While these dimensions are not critical, the dimensions give an understanding of size generally of certain components of one preferred embodiment of the invention.

Further, in each of the embodiments of the invention shown in FIGS. 27, 28a and 28b, the base member 25 (and the components mounted thereto), can be covered by a suitable cover 290 (first shown in FIG. 28d) to insulate electrically, as well as creating a local protective environment for all of the components attached to the base member 25. Such cover 290 can be made of any suitable material which provides appropriate safety and operational flexibility. Exemplary materials include plastics similar to that used for other portions of the trough member 30 and/or the control device 20 and is preferably transparent.

FIG. 28c shows a perspective view of an electrode guide assembly 280 utilized to guide, for example, an electrode 5. Specifically, a top portion 281 is attached to the base member 25. A through-hole/slot combination 282a, 282b and 282c, all serve to guide an electrode 5 therethrough. Specifically, the portion 283 specifically directs the tip 9' of the electrode 5 toward and into the liquid 3 flowing in the trough member 30. The guide 280 shown in FIG. 28c can be made of materials similar, or exactly the same, as those materials used to make other portions of the trough member 30 and/or base member 25, etc.

Figure 28D:
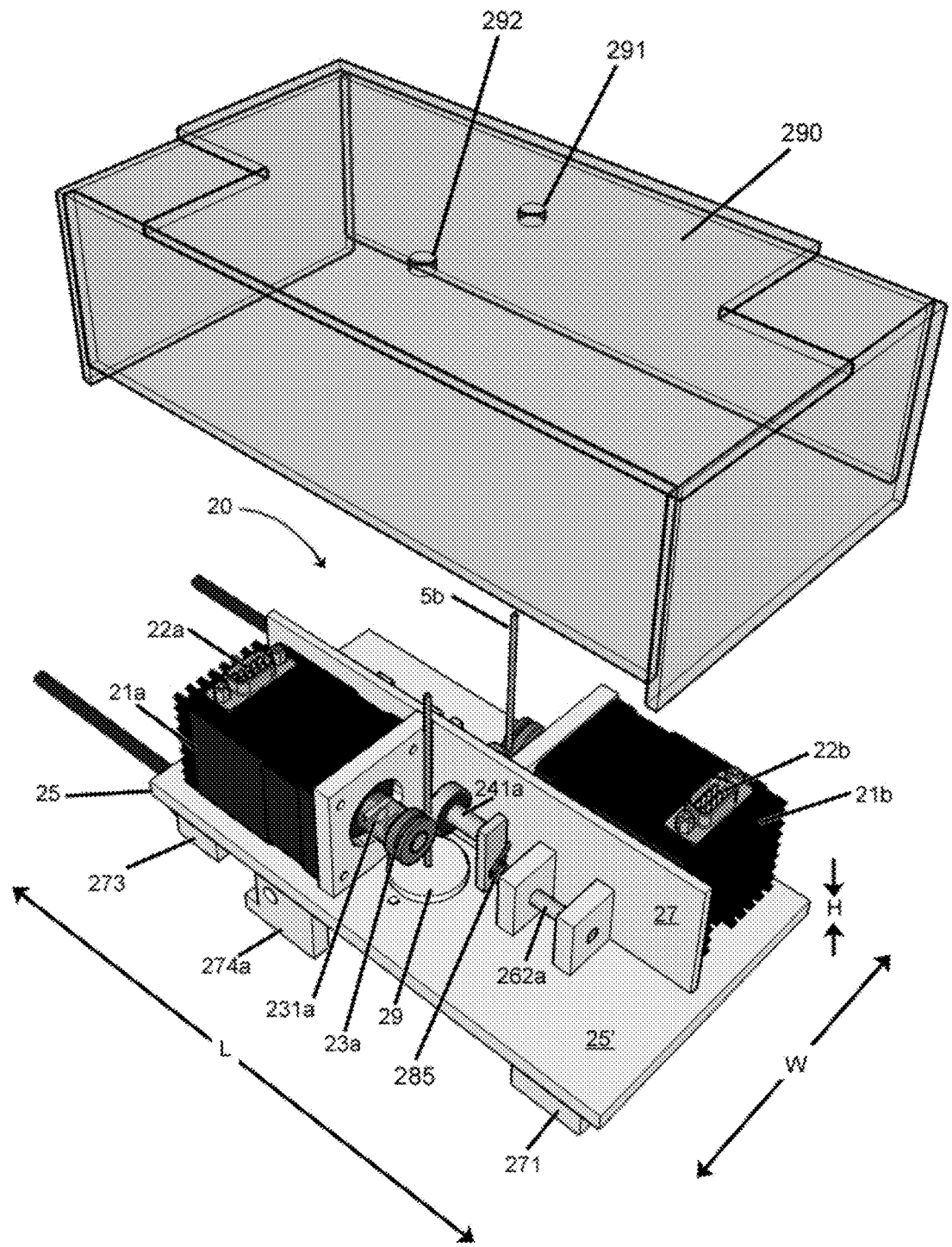

FIG. 28d shows a similar control device 20 as those shown in FIGS. 27 and 28, but also now includes a cover member 290. This cover member 290 can also be made of the same type of materials used to make the base portion 25. The cover 290 is also shown as having 2 through-holes 291 and 292 therein. Specifically, these through-holes can, for example, be aligned with excess portions of, for example, electrodes 5, which can be connected to, for example, a spool of electrode wire (not shown in these drawings).

Figure 28E:
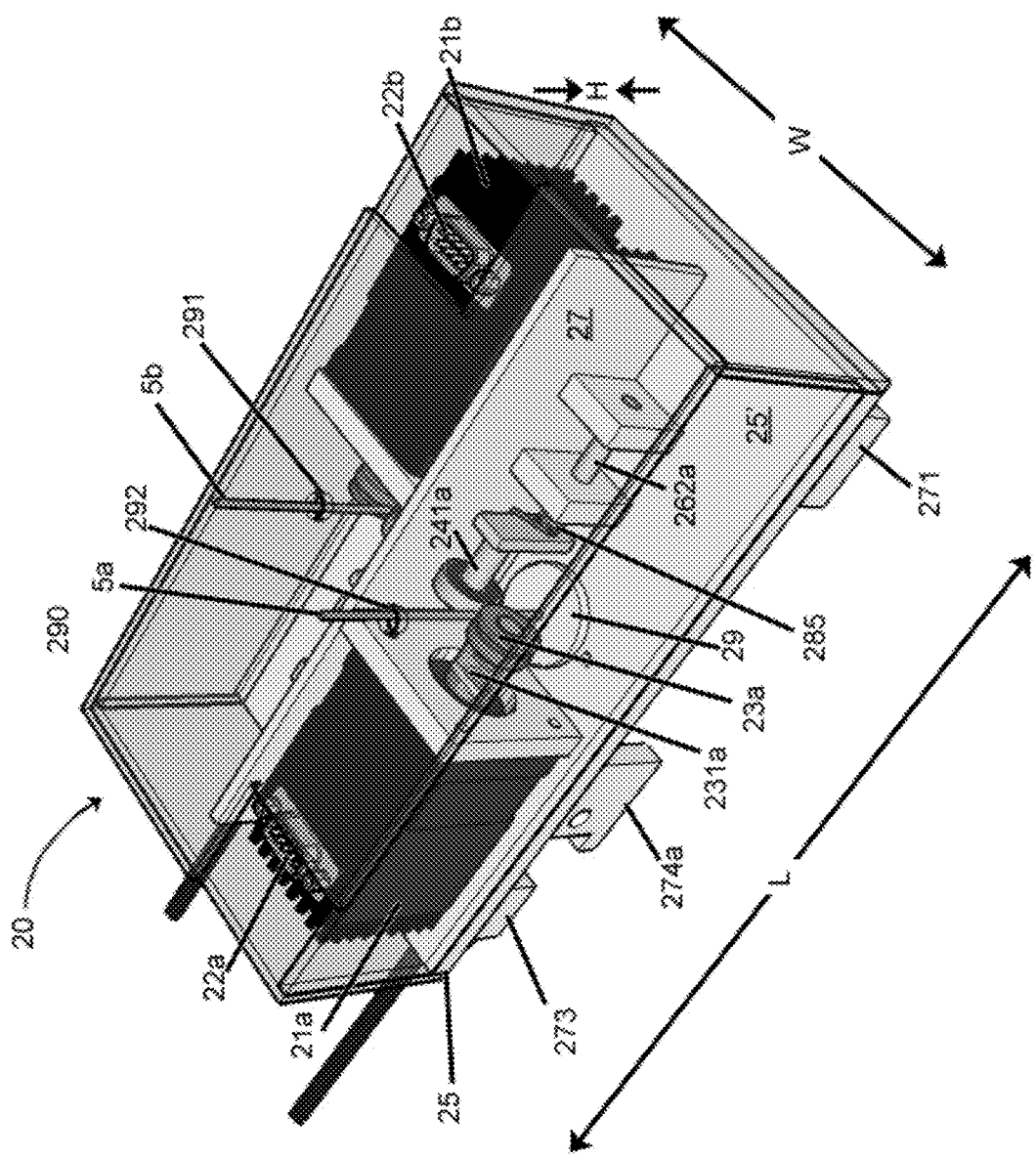

FIG. 28e shows the cover portion 290 attached to the base portion 25 with the electrodes 5a, 5b extending through the cover portion 290 through the holes 292, 291, respectively.

Figure 28F:
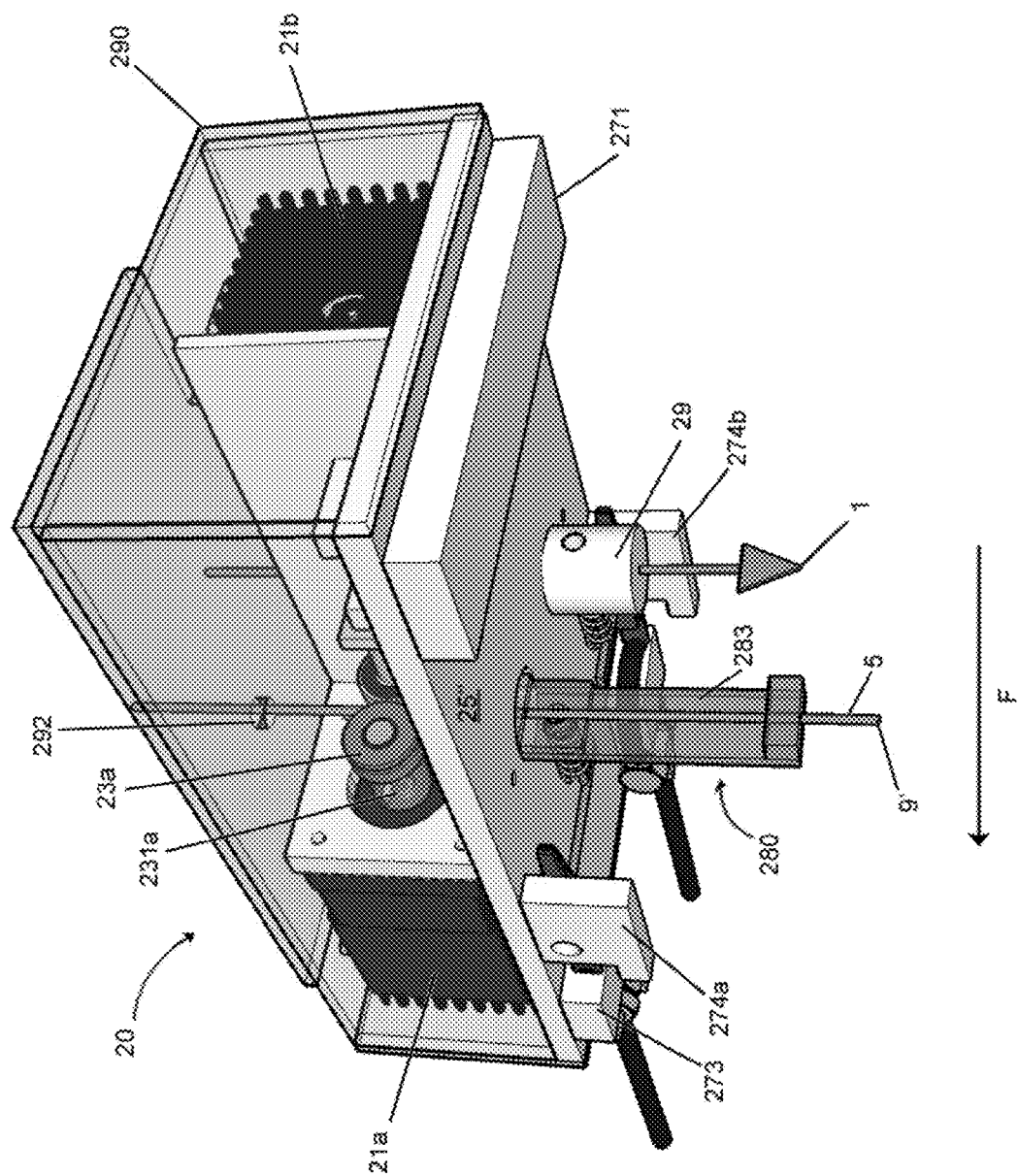

FIG. 28f shows a bottom-oriented perspective view of the control device 20 having a cover 290 thereon. Specifically, the electrode guide apparatus 280 is shown as having the electrode 5 extending therethrough. More specifically, this FIG. 28f shows an arrangement where an electrode 1 would first contact a fluid 3 flowing in the direction "F", as represented by the arrow in FIG. 28f.

Figure 28G:
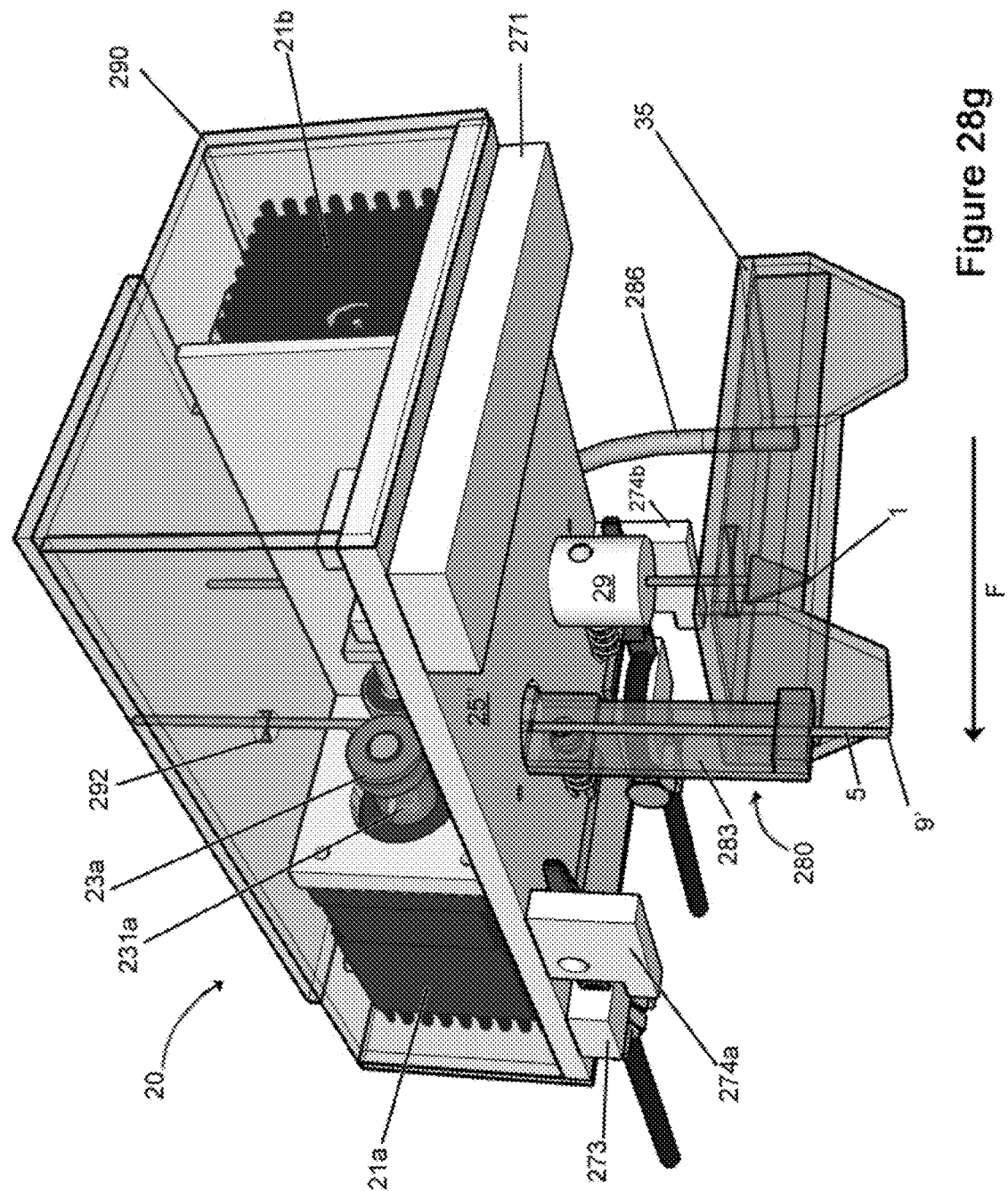

FIG. 28g shows the same apparatus as that shown in FIG. 28f with an atmosphere control device 35 added thereto. Specifically, the atmosphere control device is shown as providing a controlled atmosphere for the electrode 1. Additionally, a gas inlet tube 286 is provided. This gas inlet tube provides for flow of a desirable gas into the atmosphere control device 35 such that plasmas 4 created by the electrode 1 are created in a controlled atmosphere.

Figure 28H:
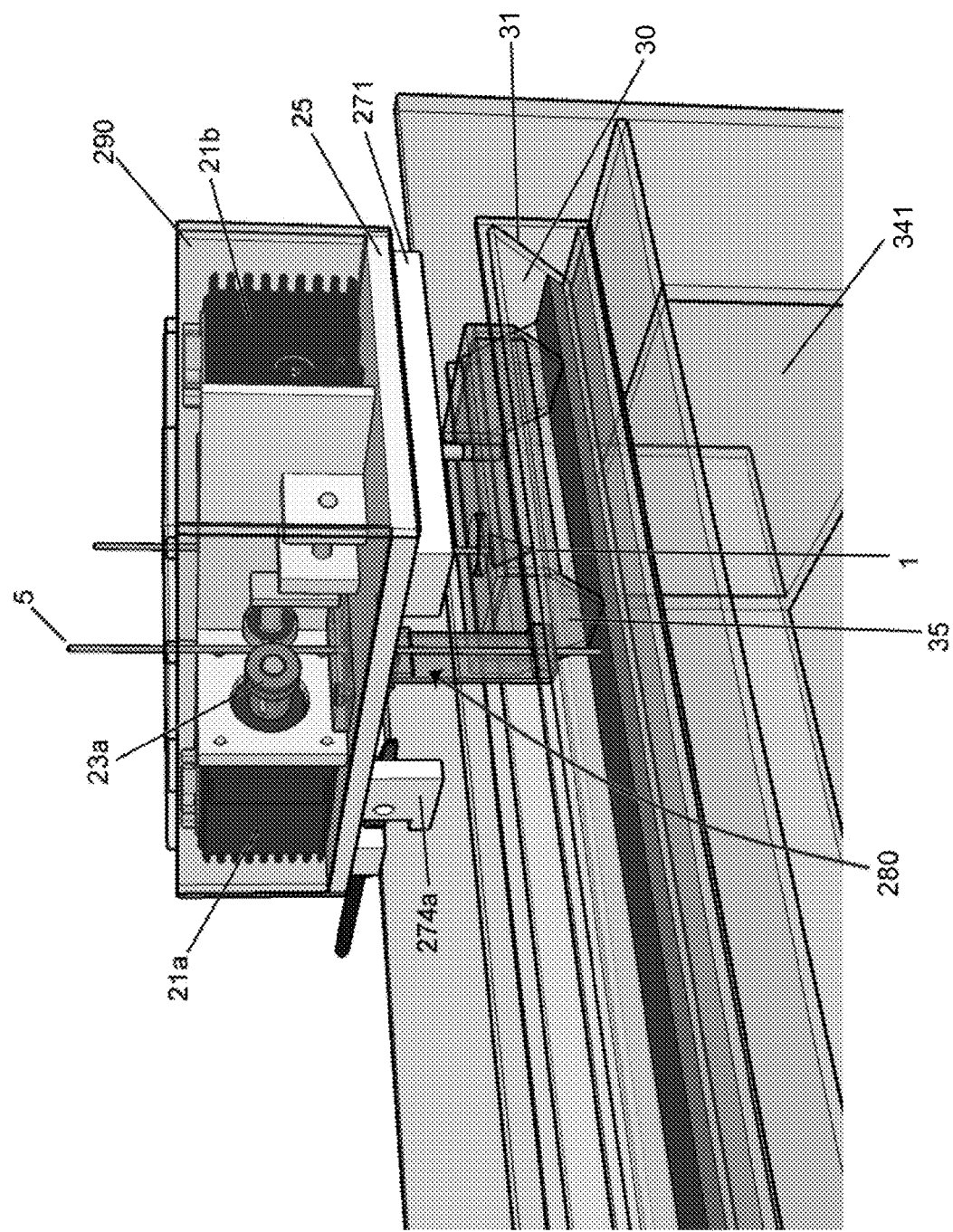

FIG. 28h shows the assembly of FIG. 28g located within a trough member 30 and a support means 341.

Figure 28I:
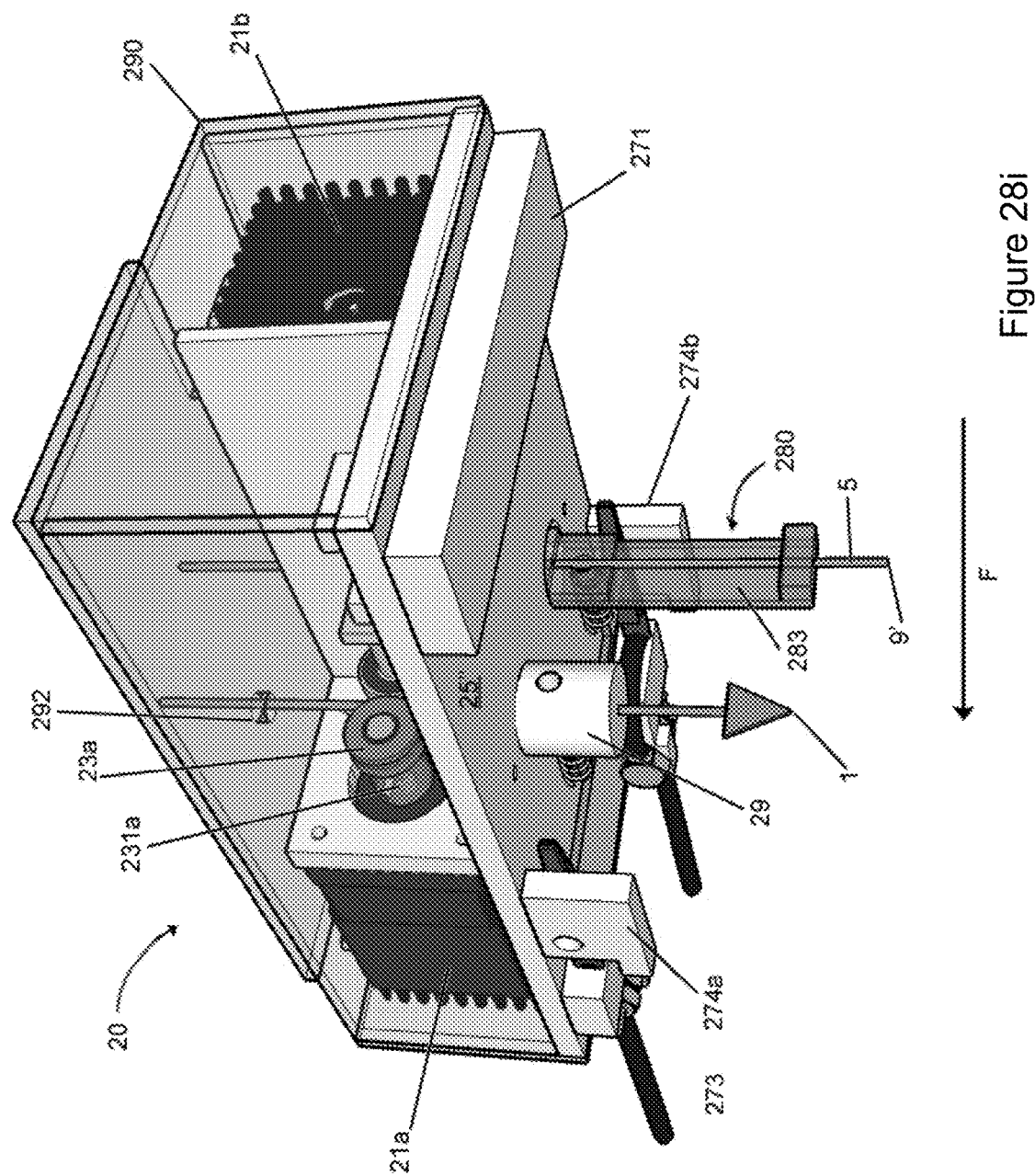

FIG. 28i is similar to FIG. 28f except now an electrode 5 is the first electrode that contacts a liquid 3 flowing in the direction of the arrow "F" within the trough member 30.

Figure 28J:
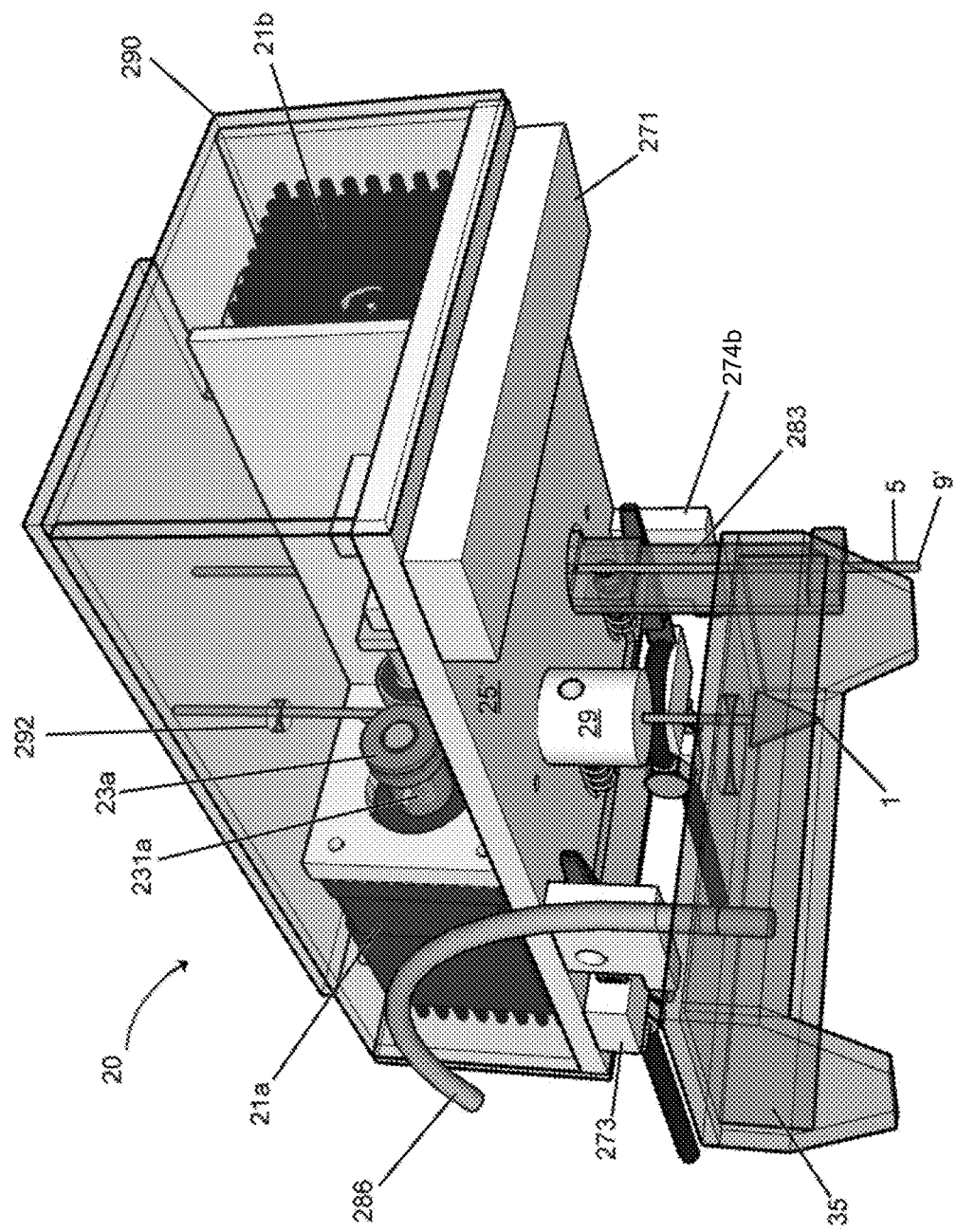

FIG. 28j corresponds to FIG. 28g except that the electrode 5 first contacts the flowing liquid 3 in the trough member 30.

Figure 28K:
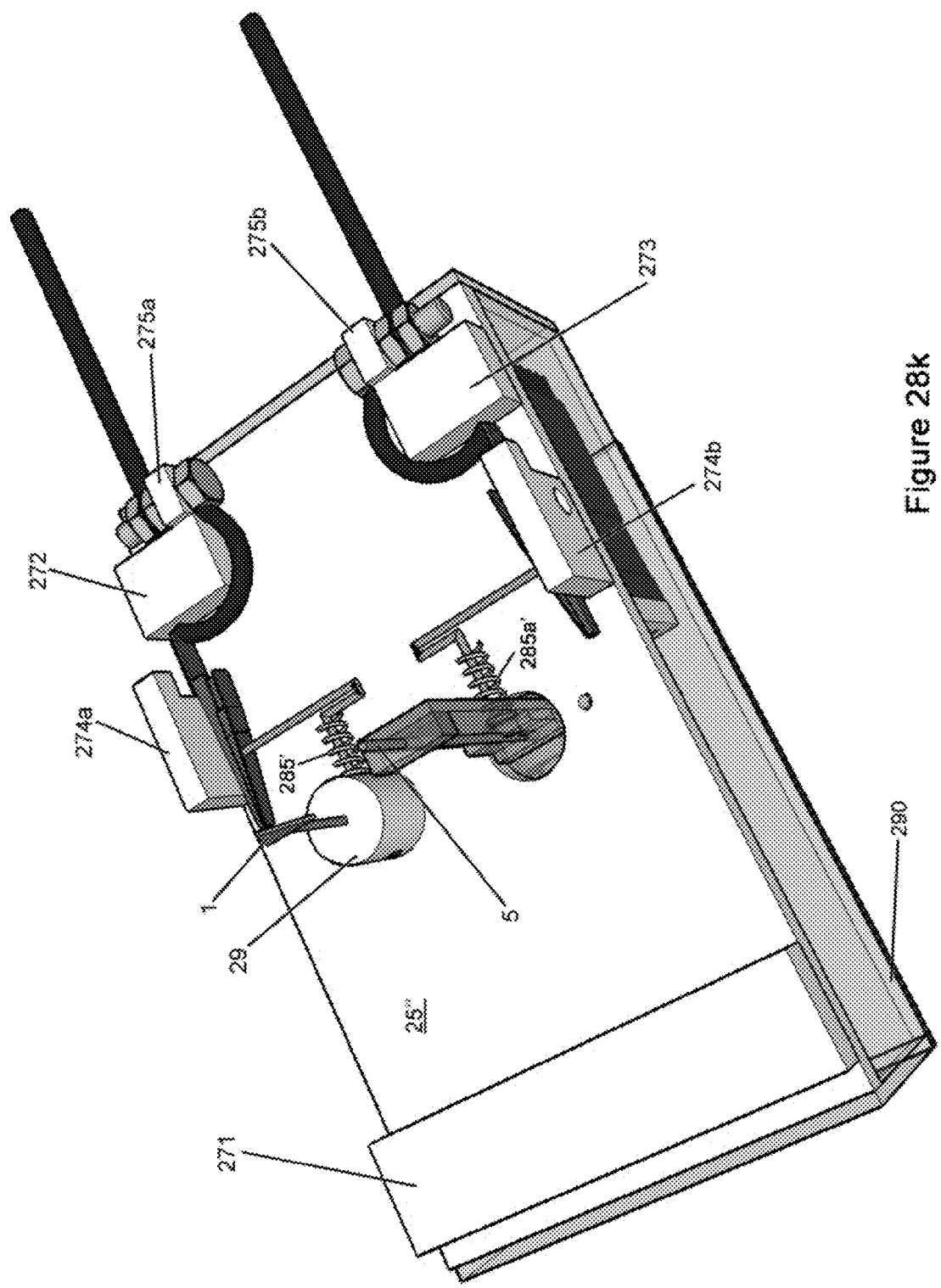

FIG. 28k shows a more detailed perspective view of the underside of the apparatus shown in the other FIG. 28's herein.

Figure 28L:
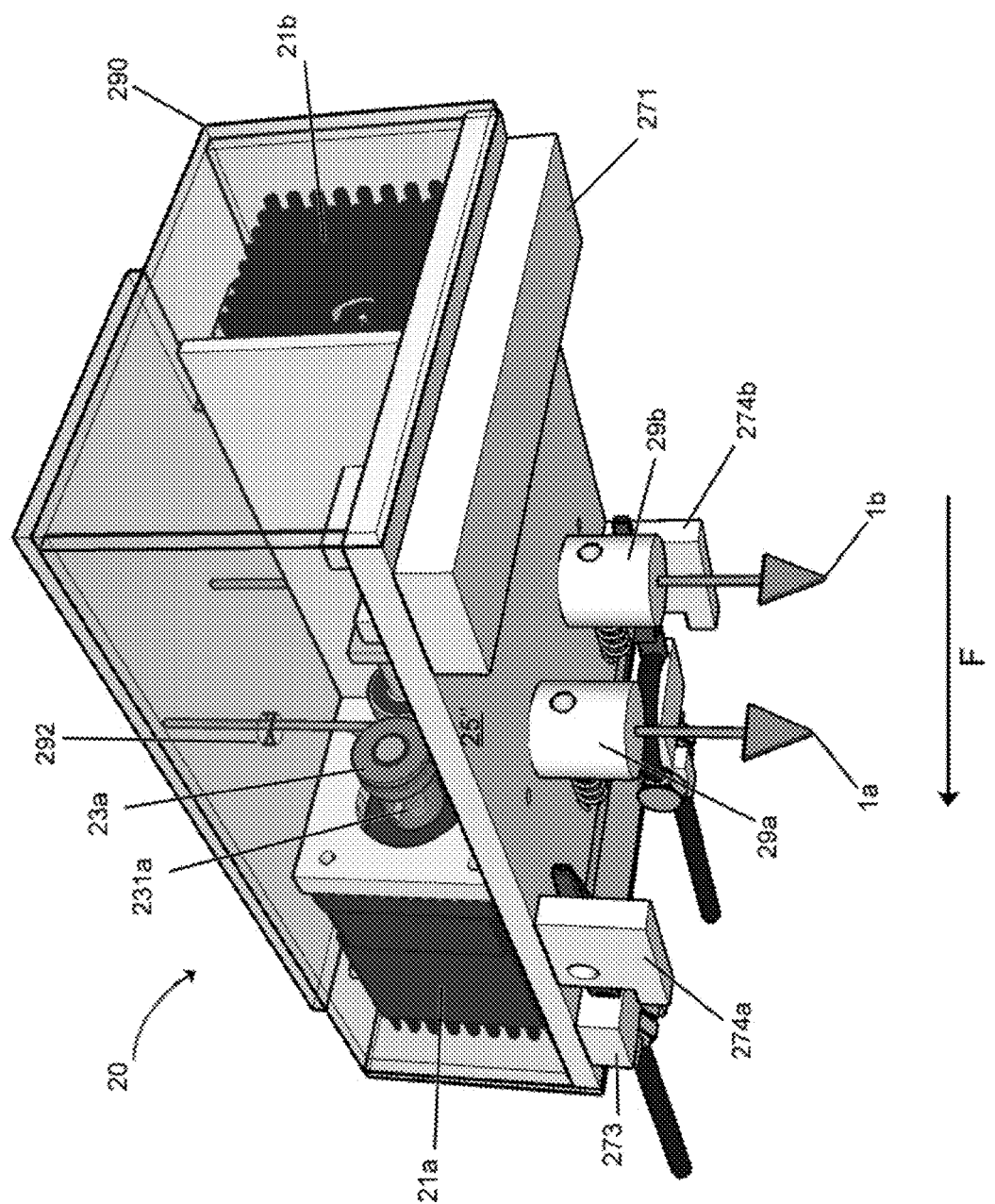

FIG. 28l shows the control device 20 similar to that shown in FIGS. 28f and 28i, except that two electrodes 1 are provided.

FIG. 29 shows another preferred embodiment of the invention wherein a refractory material 29 is combined with a heat sink 28 such that heat generated during processes practiced according to embodiments of the invention generate sufficient amounts of heat that necessitate a thermal management program. In this regard, the component 29 is made of, for example, suitable refractory component, including, for example, aluminum oxide or the like. The refractory component 29 has a transverse through-hole 291 therein which provides for electrical connections to the electrode(s) 1 and/or 5. Further a longitudinal through-hole 292 is present along the length of the refractory component 29 such that electrode assemblies 1/5 can extend therethrough. The heat sink 28 thermally communicates with the refractory member 29 such that any heat generated from the electrode assembly 1 and/or 5 is passed into the refractory member 29, into the heat sink 28 and out through the fins 282, as well as the base portion 281 of the heat sink 28. The precise number, size, shape and location of the fins 282 and base portion 281 are a function of, for example, the amount of heat required to be dissipated. Further, if significant amounts of heat are generated, a cooling means such as a fan can be caused to blow across the fins 282. The heat sink is preferably made from a thermally conductive metal such as copper, aluminum, etc.

FIG. 30 shows a perspective view of the heat sink of FIG. 29 as being added to the device shown in FIG. 27. In this regard, rather than the electrode 5a directly contacting the base portion 25, the refractory member 29 is provided as a buffer between the electrodes 1/5 and the base member 25.

A fan assembly, not shown in the drawings, can be attached to a surrounding housing which permits cooling air to blow across the cooling fins 282. The fan assembly could comprise a fan similar to a computer cooling fan, or the like. A preferred fan assembly comprises, for example, a Dynatron DF124020BA, DC brushless, 9000 RPM, ball bearing fan measuring about 40 mm×40 mm×20 mm works well. Specifically, this fan has an air flow of approximately 10 cubic feet per minute.

FIG. 31 shows a perspective view of the bottom portion of the control device 20 shown in FIG. 30a. In this FIG. 31, one electrode(s) 1a is shown as extending through a first refractory portion 29a and one electrode(s) 5a is shown as extending through a second refractory portion 29b. Accordingly, each of the electrode assemblies expressly disclosed herein, as well as those referred to herein, can be utilized in combination with the preferred embodiments of the control device shown in FIGS. 27-31. In order for the control devices 20 to be actuated, two general processes need to occur. A first process involves electrically activating the electrode(s) 1 and/or 5 (e.g., applying power thereto from a preferred power source 10), and the second general process occurrence involves determining how much power is applied to the electrode(s) and appropriately adjusting electrode 1/5 height in response to such determinations (e.g., manually and/or automatically adjusting the height of the electrodes 1/5). In the case of utilizing a control device 20, suitable instructions are communicated to the step motor 21 through the RS-232 ports 22a and 22b Important embodiments of components of the control device 20, as well as the electrode activation process, are discussed later herein.

Power Sources

A variety of power sources are suitable for use with the present invention. Power sources such as AC sources, DC sources, rectified AC sources of various polarities, etc., can be used. However, in the preferred embodiments disclosed herein, an AC power source is utilized directly, or an AC power source has been rectified to create a specific DC source of variable polarity.

FIG. 32a shows a source of AC power 62 connected to a transformer 60. In addition, a capacitor 61 is provided so that, for example, loss factors in the circuit can be adjusted. The output of the transformer 60 is connected to the electrode(s) 1/5 through the control device 20. A preferred transformer for use with the present invention is one that uses alternating current flowing in a primary coil 601 to establish an alternating magnetic flux in a core 602 that easily conducts the flux.

When a secondary coil 603 is positioned near the primary coil 601 and core 602, this flux will link the secondary coil 603 with the primary coil 601. This linking of the secondary coil 603 induces a voltage across the secondary terminals. The magnitude of the voltage at the secondary terminals is related directly to the ratio of the secondary coil turns to the primary coil turns. More turns on the secondary coil 603 than the primary coil 601 results in a step up in voltage, while fewer turns results in a step down in voltage.

Preferred transformer(s) 60 for use in various embodiments disclosed herein have deliberately poor output voltage regulation made possible by the use of magnetic shunts in the transformer 60. These transformers 60 are known as neon sign transformers. This configuration limits current flow into the electrode(s) 1/5. With a large change in output load voltage, the transformer 60 maintains output load current within a relatively narrow range.

The transformer 60 is rated for its secondary open circuit voltage and secondary short circuit current. Open circuit voltage (OCV) appears at the output terminals of the transformer 60 only when no electrical connection is present. Likewise, short circuit current is only drawn from the output terminals if a short is placed across those terminals (in which case the output voltage equals zero). However, when a load is connected across these same terminals, the output voltage of the transformer 60 should fall somewhere between zero and the rated OCV. In fact, if the transformer 60 is loaded properly, that voltage will be about half the rated OCV.

The transformer 60 is known as a Balanced Mid-Point Referenced Design (e.g., also formerly known as balanced midpoint grounded). This is most commonly found in mid to higher voltage rated transformers and most 60 mA transformers. This is the only type transformer acceptable in a "mid-point return wired" system. The "balanced" transformer 60 has one primary coil 601 with two secondary coils 603, one on each side of the primary coil 601 (as shown generally in the schematic view in FIG. 33a). This transformer 60 can in many ways perform like two transformers. Just as the unbalanced midpoint referenced core and coil, one end of each secondary coil 603 is attached to the core 602 and subsequently to the transformer enclosure and the other end of the each secondary coil 603 is attached to an output lead or terminal Thus, with no connector present, an unloaded 15,000 volt transformer of this type, will measure about 7,500 volts from each secondary terminal to the transformer enclosure but will measure about 15,000 volts between the two output terminals.

In alternating current (AC) circuits possessing a line power factor or 1 (or 100%), the voltage and current each start at zero, rise to a crest, fall to zero, go to a negative crest and back up to zero. This completes one cycle of a typical sinewave. This happens 60 times per second in a typical US application. Thus, such a voltage or current has a characteristic "frequency" of 60 cycles per second (or 60 Hertz) power. Power factor relates to the position of the voltage waveform relative to the current waveform. When both waveforms pass through zero together and their crests are together, they are in phase and the power factor is 1, or 100%. FIG. 33b shows two waveforms "V" (voltage) and "C" (current) that are in phase with each other and have a power factor of 1 or 100%; whereas FIG. 33c shows two waveforms "V" (voltage) and "C" (current) that are out of phase with each other and have a power factor of about 60%; both waveforms do not pass through zero at the same time, etc. The waveforms are out of phase and their power factor is less than 100%.

The normal power factor of most such transformers 60 is largely due to the effect of the magnetic shunts 604 and the secondary coil 603, which effectively add an inductor into the output of the transformer's 60 circuit to limit current to the electrodes 1/5. The power factor can be increased to a higher power factor by the use of capacitor(s) 61 placed across the primary coil 601 of the transformer, 60 which brings the input voltage and current waves more into phase.

The unloaded voltage of any transformer 60 to be used in the present invention is important, as well as the internal structure thereof. Desirable unloaded transformers for use in the present invention include those that are around 9,000 volts, 10,000 volts, 12,000 volts and 15,000 volts. However, these particular unloaded volt transformer measurements should not be viewed as limiting the scope acceptable power sources as additional embodiments. A specific desirable transformer for use with various embodiments of the invention disclosed herein is made by Franceformer, Catalog No. 9060-P-E which operates at: primarily 120 volts, 60 Hz; and secondary 9,000 volts, 60 mA.

FIGS. 32b and 32c show another embodiment of the invention, wherein the output of the transformer 60 that is input into the electrode assemblies 1/5 has been rectified by a diode assembly 63 or 63'. The result, in general, is that an AC wave becomes substantially similar to a DC wave. In other words, an almost flat line DC output results (actually a slight 120 Hz pulse can sometimes be obtained). This particular assembly results in two additional preferred embodiments of the invention (e.g., regarding electrode orientation). In this regard, a substantially positive terminal or output and substantially negative terminal or output is generated from the diode assembly 63. An opposite polarity is achieved by the diode assembly 63'. Such positive and negative outputs can be input into either of the electrode(s) 1 and/or 5. Accordingly, an electrode 1 can be substantially negative or substantially positive; and/or an electrode 5 can be substantially negative and/or substantially positive. Further, when utilizing the assembly of FIG. 32b, it has been found that the assemblies shown in FIGS. 29, 30 and 31 are desirable. In this regard, the wiring diagram shown in FIG. 32b can generate more heat (thermal output) than that shown in, for example, FIG. 32a under a given set of operating (e.g., power) conditions. Further, one or more rectified AC power source(s) can be particularly useful in combination with the membrane assemblies shown in, for example, FIGS. 21-26.

FIG. 34a shows 8 separate transformer assemblies 60a-60h each of which is connected to a corresponding control device 20a-20h, respectively. This set of transformers 60 and control devices 20 is utilized in one preferred embodiment discussed in the Examples section later herein.

FIG. 34b shows 8 separate transformers 60a'-60h', each of which corresponds to the rectified transformer diagram shown in FIG. 32b. This transformer assembly also communicates with a set of control devices 20a-20h and can be used as a preferred embodiment of the invention.

FIG. 34c shows 8 separate transformers 60a"-60h", each of which corresponds to the rectified transformer diagram shown in FIG. 32c. This transformer assembly also communicates with a set of control devices 20a-20h and can be used as a preferred embodiment of the invention.

Accordingly, each transformer assembly 60a-60h (and/or 60a'-60h'; and/or 60a"-60h") can be the same transformer, or can be a combination of different transformers (as well as different polarities). The choice of transformer, power factor, capacitor(s) 61, polarity, electrode designs, electrode location, electrode composition, cross-sectional shape(s) of the trough member 30, local or global electrode composition, atmosphere(s), local or global liquid 3 flow rate(s), liquid 3 local components, volume of liquid 3 locally subjected to various fields in the trough member 30, neighboring (e.g., both upstream and downstream) electrode sets, local field concentrations, the use and/or position and/or composition of any membrane 50, etc., are all factors which influence processing conditions as well as composition and/or volume of constituents produced in the liquid 3, nanoparticles and nanoparticle/solutions made according to the various embodiments disclosed herein. Accordingly, a plethora of embodiments can be practiced according to the detailed disclosure presented herein.

Electrode Height Control/Automatic Control Device

A preferred embodiment of the invention utilizes the automatic control devices 20 shown in various figures herein. The step motors 21a and 21b shown in, for example, FIGS. 27-31, are controlled by an electrical circuit diagrammed in each of FIGS. 35, 36a, 36b and 36c. In particular, the electrical circuit of FIG. 35 is a voltage monitoring circuit. Specifically, voltage output from each of the output legs of the secondary coil 603 in the transformer 60 are monitored over the points "P-Q" and the points "P'-Q'". Specifically, the resistor denoted by "$R_L$" corresponds to the internal resistance of the multi-meter measuring device (not shown). The output voltages measured between the points "P-Q" and "P'-Q'" typically, for several preferred embodiments shown in the Examples later herein, range between about 200 volts and about 4,500 volts. However, higher and lower voltages can work with many of the embodiments disclosed herein. In the Examples later herein, desirable target voltages have been determined for each electrode set 1 and/or 5 at each position along a trough member 30. Such desirable target voltages are achieved as actual applied voltages by, utilizing, for example, the circuit control shown in FIGS. 36a, 36b and 36c. These FIG. 36 refer to sets of relays controlled by a Velleman K8056 circuit assembly (having a micro-chip PIC16F630-I/P). In particular, a voltage is detected across either the "P-Q" or the "P'-Q'" locations and such voltage is compared to a predetermined reference voltage (actually compared to a target voltage range). If a measured voltage across, for example, the points "P-Q" is approaching a high-end of a predetermined voltage target range, then, for example, the Velleman K8056 circuit assembly causes a servo-motor 21 (with specific reference to FIG. 28a) to rotate in a clockwise direction so as to lower the electrode 5a toward and/or into the fluid 3. In contrast, should a measured voltage across either of the points "P-Q" or "P'-Q'" be approaching a lower end of a target voltage, then, for example, again with reference to FIG. 28a, the server motor 21a will cause the drive-wheel 23a to rotate in a counter-clockwise position thereby raising the electrode 5a relative to the fluid 3.

Each set of electrodes in each embodiment of the invention has an established target voltage range. The size or magnitude of acceptable range varies by an amount between about 1% and about 10%45% of the target voltage. Some embodiments of the invention are more sensitive to voltage changes and these embodiments should have, typically, smaller acceptable voltage ranges; whereas other embodiments of the invention are less sensitive to voltage and should have, typically, larger acceptable ranges. Accordingly, by utilizing the circuit diagram shown in FIG. 35, actual voltages output from the secondary coil 603 of the transformer 60 are measured at "$R_L$" (across the terminals "P-Q" and "P'-Q'"), and are then compared to the predetermined voltage ranges. The servo-motor 21 responds by rotating a predetermined amount in either a clockwise direction or a counter-clockwise direction, as needed. Moreover, with specific reference to FIG. 36, it should be noted that an interrogation procedure occurs sequentially by determining the voltage of each electrode, adjusting height (if needed) and then proceeding to the next electrode. In other words, each transformer 60 is connected electrically in a manner shown in FIG. 35. Each transformer 60 and associated measuring points "P-Q" and "P'-Q'" are connected to an individual relay. For example, the points "P-Q" correspond to relay number 501 in FIG. 36*a* and the points "P'-Q'" correspond to the relay 502 in FIG. 36*a*. Accordingly, two relays are required for each transformer 60. Each relay, 501, 502, etc., sequentially interrogates a first output voltage from a first leg of a secondary coil 603 and then a second output voltage from a second leg of the secondary coil 603; and such interrogation continues onto a first output voltage from a second transformer 60*b* on a first leg of its secondary coil 603, and then on to a second leg of the secondary coil 603, and so on.

The computer or logic control for the discussed interrogation voltage adjustment techniques are achieved by any conventional program or controller, including, for example, in a preferred embodiment, standard visual basic programming steps utilized in a PC. Such programming steps include interrogating, reading, comparing, and sending an appropriate actuation symbol to increase or decrease voltage (e.g., raise or lower an electrode relative to the surface 2 of the liquid 3). Such techniques should be understood by an artisan of ordinary skill.

Examples 1-12

The following examples serve to illustrate certain embodiments of the invention but should not to be construed as limiting the scope of the disclosure.

In general, each of the 12 Examples utilize certain embodiments of the invention associated with the apparatuses generally shown in FIGS. 16*b* and 16*c*. Specific differences in processing and apparatus will be apparent in each Example. The trough member 30 was made from plexiglass, all of which had a thickness of about 3 mm-4 mm (about ⅛"). The support structure 34 was also made from plexiglass which was about ¼" thick (about 6-7 mm thick). The cross-sectional shape of the trough member 30 corresponded to that shape shown in FIG. 10*b* (i.e., a truncated "V"). The base portion "R" of the truncated "V" measured about 0.5" (about 1 cm), and each side portion "S", "S'" measured about 1.5" (about 3.75 cm). The distance "M" separating the side portions "S", "S'" of the V-shaped trough member 30 was about 2¼"-2 5/16" (about 5.9 cm) (measured from inside to inside). The thickness of each portion also measured about ⅛" (about 3 mm) thick. The longitudinal length "$L_T$" (refer to FIG. 11*a*) of the V-shaped trough member 30 measured about 6 feet (about 2 meters) long from point 31 to point 32. The difference in vertical height from the end 31 of the trough member 30 to the end 32 was about ¼-½" (about 6-12.7 mm) over its 6 feet length (about 2 meters) (i.e., less than 1°).

Purified water (discussed later herein) was used as the liquid 3 in all of Examples 1-12. The depth "d" (refer to FIG. 10*b*) of the water 3 in the V-shaped trough member 30 was about 7/16" to about ½" (about 11 mm to about 13 mm) at various points along the trough member 30. The depth "d" was partially controlled through use of the dam 80 (shown in FIGS. 15*a* and 15*b*). Specifically, the dam 80 was provided near the end 32 and assisted in creating the depth "d" (shown in FIG. 10*b*) to be about ⅞"-½" (about 11-13 mm) in depth. The height "j" of the dam 80 measured about ¼" (about 6 mm) and the longitudinal length "k" measured about ½" (about 13 mm) The width (not shown) was completely across the bottom dimension "R" of the trough member 30. Accordingly, the total volume of water 3 in the V-shaped trough member 30 during operation thereof was about 26 in$^3$ (about 430 ml).

The rate of flow of the water 3 in the trough member 30 was about 150-200 ml/minute, depending on which Example was being practiced. Specifically, for example, silver-based and copper-based nanoparticle/solution raw materials made in Examples 1-3 and 5 all utilized a flow rate of about 200 ml/minute; and a zinc-based nanoparticle/solution raw material made in Example 4 utilized a flow rate of about 150 ml/minute. Such flow of water 3 was obtained by utilizing a Masterflex® L/S pump drive 40 rated at 0.1 horsepower, 10-600 rpm. The model number of the Masterflex® pump 40 was 77300-40. The pump drive had a pump head also made by Masterflex® known as Easy-Load Model No. 7518-10. In general terms, the head for the pump 40 is known as a peristaltic head. The pump 40 and head were controlled by a Masterflex® LS Digital Modular Drive. The model number for the Digital Modular Drive is 77300-80. The precise settings on the Digital Modular Drive were, for example, 150 milliliters per minute for Example 4 and 200 ml/minute for the other Examples 1-3 and 5. Tygon® Tubing having a diameter of ¼" (i.e., size 06419-25) was placed into the peristaltic head. The tubing was made by Saint Gobain for Masterflex®. One end of the tubing was delivered to a first end 31 of the trough member 30 by a flow diffusion means located therein. The flow diffusion means tended to minimize disturbance and bubbles in water 3 introduced into the trough member 30 as well as any pulsing condition generated by the peristaltic pump 40. In this regard, a small reservoir served as the diffusion means and was provided at a point vertically above the end 31 of the trough member 30 such that when the reservoir overflowed, a relatively steady flow of water 3 into the end 31 of the V-shaped trough member 30 occurred.

Additionally, the plastic portions of the control devices 20 were also made from plexiglass having a thickness of about ⅛" (about 3 mm) With reference to FIG. 27, the control devices 20 had a dimension "w" measuring about 4" (about 10 cm) and a dimension "L" measuring about 7.5" (about 19 cm). The thickness of the base portion 25 was about ¼" (about 0.5 cm). All of the other components shown in FIG. 27 are drawn very close to scale. All individual components attached to surfaces 25' and 25" were also made of plexiglass which were cut to size and glued into position.

With regard to FIGS. 16*b* and 16*c,* 8 separate electrode sets (Set 1, Set 2, Set 3,-Set 8) were attached to 8 separate control devices 20. Each of Tables 3-7 refers to each of the 8 electrode sets by "Set #". Further, within any Set #, electrodes 1 and 5, similar to the electrode assemblies shown in FIGS. 3*a* and 3*c* were utilized. Each electrode of the 8 electrode sets was set to operate within specific target voltage range. Actual target voltages are listed in each of Tables 3-7. The distance "c-c" (with reference to FIG. 14) from the centerline of each electrode set to the adjacent electrode set is also represented. Further, the distance "x" associated with any electrode(s) 1 utilized is also reported. For any electrode 5's, no distance "x" is reported. Other relevant distances are reported, for example, in each of Tables 3-7.

The size and shape of each electrode 1 utilized was about the same. The shape of each electrode 1 was that of a right triangle with measurements of about 14 mm×23 mm×27 mm. The thickness of each electrode 1 was about 1 mm Each triangular-shaped electrode 1 also had a hole therethrough at a base portion thereof, which permitted the point formed by the 23 mm and 27 mm sides to point toward the surface 2 of the water 3. The material comprising each electrode 1 was 99.95% pure (i.e., 3N5) unless otherwise stated herein. When silver was used for each electrode 1, the weight of each electrode was about 2 grams. When zinc was used for each electrode 1, the weight of each electrode was about 1.1 grams. When copper was used for each electrode 1, the weight of each electrode was about 1.5 grams.

The wires used to attach the triangular-shaped electrode 1 to the transformer 60 were, for Examples 1-4, 99.95% (3N5) silver wire, having a diameter of about 1.016 mm. The wire used to attach the triangular shaped electrode 1 in Example 5 was 99.95% pure (3N5) copper wire, also having a diameter of about 1.016 mm. Accordingly, a small loop of wire was placed through the hole in each electrode 1 to electrically connect thereto.

The wires used for each electrode 5 comprised 99.95% pure (3N5) each having a diameter of about 1.016 mm. The composition of the electrodes 5 in Examples 1-3 was silver; in Example 4 was zinc and in Example 5 was copper. All materials for the electrodes 1/5 were obtained from ESPI having an address of 1050 Benson Way, Ashland, Oreg. 97520.

The water 3 used in Examples 1-12 as an input into the trough member 30 was produced by a Reverse Osmosis process and deionization process. In essence, Reverse Osmosis (RO) is a pressure driven membrane separation process that separates species that are dissolved and/or suspended substances from the ground water. It is called "reverse" osmosis because pressure is applied to reverse the natural flow of osmosis (which seeks to balance the concentration of materials on both sides of the membrane). The applied pressure forces the water through the membrane leaving the contaminants on one side of the membrane and the purified water on the other. The reverse osmosis membrane utilized several thin layers or sheets of film that are bonded together and rolled in a spiral configuration around a plastic tube. (This is also known as a thin film composite or TFC membrane.) In addition to the removal of dissolved species, the RO membrane also separates out suspended materials including microorganisms that may be present in the water. After RO processing a mixed bed deionization filter was used. The total dissolved solvents ("TDS") after both treatments was about 0.2 ppm, as measured by an Accumet® AR20 pH/conductivity meter.

Example 1

Manufacturing Silver-Based Nanoparticles/Nanoparticle Solutions AT059 and AT038

This Example utilizes 99.95% pure silver electrodes 1 and 5. Table 3 summarizes portions of electrode design, location and operating voltages. As can be seen from Table 3, the target voltages were set to a low of about 550 volts and to a high of about 2,100 volts.

Further, bar charts of the actual and target voltages for each electrode in each of the 8 electrode sets, Set #1-Set #8, are shown in FIG. 37*a*. Still further, the actual recorded voltages as well as a function of the time of day is shown in each of FIGS. 37*b*-37*i*. Accordingly, the data contained in Table 3, as well as FIGS. 37*a*-37*i*, give a complete understanding of the electrode design in each electrode set as well as the target and actual voltages applied to each electrode for the duration of the manufacturing process.

TABLE 3

AT059
Flow Rate: 200 ml/min
Room Temperature 23 C.
Relative Humidity 23%

| Set # | Electrode Set # | Target Voltage (kV) | Distance "c-c" in/mm | Distance "x" in/mm | Average Voltage (kV) |
|---|---|---|---|---|---|
| | | | 7/177.8* | | |
| 1 | 1a | 2.11 | | 0.29/7.37 | 2.05 |
| | 5a | 1.83 | | N/A | 1.83 |
| | | | 8/203.2 | | |
| 2 | 1b | 1.09 | | 0.22/5.59 | 1.16 |
| | 5b | 1.14 | | N/A | 1.14 |
| | | | 8/203.2 | | |
| 3 | 1c | 1.02 | | 0.22/5.59 | 0.96 |
| | 5c | 0.92 | | N/A | 0.92 |
| | | | 8/203.2 | | |
| 4 | 1d | 0.90 | | 0.15/3.81 | 0.88 |
| | 5d | 0.78 | | N/A | 0.77 |
| | | | 9/228.6 | | |
| 5 | 1e | 1.26 | | 0.22/5.59 | 1.34 |
| | 5e | 0.55 | | N/A | 0.55 |
| | | | 8/203.2 | | |
| 6 | 1f | 0.96 | | 0.22/5.59 | 0.99 |
| | 5f | 0.72 | | N/A | 0.72 |
| | | | 8/203.2 | | |
| 7 | 1g | 0.89 | | 0.22/5.59 | 0.81 |
| | 5g | 0.70 | | N/A | 0.70 |
| | | | 8/203.2 | | |
| 8 | 1h | 0.63 | | 0.15/3.81 | 0.59 |
| | 5h | 0.86 | | N/A | 0.85 |
| | | | 8/203.2** | | |
| | | Output Water Temperature | | | 67 C. |

*Distance from water inlet to center of first electrode set
**Distance from center of last electrode set to water outlet

Example 2

Manufacturing Silver-Based Nanoparticles/Nanoparticle Solutions AT060 and AT036

Table 4 contains information similar to that data shown in Table 3 relating to electrode set design, voltages, distances, etc. It is clear from Table 4 that the electrode configurations Set #1 and Set #2 were the same as of Set #'s 1-8 in Table 3 and Example 1. Further electrode Sets 3-8 are all configured in the same manner and corresponded to a different electrode configuration from Set #1 and Set #2 herein, which electrode configuration corresponds to that configuration shown in FIG. 8*c*.

TABLE 4

AT060
Flow Rate: 200 ml/min
Room Temperature 23 C.
Relative Humidity 23%

| Set # | Electrode Set # | Target Voltage (kV) | Distance "c-c" in/mm | Distance "x" in/mm | Average Voltage (kV) |
|---|---|---|---|---|---|
| | | | 7/177.8* | | |
| 1 | 1a | 2.41 | | 0.37/9.4 | 2.14 |
| | 5a | 1.87 | | N/A | 1.86 |
| | | | 8/203.2 | | |
| 2 | 1b | 1.33 | | 0.26/6.6 | 1.33 |
| | 5b | 1.13 | | N/A | 1.13 |
| | | | 8/203.2 | | |

TABLE 4-continued

AT060
Flow Rate: 200 ml/min
Room Temperature 23 C.
Relative Humidity 23%

| Set # | Electrode Set # | Target Voltage (kV) | Distance "c-c" in/mm | Distance "x" in/mm | Average Voltage (kV) |
|---|---|---|---|---|---|
| 3 | 5c | 0.79 | | N/A | 0.80 |
|   | 5c' | 0.78 | | N/A | 0.79 |
|   |   |   | 8/203.2 |   |   |
| 4 | 5d | 0.85 | | N/A | 0.86 |
|   | 5d' | 0.88 | | N/A | 0.91 |
|   |   |   | 9/228.6 |   |   |
| 5 | 5e | 1.07 | | N/A | 1.06 |
|   | 5e' | 0.70 | | N/A | 0.69 |
|   |   |   | 8/203.2 |   |   |
| 6 | 5f | 0.94 | | N/A | 0.92 |
|   | 5f' | 0.92 | | N/A | 0.90 |
|   |   |   | 8/203.2 |   |   |
| 7 | 5g | 1.02 | | N/A | 1.00 |
|   | 5g' | 0.93 | | N/A | 0.91 |
|   |   |   | 8/203.2 |   |   |
| 8 | 5h | 0.62 | | N/A | 0.63 |
|   | 5h' | 0.80 | | N/A | 0.83 |
|   |   |   | 8/203.2** |   |   |
|   |   |   | Output Water Temperature |   | 73 C. |

*Distance from water inlet to center of first electrode set
**Distance from center of last electrode set to water outlet FIG. 38a shows a bar chart of target and actual average voltages for each electrode in each of the 8 electrode sets (i.e., Set #1-Set #8).

FIGS. 38b-38i show actual voltages applied to the electrodes for each of the 8 electrode sets.

The product produced according to Example 2 is referred to herein as "AT060".

Example 3

Manufacturing Silver-Based
Nanoparticles/Nanoparticle Solutions AT031

Table 5 herein sets forth electrode design and target voltages for each of the 16 electrodes in each of the eight electrode sets (i.e., Set #1-Set #8) utilized to form the product formed in this example referred to herein as "AT031".

TABLE 5

AT031
Flow Rate: 200 ml/min
Room Temperature 22.5 C.
Relative Humidity 47%

| Set # | Electrode Set # | Target Voltage (kV) | Distance "c-c" in/mm | Distance "x" in/mm | Average Voltage (kV) |
|---|---|---|---|---|---|
|   |   |   | 7/177.8* |   |   |
| 1 | 1a | 2.24 | | 0.22/5.59 | 2.28 |
|   | 5a | 1.84 | | N/A | 1.84 |
|   |   |   | 8/203.2 |   |   |
| 2 | 5b | 1.35 | | N/A | 1.36 |
|   | 5b' | 1.55 | | N/A | 1.55 |
|   |   |   | 8/203.2 |   |   |
| 3 | 5c | 1.46 | | N/A | 1.46 |
|   | 5c' | 1.54 | | N/A | 1.54 |
|   |   |   | 8/203.2 |   |   |

TABLE 5-continued

AT031
Flow Rate: 200 ml/min
Room Temperature 22.5 C.
Relative Humidity 47%

| Set # | Electrode Set # | Target Voltage (kV) | Distance "c-c" in/mm | Distance "x" in/mm | Average Voltage (kV) |
|---|---|---|---|---|---|
| 4 | 1d | 1.62 | | 0.19/4.83 | 1.61 |
|   | 5d | 1.25 | | N/A | 1.27 |
|   |   |   | 9/228.6 |   |   |
| 5 | 5e | 1.21 | | N/A | 1.21 |
|   | 5e' | 0.82 | | N/A | 0.82 |
|   |   |   | 8/203.2 |   |   |
| 6 | 5f | 0.99 | | N/A | 1.06 |
|   | 5f' | 0.92 | | N/A | 0.92 |
|   |   |   | 8/203.2 |   |   |
| 7 | 5g | 1.02 | | N/A | 1.03 |
|   | 5g' | 0.96 | | N/A | 0.95 |
|   |   |   | 8/203.2 |   |   |
| 8 | 5h | 1.00 | | N/A | 1.00 |
|   | 5h' | 0.97 | | N/A | 1.23 |
|   |   |   | 8/203.2** |   |   |
|   |   |   | Output Water Temperature |   | 83 C. |

*Distance from water inlet to center of first electrode set
**Distance from center of last electrode set to water outlet FIG. 39a shows a bar chart of target and actual average voltages applied for each of the 16 electrodes in each of the 8 electrode sets.

FIGS. 39b-39i show the actual voltages applied to each of the 16 electrodes in each of the 8 electrode sets as a function of time.

It should be noted that electrode Set #1 was the same in this Example 3 as in each of Examples 1 and 2 (i.e., an electrode configuration of 1/5). Another 1/5 configuration was utilized for each of the other electrode sets, namely Set #2 and Set #'s 5-8 were all configured in a manner according to a 5/5 configuration.

Example 4

Manufacturing Zinc-Based
Nanoparticles/Nanoparticle Solutions BT006 and BT004

Material designated herein as "BT006" was manufactured in accordance with the disclosure of Example 4. Similar to Examples 1-3, Table 6 herein discloses the precise electrode combinations in each of the 8 electrode sets (i.e, Set #1-Set #8). Likewise, target and actual voltage, distances, etc., are also reported. It should be noted that the electrode set assembly of Example 4 is similar to the electrode set assembly used in Example 1, except that 99.95% pure zinc was used only for the electrodes 5. The triangular-shaped portion of the electrodes 1 also comprised the same purity zinc, however the electrical connections to the triangular-shaped electrodes were all 99.95% pure silver-wire, discussed above herein. Also, the flow rate of the reaction 3 was lower in this Example then in all the other Examples.

TABLE 6

BT006
Flow Rate: 150 ml/min
Room Temp 73.2-74.5 F.
Relative humidity 21-22%

| Set # | Electrode Set # | Target Voltage (kV) | Distance "c-c" in/mm | Distance "x" in/mm | Average Voltage (kV) |
|---|---|---|---|---|---|
|   |   |   | 7/177.8* |   |   |
| 1 | 1a | 1.91 |   | 0.29/7.37 | 1.88 |
|   | 5a | 1.64 |   | N/A | 1.64 |
|   |   |   | 8/203.2 |   |   |
| 2 | 1b | 1.02 |   | 0.22/5.59 | 1.05 |
|   | 5b | 1.09 |   | N/A | 1.08 |
|   |   |   | 8/203.2 |   |   |
| 3 | 1c | 0.91 |   | 0.22/5.59 | 0.90 |
|   | 5c | 0.81 |   | N/A | 0.82 |
|   |   |   | 8/203.2 |   |   |
| 4 | 1d | 0.84 |   | 0.15/3.81 | 0.86 |
|   | 5d | 0.74 |   | N/A | 0.75 |
|   |   |   | 9/228.6 |   |   |
| 5 | 1e | 1.40 |   | 0.22/5.59 | 1.40 |
|   | 5e | 0.54 |   | N/A | 0.55 |
|   |   |   | 8/203.2 |   |   |
| 6 | 1f | 0.93 |   | 0.22/5.59 | 0.91 |
|   | 5f | 0.61 |   | N/A | 0.63 |
|   |   |   | 8/203.2 |   |   |
| 7 | 1g | 0.72 |   | 0.22/5.59 | 0.82 |
|   | 5g | 0.75 |   | N/A | 0.75 |
|   |   |   | 8/203.2 |   |   |
| 8 | 1h | 0.64 |   | 0.15/3.81 | 0.60 |
|   | 5h | 0.81 |   | N/A | 0.81 |
|   |   |   | 8/203.2** |   |   |
|   | Output Water Temperature |   |   |   | 64 C. |

*Distance from water inlet to center of first electrode set
**Distance from center of last electrode set to water outlet FIG. 40a shows a bar chart of the target and actual applied average voltages utilized for each of the 16 electrodes in the 8 electrode sets. Also, FIGS. 40b-40i show the actual voltages applied to each of the 16 electrodes as a function of time.

Example 5

Manufacturing Copper-Based Nanoparticles/Nanoparticle Solutions CT006

A copper-based nanoparticle solution designated as "CT006" was made according to the procedures disclosed in Example 5. In this regard, Table 7 sets forth pertinent operating parameters associated with each of the 16 electrodes in the 8 electrode sets.

TABLE 7

CT006
Flow Rate: 200 ml/min
Relative Humidity 48%
Room Temperature 23.1 C.

| Set # | Electrode Set # | Target Voltage (kV) | Distance "c-c" (in) | Distance "x" (in) | Average Voltage (kV) |
|---|---|---|---|---|---|
|   |   |   | 7/177.8* |   |   |
| 1 | 1a | 2.17 |   | 0.44/11.18 | 2.21 |
|   | 5a | 1.75 |   | N/A | 1.74 |
|   |   |   | 8/203.2 |   |   |
| 2 | 5b | 1.25 |   | N/A | 1.24 |
|   | 5b' | 1.64 |   | N/A | 1.63 |
|   |   |   | 8/203.2 |   |   |

TABLE 7-continued

CT006
Flow Rate: 200 ml/min
Relative Humidity 48%
Room Temperature 23.1 C.

| Set # | Electrode Set # | Target Voltage (kV) | Distance "c-c" (in) | Distance "x" (in) | Average Voltage (kV) |
|---|---|---|---|---|---|
| 3 | 1c | 1.45 |   | 0.22/5.59 | 1.43 |
|   | 5c | 0.83 |   | N/A | 0.83 |
|   |   |   | 8/203.2 |   |   |
| 4 | 5d | 0.77 |   | N/A | 0.77 |
|   | 5d' | 0.86 |   | N/A | 0.86 |
|   |   |   | 9/228.6 |   |   |
| 5 | 5e | 1.17 |   | N/A | 1.15 |
|   | 5e' | 0.76 |   | N/A | 0.76 |
|   |   |   | 8/203.2 |   |   |
| 6 | 5f | 0.85 |   | N/A | 0.84 |
|   | 5f' | 0.84 |   | N/A | 0.83 |
|   |   |   | 8/203.2 |   |   |
| 7 | 5g | 0.99 |   | N/A | 0.99 |
|   | 5g' | 0.87 |   | N/A | 0.86 |
|   |   |   | 8/203.2 |   |   |
| 8 | 5h | 0.85 |   | N/A | 0.85 |
|   | 5h' | 1.10 |   | N/A | 1.09 |
|   |   |   | 8/203.2** |   |   |
|   | Output Water Temperature |   |   |   | 79 C. |

*Distance from water inlet to center of first electrode set
**Distance from center of last electrode set to water outlet Further, FIG. 41a shows a bar chart of each of the average actual voltages applied to each of the 16 electrodes in the 8 electrode sets. It should be noted that the electrode configuration was slightly different than the electrode configuration in each of Examples 1-4. Specifically, electrode Set #'s 1 and 3 were of the 1/5 configuration, and all other the Sets were of the 5/5 configuration.

FIG. 41b-41i show the actual voltages applied to each of the 16 electrodes as a function of time. As above, the wires utilized for each of the electrode(s) 1 and 5 comprised wires of a diameter of about 0.04" (1.016 mm) and a 99.95% purity.

Characterization of Materials of Examples 1-5 and Mixtures Thereof

Each of the silver-based nanoparticles and nanoparticle/solutions made in Examples 1-3 (AT-059/AT-038), (AT060/AT036) and (AT031), respectively; as well as the zinc nanoparticles and nanoparticle/solutions made in Example 4 (BT-004); and the copper nanoparticles and nanoparticle-based/solutions made in Example 5 (CT-006) were physically characterized by a variety of techniques. Specifically, Tables 8 and 9 herein show each of the 5 "raw materials" made according to Examples 1-5 as well as 10 solutions or mixtures made therefrom, each of the solutions being designated "GR1-GR10" or GR1B-GR10B". The amount by volume of each of the "raw materials" is reported for each of the 10 solutions manufactured. Further, atomic absorption spectroscopy ("AAS") was performed on each of the raw materials of Examples 1-5 as well as on each of the 10 solutions GR1-GR10 derived therefrom. The amount of silver constituents, zinc constituents and/or copper constituents therein were thus determined. The atomic absorption spectroscopy results (AAS) are reported by metallic-based constituent.

TABLE 8

| ID | Silver Constituent | % by Volume | Zinc Constituent | % by Volume | Copper Constituent | % by Volume | Ag ppm (AAS) | Zn ppm (AAS) | Cu ppm (AAS) | Metal ppm (Ionic) | NO2 (ppm) | NO3 (ppm) | pH |
|---|---|---|---|---|---|---|---|---|---|---|---|---|---|
| AT-036 | AT-036 | 100.0% | | | | | 43.8 | | | 30.8 | 38.9 | 2.3 | 5.31 |
| AT-031 | AT-031 | 100.0% | | | | | 41.3 | | | 23.3 | 41.3 | 15 | 5.23 |
| AT-038 | AT-038 | 100.0% | | | | | 46 | | | 24.3 | N/A | 11.7 | 3.34 |
| BT-004 | | | BT-004 | 100.0% | | | | 23.1 | | ** | N/A | 33.7 | 3.52 |
| CT006- | | | | | CT-006 | 100.0% | | | 9.2 | | 17.3 | 5.20 | 4.38 |
| GR1 | AT-036 | 22.8% | BT-004 | 43.3% | CT-006 | 33.9% | 9.4 | 10.5 | 3.3 | * | 6.2 | 19.7 | 3.93 |
| GR2 | AT-031 | 24.2% | BT-004 | 43.3% | CT-006 | 32.5% | 8.7 | 11.4 | 2.9 | * | 7.2 | 21.5 | 3.86 |
| GR3 | AT-038 | 21.7% | BT-004 | 43.3% | CT-006 | 35.0% | 9.1 | 10.8 | 3.1 | * | N/A | 23.7 | 3.64 |
| GR4 | AT-036 | 22.8% | BT-004 | 77.2% | | | 9.5 | 19.7 | | 5.6 | N/A | 36.7 | 3.66 |
| GR5 | AT-031 | 24.2% | BT-004 | 75.8% | | | 10.4 | 18.8 | | 5.9 | N/A | 26.6 | 3.68 |
| GR6 | AT-038 | 21.7% | BT-004 | 78.3% | | | 7.6 | | | | N/A | 25.3 | 3.5 |
| GR7 | AT-036 | 45.7% | BT-004 | 54.3% | | | 17.3 | 13.3 | | 8.9 | N/A | 19.6 | 3.83 |
| GR8 | AT-036 | 16.0% | BT-004 | 84.0% | | | 7.4 | 20.0 | | 5.1 | N/A | 29.2 | 3.61 |
| GR9 | AT-036 | 70.0% | BT-004 | 10.0% | CT-006 | 20.0% | 27.1 | 2.4 | 1.8 | * | 36.2 | 3.1 | 4.54 |
| GR10 | AT-36/31/39 | 34.3% | BT-004 | 65.7% | | | 13.2 | 15.6 | | 7.3 | N/A | 23.4 | 3.62 |

N/A ph is out of testing range
\* Can not be tested due to silver and copper interaction
\*\* Zinc can not be tested with device The AAS values were obtained from a Perkin Elmer AAnalyst 300 Spectrometer system. The samples from Examples 1-5 and Solutions GR1-GR10 were prepared by adding a small amount of nitric acid or hydrochloric acid (usually 2% of final volume) and then dilution to a desirable characteristic concentration range or linear range of the specific element to improve accuracy of the result. The "desireable" range is an order of magnitude estimate based on production parameters established during product development. For pure metals analysis, a known amount of feedstock material is digested in a known amount of acid and diluted to ensure that the signal strength of the absorbance will be within the tolerance limits and more specifically the most accurate range of the detector settings, better known as the linear range.

The specific operating procedure for the Perkin Elmer AAnalyst 300 system is as follows:

I) Principle

The Perkin Elmer AAnalyst 300 system consists of a high efficiency burner system with a Universal GemTip nebulizer and an atomic absorption spectrometer. The burner system provides the thermal energy necessary to dissociate the chemical compounds, providing free analyte atoms so that atomic absorption occurs. The spectrometer measures the amount of light absorbed at a specific wavelength using a hollow cathode lamp as the primary light source, a monochromator and a detector. A deuterium arc lamp corrects for background absorbance caused by non-atomic species in the atom cloud.

II) Instrument Setup

A) Empty waste container to mark. Add deionized water to drain tubing to ensure that water is present in the drain system float assembly.

B) Ensure that the appropriate Hollow Cathode Lamp for the analyte to be analyzed is properly installed in the turret.

C) Power AAnalyst 300 and computer ON.

E) After the AAnalyst 300 has warmed up for approximately 3 minutes, start the AAWin Analyst software F) Recall Method to be analyzed.

G) Ensure that the correct Default Conditions are entered.

H) Align the Hollow Cathode Lamp.
   1) Check that a proper peak and energy level has been established for the specific lamp.
   2) Adjust the power and frequency of the lamp settings to obtain maximum energy.

I) Store Method changes in Parameter Entry, Option, Store and #.

J) Adjust Burner height.
   1) Place a white sheet of paper behind the burner to confirm the location of the light beam.
   2) Lower the burner head below the light beam with the vertical adjustment knob.
   3) Press Cont (Continuous) to display an absorbance value.
   4) Press A/Z to Autozero.
   5) Raise the burner head with the vertical adjustment knob until the display indicates a slight absorbance (0.002). Slowly lower the head until the display returns to zero. Lower the head an additional quarter turn to complete the adjustment.

K) Ignite flame.
   1) Turn Fume Hood switch ON.
   2) Open air compressor valve. Set pressure to 50 to 65 psi.
   3) Open acetylene gas cylinder valve. Set output pressure to 12 to 14 psi. Replace cylinder when pressure falls to 85 psi to prevent valve and tubing damage from the presence of acetone.
   4) Press Gases On/Off. Adjust oxidant flow to 4 Units.
   5) Press Gases On/Off. Adjust acetylene gas flow to 2 Units.
   6) Press Flame On/Off to turn flame on.
      Note: Do not directly view the lamp or flame without protective ultraviolet radiation eyewear.

L) Aspirate deionized water through the burner head several minutes.

M) Adjust Burner Position and Nebulizer.
   1) Aspirate a standard with a signal of approximately 0.2 absorbance units.
   2) Obtain maximum burner position absorbance by rotating the horizontal and rotational adjustment knobs.

3) Loosen the nebulizer locking ring by turning it clockwise. Slowly turn the nebulizer adjustment knob to obtain maximum absorbance. Lock the knob in place with the locking ring.

Note: An element, such as Magnesium, which is at a wavelength where gases do not absorb is optimal for adjusting the Burner and Nebulizer.

N) Allow 30 minutes to warm-up flame and lamp.

III) Calibration Procedure

A) Calibrate with standards that bracket the sample concentrations.

B) WinAA Analyst software will automatically create a calibration curve for your sample readings. But check to ensure that proper absorption is established with each calibration standard.

C) Enter Standard Concentration Values in the Default Conditions to calculate an AAnalyst 300 standard curve.
1) Enter the concentration of the lowest standard for STD1 using significant digits.
2) Enter the concentrations of the other standards of the calibration curve in ascending order and the concentration of the reslope standard.
3) Autozero with the blank before each standard.
4) Aspirate Standard 1, press 0 Calibrate to clear the previous curve. Aspirate the standards in numerical order.
Press standard number and calibrate for each standard.
5) Press Print to print the graph and correlation coefficient.
6) Rerun one or all standards, if necessary. To rerun Standard 3, aspirate standard and press 3 Calibrate.
7) Reslope the standard curve by pressing Reslope after aspirating the designated reslope standard.

D) The correlation coefficient should be greater than or equal to 0.990.

E) Check the calibration curve for drift, accuracy and precision with standards and controls every 20 samples.

IV) Analysis Procedure

A) Autozero with the blank before each standard, control and sample.

B) Aspirate sample and press Read Sample. The software will take 3 readings of absorbance and then average those readings. Wait until software says idle. Rerun the sample if the standard deviation is greater than 10% of the sample result.

V) Instrument Shutdown

A) Aspirate 5% Hydrochloric Acid (HCl) for 5 minutes and deionized water for 10 minutes to clean the burner head. Remove the capillary tube from the water.

B) Press Flame On/Off to turn off flame.

C) Close air compressor valve.

D) Close acetylene cylinder valve.

E) Press Bleed Gases to bleed the acetylene gas from the lines. The cylinder pressure should drop to zero.

F) Exit the software, power OFF the AAnalyst 300, and shut down the computer.

Further, the last 4 columns of Table 8 disclose "Metal PPM (Ionic)"; and $O_2$ (ppm); $NO_3$ (ppm); and "pH". Each of these sets of numbers were determined by utilizing an ion selective electrode measurement technique. In particular, a NICO ion analyzer was utilized. Precise stabilization times and actual experimental procedures for collecting the data in each of these three columns of Table 8 (and Table 9) occurs immediately below.

DEFINITIONS

Stabilization Times—After immersing the electrodes in a new solution, the mV reading normally falls rapidly at first by several mV, and then gradually, and increasingly slowly, falls to a stable reading as the ISE membrane equilibrates and the reference electrode liquid junction potential stabilizes. This equilibration may take up to 3 or 4 minutes to reach a completely stable value. Sometimes the reading begins to rise again after a short period of stability and it is important to ensure that the recording is made at the lowest point, before this rise has proceeded to any great extent. In this study it was found that it was not necessary to wait for a completely stable reading but that satisfactory results could be obtained by taking a reading after a pre-set time, so that each measurement was made at the same point of the decay curve. For optimum performance it was found that this delay time should be at least two minutes to ensure that the reading was in the shallower part of the curve.

Procedure:
1. Get two 150 mL beakers for each electrode to be used (typically 4). One beaker will be used for the solutions themselves and the other beaker will be filled with DI $H_2O$ to equalize the membranes of each electrode after each solution has been tested.
2. Obtain approximately 50 mL of the solution of interest for each electrode being used and its respective beaker. (Commonly about 200 mL for testing of Ag, NO3, NO2 and pH of a solution.)
3. If not already in place, locate and insert each desired ion selective electrode and its respective reference electrode into the appropriate receptacle. Only one electrode and its reference electrode per receptacle unless both ion selective electrodes require the use of the same reference electrode. Remove caps from each electrode and its corresponding reference electrode and place them into the electrode holder.
4. Turn on the computer associated with the NICO Ion Analyser and the software to operate it.
5. Open the 8-Channel Ion Electrode Analyser Software to operate the equipment.
6. Each ion selective electrode must be calibrated using the standards most accurate for our purposes. This calibration must be done each time the machine is turned on and for most accurate results, should be calibrated before each individual sample is tested. For each ion selective electrode, at the present time, 1 ppm, 10 ppm and 100 ppm give the best calibration for our solutions and their relative readings. Locate the "Calibrate" button on the software interface and follow the directions.
7. Each beaker is to be rinsed with DI H2O and swabbed with a lint free cloth before each use.
8. Fill each "solution" beaker with approximately 50 mL of the solution of interest and each "equalizer" beaker with approximately 100 mL of DI H2O.
9. Place each electrode into the "equalizer" beakers for approximately 15 seconds to ensure the membranes are in the same state and equal before each new solution is tested.
10. Remove electrodes from the DI H2O and wipe gently with a lint free cloth.
11. Place the electrodes into the solution so that each electrode and reference electrode is immersed at least 2 cm. Gently swirl the electrode and beaker to ensure homogeneity and good to remove any air bubbles that may be between the electrodes and the solution.
12. Let the electrodes remain undisturbed for 2-5 minutes depending on the stabilization time for the particular solution.

13. When the operator is satisfied with the reading and it occurs during the stabilization time, it must be recorded using the software. Upon hitting the "Record" button you will be prompted for a filename for this specific set of data. Also record these readings in a lab book that can be used for transferring numbers to external speadsheets and the like.
14. Remove the electrodes from the solution and discard the solution.
15. Rinse each electrode with a stream of DI H2O.
16. Rinse each 150 mL beaker with DI H2O.
17. Dry both the electrodes and the beakers with lint free cloths.
18. Return each electrode to its holder and replace caps if no further testing is to occur.

Table 9 is also included herein which contains similar data to that data shown in Table 8 (and discussed in Examples 1-5) with the only exception being AT-031. The data in Table 9 comes from procedures copied from Examples 1-5 except that such procedures were conducted at a much later point in time (months apart). The raw materials and associated solutions, summarized in Table 9 show that the raw materials, as well as solutions therefrom, are substantially constant. Accordingly, the process is very reliable and reproducible.

while allowing emitted energies to have optimum path to the XEDS detector. A sample is typically positioned about 18 mm beneath the aperture for the final lens and tilted nominally at 18° towards the XEDS detector. All work is accomplished within a vacuum chamber, maintained at about $10^{-6}$ torr.

The final lens aperture is adjusted to 200 to 300 μm in diameter and the beam spot size is adjusted to achieve an adequate x-ray photon count rate for the digital "pulse" processor. Data collection periods range between 200 and 300 seconds, with "dead-times" of less than 15%.

An aliquot of liquid sample solution is placed onto a AuPd sputtered glass slide followed by a dehydration step which includes freeze drying the solution or drying the solution under a dry nitrogen gas flow to yield particulates from the suspension. Due to the nature of the particulates, no secondary coating is required for either imaging or XEDS analysis.

FIGS. 43a(i-iv)-43e(i-iv) disclose photomicrographs, at 4 different magnifications each, corresponding to freeze-drying each of the materials produced in Examples 1-5, as well as freeze drying each of the solutions GR1-GR10 recorded in Tables 8 and 9. Specifically, FIGS. 43f(i-iv)-43o(i-iv) correspond to the solutions GR1-GR10, respectively. All of the photomicrographs were generated with an AMRAY 1820

TABLE 9

| | Solution Contents | | | | | | Analytical Results | | | | | | |
|---|---|---|---|---|---|---|---|---|---|---|---|---|---|
| ID | Silver Constituent | % by Volume | Zinc Constituent | % by Volume | Copper Constituent | % by Volume | Ag ppm (AAS) | Zn ppm (AAS) | Cu ppm (AAS) | Metal ppm Ionic | NO2 (ppm) | NO3 (ppm) | pH |
| AT-060 | AT-060 | 100.0% | | | | | 40.9 | | | 24.2 | N/A | 0.00 | 4.04 |
| AT-031 | AT-031 | 100.0% | | | | | 41.3 | | | 23.3 | 41.3 | 15 | 5.23 |
| AT-059 | AT-059 | 100.0% | | | | | 41.4 | | | 10.9 | N/A | 13.3 | 2.98 |
| BT-006 | | | BT-006 | 100.0% | | | | 24 | | ** | N/A | 20.8 | 3.13 |
| CT-006 | | | | | CT-006 | 100.0% | | | 9.2 | | 17.3 | 5.20 | 4.38 |
| GR1B | | | | | | | | | | | | | |
| GR2B | | | | | | | | | | | | | |
| GR3B | AT-059 | 24.2% | BT-006 | 41.7% | CT-006 | 34.2% | 9.99 | 9.85 | 2.91 | * | N/A | 58 | 3.27 |
| GR4B | | | | | | | | | | | | | |
| GR5B | AT-031 | 24.2% | BT-006 | 75.8% | | | 9.34 | 18.8 | | 5.5 | N/A | 42.8 | 3.25 |
| GR6B | | | | | | | | | | | | | |
| GR7B | AT-060 | 48.9% | BT-006 | 51.1% | | | 20.6 | 12.7 | | 8.7 | N/A | 30.5 | 3.38 |
| GR8B | AT-060 | 17.1% | BT-006 | 82.9% | | | 7.13 | 19.1 | | 5 | N/A | 39.4 | 3.2 |
| GR9B | AT-060 | 70.0% | BT-006 | 10.0% | CT-006 | 20.0% | 29.9 | 3.7 | 1.7 | * | N/A | 15.8 | 3.82 |
| GR10B | AT-60/31/59 | 36.4% | BT-006 | 63.6% | | | 14.2 | 15.6 | | 7 | N/A | 21.4 | 3.2 |

N/A ph is out of testing range
* Can not be tested due to silver and copper interaction
** Zinc can not be tested with device Scanning Electron Microscopy/EDS Scanning electron microscopy was performed on each of the new materials and solutions GR1-GR10 made according to Examples 1-5.

FIGS. 42a-42e show EDS results for a scanning electron microscope corresponding to each of the 5 raw materials made in Examples 1-5, respectively.

FIGS. 42f-42o show EDS analysis for each of the 10 solutions shown in Tables 8 and 9.

XEDS spectra were obtained using a EDAX Lithium drifted silicon detector system coupled to a IXRF Systems digital processor, which was interfaced with an AMRAY 1820 SEM with a LaB6 electron gun. Interpretation of all spectra generated was performed using IXRF EDS2008, version 1.0 Rev E data collection and processing software.

Instrumentation hardware and software setup entails positioning liquid samples from each Run ID on a sample stage in such a manner within the SEM to permit the area of interest to be under the electron beam for imaging purposes SEM with an LaB6 electron gun. Magnification size lens are shown on each photomicrograph.

Transmission Electron Microscopy

Transmission Electron Microscopy was performed on raw materials corresponding to the components used to manufacture GR5 and GR8, as well as the solutions GR5 and GR8. Specifically, an additional run was performed corresponding to those production parameters associated with manufacturing AT031 (i.e, the silver constituent in GR5); an additional run was performed corresponding to those production parameters associated with manufacturing AT060 (i.e., the silver constituent in GR8); and an additional run was performed corresponding to those production parameters associated with manufacturing BT006 (i.e., the zinc constituent used in both GR5 and GR8). The components were then mixed together in a similar manner as discussed above herein to result in solutions equivalent to previously manufactured GR5 and GR8.

FIGS. 43p(i)-43p(iii) disclose three different magnification TEM photomicrographs of a silver constituent made corresponding to the production parameters used to manufacture AT031.

FIGS. 43q(i)-43q(vi) disclose six different TEM photomicrographs taken at three different magnifications of a silver constituent made corresponding to the production parameters used to manufacture AT060.

FIGS. 43r(i)-43r(ii) disclose two different TEM photomicrographs taken at two different magnifications of a zinc constituent made according to the production parameters used to manufacture BT006.

FIGS. 43s(i)-43s(v) disclose five different TEM photomicrographs taken at three different magnifications of a solution GR5.

FIGS. 43t(i)-43t(x) disclose ten different TEM photomicrographs taken at three different magnifications of a solution GR8.

The samples for each of the TEM photomicrographs were prepared at room temperature. Specifically, 4 microliters of each liquid sample were placed onto a holey carbon film which was located on top of filter paper (used to wick off excess liquid). The filter paper was moved to a dry spot and this procedure was repeated resulting in 8 total microliters of each liquid sample being contacted with one portion of the holey carbon film. The carbon film grids were then mounted in a single tilt holder and placed in the loadlock of the JEOL 2100 CryoTEM to pump for about 15 minutes. The sample was then introduced into the column and the TEM microscopy work performed.

The JEOL 2100 CryoTEM operated at 200 kv accelerating potential. Images were recorded on a Gatan digital camera of ultra high sensitivity. Typical conditions were 50 micron condenser aperture, spot size 2, and alpha 3.

These TEM photomicrographs show clearly that the average particle size of those particles in FIG. 43p (i.e., those corresponding to the silver constant in GR05) are smaller than those particles shown in FIG. 43q (i.e., those corresponding to the silver constituent in GR8). Further, crystal planes are clearly shown in both sets of FIGS. 43p and 43q. Moreover, FIG. 43q show the development of distinct crystal facets, some of which correspond to the known 111 cubic structure for silver.

TEM photomicrographs 43r do not show any significant crystallization of zinc.

TEM photomicrographs 43s (corresponding to solution GR5) also show similar silver features as shown in FIG. 43p; and the photomicrographs 43t (i.e., corresponding to solution GR8) also show similar features as shown in FIG. 43 q.

Thus, these TEM photomicrographs suggest that the processing parameters utilized to manufacture GR5 resulted in somewhat smaller silver-based nanoparticles, when compared to those silver-based nanoparticles associated with GR8. The primary difference in production parameters between GR5 and GR8 was the location of the two adjustable plasmas 4 used to make the silver constituents in each solution. The zinc constituents in both of GR5 and GR8 are the same. However, the silver constituents in GR5 is made by adjustable plasmas 4 located at the First Electrode Set and the Fourth Electrode Set; whereas the silver constituent in GR8 is made by adjustable plasmas 4 located at the First and Second Electrode Sets.

UV-VIS Spectroscopy

Energy absorption spectra were obtained using US-VIS micro-spec-photometry. This information was acquired using dual beam scanning monochrometer systems capable of scanning the wavelength range of 190 nm to 1100 nm Two UV-Vis spectrometers were used to collect absorption spectra; these were a Jasco V530 and a Jasco MSV350. Instrumentation was setup to support measurement of low-concentration liquid samples using one of a number of fuzed-quartz sample holders or "cuvettes". The various cuvettes allow data to be collected at 10 mm, 1 mm or 0.1 mm optic path of sample. Data was acquired over the above wavelength range using both PMT and LED detectors with the following parameters; bandwidth of 2 nm, with data pitch of 0.5 nm, with and without a water baseline background. Both tungsten "halogen" and Hydrogen "D2" energy sources were used as the primary energy sources. Optical paths of these spectrometers were setup to allow the energy beam to pass through the samples with focus towards the center of the sample cuvettes. Sample preparation was limited to filling and capping the cuvettes and then physically placing the samples into the cuvette holder, within the fully enclosed sample compartment. Optical absorption of energy by the materials of interest was determined. Data output was measured and displayed as Absorbance Units (per Beer-Lambert's Law) versus wavelength and frequency.

Spectral signatures in a UV-Visible range were obtained for each of the raw materials produced in Examples 1-5 as well as in each of the solutions GR1-GR10 shown in Tables 8 and 9.

Specifically, FIG. 44a shows UV-Vis spectral signature of each of the 5 raw materials with a wavelength of about 190 nm-600 nm.

FIG. 44b shows the UV-Vis spectral pattern for each of the 10 solutions GR1-GR10 for the same wavelength range.

FIG. 44c shows the UV-Vis spectral pattern of each of the 10 solutions GR1-GR10 over a range of 190 nm-225 nm.

FIG. 44d is a UV-Vis spectra of each of the 10 solutions GR1-GR10 over a wavelength of about 240 nm-500 nm.

FIG. 44e is a UV-Vis spectral pattern for each of the solutions GR1-GR10 over a wavelength range of about 245 nm-450 nm.

The UV-Vis spectral data for each of FIGS. 44a-44e were obtained from a Jasco V-530 UV-Vis Spectrophotometer. Pertinent operational conditions for the collection of each UV-Vis spectral pattern are shown in FIGS. 44a-44e.

In general, UV-Vis spectroscopy is the measurement of the wavelength and intensity of absorption of near-ultraviolet and visible light by a sample. Ultraviolet and visible light are energetic enough to promote outer electrons to higher energy levels. UV-Vis spectroscopy can be applied to molecules and inorganic ions or complexes in solution.

The UV-Vis spectra have broad features that can be used for sample identification but are also useful for quantitative measurements. The concentration of an analyte in solution can be determined by measuring the absorbance at some wavelength and applying the Beer-Lambert Law.

The dual beam UV-Vis spectrophotometer was used to subtract any signals from the solvent (in this case water) in order to specifically characterize the samples of interest. In this case the reference is the feedstock water that has been drawn from the outlet of the Reverse Osmosis process discussed in the Examples section herein.

Raman Spectroscopy

Raman spectral signatures were obtained using a Renishaw Invia Spectrometer with relevant operating information shown in FIG. 45. It should be noted that no significant differences were seen for each of the GR1-GR10 blends using Raman Spectroscopy.

The reflection micro-spectrograph with Leica DL DM microscope was fitted with either a 20× (NA=0.5) water immersion or a 5× (NA=0.12) dry lens. The rear aperture of each lens was sized to equal or exceed the expanded laser beam diameter. Two laser frequencies were used, these being a multiline 50 mW Argon laser at ½ power setup for 514.5 nm and a 20 mW HeNe laser at 633 nm High resolution gratings were fitted in the monochrometer optic path which allowed continuous scans from 50 to 4000 wavenumbers (1/cm). Ten to 20 second integration times were used. Sample fluid was placed below the lens in a 50 ml beaker. Both lasers were used to investigate resonance bands, while the former laser was primarily used to obtain Raman spectra. Sample size was about 25 ml. Measurements made with the 5× dry lens were made with the objective positioned about 5 mm above the fluid to interrogate a volume about 7 mm beneath the water meniscus Immersion measurements were made with the 20× immersion lens positioned about 4 mm into the sample allowing investigation of the same spatial volume. CCD detector acquisition areas were individually adjusted for each lens to maximize signal intensity and signal-to-noise ratios.

Biological Characterization

Bioscreen Results

A Bioscreen C microbiology reader was utilized to compare the effectiveness of the raw materials made in accordance with Examples 1-5, as well as the 10 solutions GR1-GR10 made therefrom. Specific procedure for obtaining Bioscreen results follows below.

Bacterial Strains

*Escherichia coli* was obtained from the American Type Culture Collection (ATCC) under the accession number 25922. The initial pellets were reconstituted in trypticase soy broth (TSB, Becton Dickinson and Company, Sparks, Md.) and aseptically transferred to a culture flask containing 10 ml of TSB followed by overnight incubation at 37° C. in a Forma 3157 water-jacketed incubator (Thermo Scientific, Waltham, Mass., USA).

Maintenance and Storage of Bacteria

Bacterial strains were kept on trypticase soy agar (TSA, Becton Dickinson and Company, Sparks, Md.) plates and aliquots were cryogenically stored at −80° C. in MicroBank tubes (Pro-Lab Incorporated, Ontario, Canada).

Preparation of Bacterial Cultures

Microbank tubes were thawed at room temperature and opened in a NuAire Labgard 440 biological class II safety cabinet (NuAire Inc., Plymouth, Minn., USA). Using a sterile inoculating needle, one microbank bead was aseptically transferred from the stock tube into 10 ml of either Trypticase Soy Broth (TSB, Becton Dickenson and Company, Sparks, Md.) for Bioscreen analysis or Mueller-Hinton Broth (MHB, Becton Dickenson and Company, Sparks, Md.) for MIC/MLC analysis. Overnight cultures of bacterial strains were grown at 37° C. for 18 hours in a Forma 3157 water jacketed incubator (Thermo Scientific, Waltham, Mass., USA) and diluted to a 0.5 McFarland turbidity standard. Subsequently, a $10^{-1}$ dilution of the McFarland standard was performed, to give an approximate bacterial count of $1.0 \times 10^7$ CFU/ml. This final dilution must be used within 30 minutes of creation to prevent an increase in bacterial density due to cellular growth.

Dilution of Nanoparticle Solutions

Nanoparticle solutions were diluted in MHB and sterile $dH_2O$ to a 2× testing concentration yielding a total volume of 1.5 ml. Of this volume, 750 µl consisted of MHB, while the other 750 µl consisted of varying amounts of sterile $dH_2O$ and the nanoparticle solution to make a 2× concentration of the particular nanoparticle solution being tested. Testing dilutions (final concentration in reaction) ranged from 0.5 ppm Ag to 6.0 ppm Ag nanoparticle concentration with testing performed at every 0.5 ppm interval.

Preparation of Bioscreen Reaction

To determine the minimum inhibitory concentration (MIC) of nanoparticle solutions, 100 µl of the diluted bacterial culture was added to 100 µl of a particular nanoparticle solution at the desired testing concentration in the separate, sterile wells of a 100 well microtiter plate (Growth Curves USA, Piscataway, N.J., USA). Wells inoculated with both 100 µl of the diluted bacterial culture and 100 µl of a 1:1 MHB/sterile $ddH_2O$ mix served as positive controls, while wells with 100 µl of MHB and 100 µl of a 1:1 MHB/sterile $ddH_2O$ mix served as negative controls for the reaction. Plates were placed inside the tray of a Bioscreen C Microbiology Reader (Growth Curves USA, Piscataway, N.J., USA) and incubated at a constant 37° C. for 15 hours with optical density (O.D.) measurements being taken every 10 minutes. Before each O.D. measurement, plates were automatically shaken for 10 seconds at medium intensity to prevent settling of bacteria and to ensure a homogenous reaction well.

Determination of Both MIC and MLC

All data was collected using EZExperiment Software (Growth Curves USA, Piscataway, N.J., USA) and analyzed using Microsoft Excel (Microsoft Corporation, Redmond, Wash., USA). The growth curves of bacteria strains treated with different nanoparticle solutions were constructed and the MIC determined. The MIC was defined as the lowest concentration of nanoparticle solution that prevented the growth of the bacterial culture for 15 hours, as measured by optical density using the Bioscreen C Microbiology Reader.

Once the MIC was determined, the test medium from the MIC and subsequent higher concentrations was removed from each well and combined according to concentration in appropriately labeled, sterile Eppendorf tubes. TSA plates were inoculated with 100 µl of test medium and incubated overnight at 37° C. in a Forma 3157 water-jacketed incubator (Thermo Scientific, Waltham, Mass., USA). The minimum lethal concentration (MLC) was defined as the lowest concentration of nanoparticle solution that prevented the growth of the bacterial culture as measured by colony growth on TSA.

The results of the Bioscreen runs are shown in FIG. 46. It should be noted that the raw materials AT031; AT059 and AT060 had reasonable performance, whereas the raw materials BT-006 and CT-006 did not slow down growth of the *E. coli* at all. In this regard, the longer a curve remains at low optical density ("OD") the better the performance against bacteria.

In contrast, each of the solutions GR1-GR10 showed superior performance, relative to each of the raw materials AT031, AT060 and AT059. Interestingly, the combination of the raw materials associated with silver nanoparticles with those raw materials associated with both zinc and copper nanoparticles produced unexpected synergistic results.

Additional Bioscreen results are shown in FIGS. 47 and 48. Data reported in these Figures are known as "MIC" data. "MIC" stands for minimum inhibitory concentration. MIC data was only generated for GR3 and GR8. It is clear from reviewing the data in each of FIGS. 47 and 48 that appropriate MIC values for GR3 and GR8 were around 2-3 ppm Due to the unexpected favorable results shown in FIG. 46, the sequential addition of the raw material BT-006, made in accordance with Example 4, was added to the raw material AT-060 made in accordance with Example 2 (i.e., a zinc-based nanoparticle solution was added to a silver-based nanoparticle solution. The amount of silver present (as determined by atomic absorption spectroscopy) was maintained at 1 ppm. The amount of BT-006 in the nanoparticle solution added thereto is reported in FIG. 49. It is interesting to note that enhanced antimicrobial performance against *E. coli* was achieved with increasing amounts of zinc nanoparticle solutions, i.e., BT-006, (from Example 4) being added thereto. Further, FIGS. 50a-50d show additional Bioscreen information showing performance against *e. coli* by adding a conditioned water ("GZA") to the nanoparticle solution AT-060 from Example 2.

GZA raw material was made in a manner similar to the BT-006 raw material except that a platinum electrode 1/5 configuration was utilized rather than zinc.

Freeze-Drying

FIG. 54 shows another set of Bioscreen results whereby solutions referred to in Tables 8 and 9 herein as GR5 and GR8, were compared for efficacy against *E. coli*, as well as the same solutions having been first completely freeze-dried and thereafter rehydrated with water (liquid 3) such rehydration being effected to result in the same original ppm.

Freeze-drying was accomplished by placing the GR5 and GR8 solution in a plastic (nalgene) container and placing the plastic container in a BenchTop 2K freeze dryer (manufactured by Virtis) which was maintained at a temperature of about −52° C. and a vacuum of less than 100 milliliter. About 10-20 ml of solution will freeze-dry overnight.

As is shown in FIG. 54, the performance of freeze-dried and rehydrated nanoparticles is identical to the performance of the original GR5 and GR8 solutions.

Viability/Cytotoxicity Testing of Mammalian Cells

The following procedures were utilized to obtain cell viability and/or cytotoxicity measurements.

Cell Lines

*Mus musculus* (mouse) liver epithelial cells (accession number CRL-1638) and *Sus scrofa domesticus* (minipig) kidney fibrobast cells (accession number CCL-166) were obtained from the American Type Culture Collection (ATCC).

Cell Culturing from Frozen Stocks

Cell lines were thawed by gentle agitation in a Napco 203 water bath (Thermo Scientific, Waltham, Mass., USA) at 37° C. for 2 minutes. To reduce microbial contamination, the cap and O-ring of the frozen culture vial were kept above the water level during thawing. As soon as the contents of the culture vial were thawed, the vial was removed from the water, sprayed with 95% ethanol, and transferred into a NuAire Labgard 440 biological class II safety cabinet (Nu-Aire Inc., Plymouth, Minn., USA). The vial contents were then transferred to a sterile 75 $cm^2$ tissue culture flask (Corning Life Sciences, Lowell, Mass., USA) and diluted with the recommended amount of complete culture medium. Murine liver epithelial cell line CRL-1638 required propagation in complete culture media composed of 90% Dulbecco's Modified Eagle's Medium (ATCC, Manassas, Va., USA) and 10% fetal bovine serum (ATCC, Manassas, Va., USA), while minipig kidney fibroblast cell line CCL-166 was grown in complete culture media comprised of 80% Dulbecco's Modified Eagle's Medium and 20% fetal bovine serum. Cell line CRL-1638 was diluted with growth media in a 1:15 ratio, while cell line CCL-166 was diluted with growth media in a 1:10 ratio. The culture flasks were then incubated at about 37° C., utilizing a 5% $CO_2$ and 95% humidified atmosphere in a NuAire, IR Autoflow water-jacketed, $CO_2$ incubator (NuAire Inc., Plymouth, Minn., USA).

Medium Renewal and Care of Growing Cells

Every two days, old growth medium was removed from culturing flasks and replaced with fresh growth medium. Each day, observations for microbial growth, such as fungal colonies and turbidity in medium, were made with the naked eye. Additionally, cultured cells were observed under an inverted phase contrast microscope (VWR Vistavision, VWR International, and West Chester, Pa., USA) to check for both general health of the cells and cell confluency.

Subculturing of Cells

Once cells reached approximately 80% confluent growth, cells were deemed ready for subculturing. Old growth medium was removed and discarded and the cell sheet rinsed with 5 ml of prewarmed trypsin-EDTA dissociating solution (ATCC, Manassas, Va., USA). After 30 seconds of contact with the cell sheet, the trypsin-EDTA was removed and discarded. Ensuring that both the entire cell monolayer was covered and the flask was not agitated, a 3 ml volume of the prewarmed trypsin-EDTA solution was added to the cell sheet followed by incubation of the culture flask at 37° C. for about 15 minutes. After cell dissociation, trypsin-EDTA was inactivated by adding about 6 ml of complete growth medium to the cell culture flask followed by gentle pipetting to aspirate cells.

In order to count cells, 200 µl of the cell suspension was collected in a 15 ml centrifuge tube (Corning Life Sciences, Lowell, Mass., USA). Both 300 µL of phosphate buffered saline (ATCC, Manassas, Va., USA) and 500 µL of a 0.4% trypan blue solution (ATCC, Manassas, Va., USA) was added to the collected cell suspension and mixed thoroughly. After allowing to stand for about 15 minutes, 10 µl of the mixture was placed in each chamber of an iN Cyto, C-Chip disposable hemacytometer (INCYTO, Seoul, Korea) where the cells were counted with a VWR Vistavision inverted phase contrast microscope (VWR International, West Chester, Pa., USA) according to the manufacturer's instructions. The concentration of the cells in the suspension was calculated using a conversion formula based upon the cell count obtained from the hemacytometer.

Cytotoxicity Testing

The wells of black, clear bottom, cell culture-treated microtiter plates (Corning Life Sciences, Lowell, Mass., USA) were seeded with 200 µl of culture medium containing approximately 1.7×10⁴ cells as shown in FIG. 1. Cells were allowed to equilibrate in the microtiter plates at about 37° C., utilizing a 5% $CO_2$ and 95% humidified atmosphere for about 48 hours. After the equilibration period, culture medium was removed from each well and replaced with 100 µl of fresh growth medium in all wells except for those in column 3 of the plate. A 100 µl volume of fresh medium supplemented with 2× of the desired testing concentration of Hydronanon™ solution was placed in each well as shown in Table 10.

TABLE 10

Microwell plate setup for cytotoxicity testing. All outer wells (shaded area) of the plate contained only 200 µl of culture medium (no cells) to act as a blank vehicle control (VCb) for the experiment. As a positive vehicle control, wells 2B-2G (VC1) and wells 11B-11G (VC2) were seeded with both culture medium and cells. One Hydronanon ™ solution was tested on each plate ($H_x$). The highest concentration of Hydronanon ™ solution was placed in wells 3B-3D ($C_1$), while seven, 20% dilutions (C2-C7) of each solution were present in each consecutive well.

|   | 1 | 2 | 3 | 4 | 5 | 6 | 7 | 8 | 9 | 10 | 11 | 12 |
|---|---|---|---|---|---|---|---|---|---|----|----|----|
| A | VCb | VCb | VCb | VCb | VCb | VCb | VCb | VCb | VCb | VCb | VCb | VCb |
| B | VCb | VC1 | $H_1C_1$ | $H_1C_2$ | $H_1C_3$ | $H_1C_4$ | $H_1C_5$ | $H_1C_6$ | $H_1C_7$ | $H_1C_8$ | VC2 | VCb |
| C | VCb | VC1 | $H_1C_1$ | $H_1C_2$ | $H_1C_3$ | $H_1C_4$ | $H_1C_5$ | $H_1C_6$ | $H_1C_7$ | $H_1C_8$ | VC2 | VCb |
| D | VCb | VC1 | $H_1C_1$ | $H_1C_2$ | $H_1C_3$ | $H_1C_4$ | $H_1C_5$ | $H_1C_6$ | $H_1C_7$ | $H_1C_8$ | VC2 | VCb |
| E | VCb | VC1 | C | C | C | C | C | C | C | C | VC2 | VCb |
| F | VCb | VC1 | C | C | C | C | C | C | C | C | VC2 | VCb |
| G | VCb | VC1 | C | C | C | C | C | C | C | C | VC2 | VCb |
| H | VCb | VCb | VCb | VCb | VCb | VCb | VCb | VCb | VCb | VCb | VCb | VCb |

Microtiter plates were incubated with the treatment compounds 37° C., utilizing a 5% $CO_2$ and 95% humidified atmosphere for 24 hours. After incubation with nanoparticle solutions, the culture medium was removed and discarded from each well and replaced with 100 µl of fresh media containing Alamar Blue™ (Biosource International, Camarillo, Calif., USA) at a concentration of 50 µl dye/ml media. Plates were gently shaken by hand for about 10 seconds and incubated at about 37° C., utilizing a 5% $CO_2$ and 95% humidified atmosphere for 2.5 hours. Fluorescence was then measured in each well utilizing an excitation wavelength of 544 nm and an emission wavelength of 590 nm Fluorescence measurements were carried out on the Fluoroskan II fluorometer produced by Labsystems (Thermo Scientific, Waltham, Mass., USA).

Data Analysis

Cytotoxicity of the nanoparticle solutions was determined by measuring the proportion of viable cells after treatment when compared to the non-treated control cells. A percent viability of cells after treatment was then calculated and used to generate the concentration of nanoparticle at which fifty percent of cellular death occurred ($LC_{50}$). All data was analyzed using GraphPad Prism software (GraphPad Software Inc., San Diego, Calif., USA).

Results of the viability/cytotoxicity tests are shown in Figures are shown in FIGS. 51a-51h; 52a-52f; and FIGS. 53a-53h.

Figure 51A:
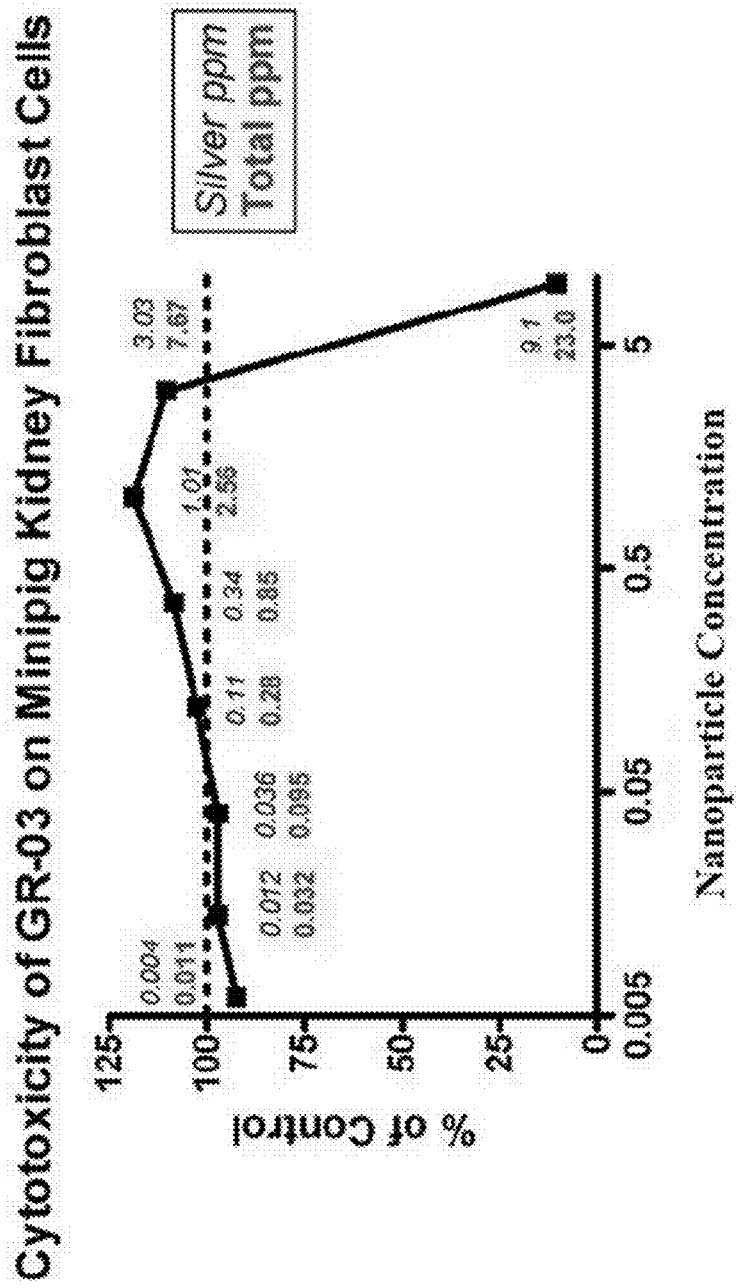
Figure 51B:
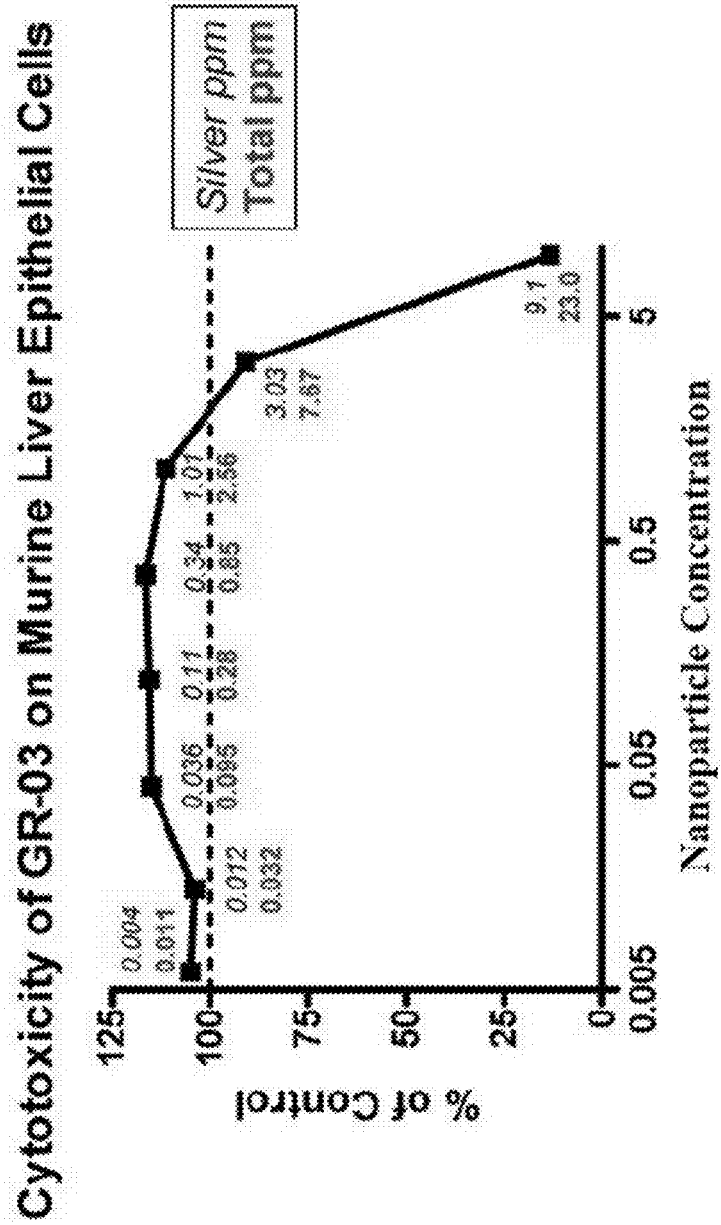

With regard to FIGS. 51a and 51b, the performance of solution "GR3" was tested against both mini-pig kidney fibroblast cells (FIG. 51a) and murine liver epithelial cells (FIG. 51b).

Figure 51C:
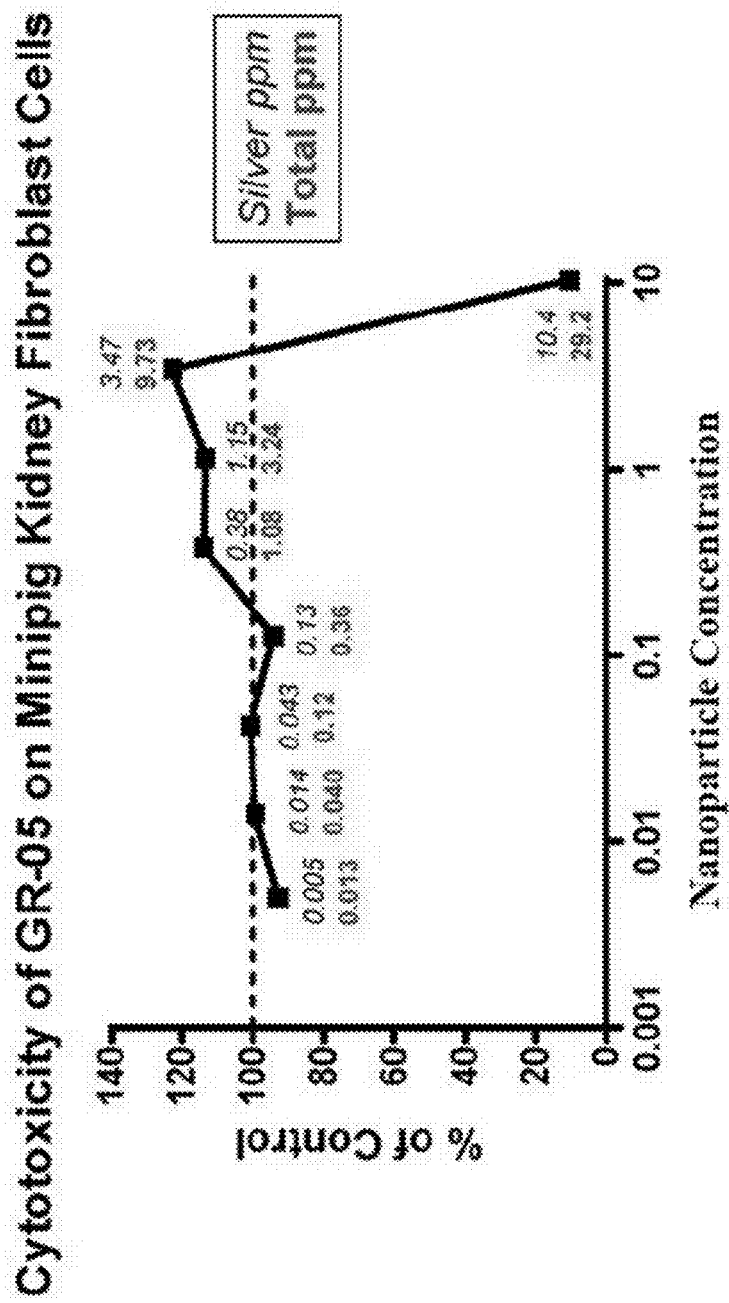
Figure 51D:
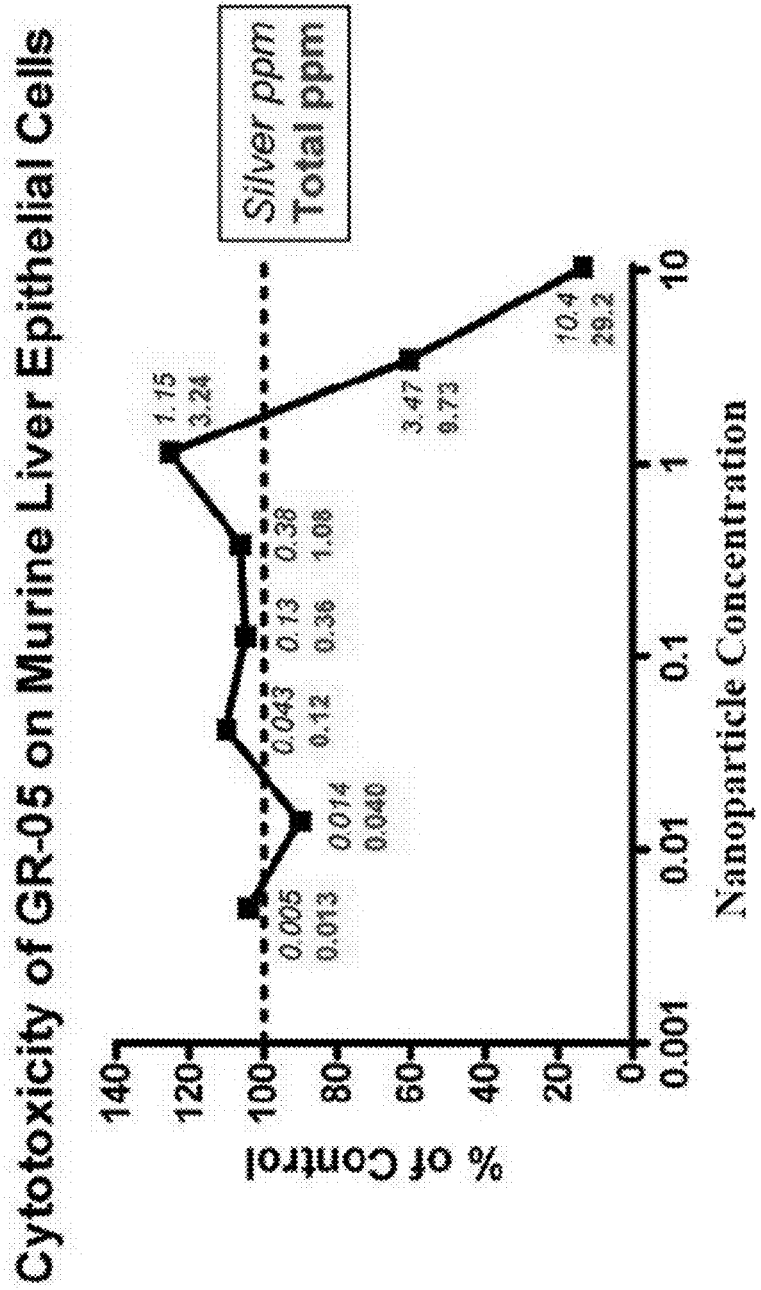
Figure 51E:
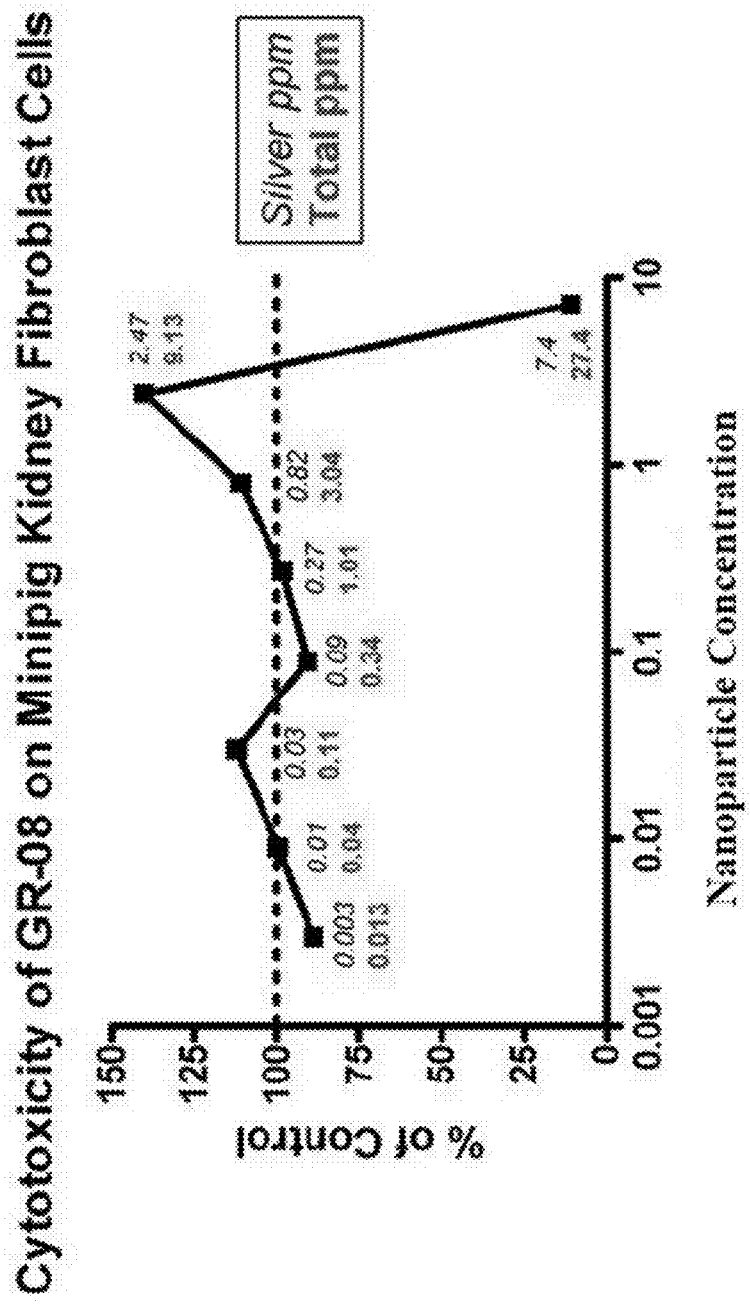
Figure 51F:
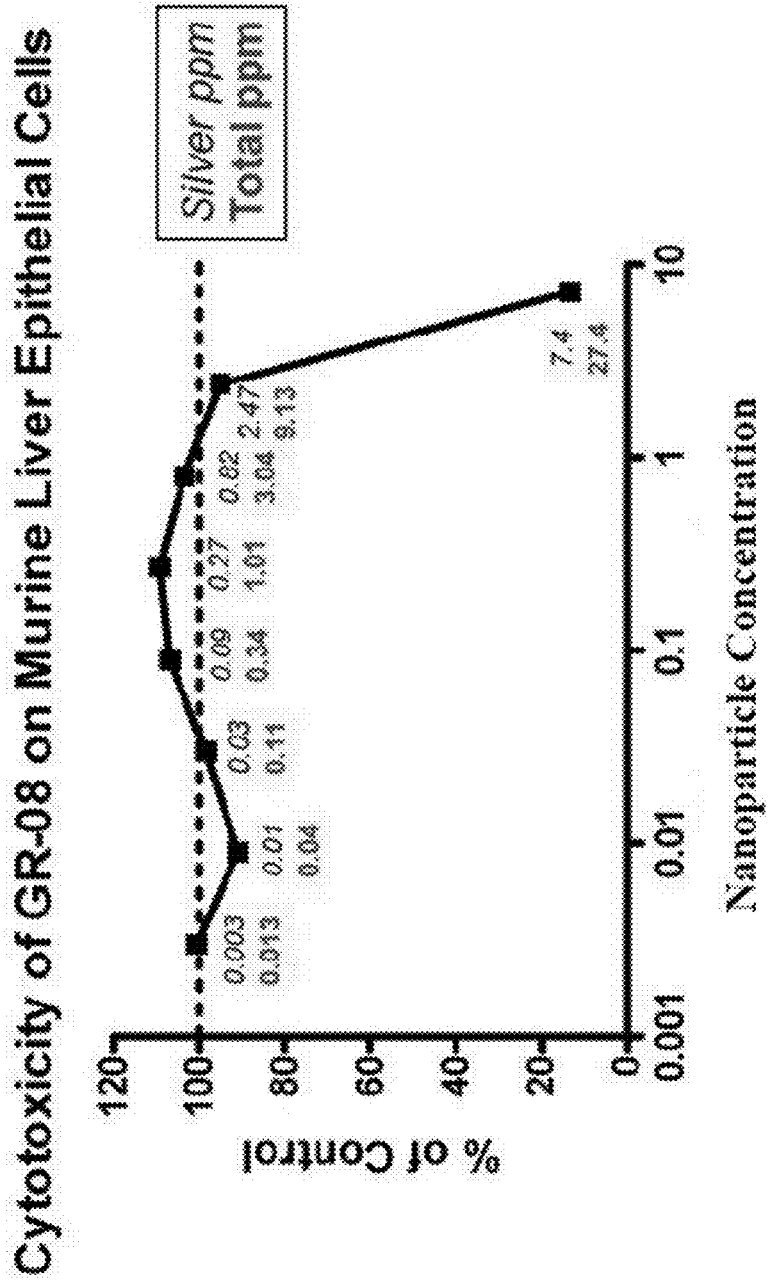
Figure 51G:
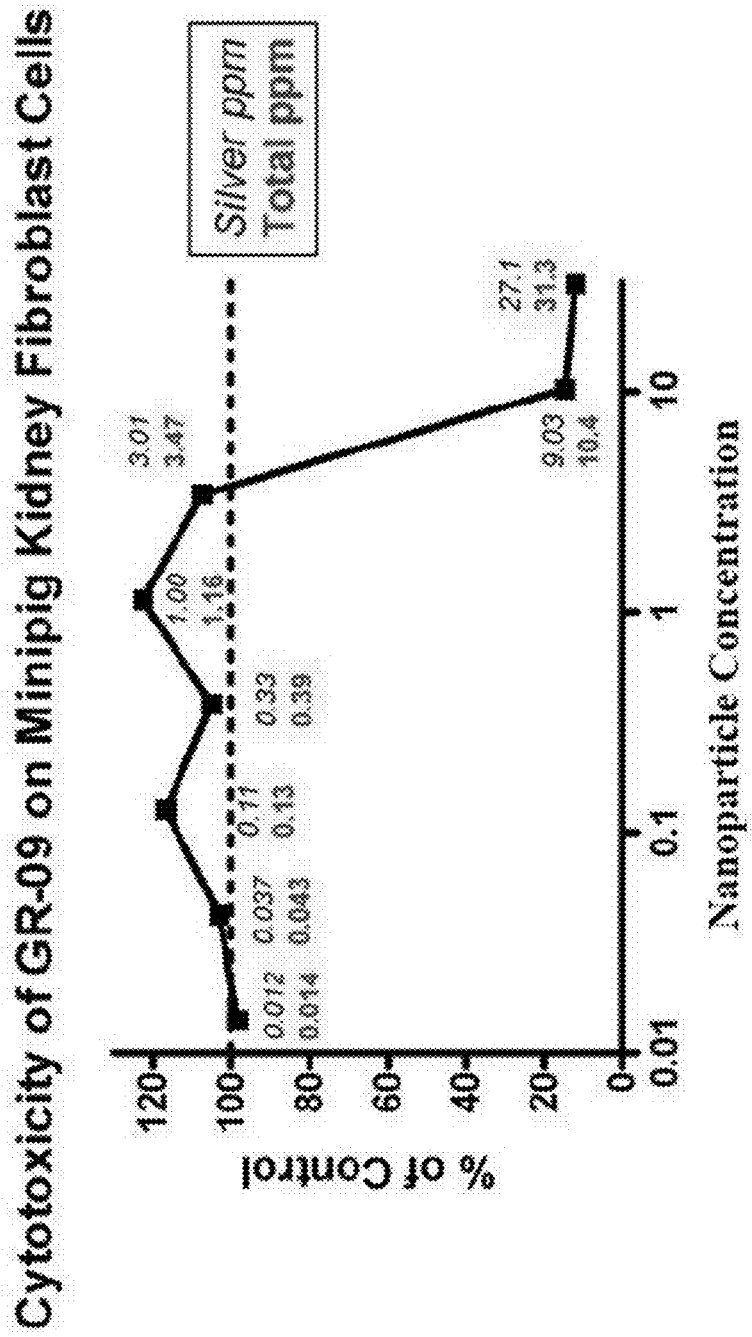
Figure 51H:
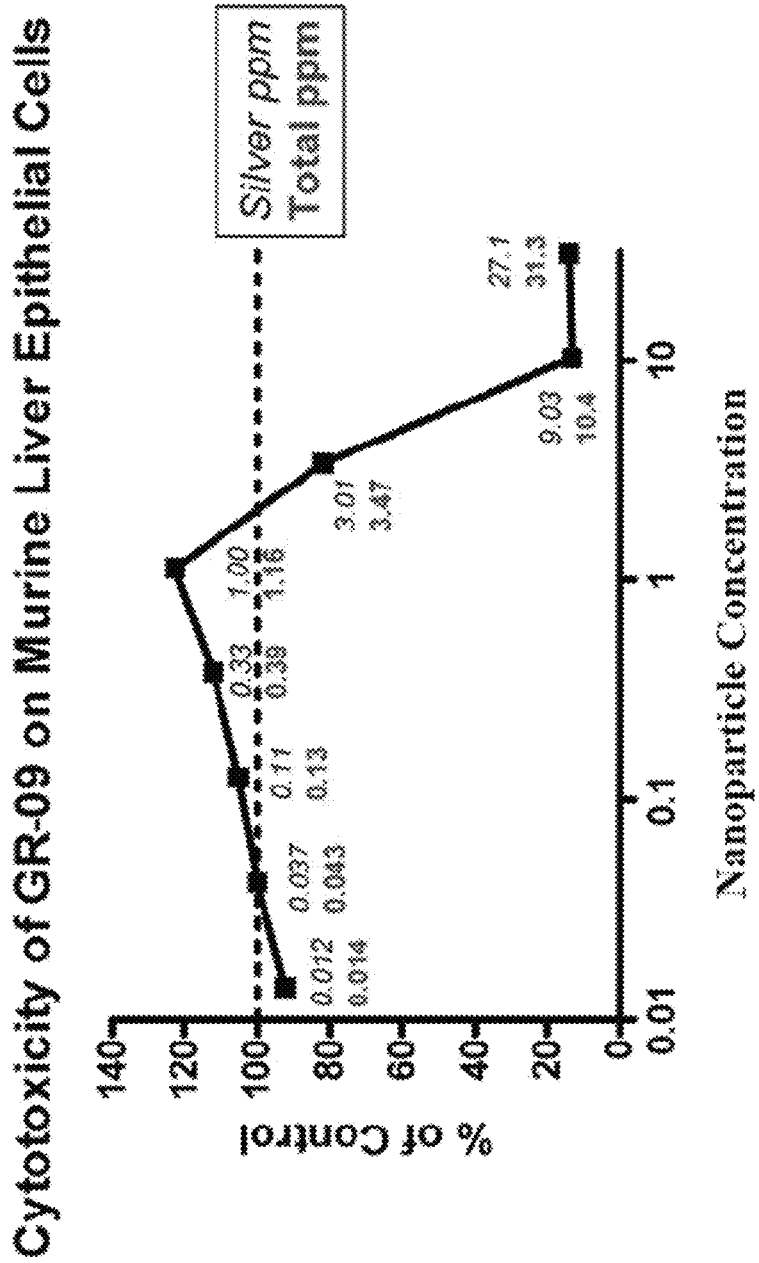
Figure 52A:
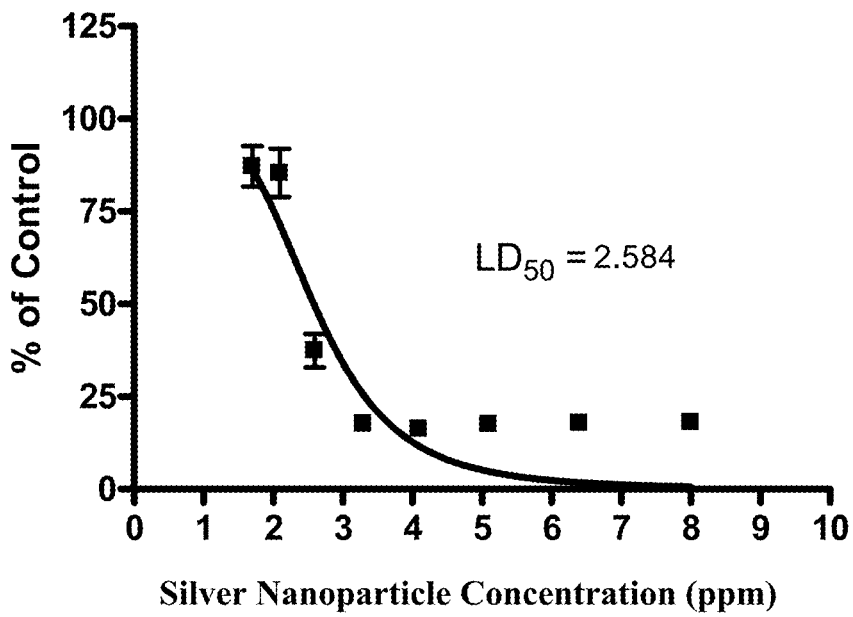
Figure 52B:
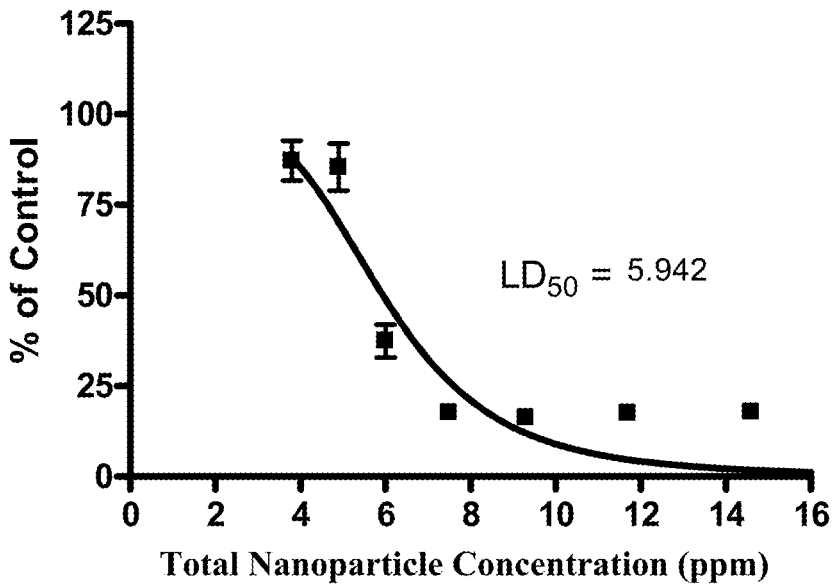
Figure 52C:
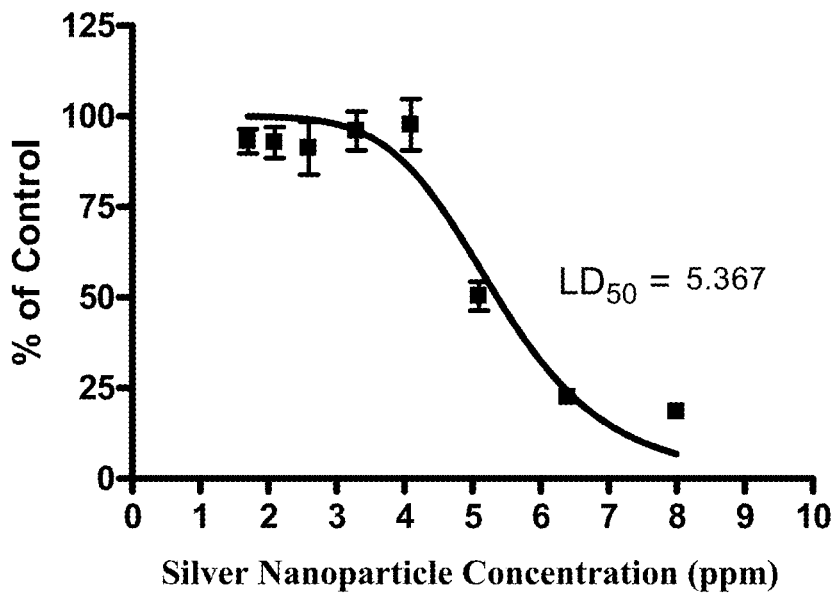
Figure 52D:
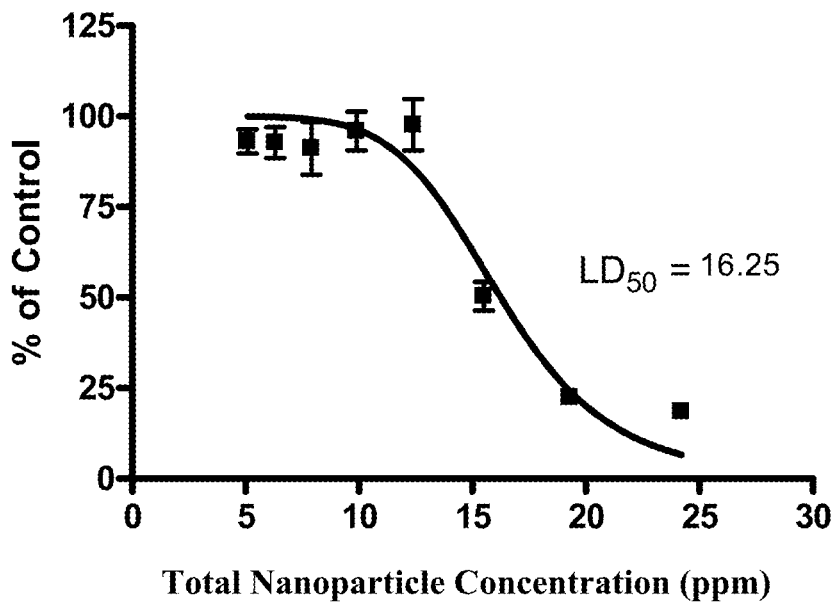
Figure 52E:
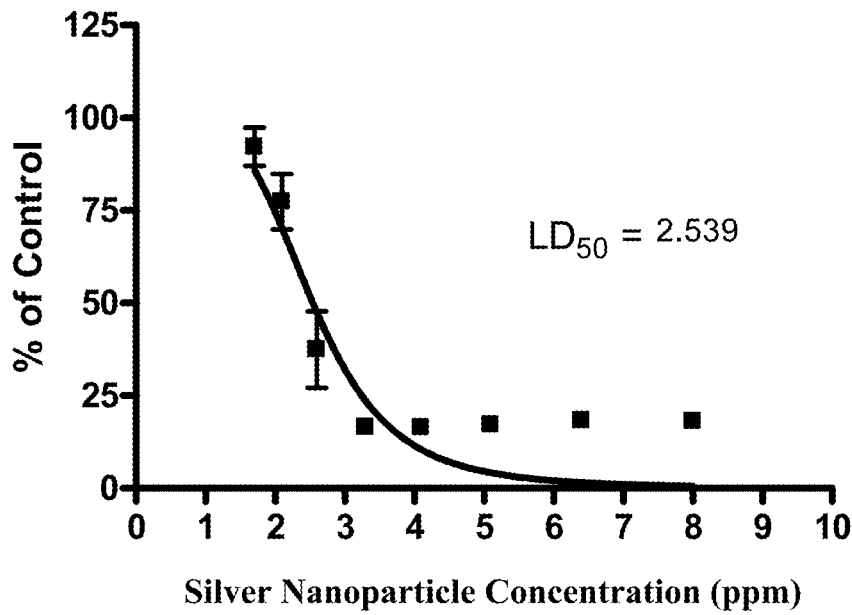
Figure 52F:
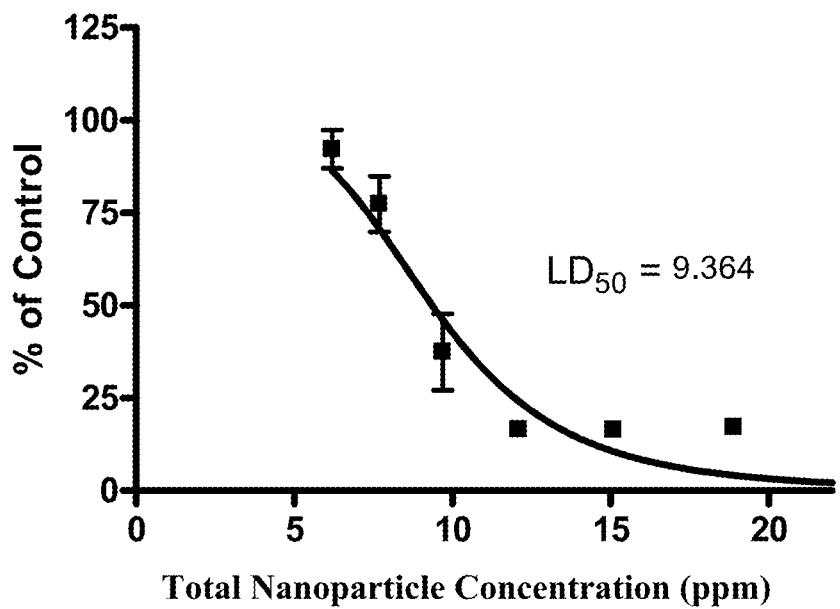
Figure 53A:
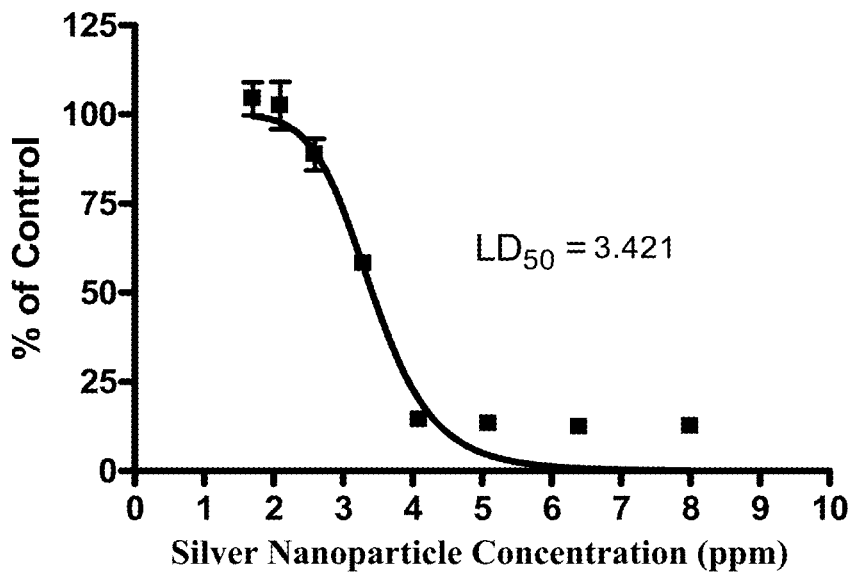
Figure 53B:
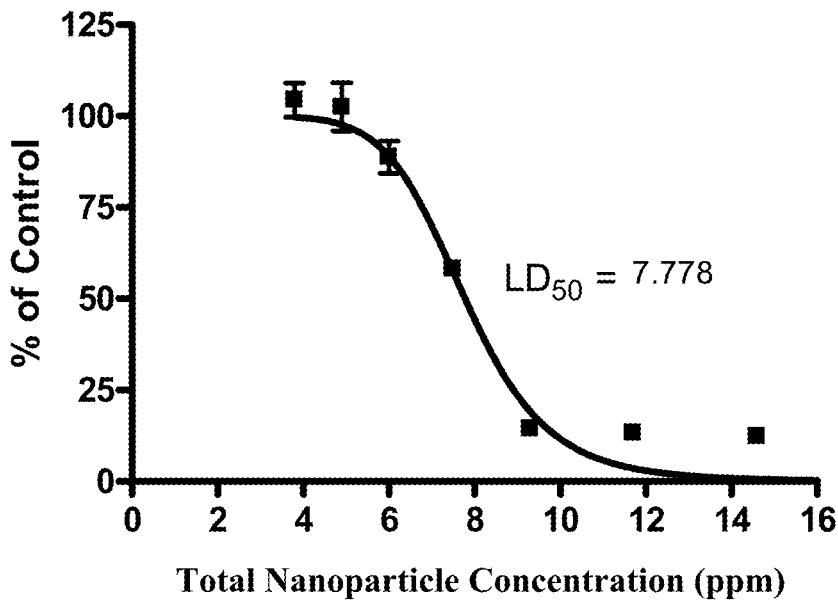
Figure 53C:
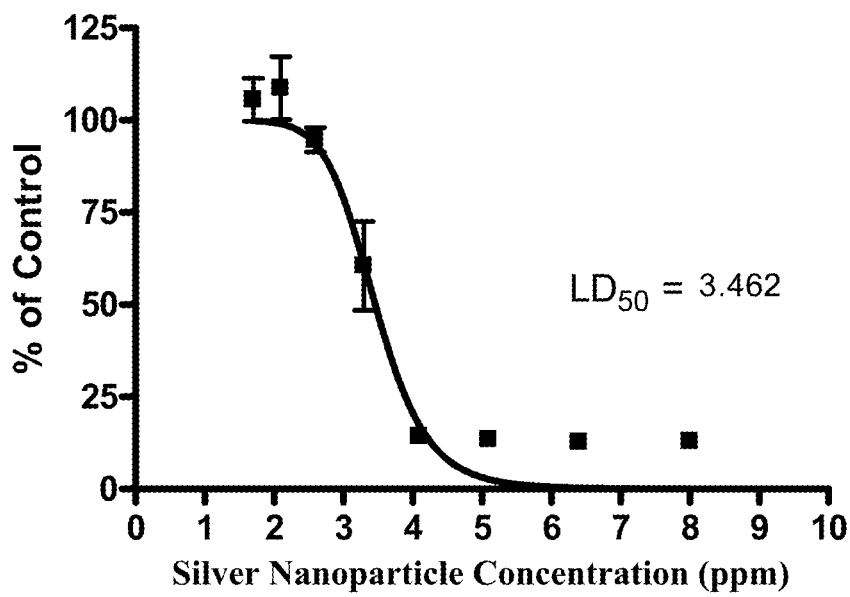
Figure 53D:
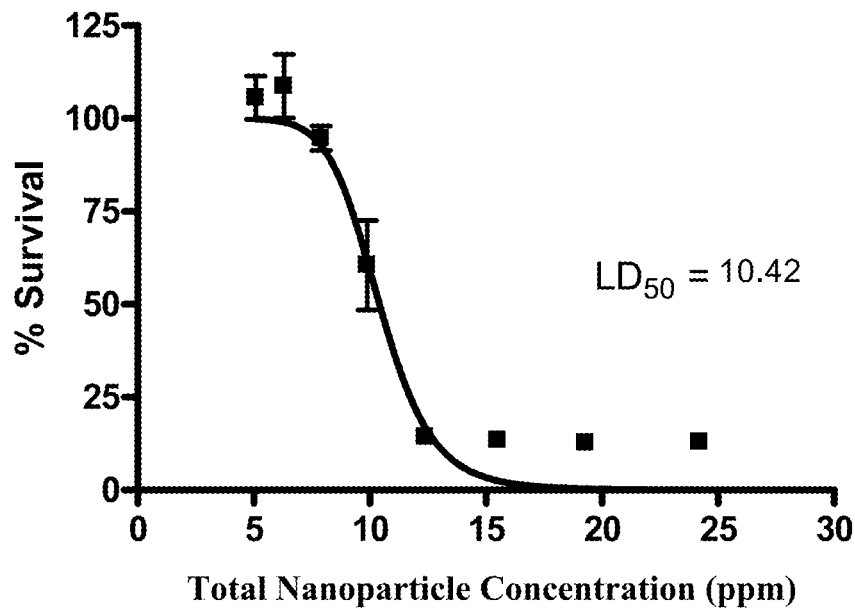
Figure 53E:
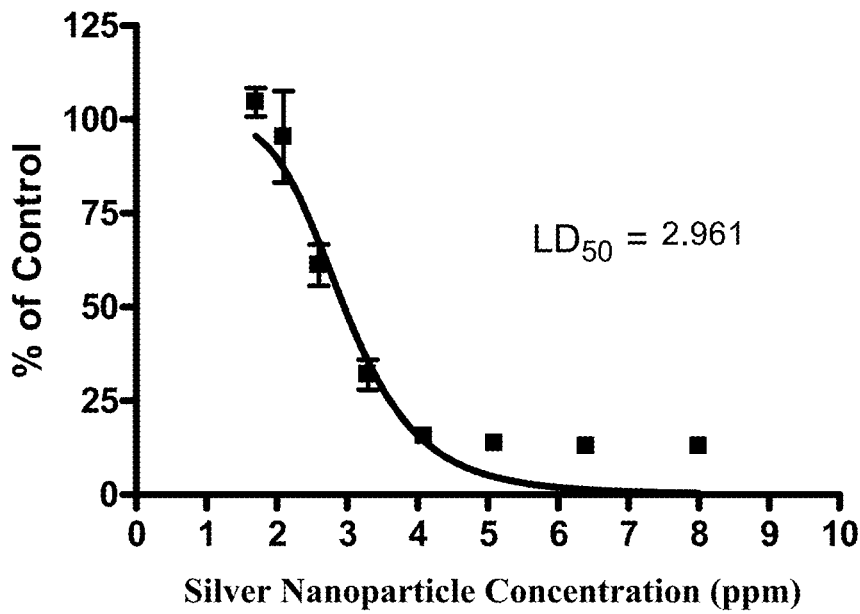
Figure 53F:
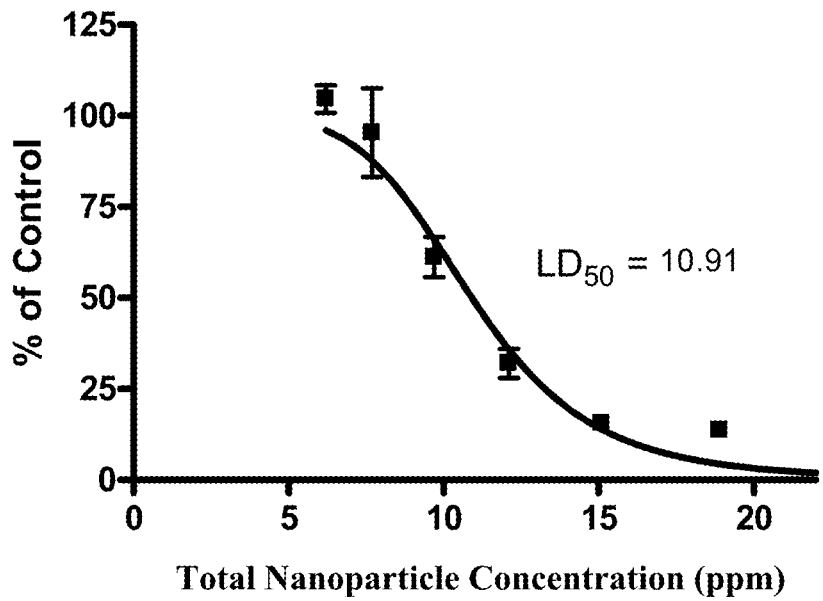
Figure 53G:
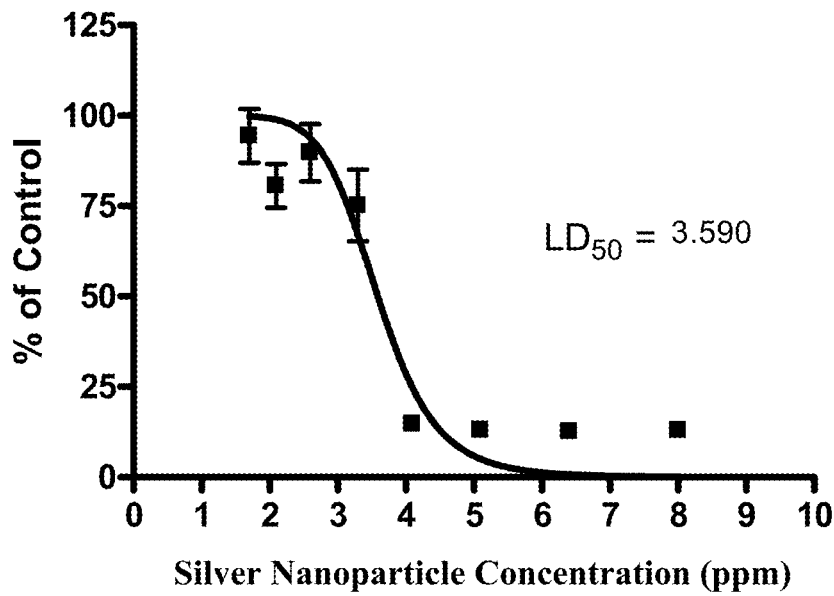
Figure 53H:
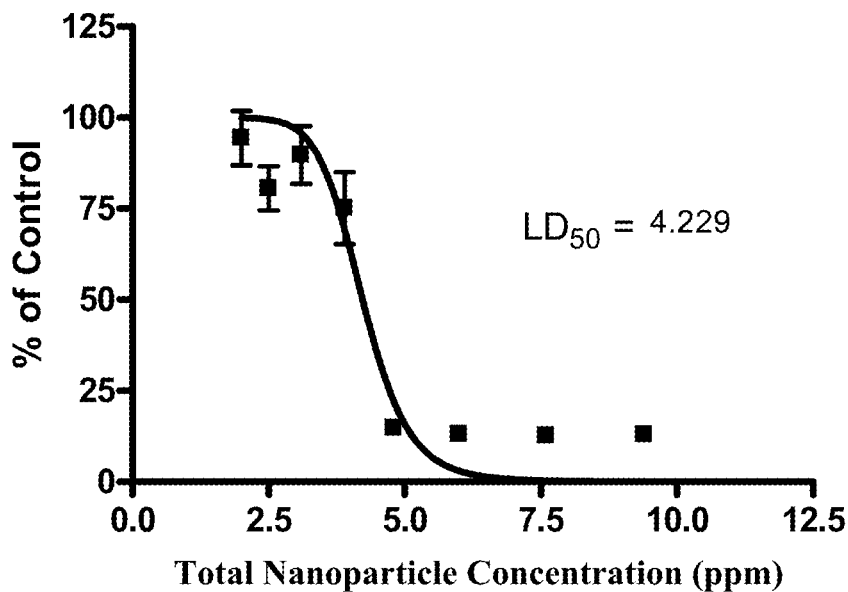

Similarly, FIGS. 51c and 51d tested the performance of GR5 against kidney cells and murine liver cells, respectively; FIGS. 51e and 51f tested the performance of GR8 against kidney cells and liver cells, respectively; and FIGS. 51g and 51h tested the performance of GR9 against kidney cells and liver cells, respectively.

In each of FIGS. 51a-51h, a biphasic response is noted. A biphasic response occurred at different concentrations for each solution and set of cells, however, the general trend or each solution tested showed that a certain concentration of nanoparticles produced according to the embodiments disclosed herein exhibited enhanced growth rates for each of the kidney and liver cells, relative to control. In this regard, any portion of any of the curves that are vertically above the dotted line corresponding to 100% (i.e., control) had a higher flourometer reading from the generated flourenscence discussed above herein. Accordingly, it is clear that particles and/or nanoparticle solutions made according to the present invention can have an enhanced growth rate effect on mammalian cells including at least, kidney and liver cells.

FIGS. 52a-52f tested a narrower response range of both silver nanoparticle concentrations and total nanoparticle concentrations. The values "$LD_{50}$" reported for each of the solutions 3, 5 and 8 in each of FIGS. 52ab, 52cd, and 52ef, respectively, correspond to the parts per million of silver-based nanoparticles (FIGS. 52a, c and e) and total nanoparticle parts per million (corresponding to FIGS. 52b, d and f). With regard to the silver nanoparticle concentration, it is clear that $LD_{50}$'s range between about 2.5 to about 5.4. In contrast, the $LD_{50}$'s for the total nanoparticle solutions vary from about 6 to about 16.

With regard to FIG. 53a-53h, "$LD_{50}$" measurements were made for each solution GR3, GR5, GR8 and GR9 against mini-pig kidney fibroblast cells. As shown in each of these Figures, the "$LD_{50}$" values for total nanoparticles present ranged from a low of about 4.3 for GR9 to a high of about 10.5-11 for each of GR5 and GR8.

Example 6

Manufacturing Silver-Based Nanoparticles/Nanoparticle Solutions AT098, AT099 and AT100 without the Use of any Plasmas This Example utilizes the same basic apparatus used to make the solutions of Examples 1-5. However, this Example does not utilize any electrode(s) 5. This Example utilizes 99.95% pure silver electrodes for each electrode 1. Tables 11a, 11b and 11c summarize portions of electrode design, configuration, location and operating voltages. As shown in Tables 11a, 11b and 11c, the target voltages were set to a low of about 2,750 volts in Electrode Set #8 and to a high of about 4,500 volts in Electrode Sets #1-3. The high of 4,500 volts essentially corresponds to an open circuit which is due to the minimal conductivity of the liquid 3 between each electrode 1, 1' in Electrode Sets #1-3

Further, bar charts of the actual and target voltages for each electrode in each electrode set, are shown in FIGS. 55a, 55b and 55c. Accordingly, the data contained in Tables 11a, 11b and 11c, as well as FIGS. 55a, 55b and 55c, give a complete understanding of the electrode design in each electrode set as well as the target and actual voltages applied to each electrode for the inventive manufacturing process. To maintain consistency with the reported electrode configurations of Examples 1-5, space for eight sets of electrodes have been included in each of Tables 11a, 11b and 11c, even though Run ID "AT100" was the only run that actually used eight sets of electrodes.

TABLE 11a

Run ID: AT098
Flow Rate: 200 ml/min

| Set # | Electrode # | Target Voltage (kV) | Distance "c-c" in/mm | Distance "x" in/mm | Average Voltage (kV) |
|---|---|---|---|---|---|
| | | | 7/177.8* | | |
| 1 | 5a | 4.54 | | N/A | 4.54 |
| | 5a' | 4.52 | | N/A | 4.51 |
| | | | 65/1651** | | |
| N/A | | | | | |
| N/A | | | | | |
| N/A | | | | | |
| N/A | | | | | |
| N/A | | | | | |
| N/A | | | | | |
| N/A | | | | | |
| | | | Output Water Temperature | | 24° C. |

*Distance from water inlet to center of first electrode set
**Distance from center of last electrode set to water outlet TABLE 11b Run ID: AT099
Flow Rate: 200 ml/min

| Set # | Electrode # | Target Voltage (kV) | Distance "c-c" in/mm | Distance "x" in/mm | Average Voltage (kV) |
|---|---|---|---|---|---|
| | | | 7/177.8* | | |
| 1 | 5a | 4.54 | | N/A | 4.53 |
| | 5a' | 4.52 | | N/A | 4.49 |
| | | | 8/203.2 | | |
| 2 | 5b | 4.55 | | N/A | 4.56 |
| | 5b' | 4.51 | | N/A | 4.52 |
| | | | 57/1447.8** | | |
| N/A | | | | | |
| N/A | | | | | |
| N/A | | | | | |
| N/A | | | | | |
| N/A | | | | | |
| N/A | | | | | |
| | | | Output Water Temperature | | 24° C. |

*Distance from water inlet to center of first electrode set
**Distance from center of last electrode set to water outlet TABLE 11c Run ID: AT100
Flow Rate: 200 ml/min

| Set # | Electrode # | Target Voltage (kV) | Distance "c-c" in/mm | Distance "x" in/mm | Average Voltage (kV) |
|---|---|---|---|---|---|
| | | | 7/177.8* | | |
| 1 | 5a | 4.53 | | N/A | 4.53 |
| | 5a' | 4.49 | | N/A | 4.49 |
| | | | 8/203.2 | | |
| 2 | 5b | 4.51 | | N/A | 4.51 |
| | 5b' | 4.48 | | N/A | 4.47 |
| | | | 8/203.2 | | |
| 3 | 5c | 4.52 | | N/A | 4.52 |
| | 5c' | 4.45 | | N/A | 4.45 |
| | | | 8/203.2 | | |
| 4 | 5d | 4.40 | | N/A | 4.40 |
| | 5d' | 4.32 | | N/A | 4.32 |
| | | | 9/228.6 | | |
| 5 | 5e | 4.38 | | N/A | 4.37 |
| | 5e' | 4.27 | | N/A | 4.26 |
| | | | 8/203.2 | | |
| 6 | 5f | 3.85 | | N/A | 3.80 |
| | 5f' | 3.71 | | N/A | 3.65 |
| | | | 8/203.2 | | |
| 7 | 5g | 3.55 | | N/A | 3.43 |
| | 5g' | 3.30 | | N/A | 3.23 |
| | | | 8/203.2 | | |
| 8 | 5h | 2.79 | | N/A | 2.76 |
| | 5h' | 2.75 | | N/A | 2.69 |
| | | | 8/203.2** | | |
| | | | Output Water Temperature | | 82° C. |

*Distance from water inlet to center of first electrode set
**Distance from center of last electrode set to water outlet Atomic Absorption Spectroscopy (AAS) samples were prepared and measurement values were obtained. Slight process modifications were incorporated into those AAS procedures discussed earlier herein. These process changes are incorporated immediately below.

The AAS values were obtained from a Perkin Elmer AAnalyst 300 Spectrometer system, as in Examples 1-5. The samples manufactured in accordance with Examples 6-12 were prepared by adding a small amount of nitric acid or hydrochloric acid (usually 2-4% of final volume) and then dilution to a desirable characteristic concentration range or linear range of the specific element to improve accuracy of the result. The "desireable" range is an order of magnitude estimate based on production parameters established during product development. For pure metals analysis, a known amount of feedstock material is digested in a known amount of acid and diluted to ensure that the signal strength of the absorbance will be within the tolerance limits and more specifically the most accurate range of the detector settings, better known as the linear range.

The specific operating procedure for the Perkin Elmer AAnalyst 300 system is as follows:

I) Principle

The Perkin Elmer AAnalyst 300 system consists of a high efficiency burner system with either a sapphire GemTip or stainless steel beaded nebulizer and an atomic absorption spectrometer. The burner system provides the thermal energy necessary to dissociate the chemical compounds, providing free analyte atoms so that atomic absorption occurs. The spectrometer measures the amount of light absorbed at a specific wavelength using a hollow cathode lamp as the primary light source, a monochromator and a detector. A deuterium arc lamp corrects for background absorbance caused by non-atomic species in the atom cloud.

II) Instrument Setup
   A) Empty waste container to mark. Add deionized water to drain tubing to ensure that water is present in the drain system float assembly.
   B) Ensure that the appropriate Hollow Cathode Lamp for the analyte to be analyzed is properly installed in the turret.
   C) Power AAnalyst 300 and computer ON.
   D) After the AAnalyst 300 has warmed up for a minimum of 30 minutes, start the AAWin Analyst software
   E) Recall Method to be analyzed.
   F) Ensure that the correct Default Conditions are entered.
   G) Align the Hollow Cathode Lamp.
      1) Allow HCL's to warm and stabilize for a minimum of 15 minutes.
      2) Check that a proper peak and energy level has been established for the specific lamp.
      3) Adjust the power and frequency of the lamp settings to obtain maximum energy.
   H) Store Method changes in Parameter Entry, Option, Store and #.
   I) Adjust Burner height.
      1) Place a white sheet of paper behind the burner to confirm the location of the light beam.
      2) Lower the burner head below the light beam with the vertical adjustment knob.
      3) Press Cont (Continuous) to display an absorbance value.
      4) Press A/Z to Autozero.
      5) Raise the burner head with the vertical adjustment knob until the display indicates a slight absorbance (0.002). Slowly lower the head until the display returns to zero. Lower the head an additional quarter turn to complete the adjustment.
   J) Ignite flame.
      1) Open air compressor valve. Set pressure to 50 to 65 psi.
      2) Open acetylene gas cylinder valve. Set output pressure to 12 to 14 psi. Replace cylinder when pressure falls to 75 psi to prevent valve and tubing damage from the presence of acetone.
      3) Press Gases On/Off. Adjust oxidant flow to 4 Units.
      4) Press Gases On/Off. Adjust acetylene gas flow to 2 Units.
      5) Press Flame On/Off to turn flame on.
         Note: Do not directly view the lamp or flame without protective ultraviolet radiation eyewear.
   K) Aspirate deionized water through the burner head to fully warm the burner head for 3 to 5 minutes.
   L) Adjust Burner Position and Nebulizer.
      1) Aspirate a standard with a signal of approximately 0.2-0.5 absorbance units.
      2) Obtain maximum burner position absorbance by rotating the horizontal, vertical and rotational adjustment knobs.
      3) Loosen the nebulizer locking ring by turning it clockwise. Slowly turn the nebulizer adjustment knob to obtain maximum absorbance. Lock the knob in place with the locking ring.
         Note: An element, such as Silver, which is at a wavelength where gases do not absorb is optimal for adjusting the Burner and Nebulizer.
III) Calibration Procedure
   A) Calibrate with standards that bracket the sample concentrations.
   B) WinAA Analyst software will automatically create a calibration curve for your sample readings. But check to ensure that proper absorption is established with each calibration standard.
   C) Enter Standard Concentration Values in the Default Conditions to calculate an AAnalyst 300 standard curve.
      1) Enter the concentration of the lowest standard for STD1 using significant digits.
      2) Enter the concentrations of the other standards of the calibration curve in ascending order and the concentration of the reslope standard.
      3) Autozero with the blank before acquiring calibration values.
      4) Aspirate Standard 1, press 0 Calibrate to clear the previous curve. Aspirate the standards in numerical order.
      Press standard number and calibrate for each standard.
      5) Press Print to print the graph and correlation coefficient.
      6) Rerun one or all standards, if necessary. To rerun Standard 3, aspirate standard and press 3 Calibrate.
   D) The correlation coefficient should be greater than or equal to 0.990.
   E) Check the calibration curve for drift, accuracy and precision with calibration standards continuously during operation, at minimum, one every 20 samples.
IV) Analysis Procedure
   A) Samples are measured in triplicate using a minimum of 3 replicates per sample.
   B) Aspirate sample and press Read Sample. The software will take 3 readings of absorbance and then average those readings. Wait until software says idle. Rerun the sample if the standard deviation is greater than 50% of the sample result.
V) Instrument Shutdown
   A) Aspirate 2% Nitric Acid ($HNO_3$) for 1-3 minutes and deionized water for 3-5 minutes to clean the burner head. Remove the capillary tube from the water and run burner-head dry for about 1 minute.
   B) Press Flame On/Off to turn off flame.
   C) Close air compressor valve.
   D) Close acetylene cylinder valve.
   E) Press Bleed Gases to bleed the acetylene gas from the lines. The cylinder pressure should drop to zero.
   F) Exit the software, power OFF the AAnalyst 300, and shut down the computer.

TABLE 11d

| Run ID | Electrode Configuration | Measured PPM |
| --- | --- | --- |
| AT098 | 0XXXXXXX | Below Detectable Limit |
| AT099 | 00XXXXXX | Less Than 0.2 PPM |
| AT100 | 00000000 | 7.1 PPM |

Table 11d shows the results obtained from Example 6. Table 11d contains a column entitled "Electrode Configuration". This column contains characters "0" and "X". The character "0" corresponds to one electrode set 5, 5'. The character "X" represents that no electrodes were present. Thus, for Run ID "AT098", only a single electrode set 5a, 5a' was utilized. No detectable amount of silver was measurable by the AAS techniques disclosed herein. Run ID "AT099" utilized two electrode sets 5a, 5a' and 5b, 5b'. The AAS techniques detected some amount of silver as being present, but that amount was less than 0.2 ppm. Run ID "AT100" utilized eight electrode sets, 5, 5'. This configuration resulted in a measured ppm of 7.1 ppm. Accordingly, it is possible to obtain metallic-based constituents (e.g., metallic-based nanoparticles/nanoparticle solution) without the use of an electrode 1 (and an associated plasma 4). However, the rate of formation of metallic-based constituents is much less than that rate obtained by using one or more plasmas 4. For example, Examples 1-3 disclosed silver-based products associated with Run ID's AT031, AT036 and AT038. Each of those Run ID's utilized two electrode sets that included adjustable plasmas 4. The measured silver ppm for each of these samples was greater than 40 ppm, which is 5-6 times more than what was measured in the product made according to Run ID AT100 in this Example 6. Thus, while it is possible to manufacture metallic-based constituents without the use of at least one adjustable plasma 4 (according to the teachings herein) the rates of formation of metallic based constituents are greatly reduced when no plasmas 4 are utilized as part of the production techniques.

Accordingly, even though eight electrode sets 5, 5 were utilized to make the product associated with Run AT100, the lack of any electrode sets including at least one electrode 1 (i.e., the lack of plasma 4), severely limited the ppm content of silver in the solution produced.

Example 7

Manufacturing Silver-Based Nanoparticles/Nanoparticle Solutions AT080, AT081, AT082, AT083, AT084, AT085, AT086 and AT097 Using Only a Single Plasma This Example utilizes the same basic apparatus used to make the solutions of Examples 1-5, however, this Example uses only a single plasma 4. Specifically, for Electrode Set #1, this Example uses a "1a, 5a" electrode configuration. Subsequent Electrode Sets #2-#8 are sequentially added. Each of Electrode Sets #2-#8 have a "5, 5'" electrode configuration. This Example also utilizes 99.95% pure silver electrodes for each of electrodes 1 and 5 in each Electrode Set.

Tables 12a-12h summarize portions of electrode design, configuration, location and operating voltages. As shown in Tables 12a-12h, the target voltages were set to a low of about 900 volts (at Electrode Set #8) and a high of about 2,300 volts (at Electrode Set #1).

Further, bar charts of the actual and target voltages for each electrode in each electrode set, are shown in FIGS. 56a, 56b, 56c, 56d, 56e, 56f, 56g and 56h. Accordingly, the data contained in Tables 12a-12h, as well as FIGS. 56a, 56b, 56c, 56d, 56e, 56f, 56g and 56h, give a complete understanding of the electrode design in each electrode set as well as the target and actual voltages applied to each electrode for the manufacturing processes. To maintain consistency with the reported electrode configurations of Examples 1-5, space for eight sets of electrodes have been included in each in each of Tables 12a, 12b, 12c, 12d, 12e, 12f, 12g and 12h even though Run ID "AT080" was the only run that actually used eight sets of electrodes.

TABLE 12a

Run ID: AT097
Flow Rate: 200 ml/min

| Set # | Electrode # | Target Voltage (kV) | Distance "c-c" in/mm | Distance "x" in/mm | Average Voltage (kV) |
|---|---|---|---|---|---|
|  |  |  | 7/177.8* |  |  |
| 1 | 1a | 1.78 |  | .26/6.8 | 1.79 |
|  | 5a | 1.82 |  | N/A | 1.79 |
|  |  |  | 65/1651** |  |  |
| N/A |  |  |  |  |  |
| N/A |  |  |  |  |  |
| N/A |  |  |  |  |  |
| N/A |  |  |  |  |  |
| N/A |  |  |  |  |  |
| N/A |  |  |  |  |  |
| N/A |  |  |  |  |  |
|  |  | Output Water Temperature |  |  | 35° C. |

*Distance from water inlet to center of first electrode set
**Distance from center of last electrode set to water outlet TABLE 12b Run ID: AT086
Flow Rate: 200 ml/min

| Set # | Electrode # | Target Voltage (kV) | Distance "c-c" in/mm | Distance "x" in/mm | Average Voltage (kV) |
|---|---|---|---|---|---|
|  |  |  | 7/177.8* |  |  |
| 1 | 1a | 2.18 |  | .26/6.8 | 2.15 |
|  | 5a | 1.63 |  | N/A | 1.67 |
|  |  |  | 8/203.2 |  |  |
| 2 | 5b | 1.05 |  | N/A | 1.05 |
|  | 5b' | 1.39 |  | N/A | 1.43 |
|  |  |  | 57/1447.8** |  |  |
| N/A |  |  |  |  |  |
| N/A |  |  |  |  |  |
| N/A |  |  |  |  |  |
| N/A |  |  |  |  |  |
| N/A |  |  |  |  |  |
| N/A |  |  |  |  |  |
|  |  | Output Water Temperature |  |  | 38° C. |

*Distance from water inlet to center of first electrode set
**Distance from center of last electrode set to water outlet TABLE 12c Run ID: AT085
Flow Rate: 200 ml/min

| Set # | Electrode # | Target Voltage (kV) | Distance "c-c" in/mm | Distance "x" in/mm | Average Voltage (kV) |
|---|---|---|---|---|---|
|  |  |  | 7/177.8* |  |  |
| 1 | 1a | 2.24 |  | .26/6.8 | 2.19 |
|  | 5a | 1.79 |  | N/A | 1.79 |
|  |  |  | 8/203.2 |  |  |
| 2 | 5b | 1.16 |  | N/A | 1.16 |
|  | 5b' | 1.24 |  | N/A | 1.23 |
|  |  |  | 8/203.2 |  |  |
| 3 | 5c | 1.12 |  | N/A | 1.14 |
|  | 5c' | 1.34 |  | N/A | 1.35 |
|  |  |  | 49/1244.6** |  |  |
| N/A |  |  |  |  |  |
| N/A |  |  |  |  |  |
| N/A |  |  |  |  |  |

TABLE 12c-continued

Run ID: AT085  
Flow Rate: 200 ml/min

| Set # | Electrode # | Target Voltage (kV) | Distance "c-c" in/mm | Distance "x" in/mm | Average Voltage (kV) |
|---|---|---|---|---|---|
| N/A | | | | | |
| N/A | | | | | |
| | | | Output Water Temperature | | 43° C. |

*Distance from water inlet to center of first electrode set  
**Distance from center of last electrode set to water outlet

TABLE 12d

Run ID: AT084  
Flow Rate: 200 ml/min

| Set # | Electrode # | Target Voltage (kV) | Distance "c-c" in/mm | Distance "x" in/mm | Average Voltage (kV) |
|---|---|---|---|---|---|
| | | | 7/177.8* | | |
| 1 | 1a | 2.29 | | .26/6.8 | 2.25 |
| | 5a | 1.95 | | N/A | 1.94 |
| | | | 8/203.2 | | |
| 2 | 5b | 1.27 | | N/A | 1.26 |
| | 5b' | 1.39 | | N/A | 1.39 |
| | | | 8/203.2 | | |
| 3 | 5c | 1.35 | | N/A | 1.34 |
| | 5c' | 1.26 | | N/A | 1.25 |
| | | | 8/203.2 | | |
| 4 | 5d | 1.31 | | N/A | 1.32 |
| | 5d' | 1.59 | | N/A | 1.56 |
| | | | 41/1041.4** | | |
| N/A | | | | | |
| N/A | | | | | |
| N/A | | | | | |
| N/A | | | | | |
| | | | Output Water Temperature | | 49° C. |

*Distance from water inlet to center of first electrode set  
**Distance from center of last electrode set to water outlet

TABLE 12e

Run ID: AT083  
Flow Rate: 200 ml/min

| Set # | Electrode # | Target Voltage (kV) | Distance "c-c" in/mm | Distance "x" in/mm | Average Voltage (kV) |
|---|---|---|---|---|---|
| | | | 7/177.8* | | |
| 1 | 1a | 2.17 | | .26/6.8 | 2.16 |
| | 5a | 1.72 | | N/A | 1.74 |
| | | | 8/203.2 | | |
| 2 | 5b | 1.10 | | N/A | 1.12 |
| | 5b' | 1.32 | | N/A | 1.34 |
| | | | 8/203.2 | | |
| 3 | 5c | 1.25 | | N/A | 1.24 |
| | 5c' | 1.12 | | N/A | 1.13 |
| | | | 8/203.2 | | |
| 4 | 5d | 1.31 | | N/A | 1.29 |
| | 5d' | 1.32 | | N/A | 1.33 |
| | | | 9/228.6 | | |
| 5 | 5e | 1.63 | | N/A | 1.64 |
| | 5e' | 1.52 | | N/A | 1.52 |
| | | | 32/812.8** | | |

TABLE 12e-continued

Run ID: AT083  
Flow Rate: 200 ml/min

| Set # | Electrode # | Target Voltage (kV) | Distance "c-c" in/mm | Distance "x" in/mm | Average Voltage (kV) |
|---|---|---|---|---|---|
| N/A | | | | | |
| N/A | | | | | |
| N/A | | | | | |
| | | | Output Water Temperature | | 56° C. |

*Distance from water inlet to center of first electrode set  
**Distance from center of last electrode set to water outlet

TABLE 12f

Run ID: AT082  
Flow Rate: 200 ml/min

| Set # | Electrode # | Target Voltage (kV) | Distance "c-c" in/mm | Distance "x" in/mm | Average Voltage (kV) |
|---|---|---|---|---|---|
| | | | 7/177.8* | | |
| 1 | 1a | 2.18 | | .26/6.8 | 2.17 |
| | 5a | 1.76 | | N/A | 1.75 |
| | | | 8/203.2 | | |
| 2 | 5b | 1.08 | | N/A | 1.09 |
| | 5b' | 1.31 | | N/A | 1.32 |
| | | | 8/203.2 | | |
| 3 | 5c | 1.26 | | N/A | 1.26 |
| | 5c' | 1.09 | | N/A | 1.08 |
| | | | 8/203.2 | | |
| 4 | 5d | 1.28 | | N/A | 1.27 |
| | 5d' | 1.25 | | N/A | 1.22 |
| | | | 9/228.6 | | |
| 5 | 5e | 1.60 | | N/A | 1.60 |
| | 5e' | 1.17 | | N/A | 1.17 |
| | | | 8/203.2 | | |
| 6 | 5f | 0.99 | | N/A | 0.98 |
| | 5f' | 1.19 | | N/A | 1.18 |
| | | | 24/609.6** | | |
| N/A | | | | | |
| N/A | | | | | |
| | | | Output Water Temperature | | 63° C. |

*Distance from water inlet to center of first electrode set  
**Distance from center of last electrode set to water outlet

TABLE 12g

Run ID: AT081  
Flow Rate: 200 ml/min

| Set # | Electrode # | Target Voltage (kV) | Distance "c-c" in/mm | Distance "x" in/mm | Average Voltage (kV) |
|---|---|---|---|---|---|
| | | | 7/177.8* | | |
| 1 | 1a | 2.23 | | .26/6.8 | 2.18 |
| | 5a | 1.77 | | N/A | 1.79 |
| | | | 8/203.2 | | |
| 2 | 5b | 1.09 | | N/A | 1.09 |
| | 5b' | 1.30 | | N/A | 1.28 |
| | | | 8/203.2 | | |
| 3 | 5c | 1.22 | | N/A | 1.21 |
| | 5c' | 1.07 | | N/A | 1.07 |
| | | | 8/203.2 | | |
| 4 | 5d | 1.27 | | N/A | 1.27 |
| | 5d' | 1.21 | | N/A | 1.21 |
| | | | 9/228.6 | | |
| 5 | 5e | 1.60 | | N/A | 1.58 |
| | 5e' | 1.26 | | N/A | 1.23 |
| | | | 8/203.2 | | |

TABLE 12g-continued

Run ID: AT081
Flow Rate: 200 ml/min

| Set # | Electrode # | Target Voltage (kV) | Distance "c-c" in/mm | Distance "x" in/mm | Average Voltage (kV) |
|---|---|---|---|---|---|
| 6 | 5f | 1.10 | | N/A | 1.09 |
|  | 5f' | 1.02 | | N/A | 0.99 |
|  |  |  | 8/203.2 |  |  |
| 7 | 5g | 1.14 | | N/A | 1.11 |
|  | 5g' | 1.34 | | N/A | 1.32 |
|  |  |  | 16/406.4** |  |  |
| N/A |  |  |  |  |  |

Output Water Temperature 72 C.
*Distance from water inlet to center of first electrode set
**Distance from center of last electrode set to water outlet

TABLE 12h

Run ID: AT080
Flow Rate: 200 ml/min

| Set # | Electrode # | Target Voltage (kV) | Distance "c-c" in/mm | Distance "x" in/mm | Average Voltage (kV) |
|---|---|---|---|---|---|
|  |  |  | 7/177.8* |  |  |
| 1 | 1a | 2.11 | | .26/6.8 | 2.13 |
|  | 5a | 1.72 | | N/A | 1.73 |
|  |  |  | 8/203.2 |  |  |
| 2 | 5b | 1.00 | | N/A | 1.00 |
|  | 5b' | 1.23 | | N/A | 1.24 |
|  |  |  | 8/203.2 |  |  |
| 3 | 5c | 1.16 | | N/A | 1.16 |
|  | 5c' | 0.97 | | N/A | 0.98 |
|  |  |  | 8/203.2 |  |  |
| 4 | 5d | 1.15 | | N/A | 1.17 |
|  | 5d' | 1.14 | | N/A | 1.14 |
|  |  |  | 9/228.6 |  |  |
| 5 | 5e | 1.47 | | N/A | 1.49 |
|  | 5e' | 1.16 | | N/A | 1.16 |
|  |  |  | 8/203.2 |  |  |
| 6 | 5f | 1.02 | | N/A | 1.02 |
|  | 5f' | 0.98 | | N/A | 0.98 |
|  |  |  | 8/203.2 |  |  |
| 7 | 5g | 1.06 | | N/A | 1.07 |
|  | 5g' | 0.94 | | N/A | 0.96 |
|  |  |  | 8/203.2 |  |  |
| 8 | 5h | 0.92 | | N/A | 0.93 |
|  | 5h' | 1.12 | | N/A | 1.14 |
|  |  |  | 8/203.2** |  |  |

Output Water Temperature 82 C.
*Distance from water inlet to center of first electrode set
**Distance from center of last electrode set to water outlet Atomic Absorption Spectroscopy (AAS) samples were prepared and measurement values were obtained, as discussed in Example 6. Table 12i shows the results. Note that Table 12i includes a column entitled "Electrode Configuration". This column contains characters of "1" and "0" and "X". The "1's" represent an electrode configuration corresponding to Electrode Set #1 (i.e., a 1, 5 combination). The "0's" represent an electrode combination of 5, 5'. The character "X" represents that no electrodes were present. Thus, for example, "AT084" is represented by "1000XXXX" which means a four electrode set combination was used to make "AT084" and the combination corresponded to Set #1=1, 5; Set #2=5, 5; Set #3=5, 5 and Set #4=5, 5 (there were no Sets after Set #4, as represented by "XXXX").

TABLE 12i

| Run ID | Electrode Configuration | Measured Ag PPM (initial) | Measured Ag PPM (10 days) | Average Particle Size Diameter Range (Initial) |
|---|---|---|---|---|
| AT097 | 1XXXXXXX | 6.5 | 6.5 | 2 nm |
| AT086 | 10XXXXXX | 14.9 | 13.4 | 3-7 nm |
| AT085 | 100XXXXX | 19.2 | 18.4 | 3-8 nm |
| AT084 | 1000XXXX | 24.1 | 22.9 | 4-8 nm |
| AT083 | 10000XXX | 30.4 | 28.1 | 6-15 nm |
| AT082 | 100000XX | 34.2 | 27.4 | 20-100 nm |
| AT081 | 1000000X | 36.7 | 29.3 | 40-120 nm |
| AT080 | 10000000 | 40.9 | 31.6 | 40-150 nm |

Table 12i includes a column entitled "Measured Ag PPM (initial)". This column corresponds to the silver content of each of the eight solutions measured within one hour of its production. As shown, the measured ppm increases with each added Electrode Set, wherein the Run AT080 produces a ppm level for silver comparable in amount to Run ID AT031 of Example 3. However, another column entitled, "Measured Ag PPM (10 days)" shows data which tells another story. Specifically, the "initial" and "10 day" PPM measurements are essentially the same (e.g., within operation error of the AAS) for samples corresponding to Run Id's AT097, AT086, AT085, AT084 and AT083. This means that essentially no significant settling of the constituent particles found in five of the eight runs occurred. However, once samples associated with Run ID AT082, AT081 and AT080 were examined after 10 days, a significant portion of the constituent particles had settled, with samples taken from Run AT080 losing about 10 ppm out of 40 ppm due to particulate settling.

In order to obtain an idea of what particle sizes were being produced in each of the eight samples associated with this Example 7, a dynamic light scattering (DLS) approach was utilized. Specifically, dynamic light scattering methods utilizing variations of scattered light intensities from an LED laser were measured over time to determine any changes in intensity from particle motion due to Brownian Motion. The instrument used to perform these measurements was a VISCOTEK 802 DLS with Dual Alternating Technology (D.A.T.).

All measurements were made using a 12 μL quartz cell, which was placed into a temperature controlled cell block. One 827.4 nm laser beam was passed through the solution to be measured. Scattering intensities were measured using a CCD detector with an optical view path mounted transversely to that of the laser. Experimental data was then mathematically transformed using variation of Einstein-Stokes and Rayleigh equations to derive values representative of particle size and distribution information. Data collection and math transforms were performed using Viscotek Omnisize version 3,0,0,291 software. This instrument hardware and software reliably provides measurements for particles with a radius from 0.8 nm to 2 μm.

This technique works best when the solution is free of micro-bubbles and particles subject to Stokes settling motion (some of which was clearly occurring in at least three of the samples in this Example 7). All vessels used to contain and prepare materials to be tested were rinsed and blow-dried to remove any debris. All water used to prepare vessels and samples was doubly deionized and 0.2 μm filtered. If solvent is needed, use only spectrographic grade isopropyl alcohol. All were rinsed with clean water after solvent exposure, and wiped only with clean lint-free cotton cloth.

An aliquot of solution sample, about 3 ml in total volume, was drawn into a small syringe and then dispensed into a clean about 4 dram glass sample vial. Two (2) syringe filters (0.45 μm) were fixed onto the syringe during this operation to doubly filter the sample, thus removing any large particles not intended as part of the solution. This sample was placed into a small vacuum chamber, where it was subjected to a 1 minute exposure to a low-level vacuum (<29.5 inches Hg) to boil the suspension, removing suspended micro-bubbles. The vacuum was drawn through a small dual-stage rotary vacuum pump such as a Varian SD-40. Using a glass Tuberculin syringe with a 20 gage or smaller blunted needle, sample was withdrawn to fill the syringe and then rinsed, then placed into the 12 μL sample cell/cuvette. Additional like-type syringes were used to withdraw used sample and rinse fluids from this cell. The filled cuvette was inspected for obvious entrapped bubbles within the optical path.

This cell was inserted into the holder located in the VISCOTEK 802 DLS. Prior to this step, the instrument was allowed to fully warm to operating temperature for about 30 minutes and operating "OmniSIZE" software loaded in the controlling computer. This software will communicate and set-up the instrument to manufacturer prescribed conditions. Select a "new" measurement. Validate that the correct sample measurement parameters are selected, i.e.; temperature of 40° C., "Target" laser attenuation value of 300 k counts per second, 3 second measurement duration, water as the solvent, spike and drift respectively at 20% and 15%. Correct if needed. Then select "Tools-Options" from the controlling menu bar. Insure proper options are annotated; i.e. resolution at 200, ignore first 2 data points, peak reporting threshold of 0 and 256 correlator channels.

Once the sample was placed into the holder, the cover lid was securely closed causing the laser shutter to open. The sample was allowed to temperature stabilize for 5 to 10 minutes. On the menu tools bar, "Auto-Attenuate" was selected to cause the adjustment of laser power to fit the measurement requirements. Once the instrument and sample was set-up, the scatter intensity graphic display was observed. Patterns should appear uniform with minimal random spikes due to entrained nano/micro-bubbles or settling large particles.

A measurement was then performed. The developing correlation curve was also observed. This curve should display a shape as an "inverted S" and not "spike" out-of-limits. If the set-up was correct, parameters were adjusted to collect 100 measurements and "run" was then selected. The instrument auto-collected data and discarded correlation curves, not exhibiting Brownian motion behavior. At measurement series completion, retained correlation curves were inspected. All should exhibit expected shape and displayed between 30% and 90% expected motion behaviors. At this point, collected data was saved and software calculated particle size information. The measurement was repeated to demonstrate reproducibility. Resultant graphic displays were then inspected. Residuals should appear randomly dispersed and data measurement point must follow calculated theoretical correlation curve. The graphic distribution display was limited to 0.8 nm to 2 μm. The Intensity Distribution and Mass Distribution histograms were reviewed to find particle sizes and relative proportions of each, present in the suspension. All information was then recorded and documented.

FIG. 57a corresponds to a representative Viscotek output for AT097; and FIG. 57b corresponds to a representative Viscotek output for AT080. The numbers reported in FIGS. 57a and 57b correspond to the radii of particles detected in each solution. It should be noted that multiple (e.g., hundreds) of data-points were examined to give the numbers reported in Table 12i, and FIGS. 57a and 57b are just a selection from those measured values.

Figure 58A:
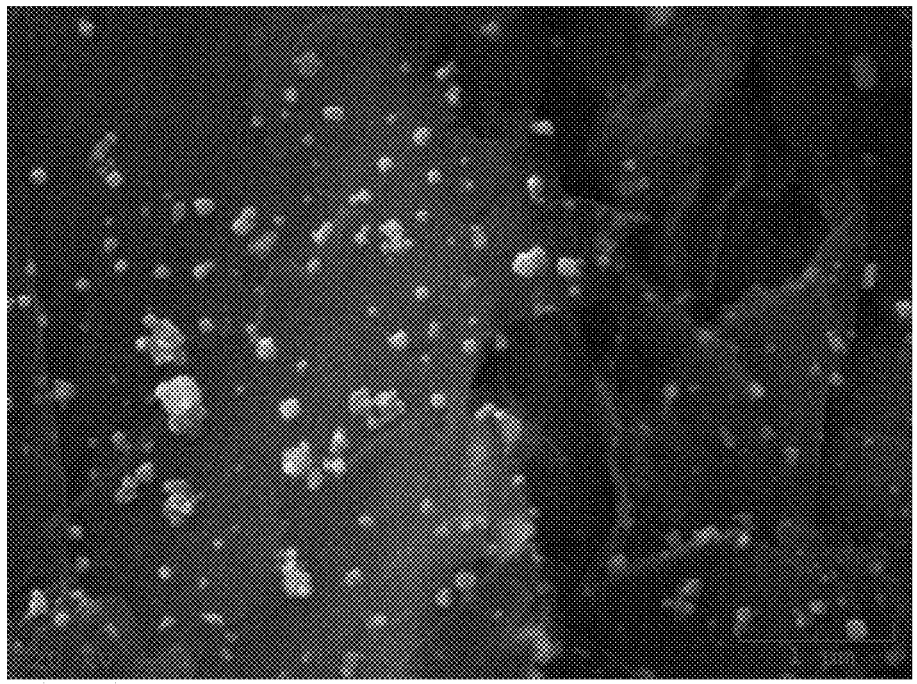
Figure 58B:
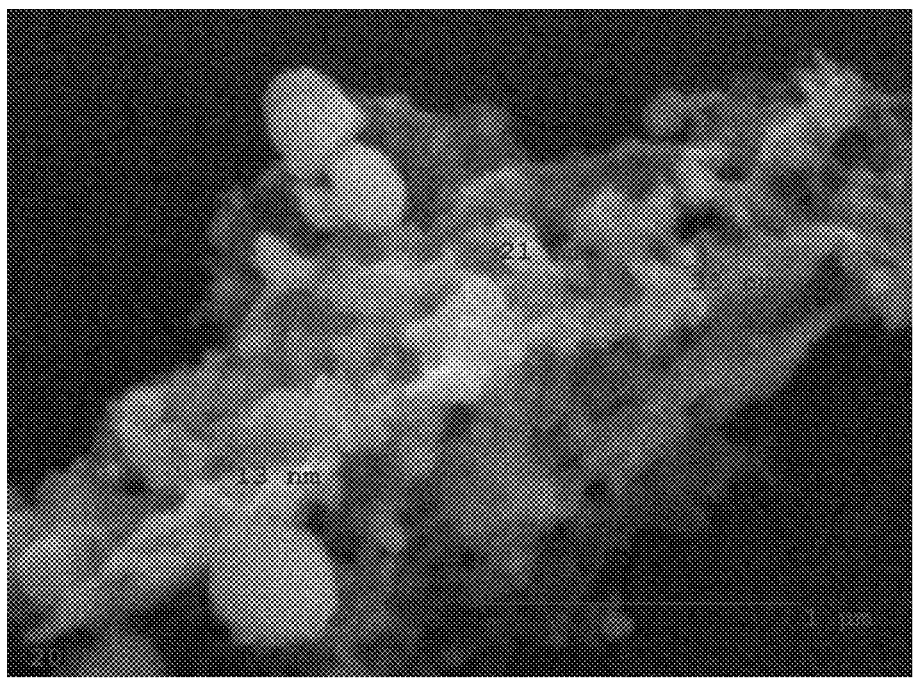
Figure 58C:
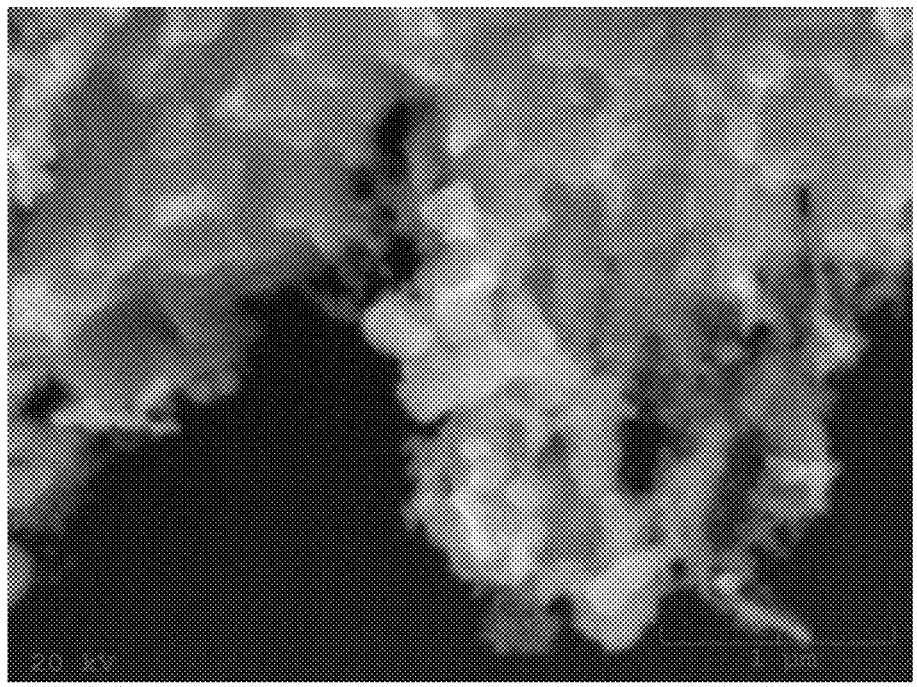
Figure 58D:
Figure 58E:
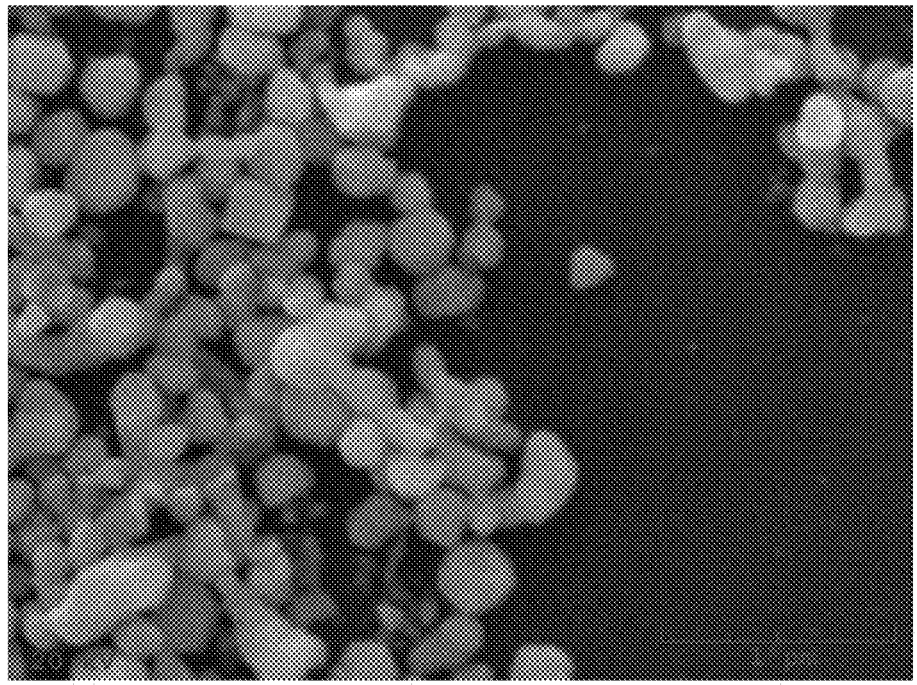
Figure 58F:
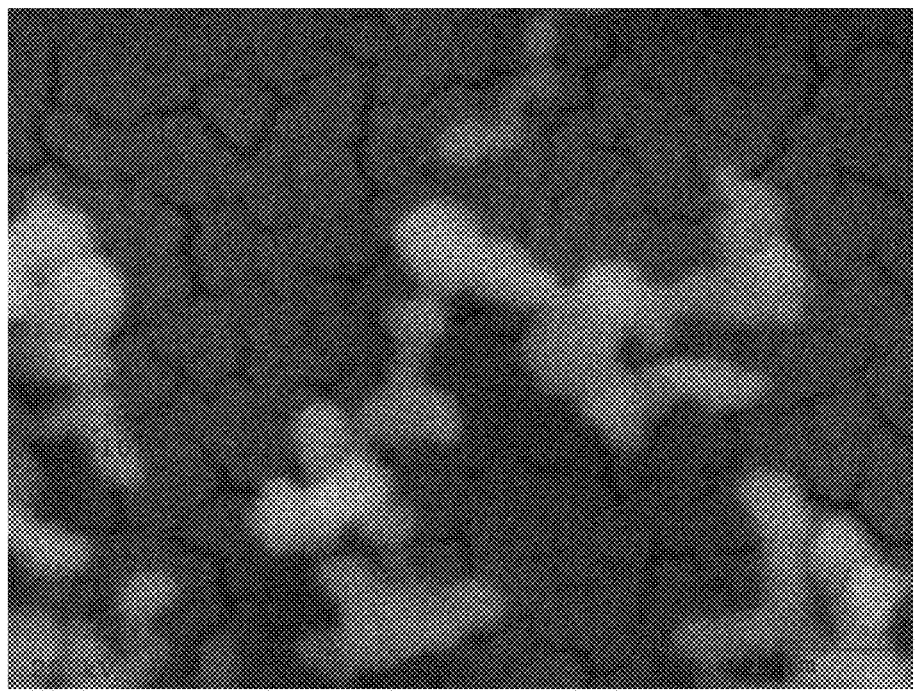

In an effort to understand further the particles produced as a function of the different electrode combinations set forth in the Example 7, SEM photomicrographs of similar magnification were taken of each dried solution corresponding to each of the eight solutions made in this Example. These SEM photomicrographs are shown in FIGS. 58a-58g. FIG. 58a corresponds to a sample from Run ID AT086 and FIG. 58g corresponds to a sample from Run ID AT080. Each SEM photomicrograph shows a "1μ" (i.e., 1 micron) bar. The general observable trend from these photomicrographs is that particle sizes gradually increase from samples AT086 through AT083, but thereafter start to increase rapidly within samples from AT082-AT080. It should be noted that the particulate matter was so small and of such low concentration that no images are available for Run ID AT097.

Figure 58G:
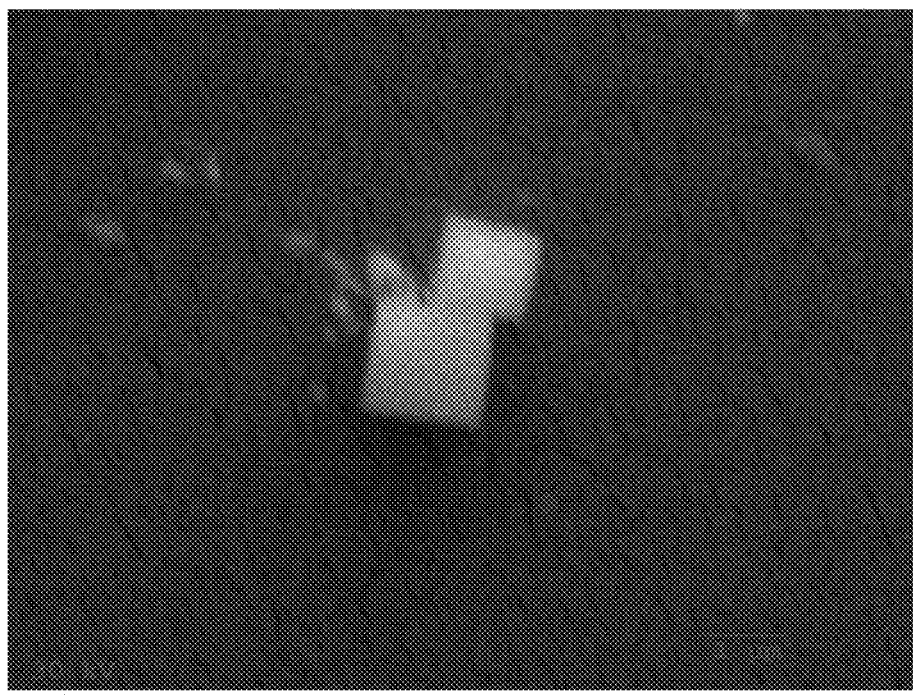

It should be noted that samples were prepared for the SEM by allowing a small amount of each solution produced to air dry on a glass slide. Accordingly, it is possible that some crystal growth may have occurred during drying. However, the amount of "growth" shown in each of samples AT082-AT080 is more than could possibly have occurred during drying alone. It is clear from the SEM photomicrographs that cubic-shaped crystals are evident in AT082, AT081 and AT080. In fact, nearly perfect cubic-shaped crystals are shown in FIG. 58g, associated with sample AT080.

Accordingly, without wishing to be bound by any particular theory or explanation, when comparing the results of Example 7 with Example 6, it becomes clear that the creation of the plasma 4 has a profound impact on this inventive process. Moreover, once the plasma 4 is established, conditions favor the production of metallic-based constituents, including silver-based nanoparticles, including the apparent growth of particles as a function of each new electrode set 5, 5' provided sequentially along the trough member 30. However, if the goal of the process is to maintain the suspension of metallic-based nanoparticles in solution, then, under the process conditions of this Example 7, some of the particles produced begin to settle out near the last three Electrode Sets (i.e., Run Id's AT082, AT081 and AT080). However, if the goal of the process is to achieve particulate matter settling, then that goal can be achieved by following the configurations in Runs AT082, AT081 and AT080.

UV-Vis spectra were obtained for each of the settled mixtures AT097-AT080. Specifically, UV-Vis spectra were obtained as discussed above herein (see the discussion in the section entitled, "Characterization of Materials of Examples 1-5 and Mixtures Thereof"). FIG. 59a shows the UV-Vis Spectra for each of samples AT097-AT080 for the wavelengths between 200 nm-220 nm. The spectra corresponding to AT097 is off the chart for this scale, so the expanded view in FIG. 59b has been provided. It is interesting to note that for each set of electrodes 5, 5' that are sequentially added along the trough member 30, the spectra associated with AT097 diminishes in amount.

UV-Vis spectra for these same eight samples are also shown in FIG. 59c. Specifically, this FIG. 59c examines wavelengths in the 220 nm-620 nm range. Interestingly, the three samples corresponding to AT080, AT081 and AT082, are all significantly above the other five spectra.

In an effort to determine efficacy against an *E. coli* bacteria (discussed in greater detail earlier herein), each of the eight solutions made according to this Example 7 were all diluted to the exact same ppm for silver in order to compare their relative efficacies in a normalized approach. In this regard, the normalization procedure was, for each of the samples, based on the ppm measurements taken after ten days of settling. Accordingly, for example, samples made according to Run AT080 were diluted from 31.6 ppm down to 4 ppm; whereas the samples associated with Run AT083 were diluted from 28.1 ppm, down to 4 ppm. These samples were then further diluted to permit Bioscreen measurements to be performed, as discussed above herein.

FIG. 60 corresponds to a Bioscreen C Microbiology Reader Run that was performed with the same ppm's of silver taken from each of samples AT097-AT080. The results in FIG. 60 are striking in that the efficacy of each of the eight solutions line up perfectly in sequence with the highest efficacy being AT086 and the lowest efficacy being AT080. It should be noted that efficacy for sample AT097 was inadvertently not included in this particular Bioscreen run. Further, while results within any Bioscreen run are very reliable for comparison purposes, results between Bioscreen runs performed at separate times may not provide reliable comparisons due to, for example, the initial bacteria concentrations being slightly different, the growth stage of the bacteria being slightly different, etc. Accordingly, no comparisons have been made in any of the Examples herein between Bioscreen runs performed at different times.

Example 8

Manufacturing Silver-Based Nanoparticles/Nanoparticle Solutions AT089, AT090 and AT091 Using One or Two Plasmas This Example utilizes the same basic apparatus used to make the solutions of Examples 1-5, however, this Example uses only a single plasma 4 to make AT090 (i.e., similar to AT080); two plasmas 4 to make AT091 (i.e., similar to AT031); and two plasmas 4 to make AT089 (first time run), wherein Electrode Set #1 and Electrode Set #8 both utilize plasmas 4. This Example also utilizes 99.95% pure silver electrodes for each of electrodes 1 and 5 in each Electrode Set.

Tables 13a, 13b and 13c summarize portions of electrode design, configuration, location and operating voltages. As shown in Tables 13a-13c, the target voltages were on average highest associated with AT089 and lowest associated with AT091.

Further, bar charts of the actual and target voltages for each electrode in each electrode set, are shown in FIGS. 61a, 61b and 61c. Accordingly, the data contained in Tables 13a-13c, as well as FIGS. 61a, 61b and 61c, give a complete understanding of the electrode design in each electrode set as well as the target and actual voltages applied to each electrode for the manufacturing processes.

TABLE 13a

Run ID: AT090
Flow Rate: 200 ml/min

| Set # | Electrode # | Target Voltage (kV) | Distance "c-c" in/mm | Distance "x" in/mm | Average Voltage (kV) |
|---|---|---|---|---|---|
| 1 | 1a | 2.03 | 7/177.8* | 0.22/5.59 | 2.09 |
|   | 5a | 1.62 |   | N/A | 1.69 |
|   |   |   | 8/203.2 |   |   |

TABLE 13a-continued

Run ID: AT090
Flow Rate: 200 ml/min

| Set # | Electrode # | Target Voltage (kV) | Distance "c-c" in/mm | Distance "x" in/mm | Average Voltage (kV) |
|---|---|---|---|---|---|
| 2 | 5b | 0.87 |   | N/A | 0.94 |
|   | 5b' | 1.08 |   | N/A | 1.11 |
|   |   |   | 8/203.2 |   |   |
| 3 | 5c | 1.04 |   | N/A | 1.10 |
|   | 5c' | 0.94 |   | N/A | 0.97 |
|   |   |   | 8/203.2 |   |   |
| 4 | 5d | 1.23 |   | N/A | 1.26 |
|   | 5d' | 1.24 |   | N/A | 1.30 |
|   |   |   | 9/228.6 |   |   |
| 5 | 5e | 1.42 |   | N/A | 1.47 |
|   | 5e' | 1.11 |   | N/A | 1.12 |
|   |   |   | 8/203.2 |   |   |
| 6 | 5f | 1.03 |   | N/A | 1.01 |
|   | 5f' | 1.01 |   | N/A | 1.03 |
|   |   |   | 8/203.2 |   |   |
| 7 | 5g | 1.15 |   | N/A | 1.13 |
|   | 5g' | 0.94 |   | N/A | 1.02 |
|   |   |   | 8/203.2 |   |   |
| 8 | 5h | 0.81 |   | N/A | 1.04 |
|   | 5h' | 1.03 |   | N/A | 1.14 |
|   |   |   | 8/203.2** |   |   |
|   | Output Water Temperature |   |   |   | 85 C. |

*Distance from water inlet to center of first electrode set
**Distance from center of last electrode set to water outlet TABLE 13b Run ID: AT091
Flow Rate: 200 ml/min

| Set # | Electrode # | Target Voltage (kV) | Distance "c-c" in/mm | Distance "x" in/mm | Average Voltage (kV) |
|---|---|---|---|---|---|
| 1 | 1a | 2.04 | 7/177.8* | 0.22/5.59 | 2.04 |
|   | 5a | 1.67 |   | N/A | 1.66 |
|   |   |   | 8/203.2 |   |   |
| 2 | 5b | 0.94 |   | N/A | 0.93 |
|   | 5b' | 1.11 |   | N/A | 1.10 |
|   |   |   | 8/203.2 |   |   |
| 3 | 5c | 1.01 |   | N/A | 0.98 |
|   | 5c' | 1.07 |   | N/A | 1.05 |
|   |   |   | 8/203.2 |   |   |
| 4 | 1d | 1.44 |   | 0.19/4.83 | 1.41 |
|   | 5d | 1.12 |   | N/A | 1.11 |
|   |   |   | 9/228.6 |   |   |
| 5 | 5e | 1.09 |   | N/A | 1.07 |
|   | 5e' | 0.56 |   | N/A | 0.55 |
|   |   |   | 8/203.2 |   |   |
| 6 | 5f | 0.72 |   | N/A | 0.71 |
|   | 5f' | 0.72 |   | N/A | 0.70 |
|   |   |   | 8/203.2 |   |   |
| 7 | 5g | 0.79 |   | N/A | 0.81 |
|   | 5g' | 0.73 |   | N/A | 0.68 |
|   |   |   | 8/203.2 |   |   |
| 8 | 5h | 0.64 |   | N/A | 0.68 |
|   | 5h' | 0.92 |   | N/A | 0.89 |
|   |   |   | 8/203.2** |   |   |

Output Water Temperature 73 C.
*Distance from water inlet to center of first electrode set
**Distance from center of last electrode set to water outlet

TABLE 13c

Run ID: AT089
Flow Rate: 200 ml/min

| Set # | Electrode # | Target Voltage (kV) | Distance "c-c" in/mm | Distance "x" in/mm | Average Voltage (kV) |
|---|---|---|---|---|---|
| | | | 7/177.8* | | |
| 1 | 1a | 2.18 | | 0.22/5.59 | 2.16 |
| | 5a | 1.80 | | N/A | 1.77 |
| | | | 8/203.2 | | |
| 2 | 5b | 0.99 | | N/A | 0.99 |
| | 5b' | 1.15 | | N/A | 1.13 |
| | | | 8/203.2 | | |
| 3 | 5c | 1.12 | | N/A | 1.14 |
| | 5c' | 1.00 | | N/A | 0.98 |
| | | | 8/203.2 | | |
| 4 | 5d | 1.33 | | N/A | 1.27 |
| | 5d' | 1.35 | | N/A | 1.32 |
| | | | 9/228.6 | | |
| 5 | 5e | 1.51 | | N/A | 1.49 |
| | 5e' | 1.16 | | N/A | 1.12 |
| | | | 8/203.2 | | |
| 6 | 5f | 1.05 | | N/A | 1.00 |
| | 5f' | 1.04 | | N/A | 1.01 |
| | | | 8/203.2 | | |
| 7 | 5g | 1.15 | | N/A | 1.11 |
| | 5g' | 1.14 | | N/A | 1.10 |
| | | | 8/203.2 | | |
| 8 | 1h | 1.23 | | 0.19/4.83 | 1.19 |
| | 5h | 1.31 | | N/A | 1.27 |
| | | | 8/203.2** | | |

Output Water Temperature 78 C.
*Distance from water inlet to center of first electrode set
Distance from center of last electrode set to water outlet Atomic Absorption Spectroscopy (AAS) samples were prepared and measurement values were obtained, as discussed in Example 6. Table 13d shows the results. Note that Table 13d includes a column entitled "Electrode Configuration". This column contains characters of "1" and "0". The "1's" represent an electrode configuration corresponding to Electrode Set #1 (i.e., a 1, 5 combination). The "0's" represent an electrode combination of 5, 5'. Thus, for example, "AT089" is represented by "10000001" which means an eight electrode set combination was used to make "AT089" and the combination corresponded to Set #1=1, 5; Sets #2-#7=5, 5; and Set #8=1, 5**.

TABLE 13d

| Run ID | Electrode Configuration | Measured Ag PPM (initial) | Measured Ag PPM (20 hours) |
|---|---|---|---|
| AT089 | 10000001 | 44.3 | 45.0 |
| AT090 | 10000000 | 40.8 | 37.2 |
| AT091 | 10010000 | 43.6 | 44.3 |

Table 13d includes a column entitled "Measured Ag PPM (initial)". This column corresponds to the silver content of each of the eight solutions measured within one hour of its production. As shown, the measured ppm for each of the three Runs were generally similar. However, another column entitled, "Measured Ag PPM (20 hours)" shows that the "initial" and "20 hours" PPM measurements are essentially the same (e.g., within operation error of the AAS) for samples corresponding to Run Id's AT089 and AT091. This means that essentially no significant settling of the constituent particles found in these runs occurred. However, the sample associated with Run ID AT090 was examined after 20 hours, a significant portion of the constituent particles had settled, with the samples taken from Run AT089 losing about 3.6 ppm out of 40 ppm due to particulate settling.

As discussed in Example 7, a dynamic light scattering (DLS) approach was utilized to obtain average particle size made in each of these three samples. The largest particles were made in AT090; and the smallest particles were made in AT091. Specifically, FIG. 62*a* corresponds to AT090; FIG. 62*b* corresponds to AT091; and FIG. 62*c* corresponds to AT089.

In an effort to determine efficacy against an *E. coli* bacteria (discussed in greater detail earlier herein), each of the three solutions made according to this Example 8 were all diluted to the exact same ppm for silver in order to compare their relative efficacies in a normalized manner. In this regard, the normalization procedure was, for each of the samples, based on the ppm measurement taken after twenty hours of settling. Accordingly, for example, samples made according to Run AT090 were diluted from 37.2 ppm down to 4 ppm; whereas the samples associated with Run AT091 were diluted from 44.0 ppm, down to 4 ppm. These samples were then further diluted to permit Bioscreen measurements to be performed, as discussed above herein. FIG. 63 corresponds to a Bioscreen C Microbiology Reader Run that was performed with the same ppm's of silver taken from each of samples AT089-AT091. The results in FIG. 63 show that the efficacy of each of the three solutions line up corresponding to the particle sizes shown in FIGS. 62*a*-62*c*, with the highest efficacy being AT091 and the lowest efficacy being AT090. Further, while results within any Bioscreen run are very reliable for comparison purposes, results between Bioscreen runs performed at separate times may not provide reliable comparisons due to, for example, the initial bacteria concentrations being slightly different, the growth stage of the bacteria being slightly different, etc. Accordingly, no comparisons have been made herein between Bioscreen runs performed at different times.

Example 9

Manufacturing Silver-Based Nanoparticles/Nanoparticle Solutions AT091, AT092, AT093, AT094 and AT095 Using Plasmas in Multiple Atmospheres This Example utilizes essentially the same basic apparatus used to make the solutions of Examples 1-5, however, this Example uses two plasmas 4 occurring in a controlled atmosphere environment. Controlled atmospheres were obtained by using the embodiment shown in FIG. 28*h*. Specifically, for Electrode Set #1 and Electrode Set #4, this Example uses a "1, 5" electrode configuration wherein the electrode 1 creates a plasma in each of the following atmospheres: air, nitrogen, reducing, ozone and helium. All other Electrode Sets #2, #3 and #5-#8, have a "5, 5'" electrode configuration. This Example also utilizes 99.95% pure silver electrodes for each of electrodes 1 and 5 in each Electrode Set.

Tables 14a-14e summarize portions of electrode design, configuration, location and operating voltages. As shown in Tables 14a-14e, the target voltages were set to a low of about 400-500 volts (reducing atmosphere and ozone) and a high of about 3,000 volts (helium atmosphere).

Further, bar charts of the actual and target voltages for each electrode in each electrode set, are shown in FIGS. 64*a*-64*e*. Accordingly, the data contained in Tables 14a-14e, as well as FIGS. 64*a*-64*e*, give a complete understanding of the electrode design in each electrode set as well as the target and actual voltages applied to each electrode for the manufacturing processes. The atmospheres used for each plasma 4 for each electrode 1 for Electrode Set #1 and Electrode Set #4 were as follows: AT091—Air; AT092—Nitrogen; AT093—Reducing or Air-Deprived; AT094—Ozone; and AT095—Helium. The atmospheres for each of Runs AT092-AT095 were achieved by utilizing the atmosphere control device 35 shown, for example, in FIG. 28h. Specifically, a nitrogen atmosphere was achieved around each electrode 1, 5 in Electrode Set #1 and Electrode Set #4 by flowing nitrogen gas (high purity) through tubing 286 into the inlet portion 37 of the atmosphere control device 35 shown in FIG. 28h. The flow rate of nitrogen gas was sufficient so as to achieve positive pressure of nitrogen gas by causing the nitrogen gas to create a positive pressure on the water 3 within the atmosphere control device 35.

Likewise, the atmosphere of ozone (AT094) was achieved by creating a positive pressure of ozone created by an ozone generator and inputted into the atmosphere control device 35, as discussed above herein. It should be noted that significant nitrogen content was probably present in the supplied ozone.

Further, the atmosphere of helium (AT095) was achieved by creating a positive pressure of helium inputted into the atmosphere control device 35, as discussed above herein.

The atmosphere of air was achieved without using the atmosphere control device 35.

The reducing atmosphere (or air-deprived atmosphere) was achieved by providing the atmosphere control device 35 around each electrode 1, 5 in Electrode Sets #1 and #4 and not providing any gas into the inlet portion 37 of the atmosphere control devices 35. In this instance, the external atmosphere (i.e., an air atmosphere) was found to enter into the atmosphere control device 35 through the hole 37 and the plasma 4 created was notably much more orange in color relative to the air atmosphere plasma.

In an effort to understand the composition of each of the plasmas 4, a "Photon Control Silicon CCD Spectrometer, SPM-002-E" (from Blue Hill Optical Technologies, Westwood, Mass.) was used to collect the spectra for each of the plasmas 4.

Specifically, in reference to FIGS. 65a and 65b, the Photon Control Silicon CCD Spectrometer 500, was used to collect spectra (200-1090 nm, 0.8/2.0 nm center/edge resolution) on each plasma 4 generated between the electrode 1 and the surface 2 of the water 3. The Spectrometer 500 was linked via a USB cable to a computer (not shown) loaded with Photon Control Spectrometer software, revision 2.2.3. A 200 nm core optical fiber patch cable 502 (SMA-905, Blue Hill Optical Technologies) was mounted on the end of a Plexiglas support 503. A laser pointer 501 (Radio Shack Ultra Slim Laser Pointer, #63-1063) was mounted on the opposite side 506 of the plexiglas support. This assembly 503 was created so that the optical cable 502 could be accurately and repeatedly positioned so that it was directly aimed toward the same middle portion of each plasma 4 formed by using the laser pointer 501 as an aiming device.

Prior to the collection of any spectra created by each plasma 4, the atmosphere control device 35 was saturated with each gas for 30 seconds and a background spectrum was collected with 2 second exposure set in the software package. The plasma 4 was active for 10 minutes prior to any data collection. The primary spot from the laser 501 was aligned with the same point each time. Three separate spectra were collected for each run and then averaged. The results of each spectra are shown in FIGS. 66a-66e (discussed later herein in this Example).

TABLE 14a

Run ID: AT091
Flow Rate: 200 ml/min
Atmosphere For Set #1 and Set #4: Air

| Set # | Electrode # | Target Voltage (kV) | Distance "c-c" in/mm | Distance "x" in/mm | Average Voltage (kV) |
|---|---|---|---|---|---|
| | | | 7/177.8* | | |
| 1 | 1a | 2.04 | | 0.22/5.59 | 2.04 |
| | 5a | 1.67 | | N/A | 1.66 |
| | | | 8/203.2 | | |
| 2 | 5b | 0.94 | | N/A | 0.93 |
| | 5b' | 1.11 | | N/A | 1.10 |
| | | | 8/203.2 | | |
| 3 | 5c | 1.01 | | N/A | 0.98 |
| | 5c' | 1.07 | | N/A | 1.05 |
| | | | 8/203.2 | | |
| 4 | 1d | 1.44 | | 0.19/4.83 | 1.41 |
| | 5d | 1.12 | | N/A | 1.11 |
| | | | 9/228.6 | | |
| 5 | 5e | 1.09 | | N/A | 1.07 |
| | 5e' | 0.56 | | N/A | 0.55 |
| | | | 8/203.2 | | |
| 6 | 5f | 0.72 | | N/A | 0.71 |
| | 5f' | 0.72 | | N/A | 0.70 |
| | | | 8/203.2 | | |
| 7 | 5g | 0.79 | | N/A | 0.81 |
| | 5g' | 0.73 | | N/A | 0.68 |
| | | | 8/203.2 | | |
| 8 | 5h | 0.64 | | N/A | 0.68 |
| | 5h' | 0.92 | | N/A | 0.89 |
| | | | 8/203.2** | | |

Output Water Temperature 73 C.
*Distance from water inlet to center of first electrode set
**Distance from center of last electrode set to water outlet TABLE 14b Run ID: AT092
Flow Rate: 200 ml/min
Atmosphere For Set #1 and Set #4: Nitrogen

| Set # | Electrode # | Target Voltage (kV) | Distance "c-c" in/mm | Distance "x" in/mm | Average Voltage (kV) |
|---|---|---|---|---|---|
| | | | 7/177.8* | | |
| 1 | 1a | 2.39 | | 0.22/5.59 | 2.27 |
| | 5a | 2.02 | | N/A | 1.99 |
| | | | 8/203.2 | | |
| 2 | 5b | 1.39 | | N/A | 1.30 |
| | 5b' | 1.51 | | N/A | 1.54 |
| | | | 8/203.2 | | |
| 3 | 5c | 1.49 | | N/A | 1.47 |
| | 5c' | 1.50 | | N/A | 1.52 |
| | | | 8/203.2 | | |
| 4 | 1d | 1.64 | | 0.19/4.83 | 1.66 |
| | 5d | 1.33 | | N/A | 1.31 |
| | | | 9/228.6 | | |
| 5 | 5e | 1.46 | | N/A | 1.47 |
| | 5e' | 1.05 | | N/A | 0.98 |
| | | | 8/203.2 | | |
| 6 | 5f | 1.18 | | N/A | 1.13 |
| | 5f' | 1.13 | | N/A | 1.11 |
| | | | 8/203.2 | | |
| 7 | 5g | 1.26 | | N/A | 1.20 |
| | 5g' | 1.17 | | N/A | 1.03 |
| | | | 8/203.2 | | |
| 8 | 5h | 0.94 | | N/A | 0.87 |
| | 5h' | 1.12 | | N/A | 1.07 |
| | | | 8/203.2** | | |

Output Water Temperature 88 C.
*Distance from water inlet to center of first electrode set
**Distance from center of last electrode set to water outlet TABLE 14c Run ID: AT093
Flow Rate: 200 ml/min
Atmosphere For Set #1 and Set #4: Reducing or Air-Deprived

| Set # | Electrode # | Target Voltage (kV) | Distance "c-c" in/mm | Distance "x" in/mm | Average Voltage (kV) |
|---|---|---|---|---|---|
| | | | 7/177.8* | | |
| 1 | 1a | 2.04 | | 0.22/5.59 | 2.02 |
| | 5a | 1.50 | | N/A | 1.49 |
| | | | 8/203.2 | | |
| 2 | 5b | 0.76 | | N/A | 0.76 |
| | 5b' | 1.02 | | N/A | 1.03 |
| | | | 8/203.2 | | |
| 3 | 5c | 0.91 | | N/A | 0.91 |
| | 5c' | 0.98 | | N/A | 0.99 |
| | | | 8/203.2 | | |
| 4 | 1d | 1.38 | | 0.19/4.83 | 1.39 |
| | 5d | 1.01 | | N/A | 0.99 |
| | | | 9/228.6 | | |
| 5 | 5e | 0.94 | | N/A | 0.92 |
| | 5e' | 0.39 | | N/A | 0.38 |
| | | | 8/203.2 | | |
| 6 | 5f | 0.60 | | N/A | 0.58 |
| | 5f' | 0.50 | | N/A | 0.48 |
| | | | 8/203.2 | | |
| 7 | 5g | 0.68 | | N/A | 0.65 |
| | 5g' | 0.55 | | N/A | 0.56 |
| | | | 8/203.2 | | |
| 8 | 5h | 0.59 | | N/A | 0.59 |
| | 5h' | 0.89 | | N/A | 0.87 |
| | | | 8/203.2** | | |

Output Water Temperature 75 C.
*Distance from water inlet to center of first electrode set
**Distance from center of last electrode set to water outlet TABLE 14d Run ID: AT094
Flow Rate: 200 ml/min
Atmosphere For Set #1 and Set #4: Ozone

| Set # | Electrode # | Target Voltage (kV) | Distance "c-c" in/mm | Distance "x" in/mm | Average Voltage (kV) |
|---|---|---|---|---|---|
| | | | 7/177.8* | | |
| 1 | 1a | 2.24 | | 0.22/5.59 | 2.20 |
| | 5a | 1.73 | | N/A | 1.74 |
| | | | 8/203.2 | | |
| 2 | 5b | 0.93 | | N/A | 0.95 |
| | 5b' | 1.16 | | N/A | 1.18 |
| | | | 8/203.2 | | |
| 3 | 5c | 1.09 | | N/A | 1.10 |
| | 5c' | 1.15 | | N/A | 1.17 |
| | | | 8/203.2 | | |
| 4 | 1d | 1.45 | | 0.19/4.83 | 1.47 |
| | 5d | 1.08 | | N/A | 1.10 |
| | | | 9/228.6 | | |
| 5 | 5e | 0.99 | | N/A | 1.00 |
| | 5e' | 0.43 | | N/A | 0.45 |
| | | | 8/203.2 | | |
| 6 | 5f | 0.64 | | N/A | 0.63 |
| | 5f' | 0.52 | | N/A | 0.56 |
| | | | 8/203.2 | | |
| 7 | 5g | 0.71 | | N/A | 0.74 |
| | 5g' | 0.63 | | N/A | 0.64 |
| | | | 8/203.2 | | |
| 8 | 5h | 0.66 | | N/A | 0.67 |
| | 5h' | 0.95 | | N/A | 0.95 |
| | | | 8/203.2** | | |

Output Water Temperature 76 C.
*Distance from water inlet to center of first electrode set
**Distance from center of last electrode set to water outlet TABLE 14e Run ID: AT095
Flow Rate: 200 ml/min
Atmosphere For Set #1 and Set #4: Helium

| Set # | Electrode # | Target Voltage (kV) | Distance "c-c" in/mm | Distance "x" in/mm | Average Voltage (kV) |
|---|---|---|---|---|---|
| | | | 7/177.8* | | |
| 1 | 1a | 3.09 | | 0.22/5.59 | 3.11 |
| | 5a | 2.98 | | N/A | 2.96 |
| | | | 8/203.2 | | |
| 2 | 5b | 2.81 | | N/A | 2.80 |
| | 5b' | 2.86 | | N/A | 2.83 |
| | | | 8/203.2 | | |
| 3 | 5c | 2.38 | | N/A | 2.38 |
| | 5c' | 2.32 | | N/A | 2.30 |
| | | | 8/203.2 | | |
| 4 | 1d | 2.64 | | 0.19/4.83 | 2.58 |
| | 5d | 2.50 | | N/A | 2.49 |
| | | | 9/228.6 | | |
| 5 | 5e | 2.06 | | N/A | 2.07 |
| | 5e' | 1.64 | | N/A | 1.63 |
| | | | 8/203.2 | | |
| 6 | 5f | 1.34 | | N/A | 1.36 |
| | 5f' | 1.31 | | N/A | 1.31 |
| | | | 8/203.2 | | |
| 7 | 5g | 1.27 | | N/A | 1.28 |
| | 5g' | 1.12 | | N/A | 1.12 |
| | | | 8/203.2 | | |
| 8 | 5h | 1.08 | | N/A | 1.08 |
| | 5h' | 1.26 | | N/A | 1.25 |
| | | | 8/203.2** | | |

Output Water Temperature 95 C.
*Distance from water inlet to center of first electrode set
Distance from center of last electrode set to water outlet Atomic Absorption Spectroscopy (AAS) samples were prepared and measurement values were obtained, as discussed in Example 6. Table 14f shows the results. Note that Table 14f includes a column entitled "Electrode Configuration". This column contains characters "1" and "0". The "1's" represent an electrode configuration corresponding to Electrode Set #1 (i.e., a 1, 5 combination). The "0's" represent an electrode combination of 5, 5'. Thus, for example, "AT091" is represented by "10010000" which means an eight electrode set combination was used to make "AT091" and the combination corresponded to Set #1=1, 5; Set #2=5, 5; Set #3=5, 5; Set #4=1, 5 and Set #5-Set #8=5, 5**.

TABLE 14f

| Run ID | Electrode Configuration | Measured Ag PPM | Atmosphere |
|---|---|---|---|
| AT091 | 10010000 | 44.0 | Air |
| AT092 | 10010000 | 40.3 | Nitrogen |
| AT093 | 10010000 | 46.8 | Reducing |
| AT094 | 10010000 | 44.5 | Ozone |
| AT095 | 10010000 | 28.3 | Helium |

Table 14f includes a column entitled "Measured Ag PPM". This column corresponds to the silver content of each of the eight solutions. As shown, the measured ppm produced in each of the atmospheres of air, nitrogen, reducing and ozone were substantially similar. However, the atmosphere of helium (i.e., AT095) produced a much lower ppm level. Also, the size of particulate matter in the AT095 solution was significantly larger than the size of the particulate matter in each of the other four solutions. The particulate sizes were determined by dynamic light scattering methods, as discussed above herein.

Figure 66A:
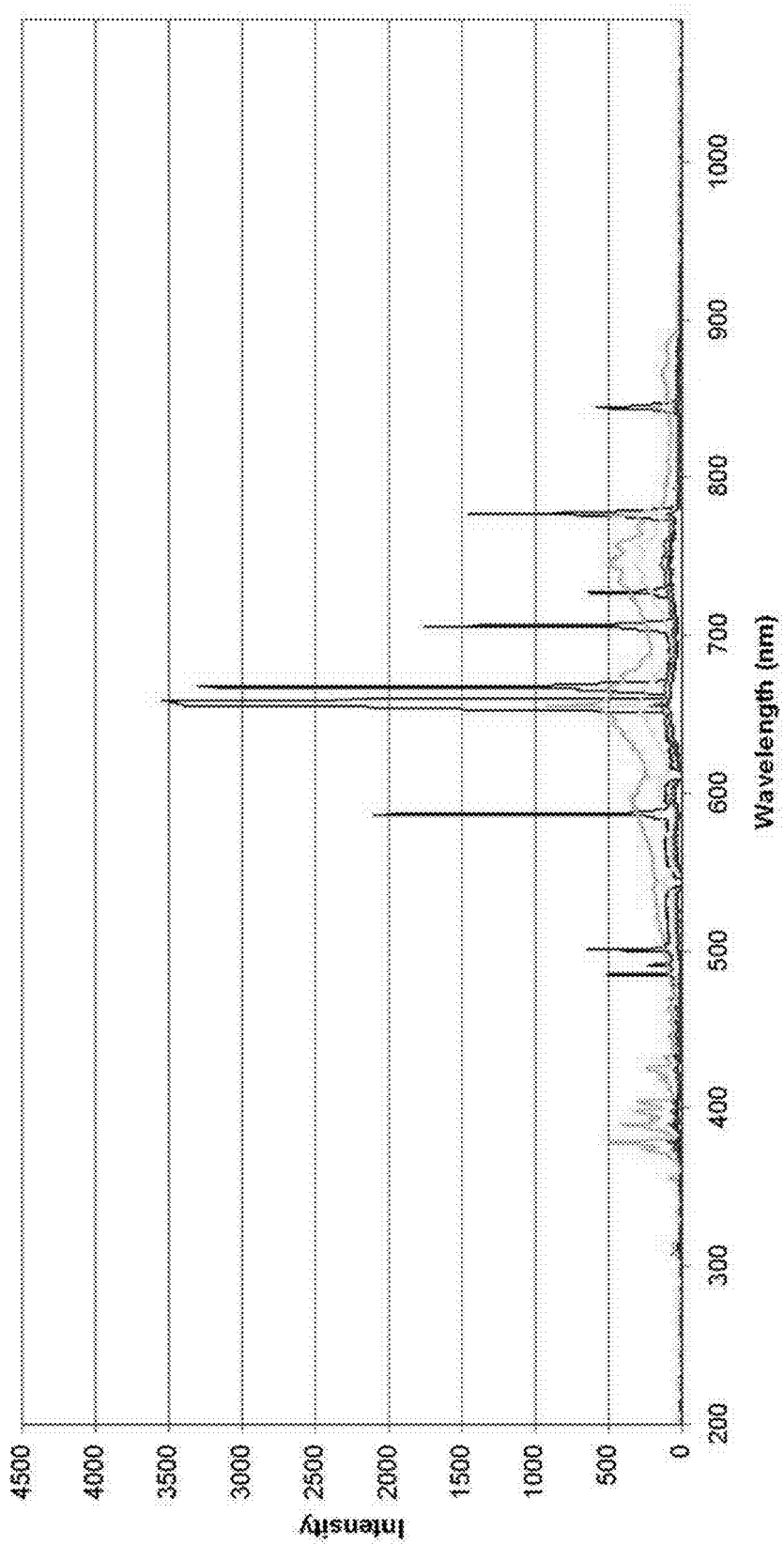
Figure 66B:
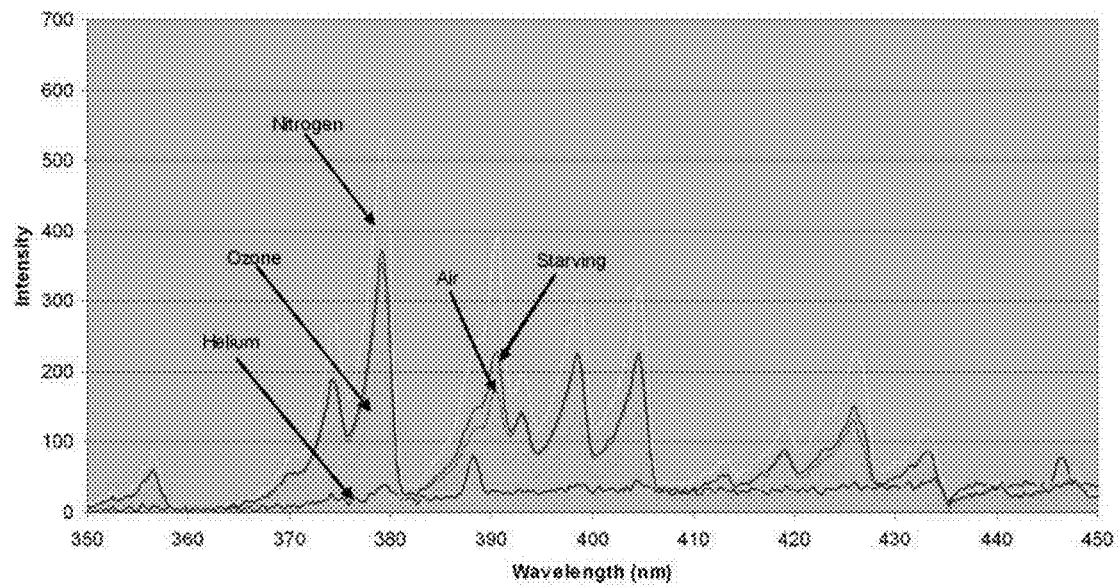
Figure 66C:
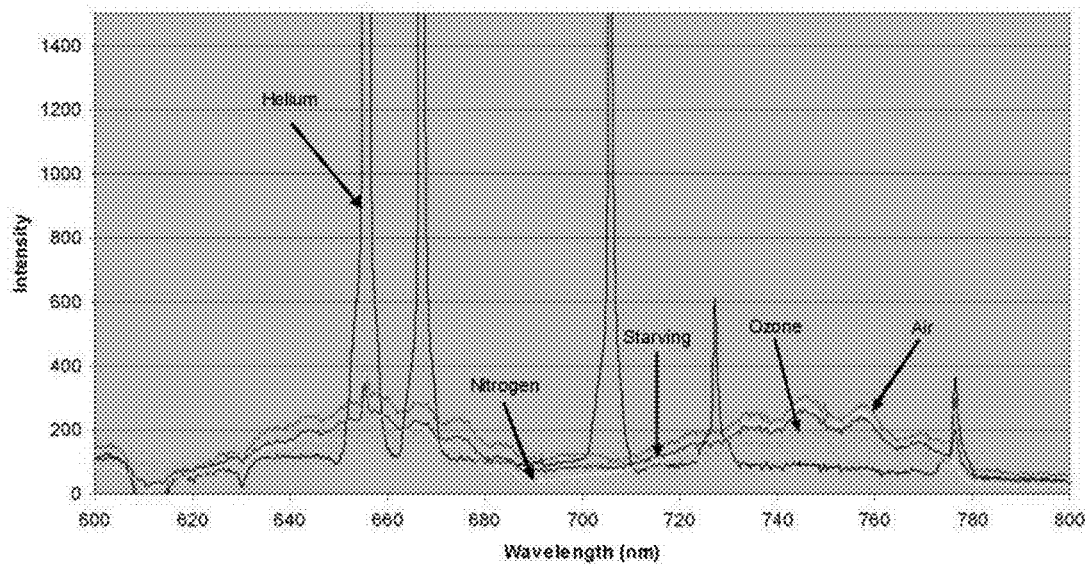
Figure 66D:
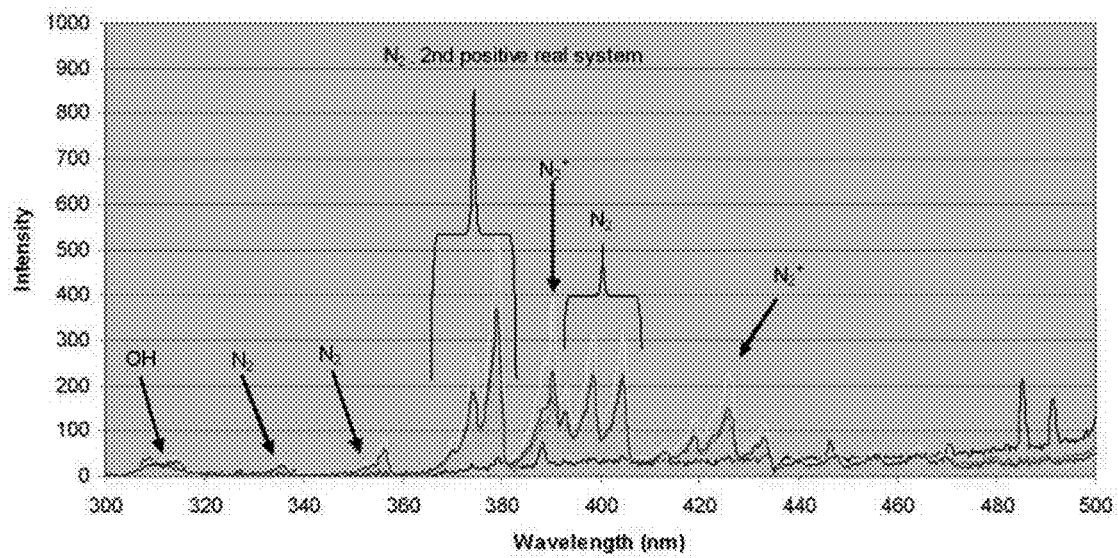
Figure 66E:
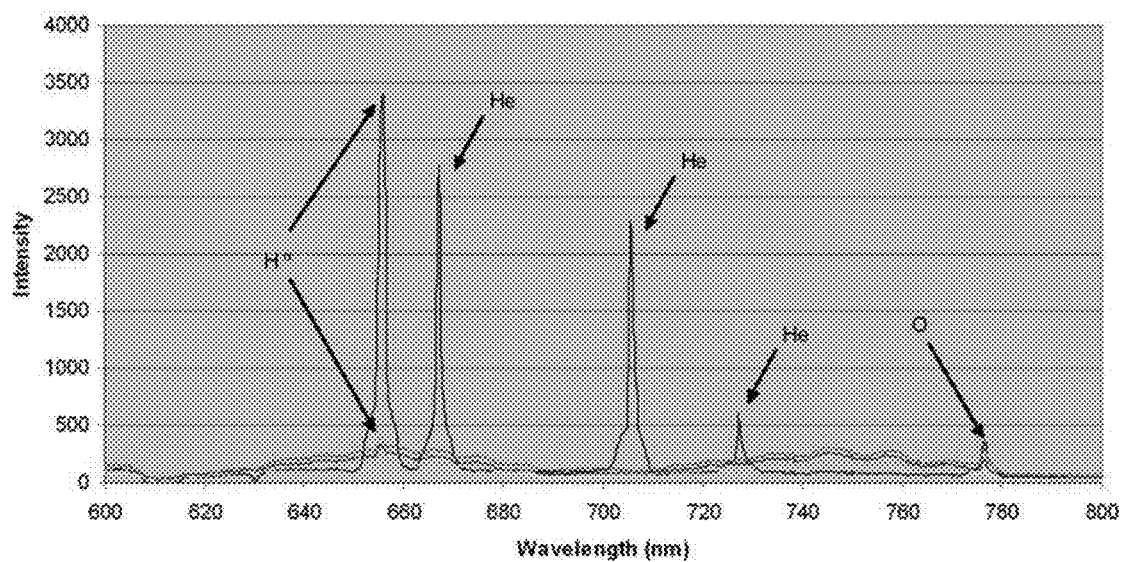
Figure 67A:
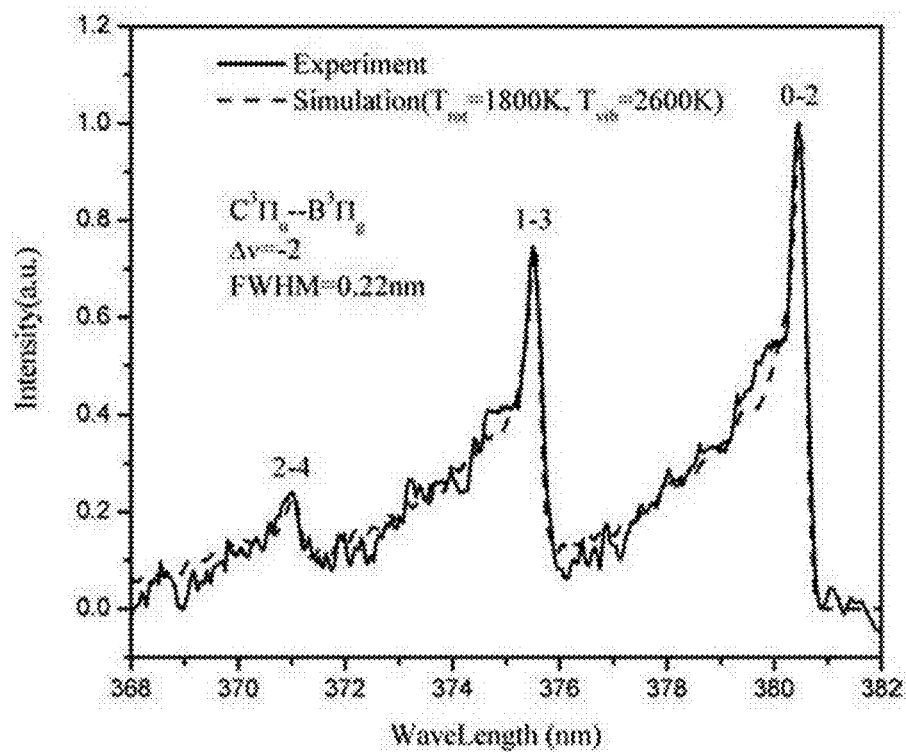
Figure 67B:
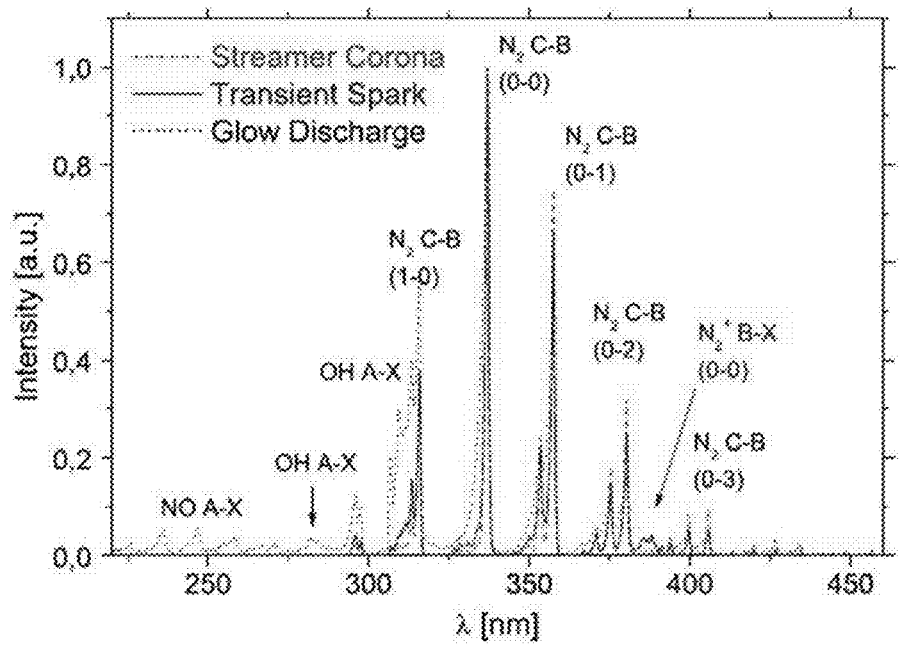
Figure 67C:
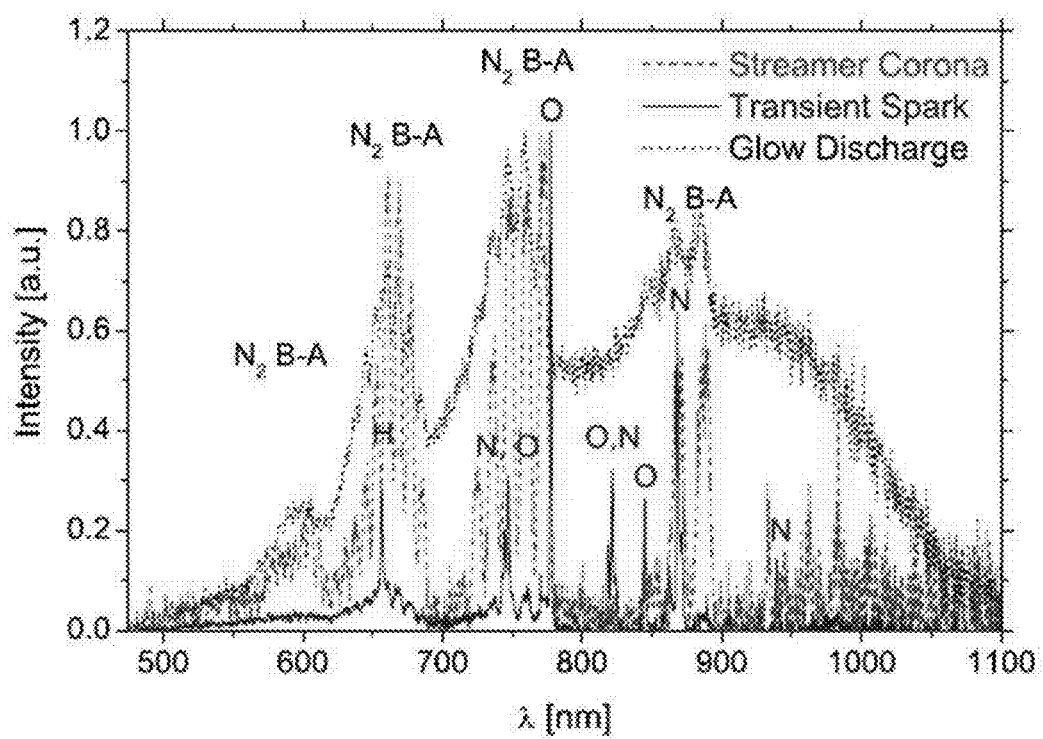
Figure 67D:
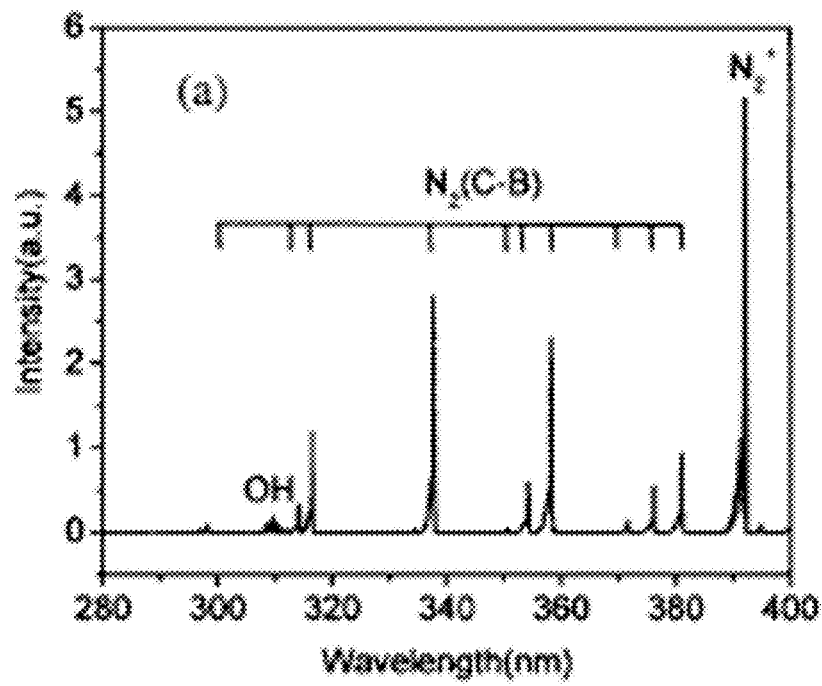
Figure 67E:
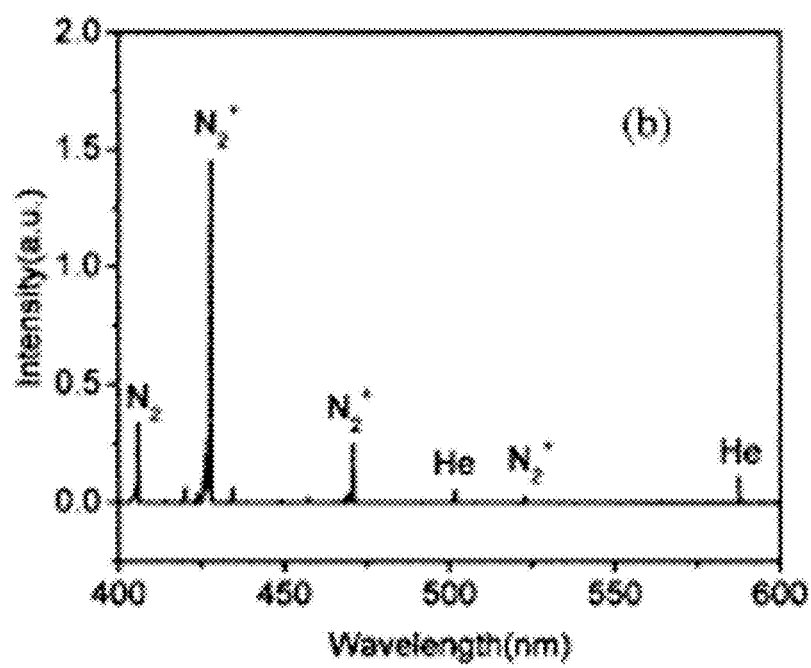
Figure 67F:
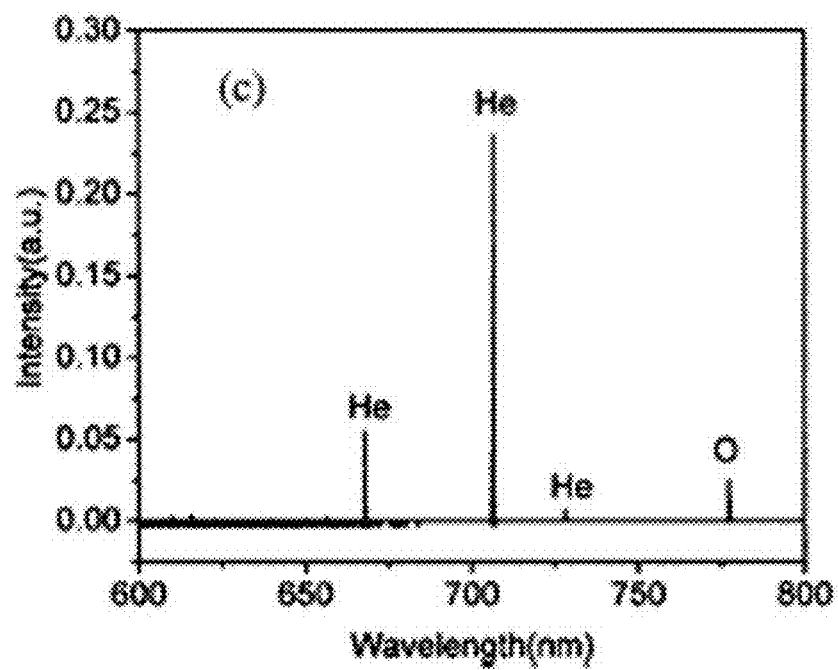

It is clear from FIGS. 66a-66e that each spectra shown therein created from the plasma 4 had a number of very prominent peaks. For example, those prominent peaks associated with each of the atmospheres of air, nitrogen, reducing and ozone all have strong similarities. However, the spectral peaks associated with the spectra creating by the plasma 4 (i.e., when helium was provided as the atmosphere) are quite different from the other four peaks. In this regard, FIG. 66a shows the complete spectral response for each plasma 4 for each of the gasses used in this Example over the entire wavelength range of 200-1000 nm FIGS. 66b and 66c focus on certain portions of the spectra of interest and identify by name the atmospheres associated with each spectrum. FIGS. 66d and 66e identify specific common peaks in each of these spectra. Specifically, FIGS. 67a-67f are excerpted from the articles discussed above herein. Those FIGS. 67a-67f assist in identifying the active peaks in the plasma 4 of this Example 9. It is clear that spectral peaks associated with the helium atmosphere are quite different from spectral peaks associated with the other four atmospheres.

In an effort to determine efficacy against an *E. coli* bacteria (discussed in greater detail earlier herein), each of the five solutions made according to this Example 9 were all diluted to the exact same ppm for silver in order to compare their relative efficacies in a normalized manner. Accordingly, for example, samples made according to Run AT091 were diluted from 44.0 ppm down to 4 ppm; whereas the samples associated with Run AT095 were diluted from 28.3 ppm, down to 4 ppm. These samples were then further diluted to permit Bioscreen measurements to be performed, as discussed above herein. FIG. 68 corresponds to a Bioscreen C Microbiology Reader Run that was performed with the same ppm's of silver taken from each of samples AT091-AT095. The results in FIG. 68 show the highest efficacy being AT094 and AT096 (note: AT096 was made according to Example 10, and shall be discussed in greater detail therein) and the lowest efficacy being AT095. Further, while results within any Bioscreen run are very reliable for comparison purposes, results between Bioscreen runs performed at separate times may not provide reliable comparisons due to, for example, the initial bacteria concentrations being slightly different, the growth stage of the bacteria being slightly different, etc. Accordingly, no comparisons have been made herein between Bioscreen runs performed at different times.

Example 10

Manufacturing Silver-Based Nanoparticles/Nanoparticle Solution AT096, Using a Diode Bridge to Rectify an AC Power Source to Form Plasmas This Example utilizes essentially the same basic apparatus used to make the solutions of Examples 1-5, however, this Example uses two plasmas 4 formed by a DC-like Power Source (i.e., a diode bridge-rectified power source). Specifically, for Electrode Set #1 and Electrode Set #4, this Example uses a "1, 5" electrode configuration wherein the electrode 1 creates a plasma 4 in accordance with the power source shown in FIG. 32c. All other Electrode Sets #2, #3 and #5-#8, had a "5, 5'" electrode configuration. This Example also utilizes 99.95% pure silver electrodes for each of electrodes 1 and 5 in each Electrode Set.

Table 15 summarizes portions of electrode design, configuration, location and operating voltages. As shown in Table 15, the target voltages were set to a low of about 400 volts (Electrode Set #4) and a high of about 1,300 volts (Electrode Set #3).

Further, bar charts of the actual and target voltages for each electrode in each electrode set, are shown in FIG. 69. Accordingly, the data contained in Table 15, as well as FIG. 69, give a complete understanding of the electrode design in each electrode set as well as the target and actual voltages applied to each electrode for the manufacturing processes.

TABLE 15

Run ID: AT096
Flow Rate: 200 ml/min

| Set # | Electrode # | Target Voltage (kV) | Distance "c-c" in/mm | Distance "x" in/mm | Average Voltage (kV) |
|---|---|---|---|---|---|
| | | | 7/177.8* | | |
| 1 | 1a | 0.76 | | 0.19/4.83 | 0.69 |
| | 5a | 0.68 | | N/A | 0.68 |
| | | | 8/203.2 | | |
| 2 | 5b | 1.25 | | N/A | 1.22 |
| | 5b' | 1.13 | | N/A | 1.11 |
| | | | 8/203.2 | | |
| 3 | 5c | 1.18 | | N/A | 1.15 |
| | 5c' | 1.28 | | N/A | 1.27 |
| | | | 8/203.2 | | |
| 4 | 1d | 0.41 | | 0.19/4.83 | 0.47 |
| | 5d | 0.64 | | N/A | 0.63 |
| | | | 9/228.6 | | |
| 5 | 5e | 1.02 | | N/A | 0.99 |
| | 5e' | 0.93 | | N/A | 0.91 |
| | | | 8/203.2 | | |
| 6 | 5f | 0.76 | | N/A | 0.74 |
| | 5f' | 0.76 | | N/A | 0.76 |
| | | | 8/203.2 | | |
| 7 | 5g | 0.91 | | N/A | 0.90 |
| | 5g' | 0.80 | | N/A | 0.79 |
| | | | 8/203.2 | | |
| 8 | 5h | 0.75 | | N/A | 0.74 |
| | 5h' | 0.93 | | N/A | 0.93 |
| | | | 8/203.2** | | |

Output Water Temperature 80 C.
*Distance from water inlet to center of first electrode set
**Distance from center of last electrode set to water outlet Atomic Absorption Spectroscopy (AAS) samples were prepared and measurement values were obtained, as discussed in Example 6. Table 15a shows the results. Note that Table 15a includes a column entitled "Electrode Configuration". This column contains characters "1*" and "0". The "1*" represents an electrode configuration corresponding to Electrode Set #1 (i.e., a 1, 5 combination, wherein the electrode 1 is negatively biased and the electrode 5 is positively biased. The "0"s" represent an electrode combination of 5, 5'.

TABLE 15a

| Run ID | Electrode Configuration | Measured Ag PPM | Atmosphere |
|---|---|---|---|
| AT096 | 1*001*0000 | 51.2 | Air |

Table 15a includes a column entitled "Measured Ag PPM". This column corresponds to the silver content of the solution. As shown, the measured ppm was 51.2 ppm, which was substantially higher than any other samples made by the other eight electrode sets utilized in any other Example.

In an effort to determine efficacy against an *E. coli* bacteria (discussed in greater detail earlier herein), this solution AT096 was tested against each of the five solutions made according to Example 9 above herein. Specifically, all of the five solutions from Example 9 and AT096 were diluted to the exact same ppm for silver in order to compare their relative efficacies in a normalized manner as discussed in Example 9. FIG. 68 corresponds to a Bioscreen C Microbiology Reader Run that was performed with the same ppm's of silver taken from each of samples AT092-AT096. The results in FIG. 68 show that AT096 was among the best performing solutions. Further, while results within any Bioscreen run are very reliable for comparison purposes, results between Bioscreen runs performed at separate times may not provide reliable comparisons due to, for example, the initial bacteria concentrations being slightly different, the growth stage of the bacteria being slightly different, etc. Accordingly, no comparisons have been made herein between Bioscreen runs performed at different times.

The atmosphere used for AT096 was air, and the corresponding spectra of the air plasma is shown in FIGS. 70a, 70b and 70c. These spectra are similar to those set forth in FIGS. 66a, 66b and 66c. Additionally, FIGS. 70a, 70b and 70c show spectra associated with the atmospheres of nitrogen, reducing or air-deprived and helium, all produced according to the set-up conforming to that used to make the plasma 4 in AT096. These atmospheres and the measurements associated therewith, were made in accordance with the teachings in Example 9.

Similarly, FIGS. 71a, 71b and 71c show a similar set of spectra taken from plasmas 4 when the polarity of the electrode 1 used earlier in this Example has been reversed. In this regard, all of the atmospheres for air, nitrogen, reducing or air-deprived, ozone and helium are also utilized but in this case the electrode 1 has become positively biased and the electrode 5 (i.e., the surface 2 of the water 3) has become negatively biased.

Example 11

Efficacy and Cytotoxicity Testing of Related Nanoparticle Solutions

This Example follows the teachings of Examples 2 [AT060], 3 [AT031-AT064] and 4 [BT006-BT012] to manufacture two different silver-based nanoparticle/nanoparticle solutions and one zinc-based nanoparticle/nanoparticle solution. Additionally, a new and different solution (i.e., PT001) based in part on the inventive process for making BT006 and BT012 was also produced. Once produced, three solutions were tested for efficacy and cytotoxicity.

Specifically, the solution made by the method of Example 2 (i.e., AT060) was tested for cytotoxicity against Murine Liver Epithelial Cells, as discussed above herein. The results are shown in FIG. 72a. Likewise, a solution produced according to Example 3 (i.e., AT031) was made "AT064" and was also likewise tested for cytotoxicity. The results are shown in FIG. 72b. Further, material produced according to Example 4 (i.e., BT006) was made and designated "BT012" and was likewise tested for cytotoxicity. The results are shown in FIG. 72c.

Mixtures of the materials (i.e., AT060, AT064 and BT012) were then made in order to form GR5 and GR8, in accordance with what is shown in Table 8 herein relating to the solutions GR5 and GR8. Specifically, AT064 and BT012 were mixed together to form GR5; and AT060 and BT012 were mixed together to form GR8 to result in the amounts of silver and zinc in each being the same as what is shown in Table 8.

Once the solutions of GR5 and GR8 were formed, the cytotoxicity for each was measured. Specifically, as shown in FIG. 73a and FIG. 73b the cytotocicity of GR5 was determined. In this regard, the $LD_{50}$ for GR5, based on silver nanoparticle concentration, was 5.092; whereas the $LD_{50}$ based on total nanoparticle concentration (i.e., both silver and zinc) was 15.44.

In comparison, FIG. 74a shows the $LD_{50}$, based on silver nanoparticle concentration, for GR8, which was 4.874. Similarly, FIG. 74b shows the $LD_{50}$ equal to 18.05 regarding the total nanoparticle concentration (i.e., total of silver and zinc particles) in GR8.

The other inventive material in this Example 11, "PT001", was made by the following process. Electrode Set #1 was a 1, 5 combination. Electrode Set #2 was also a 1, 5 combination. There were no electrode sets at positions 2-8. Accordingly, the designation for this electrode combination was a "11XXXXXX". The composition of each of electrodes 1 and 5 in both Electrode Sets #1 and #2 were high-purity platinum (i.e., 99.999%). Table 16a sets forth the specific run conditions for PT001.

Further, bar charts of the actual and target voltages for each electrode in each electrode set, are shown in FIG. 75. Accordingly, the data contained in Table 16a, as well as in FIG. 75, give a complete understanding of the electrode design in each electrode set as well as the target and actual voltages applied to each electrode for the manufacturing processes.

TABLE 16a

Run ID: PT001
Flow Rate: 150 ml/min

| Set # | Electrode # | Target Voltage (kV) | Distance "c-c" in/mm | Distance "x" in/mm | Average Voltage (kV) |
|---|---|---|---|---|---|
| | | | 7/177.8* | | |
| 1 | 1a | 1.90 | | .22/5.59 | 2.00 |
| | 5a | 1.37 | | N/A | 1.51 |
| | | | 8/203.2 | | |
| 2 | 1b | 0.78 | | .22/5.59 | 0.87 |
| | 5b | 0.19 | | N/A | 0.18 |
| | | | 57/1447.8** | | |
| N/A | | | | | |
| N/A | | | | | |
| N/A | | | | | |
| N/A | | | | | |
| N/A | | | | | |
| N/A | | | | | |

Output Water Temperature 49 C.
*Distance from water inlet to center of first electrode set
**Distance from center of last electrode set to water outlet The solution PT001 was then treated as if it had an equivalent volume of zinc-based nanoparticles equivalent to those present in BT012 (i.e., 23 ppm zinc). In other words, a volume of about 150 ml of PT001 was added to about 50 ml of AT064 to produce GR5* and a volume of about 170 ml of PT001 was added to about 33 ml of AT060 to produce GR8*. Once mixed, these new material solutions (i.e., GR5* and GR8*) were allowed to sit for 24 hours prior to being tested for cytotoxicity.

FIG. 76a shows that the $LD_{50}$ for GR5* was 8.794 (i.e., based on total silver nanoparticle concentration). This compares with an $LD_{50}$ for silver alone in AT064 of 7.050; and an $LD_{50}$ for GR5 (based on silver concentration alone) of 5.092.

Likewise, FIG. 76b shows the cytotoxicity of GR8* as a function of silver nanoparticle concentration. The $LD_{50}$ (i.e., based on silver nanoparticle concentration) for GR8* is 7.165. This compares directly to an $LD_{50}$ for AT060 of 9.610 and an $LD_{50}$ for GR8 (based on silver concentration alone) of 4.874.

Accordingly, the $LD_{50}$ of each of GR5* and GR8* was higher than the corresponding $LD_{50}$'s of GR5 and GR8, respectively (i.e., with regard to the silver content in each of the mixes GR5 and GR8).

The biological efficacies against *E. coli* of each of GR5 and GR5* were then compared. Specifically, FIG. 77a shows a Bioscreen reaction, run according to the procedures discussed above herein. In this Bioscreen reaction, it is clear that the performance of GR5 and GR5* were substantially identical.

Likewise, a comparison between the biological efficacy against *E. coli* was also performed for GR8 and GR8*. This comparison is shown in FIG. 77b. GR8 and GR8* both had substantially identical biological performance.

Accordingly, this Example shows that cytotoxicity of solutions GR5 and GR8 can be lowered by utilizing the solution PT001 instead of BT012 in each of the mixes GR5 and GR8. Moreover, such cytotoxicity is lowered without sacrificing biological efficacy against *E. coli*, as shown in FIGS. 77a and 77b.

However, it should be understood that other in vivo benefits can be obtained by the presence of, for example, the material corresponding to BT012 in the solutions GR5 and GR8.

Example 12

Comparison of Biological Performance of Two Different Silver-Based Nanoparticles/Nanoparticle Solutions by Adding Variable Zinc Nanoparticles/Nanoparticle Solutions and Related Aging Study The materials disclosed in Example 11, namely AT064 and AT060 and an equivalent to BT012 (i.e., BT013) were mixed together in varying proportions to determine if any differences in biological efficacy could be observed (e.g., similar to the studies shown in FIGS. 49 and 50). However, in this study, biological efficacy as a function of time elapsed between mixing the solutions together and testing for biological efficacy was investigated.

Specifically, FIG. 78a shows biological efficacy results of a variety of mixtures of AT064 with BT013 wherein the amount of AT064 remains at a constant ppm relative to the amount of BT013 added. Accordingly, this resulted in an increasing sequence of zinc being added as follows 2 ppm Zn, 4 ppm Zn, 8 ppm Zn and 13 ppm Zn. These differing amounts of Zn additions were achieved by a similar approach used for generating the data associated with FIGS. 49 and 50. FIG. 78a clearly shows that the biological performance of AT064 was enhanced by adding BT013. Note that efficacy tests were begun immediately after mixing AT064 and BT013 together. Specifically, FIG. 78a shows biological performance of the various silver-zinc mixtures wherein such mixtures were mixed as close in time as possible ($\Delta t=0$) to beginning the Bioscreen run. The 13 ppm Zn added showed great enhanced performance relative to AT064 as well as the other lower ppm zinc levels. However, only slight differences in performance existed between 2 ppm, 4 ppm and 8 ppm Zn additions, relative to each other. These relative performances were greatly enhanced in FIG. 78b.

Specifically, FIG. 78b shows a $\Delta t=1$, which corresponds to allowing the raw materials AT064 and BT013 to sit undisturbed after being mixed together for approximately 24 hours prior to being placed in the Bioscreen test. Clear distinctions in biological efficacy are seen between all of the Zn ppm additions to AT064, with the 13 ppm still performing equal to the negative control after 0.8 days. Accordingly, enhanced performance by mixing of BT013 with AT064 was achieved by allowing a period of time to elapse after mixing, prior to biological efficacy testing.

FIG. 79a shows slightly different results from FIG. 78a. Particularly, FIG. 79a shows the changes in biological efficacy of AT060 when mixed with 2 ppm Zn, 4 ppm Zn, 8 ppm Zn and 13 ppm Zn. In contrast to FIG. 78a, the 2 ppm and 4 ppm zinc additions to AT060 did not show any change in biological efficacy after mixing together and conducting immediate biological testing. Accordingly, with $\Delta t=0$ in this experiment, which corresponds to mixing AT060 with BT013 and immediately testing in the Bioscreen, no enhancement in efficacy was observed for the addition of 2 ppm and 4 ppm Zn. Slightly enhanced performance of AT060 was observed with 8 ppm Zn and 13 ppm Zn.

However, the biological efficacy results are dramatically different in FIG. 79b. In this efficacy experiment, the components AT060 and BT013 were allowed to sit together for $\Delta t=1$, which corresponds to approximately 24 hours. After allowing the materials AT060 and BT013 to sit for approximately 24 hours, and then subsequent Bioscreen testing was performed, a spread in efficacy, similar to that shown in FIG. 78b, was observed. Specifically, there are clear biological efficacy distinctions that exist between AT060 with additions of each of 2 ppm, 4 ppm, 8 ppm and 13 ppm of Zn added thereto, respectively.

Additional biological efficacy tests were run to determine if additional "hold time" had any further enhancing effects. Specifically, the data in FIG. 79c correspond to a "hold time" of $\Delta t=2$ (i.e., approximately 48 hours) prior to testing for efficacy changes of AT060 as a function of increasing Zn ppm concentration. It was determined that the efficacy changes shown in FIG. 79c were substantially identical to the efficacy changes shown in FIG. 79b. Accordingly, it is clear that reactions which occurred in FIG. 79b did not seem to occur to any greater extent between 24 hours and 48 hours.

In an effort to clarify the differences in biological efficacy observed in FIG. 78a vs. FIG. 78b, and in FIG. 79a vs. FIGS. 79b and 79c, a dynamic light scattering ("DLS") experiment was performed, according to the procedures discussed above herein.

Specifically, two sets of DLS tests were performed. The first test mixed together AT064 and BT013 in proportion to produce GR5 (i.e., about 50 ml of AT064 and about 150 ml of BT013). The second test mixed together AT060 and BT013 in proportion to produce GR8 (i.e., about 33 ml of AT060 and about 170 ml of BT013).

The results of the DLS measurements as a function of time after mixing the aforementioned materials together are shown in FIGS. 80 and 81. Specifically, FIGS. 80a-80f show DLS size measurements taken at six different times, namely, $t=0$; $t=80$ minutes; $t=5$ hours; $t=5.5$ hours; $t=6$ hours; and $t=21$ hours. Similarly, FIGS. 81a-81e show DLS size measurements taken at five different times, namely, $t=0$; $t=80$ minutes; $t=4$ hours; $t=5$ hours; and $t=21$ hours.

It is clear from the results shown in FIGS. 80 and 81, that one or more reaction(s) are occurring between AT064 and BT013; as well as one or more reaction(s) occurring between AT060 and BT013. While the initial particle sizes of AT064 and AT060 may be different, according to, for example, the TEM photomicrographs of FIG. 43, discussed earlier herein, the concentration and nature of solutions containing Ag and solutions containing Zn are different in each of GR5 and GR8. In any event, DLS measurements of both mixtures comprising GR5 and GR8 show relatively large particle sizes being present. Perhaps some particle agglomentation may be occurring. However, after a period of 5-6 hours, DLS measurements indicate the detected particle sizes have significantly diminished. Further, after 21 hours, the DLS measurements suggest that the detected particle sizes were substantially equivalent.

Without wishing to be bound by any particular theory or explanation, it appears that particle size and biological performance (e.g., efficacy against *E. coli*) are related.

The invention claimed is:

1. A process for creating silver and zinc constituents in water comprising:
    flowing water through at least one first trough member, said water having an upper surface and a flow direction;
    providing at least one plasma-forming electrode comprising metallic silver;
    creating at least one plasma between said at least one plasma-forming electrode and at least a portion of said upper surface of said water;
    providing at least one set of electrodes comprising silver in contact with said water and located downstream in said flow direction from said at least one plasma-forming electrode;
    conducting at least one electrochemical reaction at said at least one set of electrodes comprising silver to produce at least some silver constituents within said water;
    flowing a second water through at least one second trough member, said second water having an upper surface and a flow direction;
    providing at least one metallic electrode set comprising a plasma-forming electrode comprising zinc and a liquid-contacting electrode comprising zinc;
    creating at least one plasma between said at least one plasma-forming electrode comprising zinc and at least a portion of said upper surface of said second water to produce at least some zinc constituents in said second water from said at least one zinc electrode set;
    mixing together said at least some silver constituents within said water and said at least some zinc constituents within said second water.

2. The process of claim 1, wherein said at least one first trough member comprises a conduit with at least one inlet and at least one outlet which permits said water to flow therein and said at least one second trough member comprises a conduit with at least one inlet and at least one outlet which permits said second water to flow therein.

3. The process of claim 1, wherein each said at least one plasma comprises an adjustable plasma.

4. The process of claim 1, wherein each said at least one plasma-forming electrode provides at least one species therefrom that is present in said at least one plasma.

5. The process of claim 1, wherein said at least some silver constituents comprise metallic nanoparticles.

6. The process of claim 1, wherein said at least some silver constituents comprise metallic ions.

7. The process of claim 1, wherein said at least some zinc constituents comprise metallic ions.

8. The process of claim 1, wherein at least one first power source is connected electrically between said at least one set of electrodes comprising silver to cause said at least one electrochemical reaction to occur within said water.

9. The process of claim 1, wherein at least one first power source is provided between said plasma-forming electrode comprising zinc, and said liquid-contacting electrode comprising zinc to cause said at least one electrochemical reaction to occur.

10. The process of claim 1, wherein said flowing water comprises water that is pumped through said at least one first trough member, said at least one trough member having an inlet portion and an outlet portion.

11. The process of claim 1, wherein said second flowing water comprises water that is pumped through said at least one second trough member, said at least one trough member having an inlet portion and an outlet portion.

12. The process of claim 1, further comprising at least one control device for adjusting the location of said at least one set of electrodes comprising silver relative to the surface of the water.

13. The process of claim 12, wherein said at least one control device maintains a substantially constant voltage across said at least one set of electrodes comprising silver by adjusting the amount of contact of said electrodes comprising silver with said flowing water.

14. The process of claim 13, wherein said substantially constant voltage is maintained within a range of 630-1550 Volts.

15. The process of claim 12, wherein said at least one control device maintains a substantially constant voltage across said at least one metallic zinc electrode set by adjusting the location of said plasma-forming electrode comprising zinc relative to the upper surface of said second water.

16. The process of claim 15, wherein said substantially constant voltage is maintained within a range of 600-1880 Volts.

17. The process of claim 1, further comprising at least one control device for adjusting the location of said at least one metallic electrode set relative to the surface of the water.

18. The process of claim 1, wherein said at least one set of electrodes comprising silver comprises at least four sets of electrodes comprising silver.

19. The process of claim 1, wherein said at least one metallic zinc electrode set comprises at least four sets of electrodes comprising metallic zinc.

20. The process of claim 1, wherein said at least one first trough member with said at least one second trough member together comprise a top portion of a "Y"-shape, and said at least some silver constituents and said at least some zinc constituents mix together at the bottom portion of the "Y"-shaped trough.

21. The process of claim 20, wherein said mixing together occurs at a portion of the "Y"-shape wherein the top and bottom portions of the "Y"-shaped trough join together.

22. The process of claim 1, wherein said mixing together occurs by separately collecting outputs from each of said first and second trough members and mixing together such collected outputs in another vessel.

23. A process for creating silver constituents in water and zinc constituents in water comprising:
    flowing water through at least one first trough member, said water having an upper surface and a flow direction;
    providing at least one plasma-forming electrode comprising metallic silver;
    creating at least one plasma between said at least one plasma-forming electrode and at least a portion of said upper surface of said water;

providing at least one set of electrodes comprising silver in contact with said water and located downstream in said flow direction from said at least one plasma-forming electrode;

conducting at least one electrochemical reaction at said at least one set of electrodes comprising silver to produce at least some silver constituents within said water;

flowing a second water through at least one second trough member, said at least one second water having an upper surface and a flow direction;

providing at least two zinc electrode sets, each zinc electrode set comprising a plasma-forming electrode comprising zinc and another electrode comprising zinc in electrical connection with said plasma-forming electrode through said second water;

creating at least one plasma between each of said at least one plasma-forming electrode and at least a portion of said upper surface of said second water to produce at least some zinc constituents from said at least two zinc electrode sets in said second water;

mixing together said at least some silver constituents within said water and said at least some zinc constituents within said second water.

\* \* \* \* \*